(12) United States Patent
Bair et al.

(10) Patent No.: US 11,919,839 B2
(45) Date of Patent: *Mar. 5, 2024

(54) ALPHA-CINNAMIDE COMPOUNDS AND COMPOSITIONS AS HDAC8 INHIBITORS

(71) Applicant: Valo Health, Inc., Boston, MA (US)

(72) Inventors: Kenneth W. Bair, Wellesley, MA (US); Nicholas Barczak, Waterford, CT (US); Bingsong Han, Westwood, MA (US); David R. Lancia, Jr., Boston, MA (US); Cuixian Liu, Madison, CT (US); Matthew W. Martin, Arlington, MA (US); Pui Yee Ng, Lexington, MA (US); Aleksandra Rudnitskaya, Roslindale, MA (US); Jennifer R. Thomason, Clinton, MA (US); Mary-Margaret Zablocki, Revere, MA (US); Xiaozhang Zheng, Lexington, MA (US)

(73) Assignee: VALO HEALTH, INC., Boston, MA (US)

( * ) Notice: Subject to any disclaimer, the term of this patent is extended or adjusted under 35 U.S.C. 154(b) by 138 days.

This patent is subject to a terminal disclaimer.

(21) Appl. No.: 17/238,529

(22) Filed: Apr. 23, 2021

(65) Prior Publication Data
US 2022/0073452 A1    Mar. 10, 2022

Related U.S. Application Data

(63) Continuation of application No. 16/689,252, filed on Nov. 20, 2019, now Pat. No. 10,988,441, which is a
(Continued)

(51) Int. Cl.
*C07C 259/06* (2006.01)
*A61K 31/185* (2006.01)
*A61K 31/277* (2006.01)
*A61K 31/397* (2006.01)
*A61K 31/4035* (2006.01)
(Continued)

(52) U.S. Cl.
CPC .......... *C07C 259/06* (2013.01); *A61K 31/185* (2013.01); *A61K 31/277* (2013.01); *A61K 31/397* (2013.01); *A61K 31/4035* (2013.01); *A61K 31/407* (2013.01); *A61K 31/417* (2013.01); *A61K 31/4184* (2013.01); *A61K 31/435* (2013.01); *A61K 31/438* (2013.01); *A61K 31/44* (2013.01); *A61K 31/4439* (2013.01); *A61K 31/451* (2013.01); *A61K 31/495* (2013.01); *A61K 31/5377* (2013.01); *C07D 207/10* (2013.01); *C07D 207/267* (2013.01); *C07D 209/08* (2013.01); *C07D 209/42* (2013.01); *C07D 209/44* (2013.01); *C07D 209/46* (2013.01); *C07D 211/16* (2013.01); *C07D 211/58* (2013.01); *C07D 213/56* (2013.01); *C07D 213/65* (2013.01); *C07D 213/75* (2013.01); *C07D 213/81* (2013.01); *C07D 215/12* (2013.01); *C07D 221/20* (2013.01); *C07D 231/14* (2013.01); *C07D 231/18* (2013.01); *C07D 233/36* (2013.01); *C07D 233/38* (2013.01); *C07D 233/68* (2013.01); *C07D 235/14* (2013.01); *C07D 235/30* (2013.01); *C07D 239/20* (2013.01); *C07D 239/22* (2013.01); *C07D 241/08* (2013.01); *C07D 241/12* (2013.01); *C07D 249/18* (2013.01); *C07D 257/04* (2013.01); *C07D 261/18* (2013.01); *C07D 277/56* (2013.01); *C07D 295/155* (2013.01); *C07D 295/192* (2013.01); *C07D 307/68* (2013.01); *C07D 317/68* (2013.01); *C07D 333/70* (2013.01); *C07D 401/04* (2013.01); *C07D 401/12* (2013.01); *C07D 401/14* (2013.01); *C07D 405/12* (2013.01); *C07D 409/04* (2013.01); *C07D 409/12* (2013.01); *C07D 417/04* (2013.01); *C07D 417/12* (2013.01); *C07D 471/04* (2013.01); *C07D 471/10* (2013.01); *C07D 487/04* (2013.01); *C07D 487/08* (2013.01); *C07D 487/10* (2013.01); *C07D 491/10* (2013.01); *C07D 493/08* (2013.01); *C07D 495/10* (2013.01);
(Continued)

(58) Field of Classification Search
CPC .................................................. C07C 259/06
See application file for complete search history.

(56) References Cited

U.S. PATENT DOCUMENTS

| 4,820,828 A | 4/1989 | Demers et al. |
| 4,977,188 A | 12/1990 | Kneen et al. |

(Continued)

FOREIGN PATENT DOCUMENTS

| CN | 1073571 A | 6/1993 |
| CN | 101163696 A | 4/2008 |

(Continued)

OTHER PUBLICATIONS

Benedettti et al. Targeting Histone Deacetylases in Diseases: Where Are We?, Antioxid Redox Signal, 23(1): 99-126 (2015).
(Continued)

*Primary Examiner* — Brian J Davis
(74) *Attorney, Agent, or Firm* — Dechert LLP; John P. Rearick; Erica M. D'Amato

(57) ABSTRACT

The present invention relates to inhibitors of histone deacetylases, in particular HDAC8, that are useful for the treatment of cancer and other diseases and disorders, as well as the synthesis and applications of said inhibitors.

20 Claims, No Drawings

Related U.S. Application Data continuation of application No. 16/387,937, filed on Apr. 18, 2019, now Pat. No. 10,508,077, which is a continuation of application No. 15/925,559, filed on Mar. 19, 2018, now Pat. No. 10,266,487, which is a continuation of application No. 15/688,732, filed on Aug. 28, 2017, now abandoned, which is a continuation of application No. 15/067,605, filed on Mar. 11, 2016, now Pat. No. 9,745,253.

(60) Provisional application No. 62/270,371, filed on Dec. 21, 2015, provisional application No. 62/184,335, filed on Jun. 25, 2015, provisional application No. 62/132,895, filed on Mar. 13, 2015.

(51) Int. Cl.

| | |
|---|---|
| A61K 31/407 | (2006.01) |
| A61K 31/417 | (2006.01) |
| A61K 31/4184 | (2006.01) |
| A61K 31/435 | (2006.01) |
| A61K 31/438 | (2006.01) |
| A61K 31/44 | (2006.01) |
| A61K 31/4439 | (2006.01) |
| A61K 31/451 | (2006.01) |
| A61K 31/495 | (2006.01) |
| A61K 31/5377 | (2006.01) |
| C07D 207/10 | (2006.01) |
| C07D 207/267 | (2006.01) |
| C07D 209/08 | (2006.01) |
| C07D 209/42 | (2006.01) |
| C07D 209/44 | (2006.01) |
| C07D 209/46 | (2006.01) |
| C07D 211/16 | (2006.01) |
| C07D 211/58 | (2006.01) |
| C07D 213/56 | (2006.01) |
| C07D 213/65 | (2006.01) |
| C07D 213/75 | (2006.01) |
| C07D 213/81 | (2006.01) |
| C07D 215/12 | (2006.01) |
| C07D 221/20 | (2006.01) |
| C07D 231/14 | (2006.01) |
| C07D 231/18 | (2006.01) |
| C07D 233/36 | (2006.01) |
| C07D 233/38 | (2006.01) |
| C07D 233/68 | (2006.01) |
| C07D 235/14 | (2006.01) |
| C07D 235/30 | (2006.01) |
| C07D 239/20 | (2006.01) |
| C07D 239/22 | (2006.01) |
| C07D 241/08 | (2006.01) |
| C07D 241/12 | (2006.01) |
| C07D 249/18 | (2006.01) |
| C07D 257/04 | (2006.01) |
| C07D 261/18 | (2006.01) |
| C07D 277/56 | (2006.01) |
| C07D 295/155 | (2006.01) |
| C07D 295/192 | (2006.01) |
| C07D 307/68 | (2006.01) |
| C07D 317/68 | (2006.01) |
| C07D 333/70 | (2006.01) |
| C07D 401/04 | (2006.01) |
| C07D 401/12 | (2006.01) |
| C07D 401/14 | (2006.01) |
| C07D 405/12 | (2006.01) |
| C07D 409/04 | (2006.01) |
| C07D 409/12 | (2006.01) |
| C07D 417/04 | (2006.01) |
| C07D 417/12 | (2006.01) |
| C07D 471/04 | (2006.01) |
| C07D 471/10 | (2006.01) |
| C07D 487/04 | (2006.01) |
| C07D 487/08 | (2006.01) |
| C07D 487/10 | (2006.01) |
| C07D 491/10 | (2006.01) |
| C07D 493/08 | (2006.01) |
| C07D 495/10 | (2006.01) |
| C07D 498/04 | (2006.01) |
| C07D 513/10 | (2006.01) |

(52) U.S. Cl.
CPC ......... *C07D 498/04* (2013.01); *C07D 513/10* (2013.01); *Y02A 50/30* (2018.01)

(56) References Cited

U.S. PATENT DOCUMENTS

| | | |
|---|---|---|
| 5,234,923 A | 8/1993 | Poss et al. |
| 5,312,820 A | 5/1994 | Ashton et al. |
| 5,424,204 A | 6/1995 | Aoyama et al. |
| 5,466,704 A | 11/1995 | Poss |
| 5,534,654 A | 7/1996 | Ohtani et al. |
| 5,559,127 A | 9/1996 | Hartman et al. |
| 5,633,268 A | 5/1997 | Kirstgen et al. |
| 5,648,368 A | 7/1997 | Egbertson et al. |
| 5,814,651 A | 9/1998 | Duplantier et al. |
| 5,851,233 A | 12/1998 | Pedersen et al. |
| 5,859,010 A | 1/1999 | Petersen et al. |
| 5,939,452 A | 8/1999 | Dombroski et al. |
| 6,051,601 A | 4/2000 | Dombroski et al. |
| 6,069,156 A | 5/2000 | Oku et al. |
| 6,080,770 A | 6/2000 | Andersen et al. |
| 6,087,355 A | 7/2000 | Cho et al. |
| 6,211,197 B1 | 4/2001 | Belley et al. |
| 6,355,669 B1 | 3/2002 | Yamauchi et al. |
| 6,465,507 B2 | 10/2002 | Tang et al. |
| 6,541,661 B1 | 4/2003 | Delorme et al. |
| 6,548,517 B2 | 4/2003 | Marlowe et al. |
| 6,593,322 B1 | 7/2003 | Bhagwat et al. |
| 6,727,267 B2 | 4/2004 | Jaen et al. |
| 6,759,422 B2 | 7/2004 | Jensen et al. |
| 6,797,828 B1 | 9/2004 | Shibasaki et al. |
| 6,872,542 B1 | 3/2005 | Hultgren et al. |
| 6,884,808 B2 | 4/2005 | Kikuchi et al. |
| 6,960,572 B2 | 11/2005 | Shakespeare et al. |
| 7,067,551 B2 | 6/2006 | Remiszewski et al. |
| 7,084,189 B2 | 8/2006 | Banning et al. |
| 7,135,493 B2 | 11/2006 | Urano et al. |
| 7,342,022 B2 | 3/2008 | Berg et al. |
| 7,375,228 B2 | 5/2008 | Bressi et al. |
| 7,399,786 B2 | 7/2008 | Dey et al. |
| 7,402,603 B2 | 7/2008 | Chen et al. |
| 7,435,729 B2 | 10/2008 | Gayo-Fung et al. |
| 7,507,858 B2 | 3/2009 | Belvedere et al. |
| 7,517,898 B2 | 4/2009 | Liu et al. |
| 7,557,127 B2 | 7/2009 | Ishibashi et al. |
| 7,557,140 B2 | 7/2009 | Kalvinsh et al. |
| 7,592,478 B2 | 9/2009 | Diaz et al. |
| 7,615,640 B2 | 11/2009 | Horiuchi et al. |
| 7,626,031 B2 | 12/2009 | Xu et al. |
| 7,662,823 B2 | 2/2010 | Wang et al. |
| 7,683,185 B2 | 3/2010 | Joel et al. |
| 7,687,640 B2 | 3/2010 | Kimura et al. |
| 7,772,245 B2 | 8/2010 | Anandan et al. |
| 7,820,711 B2 | 10/2010 | Buggy et al. |
| 7,842,727 B2 | 11/2010 | Lan-Hargest et al. |
| 7,858,635 B2 | 12/2010 | Makings et al. |
| 7,880,020 B2 | 2/2011 | Watkins et al. |
| 7,897,602 B2 | 3/2011 | Huang et al. |
| 7,977,334 B2 | 7/2011 | Trieselmann et al. |
| 7,981,895 B2 | 7/2011 | Watkins et al. |

(56) References Cited

U.S. PATENT DOCUMENTS

| | | |
|---|---|---|
| 7,985,763 B2 | 7/2011 | Wang et al. |
| 7,999,001 B2 | 8/2011 | Aman et al. |
| 8,003,624 B2 | 8/2011 | McCormick et al. |
| 8,026,280 B2 | 9/2011 | Lan-Hargest et al. |
| 8,058,427 B2 | 11/2011 | Hsieh et al. |
| 8,093,220 B2 | 1/2012 | Atadja |
| 8,173,675 B2 | 5/2012 | Koradin et al. |
| 8,198,284 B2 | 6/2012 | Shie et al. |
| 8,207,177 B2 | 6/2012 | Langston et al. |
| 8,207,179 B2 | 6/2012 | Engelhardt et al. |
| 8,236,963 B2 | 8/2012 | Schwarz et al. |
| 8,242,175 B2 | 8/2012 | Mai et al. |
| 8,273,785 B2 | 9/2012 | Cai et al. |
| 8,324,221 B2 | 12/2012 | Banka et al. |
| 8,349,884 B2 | 1/2013 | Benting et al. |
| 8,383,818 B2 | 2/2013 | Zheng et al. |
| 8,420,052 B2 | 4/2013 | Kolb et al. |
| 8,420,698 B2 | 4/2013 | Lan-Hargest et al. |
| 8,426,428 B2 | 4/2013 | Miller |
| 8,476,255 B2 | 7/2013 | Rajagopal et al. |
| 8,476,308 B2 | 7/2013 | Shi et al. |
| 8,486,990 B2 | 7/2013 | Napper et al. |
| 8,497,295 B2 | 7/2013 | Makings et al. |
| 8,513,297 B2 | 8/2013 | Boiteau et al. |
| 8,551,988 B2 | 10/2013 | Chen et al. |
| 8,592,399 B2 | 11/2013 | Gill et al. |
| 8,598,374 B2 | 12/2013 | Shi et al. |
| 8,637,547 B2 | 1/2014 | Davidson et al. |
| 8,673,586 B2 | 3/2014 | Meutermans et al. |
| 8,686,025 B2 | 4/2014 | Old et al. |
| 8,716,323 B2 | 5/2014 | Das et al. |
| 8,754,237 B2 | 6/2014 | Bradner et al. |
| 8,765,810 B2 | 7/2014 | Greene et al. |
| 8,835,501 B2 | 9/2014 | Bastin et al. |
| 8,853,415 B2 | 10/2014 | Hadida Ruah et al. |
| 8,912,331 B2 | 12/2014 | Muthuppalaniappan et al. |
| 8,927,576 B2 | 1/2015 | Gu |
| 9,630,922 B2 | 4/2017 | Ng et al. |
| 9,637,453 B2 | 5/2017 | Ng et al. |
| 9,745,253 B2 | 8/2017 | Bair et al. |
| 10,266,487 B2 | 4/2019 | Bair et al. |
| 10,508,077 B2 | 12/2019 | Bair et al. |
| 10,988,441 B2 | 4/2021 | Bair et al. |
| 2002/0019395 A1 | 2/2002 | Zhu et al. |
| 2002/0045641 A1 | 4/2002 | Hamilton et al. |
| 2002/0128256 A1 | 9/2002 | Brugnara et al. |
| 2003/0152557 A1 | 8/2003 | Besterman et al. |
| 2003/0199558 A1 | 10/2003 | Dooley et al. |
| 2004/0077726 A1 | 4/2004 | Watkins et al. |
| 2005/0090498 A1 | 4/2005 | Samizu et al. |
| 2005/0137234 A1 | 6/2005 | Bressi et al. |
| 2005/0159470 A1 | 7/2005 | Bressi et al. |
| 2005/0261327 A1 | 11/2005 | Bock et al. |
| 2006/0105445 A1 | 5/2006 | Godl et al. |
| 2006/0235012 A1 | 10/2006 | Davidson et al. |
| 2007/0088051 A1 | 4/2007 | McConnell et al. |
| 2007/0167499 A1 | 7/2007 | Stunkel et al. |
| 2008/0234271 A1 | 9/2008 | Guckian et al. |
| 2008/0269298 A1 | 10/2008 | Andrews et al. |
| 2009/0023729 A1 | 1/2009 | Nakamura et al. |
| 2009/0088432 A1 | 4/2009 | Banerjee et al. |
| 2009/0118146 A1 | 5/2009 | Negoro et al. |
| 2009/0203697 A1 | 8/2009 | Kimura et al. |
| 2009/0215813 A1 | 8/2009 | Katopodis |
| 2009/0275570 A1 | 11/2009 | Daly et al. |
| 2010/0068181 A1 | 3/2010 | Paliwal et al. |
| 2010/0069388 A1 | 3/2010 | Inoue et al. |
| 2011/0053925 A1 | 3/2011 | Cho et al. |
| 2011/0065734 A1 | 3/2011 | Bar et al. |
| 2011/0224242 A1 | 9/2011 | Giethlen et al. |
| 2011/0237633 A1 | 9/2011 | Panicker et al. |
| 2011/0306671 A1 | 12/2011 | Carson et al. |
| 2012/0046238 A1 | 2/2012 | Hsieh et al. |
| 2012/0101099 A1 | 4/2012 | Selvakumar et al. |
| 2012/0148670 A1 | 6/2012 | Kim et al. |
| 2012/0270824 A1 | 10/2012 | Ernst et al. |
| 2012/0322769 A1 | 12/2012 | Yang et al. |
| 2013/0040998 A1 | 2/2013 | Bradner et al. |
| 2013/0150326 A1 | 6/2013 | Roppe et al. |
| 2013/0203714 A1 | 8/2013 | Bradbury et al. |
| 2013/0245000 A1 | 9/2013 | Thotapally et al. |
| 2013/0323269 A1 | 12/2013 | Manoharan et al. |
| 2014/0018368 A1 | 1/2014 | Cai et al. |
| 2014/0024608 A1 | 1/2014 | Deziel et al. |
| 2014/0128408 A1 | 5/2014 | Kozikowski et al. |
| 2014/0155439 A1 | 6/2014 | Donald et al. |
| 2014/0235579 A1 | 8/2014 | McCall et al. |
| 2014/0275076 A1 | 9/2014 | Tsuboi et al. |
| 2014/0288119 A1 | 9/2014 | Breslow et al. |
| 2014/0323531 A1 | 10/2014 | Davidson et al. |
| 2014/0364413 A1 | 12/2014 | Player et al. |
| 2014/0364477 A1 | 12/2014 | Chen et al. |
| 2015/0045367 A1 | 2/2015 | Verner et al. |
| 2015/0045368 A1 | 2/2015 | Bregman et al. |
| 2015/0073013 A1 | 3/2015 | Cooymans et al. |
| 2016/0221972 A1 | 8/2016 | Zheng et al. |
| 2016/0221973 A1 | 8/2016 | Zheng et al. |
| 2016/0221997 A1 | 8/2016 | Zheng et al. |
| 2016/0222022 A1 | 8/2016 | Zheng et al. |
| 2016/0222028 A1 | 8/2016 | Zheng et al. |
| 2016/0264518 A1 | 9/2016 | Bair et al. |
| 2016/0304456 A1 | 10/2016 | Ng et al. |
| 2016/0304462 A1 | 10/2016 | Ng et al. |
| 2017/0066729 A1 | 3/2017 | Zheng et al. |
| 2018/0044282 A1 | 2/2018 | Bair et al. |
| 2018/0297939 A1 | 10/2018 | Bair et al. |
| 2019/0241506 A1 | 8/2019 | Bair et al. |
| 2020/0331847 A1 | 10/2020 | Bair et al. |

FOREIGN PATENT DOCUMENTS

| | | |
|---|---|---|
| CN | 101312976 A | 11/2008 |
| CN | 102036955 A | 4/2011 |
| CN | 103373997 A | 10/2013 |
| CN | 103374021 A | 10/2013 |
| CN | 103524372 A | 1/2014 |
| CN | 103739482 A | 4/2014 |
| CN | 103755595 A | 4/2014 |
| CN | 103936752 A | 7/2014 |
| EP | 133534 A2 | 2/1985 |
| EP | 706795 A2 | 4/1996 |
| EP | 769498 A1 | 4/1997 |
| EP | 943339 A2 | 9/1999 |
| EP | 963755 A2 | 12/1999 |
| ES | 2336746 A1 | 4/2010 |
| JP | H06130434 A | 5/1994 |
| JP | H09268125 A | 10/1997 |
| JP | 2005145928 A | 6/2005 |
| JP | 2010077096 A | 4/2010 |
| JP | 4834699 B2 | 12/2011 |
| JP | 4846769 B2 | 12/2011 |
| JP | 2013177329 A | 9/2013 |
| KR | 2014087961 | 7/2014 |
| WO | WO-9001929 A1 | 3/1990 |
| WO | WO-9513264 A1 | 5/1995 |
| WO | WO-9618770 A2 | 6/1996 |
| WO | WO-97/11065 A1 | 3/1997 |
| WO | WO-9748786 A1 | 12/1997 |
| WO | WO-9855449 A1 | 12/1998 |
| WO | WO-9903498 A1 | 1/1999 |
| WO | WO-0230879 A2 | 4/2002 |
| WO | WO-2005/025557 A1 | 3/2005 |
| WO | WO-2005/065681 A1 | 7/2005 |
| WO | WO-2005/086898 A2 | 9/2005 |
| WO | WO-2006/016680 A1 | 2/2006 |
| WO | WO-2006/029575 A1 | 3/2006 |
| WO | WO-2006/083869 A2 | 8/2006 |
| WO | WO-2006/101456 A1 | 9/2006 |
| WO | WO-2007/030455 A2 | 3/2007 |
| WO | WO-2007/104834 A1 | 9/2007 |
| WO | WO-2008/087514 A2 | 7/2008 |
| WO | WO-2008/090585 A2 | 7/2008 |
| WO | WO-2009/041708 A1 | 4/2009 |
| WO | WO-2010/010148 A1 | 1/2010 |

(56) References Cited

FOREIGN PATENT DOCUMENTS

| WO | WO-2010/017827 A1 | 2/2010 |
| WO | WO-2010/119881 A1 | 10/2010 |
| WO | WO-2011/103189 A1 | 8/2011 |
| WO | WO-2011/106650 A2 | 9/2011 |
| WO | WO-2011/159297 A1 | 12/2011 |
| WO | WO-2012/117021 A2 | 9/2012 |
| WO | WO-2012/117421 A1 | 9/2012 |
| WO | WO-2012/164074 A1 | 12/2012 |
| WO | WO-2013/024427 A1 | 2/2013 |
| WO | WO-2013/040527 A1 | 3/2013 |
| WO | WO-2013/092460 A1 | 6/2013 |
| WO | WO-2013/101600 A1 | 7/2013 |
| WO | WO-2013/113838 A1 | 8/2013 |
| WO | WO-2013/113841 A1 | 8/2013 |
| WO | WO-2013/174947 A1 | 11/2013 |
| WO | WO-2013/186229 A1 | 12/2013 |
| WO | WO-2014/037340 A1 | 3/2014 |
| WO | WO-2014/046544 A1 | 3/2014 |
| WO | WO-2014/070983 A1 | 5/2014 |
| WO | WO-2014/124651 A1 | 8/2014 |
| WO | WO-2014/131855 A1 | 9/2014 |
| WO | WO-2014/140365 A1 | 9/2014 |
| WO | WO-2014/200882 A1 | 12/2014 |
| WO | WO-2015/026935 A2 | 2/2015 |
| WO | WO-2015/157504 A1 | 10/2015 |
| WO | WO-2016/126721 A1 | 8/2016 |
| WO | WO-2016/126722 A1 | 8/2016 |
| WO | WO-2016/126724 A1 | 8/2016 |
| WO | WO-2016/126725 A1 | 8/2016 |
| WO | WO-2016/126726 A1 | 8/2016 |
| WO | WO-2017/218950 A1 | 12/2017 |

OTHER PUBLICATIONS

Database CAPLUS in STN, Acc. No. 2002:293604, Watkins et al., WO 2002/030879 A2 (Apr. 18, 2002) (abstract).

Database CAPLUS in STN, Acc. No. 2005:442293, Mai et al., Medicinal Chemistry (2005), 1(3), pp. 245-254 (abstract).

Dessolin, M. et al. Reactivity of hydroxamic acids towards activated esters. Kinetic study, Lab. Chim. Org. Biol., 7: 2573-80 (1970).

Finn, P et al., Novel Sulfonamide Derivatives as Inhibitors of Histone Deacetylase, Helvetica Chimica Acta, 88: 1630-1657 (2005).

Huang, et al., Synthesis and Biological Evaluation of ortho-Aryl N-Hydroxycinnamides as Potent Histone Deacetylase (HDAC) 8 Isoform-Selective Inhibitors, Chem Med Chem, 7: 1815-1824 (2012).

International Search Report for PCT/US2016/022029, 6 pages (dated May 2, 2016).

Mai, A. et al., Synthesis and biological evaluation of 2-, 3-, and 4-acylaminocinnamyl-N-hydroxyamides as novel synthetic HDAC inhibitors, Medicinal Chemistry, 1(3): 245-254 (2005).

Plumb, J. et al. Pharmacodynamic Response and Inhibition of Growth of Human Tumor Xenografts by the Novel Histone Deacetylase Inhibitor PXD101, Molecular Cancer Therapeutics, 2: 721-828 (2003).

Tang et al. Histone deacetylases as targets for treatment of multiple diseases, Clin Sci., 124(11):651-62 (2013).

West and, Johnstone. New and emerging HDAC inhibitors for cancer treatment. J. Clin Invest., 124(1):30-9 (2014).

ALPHA-CINNAMIDE COMPOUNDS AND COMPOSITIONS AS HDAC8 INHIBITORS

CROSS-REFERENCE TO RELATED APPLICATIONS

This application claims the benefit of priority of U.S. Provisional Application No. 62/132,895, filed Mar. 13, 2015, U.S. Provisional Application No. 62/184,335, filed Jun. 25, 2015 and U.S. Provisional Application No. 62/270,371, filed Dec. 21, 2015, all of which are incorporated herein by reference.

FIELD OF THE INVENTION

The subject of this invention is applicable to the treatment of cancer, neurodegeneration, and inflammation. Furthermore, the inhibition of histone deacetylases has also been associated with other diseases including autoimmune, infectious, metabolic, or cardiovascular diseases or disorders. The present invention relates to compounds and compositions for inhibition of histone deacetylases, in particular HDAC8, as well as their synthesis and applications.

BACKGROUND OF THE INVENTION

Histone deacetylases (HDACs) are enzymes that regulate epigenetics by removal of acetyl groups from the lysine residues of proteins, including histones. The family of zinc-dependent histone deacetylases has been variously implicated in different disease states, including cancer, neurodegeneration, inflammation, and autoimmune, infectious, metabolic, hematologic, and cardiovascular dysfunctions. Three broad spectrum HDAC inhibitors have been approved for the treatment of cancer: vorinostat (cutaneous T cell lymphoma and multiple myeloma), romidepsin (peripheral T-cell lymphoma), and belinostat (peripheral T-cell lymphoma). However, there continues to be a need for an improved efficacy-safety profile and for efficacy against other types of cancer. While the potential for HDAC inhibitors as treatment for non-oncology indications has been recognized, one has yet to be approved.

As a regulator of the common post-translational modification of protein acetylation, the zinc-dependent histone deacetylases play a critical role in diverse cellular processes. Inhibitors of histone deacetylases have been approved as treatment for cutaneous T cell lymphoma and peripheral T-cell lymphoma. The potential remains for HDAC inhibition as a therapy for other types of cancer. For non-oncology therapies, HDAC inhibition will provide a novel pharmacological strategy.

SUMMARY OF THE INVENTION

One aspect of the present invention relates to compounds of Formula (I):

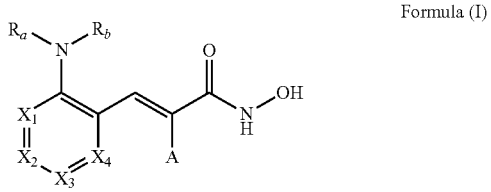

Formula (I)

and pharmaceutically acceptable salts, enantiomers, hydrates, solvates, prodrugs, and tautomers thereof, wherein:

$X_1$, $X_2$, $X_3$, and $X_4$ are independently CH or N, wherein no more than two of $X_1$, $X_2$, $X_3$, and $X_4$ are N and are not contiguous;

$R_a$ is hydrogen or alkyl;

$R_b$ is hydrogen, —$(CH_2)_nR_c$, —$C(O)R_c$, —$C(O)NHR_c$, or —$S(O)_2R_c$, or alternatively, $R_a$ and $R_b$ are combined to form a heterocycle, wherein said heterocycle is optionally substituted with one or more $R_d$;

$R_c$ is hydrogen, $C_1$-$C_6$, alkyl, $C_3$-$C_8$ cycloalkyl, 3-to-12 membered heterocycloalkyl, aryl, or heteroaryl, wherein alkyl, cycloalkyl, heterocycloalkyl, aryl, or heteroaryl are optionally substituted with one or more $R_d$ or $R_e$;

$R_d$ is hydrogen, hydroxyl, $C_1$-$C_6$ alkyl, $C_1$-$C_6$ haloalkyl, $C_1$-$C_6$ alkoxy, cyano, oxo, $C_3$-$C_8$ cycloalkyl, 3-to-12 membered heterocycloalkyl, aryl, heteroaryl, —$(CH_2)_nR_c$, —$(CH_2)_nO(CH_2)_mR_c$, —$(CH_2)_nNR_eR_f$, —$C(O)(CH_2)_nR_e$, $(CH_2)_nC(O)OR_e$, —$C(O)(CH_2)_nSR_e$, —$(CH_2)_nC(O)NR_eR_f$, —$NH(CH_2)_nR_e$, —$NHC(O)(CH_2)_nR_e$, —$NHC(O)(CH_2)_nOR_e$, —$NHC(O)CH_2)_nSR_e$, —$NHS(O)_2R_e$, —$OR_e$, or —$S(O)_2R_e$, wherein alkyl, haloalkyl, alkoxy, cycloalkyl, heterocycloalkyl, aryl, or heteroaryl are optionally substituted with one or more $R_e$ or $R_f$;

or two $R_d$ when attached to the same carbon atom can form a $C_3$-$C_{12}$ spirocycle or a 3- to 12-membered spiroheterocycle, wherein the spirocycle or the spiroheterocycle are optionally substituted with one or more $R_e$ or $R_f$;

$R_e$ is hydrogen, hydroxyl, $C_1$-$C_6$ alkyl, $C_1$-$C_6$ alkoxy, $C_3$-$C_8$ cycloalkyl, heterocycloalkyl, aryl, or heteroaryl, wherein alkyl, alkoxy, cycloalkyl, heterocycloalkyl, aryl, heteroaryl, —$C(O)(CH_2)_nR_f$, or —$(CH_2)_nC(O)R_f$, are optionally substituted with one or more $R_f$;

$R_f$ is hydrogen, $C_1$-$C_6$ alkyl, $C_1$-$C_6$ haloalkyl, $C_1$-$C_6$ alkoxy, $C_1$-$C_6$ haloalkoxy, cyano, oxo, cycloalkyl, 3-to-12 membered heterocycloalkyl, aryl, heteroaryl, ($C_1$-$C_6$)alkylaryl, halogen, —$(CH_2)_nO(CH_2)_mCH_3$, —$(CH_2)_nN(CH_3)_2$, —$(CH_2)_nO(CH_2)_mN(CH_3)_2$, —$(CH_2)_nNR_eR_f$, —$N(CH_3)S(O)_2CH_3$, —$S(CH_2)_mCH_3$, or —$S(O)_2(CH_2)_mCH_3$, wherein alkyl, haloalkyl, alkoxy, haloalkoxy, cycloalkyl, heterocycloalkyl, aryl, or heteroaryl are optionally substituted with one or more alkyl, haloalkyl, alkoxy, haloalkoxy, cyano, oxo, halogen, cycloalkyl, heterocycloalkyl, aryl, or heteroaryl;

A is hydrogen or fluorine;

n is 0, 1, 2, 3, or 4; and m is 0, 1, 2, 3, or 4, with the proviso that:

(1) both $R_a$ and $R_b$ cannot simultaneously be H nor simultaneously Me; or (2) when $R_a$ is H and $R_b$ is —$C(O)R_c$, then $R_c$ cannot be phenyl, 1-naphthyl, 2-naphthyl, 4-biphenyl, 1-styryl or alkyl with unsubstituted phenyl.

Another aspect of the present invention relates to compounds of Formula (II):

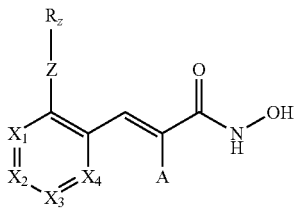

Formula (II)

and pharmaceutically acceptable salts, enantiomers, hydrates, solvates, prodrugs, and tautomers thereof, wherein:

$X_1$, $X_2$, $X_3$, and $X_4$ are independently CH or N, wherein no more than two of $X_1$, $X_2$, $X_3$, and $X_4$ are N and are not contiguous;

Z is C(O) or S(O)$_2$;

$R_z$ is —NR$_a$R$_b$ or —(CH$_2$)$_n$R$_c$;

$R_a$ is hydrogen or C$_1$-C$_6$ alkyl;

$R_b$ is hydrogen, —(CH$_2$)$_n$R$_c$, —C(O)R$_c$, —C(O)NHR$_c$, or —S(O)$_2$R$_c$;

or alternatively, $R_a$ and $R_b$ are combined to form a heterocycle, wherein said heterocycle is optionally substituted with one or more R$_d$;

$R_c$ is hydrogen, C$_1$-C$_6$ alkyl, C$_3$-C$_8$ cycloalkyl, 3-12 membered heterocycloalkyl, C$_6$-C$_{12}$ aryl, or 5-12 membered heteroaryl, wherein said alkyl, cycloalkyl, heterocycloalkyl, aryl, or heteroaryl are optionally substituted with one or more R$_d$ or R$_e$;

$R_d$ is hydrogen, hydroxyl, C$_1$-C$_6$ alkyl, C$_1$-C$_6$ haloalkyl, C$_1$-C$_6$ alkoxy, cyano, oxo, C$_3$-C$_8$ cycloalkyl, 3-12 membered heterocycloalkyl, C$_6$-C$_{12}$ aryl, 5-12 membered heteroaryl, —(CH$_2$)$_n$R$_e$, —(CH$_2$)$_n$O(CH$_2$)$_m$R$_e$, —(CH$_2$)$_n$NR$_e$R$_f$, —C(O)(CH$_2$)$_n$R$_e$, —(CH$_2$)(C(O)OR$_e$, —C(O)(CH$_2$)$_n$SR$_e$, —(CH$_2$)$_n$C(O)NR$_e$R$_f$, —NH(CH$_2$)$_n$R$_e$, —NHC(O)(CH$_2$)$_n$R$_e$, —NHC(O)(CH$_2$)$_n$OR$_e$, —NHC(O)(CH$_2$)$_n$SR$_e$, —NHS(O)$_2$R$_e$, —OR$_e$, or —S(O)$_2$R$_e$, wherein said alkyl, haloalkyl, alkoxy, cycloalkyl, heterocycloalkyl, aryl, or heteroaryl are optionally substituted with one or more R$_e$ or R$_f$;

$R_e$ is hydrogen, hydroxyl, C$_1$-C$_6$ alkyl, C$_2$-C$_6$ alkenyl, C$_1$-C$_6$, alkoxy, C$_3$-C$_8$ cycloalkyl, 3-12 membered heterocycloalkyl, C$_6$-C$_{12}$ aryl, 5-12 membered heteroaryl, wherein said alkyl, alkoky, cycloalkyl, heterocycloalkyl, aryl, or heteroaryl are optionally substituted with one or more R$_f$;

$R_f$ is hydrogen, C$_1$-C$_6$ alkyl, C$_1$-C$_6$ haloalkyl, C$_1$-C$_6$ alkoxy, C$_1$-C$_6$ haloalkoxy, cyano, oxo, C$_3$-C$_8$ cycloalkyl, 3-12 membered heterocycloalkyl, C$_6$-C$_{12}$ aryl, 5-12 membered heteroaryl, halogen, —(CH$_2$)$_n$O(CH$_2$)$_m$CH$_3$, —(CH$_2$)$_n$N(CH$_3$)$_2$, —(CH$_2$)$_n$O(CH$_2$)$_m$N(CH$_3$)$_2$, —(CH$_2$)$_n$NR$_e$R$_f$, —N(CH$_3$)S(O)$_2$CH$_3$, —S(CH$_2$)$_m$CH$_3$, or —S(O)$_2$(CH$_2$)$_m$CH$_3$, —(CH$_2$)$_n$NHC(O)R$_g$, C(O)OR$_g$, —OR$_g$, wherein said alkyl, haloalkyl, alkoxy, haloalkoxy, cycloalkyl, heterocycloalkyl, aryl, or heteroaryl are optionally substituted with one or more C$_1$-C$_6$ alkyl, C$_1$-C$_6$ haloalkyl, C$_1$-C$_6$ alkoxy, C$_1$-C$_6$ haloalkoxy, cyano, oxo, halogen, C$_3$-C$_8$ cycloalkyl, 3-12 membered heterocycloalkyl, C$_6$-C$_{12}$ aryl, or 5-12 membered heteroaryl;

$R_g$ is C$_1$-C$_6$ alkyl or C$_6$-C$_{12}$ aryl;

A is hydrogen or fluorine, n is 0, 1, 2, 3, or 4; and m is 0, 1, 2, 3, or 4;

with the proviso that when Z is S(O)$_2$, R$_z$ cannot be —NR$_a$R$_b$.

Another aspect of the present invention relates to a pharmaceutical composition comprising a compound of Formula (I) and/or Formula (II), or a pharmaceutically acceptable salt, enantiomer, hydrate, solvate, prodrug, isomer, or tautomer thereof and a pharmaceutically acceptable carrier.

In another aspect, the present invention relates to a method of modulating HDAC8. The method comprises administering to a patient in need thereof a therapeutically effective amount of a compound of Formula (I) and/or Formula (II), or a pharmaceutically acceptable salt, enantiomer, hydrate, solvate, prodrug, isomer, or tautomer thereof.

Another aspect of the present invention relates to a method of inhibiting HDAC8. The method comprises administering to a patient in need thereof a therapeutically effective amount of a compound of Formula (I) and/or Formula (II), or a pharmaceutically acceptable salt, enantiomer, hydrate, solvate, prodrug, isomer, or tautomer thereof.

In another aspect, the present invention relates to a method of inhibiting HDAC8. The method comprises administering to a patient in need thereof a therapeutically effective amount of a pharmaceutical composition of Formula (I) and/or Formula (II).

Another aspect of the present invention relates to a method of treating, preventing, inhibiting, or eliminating a disease or disorder in a patient associated with the inhibition of HDAC8 The method comprises administering to a patient in need thereof a therapeutically effective amount of a compound of Formula (I) and/or Formula (II).

DETAILED DESCRIPTION OF THE INVENTION

The invention is of small molecule therapeutic agents of Formula (I) and Formula (II). These novel compounds and compositions containing the compounds are used as inhibitors of Zinc-dependent histone deacetylases, in particular the HDAC8 isozyme, for the treatment of human diseases or disorders including oncological, neurological, inflammatory, autoimmune, infectious, metabolic, hematologic, or cardiovascular diseases or disorders (Benedetti et al, Tang et al, West and Johnstone, Dallavalle et al, Kalin et al). Use of public & proprietary crystal structure information of HDAC ligand-protein complexes as well as computational chemistry tools (docking & scoring) of newly conceived scaffolds led to design ideas that were iteratively refined to optimize key recognition features between ligand and receptor known to be necessary for potency. Compounds were synthesized by multi-step synthesis and characterized in biological activity assays.

One aspect of the present invention relates to compounds of Formula (I):

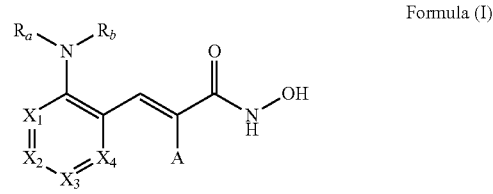

Formula (I)

and pharmaceutically acceptable salts, enantiomers, hydrates, solvates, prodrugs, and tautomers thereof, wherein $X_1$, $X_2$, $X_3$, $X_4$, $R_a$, $R_b$, and A are as described above.

Another aspect of the present invention relates to compounds of Formula (II):

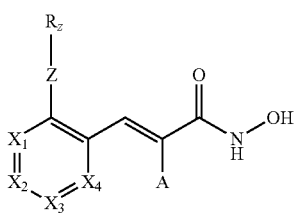

Formula (II)

and pharmaceutically acceptable salts, enantiomers, hydrates, solvates, prodrugs, and tautomers thereof, wherein $X_1$, $X_2$, $X_3$, $X_4$, Z, $R_z$, and A are as described above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

As used above, and throughout this disclosure, the following terms, unless otherwise indicated, shall be understood to have the following meanings. If a definition is missing, the conventional definition as known to one skilled in the art controls.

As used herein, the terms "including," "containing," and "comprising" are used in their open, non-limiting sense.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently A "patient" is a mammal, e.g., a human, mouse, rat, guinea pig, dog, cat, horse, cow, pig, or non-human primate, such as a monkey, chimpanzee, baboon or rhesus. "Patient" includes both human and animals.

The term "inhibitor" refers to a molecule such as a compound, a drug, enzyme, or a hormone that blocks or otherwise interferes with a particular biologic activity.

The terms "effective amount" or "therapeutically effective amount" when used in connection with a compound refer to a sufficient amount of the compound to provide the desired biological result. That result can be reduction and/or alleviation of the signs, symptoms, or causes of a disease, or any other desired alteration of a biological system. For example, an "effective amount" for therapeutic use is the amount of the composition comprising a compound as disclosed herein required to provide a clinically significant decrease in a disease. An appropriate "effective amount" in any individual case may be determined by one of ordinary skill in the art using routine experimentation. Thus, the expression "effective amount" generally refers to the quantity for which the active substance has therapeutic effects. In the present case the active substance is the inhibitor of HDAC8.

As used herein, the terms "treat" or "treatment" are synonymous with the term "prevent" and are meant to indicate a postponement of development of diseases, preventing the development of diseases, and/or reducing severity of such symptoms that will or are expected to develop. Thus, these terms include ameliorating existing disease symptoms, preventing additional symptoms, ameliorating or preventing the underlying causes of symptoms, inhibiting the disorder or disease, e.g., arresting the development of the disorder or disease, relieving the disorder or disease, causing regression of the disorder or disease, relieving a condition caused by the disease or disorder, or stopping or alleviating the symptoms of the disease or disorder.

The term "disorder" is used in this disclosure to mean, and is used interchangeably with, the terms disease, condition, or illness, unless otherwise indicated.

By using the terms "pharmaceutically acceptable" or "pharmacologically acceptable" it is intended to mean a material which is not biologically, or otherwise, undesirable—the material may be administered to an individual without causing any substantially undesirable biological effects or interacting in a deleterious manner with any of the components of the composition in which it is contained.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject. Excipients should be selected on the basis of compatibility and the release profile properties of the desired dosage form. Exemplary carrier materials include, e.g., binders, suspending agents, disintegration agents, filling agents, surfactants, solubilizers, stabilizers, lubricants, wetting agents, diluents, and the like.

The term "pharmaceutically compatible carrier materials" may comprise, e.g., acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassiun phosphate, sodium stearoyl lactylate, carrageenan, monoglyceride, diglyceride, pregelatinized starch, and the like. See, e.g., Hoover, John E., *Remington's Pharmaceutical Sciences*, Mack Publishing Co., Easton, Pa. 1975.

As used herein, the term "subject" encompasses mammals and non-mammals. Examples of mammals include, but are not limited to, any member of the class Mammalia: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the present invention, the mammal is a human.

The present invention also includes "prodrugs" of compounds of the invention. The term "prodrug" means a compound which is convertible in vivo by metabolic means (e.g., by hydrolysis) to a disclosed compound or active ingredient. Prodrugs can be prepared by techniques known to one skilled in the art. These techniques generally modify appropriate functional, e.g., a hydroxy, amino, carboxylic, etc., groups in a given compound. These modified functional groups, however, regenerate original functional groups by routine manipulation or in vivo. Examples of prodrugs include, but are not limited to esters (e.g., acetate, formate, and benzoate derivatives), carbamates (e.g., N,N-dimethylaminocarbonyl) of hydroxy or amino functional groups in compounds of the invention, amides (e.g., trifluoroacetylamino, acetylamino, and the like), and the like. Since prodrugs are known to enhance numerous desirable qualities of pharmaceuticals (e.g., solubility, bioavailability, manufacturing, transport, pharmacodynamics, etc.), the compounds of the present invention may be delivered in prodrug form Prodrugs, for instance, may be bioavailable by oral administration even when the parent drug is not. Thus, the present invention is intended to cover prodrugs of the presently claimed compounds, methods of delivering the same, and compositions containing the same. Generally speaking, prodrugs are derivatives of per se drugs that after administration undergo conversion or metabolism to the physiologically active species. The conversion may be spontaneous, such as hydrolysis in the physiological environment, or may be enzyme-catalyzed. Prodrugs include compounds that can be oxidized, reduced, aminated, deaminated, hydroxylated, dehydroxylated, hydrolyzed, esterified, alkylated, dealkylated, acylated, deacylated, phosphorylated, and/or dephosphorylated to produce the active compound.

The term "$IC_{50}$", as used herein, refers to concentrations at which a measurable activity, phenotype or response, for example growth or proliferation of cells such as tumor cells, is inhibited by 50%. $IC_{50}$ values can be estimated from an appropriate dose-response curve, for example by eye or by using appropriate curve fitting or statistical software More accurately, $IC_{50}$ values may be determined using non-linear regression analysis.

The terms "administered", "administration", or "administering" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body, including an animal, in need of treatment by bringing such individual in contact with, or otherwise exposing such individual to, such compound.

As used herein, "alkyl" means a straight chain or branched saturated chain having from 1 to 10 carbon atoms. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl and the like, and longer alkyl groups, such as heptyl, and octyl and the like. An alkyl group can be unsubstituted or substituted. Alkyl groups containing three or more carbon atoms may be straight, or branched. As used herein, "lower alkyl" means an alkyl having from 1 to 6 carbon atoms.

As used herein, an "alkenyl" includes an unbranched or branched hydrocarbon chain containing 2-12 carbon atoms. The "alkenyl" group contains at least one double bond. The double bond of an alkenyl group can be unconjugated or conjugated to another unsaturated group. Examples of alkenyl groups include, but are not limited to, ethylenyl, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl and the like. An alkenyl group can be unsubstituted or substituted. Alkenyl, as defined herein, may also be branched or straight.

As used herein, "alkynyl" includes an unbranched or branched unsaturated hydrocarbon chain containing 2-12 carbon atoms. The "alkynyl" group contains at least one triple bond. The triple bond of an alkynyl group can be unconjugated or conjugated to another unsaturated group. Examples of alkynyl groups include, but are not limited to, ethynyl, propynyl, butynyl, pentynyl, hexynyl, methylpropynyl, 4-methyl-1-butynyl, 4-propyl-2-pentynyl, 4-butyl-2-hexynyl and the like. An alkynyl group can be unsubstituted or substituted.

The term "hydroxyl" or "hydroxy" means an OH group;

The term "alkoxy" as used herein refers to a straight or branched chain saturated hydrocarbon containing 1-12 carbon atoms containing a terminal "O" in the chain, i.e., —O(alkyl). Examples of alkoxy groups include, without limitation, methoxy, ethoxy, propoxy, butoxy, t-butoxy, or pentoxy groups.

It should also be noted that any carbon as well as heteroatom with unsatisfied valences in the text, schemes, examples and Tables herein is assumed to have the sufficient number of hydrogen atom(s) to satisfy the valences.

As used herein, references to hydrogen may also refer to a deuterium substitution if desired. The term "deuterium" as used herein means a stable isotope of hydrogen having odd numbers of protons and neutrons.

The term "halo" or "halogen" refers to fluorine, chlorine, bromine, or iodine.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amino" as used herein means a substituent containing at least one nitrogen atom. Specifically, $NH_2$, —NH(alkyl) or alkylamino, —N(alkyl)$_2$ or dialkylamino, amide-, carbamide-, urea, and sulfamide substituents are included in the term "amino".

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic or polycyclic aromatic radical of 5 to 18 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. The substituents can themselves be optionally substituted. Examples include, but are not limited to, benzothiophene, furyl, thienyl, pyrrolyl, pyridyl, pyrazinyl, pyrazolyl, pyridazinyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, benzoimidazolyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1□²-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1.4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may have an unsaturated or partially saturated ring fused with a fully saturated ring.

As used herein, the term "cycloalkyl" refers to a saturated or partially saturated, monocyclic, fused or spiro polycyclic, carbocycle having from 3 to 18 carbon atoms per ring. The cycloalkyl ring or carbocycle may be optionally substituted by one or more substituents, e.g., 1 to 5 substituents, at any point of attachment. The substituents can themselves be optionally substituted Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, bicyclo[2.2.2]octenyl, decahydronaphthalenyl, octahydro-1H-indenyl, cyclopentenyl, cyclohexenyl, cyclohexa-1,4-dienyl, cyclohexa-1,3-dienyl, 1,2,3,4-tetrahydronaphthalenyl, octahydropentalenyl, 3a,4,5,6,7,7a-hexahydro-1H-indenyl, 1,2,3,3a-tetraliydropentalenyl, bicyclo[3.1.0]hexanyl, bicyclo[2.1.0]pentanyl, spiro[3.3]heptanyl, bicyclo[2.2.1]heptanyl, bicyclo[2.2.1]hept-2-enyl, bicyclo[2.2.2]octanyl, 6-methylbicyclo[3.1.1]heptanyl, 2,6,6-trimethylbicyclo[3.1.1]heptanyl, and derivatives thereof.

As used herein, the term "heterocycloalkyl" refers to a saturated or partially saturated monocyclic, or fused or spiro, polycyclic, ring structure of 3-to-18 atoms containing carbon and heteroatoms taken from oxygen, nitrogen, or sulfur and wherein there is not delocalized n-electrons (aromaticity) shared among the ring carbon or heteroatoms. The heterocycloalkyl ring structure may be substituted by one or more substituents. The substituents can themselves be optionally substituted. Examples of heterocyclyl rings include, but are not limited to, oxetanyl, azetidinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, homotropanyl, dihydrothiophen-2(3H)-onyl, tetrahydrothiophene 1,1-dioxide, 2,5-dihydro-1H-pyrrolyl, imidazolidin-2-one, pyrrolidin-2-one, dihydrofuran-2(3H)-one, 1,3-dioxolan-2-one, isothiazolidine 1,1-dioxide, 4,5-dihydro-1H-imidazolyl, 4,5-dihydrooxazolyl, oxiranyl, pyrazolidinyl, 4H-1,4-thiazinyl, thiomorpholinyl, 1,2,3,4-tetrahydropyridinyl, 1,2,3,4-tetrahydropyrazinyl, 1,3-oxazinan-2-one, tetrahydro-2H-thiopyran 1,1-dioxide, 7-oxabicyclo[2.2.1]heptanyl, 1,2-thiazepane 1,1-dioxide, octahydro-2H-quinolizinyl, 1,3-diazabicyclo[2.2.2]octanyl, 2,3-dihydrobenzo[b][1,4]dioxine, 3-azabicyclo[3.2.1]octanyl, 8-azaspiro[4.5]decane, 8-oxa-3-azabicyclo[3.2.1]octanyl, 2-azabicyclo[2.2.1]heptane, 2,8-diazaspiro[5.5]undecanyl, 2-azaspiro[5.5]undecanyl, 3-azaspiro[5.5]undecanyl, decahydroisoquinolinyl, 1-oxa-8-azaspiro[4.5]decanyl, 8-azabicyclo[3.2.1]octanyl, 1,4'-bipiperidinyl, azepanyl, 8-oxa-3-azabicyclo[3.2.1]octanyl, 3,4-dihydro-2H-benzo[b][1,4]oxazinyl, 5,6,7,8-tetrahydroimidazo[1,2-a]pyridinyl, 1,4-diazepanyl, phenoxathiinyl, benzo[d][1,3]dioxolyl, 2,3-dihydrobenzofuranyl, 2,3-dihydrobenzo[b][1,4]dioxinyl, 4-(piperidin-4-yl)morpholinyl, 3-azaspiro[5.5]undecanyl, decahydroquinolinyl, piperazin-2-one, 1-(pyrrolidin-2-ylmethyl)pyrrolidinyl, 1,3'-bipyrrolidinyl, and 6,7,8,9-tetrahydro-1H,5H-pyrazolo[1,2-a][1,2]diazepinyl.

"Spirocycloalkyl" or "spirocyclyl" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A (C3-C12) spirocycloalkyl is a spirocycle containing between 3 and 12 carbon atoms. One or more of the carbon atoms can be substituted with a heteroatom.

The term "spiroheterocycloalkyl" or "spiroheterocyclyl" is understood to mean a spirocycle wherein at least one of the rings is a heterocycle (e.g., at least one of the rings is furanyl, morpholinyl, or piperadinyl).

The term "-alkylaryl" refers to aryl groups connected to an adjacent $C_1$-$C_6$alkyl wherein the linkage is located at the alkyl end. Accordingly, groups such as benzyl, phenylethyl, or mesitylenyl constitute exemplary representatives of alkylaryl of the present invention Numerical ranges, as used herein, are intended to include sequential integers. For example, a range expressed as "from 0 to 4" would include 0, 1, 2, 3 and 4.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, oxo, -halogen, $C_1$-$C_6$ alkyl, $C_1$-$C_6$, alkoxy, $C_1$-$C_6$ haloalkyl, $C_1$-$C_6$ haloalkoxy, —$OC_1$-$C_6$ alkenyl, —$OC_1$-$C_6$, alkynyl, —$C_1$-$C_6$ alkenyl, —$C_1$-$C_6$ alkynyl, —OH, CN (cyano), —$CH_2CN$, —$OP(O)(OH)_2$, —C(O)OH, —OC(O)$C_1$-$C_6$ alkyl, —C(O)$C_1$-$C_6$ alkyl, —C(O)—$C_0$-$C_6$ alkylenyl-cycloalkyl, —C(O)—$C_0$-$C_6$ alkylenyl-heterocycloalkyl, —C(O)—$C_0$-$C_6$ alkylenyl-aryl, —C(O)—$C_0$-$C_6$ alkylenyl-heteroaryl, —OC(O)O$C_1$-$C_6$ alkyl, $NH_2$, NH($C_1$-$C_6$ alkyl), N($C_1$-$C_6$ alkyl)$_2$, —C(O)$NH_2$, —C(O)NH($C_1$-$C_6$ alkyl), —C(O)N($C_1$-$C_6$ alkyl)$_2$, —C(O)NH cycloalkyl, —C(O)N($C_1$-$C_6$ alkyl)cycloalkyl, —C(O)NHheterocycloalkyl, —C(O)N($C_1$-$C_6$ alkyl)heterocycloalkyl, —C(O)NHaryl, —C(O)N($C_1$-$C_6$ alkyl)aryl, —C(O)NHheteroaryl, —C(O)N($C_1$-$C_6$ alkyl)heteroaryl, —$S(O)_2$—$C_1$-$C_6$ alkyl, —$S(O)_2$—$C_1$-$C_6$ haloalkyl, —$S(O)_2$-cycloalkyl, —$S(O)_2$-heterocycloalkyl, —$S(O)_2$-aryl, —$S(O)_2$-heteroaryl —$C_0$-$C_6$ alkylenyl-$S(O)_2NH_2$, —$S(O)_2NHC_1$-$C_6$ alkyl, —$S(O)_2N(C_1$-$C_6$ alkyl)$_2$, —$S(O)_2$NHcycloalkyl, —$S(O)_2$NHheterocycloalkyl, —$S(O)_2$NHaryl, —$S(O)_2$NHhetereoaryl, —$NHS(O)_2C_1$-$C_6$ alkyl, —N($C_1$-$C_6$ alkyl)$S(O)_2$($C_1$-$C_6$ alkyl), —$NHS(O)_2$aryl, —N($C_1$-$C_6$ alkyl)$S(O)_2$ aryl, —$NHS(O)_2$ heteroaryl, —N($C_1$-$C_6$ alkyl)$S(O)_2$ heteroaryl, —$NHS(O)_2$ cycloalkyl, —N($C_1$-$C_6$ alkyl)$S(O)_2$cycloalkyl, —$NHS(O)_2$ heterocycloalkyl, —N($C_1$-$C_6$ alkyl)$S(O)_2$ heterocycloalkyl, —N($C_1$-$C_6$ alkyl)$S(O)_2$ aryl, —$C_0$-$C_6$ alkylenyl-aryl, —$C_0$-$C_6$ alkylenyl-heteroaryl, —$C_0$-$C_6$ alkylenyl-cycloalkyl, —$C_0$-$C_6$ alkylenyl-heterocycloalkyl, —O-aryl, —NH-aryl, and N($C_1$-$C_6$ alkyl)aryl. The substituents can themselves be optionally substituted. When a multifunctional moiety is shown, the point of attachment to the core is indicated by a line, e.g., (cycloalkyloxy)alkyl- refers to alkyl being the point of attachment to the core while cycloalkyl is attached to alkyl via the oxy group. "Optionally substituted" also refers to "substituted" or "unsubstituted", with the meanings described above.

The term "oxy" as used herein refers to an "—O—" group.

The term "oxo" as used herein refers to an "=O" group.

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "salt(s)", as employed herein, denotes acidic salts formed with inorganic and/or organic acids, as well as basic salts formed with inorganic and/or organic bases. In addition, when a compound of the Formula contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula may be formed, for example, by reacting a compound of Formula with an amount of acid or base, such as an equivalent amount, in a medium such as one in which the salt precipitates or in an aqueous medium followed by lyophilization.

In another embodiment of the invention, the compounds of Formula (I) and Formula (II) are enantiomers. In some embodiments the compounds are the (S)-enantiomer. In other embodiments the compounds are the (R)-enantiomer. In yet other embodiments, the compounds of Formula (I) or Formula (II) may be (+) or (−) enantiomers.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans-configuration. All tautomeric forms are also intended to be included.

Compounds of the various Formulae, and salts, solvates, esters and prodrugs thereof, may exist in their tautomeric form (for example, as an amide or imino ether). All such tautomeric forms are contemplated herein as part of the present invention.

The compounds of the various Formulae may contain asymmetric or chiral centers, and, therefore, exist in different stereoisomeric forms. It is intended that all stereoisomeric forms of the compounds of the various Formulae as well as mixtures thereof, including racemic mixtures, form part of the present invention. In addition, the present invention embraces all geometric and positional isomers. For example, if a compound of the various Formulae incorporates a double bond or a fused ring, both the cis- and trans-forms, as well as mixtures, are embraced within the scope of the invention. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the various Formulae may be atropisomers (e.g., substituted biaryls) and are considered as part of this invention. Enantiomers can also be separated by use of a chiral HPLC column.

It is also possible that the compounds of Formula (I) and Formula (II) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the various Formulae incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations: The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H (or D), $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of the various Formulae (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances Isotopically labelled compounds of the various Formulae can generally be prepared by following procedures analogous to those disclosed in the Schemes and/or in the Examples herein below, by substituting an appropriate isotopically labelled reagent for a non-isotopically labelled reagent.

The compounds of Formula (I) and Formula (II) may form salts which are also within the scope of this invention. Reference to a compound of the Formula herein is understood to include reference to salts thereof, unless otherwise indicated.

The invention is directed to compounds as described herein and pharmaceutically acceptable salts, enantiomers, hydrates, solvates, prodrugs, isomers, or tautomers thereof, and pharmaceutical compositions comprising one or more compounds as described herein, or pharmaceutically acceptable salts, enantiomers, hydrates, solvates, prodrugs, isomers, or tautomers thereof.

Compounds of the Invention

The present invention relates to compounds, or pharmaceutically acceptable salts or isomers thereof, capable of modulating HDAC8, which are useful for the treatment of diseases and disorders associated with modulation of HDAC8. The invention further relates to compounds, or pharmaceutically acceptable salts or isomers thereof, which are useful for inhibiting HDAC8.

Another aspect of the present invention is the provision of pharmaceutical compositions comprising therapeutically effective amounts of at least one compound of Formula (I) or Formula (II).

One aspect of the present invention relates to compounds of Formula (I):

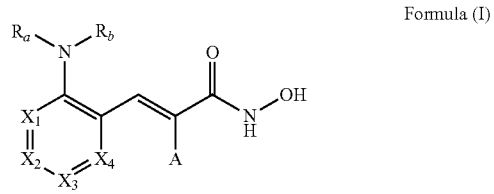

Formula (I)

and pharmaceutically acceptable salts, enantiomers, hydrates, solvates, prodrugs, and tautomers thereof, wherein $X_1$, $X_2$, $X_3$, $X_4$, $R_a$, $R_b$, and A are as described above. In some embodiments of the compounds of Formula I, $X_1$ is N and $X_2$, $X_3$, $X_4$ are all CH. In other embodiments of the compounds of Formula I, $X_2$ is N and $X_1$, $X_3$, and $X_4$ are all CH. In other embodiments of the compounds of Formula I, $X_3$ is N and $X_1$, $X_2$, and $X_4$ are all CH. In other embodiments of the compounds of Formula I, $X_2$ is N and $X_1$, $X_3$, and $X_4$ are all CH. In some embodiments of the compounds of Formula I $X_1$ and $X_3$ are N and $X_2$ and $X_4$ are CH. In some embodiments of the compounds of Formula I $X_1$ and $X_4$ are N and $X_2$ and $X_3$ are CH. In some embodiments of the compounds of Formula I $X_2$ and $X_4$ are N and $X_1$ and $X_3$ are CH. In some embodiments of the compounds of Formula I, $X_1$, $X_2$, $X_3$, $X_4$ are all CH.

In some embodiments of the compounds of Formula I, $R_a$ is H or $C_1$-$C_6$ alkyl. In other embodiments of the compounds of Formula I, $R_a$ is $C_1$-$C_6$ alkyl. In other embodiments of the compounds of Formula I, $R_a$ is H. In other embodiments of the compounds of Formula I, $R_b$ is hydrogen, —(CH$_2$)$_n$R$_c$, —C(O)R$_c$, —C(O)NHR$_c$, or —S(O)$_2$R$_c$. In other embodiments of the compounds of Formula I, $R_b$ is —(CH$_2$)$_n$R$_c$, —C(O)R$_c$, —C(O)NHR$_c$, or —S(O)$_2$R$_c$. In other embodiments of the compounds of Formula I, $R_b$ is —C(O)R$_c$ or —S(O)$_2$R$_c$. In other embodiments of the compounds of Formula I, $R_b$ is —C(O)R$_c$. In other embodiments of the compounds of Formula I, $R_b$ is —S(O)$_2$R$_c$.

In other embodiments of the compounds of Formula I, $R_a$ and $R_b$ are combined to form a heterocycle. In other embodiments of the compounds of Formula I, $R_a$ and $R_b$ are combined to form a heterocycle optionally substituted with one or more $R_d$.

In some embodiments of the compounds of Formula I, two $R_d$ when attached to the same carbon atom can form a $C_3$-$C_{12}$ spirocycle or a 3- to 12-membered spiroheterocycle. In some embodiments of the compounds of Formula I, two $R_d$ when attached to the same carbon atom can form a $C_3$-$C_{12}$ spirocycle. In some embodiments of the compounds of Formula I, two $R_d$ when attached to the same carbon atom can form a 3- to 12-membered spiroheterocycle. In other embodiments, two Rd when attached to the same carbon atom can form a $C_3$-$C_{12}$ spirocycle or a 3- to 12-membered spiroheterocycle optionally substituted with one or more $R_e$ or $R_f$.

In some embodiments of the compounds of Formula I, A is hydrogen or fluorine. In some embodiments of the compounds of Formula I, A is fluorine. In other embodiments of the compounds of Formula I, A is hydrogen.

Another aspect of the present invention relates to compounds of Formula (II):

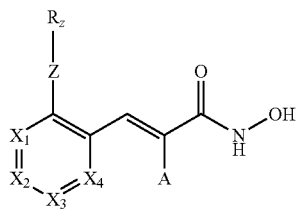

Formula (II)

and pharmaceutically acceptable salts, enantiomers, hydrates, solvates, prodrugs, and tautomers thereof, wherein $X_1$, $X_2$, $X_3$, $X_4$, Z, $R_z$, and A are as described above.

In some embodiments of the compounds of Formula II, $X_1$ is N and $X_2$, $X_3$, $X_4$ are all CH. In other embodiments of the compounds of Formula II, $X_2$ is N and $X_1$, $X_3$, and $X_4$ are all CH. In other embodiments of the compounds of Formula II, $X_3$ is N and $X_1$, $X_2$, and $X_4$ are all CH. In other embodiments of the compounds of Formula II, $X_2$ is N and $X_1$, $X_3$, and $X_4$ are all CH. In some embodiments of the compounds of Formula II $X_1$ and $X_3$ are N and $X_2$ and $X_4$ are CH. In some embodiments of the compounds of Formula II $X_1$ and $X_4$ are N and $X_2$ and $X_3$ are CH. In some embodiments of the compounds of Formula II $X_2$ and $X_4$ are N and $X_1$ and $X_3$ are CH. In some embodiments of the compounds of Formula II, $X_1$, $X_2$, $X_3$, $X_4$ are all CH.

In some embodiments of the compounds of Formula II, Z is C(O) or S(O)$_2$. In other embodiments of the compounds of Formula II, Z is C(O). In other embodiments of the compounds of Formula II, Z is S(O)$_2$. In other embodiments of the compounds of Formula II, A is hydrogen or fluorine. In some embodiments of the compounds of Formula II, A is fluorine. In other embodiments of the compounds of Formula II, A is hydrogen.

In some embodiments of the compounds of Formula II, $R_z$ is —NR$_a$R$_b$ or (CH$_2$)$_n$R$_c$. In some embodiments of the compounds of Formula II, R$_z$ is —NR$_a$R$_b$. In some embodiments of the compounds of Formula II, R$_z$ is —(CH$_2$)$_n$R$_c$. In further embodiments of the compounds of Formula II, R$_b$ is H or C$_1$-C$_6$ alkyl. In yet further embodiments, R$_a$ is C$_1$-C$_6$ alkyl. In yet other embodiments of Formula II, R$_a$ is H. In other embodiments of the compounds of Formula II, R$_b$ is hydrogen, —(CH$_2$)$_n$R$_c$, —C(O)R$_c$, —C(O)NHR$_c$, or —S(O)$_2$R$_c$. In other embodiments of the compounds of Formula II, R$_b$ is —(CH$_2$)$_n$R$_c$, —C(O)R$_c$, —C(O)NHR$_c$, or —S(O)$_2$R$_c$. In other embodiments of the compounds of Formula II, R$_b$ is —C(O)R$_c$ or —S(O)$_2$R$_c$. In other embodiments of the compounds of Formula II, R$_b$ is —C(O)R$_c$. In other embodiments of the compounds of Formula II, R$_b$ is —S(O)$_2$R$_c$.

In other embodiments of the compounds of Formula II, R$_a$ and R$_b$ are combined to form a heterocycle. In other embodiments of the compounds of Formula II, R$_a$ and R$_b$ are combined to form a heterocycle optionally substituted with one or more R$_d$.

In some embodiments of the compounds of Formula II, R$_c$ is hydrogen, C$_1$-C$_6$ alkyl, C$_3$-C$_8$ cycloalkyl, 3-to-12 membered heterocycloalkyl, aryl, or heteroaryl. In other embodiments, R$_c$ is hydrogen, C$_1$-C$_6$ alkyl, C$_1$-C$_6$ cycloalkyl, 3-to-12 membered heterocycloalkyl. In other embodiments, R$_c$ is C$_1$-C$_6$ alkyl, C$_3$-C$_8$ cycloalkyl, 3-to-12 membered heterocycloalkyl, aryl, or heteroaryl. In other embodiments, R$_c$ is hydrogen. In other embodiments, R$_c$ is C$_1$-C$_6$ alkyl.

In one embodiment of the invention illustrative compounds include:
(E)-3-(2-((1H-benzo[d]imidazol-2-yl)amino)phenyl)-N-hydroxyacrylamide (I-1);
(E)-N-hydroxy-3-(2-(((1-(2-methoxyethyl)-1H-benzo[d]imidazol-2-yl)methyl)amino)phenyl)acrylamide (I-2);
(E)-N-hydroxy-3-(2-((1-(2-methoxyethyl)-1H-benzo[d]imidazol-2-yl)amino)phenyl)acrylamide (I-3);
(E)-N-hydroxy-3-(2-(((6-(trifluoromethyl)-1H-benzo[d]imidazol-2-yl)methyl)amino)phenyl)acrylamide (I-4);
(E)-N-hydroxy-3-(2-(3-(3-(trifluoromethyl)phenyl)ureido)phenyl)acrylamide (I-5);
(E)-1-hydroxy-N-(2-(3-(hydroxyamino)-3-oxoprop-1-en-1-yl)phenyl)cyclobutane-1-carboxamide (I-6),
(E)-N-hydroxy-3-(2-((3-(trifluoromethyl)phenyl)sulfonamido)phenyl)acrylamide (I-7);
(E)-3-(2-(4-aminopiperidin-1-yl)phenyl)-N-hydroxyacrylamide (I-8);
(E)-N-hydroxy-3-(2-(4-(2-(4-methoxyphenyl)acetamido)piperidin-1-yl)phenyl)acrylamide (I-9);
(E)-3-(2-(4-(2-(4-chlorophenoxy)acetamido)piperidin-1-yl)phenyl)-N-hydroxyacrylamide (I-10);
(E)-N-(1-(2-(3-(hydroxyamino)-3-oxoprop-1-en-1-yl)phenyl)piperidin-4-yl)-1,8-naphthyridine-2-carboxamide (I-11);
(E)-N-(1-(2-(3-(hydroxyamino)-3-oxoprop-1-en-1-yl)phenyl)piperidin-4-yl)-1-methylazetidine-3-carboxamide (I-12);
(E)-3-(2-(4-(2-(4-chlorophenyl)acetamido)piperidin-1-yl)phenyl)-N-hydroxyacrylamide (I-13);
(E)-N-(1-(2-(3-(hydroxyamino)-3-oxoprop-1-en-1-yl)phenyl)piperidin-4-yl)-3-methylbenzamide (I-14);
(E)-5-(4-chlorophenyl)-N-(1-(2-(3-(hydroxyamino)-3-oxoprop-1-en-1-yl)phenyl)piperidin-4-yl)-2-methylfuran-3-carboxamide (I-15),
(E)-N-(1-(2-(3-(hydroxyamino)-3-oxoprop-1-en-1-yl)phenyl)piperidin-4-yl)-5-methyl-1-phenyl-1H-pyrazole-4-carboxamide (I-16),
(E)-3-(2-(4-((2-((dimethylamino)methyl)benzyl)amino)piperidin-1-yl)phenyl)-N-hydroxyacrylamide (I-17),
(E)-3-(2-(4-((3-((dimethylamino)methyl)benzyl)amino)piperidin-1-yl)phenyl)-N-hydroxyacrylamide (I-18);
(E)-N-hydroxy-3-(2-(4-(tetrahydrofuran-2-carbonyl)piperazin-1-yl)phenyl)acrylamide (I-19),
(E)-3-(2-(4-(2,3-dihydro-1H-indene-2-carbonyl)piperazin-1-yl)phenyl)-N-hydroxyacrylamide (I-20);

(E)-N-hydroxy-3-(2-(4-(1-(methoxymethyl)cyclobutane-1-carbonyl)piperazin-1-yl)phenyl)acrylamide (I-21);
(E)-N-hydroxy-3-(2-(4-(pyrazolo[1,5-a]pyridine-2-carbonyl)piperazin-1-yl)phenyl)acrylamide (I-22);
(E)-3-(2-(4-(4,4-difluorocyclohexane-1-carbonyl)piperazin-1-yl)phenyl)-N-hydroxyacrylamide (I-23),
(E)-N-hydroxy-3-(2-(4-(2-(tetrahydro-1H-pyrrolizin-7a(5H)-yl)acetyl)piperazin-1-yl)phenyl)acrylamide (I-24);
(E)-3-(2-(4-(1H-indole-2-carbonyl)piperazin-1-yl)phenyl)-N-hydroxyacrylamide (I-25);
(E)-N-hydroxy-3-(2-(4-((1-methylethyl)sulfonamido)piperidin-1-yl)phenyl)acrylamide (I-26);
(E)-3-(2-(4-(cyclopentanesulfonamido)piperidin-1-yl)phenyl)-N-hydroxyacrylamide (I-27);
(E)-3-(2-(4-((2,3-dihydrobenzo[b][1,4]dioxin-6-yl)sulfonyl)piperazin-1-yl)phenyl)-N-hydroxyacrylamide (I-28);
(E)-N-hydroxy-3-(2-(4-((2-(trifluoromethoxy)phenyl)sulfonyl)piperazin-1-yl)phenyl)acrylamide (I-29);
(E)-3-(2-(4-((4-(difluoromethoxy)phenyl)sulfonyl)piperazin-1-yl)phenyl)-N-hydroxyacrylamide (I-30),
(E)-N-hydroxy-3-(2-(4-((2-methoxyphenyl)sulfonyl)piperazin-1-yl)phenyl)acrylamide (I-31),
(E)-N-((5-((4-(2-(3-(hydroxyamino)-3-oxoprop-1-en-1-yl)phenyl)piperazin-1-yl)sulfonyl)thiophen-2-yl)methyl)benzamide (I-32);
(E)-3-(2-(4-((5-chloro-3-methylbenzo[b]thiophen-2-yl)sulfonyl)piperazin-1-yl)phenyl)-N-hydroxyacrylamide (I-33);
(E)-3-(2-(4-((2,5-dimethoxyphenyl)sulfonyl)piperazin-1-yl)phenyl)-N-hydroxyacrylamide (I-34);
(E)-2-(3-(hydroxyamino)-3-oxoprop-1-en-1-yl)-N-(2-(trifluoromethyl)-[1,1'-biphenyl]-4-yl)benzamide (II-1).
(E)-2-(3-(hydroxyamino)-3-oxoprop-1-en-1-yl)-N-phenylbenzamide (II-2);
(E)-N-(4-ethylphenyl)-2-(3-(hydroxyamino)-3-oxoprop-1-en-1-yl)benzamide (II-3);
(E)-N-(cyclohexylmethyl)-2-(3-(hydroxyamino)-3-oxoprop-1-en-1-yl)benzamide (II-4);
(E)-2-(3-(hydroxyamino)-3-oxoprop-1-en-1-yl)-N-(4-methoxybenzyl)benzamide (II-5);
(E)-N-(4-fluorophenethyl)-2-(3-(hydroxyamino)-3-oxoprop-1-en-1-yl)benzamide (II-6);
(E)-N-([1,1'-biphenyl]-4-ylmethyl)-2-(3-(hydroxyamino)-3-oxoprop-1-en-1-yl)benzamide (II-7);
(E)-3-(2-(4-acetamidopiperidine-1-carbonyl)phenyl)-N-hydroxyacrylamide (II-8);
(E)-3-(2-(3H-spiro[isobenzofuran-1,4'-piperidine]-1'-carbonyl)phenyl)-N-hydroxyacrylamide (II-9);
(E)-3-(2-(3-(1,1-dioxidothiomorpholino)azetidine-1-carbonyl)phenyl)-N-hydroxyacrylamide (II-10);
(E)-2-(3-(hydroxyamino)-3-oxoprop-1-en-1-yl)-N-(1-(methoxymethyl)cyclopropyl)-N-methylbenzamide (II-11);
(E)-3-(2-(7-azabicyclo[2.2.1]heptane-7-carbonyl)phenyl)-N-hydroxyacrylamide (II-12);
(E)-N-hydroxy-3-(2-(4-(1-(pyrazin-2-yl)cyclopropane-1-carbonyl)piperazin-1-yl)phenyl)acrylamide (I-35);
(E)-N-hydroxy-3-(2-(4-(1-phenylcyclopropane-1-carbonyl)piperazin-1-yl)phenyl)acrylamide (I-36);
(E)-N-hydroxy-3-(2-(4-(1-phenylcyclobutane-1-carbonyl)piperazin-1-yl)phenyl)acrylamide (I-37);
(E)-N-(2-(3-(hydroxyamino)-3-oxoprop-1-en-1-yl)phenyl)-1-(2-(trifluoromethyl)phenyl)-1H-imidazole-2-carboxamide (I-38);
(E)-3-(2-(((1H-benzo[d]imidazol-2-yl)methyl)amino)phenyl)-N-hydroxyacrylamide (I-39);
(E)-3-(2-(benzylamino)phenyl)-N-hydroxyacrylamide (I-40);
(E)-N-(2-(3-(hydroxyamino)-3-oxoprop-1-en-1-yl)phenyl)-3-(trifluoromethyl)benzamide (I-41);
(E)-3-acetamido-N-(2-(3-(hydroxyamino)-3-oxoprop-1-en-1-yl)phenyl)benzamide (I-42);
(E)-3-(2-((3-acetamidobenzyl)amino)phenyl)-N-hydroxyacrylamide (I-43),
(E)-3-cyano-N-(2-(3-(hydroxyamino)-3-oxoprop-1-en-1-yl)phenyl)benzamide (I-44);
(E)-3-(2-((3-cyanobenzyl)amino)phenyl)-N-hydroxyacrylamide (I-45);
(E)-N-hydroxy-3-(2-((3-(trifluoromethyl)benzyl)amino)phenyl)acrylamide (I-46);
tert-butyl-(E)-9-((2-(3-(hydroxyamino)-3-oxoprop-1-en-1-yl)phenyl)carbamoyl)-3-azaspiro[5.5]undecane-3-carboxylate (I-47);
(E)-N-hydroxy-3-(2-((3-(3-hydroxypropyl)benzyl)amino)phenyl)acrylamide (I-48);
(E)-N-(2-(3-(hydroxyamino)-3-oxoprop-1-en-1-yl)phenyl)-3-(3-hydroxypropyl)benzamide (I-49);
tert-butyl-(E)-9-(2-(3-(hydroxyamino)-3-oxoprop-1-en-1-yl)phenyl)-3,9-diazaspiro[5.5]undecane-3-carboxylate (I-50)
(E)-3-(2-(((6-cyano-1H-benzo[d]imidazol-2-yl)methyl)amino)phenyl)-N-hydroxyacrylamide (I-51);
(E)-3-(2-(3,9-diazaspiro[5.5]undecan-3-yl)phenyl)-N-hydroxyacrylamide (I-52);
(E)-3-(2-((3-(3-amino-3-oxopropyl)benzyl)amino)phenyl)-N-hydroxyacrylamide (I-53);
(E)-N-(2-(3-(hydroxyamino)-3-oxoprop-1-en-1-yl)phenyl)-N-methyl-3-(trifluoromethyl)benzamide (I-54)
(E)-3-(2-((cyclohexylmethyl)amino)phenyl)-N-hydroxyacrylamide (I-55);
(E)-N-(2-(3-(hydroxyamino)-3-oxoprop-1-en-1-yl)phenyl)cyclohexanecarboxamide (I-56);
(E)-N-hydroxy-3-(2-(piperidin-1-yl)phenyl)acrylamide (I-57);
tert-butyl (E)-4-(2-(3-(hydroxyamino)-3-oxoprop-1-en-1-yl)phenyl)piperazine-1-carboxylate (I-58);
(E)-N-hydroxy-3-(2-(piperazin-1-yl)phenyl)acrylamide (I-59);
tert-butyl (E)-(1-(2-(3-(hydroxyamino)-3-oxoprop-1-en-1-yl)phenyl)piperidin-4-yl)carbamate (I-60);
(E)-N-(2-(3-(hydroxyamino)-3-oxoprop-1-en-1-yl)phenyl)-4-(trifluoromethyl)benzamide (I-61);
(E)-N-(2-(3-(hydroxyamino)-3-oxoprop-1-en-1-yl)phenyl)-1H-indole-5-carboxamide (I-62);
(E)-3-(2-(2(1, 1-dioxidothiomorpholino)propanamido)phenyl)-N-hydroxyacrylamide (I-63);
(E)-N-(2-(3-(hydroxyamino)-3-oxoprop-1-en-1-yl)phenyl)-1-phenylcyclopropane-1-carboxamide (I-64);
(E)-N-(2-(3-(hydroxyamino)-3-oxoprop-1-en-1-yl)phenyl)-1,2,3,4-tetrahydronaphthalene-2-carboxamide (I-65);
(E)-N-hydroxy-3-(2-(2-(p-tolyl)acetamido)phenyl)acrylamide (I-66);
(E)-N-(2-(3-(hydroxyamino)-3-oxoprop-1-en-1-yl)phenyl)-4-methylpentanamide (I-67);
(E)-3-(2-(2-cyclopentylacetamido)phenyl)-N-hydroxyacrylamide (I-68);
(E)-N-hydroxy-3-(2-isobutyramidophenyl)acrylamide (I-69),
(E)-4-(difluoromethoxy)-N-(2-(3-(hydroxyamino)-3-oxoprop-1-en-1-yl)phenyl)benzamide (I-70);
(E)-N-(2-(3-(hydroxyamino)-3-oxoprop-1-en-1-yl)phenyl)-2-phenoxybenzamide (I-71);

(E)-N-(2-(3-(hydroxyamino)-3-oxoprop-1-en-1-yl)phenyl)-4-(1H-pyrazol-1-yl)benzamide (I-72);
(1S,2R)—N-(2-((E)-3-(hydroxyamino)-3-oxoprop-1-en-1-yl)phenyl)-2-phenylcyclopropane-1-carboxamide (I-73);
(E)-N-(2-(3-(hydroxyamino)-3-oxoprop-1-en-1-yl)phenyl)-5,6-dihydro-4H-pyrrolo[1,2-b]pyrazole-2-carboxamide (I-74);
(E)-N-(2-(3-(hydroxyamino)-3-oxoprop-1-en-1-yl)phenyl)-2-(pyridin-3-yl)thiazole-4-carboxamide (1-75);
(E)-N-(2-(3-(hydroxyamino)-3-oxoprop-1-en-1-yl)phenyl)-2-(pyridin-3-yl)thiazole-5-carboxamide (I-76);
(E)-N-(2-(3-(hydroxyamino)-3-oxoprop-1-en-1-yl)phenyl)-1H-indole-2-carboxamide (I-77);
(E)-N-(2-(3-(hydroxyamino)-3-oxoprop-1-en-1-yl)phenyl)-5-(1-methyl-3-(trifluoromethyl)-1H-pyrazol-5-yl)thiophene-2-carboxamide (I-78);
(E)-1-ethyl-N-(2-(3-(hydroxyamino)-3-oxoprop-1-en-1-yl)phenyl)-1H-indole-2-carboxamide (I-79).
(E)-N-(2-(3-(hydroxyamino)-3-oxoprop-1-en-1-yl)phenyl)-1,3-dimethyl-1H-pyrazole-5-carboxamide (I-80);
(E)-N-(2-(3-(hydroxyamino)-3-oxoprop-1-en-1-yl)phenyl)-2,3-dihydro-1H-indene-2-carboxamide (I-81);
(E)-N-(2-(3-(hydroxyamino)-3-oxoprop-1-en-1-yl)phenyl)pyrazolo[1,5-a]pyridine-2-carboxamide (I-82),
(1S,2S)—N-(2-((E)-3-(hydroxyamino)-3-oxoprop-1-en-1-yl)phenyl)-2-phenylcyclopropane-1-carboxamide (I-83);
(E)-N-(2-(3-(hydroxyamino)-3-oxoprop-1-en-1-yl)phenyl)spiro[2.5]octane-6-carboxamide (I-84);
(E)-N-(2-(3-(hydroxyamino)-3-oxoprop-1-en-1-yl)phenyl)-3-(methylsulfonyl)imidazo[1,5-a]pyridine-1-carboxamide (I-85);
(E)-3-(2-((4-chlorobenzyl)amino)phenyl)-N-hydroxyacrylamide (I-86);
(E)-N-hydroxy-3-(2-(((5-isopropylpyridin-2-yl)methyl)amino)phenyl)acrylamide (I-87);
(E)-N-hydroxy-3-(2-((quinolin-4-ylmethyl)amino)phenyl)acrylamide (I-88);
(E)-N-hydroxy-3-(2-((pyridin-2-ylmethyl)amino)phenyl)acrylamide (I-89);
(E)-N-hydroxy-3-(2-(((5-methoxypyridin-3-yl)methyl)amino)phenyl)acrylamide (I-90);
(E)-N-hydroxy-3-(2-(((thiazol-2-ylmethyl)amino)phenyl)acrylamide (I-91);
(E)-N-hydroxy-3-(2-((4-(pyridin-2-yl)benzyl)amino)phenyl)acrylamide (I-92);
(E)-N-hydroxy-3-(2-((pyridin-3-ylmethyl)amino)phenyl)acrylamide (I-93);
(E)-3-(2-(((1,3-dimethyl-1H-pyrazol-5-yl)methyl)amino)phenyl)-N-hydroxyacrylamide (I-94);
(E)-N-hydroxy-3-(2-((4-(methylsulfonyl)benzyl)amino)phenyl)acrylamide (I-95);
(E)-3-(2-((4-(1H-tetrazol-5-yl)benzyl)amino)phenyl)-N-hydroxyacrylamide (I-96);
(E)-N-hydroxy-3-(2-((3-morpholinobenzyl)amino)phenyl)acrylamide (I-97);
(E)-N-hydroxy-3-(2-(((2-morpholinopyridin-4-yl)methyl)amino)phenyl)acrylamide (I-98);
(E)-N-hydroxy-3-(2-(((6-phenylpyridin-3-yl)methyl)amino)phenyl)acrylamide (I-99);
(E)-N-hydroxy-3-(2-((3-(methylsulfonyl)benzyl)amino)phenyl)acrylamide (I-100);
(E)-N-hydroxy-3-(2-((3-(morpholinomethyl)benzyl)amino)phenyl)acrylamide (I-101);
(E)-3-(2-(((1H-pyrrolo[2,3-b]pyridin-2-yl)methyl)amino)phenyl)-N-hydroxyacrylamide (I-102);
(E)-N-hydroxy-3-(2-((imidazo[1,2-a]pyridin-6-ylmethyl)amino)phenyl)acrylamide (I-103),
(E)-N-hydroxy-3-(2-(((3-(4-(trifluoromethyl)phenyl)-1H-pyrazol-4-yl)methyl)amino)phenyl)acrylamide (I-104);
(E)-N-hydroxy-3-(2-(((2-(isopropylamino)pyrimidin-5-yl)methyl)amino)phenyl)acrylamide (I-105);
(E)-N-hydroxy-3-(2-(((tetrahydrofuran-3-yl)methyl)amino)phenyl)acrylamide (I-106);
(E)-3-(3-amino-3-oxopropyl)-N-(2-(3-(hydroxyamino)-3-oxoprop-1-en-1-yl)phenyl)benzamide (I-107);
(E)-3-(2-(3-(hydroxyamino)-3-oxoprop-1-en-1-yl)phenyl)-3-azaspiro[5.5]undecane-9-carboxamide (I-108);
tert-butyl (E)-9-(2-(3-(hydroxyamino)-3-oxoprop-1-en-1-yl)phenyl)-2,9-diazaspiro[5.5]undecane-2-carboxylate (I-109);
(E)-3-(2-(2,9-diazaspiro[5.5]undecan-9-yl)phenyl)-N-hydroxyacrylamide (I-110);
tert-butyl (E)-2-(2-(3-(hydroxyamino)-3-oxoprop-1-en-1-yl)phenyl)-2,8-diazaspiro[4.5]decane-8-carboxylate (I-111);
tert-butyl (E)-7-(2-(3-(hydroxyamino)-3-oxoprop-1-en-1-yl)phenyl)-2,7-diazaspiro[4.4]nonane-2-carboxylate (I-112);
(E)-3-(2-(2,7-diazaspiro[4.4]nonan-2-yl)phenyl)-N-hydroxyacrylamide (I-113);
benzyl (E)-(2-(2-(3-(hydroxyamino)-3-oxoprop-1-en-1-yl)phenyl)-5,5-dioxido-5-thia-2-azaspiro[3.4]octan-7-yl)carbamate (1-114);
(E)-3-(2-(2,8-diazaspiro[4.5]decan-2-yl)phenyl)-N-hydroxyacrylamide (I-115);
(E)-N-hydroxy-3-(2-(((6-(3-hydroxypropyl)-1H-benzo[d]imidazol-2-yl)methyl)amino)phenyl)acrylamide (I-116);
(E)-3-(2-(7-amino-5,5-dioxido-5-thia-2-azaspiro[3.4]octan-2-yl)phenyl)-N-hydroxyacrylamide (I-117);
(E)-N-(2-(3-(hydroxyamino)-3-oxoprop-1-en-1-yl)phenyl)-N-isopropyl-3-(trifluoromethyl)benzamide (I-118);
(E)-N-hydroxy-3-(2-(methyl(3-(trifluoromethyl)benzyl)amino)phenyl)acrylamide (I-119);
(E)-N-cyclohexyl-2-(3-(hydroxyamino)-3-oxoprop-1-en-1-yl)benzamide (II-13);
(E)-N-hydroxy-3-(2-(((2-(trifluoromethyl)-[1,1'-biphenyl]-4-yl)methyl)amino)phenyl)acrylamide (I-120);
(E)-3-(2-(((4,5-dichloro-1-methyl-1H-imidazol-2-yl)methyl)amino)phenyl)-N-hydroxyacrylamide (I-121);
(E)-N-(3-(3-(hydroxyamino)-3-oxoprop-1-en-1-yl)pyridin-2-yl)-3-(trifluoromethyl)benzamide (I-122);
(E)-N-(4-(3-(hydroxyamino)-3-oxoprop-1-en-1-yl)pyridin-3-yl)-3-(trifluoromethyl)benzamide (I-123);
(E)-N-(2-(3-(hydroxyamino)-3-oxoprop-1-en-1-yl)pyridin-3-yl)-3-(trifluoromethyl)benzamide (I-124);
(E)-N-(1-(2-(3-(hydroxyamino)-3-oxoprop-1-en-1-yl)phenyl)piperidin-4-yl)pentanamide (I-125);
(E)-N-(1-(2-(3-(hydroxyamino)-3-oxoprop-1-en-1-yl)phenyl)piperidin-4-yl)cyclohexanecarboxamide (I-126);
(E)-N-(1-(2-(3-(hydroxyamino)-3-oxoprop-1-en-1-yl)phenyl)piperidin-4-yl)-1-(methylsulfonyl)piperidine-3-carboxamide (I-127);
(E)-N-hydroxy-3-(2-(4-(2-(thiophen-2-yl)acetamido)piperidin-1-yl)phenyl)acrylamide (I-128);
(E)-3-(2-(4-(2-((4-fluorophenyl)thio)acetamido)piperidin-1-yl)phenyl)-N-hydroxyacrylamide (I-129);
(E)-4,4,4-trifluoro-N-(1-(2-(3-(hydroxyamino)-3-oxoprop-1-en-1-yl)phenyl)piperidin-4-yl)butanamide (I-130);
(E)-3-(2-(4-(2-(ethylthio)acetamido)piperidin-1-yl)phenyl)-N-hydroxyacrylamide (I-131);
(E)-N-(1-(2-(3-(hydroxyamino)-3-oxoprop-1-en-1-yl)phenyl)piperidin-4-yl)nicotinamide (I-132);

(E)-N-(1-(2-(3-(hydroxyamino)-3-oxoprop-1-en-1-yl)phenyl)piperidin-4-yl)-4-(methylamino)benzamide (I-133);
(E)-N-(1-(2-(3-(hydroxyamino)-3-oxoprop-1-en-1-yl)phenyl)piperidin-4-yl)-5-methyl-1H-pyrazole-3-carboxamide (I-134);
(E)-N-hydroxy-3-(2-(4-(2-(1-(methylsulfonyl)piperidin-4-yl)acetamido)piperidin-1-yl)phenyl)acrylamide (I-135);
(E)-N-(1-(2-(3-(hydroxyamino)-3-oxoprop-1-en-1-yl)phenyl)piperidin-4-yl)-4-(methylsulfonyl)butanamide (I-136);
(E)-N-hydroxy-3-(2-(4-(3-(2-oxopyrrolidin-1-yl)propanamido)piperidin-1-yl)phenyl)acrylamide (I-137);
(E)-3-(2-(4-(2-(1,1-dioxidothiomorpholino)acetamido)piperidin-1-yl)phenyl)-N-hydroxyacrylamide (I-138);
(E)-N-hydroxy-3-(2-(4-(2-(4-hydroxy-3-methoxyphenyl)acetamido)piperidin-1-yl)phenyl)acrylamide (I-139);
(E)-N-(1-(2-(3-(hydroxyamino)-3-oxoprop-1-en-1-yl)phenyl)piperidin-4-yl)-2,3-dihydro-1H-indene-2-carboxamide (I-140);
(E)-N-(1-(2-(3-(hydroxyamino)-3-oxoprop-1-en-1-yl)phenyl)piperidin-4-yl)-2-(o-tolyloxy)nicotinamide (I-141);
(E)-4,4-difluoro-N-(1-(2-(3-(hydroxyamino)-3-oxoprop-1-en-1-yl)phenyl)piperidin-4-yl)cyclohexane-1-carboxamide (I-142),
(E)-N-hydroxy-3-(2-(4-(3-(1-methylcyclopropyl)propanamido)piperidin-1-yl)phenyl)acrylamide (I-143);
(E)-N-hydroxy-3-(2-(4-(2-(N-methylmethylsulfonamido)acetamido)piperidin-1-yl)phenyl)acrylamide (I-144);
(E)-N-(1-(2-(3-(hydroxyamino)-3-oxoprop-1-en-1-yl)phenyl)piperidin-4-yl)-6,7-dihydro-5H-pyrazolo[5,1-b][1,3]oxazine-3-carboxamide (I-145);
(E)-N-hydroxy-3-(2-(4-(2-(tetrahydro-1H-pyrrolizin-7a(5H)-yl)acetamido)piperidin-1-yl)phenyl)acrylamide (I-146);
(E)-N-(1-(2-(3-(hydroxyamino)-3-oxoprop-1-en-1-yl)phenyl)piperidin-4-yl)-1,6-naphthyridine-2-carboxamide (I-147);
(E)-1-(difluoromethyl)-N-(1-(2-(3-(hydroxyamino)-3-oxoprop-1-en-1-yl)phenyl)piperidin-4-yl)-1H-pyrazole-5-carboxamide (I-148);
(E)-3,3-difluoro-N-(1-(2-(3-(hydroxyamino)-3-oxoprop-1-en-1-yl)phenyl)piperidin-4-yl)cyclobutane-1-carboxamide (I-149);
(E)-3-(2-(4-(2-cyclopropylacetamido)piperidin-1-yl)phenyl)-N-hydroxyacrylamide (I-150);
(E)-3-(2-(4-(2-(1,1-dioxidotetrahydro-2H-thiopyran-4-yl)acetamido)piperidin-1-yl)phenyl)-N-hydroxyacrylamide (I-151);
(E)-N-hydroxy-3-(2-(4-(2-(phenylthio)acetamido)piperidin-1-yl)phenyl)acrylamide (I-152);
(E)-N-(1-(2-(3-(hydroxyamino)-3-oxoprop-1-en-1-yl)phenyl)piperidin-4-yl)-1H-indole-5-carboxamide (I-153);
(E)-N-(1-(2-(3-(hydroxyamino)-3-oxoprop-1-en-1-yl)phenyl)piperidin-4-yl)-5-isopropylpicolinamide (I-154);
(E)-N-(1-(2-(3-(hydroxyamino)-3-oxoprop-1-en-1-yl)phenyl)piperidin-4-yl)-1H-indole-2-carboxamide (I-155);
(E)-N-hydroxy-3-(2-(4-(2-(4-(methylthio)phenyl)acetamido)piperidin-1-yl)phenyl)acrylamide (I-156);
(E)-N-(1-(2-(3-(hydroxyamino)-3-oxoprop-1-en-1-yl)phenyl)piperidin-4-yl)-4-methylpentanamide (I-157);
(E)-3-(2-(4-(2-(2,5-dimethylthiazol-4-yl)acetamido)piperidin-1-yl)phenyl)-N-hydroxyacrylamide (I-158);
(E)-N-(1-(2-(3-(hydroxyamino)-3-oxoprop-1-en-1-yl)phenyl)piperidin-4-yl)furan-3-carboxamide (I-159);
(E)-N-(1-(2-(3-(hydroxyamino)-3-oxoprop-1-en-1-yl)phenyl)piperidin-4-yl)-6-(1H-pyrrol-1-yl)nicotinamide (I-160);
(E)-N-(1-(2-(3-(hydroxyamino)-3-oxoprop-1-en-1-yl)phenyl)piperidin-4-yl)-1H-benzo[d][1,2,3]triazole-5-carboxamide (I-161);
(E)-3-(2-(4-(2-((dimethylamino)methyl)benzyl)piperazin-1-yl)phenyl)-N-hydroxyacrylamide (I-162);
(E)-3-(2-(4-(4-fluorobenzyl)piperazin-1-yl)phenyl)-N-hydroxyacrylamide (I-163);
(E)-3-(2-(4-(2-fluorobenzyl)piperazin-1-yl)phenyl)-N-hydroxyacrylamide (I-164);
(E)-N-hydroxy-3-(2-(4-((6-(trifluoromethyl)pyridin-3-yl)methyl)piperazin-1-yl)phenyl)acrylamide (1-165);
(E)-N-hydroxy-3-(2-(4-(3-phenylpropyl)piperazin-1-yl)phenyl)acylamide (I-166);
(E)-N-hydroxy-3-(2-(4-((tetrahydrofuran-3-yl)methyl)piperazin-1-yl)phenyl)acrylamide (I-167);
(E)-N-hydroxy-3-(2-(4-(pyridin-2-ylmethyl)piperazin-1-yl)phenyl)acrylamide (I-168);
(E)-N-hydroxy-3-(2-(4-((5-methoxypyridin-3-yl)methyl)piperazin-1-yl)phenyl)acrylamide (I-169);
(E)-N-hydroxy-3-(2-(4-(thiazol-2-ylmethyl)piperazin-1-yl)phenyl)acrylamide (I-170);
(E)-N-hydroxy-3-(2-(4-(3-(trifluoromethyl)benzyl)piperazin-1-yl)phenyl)acrylamide (I-171);
(E)-N-hydroxy-3-(2-(4-(4-methoxybenzyl)piperazin-1-yl)phenyl)acrylamide (I-172);
(E)-3-(2-(4-((2,2-difluorobenzo[d][1,3]dioxol-5-yl))methyl)piperazin-1-yl)phenyl)-N-hydroxyacrylamide (I-173);
(E)-N-hydroxy-3-(2-(4-(2-(trifluoromethyl)benzyl)piperazin-1-yl)phenyl)acrylamide (I-174),
(E)-3-(2-(4-((6-chlorobenzo[d][1,3]dioxol-5-yl)methyl)piperazin-1-yl)phenyl)-N-hydroxyacrylamide (I-175);
(E)-3-(2-(4-(2-(difluoromethoxy)benzyl)piperazin-1-yl)phenyl)-N-hydroxyacrylamide (I-176);
(E)-3-(2-(4-butylpiperazin-1-yl)phenyl)-N-hydroxyacrylamide (I-177);
(E)-3-(2-(4-hexylpiperazin-1-yl)phenyl)-N-hydroxyacrylamide (I-178);
(E)-N-hydroxy-3-(2-(4-(pyridin-3-ylmethyl)piperazin-1-yl)phenyl)acylamide (I-179);
(E)-N-hydroxy-3-(2-(4-((1-methyl-1H-imidazol-5-yl)methyl)piperazin-1-yl)phenyl)acrylamide (I-180);
(E)-N-hydroxy-3-(2-(4-((1-methyl-1H-imidazol-2-yl)methyl)piperazin-1-yl)phenyl)acrylamide (I-181);
(E)-N-hydroxy-3-(2-(4-(6-(pyrrolidin-1-yl)pyridin-3-yl)methyl)piperazin-1-yl)phenyl)acrylamide (I-182);
(E)-3-(2-(4-((1,3-dimethyl-1H-pyrazol-5-yl)methyl)piperazin-1-yl)phenyl)-N-hydroxyacrylamide (I-183);
(E)-N-hydroxy-3-(2-(4-(4,4,4-trifluorobutyl)piperazin-1-yl)phenyl)acrylamide (I-184);
(E)-N-hydroxy-3-(2-(4-((4-methylthiazol-2-yl)methyl)piperazin-1-yl)phenyl)acrylamide (I-185);
(E)-3-(2-(4-((1-((dimethylamino)methyl)cyclopentyl)methyl)piperazin-1-yl)phenyl)-N-hydroxyacrylamide (I-186);
(E)-3-(2-(4-((1,4-dimethylpiperidin-4-yl)methyl)piperazin-1-yl)phenyl)-N-hydroxyacrylamide (I-187),
(E)-N-hydroxy-3-(2-(4-(imidazo[1,2-a]pyridin-2-ylmethyl)piperazin-1-yl)phenyl)acrylamide (I-188);
(E)-3-(2-(4-(benzo[d]thiazol-2-ylmethyl)piperazin-1-yl)phenyl)-N-hydroxyacrylamide (I-189);
(E)-N-hydroxy-3-(2-(4-((thiazol-2-ylmethyl)amino)piperidin-1-yl)phenyl)acrylamide (I-190);
(E)-3-(2-(4-(((2-(difluoromethoxy)benzyl)amino)piperidin-1-yl)phenyl)-N-hydroxyacrylamide (I-191);
(E)-3-(2-(4-((benzo[d]thiazol-2-ylmethyl)amino)piperidin-1-yl)phenyl)-N-hydroxyacrylamide (I-192);

(E)-3-(2-(4-acetylpiperazin-1-yl)phenyl)-N-hydroxyacrylamide (I-193);
(E)-N-hydroxy-3-(2-(4-(2-(methylthio)acetyl)piperazin-1-yl)phenyl)acrylamide (I-194);
(E)-N-hydroxy-3-(2-(4-(2-(4-methoxyphenyl)acetyl)piperazin-1-yl)phenyl)acrylamide (I-195);
(E)-N-hydroxy-3-(2-(4-(2-(thiophen-2-yl)acetyl)piperazin-1-yl)phenyl)acrylamide (I-196);
(E)-3-(2-(4-(2-(ethylthio)acetyl)piperazin-1-yl)phenyl)-N-hydroxyacrylamide (I-197);
(E)-N-hydroxy-3-(2-(4-(5-methyl-1H-pyrazole-3-carbonyl)piperazin-1-yl)phenyl)acrylamide (I-198);
(E)-N-hydroxy-3-(2-(4-(1-methyl-1H-imidazole-5-carbonyl)piperazin-1-yl)phenyl)acrylamide (I-199);
(E)-N-hydroxy-3-(2-(4-(4-methylthiazole-5-carbonyl)piperazin-1-yl)phenyl)acrylamide (I-200);
(E)-N-hydroxy-3-(2-(4-(4-(methylsulfonyl)butanoyl)piperazin-1-yl)phenyl)acrylamide (I-201);
(E)-3-(2-(4-(5-fluoropicolinoyl)piperazin-1-yl)phenyl)-N-hydroxyacrylamide (I-202);
(E)-N-hydroxy-3-(2-(4-(2-(4-hydroxy-3-methoxyphenyl)acetyl)piperazin-1-yl)phenyl)acrylamide (I-203);
(E)-3-(2-(4-(6,7-dihydro-5H-pyrazolo[5,1-b][1,3]oxazine-3-carbonyl)piperazin-1-yl)phenyl)-N-hydroxyacrylamide (I-204);
(E)-3-(2-(4-(3,3-difluorocyclobutane-1-carbonyl)piperazin-1-yl)phenyl)-N-hydroxyacrylamide (I-205);
(E)-3-(2-(4-(1H-pyrazole-4-carbonyl)piperazin-1-yl)phenyl)-N-hydroxyacrylamide (I-206);
(E)-3-(2-(4-(benzo[d][1,3]dioxole-5-carbonyl)piperazin-1-yl)phenyl)-N-hydroxyacrylamide (I-207);
(E)-3-(2-(4-(1H-indole-5-carbonyl)piperazin-1-yl)phenyl)-N-hydroxyacrylamide (I-208);
(E)-N-hydroxy-3-(2-(4-(1-methylpiperidine-3-carbonyl)piperazin-1-yl)phenyl)acrylamide (I-209);
(E)-3-(2-(4-(2-(4-chlorophenyl)acetyl)piperazin-1-yl)phenyl)-N-hydroxyacrylamide (I-210),
(E)-3-(2-(4-(2-(2,5-dimethylthiazol-4-yl)acetyl)piperazin-1-yl)phenyl)-N-hydroxyacrylamide (I-211);
(E)-3-(2-(4-(4-(difluoromethoxy)benzoyl)piperazin-1-yl)phenyl)-N-hydroxyacrylamide (I-212);
(E)-3-(2-(4-(3-fluoro-4-methoxybenzoyl)piperazin-1-yl)phenyl)-N-hydroxyacrylamide (I-213);
(E)-3-(2-(4-(5-(4-chlorophenyl)-2-methylfuran-3-carbonyl)piperazin-1-yl)phenyl)-N-hydroxyacrylamide (I-214),
(E)-3-(2-(4-(1H-benzo[d][1,2,3]triazole-5-carbonyl)piperazin-1-yl)phenyl)-N-hydroxyacrylamide (I-215);
(E)-N-hydroxy-3-(2-(isopropyl(3-(trifluoromethyl)benzyl)amino)phenyl)acrylamide (I-216);
(E)-N-hydroxy-3-(2-(((2-(trifluoromethyl)-[1,1'-biphenyl]-4-yl)amino)methyl)pyridin-3-yl)acrylamide (I-217);
(E)-3-(2-(4-((5-chloro-1,3-dimethyl-1H-pyrazole)-4-sulfonamido)piperidin-1-yl)phenyl)-N-hydroxyacrylamide (I-218),
(E)-N-hydroxy-3-(2-(4-(1-methyl-1H-pyrazole)-3-sulfonamido)piperidin-1-yl)phenyl)acrylamide (I-219);
(E)-3-(2-(4-((3,5-dimethylisoxazole)-4-sulfonamido)piperidin-1-yl)phenyl)-N-hydroxyacrylamide (I-220);
(E)-N-hydroxy-3-(2-(4-(pyridine-3-sulfonamido)piperidin-1-yl)phenyl)acrylamide (I-221);
(E)-3-(2-(4-((4-fluorophenyl)sulfonamido)piperidin-1-yl)phenyl)-N-hydroxyacrylamide (I-222);
(E)-3-(2-(4-((4-chlorophenyl)sulfonamido)piperidin-1-yl)phenyl)-N-hydroxyacrylamide (I-223);
(E)-N-hydroxy-3-(2-(4-((4-(trifluoromethyl)phenyl)sulfonamido)piperidin-1-yl)phenyl)acrylamide (I-224);
(E)-N-hydroxy-3-(2-(4-((4-isopropylphenyl)sulfonamido)piperidin-1-yl)phenyl)acrylamide (I-225);
(E)-N-hydroxy-3-(2-(4-((6-(trifluoromethyl)pyridine)-3-sulfonamido)piperidin-1-yl)phenyl)acrylamide (I-226);
(E)-3-(2-(4-(ethylsulfonamido)piperidin-1-yl)phenyl)-N-hydroxyacrylamide (I-227);
(E)-3-(2-(4-(((4-fluorophenyl)methyl)sulfonamido)piperidin-1-yl)phenyl)-N-hydroxyacrylamide (I-228);
(E)-3-(2-(4-(((3-chlorophenyl)methyl)sulfonamido)piperidin-1-yl)phenyl)-N-hydroxyacrylamide (I-229);
(E)-N-hydroxy-3-(2-(4-((1-methyl-1H-imidazole)-2-sulfonamido)piperidin-1-yl)phenyl)acrylamide (I-230);
(E)-3-(2-(4-((2,3-dihydrobenzo[b][1,4]dioxine)-6-sulfonamido)piperidin-1-yl)phenyl)-N-hydroxyacrylamide (I-231);
(E)-N-hydroxy-3-(2-(4-(isoquinoline-5-sulfonamido)piperidin-1-yl)phenyl)acrylamide (I-232);
(E)-3-(2-(4-((3,4-dimethoxyphenyl)sulfonamido)piperidin-1-yl)phenyl)-N-hydroxyacrylamide (I-233);
(E)-3-(2-(4-((4-(difluoroethoxy)phenyl)sulfonamido)piperidin-1-yl)phenyl)-N-hydroxyacrylamide (I-234);
(E)-3-(2-(4-(((3-fluorophenyl)methyl)sulfonamido)piperidin-1-yl)phenyl)-N-hydroxyacrylamide (I-235),
(E)-N-hydroxy-3-(2-(4-((3-oxo-3,4-dihydro-2H-benzo[b][1,4]oxazine)-6-sulfonamido)piperidin-1-yl)phenyl)acrylamide (I-236);
(E)-N-hydroxy-3-(2-(4-((1-methyl-1H-imidazole)-4-sulfonamido)piperidin-1-yl)phenyl)acrylamide (I-237);
(E)-N-hydroxy-3-(2-(4-((2-methoxyphenyl)sulfonamido)piperidin-1-yl)phenyl)acrylamide (I-238);
(E)-3-(2-(4-(((4-chloro-2-fluorophenyl)methyl)sulfonamido)piperidin-1-yl)phenyl)-N-hydroxyacrylamide (I-239);
(E)-N-((5-(N-(1-(2-(3-(hydroxyamino)-3-oxoprop-1-en-1-yl)phenyl)piperidin-4-yl)sulfamoyl)thiophen-2-yl)methyl)benzamide (I-240);
(E)-3-(2-(4-(cyclopropanesulfonamido)piperidin-1-yl)phenyl)-N-hydroxyacrylamide (I-241);
(E)-3-(2-(4-((2,5-dimethoxyphenyl)sulfonamido)piperidin-1-yl)phenyl)-N-hydroxyacrylamide (I-242);
(E)-3-(2-(4-((5-chloro-1,3-dimethyl-1H-pyrazol-4-yl)sulfonyl)piperazin-1-yl)phenyl)-N-hydroxyacrylamide (I-243),
(E)-N-hydroxy-3-(2-(4-((1-methyl-1H-pyrazol-3-yl)sulfonyl)piperazin-1-yl)phenyl)acrylamide (I-244);
(E)-3-(2-(4-((3,5-dimethylisoxazol-4-yl)sulfonyl)piperazin-1-yl)phenyl)-N-hydroxyacrylamide (I-245);
(E)-N-hydroxy-3-(2-(4-(pyridin-3-ylsulfonyl)piperazin-1-yl)phenyl)acrylamide (I-246);
(E)-N-hydroxy-3-(2-(4-(o-tolylsulfonyl)piperazin-1-yl)phenyl)acrylamide (I-247);
(E)-N-hydroxy-3-(2-(4-((6-(trifluoromethyl)pyridin-3-yl)sulfonyl)piperazin-1-yl)phenyl)acrylamide (I-248);
(E)-N-hydroxy-3-(2-(4-(isopropylsulfonyl)piperazin-1-yl)phenyl)acrylamide (I-249);
(E)-3-(2-(4-(cyclopentylsulfonyl)piperazin-1-yl)phenyl)-N-hydroxyacrylamide (I-250);
(E)-3-(2-(4-((4-fluorobenzyl)sulfonyl)piperazin-1-yl)phenyl)-N-hydroxyacrylamide (I-251);
(E)-N-hydroxy-3-(2-(4-((1-methyl-1H-imidazol-2-yl)sulfonyl)piperazin-1-yl)phenyl)acrylamide (I-252);
(E)-3-(2-(4-((5-chlorothiophen-2-yl)sulfonyl)piperazin-1-yl)phenyl)-N-hydroxyacrylamide (I-253);
(E)-N-hydroxy-3-(2-(4-(isoquinolin-5-ylsulfonyl)piperazin-1-yl)phenyl)acrylamide (I-254);
(E)-N-hydroxy-3-(2-(4-((tetrahydro-2H-pyran-4-yl)sulfonyl)piperazin-1-yl)phenyl)acrylamide (I-255);

(E)-3-(2-(4-((3,4-dimethoxyphenyl)sulfonyl)piperazin-1-yl)phenyl)-N-hydroxyacrylamide (I-256);
(E)-3-(2-(4-((3-fluorobenzyl)sulfonyl)piperazin-1-yl)phenyl)-N-hydroxyacrylamide (I-257);
(E)-N-hydroxy-3-(2-(4-((1-methyl-1H-imidazol-4-yl)sulfonyl)piperazin-1-yl)phenyl)acrylamide (I-258);
(E)-3-(2-(4-((4-chloro-2-fluorobenzyl)sulfonyl)piperazin-1-yl)phenyl)-N-hydroxyacrylamide (I-259);
(E)-3-(2-(4-(cyclopropylsulfonyl)piperazin-1-yl)phenyl)-N-hydroxyacrylamide (I-260);
tert-butyl (E)-3-(2-(3-(hydroxyamino)-3-oxoprop-1-en-1-yl)phenyl)-4-oxoimidazolidine-1-carboxylate (I-261);
(E)-N-hydroxy-3-(2-(2-oxo-3-phenylpyrrolidin-1-yl)phenyl)acrylamide (I-262);
tert-butyl (E)-4-(2-(3-(hydroxyamino)-3-oxoprop-1-en-1-yl)phenyl)-3-oxopiperazine-1-carboxylate (I-263);
(E)-5-(tert-butyl)-N-(2-(3-(hydroxyamino)-3-oxoprop-1-en-1-yl)phenyl)-2-methylfuran-3-carboxamide (I-265);
(E)-1-(4-chlorophenyl)-N-(2-(3-(hydroxyamino)-3-oxoprop-1-en-1-yl)phenyl)-5-(trifluoromethyl)-1H-pyrazole-4-carboxamide (I-266),
(E)-N-(2-(3-(hydroxyamino)-3-oxoprop-1-en-1-yl)phenyl)-2-phenethylbenzamide (I-267);
(E)-2-(4-chlorophenoxy)-N-(2-(3-(hydroxyamino)-3-oxoprop-1-en-1-yl)phenyl)benzamide (I-268);
(E)-3-chloro-N-(2-(3-(hydroxyamino)-3-oxoprop-1-en-1-yl)phenyl)benzo[b]thiophene-2-carboxamide (I-269);
(E)-N-(2-(3-(hydroxyamino)-3-oxoprop-1-en-1-yl)phenyl)-1-propyl-1H-indole-2-carboxamide (I-270).
(E)-N-(2-(3-(hydroxyamino)-3-oxoprop-1-en-1-yl)phenyl)-2-methyl-5-phenylfuran-3-carboxamide (I-271);
(E)-5-(4-chlorophenyl)-N-(2-(3-(hydroxyamino)-3-oxoprop-1-en-1-yl)phenyl)-2-methylfuran-3-carboxamide (I-272);
(E)-N-(2-(3-(hydroxyamino)-3-oxoprop-1-en-1-yl)phenyl)-6-(1H-pyrrol-1-yl)nicotinamide (I-273);
(E)-1-ethyl-N-(2-(3-(hydroxyamino)-3-oxoprop-1-en-1-yl)phenyl)-3-methyl-1H-pyrazole-5-carboxamide (I-274);
(E)-3-(2,6-dichlorophenyl)-N-(2-(3-(hydroxyamino)-3-oxoprop-1-en-1-yl)phenyl)-5-methylisoxazole-4-carboxamide (I-275);
(E)-N-(2-(3-(hydroxyamino)-3-oxoprop-1-en-1-yl)phenyl)-2-phenyl-4-propylthiazole-5-carboxamide (I-276);
(E)-N-(2-(3-(hydroxyamino)-3-oxoprop-1-en-1-yl)phenyl)-4-methyl-2-phenylthiazole-5-carboxamide (I-277);
(E)-N-(2-(3-(hydroxyamino)-3-oxoprop-1-en-1-yl)phenyl)-3-methyl-2-(o-tolyl)butanamide (I-278);
(E)-3-(2-(2-cyclopentyl-2-phenylacetamido)phenyl)-N-hydroxyacrylamide (I-279);
(E)-N-(2-(3-(hydroxyamino)-3-oxoprop-1-en-1-yl)phenyl)-2-(p-tolylthio)nicotinamide (I-280);
(E)-N-(2-(3-(hydroxyamino)-3-oxoprop-1-en-1-yl)phenyl)-2-phenoxybutanamide (I-281);
(1S,2R,4R)—N-(2-((E)-3-(hydroxyamino)-3-oxoprop-1-en-1-yl)phenyl)-7-oxabicyclo[2.2.1]heptane-2-carboxamide (I-282);
(E)-2-(tert-butyl)-N-(2-(3-(hydroxyamino)-3-oxoprop-1-en-1-yl)phenyl)-4-methylthiazole-5-carboxamide (I-283);
(E)-N-(2-(3-(hydroxyamino)-3-oxoprop-1-en-1-yl)phenyl)-3-methoxy-5-phenylthiophene-2-carboxamide (I-284);
(E)-N-(2-(3-(hydroxyamino)-3-oxoprop-1-en-1-yl)phenyl)-2-(1-methyl-1H-pyrazol-4-yl)thiazole-5-carboxamide (I-285);
(E)-N-(2-(3-(hydroxyamino)-3-oxoprop-1-en-1-yl)phenyl)-3-methyl-4-(1H-tetrazol-1-yl)benzamide (I-286);
(E)-4-((1H-benzo[d][1,2,3]triazol-1-yl)methyl)-N-(2-(3-(hydroxyamino)-3-oxoprop-1-en-1-yl)phenyl)benzamide (I-287);
(E)-4-((3,5-dimethyl-1H-pyrazol-1-yl)methyl)-N-(2-(3-(hydroxyamino)-3-oxoprop-1-en-1-yl)phenyl)benzamide (I-288);
(E)-N-hydroxy-3-(2-(4-(2-(2-methylthiazol-4-yl)propanoyl)piperazin-1-yl)phenyl)acrylamide (I-289);
(E)-3-(2-(5,6-dichloroisoindolin-2-yl)phenyl)-N-hydroxyacrylamide (I-290);
(E)-3-(2-(4-(2-(4-chlorophenyl)propanoyl)piperazin-1-yl)phenyl)-N-hydroxyacrylamide (I-291);
(E)-N-hydroxy-3-(2-(3-(4-methoxybenzyl)-5-oxoimidazolidin-1-yl)phenyl)acrylamide (I-292);
(E)-N-hydroxy-3-(2-(4-(4-methoxybenzyl)-2-oxopiperazin-1-yl)phenyl)acrylamide (I-293);
(E)-3-(2-(4-(1-(4-chlorophenyl)cyclopropane-1-carbonyl)piperazin-1-yl)phenyl)-N-hydroxyacrylamide (I-294);
(E)-N-hydroxy-3-(2-(4-(2-(pyridin-3-yl)acetyl)piperazin-1-yl)phenyl)acrylamide (I-295);
(E)-N-(4-butylphenyl)-2-(3-(hydroxyamino)-3-oxoprop-1-en-1-yl)benzamide (II-14);
(E)-N-hydroxy-3-(2-(4-(2-(pyridin-2-yl)acetyl)piperazin-1-yl)phenyl)acrylamide (I-296);
(E)-N-hydroxy-3-(2-(4-(2-methyl-3-phenylpropanoyl)piperazin-1-yl)phenyl)acrylamide (I-297);
(E)-3-(2-(4-(1,3-dimethyl-1H-pyrazole-5-carbonyl)piperazin-1-yl)phenyl)-N-hydroxyacrylamide (I-298);
(E)-N-hydroxy-3-(2-(pyrrolidine-1-carbonyl)phenyl)acrylamide (II-15);
(E)-N-hydroxy-3-(2-(piperidine-1-carbonyl)phenyl)acrylamide (II-16);
(E)-3-(2-(4,4-difluoropiperidine-1-carbonyl)phenyl)-N-hydroxyacrylamide (II-17);
(E)-2-(3-(hydroxyamino)-3-oxoprop-1-en-1-yl)-N-methyl-N-(3-(trifluoromethyl)benzyl)benzamide (II-18),
(E)-3-(2-(4-(4-chlorophenethyl)piperazin-1-yl)phenyl)-N-hydroxyacrylamide (I-299);
(E)-N-hydroxy-3-(2-(4-(2-phenylpropyl)piperazin-1-yl)phenyl)acrylamide (I-300),
tert-butyl (E)-(1-(2-(3-(hydroxyamino)-3-oxoprop-1-en-1-yl)phenyl)pyrrolidin-3-yl)carbamate (I-301);
(E)-N-hydroxy-3-(2-(2-oxo-3-phenylimidazolidin-1-yl)phenyl)acrylamide (I-302),
(E)-N-(2-(3-(hydroxyamino)-3-oxoprop-1-en-1-yl)phenyl)-2-(4-(trifluoromethyl)phenoxy)benzamide (I-303);
(E)-N-(2-(3-(hydroxyamino)-3-oxoprop-1-en-1-yl)phenyl)-2-(2-methoxyphenoxy)benzamide (I-304):
(E)-N-(2-(3-(hydroxyamino)-3-oxoprop-1-en-1-yl)phenyl)-2-morpholinoisonicotinamide (I-305);
(E)-2-(4-fluorophenoxy)-N-(2-(3-(hydroxyamino)-3-oxoprop-1-en-1-yl)phenyl)benzamide (I-306);
(E)-3-(2-(3-acetamidopyrrolidin-1-yl)phenyl)-N-hydroxyacrylamide (I-307);
(E)-N-hydroxy-3-(2-(1-oxoisoindolin-2-yl)phenyl)acrylamide (I-308),
(E)-N-hydroxy-3-(2-(2-oxo-4-phenylpyrrolidin-1-yl)phenyl)acrylamide (I-309);
tert-butyl (E)-2-(2-(3-(hydroxyamino)-3-oxoprop-1-en-1-yl)phenyl)-1-oxo-2,8-diazaspiro[4.5]decane-8-carboxylate (I-310);
(E)-2-(2-fluorophenyl)-N-(2-(3-(hydroxyamino)-3-oxoprop-1-en-1-yl)phenyl)thiazole-5-carboxamide (I-311),
(E)-N-(2-(3-(hydroxyamino)-3-oxoprop-1-en-1-yl)phenyl)-2-(pyridin-2-yl)thiazole-5-carboxamide (I-312);
(E)-N-(2-(3-(hydroxyamino)-3-oxoprop-1-en-1-yl)phenyl)-3-morpholinoisonicotinamide (I-313);

(E)-N-(2-(3-(hydroxyamino)-3-oxoprop-1-en-1-yl)phenyl)-2-(pyridin-3-yloxy)benzamide (I-314);

(E)-3-(2-(4-((2,4-dimethylthiazol-5-yl)methyl)piperazin-1-yl)phenyl)-N-hydroxyacrylamide (I-315);

(E)-3-(2-((1S,4S)-5-(2-(4-chlorophenyl)acetyl)-2,5-diazabicyclo[2.2.1]heptan-2-yl)phenyl)-N-hydroxyacrylamide (I-316);

(E)-3-(2-((1S,4S)-5-((1,3-dimethyl-1H-pyrazol-5-yl)methyl)-2,5-diazabicyclo[2.2.1]heptan-2-yl)phenyl)-N-hydroxyacrylamide (I-317);

(E)-N-hydroxy-3-(2-(4-phenylpiperazine-1-carbonyl)phenyl)acrylamide (II-19);

(E)-N-hydroxy-3-(2-(4-(pyridin-4-yl)piperazine-1-carbonyl)phenyl)acrylamide (II-20);

(E)-N-hydroxy-3-(2-(4-phenethylpiperazine-1-carbonyl)phenyl)acrylamide (II-21), (E)-N-hydroxy-3-(2-(4-(pyrazin-2-yl)piperazine-1-carbonyl)phenyl)acrylamide (I-22);

(E)-N-hydroxy-3-(2-(4-(trifluoromethyl)piperidine-1-carbonyl)phenyl)acrylamide (II-23);

(E)-3-(2-(1,1-dioxidothiomorpholine-4-carbonyl)phenyl)-N-hydroxyacrylamide (II-24);

(E)-N-hydroxy-3-(2-(2-methyl-4,5,6,7-tetrahydro-2H-pyrazolo[4,3-c]pyridine-5-carbonyl)phenyl)acrylamide (II-25);

(E)-3-(2-(4-(3,5-di methyl-4H-1,2,4-triazol-4-yl)piperidine-1-carbonyl)phenyl)-N-hydroxyacrylamide (II-26);

(E)-3-(2-(3-((1H-imidazol-1-yl)methyl)piperidine-1-carbonyl)phenyl)-N-hydroxyacrylamide (II-27), (E)-3-(2-(3,3-difluoropyrrolidine-1-carbonyl)phenyl)-N-hydroxyacrylamide (II-28);

(E)-N-(1-(2-(3-(hydroxyamino)-3-oxoprop-1-en-1-yl)phenyl)pyrrolidin-3-yl)benzamide (I-318), (E)-N-(2-(3-(hydroxyamino)-3-oxoprop-1-en-1-yl)phenyl)-2-morpholinothiazole-5-carboxamide (I-319);

(E)-3-(2-chlorophenyl)-N-(2-(3-(hydroxyamino)-3-oxoprop-1-en-1-yl)phenyl)-5-methylisoxazole-4-carboxamide (I-320), (E)-N-hydroxy-3-(2-(4-(1-(pyridin-3-yl)cyclopropane-1-carbonyl)piperazin-1-yl)phenyl)acrylamide (I-321);

(E)-N-hydroxy-3-(2-(4-(1-(trifluoromethyl)cyclopropane-1-carbonyl)piperazin-1-yl)phenyl)acrylamide (I-322);

(E)-3-(4-fluorophenyl)-N-(2-(3-(hydroxyamino)-3-oxoprop-1-en-1-yl)phenyl)-5-methylisoxazole-4-carboxamide (I-323);

(E)-3-(2-((1-(2-(4-chlorophenyl)acetyl)piperidin-4-yl)sulfonyl)phenyl)-N-hydroxyacrylamide (II-29);

(E)-3-(2-((1-benzylpiperidin-4-yl)sulfonyl)phenyl)-N-hydroxyacrylamide (II-30);

(Z)—N-(2-(2-fluoro-3-(hydroxyamino)-3-oxoprop-1-en-1-yl)phenyl)-3-(trifluoromethyl)benzamide (I-324);

(Z)—N-(2-(2-fluoro-3-(hydroxyamino)-3-oxoprop-1-en-1-yl)phenyl)-2-phenoxybenzamide (I-325);

(E)-N-hydroxy-3-(2-(4-methylpiperazin-1-yl)phenyl)acrylamide (I-326);

(R,E)-N-hydroxy-3-(2-(2-oxo-3-phenylpyrrolidin-1-yl)phenyl)acrylamide (I-327), (S,E)-N-hydroxy-3-(2-(2-oxo-3-phenylpyrrolidin-1-yl)phenyl)acrylamide (I-328);

(E)-3-(2-((1S,4S)-5-(1-(4-chlorophenyl)cyclopropane-1-carbonyl)-2,5-diazabicyclo[2.2.1]heptan-2-yl)phenyl)-N-hydroxyacrylamide (I-329);

(E)-3-(2-((1-(4-fluorobenzyl)pyrrolidin-3-yl)amino)phenyl)-N-hydroxyacrylamide (I-330);

(E)-3-(2-(4-(2-(4-fluorophenyl)acetamido)piperidin-1-yl)phenyl)-N-hydroxyacrylamide (I-331);

(E)-N-(2-(3-(hydroxyamino)-3-oxoprop-1-en-1-yl)phenyl)-4-methoxybenzamide (I-332);

(E)-N-(2-(3-(hydroxyamino)-3-oxoprop-1-en-1-yl)phenyl)-1-methylpiperidine-3-carboxamide (I-333);

(E)-3-(2-(2-(benzo[d][1,3]dioxol-5-yl)acetamido)phenyl)-N-hydroxyacrylamide (I-334);

(E)-N-(2-(3-(hydroxyamino)-3-oxoprop-1-en-1-yl)phenyl)-2,3-dihydrobenzofuran-5-carboxamide (I-335), (E)-N-(2-(3-(hydroxyamino)-3-oxoprop-1-en-1-yl)phenyl)furan-3-carboxamide (I-336);

(E)-N-(2-(3-(hydroxyamino)-3-oxoprop-1-en-1-yl)phenyl)quinoline-4-carboxamide (I-337);

(E)-N-hydroxy-3-(2-(2-(2-oxopiperidin-1-yl)acetamido)phenyl)acrylamide (I-338);

(E)-N-(2-(3-(hydroxyamino)-3-oxoprop-1-en-1-yl)phenyl)-2-(1H-pyrrol-1-yl)benzamide (I-339);

(E)-3-(2-(2-cyanoacetamido)phenyl)-N-hydroxyacrylamide (I-340), (E)-N-(2-(3-(hydroxyamino)-3-oxoprop-1-en-1-yl)phenyl)quinoline-2-carboxamide (I-341), (S,E)-N-(2-(3-(hydroxyamino)-3-oxoprop-1-en-1-yl)phenyl)tetrahydrofuran-2-carboxamide (I-342);

(E)-N-(2-(3-(hydroxyamino)-3-oxoprop-1-en-1-yl)phenyl)-1-methyl-1H-indole-2-carboxamide (I-343);

(E)-N-(2-(3-(hydroxyamino)-3-oxoprop-1-en-1-yl)phenyl)-5-methyl-1-phenyl-1H-pyrazole-4-carboxamide (I-344);

(E)-N-(2-(3-(hydroxyamino)-3-oxoprop-1-en-1-yl)phenyl)-1-phenyl-5-propyl-1H-pyrazole-4-carboxamide (I-345);

(E)-N-(2-(3-(hydroxyamino)-3-oxoprop-1-en-1-yl)phenyl)-2-methyl-4-phenylthiazole-5-carboxamide (I-346), (E)-N-(2-(3-(hydroxyamino)-3-oxoprop-1-en-1-yl)phenyl)-4-(5-oxo-4,5-dihydro-1H-pyrazol-1-yl)benzamide (I-347);

(E)-N-(2-(3-(hydroxyamino)-3-oxoprop-1-en-1-yl)phenyl)-5,6,7,8-tetrahydroquinoline-3-carboxamide (I-348);

(E)-5-chloro-N-(2-(3-(hydroxyamino)-3-oxoprop-1-en-1-yl)phenyl)-H-indole-3-carboxamide (I-349);

(E)-6-fluoro-N-(2-(3-4hydroxyamino)-3-oxoprop-1-en-1-yl)phenyl)quinoline-2-carboxamide (I-350);

(E)-N-(2-(3-(hydroxyamino)-3-oxoprop-1-en-1-yl)phenyl)furo[3,2-b]pyridine-2-carboxamide (I-351);

(E)-N-(2-(3-(hydroxyamino)-3-oxoprop-1-en-1-yl)phenyl)-3-phenylisoxazole-5-carboxamide (I-352), (E)-N-(2-(3-(hydroxyamino)-3-oxoprop-1-en-1-yl)phenyl)-4-(1H-imidazol-2-yl)benzamide (I-353);

(E)-N-(2-(3-(hydroxyamino)-3-oxoprop-1-en-1-yl)phenyl)-4-(1H-1,2,4-triazol-5-yl)benzamide (I-354);

(E)-N-(2-(3-(hydroxyamino)-3-oxoprop-1-en-1-yl)phenyl)-4-(1H-imidazol-1-yl)benzamide (I-355);

(E)-3-(2-((4-((dimethylamino)methyl)benzyl)amino)phenyl)-N-hydroxyacrylamide (I-356);

(E)-3-(2-((3-(2-(dimethylamino)ethyl)benzyl)amino)phenyl)-N-hydroxyacrylamide (I-357);

(E)-N-hydroxy-3-(2-((4-isopropylbenzyl)amino)phenyl)acrylamide (I-358);

(E)-N-hydroxy-3-(2-((pyridin-4-ylmethyl)amino)phenyl)acrylamide (I-359);

(E)-3-(2-(((5-fluoropyridin-2-yl)methyl)amino)phenyl)-N-hydroxyacrylamide (I-360);

(E)-3-(2-((2,5-difluorobenzyl)amino)phenyl)-N-hydroxyacrylamide (I-361);

(E)-3-(2-((3,5-dichlorobenzyl)amino)phenyl)-N-hydroxyacrylamide (I-362);

(E)-N-hydroxy-3-(2-((4-(trifluoromethoxy)benzyl)amino)phenyl)acrylamide (I-363), (E)-N-hydroxy-3-(2-((3-phenoxybenzyl)amino)phenyl)acrylamide (I-364);

(E)-N-hydroxy-3-(2-((4-phenoxybenzyl)amino)phenyl) acrylamide (I-365);
(E)-N-hydroxy-3-(2-((3-(trifluoromethoxy)benzyl)amino) phenyl)acrylamide (I-366);
(E)-N-hydroxy-3-(2-((2-(trifluoromethoxy)benzyl)amino) phenyl)acrylamide (I-367);
(E)-N-hydroxy-3-(2-((quinolin-2-ylmethyl)amino)phenyl) acrylamide (I-368),
(E)-N-hydroxy-3-(2-(((1-methyl-1H-imidazol-5-yl)methyl) amino)phenyl)acrylamide (I-369);
(E)-N-hydroxy-3-(2-((imidazo[1,2-a]pyridin-2-ylmethyl) amino)phenyl)acrylamide (I-370);
(E)-N-hydroxy-3-(2-((isoquinolin-5-ylmethyl)amino)phenyl)acrylamide (I-371);
(E)-N-hydroxy-3-(2-(((2-morpholinothiazol-5-yl)methyl) amino)phenyl)acrylamide (I-372),
(E)-N-hydroxy-3-(2-((naphthalen-2-ylmethyl)amino)phenyl)acrylamide (I-373);
(E)-3-(2-((4-(1,3,4-oxadiazol-2-yl)benzyl)amino)phenyl)-N-hydroxyacrylamide (I-374);
(E)-N-hydroxy-3-(2-((naphthalen-1-ylmethyl)amino)phenyl)acrylamide (I-375),
(E)-3-(2-(((1H-pyrrolo[2,3-b]pyridin-3-yl)methyl)amino) phenyl)-N-hydroxyacrylamide (I-376);
(E)-N-hydroxy-3-(2-((4-morpholinobenzyl)amino)phenyl) acrylamide (I-377);
(E)-3-(2-((4-(1,1-dioxidothiomorpholino)benzyl)amino) phenyl)-N-hydroxyacrylamide (I-378);
(E)-3-(2-(((1H-indazol-6-yl)methyl)amino)phenyl)-N-hydroxyacrylamide (I-379);
(E)-3-(2-((4-(1H-1,2,4-triazol-1-yl)benzyl)amino)phenyl)-N-hydroxyacrylamide (I-380);
(E)-N-hydroxy-3-(2-(((6-oxo-1,6-dihydropyridin-3-yl) methyl)amino)phenyl)acrylamide (I-381);
(E)-N-hydroxy-3-(2-(((6-isopropylpyridin-3-yl)methyl) amino)phenyl)acrylamide (I-382);
(E)-3-(2-((4-(tert-butoxy)benzyl)amino)phenyl)-N-hydroxyacrylamide (I-383);
(E)-N-hydroxy-3-(2-(((1-isopropylpiperidin-4-yl)methyl) amino)phenyl)acrylamide (I-384);
(E)-3-(2-(((6-(3-amino-3-oxopropyl)-1H-benzo[d]imidazol-2-yl)methyl)amino)phenyl)-N-hydroxyacrylamide (I-385);
(E)-N-(1-(2-(3-(hydroxyamino)-3-oxoprop-1-en-1-yl)phenyl)piperidin-4-yl)cyclobutanecarboxamide (I-386).
(E)-N-(1-(2-(3-(hydroxyamino)-3-oxoprop-1-en-1-yl)phenyl)piperidin-4-yl)-6-oxo-1,4,5,6-tetrahydropyridazine-3-carboxamide (I-387);
(E)-N-(1-(2-(3-(hydroxyamino)-3-oxoprop-1-en-1-yl)phenyl)piperidin-4-yl)-5-methylpyrazine-2-carboxamide (I-388);
(E)-N-(1-(2-(3-(hydroxyamino)-3-oxoprop-1-en-1-yl)phenyl)piperidin-4-yl)-1-methyl-1H-imidazole-5-carboxamide (I-389);
(E)-3-(2-(4-(2-(dimethylamido)acetamido)piperidin-1-yl) phenyl)-N-hydroxyacrylamide (I-390),
(E)-5-fluoro-N-(1-(2-(3-(hydroxyamino)-3-oxoprop-1-en-1-yl)phenyl)piperidin-4-yl)picolinamide (I-391);
(E)-N-(1-(2-(3-(hydroxyamino)-3-oxoprop-1-en-1-yl)phenyl)piperidin-4-yl)benzo[d]thiazole-6-carboxamide (I-392);
(E)-N-(1-(2-(3-(hydroxyamino)-3-oxoprop-1-en-1-yl)phenyl)piperidin-4-yl)-1-(methoxymethyl)cyclobutane-1-carboxamide (I-393);
(E)-N-(1-(2-(3-(hydroxyamino)-3-oxoprop-1-en-1-yl)phenyl)piperidin-4-yl)pyrazolo[1,5-a]pyridine-2-carboxamide (I-394);

(E)-3-(2-(4-(3-((dimethylamino)methyl)benzyl)piperazin-1-yl)phenyl)-N-hydroxyacrylamide (I-395);
(E)-3-(2-(4-(4-(2-(dimethylamino)ethoxy)benzyl)piperazin-1-yl)phenyl)-N-hydroxyacrylamide (I-396);
(E)-N-hydroxy-3-(2-(4-(4-isopropylbenzyl)piperazin-1-yl) phenyl)acrylamide (I-397);
(E)-N-hydroxy-3-(2-(4-(3-methylbenzyl)piperazin-1-yl) phenyl)acrylamide (I-398);
(E)-N-hydroxy-3-(2-(4-((5-isopropylpyridin-2-yl)methyl) piperazin-1-yl)phenyl)acrylamide (I-399);
(E)-N-hydroxy-3-(2-(4-(pyridin-4-ylmethyl)piperazin-1-yl) phenyl)acrylamide (I-400);
(E)-N-hydroxy-3-(2-(4-(4-isopropoxybenzyl)piperazin-1-yl)phenyl)acrylamide (I-401);
(E)-3-(2-(4-(benzo[d][1,3]dioxol-5-ylmethyl)piperazin-1-yl)phenyl)-N-hydroxyacrylamide (1402);
(E)-N-hydroxy-3-(2-(4-((6-morpholinopyridin-3-yl)methyl) piperazin-1-yl)phenyl)acrylamide (I-403);
(E)-N-hydroxy-3-(2-(4-((tetrahydro-2H-pyran-4-yl)methyl) piperazin-1-yl)phenyl)acrylamide (I-404);
(E)-3-(2-(4-((1H-pyrol-2-yl)methyl)piperazin-1-yl)phenyl)-N-hydroxyacrylamide (I-405);
(E)-3-(2-(4-((1H-indol-5-yl)methyl)piperazin-1-yl)phenyl)-N-hydroxyacrylamide (I-406);
(E)-3-(2-(4-(1-((S)-3-formylpiperidin-1-yl)ethyl)piperazin-1-yl)phenyl)-N-hydroxyacrylamide (I-407);
(E)-3-(2-(4-(1-(4-formylpiperidin-1-yl)-2-methylpropyl) piperazin-1-yl)phenyl)-N-hydroxyacrylamide (I-408);
(E)-3-(2-(4-((1H-indol-2-yl)methyl)piperazin-1-yl)phenyl)-N-hydroxyacrylamide (I-409);
(E)-3-(2-(4-((4-(2-(dimethylamino)ethoxy)benzyl)amino) piperidin-1-yl)phenyl)-N-hydroxyacrylamide (I-410);
(E)-3-(2-(4-((4-fluorobenzyl)amino)piperidin-1-yl)phenyl)-N-hydroxyacrylamide (I-411);
(E)-3-(2-(4-((cyclohexylmethyl)amino)piperidin-1-yl)phenyl)-N-hydroxyacrylamide (I-412);
(E)-3-(2-(4-((2-fluorobenzyl)amino)piperidin-1-yl)phenyl)-N-hydroxyacrylamide (I-413);
(E)-N-hydroxy-3-(2-(4-((4-isopropylbenzyl)amino)piperidin-1-yl)phenyl)acrylamide (I-414);
(E)-N-hydroxy-3-(2-(4-((3-methylbenzyl)amino)piperidin-1-yl)phenyl)acrylamide (I-415);
(E)-N-hydroxy-3-(2-(4-(((6-(trifluoromethyl)pyridin-3-yl) methy)amino)piperidin-1-yl)phenyl)acrylamide (I-416);
(E)-N-hydroxy-3-(2-(4-(((5-isopropylpyridin-2-yl)methyl) amino)piperidin-1-yl)phenyl)acrylamide (I-417);
(E)-N-hydroxy-3-(2-(4-((pyridin-4-ylmethyl)amino)piperidin-1-yl)phenyl)acrylamide (I-418),
(E)-N-hydroxy-3-(2-(4-((3-(trifluoromethyl)benzyl)amino) piperidin-1-yl)phenyl)acrylamide (I-419);
(E)-N-hydroxy-3-(2-(4-((4-isopropoxybenzyl)amino)piperidin-1-yl)phenyl)acrylamide (I-420);
(E)-N-hydroxy-3-(2-(4-((4-methoxybenzyl)amino)piperidin-1-yl)phenyl)acrylamide (I-421),
(E)-3-(2-(4-((benzo[d][1,3]dioxol-5-ylmethyl)amino)piperidin-1-yl)phenyl)-N-hydroxyacrylamide (I-422);
(E)-3-(2-(4-(((2,2-difluorobenzo[d][1,3]dioxol-5-yl)methyl) amino)piperidin-1-yl)phenyl)-N-hydroxyacrylamide (I-423):
(E)-N-hydroxy-3-(2-(4-((2-(trifluoromethyl)benzyl)amino) piperidin-1-yl)phenyl)acrylamide (I-424);
(E)-3-(2-(4-(((6-chlorobenzo[d][1,3]dioxol-5-yl)methyl) amino)piperidin-1-yl)phenyl)-N-hydroxyacrylamide (I-425),
(E)-N-hydroxy-3-(2-(4-(((6-morpholinopyridin-3-yl) methyl)amino)piperidin-1-yl)phenyl)acrylamide (I-426);

(E)-N-hydroxy-3-(2-(4-((pyridin-3-ylmethyl)amino)piperidin-1-yl)phenyl)acylamide (I-427);
(E)-N-hydroxy-3-(2-(4-(((tetrahydro-2H-pyran-4-yl)methyl)amino)piperidin-1-yl)phenyl)acrylamide (I-428);
(E)-N-hydroxy-3-(2-(4-(((1-methyl-1H-imidazol-5-yl)methyl)amino)piperidin-1-yl)phenyl)acrylamide (I-429);
(E)-3-(2-(4-(((1H-pyrrol-2-yl)methyl)amino)piperidin-1-yl)phenyl)-N-hydroxyacrylamide (I-430),
(E)-3-(2-(4-(((1H-indol-5-yl)methyl)amino)piperidin-1-yl)phenyl)-N-hydroxyacrylamide (I-431)
(E)-3-(2-(4-(((1,3-dimethyl-1H-pyrazol-5-yl)methyl)amino)piperidin-1-yl)phenyl)-N-hydroxyacrylamide (I-432);
(E)-3-(2-(4-((1-((S)-3-formylpiperidin-1-yl)ethyl)amino)piperidin-1-yl)phenyl)-N-hydroxyacrylamide (I-433),
(E)-3-(2-(4-((1-(4-formylpiperidin-1-yl)-2-methylpropyl)amino)piperidin-1-yl)phenyl)-N-hydroxyacrylamide (I-434);
(E)-3-(2-(4-(((1-((dimethylamino)methyl)cyclopentyl)methyl)amino)piperidin-1-yl)phenyl)-N-hydroxyacrylamide (I-435);
(E)-3-(2-(4-(((1H-indol-2-yl)methyl)amino)piperidin-1-yl)phenyl)-N-hydroxyacrylamide (I-436)
(E)-3-(2-(4-(((1,4-dimethylpiperidin-4-yl)methyl)amino)piperidin-1-yl)phenyl)-N-hydroxyacrylamide (I-437),
(E)-N-hydroxy-3-(2-(4-pentanoylpiperazin-1-yl)phenyl)acrylamide (I-438);
(E)-N-hydroxy-3-(2-(4-(2-(pyridin-3-yl)thiazole-4-carbonyl)piperazin-1-yl)phenyl)acrylamide (I-439);
(E)-3-(2-(4-(cyclohexanecarbonyl)piperazin-1-yl)phenyl)-N-hydroxyacrylamide (I-440);
(E)-3-(2-(4-(2-((4-fluorophenyl)thio)acetyl)piperazin-1-yl)phenyl)-N-hydroxyacrylamide (I-441);
(E)-N-hydroxy-3-(2-(4-(4,4,4-trifluorobutanoyl)piperazin-1-yl)phenyl)acrylamide (I-442);
(E)-N-hydroxy-3-(2-(4-nicotinoylpiperazin-1-yl)phenyl)acrylamide (I-443);
(E)-N-hydroxy-3-(2-(4-(4-(methylamino)benzoyl)piperazin-1-yl)phenyl)acrylamide (I-444);
(E)-N-hydroxy-3-(2-(4-(2-(1-(methylsulfonyl)piperidin-4-yl)acetyl)piperazin-1-yl)phenyl)acrylamide (I-445);
(E)-3-(2-(4-(dimethylglycyl)piperazin-1-yl)phenyl)-N-hydroxyacrylamide (I-446);
(E)-N-hydroxy-3-(2-(4-(3-(2-oxopyrrolidin-1-yl)propanoyl)piperazin-1-yl)phenyl)acrylamide (I-447);
(E)-3-(2-(4-(2-(1,1-dioxidothiomorpholino)acetyl)piperazin-1-yl)phenyl)-N-hydroxyacrylamide (I-448);
(E)-3-(2-(4-(benzo[d]thiazole-6-carbonyl)piperazin-1-yl)phenyl)-N-hydroxyacrylamide (I-449);
(E)-N-hydroxy-3-(2-(4-(2-(o-tolyloxy)nicotinoyl)piperazin-1-yl)phenyl)acrylamide (I-450),
(E)-N-hydroxy-3-(2-(4-(1-(pyrrolidin-1-yl)cyclopentane-1-carbonyl)piperazin-1-yl)phenyl)acrylamide (I-451);
(E)-N-hydroxy-3-(2-(4-(1-methyl-1H-pyrazole-5-carbonyl)piperazin-1-yl)phenyl)acrylamide (I-452);
ethyl (E)-(4-(4-(2-(3-(hydroxyamino)-3-oxoprop-1-en-1-yl)phenyl)piperazin-1-yl)-4-oxobutyl)carbamate (1-453);
(E)-N-hydroxy-3-(2-(4-(3-(1-methylcyclopropyl)propanoyl)piperazin-1-yl)phenyl)acrylamide (I-454);
(E)-N-hydroxy-3-(2-(4-(N-methyl-N-(methylsulfonyl)glycyl)piperazin-1-yl)phenyl)acrylamide (I-455);
(E)-3-(2-(4-(2-(4,4-dimethyl-2,5-dioxoimidazolidin-1-yl)acetyl)piperazin-1-yl)phenyl)-N-hydroxyacrylamide (I-456);
(E)-3-(2-(4-(1,4-dimethylpiperazine-2-carbonyl)piperazin-1-yl)phenyl)-N-hydroxyacrylamide (I-457);
(E)-3-(2-(4-(1-(difluoromethyl)-1H-pyrazole-5-carbonyl)piperazin-1-yl)phenyl)-N-hydroxyacrylamide (I-458);
(E)-N-hydroxy-3-(2-(4-(1-methylazetidine-3-carbonyl)piperazin-1-yl)phenyl)acrylamide (I-459);
(E)-3-(2-(4-(2-cyclopropylacetyl)piperazin-1-yl)phenyl)-N-hydroxyacrylamide (I-460);
(E)-3-(2-(4-(2-(1,1-dioxidotetrahydro-2H-thiopyran-4-yl)acetyl)piperazin-1-yl)phenyl)-N-hydroxyacrylamide (I-461);
(E)-N-hydroxy-3-(2-(4-(2-(3-methoxyphenoxy)acetyl)piperazin-1-yl)phenyl)acrylamide (I-462);
(E)-N-hydroxy-3-(2-(4-(2-(phenylthio)acetyl)piperazin-1-yl)phenyl)acrylamide (I-463);
(E)-N-hydroxy-3-(2-(4-(4-(trifluoromethyl)benzoyl)piperazin-1-yl)phenyl)acrylamide (I-464);
(E)-N-hydroxy-3-(2-(4-(5-isopropylpicolinoyl)piperazin-1-yl)phenyl)acrylamide (I-465),
(E)-3-(2-(4-(2-(benzo[b]thiophen-3-yl)acetyl)piperazin-1-yl)phenyl)-N-hydroxyacrylamide (I-466);
(E)-N-hydroxy-3-(2-(4-(2-(4-(methylthio)phenyl)acetyl)piperazin-1-yl)phenyl)acrylamide (I-467),
(E)-3-(2-(4-(2-(4-fluorophenyl)acetyl)piperazin-1-yl)phenyl)-N-hydroxyacrylamide (I-468);
(E)-N-hydroxy-3-(2-(4-(4-methylpentanoyl)piperazin-1-yl)phenyl)acrylamide (I-469);
(E)-N-hydroxy-3-(2-(4-(3-methylbenzoyl)piperazin-1-yl)phenyl)acrylamide (I-470);
(E)-3-(2-(4-(furan-3-carbonyl)piperazin-1-yl)phenyl)-N-hydroxyacrylamide (I-471);
(E)-3-(2-(4-(2-chloronicotinoyl)piperazin-1-yl)phenyl)-N-hydroxyacrylamide (I-472);
(E)-3-(2-(4-(6-(1H-pyrrol-1-yl)nicotinoyl)piperazin-1-yl)phenyl)-N-hydroxyacrylamide (I-473);
(E)-N-hydroxy-3-(2-(4-(5-methyl-1-phenyl-1H-pyrazole-4-carbonyl)piperazin-1-yl)phenyl)acrylamide (I-474);
(E)-3-(2-(4-(3-amino-4-methylbenzoyl)piperazin-1-yl)phenyl)-N-hydroxyacrylamide (I-475);
(E)-3-(2-(4-(3-aminobenzoyl)piperazin-1-yl)phenyl)-N-hydroxyacrylamide (I-476);
(E)-N-hydroxy-3-(2-(4-(2-(trifluoromethyl)thiazole-4-carbonyl)piperazin-1-yl)phenyl)acrylamide (I-477);
(E)-3-(2-(4-((E)-3-(3-ethoxyphenyl)acryloyl)piperazin-1-yl)phenyl)-N-hydroxyacrylamide (I-478);
(E)-3-(2-(4-((4-butylphenyl)sulfonamido)piperidin-1-yl)phenyl)-N-hydroxyacrylamide (I-479);
(E)-N-hydroxy-3-(2-(4-((4-isopropylphenyl)sulfonyl)piperazin-1-yl)phenyl)acrylamide (I-480);
(E)-N-hydroxy-3-(2-(4-((5-(2-(methylthio)pyrimidin-4-yl)thiophen-2-yl)sulfonyl)piperazin-1-yl)phenyl)acrylamide (I-481);
(E)-3-(2-(4-((4-acetamido-3-chlorophenyl)sulfonyl)piperazin-1-yl)phenyl)-N-hydroxyacrylamide (I-482);
(E)-N-(2-(3-(hydroxyamino)-3-oxoprop-1-en-1-yl)phenyl)-2,4-diphenylthiazole-5-carboxamide (I-483):
(E)-2-(2,4-dimethylphenoxy)-N-(2-(3-(hydroxyamino)-3-oxoprop-1-en-1-yl)phenyl)nicotinamide (I-484);
(E)-N-(2-(3-(hydroxyamino)-3-oxoprop-1-en-1-yl)phenyl)-2-(o-tolyloxy)nicotinamide (I-485);
(E)-2-(4-chloro-2-methylphenoxy)-N-(2-(3-(hydroxyamino)-3-oxoprop-1-en-1-yl)phenyl)nicotinamide (I-486);
(E)-N-(2-(3-(hydroxyamino)-3-oxoprop-1-en-1-yl)phenyl)-3-methyl-1-phenyl-1H-pyrazole-4-carboxamide (I-487);
(E)-N-(2-(3-(hydroxyamino)-3-oxoprop-1-en-1-yl)phenyl)-6,7-dihydro-5H-pyrazolo[5,1-b][1,3]oxazine-3-carboxamide (I-488);

(E)-5-chloro-N-(2-(3-(hydroxyamino)-3-oxoprop-1-en-1-yl)phenyl)-3-methylbenzofuran-2-carboxamide (I-489);

(3S,4S)-1-(2-ethoxyethyl)-N-(2-((E)-3-(hydroxyamino)-3-oxoprop-1-en-1-yl)phenyl)-4-(trifluoromethyl)pyrrolidine-3-carboxamide (I-490);

(E)-N-(2-(3-(hydroxyamino)-3-oxoprop-1-en-1-yl)phenyl)-4-(2-methyl-1H-imidazol-1-yl)benzamide (I-491);

(E)-N-hydroxy-3-(2-(2-(2-methylindolin-1-yl)acetamido)phenyl)acrylamide (I-492);

(E)-3-((1H-imidazol-1-yl)methyl)-N-(2-(3-(hydroxyamino)-3-oxoprop-1-en-1-yl)phenyl)benzamide (I-493);

(E)-N-(2-(3-(hydroxyamino)-3-oxoprop-1-en-1-yl)phenyl)-3-((2-methyl-1H-imidazol-1-yl)methyl)benzamide (I-494), (E)-3-(2-(4-benzyl-2-oxopiperazin-1-yl)phenyl)-N-hydroxyacrylamide (I-495);

(E)-N-hydroxy-3-(2-(3-(2-hydroxypropan-2-yl)azetidine-1-carbonyl)phenyl)acrylamide (II-31);

(E)-N-hydroxy-3-(2-(3-oxopiperazine-1-carbonyl)phenyl)acrylamide (II-32);

(E)-2-(3-(hydroxyamino)-3-oxoprop-1-en-1-yl)-N-((6-isopropylpyridin-3-yl)methyl)-N-methylbenzamide (II-33);

(E)-2-(3-(hydroxyamino)-3-oxoprop-1-en-1-yl)-N-methyl-N-(1-methylpiperidin-4-yl)benzamide (II-34);

(E)-3-(4-chlorophenyl)-N-(2-(3-(hydroxyamino)-3-oxoprop-1-en-1-yl)phenyl)isoxazole-4-carboxamide (I-496);

(E)-3-(2-(3-(2-(4-chlorophenyl)acetamido)-2-oxopyrrolidin-1-yl)phenyl)-N-hydroxyacrylamide (I-497);

(E)-N-hydroxy-3-(2-((1-phenylpiperidin-4-yl)sulfonyl)phenyl)acrylamide (II-35)

(E)-N-hydroxy-3-(2-((1 S,4S)-5-(oxetan-3-ylmethyl)-2,5-diazabicyclo[2.2.1]heptan-2-yl)phenyl)acrylamide (I-498);

(E)-3-(2-((1-(4-fluorophenyl)pyrrolidin-3-yl)amino)phenyl)-N-hydroxyacrylamide (I-499);

(E)-N-hydroxy-3-(2-(2-oxo-3-(4-(trifluoromethoxy)phenyl)imidazolidin-1-yl)phenyl)acrylamide (I-500);

(E)-3-(2-(3-(4-fluorophenyl)-2-oxoimidazolidin-1-yl)phenyl)-N-hydroxyacrylamide (I-501);

(E)-N-hydroxy-3-(2-(2-oxo-3-(4-(trifluoromethyl)phenyl)imidazolidin-1-yl)phenyl)acrylamide (I-502);

(E)-N-hydroxy-3-(2-(2-oxo-4-(4-(trifluoromethoxy)phenyl)piperazin-1-yl)phenyl)acrylamide (I-503);

(E)-3-(2-(4-(4-fluorophenyl)-2-oxopiperazin-1-yl)phenyl)-N-hydroxyacrylamide (I-504);

(E)-N-hydroxy-3-(2-(2-oxo-4-(4-(trifluoromethyl)phenyl)piperazin-1-yl)phenyl)acrylamide (I-505);

(E)-N-(2-(3-(hydroxyamino)-3-oxoprop-1-enyl)phenyl)benzamide (I-506);

(E)-2-(3-(hydroxyamino)-3-oxoprop-1-en-1-yl)-N-(3-(trifluoromethyl)phenyl)benzamide (II-36)

(E)-3-(2-(((4,5-dichloro-1H-imidazol-2-yl)methyl)amino)phenyl)-N-hydroxyacrylamide (I-515);

(E)-N-hydroxy-3-(2-((3-(trifluoromethyl)phenylamino)methyl)pyridin-3-yl)acrylamide (I-516);

Ethyl (E)-3-(2-(2-oxo-3-phenylpyrrolidin-1-yl)phenyl)acrylate (I-521);

(E)-3-(2-(4-((1-acetylpiperidin-3-yl)methyl)piperazin-1-yl)phenyl)-N-hydroxyacrylamide (I-522);

(E)-N-hydroxy-3-(2-(4-((1-isobutyrylpiperidin-4-yl)methyl)piperazin-1-yl)phenyl)acrylamide (I-523);

(E)-3-(2-(4-(((1-acetylpiperidin-3-yl)methyl)amino)piperidin-1-yl)phenyl)-N-hydroxyacrylamide (I-524);

ethyl (E)-3-(2-(4-bromobenzamido)phenyl)acrylate (1-525);

(E)-N-hydroxy-3-(2-(2-oxo-4-(phenylsulfonyl)piperazin-1-yl)phenyl)acrylamide (I-526);

(E)-N-hydroxy-3-(2-(2-oxo-4-((4-(trifluoromethoxy)phenyl)sulfonyl)piperazin-1-yl)phenyl)acrylamide (I-527);

(E)-4-(2-(3-(hydroxyamino)-3-oxoprop-1-en-1-yl)phenyl)-3-oxo-N-(4-(trifluoromethoxy)phenyl)piperazine-1-carboxamide (I-528):

(E)-4-(2-(3-(hydroxyamino)-3-oxoprop-1-en-1-yl)phenyl)-N-(4-methoxyphenyl)-3-oxopiperazine-1-carboxamide (I-529);

(E)-3-(2-(4-(4-fluorobenzyl)-2-oxopiperazin-1-yl)phenyl)-N-hydroxyacrylamide (I-530);

(E)-N-hydroxy-3-(2-(4-(4-methoxybenzoyl)-2-oxopiperazin-1-yl)phenyl)acrylamide (I-531);

(E)-N-hydroxy-3-(2-(2-oxo-4-(4-(trifluoromethyl)benzoyl)piperazin-1-yl)phenyl)acrylamide (1-532);

(E)-N-hydroxy-3-(2-(2-oxo-4-(p-tolyl)piperazin-1-yl)phenyl)acrylamide (I-533);

(E)-2-(4-chloro-2-fluorophenoxy)-N-(2-(3-(hydroxyamino)-3-oxoprop-1-en-1-yl)phenyl)benzamide (I-534);

(E)-N-(2-(3-(hydroxyamino)-3-oxoprop-1-en-1-yl)phenyl)-2-((6-methylpyridin-3-yl)oxy)benzamide (I-535);

(E)-N-(2-(3-(hydroxyamino)-3-oxoprop-1-en-1-yl)phenyl)-3-phenoxybenzamide (I-536);

N-{2-[(1E)-2-(hydroxycarbamoyl)eth-1-en-1-yl]phenyl}-3-phenoxypyridine-2-carboxamide tert-butyl (I-537);

(E)-9-(2-(3-(hydroxyamino)-3-oxoprop-1-en-1-yl)phenyl)-1,9-diazaspiro[5.5]undecane-1-carboxylate (I-538);

N-{2-[(1E)-2-(hydroxycarbamoyl)eth-1-en-1-yl]phenyl}-5-phenoxy-1,3-thiazole-4-carboxamide (I-539);

(E)-N-(2-(3-(hydroxyamino)-3-oxoprop-1-en-1-yl)phenyl)-2-((6-(trifluoromethyl)pyridin-3-yl)oxy)benzamide (I-540);

tert-butyl (E)-7-(2-(3-(hydroxyamino)-3-oxoprop-1-en-1-yl)phenyl)-1,7-diazaspiro[4.4]nonane-1-carboxylate (I-541);

tert-butyl (E)-5-(2-(3-(hydroxyamino)-3-oxoprop-1-en-1-yl)phenyl)-2,5-diazaspiro[3.4]octane-2-carboxylate (I-542);

tert-butyl (E)-2-(2-(3-(hydroxyamino)-3-oxoprop-1-en-1-yl)phenyl)-2,6-diazaspiro[4.5]decane-6-carboxylate (I-543);

N-{2-[(1E)-2-(hydroxycarbamoyl)eth-1-en-1-yl]phenyl}-4-phenoxy-1,3-thiazole-2-carboxamide (I-544);

(E)-3-(2-(1-acetyl-1,7-diazaspiro[4.4]nonan-7-yl)phenyl)-N-hydroxyacrylamide (I-545);

(E)-2-(4-fluoro-2-methoxyphenoxy)-N-(2-(3-(hydroxyamino)-3-oxoprop-1-en-1-yl)phenyl)benzamide (I-546);

(E)-3-(2-(2-acetyl-2,5-diazaspiro[3.4]octan-5-yl)phenyl)-N-hydroxyacrylamide (I-547);

N-{2-[(1E)-2-(hydroxycarbamoyl)eth-1-en-1-yl]phenyl}-2-[(1-methyl-1H-pyrazol-4-yl)oxy]benzamide (I-548);

N-(4-chloro-2-[(1E)-2-(hydroxycarbamoyl)eth-1-en-1-yl]phenyl)-2-(4-fluorophenoxy)benzamide (I-549);

tert-butyl (E)-2-(2-(3-(hydroxyamino)-3-oxoprop-1-en-1-yl)phenyl)-2,5-diazaspiro[3.4]octane-5-carboxylate (I-550);

2-(5-fluoro-2-methoxyphenoxy)-N-{2-[(1E)-2-(hydroxycarbamoyl)eth-1-en-1-yl]phenyl}benzamide (I-551);

N-{2-[(1E)-2-(hydroxycarbamoyl)eth-1-en-1-yl]phenyl}-2-(3-methoxyphenoxy)benzamide (I-552);

N-{2-[(1E)-2-(hydroxycarbamoyl)eth-1-en-1-yl]phenyl}-2-[(3-methoxypyridin-4-yl)oxy]benzamide (I-553);

(E)-3-(2-(2-(4-fluorobenzoyl)-2,5-diazaspiro[3.4]octan-5-yl)phenyl)-N-hydroxyacrylamide (I-554);

N-{4-fluoro-2-[(1E)-2-(hydroxycarbamoyl)eth-1-en-1-yl]phenyl}-2-(4-fluorophenoxy)benzamide (I-555);

2-(4-fluorophenoxy)-N-{2-[(1E)-2-(hydroxycarbamoyl)eth-1-en-1-yl]-4-(trifluoromethyl)phenyl}benzamide (I-556);

2-(4-fluorophenoxy)-N-{2-[(1E)-2-(hydroxycarbamoyl)eth-1-en-1-yl]-4-(trifluoromethoxy)phenyl}benzamide (I-557);

N-{4-fluoro-2-[(1E)-2-(hydroxycarbamoyl)eth-1-en-1-yl]phenyl}-2-[(1-methyl-1H-pyrazol-4-yl)oxy]benzamide (I-558);

N-{2-[(1E)-2-(hydroxycarbamoyl)eth-1-en-1-yl]phenyl}-2-(4-methoxyphenoxy)benzamide (I-559):

N-{4-chloro-2-[(1E)-2-(hydroxycarbamoyl)eth-1-en-1-yl]phenyl}-2-[(6-methylpyridin-3-yl)oxy]benzamide (I-560);

(E)-N-hydroxy-3-(2-(2-(2-phenylacetyl)-2,5-diazaspiro[3.4]octan-5-yl)phenyl)acrylamide (I-561);

(E)-3-(2-(2-(2-(4-fluorophenyl)acetyl)-2,5-diazaspiro[3.4]octan-5-yl)phenyl)-N-hydroxyacrylamide (I-562);

N-{3-chloro-2-[(1E)-2-(hydroxycarbamoyl)eth-1-en-1-yl]phenyl}-2-(4-fluorophenoxy)benzamide (I-563);

N-{5-chloro-2-[(1E)-2-(hydroxycarbamoyl)eth-1-en-1-yl]phenyl}-2-(4-fluorophenoxy)benzamide (I-564);

(E)-3-(2-(2-(cyclopentanecarbonyl)-2,5-diazaspiro[3.4]octan-5-yl)phenyl)-N-hydroxyacrylamide (I-565);

(E)-N-hydroxy-3-(2-(2-(3,3,3-trifluoropropanoyl)-2,5-diazaspiro[3.4]octan-5-yl)phenyl)acrylamide (I-566);

(E)-3-(2-(2-(cyclohexanecarbonyl)-2,5-diazaspiro[3.4]octan-5-yl)phenyl)-N-hydroxyacrylamide (I-567);

(E)-N-hydroxy-3-(2-(2-(1-methylcyclohexane-1-carbonyl)-2,5-diazaspiro[3.4]octan-5-yl)phenyl)acrylamide (I-568);

(E)-N-hydroxy-3-(2-(2-pivaloyl-2,5-diazaspiro[3.4]octan-5-yl)phenyl)acrylamide (I-569);

N-(4-chloro-2-[(1E)-2-(hydroxycarbamoyl)eth-1-en-1-yl]phenyl)-2-phenoxypyridine-3-carboxamide (I-570);

N-(4-chloro-2-[(E)-2-(hydroxycarbamoyl)eth-1-en-1-yl]phenyl)-3-phenoxypyridine-2-carboxamide (I-571);

N-4-chloro-2-[(1E)-2-(hydroxycarbamoyl)eth-1-en-1-yl]phenyl)-2-(4-chlorophenoxy)pyridine-3-carboxamide (I-572);

N-{4-chloro-2-[(1E)-2-(hydroxycarbamoyl)eth-1-en-1-yl]phenyl}-2-(4-methoxyphenoxy)benzamide (I-573); (E)-3-(2-(1-(cyclopentanecarbonyl)-1,7-diazaspiro[4.4]nonan-7-yl)phenyl)-N-hydroxyacrylamide (I-574);

(E)-3-(2-(1-(4-fluorobenzoyl)-1,7-diazaspiro[4.4]nonan-7-yl)phenyl)-N-hydroxyacrylamide (I575);

(E)-N-hydroxy-3-(2-(1-(3,3,3-trifluoropropanoyl)-1,7-diazaspiro[4.4]nonan-7-yl)phenyl)acrylamide (I-576);

(E)-3-(2-(1-(cyclohexanecarbonyl)-1,7-diazaspiro[4.4]nonan-7-yl)phenyl)-N-hydroxyacrylamide (I-577); (E)-3-(2-(1-benzoyl-1,7-diazaspiro[4.4]nonan-7-yl)phenyl)-N-hydroxyacrylamide (I-578);

(E)-N-hydroxy-3-(2-(1-(2-phenylacetyl)-1,7-diazaspiro[4.4]nonan-7-yl)phenyl)acrylamide (I-579);

(E)-N-hydroxy-3-(2-(1-(3-phenylpropanoyl)-1,7-diazaspiro[4.4]nonan-7-yl)phenyl)acrylamide (1-580);

(E)-N-hydroxy-3-(2-(1-(4-(trifluoromethyl)benzoyl)-1,7-diazaspiro[4.4]nonan-7-yl)phenyl)acrylamide (I-581);

(E)-3-(2-(4-(4-chloro-3-(trifluoromethyl)phenyl)-2-oxopiperazin-1-yl)phenyl)-N-hydroxyacrylamide (I-582):

(E)-3-(2-(4-(3,4-dichlorophenyl)-2-oxopiperazin-1-yl)phenyl)-N-hydroxyacrylamide (I-583); and tert-butyl (E)-2-(2-(3-(hydroxyamino)-3-oxoprop-1-en-1-yl)phenyl)-2,5-diazaspiro[3.5]nonane-5-carboxylate (I-584).

In another embodiment of the invention, the compounds of Formula I may be of the Formula (I-a):

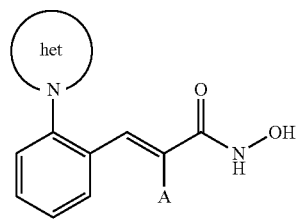

Formula (I-a)

and pharmaceutically acceptable salts, enantiomers, hydrates, solvates, prodrugs, or tautomers thereof,
wherein:
het represents a 3-to-12 membered heterocycle, wherein said heterocycle is optionally substituted with one or more $R_d$.

In another embodiment of the invention, the compounds of Formula I may be of the Formula (I-b):

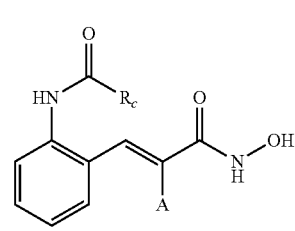

Formula (I-b)

and pharmaceutically acceptable salts, enantiomers, hydrates, solvates, prodrugs, or tautomers thereof.

In another embodiment of the invention, the compounds of Formula I may be of the Formula (I-c):

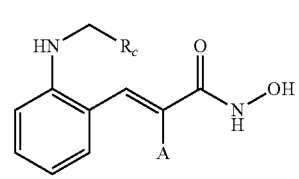

Formula (I-c)

and pharmaceutically acceptable salts, enantiomers, hydrates, solvates, prodrugs, or tautomers thereof.

In other embodiments of the compounds of Formula I, $X_1$ is N. Yet in other embodiments of the compounds of Formula I, $X_2$ is N. In other embodiments of the compounds of Formula I, $X_3$ is N. In other embodiments of the compounds of Formula I, $X_4$ is N Yet in other embodiments of the invention, the compounds of Formula II may be of the Formula (II-a)

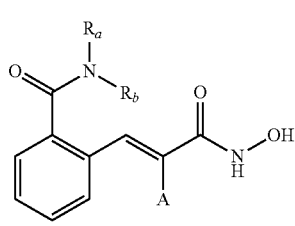

Formula (II-a)

or a pharmaceutically acceptable salt, enantiomer, hydrate, solvate, prodrug, or tautomer thereof.

In other embodiments of the invention, the compounds of Formula II may be of the Formula (II-b):

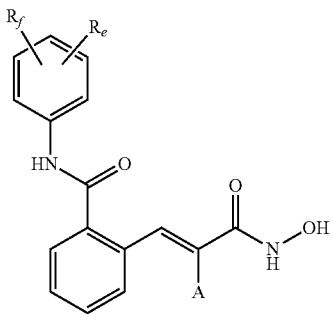

Formula (II-b)

or a pharmaceutically acceptable salt, enantiomer, hydrate, solvate, prodrug, or tautomer thereof.

In other embodiments of the invention, the compounds of Formula II may be of the Formula (II-c):

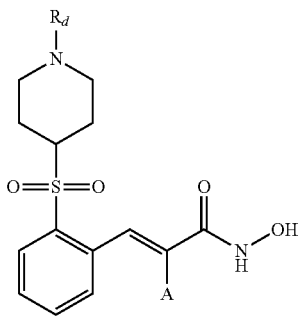

Formula (II-c)

or a pharmaceutically acceptable salt, enantiomer, hydrate, solvate, prodrug, or tautomer thereof.

In other embodiments of the compounds of Formula II, $X_1$ is N. Yet in other embodiments of the compounds of Formula II, $X_2$ is N. In other embodiments of the compounds of Formula II, $X_3$ is N. In other embodiments of the compounds of Formula II, $X_4$ is N An aspect of the present invention concerns compounds which are, or can be, inhibitors of HDAC8.

An aspect of the present invention concerns the use of an inhibitor of HDAC8 for the preparation of a medicament used in the treatment, prevention, inhibition or elimination of tumors.

An aspect of the present invention concerns the use of an inhibitor of HDAC8 for the preparation of a medicament used in the treatment, prevention, inhibition or elimination of cancer.

Another aspect of the present invention is a pharmaceutical composition comprising the compound of Formula (I) and/or Formula (II) and a pharmaceutically acceptable carrier.

Another aspect of the present invention is a pharmaceutical composition comprising the compound of Formula (I) and/or Formula (II) and a pharmaceutically acceptable carrier comprising therapeutically effective amounts of one or more additional therapeutic agents. In some embodiment the present invention relates to a pharmaceutical composition comprising the compound of Formula (I) and/or Formula (II) and a pharmaceutically acceptable carrier comprising therapeutically effective amounts of one or more additional therapeutic agents, wherein said additional therapeutic agents are selected from the group consisting of cytotoxic agent, cisplatin, doxorubicin, taxotere, etoposide, irinotecan, camptostar, topotecan, paclitaxel, docetaxel, the epothilones, tamoxifen, 5-fluorouracil, methotrexate, temozolomide, cyclophosphamide, Lonafarib, Tipifarnib, 4-((5-((4-(3-chlorophenyl)-3-oxopiperazin-1-yl)methyl)-1H-imidazol-1-yl)methyl)benzonitrile hydrochloride, (R)-1-((1H-imidazol-5-yl)methyl)-3-benzyl-4-(thiophen-2-ylsulfonyl)-2,3,4,5-tetrahydro-1H-benzo[e][1,4]diazepine-7-carbonitrile, Cetuximab, GLEEVEC®, Intron®, Peg-Intron®, aromatase combinations, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin. Dacarbazine, Floxuridine, Cytarabine, 6-Mercaptopurine, 6-Thioguanine, Fludarabine phosphate, leucovirin, oxaliplatin (ELOXATIN®), Pentostatine, Vinblastine, Vincristine, Vindesine, Bleomycin, Dactinomycin, Daunorubicin, Epirubicin, Idarubicin, Mithramycin™, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrol acetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Rituximab, Campath, leucovorin, dexamethasone, bicalutamide, carboplatin, chlorambucil, cisplatin, letrozole, megestrol, and valrubicin.

Another aspect of the present invention is directed to a method of inhibiting HDAC8 in a patient comprising administering to the patient in need thereof an effective amount of the compound of Formula (I) and/or Formula (II).

Another aspect of the present invention is directed to a method of inhibiting HDAC8 in a patient comprising administering to the patient in need thereof an effective amount of the pharmaceutical composition comprising the compound of Formula (I) and/or Formula (II) and a pharmaceutically acceptable carrier.

Another aspect of the present invention is directed to a method of treating, preventing, inhibiting, or eliminating a disease or disorder associated with the activity of HDAC8 in a patient comprising administering to said patient in need thereof a therapeutically effective amount of the compound of Formula (I) and/or Formula (II).

One embodiment of the present invention relates a method of treating, preventing, inhibiting, or eliminating a disease or disorder associated with the activity of HDAC8 in a patient comprising administering to said patient in need thereof a therapeutically effective amount of the compound of Formula (I) and/or Formula (II), and further comprising administering to said patient in need thereof a therapeutically effective amount of another therapeutic agent.

Method of Synthesizing the Compounds

The compounds of the present invention may be made by a variety of methods, including standard chemistry. One suitable synthetic route is depicted in the Scheme provided below.

The compounds of the present invention, i.e., compounds of Formula (I) and Formula (II), or a pharmaceutically acceptable salt, enantiomer, hydrate, solvate, prodrug, isomer, or tautomer thereof, may be prepared by methods known in the art of organic synthesis as set forth in part by the following synthetic scheme. In the scheme described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I) and Formula (II).

Those skilled in the art will recognize if a stereocenter exists in the compounds of Formula (I) or Formula (II). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Illustrative methods include but are not limited to those methods described below. Compounds of the present invention can be synthesized by following the steps outlined in General Schemes 1, 2, 3 and 4. Starting materials are either commercially available or made by known procedures in the reported literature or as illustrated.

Substituted α-cinnamides of Formula I can be prepared according to the general procedure outlined in Scheme 1. Aryl amines (2) are readily accessible from aryl acrylate (1) and a variety of amines via palladium- or copper-mediated cross-couplings. Subsequent treatment with hydroxylamine and sodium hydroxide affords the desired α-cinnamide compounds of Formula I.

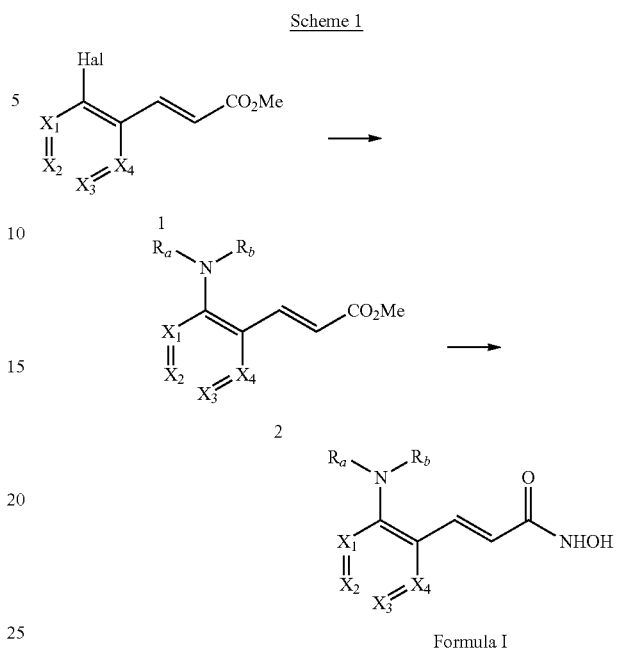

Scheme 1

Alternatively, acrylateamine (4) can be acylated with a number of carboxylic acids or acid chlorides under standard conditions to afford amide (5) (Scheme 2). Subsequent treatment with hydroxylamine and sodium hydroxide affords the desired α-cinnamide compounds (6).

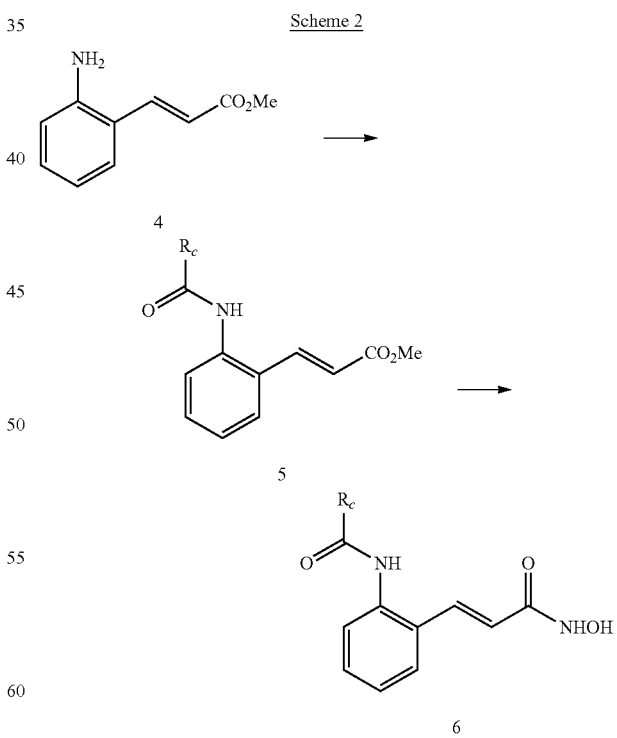

Scheme 2

Compounds of Formula II can be prepared according to the procedure outlined in Scheme 3. Treatment of aldehyde 7 with tert-butyl 2-(diethoxyphosphoryl)acetate in the presence of base affords acrylate 8. The addition of trifluoroacetic acid provides carboxylic acid 9, which when treated with hydroxylamine in the presence of isopropylchloroformate and base affords the desired α-cinnamide compounds of Formula II.

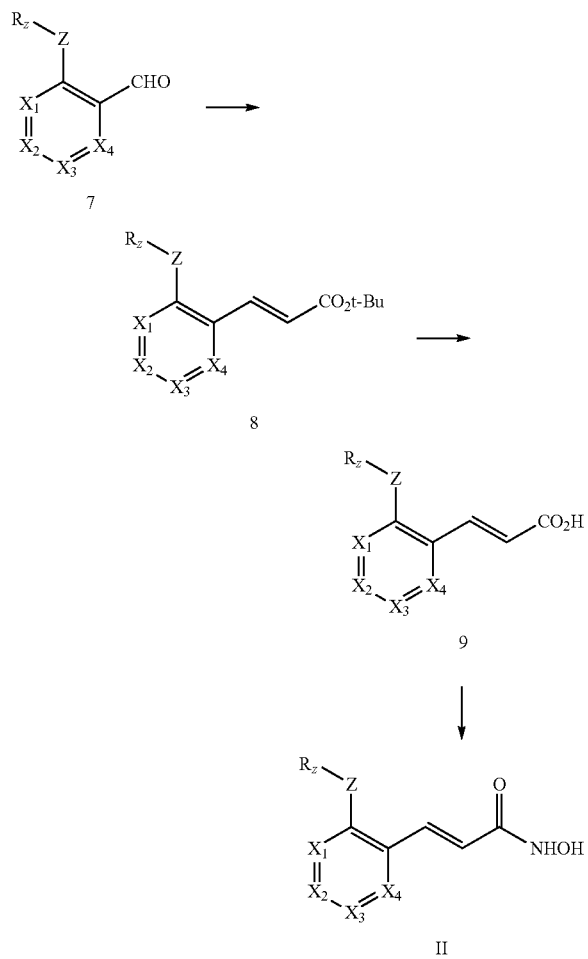

Compounds such as 17 could be readily prepared as outlined in Scheme 4. Treatment of acrylate (1) with compound (13) affords sulfide (14) which can be oxidized to the sulfone (15) under standard conditions such as m-chloroperoxybenzoic acid. Subsequent treatment with hydroxylamine and sodium hydroxide affords the desired α-cinnamide compounds (17).

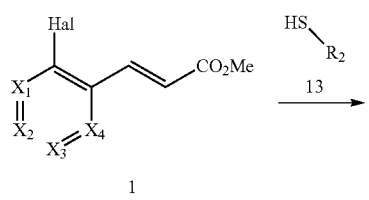

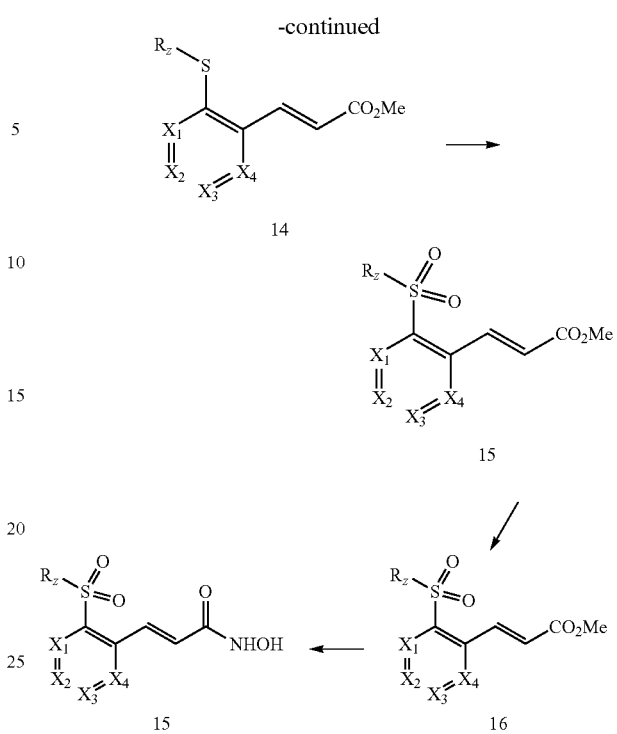

Methods of Using the Disclosed Compounds

One aspect of the present invention relates to a method of modulating HDAC8, comprising administering to a patient in need thereof a therapeutically effective amount of a compound of Formula (I) and/or Formula (II).

Another aspect of the present invention relates to a method of inhibiting HDAC8, comprising administering to a patient in need thereof a therapeutically effective amount of a compound of Formula (I) and/or Formula (II).

In another aspect, the present invention relates to a method of inhibiting HDAC8, comprising administering to a patient in need thereof a therapeutically effective amount of the pharmaceutical composition comprising a compound of Formula (I) and/or Formula (II).

Another aspect of the present invention relates to a method of treating, preventing, inhibiting, or eliminating a disease or disorder in a patient associated with the inhibition of HDAC8, the method comprising administering a therapeutically effective amount of a compound of Formula (I) and/or Formula (II).

One therapeutic use of the compounds of the present invention is to treat proliferative diseases or disorders such as cancer. Cancer can be understood as abnormal or unregulated cell growth within a patient and can include colon cancer, lung cancer, neuroblastoma, ovarian cancer, hepatocellular carcinoma, gastric cancer, prostate cancer, pancreatic cancer, renal cancer and leukemias such as acute myeloid leukemia and acute lymphoblastic leukemia. Additional cancer types include T-cell lymphoma (e.g., cutaneous T-cell lymphoma, peripheral T-cell lymphoma), B-cell lymphoma and multiple myeloma. In other embodiments, treating proliferative disease or disorders can include any cancer where there is evidence of an increase in Treg/effector T cell ratio or in an absolute Treg number, either in the periphery or in the tumor microenvironment or tertiary lymphoid structures, or increased expression of T cell tolerance-related genes. Such proliferative diseases or disorders can include but are not limited to: any Kras mutant carrying tumor (http://cancerimmunolres.aacrjournals.org/content/early/2016/02/13/2326-6066.CIR-15-0241.long); renal cell carcinoma; lung carcinoma; cervical cancer; prostate cancer, ovarian cancer; head and neck cancer; lymphoma; colorectal cancer, non small cell lung carcinoma; breast cancers (Gobert, M. et al. (2009) Cancer Res. 69, 2000-2009); and bladder cancer.

One therapeutic use of the compounds of the present invention is to treat neurological diseases or disorders or neurodegeneration. Neurological disorders are understood as disorders of the nervous system (e.g., the brain and spinal cord). Neurological disorders and diseases can include but are not limited to epilepsy, attention deficit disorder (ADD), Alzheimer's disease, Parkinson's Disease, Huntington's Disease, Muscular dystrophy, essential tremor, central nervous system trauma caused by tissue injury, oxidative stress-induced neuronal or axomal degeneration, ALS, and multiple sclerosis.

Another therapeutic use of the compounds of the present invention is also to treat inflammatory diseases or disorders. Inflammation can be understood as a host's response to an initial injury or infection. Symptoms of inflammation can include but are not limited to redness, swelling, pain, heat and loss of function. Inflammation may be caused by the upregulation of pro-inflammatory cytokines such as IL-1β, and increased expression of the FOXP3 transcription factor. In some embodiments, the inflammatory diseases include fibrosis or fibrotic diseases. Types of fibrotic diseases include but are not limited to lung fibrosis or pulmonary fibrosis, Liver fibrosis; Heart fibrosis; Mediastinal fibrosis; Retroperitoneal cavity fibrosis; Bone marrow fibrosis; Skin fibrosis; and Scleroderma or systemic sclerosis.

Another therapeutic use of the compounds of the present invention is also to treat autoimmune diseases or disorders. Autoimmune disorders are understood as disorders wherein a host's own immune system responds to tissues and substances occurring naturally in the host's body. Autoimmune diseases can include but are not limited to rheumatoid arthritis, Crohn's disease, type-1 diabetes, systemic juvenile idiopathic arthritis; inflammatory bowel disease; allograft transplantation; eczema, psoriasis, idiopathic thrombocytopenic purpra, autoimmune thrombocytopenia, acquired immune thrombocytopenia, autimmune neutropenia, autoimmune hemolytic anemia, parvovirus B19-associated red cell aplasia, acquired antifactor VIII autoimmunity, acquired von Willebrand disease, monoclonal gammopathy, aplastic anemia, pure red cell aplasia, Diamond-Blackfan anemia, hemolytic disease of the newborn, immune mediated-refractoriness to platelet transfusion, hemolytic uremic syndrome, Evan's syndrome, Guillain-Barre syndrome, chronic demyelinating polyradiculoneuropathy, paraproteinemic IgM demyelinating polyneuropathy, Lamber-Eaton myasthenic syndeom, myasthenia gravis, multifocal motor neuropathy, stiff man syndrome, paraneoplastic encephalomyelitis, sensory neuropathy with anti-Hu antibodies, myelitis, autoimmune diabetic neuropathy, acute idiopathic neuropathy, toxic epidermal necrolysis, gangrene, granuloma, pemphigus vulgaris, bullous pemphigoid, vitiligo, scleroderma, atomic dermatis, systemic and diffuse sclerosis, primary biliary cirrhosis, Celiac disease, dermatitis herpetiformis, cryptogenic cirrhosis, reactive arthritis, Hashimoto's thryroditis, Wegner's granulomoatosis, micropolyarterits, Churg-Strauss syndrome Type I and Type II autoimmune polyglandular syndromes, linear IgA disease, epidermolysis bullosa acquisita, erythema nodosa, pemphigoid gestationis, cicatricial pemphigoid, mixed essential cryoglobulinemia, chronic bullous disease of childhood, Goodpasture's syndrome, sclerosis cholangitis, ankylosing spondylitis, Bechet's syndrome temporal arteritis, Takayasu's arteritis, autoimmune urticaria, and Kawasaki's disease.

Another therapeutic use of the compounds of the present invention is also to treat infectious diseases or disorders. Infections or infectious diseases are caused by the invasion of a foreign pathogen. The infection may be caused by, for instance, a bacteria, a fungus, or virus. Bacterial infections include, but are not limited to *streptococcus* infections, mycobacterial infections, *bacillus* infections, *Salmonella* infections, *Vibrio* infections, spirochete infections, and *Neisseria* infections. Viral infections include, but are not limited to herpes virus infections, hepatitis virus infections, west nile virus infections, flavivirus infections, influenza virus infections, rhinovirus infections, papillomavirus infections, paromyxovirus infections, parainfluenza virus infections, and retrovirus infections. In particular embodiments, the compounds of the present invention are useful for treating infections which result in an inflammatory cytokine burst. Nonlimiting examples of such infections include Ebola and other viral hemorghagic fever-causing viruses, and Malaria.

Another therapeutic use of the compounds of the present invention is also to treat and/or prevent allergy and unwanted immune responses associated with allergy. A non-limiting list of allergies and related conditions includes, pollen allergy (e.g. Japanese Cedar Pollen), mold allergy, food allergies (including, but not limited to peanut, tree nut, milk, soy, gluten, and egg allergies), animal allergies (e.g. allergies to dogs, cats, rabbits), dust mite allergy, atopic dermatitis, allergic rhinitis, allergic otitis, allergic asthma, dry eye, ocular allergy, allergic urticaria, contact dermatitis, anaphalaxis, eosinophilic esophagitis.

Yet another therapeutic use of the compounds of the present invention is also to treat metabolic diseases or disorders. Metabolic diseases can be characterized as abnormalities in the way that a subject stores energy. Metabolic disorders can include but are not limited to metabolic syndrome, diabetes, obesity, high blood pressure, non-alcoholic fatty liver disease and heart failure.

Yet another therapeutic use of the compounds of the present invention is also to treat hematologic disorders. Hematologic diseases primarily affect the blood. Hematologic disorders can include but are not limited to anemia, multiple myeloma, lymphoma, and leukemia.

Yet another therapeutic use of the compounds of the present invention is also to prevent and/or treat transplant rejection. Tissues that are transplanted include (but are not limited to) whole organs such as kidney, liver, heart, lung, organ components such as skin grafts and the cornea of the eye; and cell suspensions such as bone marrow cells and cultures of cells selected and expanded from bone marrow or circulating blood, and whole blood transfusions.

Yet another therapeutic use of the compounds of the present invention is also to treat cardiovascular diseases or disorders. Cardiovascular diseases affect the heart and blood vessels of a patient. Exemplary conditions include but are not limited to cardiovascular stress, pressure overload, chronic ischemia, infarction-reperfusion injury, hypertension, Brain infarct after cerebral artery occlusion; atherosclerosis, peripheral artery disease, cardiac hypertrophy, cardiac arrhythmias, stroke, and heart failure.

Another therapeutic use of the compounds of the present invention is for purging the reservoir of latently infected memory CD4+ T cells in HIV+ patients (Matalon, et al., Mol Med. 2011; 17(5-6): 466-472).

The present invention also relates to the use of an inhibitor of HDAC8 for the preparation of a medicament used in the treatment, prevention, inhibition or elimination of a disease or disorder mediated by HDAC8, wherein the medicament comprises a compound of Formula (I) and/or Formula (II).

In another aspect, the present invention the present invention relates to a method for the manufacture of a medicament for treating, preventing, inhibiting, or eliminating a disease or disorder mediated by HDAC8, wherein the medicament comprises a compound of Formula (I) and/or Formula (II).

Another aspect of the present invention relates to a pharmaceutical composition for use in a method for treating a disease or disorder mediated by HDAC8, wherein the pharmaceutical composition comprises a compound of Formula (I) and/or Formula (II).

In yet another aspect, the present invention relates to a compound for use in a method for treating a disease or disorder mediated by HDAC8, wherein the use comprises a compound of Formula (I) and/or Formula (II).

The present invention also relates to the use of an inhibitor of HDAC8 for the preparation of a medicament used in the treatment, prevention, inhibition or elimination of tumors, wherein the medicament comprises a compound of Formula (I) and/or Formula (II).

The present invention further relates to the use of an inhibitor of HDAC8 for the preparation of a medicament used in the treatment, prevention, inhibition or elimination of cancer, wherein the medicament comprises a compound of Formula (I) and/or Formula (II).

Another embodiment of the present invention relates to a compound of Formula (T) and/or Formula (II), or a pharmaceutically acceptable salt, enantiomer, hydrate, solvate, prodrug, isomer, or tautomer thereof, or a pharmaceutical composition comprising a compound of the present invention, or a pharmaceutically acceptable salt, enantiomer, hydrate, solvate, prodrug, isomer, or tautomer thereof, and a pharmaceutically acceptable carrier which provides, upon administration to a human, a decrease in tumor burden and/or metastases. The pharmaceutical composition can be administered by oral means or other suitable means.

In another embodiment, the present invention relates to a compound of Formula (I) and/or Formula (II) or a pharmaceutical composition comprising a compound of the present invention and a pharmaceutically acceptable carrier used for the treatment of cancers including but not limited to cervix, colon, breast, lung, and stomach cancers; hematologic cancer, such as but not limited to leukaemia, lymphoma and multiple myeloma; midline carcinomas, mesenchymal, hepatic, renal and neurological tumors; and melanoma, squamous cell carcinoma and cutaneous T-cell lymphoma.

The disclosed compounds of the invention can be administered in effective amounts to treat or prevent a disorder and/or prevent the development thereof in subjects.

The present invention also relates to a pharmaceutical composition comprising a compound of Formula (I) and/or Formula (II) and a pharmaceutically acceptable carrier. The pharmaceutical acceptable carrier may further include an excipient, diluent, additive, or surfactant.

The compounds or pharmaceutical compositions of the invention may be administered via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compounds or compositions can be in solid, semisolid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

In one embodiment, the present invention relates to a method of preparing a pharmaceutical composition of the present invention by mixing at least one pharmaceutically acceptable compound of the present invention, and, optionally, one or more pharmaceutically acceptable carriers, additives, or excipients.

In another embodiment, the present invention relates to a method of preparing a pharmaceutical composition of the present invention by mixing at least one pharmaceutically acceptable compound of the present invention and one or more additional therapeutic agents.

According to one embodiment of the invention, the additional therapeutic agents may be selected from the group consisting of cytotoxic agent cisplatin, doxorubicin, taxotere, etoposide, irinotecan, camptostar, topotecan, paclitaxel, docetaxel, the epothilones, tamoxifen, 5-fluorouracil, methotrexate, temozolomide, cyclophosphamide, Lonafarib, Tipifarnib, 4-((5-((4-(3-chlorophenyl)-3-oxopiperazin-1-yl)methyl)-1H-imidazol-1-yl)methyl)benzonitrile hydrochloride, (R)-1-((1H-imidazol-5-yl)methyl)-3-benzyl-4-(thiophen-2-ylsulfonyl)-2,3,4,5-tetrahydro-1H-benzo[e][1,4]diazepine-7-carbonitrile, Cetuximab, GLEEVEC®, Intron®, Peg-Intron®, aromatase combinations, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, leucovirin, oxaliplatin (ELOXATIN®), Pentostatine, Vinblastine, Vincristine, Vindesine, Bleomycin, Dactinomycin, Daunorubicin, Epirubicin, Idarubicin, Mithramycin™, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrol acetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Rituximab, Campath, leucovorin, dexamethasone, bicalutamide, carboplatin, chlorambucil, cisplatin, letrozole, megestrol, and vairubicin.

The dosage forms of the present invention, may contain a mixture of one or more compounds of this invention, and may include additional materials known to those skilled in the art as pharmaceutical excipients. Stabilizing additives may be incorporated into the delivery agent solution. With some drugs, the presence of such additives promotes the stability and dispersibility of the agent in solution. The stabilizing additives may be employed at a concentration ranging from about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. In one embodiment, the stabilizing additives are gum acacia, gelatin and methyl cellulose.

Examples of pharmaceutical excipients and additives include, but are not limited to: acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid), Aerosol propellants (butane, dichlorodifluoromethane, dichlorotetrafluoroethane, isobutane, propane, trichloromonofluoromethane); Air displacements (carbon dioxide, nitrogen), Alcohol denaturants (denatonium benzoate, methyl isobutyl ketone, sucrose octaacetate); Alkalizing agents (strong ammonia solution, ammonium carbonate, diethanolamine, diisopropanolamine, potassium hydroxide, sodium bicarbonate, sodium borate, sodium carbonate, sodium hydroxide, trolamine); Anticaking agents (see glidant), Antifoaming agents (dimethicone, simethicone); Antimicrobial preservatives (benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, ascorbyl palmitate, butylated hydroxyanisole, butylated hydroxytoluene, hypophosphorous acid, monothioglycerol, propyl gallate sodium formaldehyde sulfoxylate sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Capsule lubricants (see tablet and capsule lubricant); Chelating agents (edetate disodium, ethylenediaminetetraacetic acid and salts, edetic acid); Coating agents (sodium carboxymethylcellulose, cellulose acetate, cellulose acetate phthalate ethylcellulose, gelatin, pharmaceutical glaze, hydroxypropyl cellulose, hydroxypropyl methylcellulose, hydroxypropyl methylcellulose phthalate methacrylic acid copolymer, methylcellulose, polyethylene glycol, polyvinyl acetate phthalate shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolamide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate monosodium glutamate, orange flower oil, peppermint, peppermint oil, peppermint spirit, rose oil, stronger rose water, thymol, tolu balsam tincture, vanilla, vanilla tincture, vanillin); Glidants and/or anticaking agents (calcium silicate, magnesium silicate, colloidal silicon dioxide, talc); Humectants (glycerin, hexylene glycol, propylene glycol, sorbitol); Plasticizers (castor oil, diacetylated monoglycerides, diethyl phthalate glycerin, mono- and di-acetylated monoglycerides, polyethylene glycol, propylene glycol, triacetin, triethyl citrate); Polymers (e.g., cellulose acetate, alkyl celluloses, hydroxyalkylcelluloses, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water), Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Tablet disintegrants (alginic acid, microcrystalline cellulose, croscarmellose sodium, crospovidone, polacrilin potassium, sodium starch glycolate starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane); Vehicle, solid carrier (sugar spheres); Vehicle: sterile (bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol) may be used as excipients. This list is not meant to be exclusive, but instead merely representative of the classes of excipients and the particular excipients which may be used in dosage forms of the present invention.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures, e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier, and/or g) an agent that enhances absorption of the compound such as cyclodextrin, hydroxypropyl-cyclodextrin, PEG400, PEG200.

For preparing pharmaceutical compositions from the compounds described in this disclosure inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. For example, water or water-propylene glycol solutions for parenteral injection or addition of sweeteners and opacifiers for oral solutions, suspensions and emulsions. Liquid form preparations may also include solutions for intranasal administration.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension Proteins such as albumin, chylomicron particles, or serum proteins can be used to solubilize the disclosed compounds.

Parental injectable administration is generally used for subcutaneous, intramuscular or intravenous injections and infusions Injectables can be prepared in conventional forms, either as liquid solutions or suspensions or solid forms suitable for dissolving in liquid prior to injection.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

If formulated as a fixed dose, such combination products employ the compounds of this invention within the dosage range described herein, or as known to those skilled in the art.

Since the compounds of this invention are intended for use in pharmaceutical compositions a skilled artisan will understand that they can be provided in substantially pure forms for example, at least 60% pure, more suitably at least 75% pure, preferably at least 85% pure and most preferably at least 98% pure (w/w).

The pharmaceutical preparation may be in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, from about 1 mg to about 500 mg, from about 1 mg to about 250 mg, or from about 1 mg to about 25 mg, according to the particular application.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. Effective dosage amounts of the disclosed compounds, when used for the indicated effects, range from about 0.5 ng to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses A typical recommended daily dosage regimen for oral administration can range from about 1 mg/day to about 500 mg/day or 1 mg/day to 200 mg/day, in two to four divided doses.

The compounds of Formula (I) and Formula (II) can form salts which are also within the scope of this invention. Reference to a compound of the Formula herein is understood to include reference to salts thereof, unless otherwise indicated.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, all materials were obtained from commercial suppliers and were used without further purification. Anhydrous solvents were obtained from Sigma-Aldrich (Milwaukee, Wis.) and used directly. All reactions involving air- or moisture-sensitive reagents were performed under a nitrogen atmosphere.

Unless otherwise noted, mass-triggered HPLC purification and/or purity and low resolution mass spectral data were measured using either: (1) Waters Acquity ultra performance liquid chromatography (UPLC) system (Waters Acquity UPLC with Sample Organizer and Waters Micromass ZQ Mass Spectrometer) with UV detection at 220 nm and a low resonance electrospray positive ion mode (ESI) (Column. Acquity UPLC BEH $C_{18}$ 1.7 μm 2.1×50 mm; gradient: 5-100% Solvent B (95/5/0.09%: Acetonitrile/Water/Formic Acid) in Solvent A (95/5/0.1%: 10 mM Ammonium Formate/Acetonitrile/Formic Acid) for 2.2 min then 100-5% Solvent B in Solvent A for 0.01 min then hold at 5% Solvent B in Solvent A for 0.29 min) or (2) Waters HT2790 Alliance high performance liquid chromatography (HPLC) system (Waters 996 PDA and Waters ZQ Single Quad Mass Spectrometer) with UV detection at 220 nm and 254 nm and a low resonance electrospray ionization (positive/negative) mode (ESI) (Column: XBridge Phenyl or C18, 5 μm 4.6×50 mm; gradient: 5-95% Solvent B (95% methanol/5% water with 0.1% Formic Acid) in Solvent A (95% water/5% methanol with 0.1% Formic Acid) for 2.5 min then hold at 95% Solvent B in Solvent A for 1 min (purity and low resolution MS only).

Unless otherwise noted, proton nuclear magnetic resonance (NMR) spectra were obtained on either: (1) Bruker BBFO ASCEND™400 AVANCE III spectrometer at 400 MHz or (2) Bruker BBFO ULTRASHIELD™300 AVANCE III spectrometer at 300 MHz spectrometers at 300 MHz. Spectra are given in ppm (δ) and coupling constants, J, are reported in Hertz. Tetramethylsilane (TMS) was used as an internal standard Mass spectra were collected using a Waters ZQ Single Quad Mass Spectrometer (ion trap electrospray ionization (ESI)).

LCMS Method
- Column: Shim-pack XR-ODS, 3.0*50 mm, 2.2 um;
- Mobile phase A: Water/0.05% TFA,
- Mobile phase B: ACN/0.05% TFA,
- Flow rate: 1.0 mL/min;
- LC Gradient: 5% B to 100% B in 2.2 min, hold 1.0 min; 254 nm, 220 nm.

Abbreviations used in the following examples and elsewhere herein are:
ACN acetonitrile
DCE 1,2-dichloroethane
DCM dichloromethane or methylene chloride
DIEA N,N-diisopropylethylamine
DMA N,N-Dimethylacetamide
DMF N,N-dimethylformamide
DMSO dimethylsulfoxide DMTMM 4-(4,6-Dimethoxy-1,3,5-triazin-2-yl)-4-methylmorpholinium chloride
dppf bis(diphenylphosphino)ferrocene
EtOAc ethyl acetate
h hours
HATU 2-(3H-[1,2,3]triazolo[4,5-b]pyridin-3-yl)-1,1,3,3-tetramethyl-isouronium hexafluorophosphate
HCl hydrogen chloride
HPLC high performance liquid chromatography
LC/M liquid chromatography/mass spectrometry
LiOH lithium hydroxide
$K_2CO_3$ potassium carbonate
MeOH methanol
MS mass spectrometry
NaOH sodium hydroxide
$Na_2SO_4$ sodium sulfate
NMM 4-Methylmorpholine
$Pd_2(dba)_3$ tris(dibenzylideneacetone)dipalladium
$PPh_3$ triphenylphosphine
Rt room temperature
TEA triethylamine
TFA trifluoroacetic acid
THF tetrahydrofuran Example 1—Intermediate Int-1: (E)-methyl 3-(2-aminophenyl)acrylate

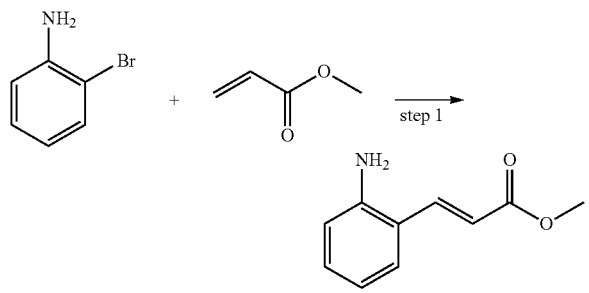

Step-1: (E)-methyl 3-(2-aminophenyl)acrylate. Into a 1-L 3-necked round-bottom flask, was placed 2-bromoaniline (55 g, 319.72 mmol, 1.00 equiv), N,N-dimethylformamide (500 mL), methyl prop-2-enoate (275 g, 3.19 mot, 10.00 equiv), TEA (97 g, 958.59 mmol, 3.00 equiv), Pd(dppf)Cl₂·CH₂Cl₂ (13 g, 0.05 equiv) and water (0.5 mL). The resulting solution was stirred overnight at 110° C. The reaction mixture was then cooled to room temperature and poured into 2 L of water, extracted with 3×800 mL of ethyl acetate, washed with 1000 mL of brine, dried over anhydrous sodium sulfate and concentrated under vacuum. The residue was applied onto a silica gel column with ethyl acetate/petroleum ether (1:4). The collected fraction was concentrated under vacuum to give (E)-methyl 3-(2-aminophenyl)acrylate (17.6 g, 31%) as a green solid ¹H-NMR (DMSO, 400 MHz) δ (ppm): 7.90 (d, J=16 Hz, 1H), 7.45 (d, J=8 Hz, 1H), 7.10-7.06 (m, 1H), 6.70 (d, J=8.4 Hz, 1H), 6.54 (t, J=7.2 Hz, 1H), 6.37 (d, J=15.6 Hz, 1H), 5.62 (s, 2H), 3.71 (s, 3H). MS: (ES, m/z): 178 [M+H]⁺.

Example 2—Intermediate Int-2: (E)-methyl 3-(2-bromophenyl)acrylate

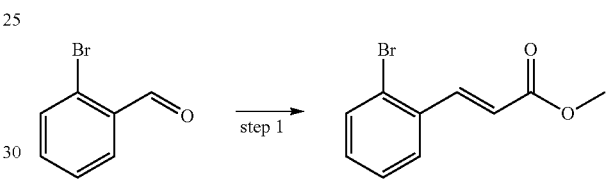

Step-1: (E)-methyl 3-(2-bromophenyl)acrylate

Into a 250-mL round-bottom flask purged and maintained with an inert atmosphere of nitrogen, was placed methyl 2-(dimethoxyphosphoryl)acetate (12 g, 65.89 mmol, 1.20 equiv), tetrahydrofuran (100 mL). This was followed by the addition of sodium hydride (60% in oil, 2.4 g, 60.00 mmol, 1.11 equiv) at 0° C. The mixture was stirred for 30 min at 0° C. Then 2-bromobenzaldehyde (10 g, 54.05 mmol, 1.00 equiv) was added at 0° C. The resulting solution was stirred for additional 10 min at 0° C. The reaction mixture was then poured into 500 mL of water, extracted with 500 mL of ethyl acetate, washed with 50 mL of brine, dried over anhydrous sodium sulfate and concentrated under vacuum. The residue was applied onto a silica gel column with ethyl acetate/petroleum ether (1:5). The collected fraction was concentrated under vacuum to give (E)-methyl 3-(2-bromophenyl)acrylate (9 g, 69%) as yellow oil. ¹H-NMR (DMSO, 400 MHz) δ(ppm): 7.90-7.85 (m, 2H), 7.66 (d, J=8 Hz, 1H), 7.40 (t, J=7.6 Hz, 1H), 7.35-7.30 (m, 1H), 6.62 (d, J=15.6 Hz, 1H), 3.75 (s, 3H). MS: (ES, m/z): 241 [M+H]⁺.

Example 3—Intermediate Int-3: (E)-tert-butyl 3-(2-bromophenyl)acrylate

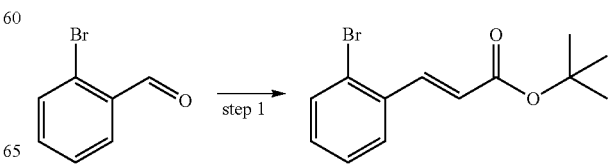

Step-1: Synthesis of (E)-tert-butyl 3-(2-bromophenyl)acrylate

Into a 250-mL 3-necked round-bottom flask purged and maintained with an inert atmosphere of nitrogen, was placed a solution of sodium hydride (60%, 1.32 g, 55.00 mmol, 1.10 equiv) in tetrahydrofuran (100 mL). This was followed by the addition of a solution of tert-butyl 2-(diethoxyphosphoryl)acetate (9.1 g, 36.08 mmol, 1.20 equiv) in tetrahydrofuran (10 mL) dropwise with stirring at 0° C. The resulting solution was stirred for 30 min at 0° C. To this was added a solution of 2-bromobenzaldehyde (5.55 g, 30.00 mmol, 1.00 equiv) in tetrahydrofuran (10 mL) dropwise with stirring at 0° C. The resulting solution was allowed to react overnight at room temperature. The reaction mixture was poured into 250 mL of water, extracted with 200 mL of ethyl acetate, washed with 500 mL of brine, dried over anhydrous sodium sulfate and concentrated under vacuum. The residue was applied onto a silica gel column with ethyl acetate/petroleum ether (1:10). The collected fraction was concentrated under vacuum to give (E)-tert-butyl 3-(2-bromophenyl)acrylate (7.1 g, 84%) as colorless oil. $^1$H-NMR (DMSO, 400 MHz) δ(ppm): 7.92 (m, 1H), 7.83 (d, J=15.6 Hz, 1H), 7.72-7.70 (m, 1H), 7.44-7.41 (m, 1H), 7.40-7.33 (m, 1H), 6.57 (d, J=16 Hz, 1H), 1.50 (s, 9H). MS: (ES, m/z): 283[M+H]$^+$.

Example 4—Intermediate Int-4: (E)-2-(3-tert-butoxy-3-oxoprop-1-enyl)benzoic acid

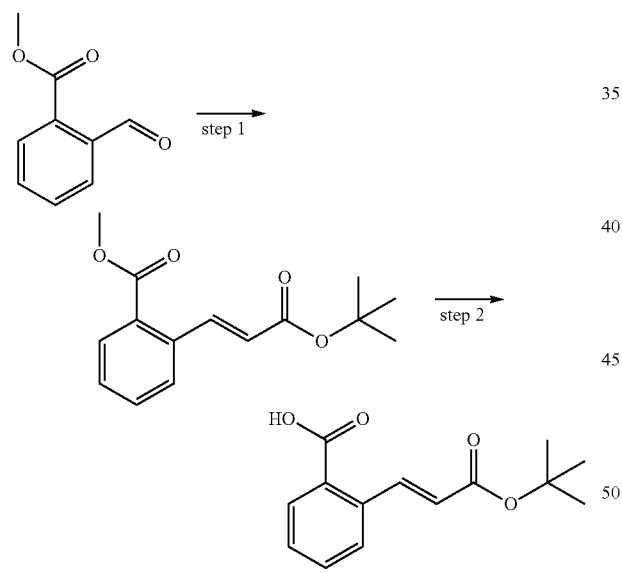

Step-1: Synthesis of (E)-methyl 2-(3-tert-butoxy-3-oxoprop-1-enyl)benzoate

Into a 500-mL round-bottom flask, was placed tetrahydrofuran (150 mL) and sodium hydride (60%, 1.3 g, 54.17 mmol, 1.10 equiv). This was followed by the addition of tert-butyl 2-(diethoxyphosphoryl)acetate (9.2 g, 36.47 mmol, 1.20 equiv) dropwise with stirring at 0° C. The resulting solution was stirred for 30 min at room temperature. To the above was added a solution of methyl 2-formylbenzoate (5 g, 30.46 mmol, 1.00 equiv) in tetrahydrofuran (10 mL) dropwise with stirring at 0° C. The resulting solution was allowed to react for an additional 4 h at room temperature. The reaction was then quenched by the addition of 200 mL of water, extracted with 3×200 mL of ethyl acetate, dried over anhydrous sodium sulfate and concentrated under vacuum. The residue was applied onto a silica gel column with ethyl acetate/petroleum ether (1:10). The collected fraction was concentrated under vacuum to give (E)-methyl 2-(3-tert-butoxy-3-oxoprop-1-enyl)benzoate (5.6 g, 70%) as yellow oil. MS: (ES, m/z): 263[M+H]$^+$.

Step-2: Synthesis of (E)-2-(3-tert-butoxy-3-oxoprop-1-enyl)benzoic acid

Into a 500-mL round-bottom flask, was placed (E)-methyl 2-(3-tert-butoxy-3-oxoprop-1-enyl)benzoate (4 g, 15.25 mmol, 1.00 equiv), tetrahydrofuran (76 mL) and a solution of LiOH (1.8 g, 75.16 mmol, 5.00 equiv) in water (76 mL). The resulting solution was stirred for 3 h at room temperature and then concentrated under vacuum to remove tetrahydrofuran. The solution was then extracted with 50 mL of ethyl acetate and the aqueous phase was collected. The pH of the aqueous solution was adjusted to 6 with HCl (6 mol/L). The resulting solution was extracted with 2×200 mL of dichloromethane, dried over anhydrous sodium sulfate and concentrated under vacuum. This gave (E)-2-(3-tert-butoxy-3-oxoprop-1-enyl)benzoic acid (4.2 g, crude) as a white solid. $^1$H-NMR (DMSO, 300 MHz) δ(ppm): 8.35 (d, J=15.9 Hz, 1H), 7.89-7.82 (m, 2H), 7.61-7.48 (m, 2H), 6.41 (d, J=15.9 Hz, 1H), 1.50 (s, 3H). MS: (ES, m/z): 249[M+H]$^+$.

Example 5—Intermediate Int-5: (E)-methyl 3-(2-(bromomethyl)pyridin-3-yl)acrylate

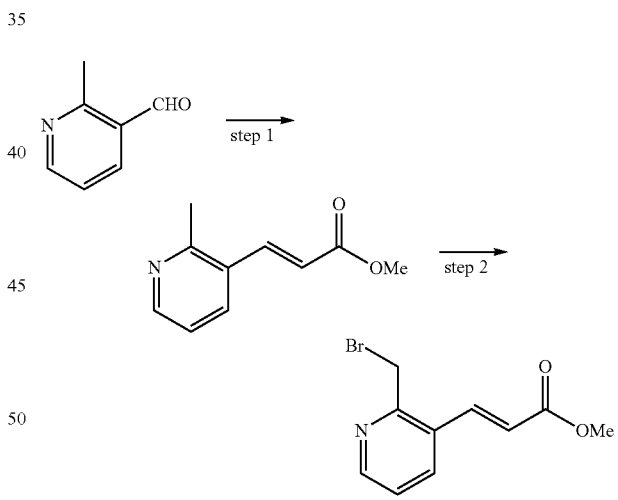

Step-1: Synthesis of (E)-methyl 3-(2-methylpyridin-3-yl)acrylate

Into a 250-mL 3-necked round-bottom flask purged and maintained with an inert atmosphere of nitrogen, was placed sodium hydride (60%, 1.09 g, 1.10 equiv) in tetrahydrofuran (50 mL). This was followed by the addition of methyl 2-(dimethoxyphosphoryl)acetate (5.41 g, 29.71 mmol, 1.20 equiv) dropwise with stirring at 0° C. The resulting solution was stirred for 30 min at 0° C. To this was added a solution of 2-methylpyridine-3-carbaldehyde (3 g, 24.77 mmol, 1.00 equiv) in tetrahydrofuran (20 mL) dropwise with stirring at 0° C. The resulting solution was stirred for 4 h at room temperature. The reaction was then quenched by the addition of 100 mL of water, extracted with 2×300 mL of ethyl acetate, washed with 1×150 mL of brine, dried over anhydrous sodium sulfate and concentrated under vacuum. The residue was applied onto a silica gel column with ethyl acetate/petroleum ether (1:2). The collected fraction was concentrated under vacuum to give (E)-methyl 3-(2-methylpyridin-3-yl)acrylate (3.3 g, 75%) as yellow oil. MS. (ES, m/z): 178[M+H]+.

Step-2: Synthesis of (E)-methyl 3-(2-(bromomethyl)pyridin-3-yl)acrylate

Into a 50-mL round-bottom flask, was placed (E)-methyl 3-(2-methylpyridin-3-yl)acrylate (1 g, 5.64 mmol, 1.00 equiv), CCl₄ (12 mL), NBS (1.11 g, 6.24 mmol, 1.10 equiv), AIBN (93 mg, 0.57 mmol, 0.10 equiv). The resulting solution was stirred overnight at 70° C. The reaction mixture was cooled to room temperature and poured into 50 mL of water, extracted with 2×50 mL of dichloromethane, washed with 100 mL of brine, dried over anhydrous sodium sulfate and concentrated under vacuum. The residue was applied onto a silica gel column with ethyl acetate/petroleum ether (1:2). The collected fraction was concentrated under vacuum to give (E)-methyl 3-(2-(bromomethyl)pyridin-3-yl)acrylate (181 mg, 13%) as red oil. MS: (ES, m/z): 256[M+H]+.

Example 6—Intermediate Int-6: (E)-methyl 3-(3-bromopyridin-4-yl)acrylate

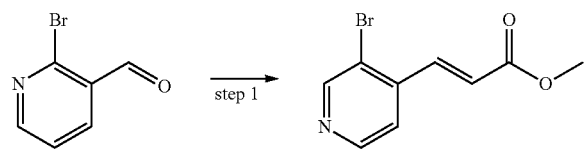

Step-1: Synthesis of (E)-methyl 3-(3-bromopyridin-4-yl)acrylate

Into a 500-mL 3-necked round-bottom flask purged and maintained with an inert atmosphere of nitrogen, was placed a solution of sodium hydride (60%, 476 mg, 19.83 mmol, 1.10 equiv) in tetrahydrofuran (70 mL). To this was added a solution of methyl 2-(dimethoxyphosphoryl)acetate (2.36 g, 12.96 mmol, 1.20 equiv) in tetrahydrofuran (70 mL). The resulting solution was stirred for 30 min at 0° C., then to this was added a solution of 3-bromopyridine-4-carbaldehyde (2 g, 10.75 mmol, 1.00 equiv) in tetrahydrofuran (60 mL). The resulting solution was allowed to react with stirring for 2 h at room temperature. Then was poured into 100 mL of water, extracted with 100 mL of ethyl acetate, dried over anhydrous sodium sulfate and concentrated under vacuum. The residue was applied onto a silica gel column with ethyl acetate/petroleum ether (1:10). The collected fraction was concentrated under vacuum to give (E)-methyl 3-(3-bromopyridin-4-yl)acrylate (1.5 g, 58%) as a white solid. MS: (ES, m/z): 242[M+H]+.

Intermediates (E)-methyl 3-(2-bromopyridin-3-yl)acrylate and (E)-methyl 3-(3-bromopyridin-2-yl)acrylate were synthesized according to the procedure above for (E)-methyl 3-(3-bromopyridin-4-yl)acrylate.

Example 7—Intermediate Int-7: (Z)-ethyl 3-(2-aminophenyl)-2-fluoroacrylate

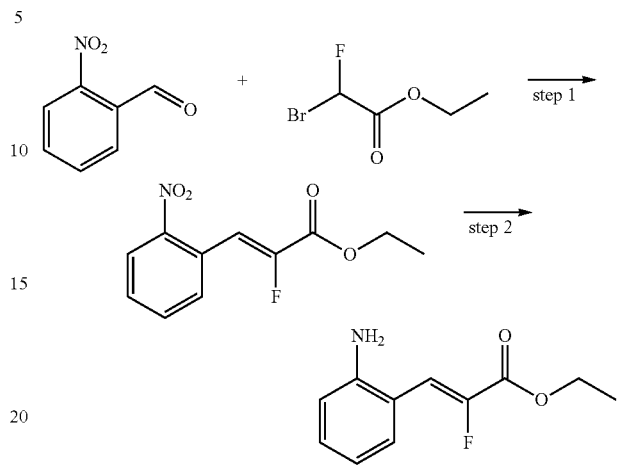

Step-1: Synthesis of (Z)-ethyl 2-fluoro-3-(2-nitrophenyl)acrylate

Into a 250-mL round-bottom flask, was placed PPh₃ (10 g, 38.13 mmol, 1.20 equiv), ethyl 2-bromo-2-fluoroacetate (7 g, 37.84 mmol, 1.20 equiv), 2-nitrobenzaldehyde (4.8 g, 31.76 mmol, 1.00 equiv) and zinc-copper couple (3.4 g). The resulting mixture was stirred for 4 h at 130° C. in an oil bath. The reaction was then cooled to room temperature and quenched by the addition of 100 mL of water. The resulting solution was extracted with 3×100 mL of ethyl acetate, washed with 2×100 mL of brine, dried over anhydrous sodium sulfate and concentrated under vacuum. The residue was applied onto a silica gel column with ethyl acetate/petroleum ether (1:10). The collected fraction was concentrated under vacuum to give (Z)-ethyl 2-fluoro-3-(2-nitrophenyl)acrylate (2.1 g, 28%) as a yellow solid. GCMS: (EI, m/z): 239[M].

Step-2: Synthesis of (Z)-ethyl 3-(2-aminophenyl)-2-fluoroacrylate

Into a 250-mL 3-necked round-bottom flask, was placed (Z)-ethyl 2-fluoro-3-(2-nitrophenyl)acrylate (2.1 g, 8.78 mmol, 1.00 equiv), ethanol (24 mL), water (6 mL) and iron (2.95 g, 6.00 equiv). This was followed by the addition of NH₄Cl (940 mg, 17.57 mmol, 2.00 equiv) in portions with stirring at 90° C. The resulting solution was stirred for 3 h at 90° C. in an oil bath. The solids were filtered out. The filtrate was concentrated under vacuum. The residue was dissolved in 100 mL of water, and then extracted with 3×100 mL of ethyl acetate, washed with 100 mL of brine, dried over anhydrous sodium sulfate and concentrated under vacuum. The crude product was applied onto a silica gel column with ethyl acetate/petroleum ether (1:10). The collected fraction was concentrated under vacuum to give (Z)-ethyl 3-(2-aminophenyl)-2-fluoroacrylate (1.1 g, 60%) as a yellow solid. MS: (ESI, m/z): 210[M+H]+.

Example 8—Intermediate Int-8: 2-bromo-1-(2-methoxyethyl)-11H-benzo[d]imidazole

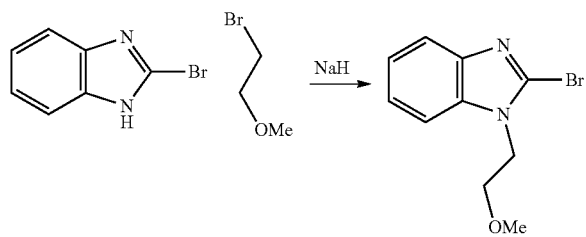

Sodium hydride (60% dispersion in mineral oil, 0.665 g, 16.63 mmol) was added to a solution of 2-bromo-1H-benzo[d]imidazole (2.73 g, 13.86 mmol) in DMF (30 mL), and the reaction stirred for 10 minutes at ambient temperature. 1-Bromo-2-methoxyethane (1.541 ml, 16.63 mmol) was added, and reaction stirred overnight at ambient temperature. The reaction was diluted with ethyl acetate and washed several times with brine. The organic layer was separated and dried over anhydrous magnesium sulfate, filtered and concentrated. The residue was purified via column chromatography on a 100 gram silica gel column eluting with 20-40% ethyl acetate-hexane. The desired fractions were combined and concentrated to afford 2-bromo-1-(2-methoxyethyl)-1H-benzo[d]imidazole (2.9 g, 82%) as an orange oil. $^1$H NMR (300 MHz, DMSO-$d_6$) δ ppm 7.54-7.67 (m, 2H) 7.14-7.34 (m, 2H) 4.42 (t, J=5.28 Hz, 2H) 3.67 (t, J=5.28 Hz, 2H) 3.20 (s, 3H).

Example 9—Intermediate Int-9: (E)-3-(2-(2-oxoimidazolidin-1-yl)phenyl)acrylate hydrochloride

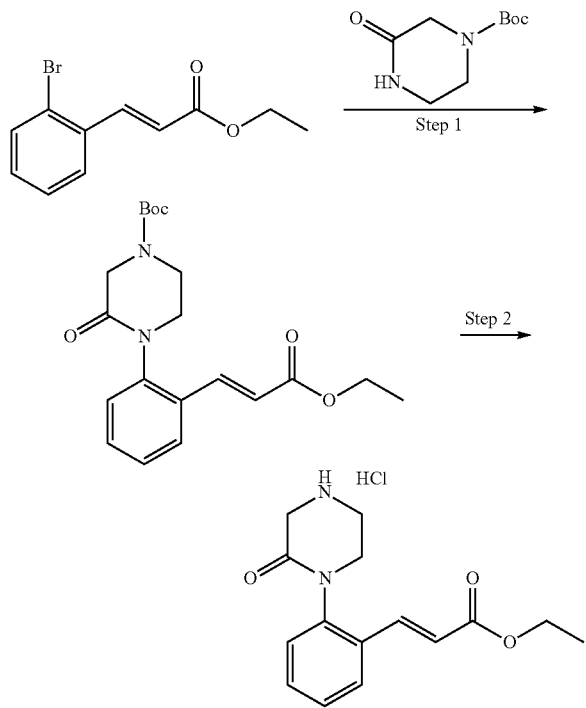

Step-1: Synthesis of tert-butyl (E)-4-(2-(3-ethoxy-3-oxoprop-1-en-1-yl)phenyl)-3-oxopiperazine-1-carboxylate A 10-mL microwave vial was equipped with a stir bar and ethyl (E)-3-(2-bromophenyl)acrylate (0.206 g, 0.806 mmol, 1.0 equiv), tert-butyl 3-oxopiperazine-1-carboxylate (0.200 g, 0.999 mmol, 1.2 equiv), potassium phosphate tribasic (0.513 g, 242 mmol, 3.0 equiv), (1R,2R)—N1,N2-dimethylcyclohexane-1,2-diamine (0.115 g, 0.806 mmol, 1.0 equiv), and copper (I) iodide (0.0307 g, 0.161 mmol, 0.2 equiv) in DMF (3 mL). The resulting mixture was heated to 100'C for 3 hours in the microwave. The reaction mixture was diluted with 25 mL EtOAc and washed with 20 mL H$_2$O. The organic layer was separated and the aqueous layer was extracted twice with 10 mL EtOAc. Organic layers were combined and filtered through a 5 g Silicycle SiliaMetS-DMT column. EtOAc was removed under reduced pressure to afford (0.287 g, 95% crude yield) of tert-butyl (E)-4-(2-(3-ethoxy-3-oxoprop-1-en-1-yl)phenyl)-3-oxopiperazine-1-carboxylate. MS (ESI, m/z): 375 [M+H]$^+$.

Step-2: Synthesis of ethyl (E)-3-(2-(2-oxoimidazolidin-1-yl)phenyl)acrylate hydrochloride Intermediate from Step-1: tert-butyl (E)-4-(2-(3-ethoxy-3-oxoprop-1-en-1-yl)phenyl)-3-oxopiperazine-1-carboxylate (0.287 g, 0.766 mmol, 1.0 equiv) was dissolved in EtOAc (3 mL). 4M % HCl in 1,4-Dioxane (1.92 mL, 7.66 mmol, 10.0 equiv) was added. The reaction was heated at 50° C. for 18 hours. The reaction was concentrated to dryness. The residue was brought up in 3 mL of diethyl ether and warmed to 35° C. Upon cooling to room temperature, a precipitate formed. The precipitate was collected by vacuum filtration to afford (0.094 g, 52% crude yield) of ethyl (E)-3-(2-(2-oxopiperazin-1-yl)phenyl)acrylate hydrochloride as a pale pink solid. MS (ESI, m/z): 275 [M+H]$^+$.

Example 10—Intermediate Int-10: (E)-5-(2-(3-methoxy-3-oxoprop-1-en-1-yl)phenyl)-2,5-diazabicyclo[2.2.1]heptan-2-ium chloride

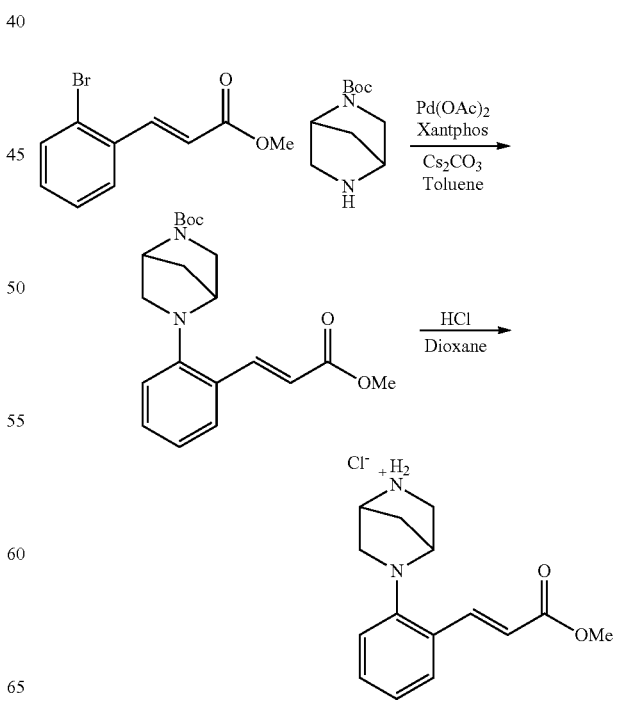

Step-1: A thick-walled pressure vessel with teflon screw-top and stirbar was charged with methyl-(E)-3-(2-bromophenyl)acrylate (1.00 g, 4.15 mmol, 1.00 equiv), tert-butyl-2,5-diazabicyclo[2.2.1]heptane-2-carboxylate (0.905 g, 4.56 mmol, 1.10 equiv), cesium carbonate (2.70 g, 8.3 mmol, 2.0 equiv), palladium(II) acetate (65 mg, 0.29 mmol, 0.07 equiv), and xantphos (360 mg, 0.62, 0.14 equiv). The vessel was brought into a glovebox and dry toluene (10 mL) was added. The vessel was sealed, removed from the glovebox and heated at 90° C. overnight. The reaction mixture was then cooled to room temperature and diluted with 50 mL of EtOAc, then washed with 10% K₂CO₃, 1M HCl, and brine. The organic phase was dried with Na₂SO₄, the solvent was removed and the brown oil was purified via flash column chromatography on silica gel (40% EtOAc/Hexane, R$_f$=0.55) to afford a bright yellow solid (1.00 g, 67%).

Step-2: The yellow solid was dissolved in an anhydrous solution of 4M HCl/Dioxane and stirred for 24 hours. The reaction mixture was evaporated to dryness, then triturated from hexanes and isolated by filtration to afford (E)-5-(2-(3-methoxy-3-oxoprop-1-en-1-yl)phenyl)-2,5-diazabicyclo[2.2.1]heptan-2-ium chloride as an off-white powder. ¹H NMR (400 MHz, DMSO-d₆) δ 9.76 (br s, 1H), 9.09 (br s, 1H), 7.77 (d, J=16 Hz, 1H), 7.57 (dd, J=7.6, 1.4 Hz, 1H), 7.30 (t, J=8.2 Hz, 1H), 7.03 (d, J=8.6 Hz, 1H), 6.93 (t, J=7.4 Hz, 1H), 6.39 (d, J=16.0 Hz, 1H), 4.33 (d, J=14.8 Hz, 2H), 3.71 (s, 3H), 3.52 (d, J=10.1 Hz, 1H), 3.44 (d, J=10.1 Hz, 1H), 3.31-3.18 (m, 2H), 2.12 (d, J=10.5 Hz, 1H), 1.92 (d, J=10.5 Hz, 1H); ¹³C NMR (100 MHz, DMSO-d₆) δ 166.9, 147.8, 142.9, 130.7, 129.2, 124.4, 120.5, 117.0, 116.6, 58.5, 57.6, 56.0, 51.5, 48.6, 34 9; LRMS (ESI, m/z) calculated for $C_{15}H_{19}N_2O_2$ [M+H]⁺ 259.14, found 259.07.

The following intermediates are prepared similarly to Example 10

TABLE 1

| ID | Structure | Name | ¹H-NMR (CDCl₃, 400 MHz) δ (ppm): and ¹³C NMR | LC-MS [M + 1]+ |
|---|---|---|---|---|
| Int-11 | 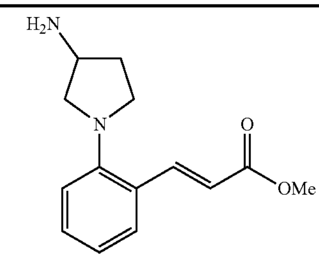 | Methyl (E)-3-(2-(3-aminopyrrolidin-1-yl)phenyl)acrylate | (400 MHz, DMSO-d₆) δ 9.65 (br s, 1H), 8.51 (br s, 2H), 7.92 (d, J = 16 Hz, 1H), 7.55 (dd, J = 7.4, 1.6 Hz, 1H), 7.30 (dt, J = 7.0, 1.6 Hz, 1H), 6.96-6.91 (m, 2H), 6.40 (d, J = 16 Hz, 1H), 3.84 (br s, 1H), 3.72 (s, 3H), 3.49-3.44 (m, 2H), 3.24 (dd, J = 10.5, 3.9 Hz, 1H), 2.80-2.70 (m, 1H), 2.52-2.44 (m, 1H), 3.17-3.11 (m, 1H), 2.30-2.21 (m, 1H), 2.06-1.98 (m, 1H); ¹³C NMR (100 MHz, DMSO-d₆) δ 169.9, 148.6, 143.5, 130.8, 128.8, 124.6, 120.7, 116.4, 66.4, 55.3, 51.4, 50.5, 49.1, 29.4; | 247.06 |
| Int-12 | 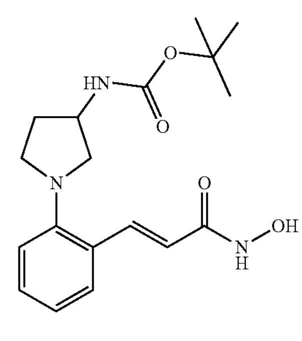 [SMILES: CC(C)(C)OC(=O)NC1CCN(c2ccccc2/C=C/C(=O)NO)C1] | N-(1-{2-[(1E)-2-(hydroxycarbamoyl)eth-1-en-1-yl]phenyl}pyrrolidin-3-yl)benzamide | (400 MHz, DMSO-d₆) δ 9.76 (br s, 1H), 9.09 (br s, 1H), 8.00 (d, J = 16 Hz, 1H), 7.42 (dd, J = 7.6, 1.4 Hz, 1H), 7.26 (t, J = 8.2 Hz, 1H), 6.93-6.85 (m, 2H), 6.27 (d, J = 16.0 Hz, 1H), 4.84 (br s, 1H), 4.31 (br s, 1H), 3.49-3.41 (m, 2H), 3.20-3.08 (m, 2H), 2.32-2.23 (m, 1H), 1.89-1.82 (m, 1H), 1.45 (s, 9H); ¹³C NMR (100 MHz, DMSO-d₆) δ 162.9, 155.1, 151.1, 135.0, 130.2, 128.8, 127.4, 123.6, 119.42, 119.30, 77.4, 53.2, 51.4, 48.6, 32.8, 28.2 | 348.25 |
| Int-13 | 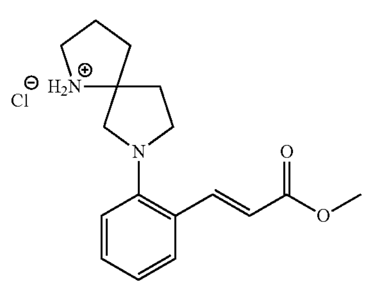 [SMILES: [Cl-] ; COC(=O)/C=C/c1ccccc1N1CCC2(CCC[NH2+]2)C1] | (E)-7-(2-(3-Methoxy-3-oxoprop-1-en-1-yl)phenyl)-1,7-diazaspiro[4.4]nonan-1-ium chloride | (400 MHz, DMSO-d₆) δ 9.65 (br s, 1H), 9.49 (br s, 1H), 7.91 (d, J = 16.0 Hz, 1H), 7.55 (dd, J = 8.2, 1.6 Hz, 1H), 7.30 (dt, J = 7.8, 1.6 Hz, 1H), 6.95-6.92 (m, 2H), 6.40 (d, J = 16.0 Hz, 1H), 3.70 (s, 3H), 3.52-3.44 (m, 2H), 3.34 (d, J = 10.5 Hz, 1H), 3.29-3.21 (m, 2H), 3.15-3.10 (m, 1H), 2.42-2.35 (m, 1H), 2.13-1.95 (m, 5H) | 273.08 |

TABLE 1-continued

| ID | Structure | Name | $^1$H-NMR (CDCl$_3$, 400 MHz) δ (ppm): and $^{13}$C NMR | LC-MS [M + 1]+ |
|---|---|---|---|---|
| Int-14 | 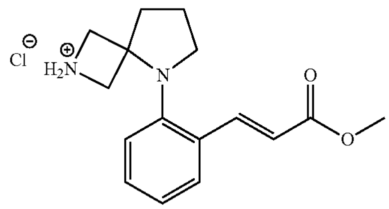 [SMILES: [Cl-] ; COC(=O)/C=C/c1ccccc1N1CCCC12C[NH2+]C2] | (E)-5-(2-(3-Methoxy-3-oxoprop-1-en-1-yl)phenyl)-2,5-diazaspiro[3.4]octan-2-ium chloride | (400 MHz, DMSO-d$_6$) δ 9.52 (br s, 1H), 8.38 (br s, 1H), 7.87 (dd, J = 7.8, 1.6 Hz, 1H), 7.81 (d, J = 16 Hz, 1H), 7.30 (dt, J = 7.4, 1.6 Hz, 1H), 7.32-7.27 (m, 2H), 6.51 (d, J = 16 Hz, 1H), 3.70 (s, 3H), 3.68-3.58 (m, 3H), 3.48-3.45 (m, 1H), 3.18 (t, J = 6.6 Hz, 2H), 2.40 (t, J = 7.0 Hz, 2H), 1.94-1.87 (m, 2H) | 287.04 |

Example 11—Intermediate Int-15: (E)-4-((2-(3-methoxy-3-oxoprop-1-en-1-yl)phenyl)sulfonyl)piperidin-1-ium chloride

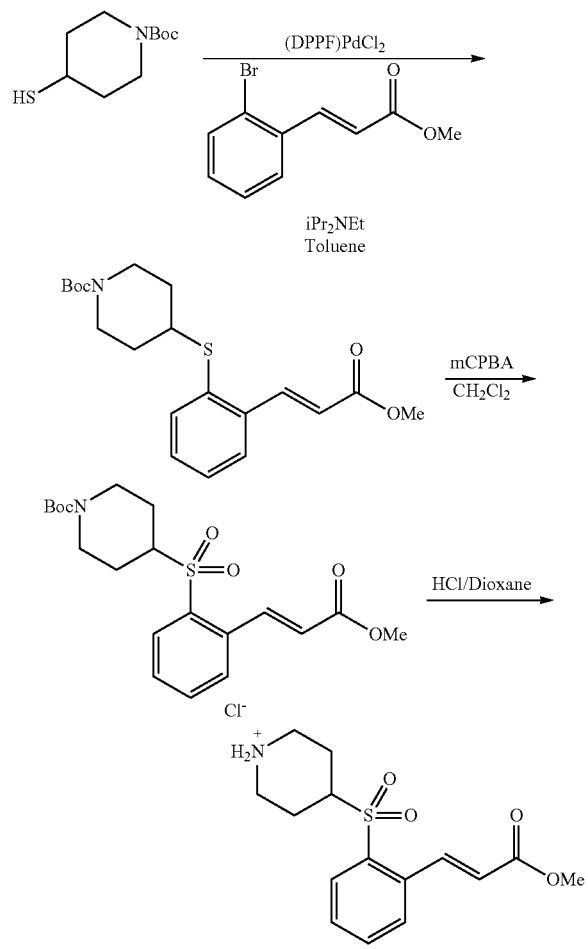

Step-1: A 50 mL glass pressure vessel was charged with the tert-butyl-4-mercaptopiperidine-1-carboxylate (239 mg, 1.10 mmol, 1.10 equiv) and the (dppf) PdCl$_2$·DCM (41 mg, 0.050 mmol, 0.05 equiv). Then the vessel was brought into a nitrogen atmosphere glove-box. In the glovebox, methyl-(E)-3-(2-bromophenyl)acrylate (241 mg, 1.00 mmol) and a solution of N-ethyl-N,N-diisopropylamine (200 uL, 1.1 mmol, 0.1 equiv) in toluene (3 mL) were added. The vessel was sealed and brought outside the glovebox where it was heated at 110° C. for 3 hours. The reaction mixture was then cooled to room temperature and diluted with 50 mL of EtOAc, and 50 mL of water. The layers were separated and the organic layer was washed with brine, then dried over Na$_2$SO$_4$. The solvent was removed, and the residue was passed through a small plug of silica gel eluting with 40% EtOAc/Hexane. The solvent was removed to afford a viscous residue (328 mg, 87%).

Step-2: The viscous residue was dissolved in 10 ml of dry DCM. Then m-chloroperbenzoic acid (375 mg, 2.18 mmol, 2.5 equiv) was added. The reaction mixture stirred at room temperature for 16 h. The DCM was removed in vacuo and the mixture was partitioned between 50 mL of EtOAc and 50 mL of 10% K$_2$CO$_3$. The layers were separated and the organic phase was washed with brine (1×50 mL), and dried over Na$_2$SO$_4$. Filtration and solvent removal yielded a white solid (345 mg, 97%) which was carried forward without further purification.

Step-3: Tert-butyl-(E)-4-((2-(3-methoxy-3-oxoprop-1-en-1-yl)phenyl)sulfonyl)piperidine-1-carboxylate (345 mg, 0.842 mmol, 1.00 equiv) was dissolved in 5 mL of anhydrous 4M HCl/dioxane. The reaction mixture stirred at room temperature for 24 hours. The mixture was evaporated to dryness and then triturated from hexanes to yield (E)-4-((2-(3-methoxy-3-oxoprop-1-en-1-yl)phenyl)sulfonyl)piperidin-1-ium chloride as a white powder (290 mg, 100%). $^1$H NMR (400 MHz, DMSO-d$_6$) δ 9.22 (br s, 1H), 8.66 (br s), 8.42 (d, J=16.0 Hz, 1H), 8.06 (d, J=7.8 Hz, 1H), 7.92 (d, J=7.8 Hz, 1H), 7.82 (t, J=7.4 Hz, 1H), 7.72 (t, J=7.4 Hz, 1H), 6.67 (d, J=15.6 Hz, 1H), 3.74 (s, 3H), 3.30 (d, J=12.9 Hz, 2H), 3.56-3.52 (m, 1H), 2.90-2.82 (m, 2H), 1.92-1.89 (m, 2H), 1.84-1.73 (m, 2H), $^{13}$C NMR (100 MHz, DMSO-d$_6$) δ 166.0, 139.7, 134.8, 134.5, 134.3, 131.4, 130.7, 129.5, 122.8, 66.3, 57.7, 54.9, 51.8, 41.5, 21.5; LRMS (ESI, m/z) calculated for C$_{15}$H$_{20}$NO$_4$S [M+H]$^+$ 310.11, found 309.98.

Example 12—Intermediate Int-16: N-(3-(bromomethyl)phenyl)acetamide

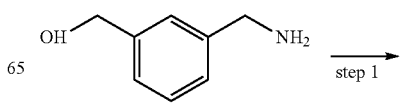

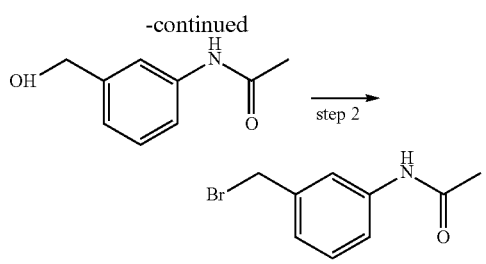

Step-1: Synthesis of N-(3-(hydroxymethyl)phenyl)acetamide

Into a 50-mL 3-necked round-bottom flask, was placed a solution of (3-aminophenyl)methanol (1.88 g, 15.22 mmol, 1.00 equiv) in tetrahydrofuran (10 mL) and triethylamine (7.42 g, 73.36 mmol, 5.00 equiv) This was followed by the addition of acetyl acetate (1.63 g, 15.99 mmol, 1.09 equiv) dropwise with stirring at 0° C. The resulting solution was stirred for 4 h at room temperature. The reaction was then quenched by the addition of 30 mL of water, extracted with 5×50 mL of ethyl acetate, dried over anhydrous magnesium sulfate and concentrated under vacuum to give N-(3-(hydroxymethyl)phenyl)acetamide (2.37 g, crude) as a brown solid. MS: (ES, m/z): 166[M+H]$^+$.

Step-2: Synthesis of N-(3-(bromomethyl)phenyl)acetamide

Into a 100-mL 3-necked round-bottom flask, was placed a solution of N-(3-(hydroxymethyl)phenyl)acetamide ((1.63 g, 9.86 mmol, 1.00 equiv) in dichloromethane (48 mL), triphenylphosphane (3.88 g, 14.79 mmol, 1.50 equiv). This was followed by the addition of a solution of tetrabromomethane (4.92 g, 14.82 mmol, 1.50 equiv) in ACN (16 mL) dropwise with stirring at 0° C. The resulting solution was stirred for 5 h at room temperature. The reaction was concentrated under vacuum. The residue was applied onto a silica gel column with ethyl acetate/petroleum ether (1/1). The collected fraction was concentrated to give N-(3-(bromomethyl)phenyl)acetamide (918.3 mg, 41%) of the title compound as a pink solid.

Example 13—Intermediate Int-17: ethyl (E)-3-(2-amino-5-chlorophenyl)acrylate

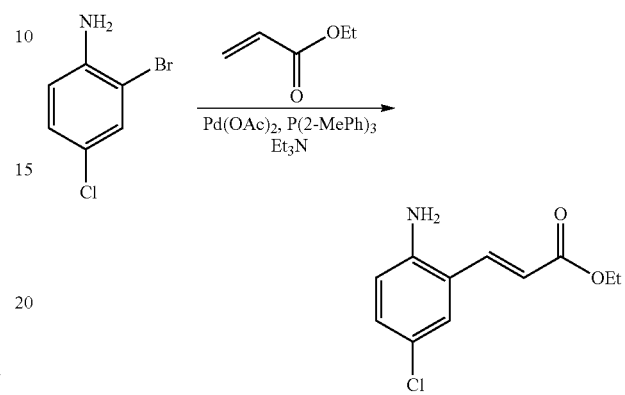

To a sealed tube is added 2-bromo-4-chloroaniline (1 g, 4.84 mmol), CH$_3$CN (15 mL), Et$_3$N (10 mL) and ethyl acrylate (0.58 g, 5.8 mmol) Pd(OAc)$_2$ (87 mg, 0.39 mmol) and tri-o-tolylphosphine (177 mg, 0.58 mml) are added and the mixture is heated at 110° C. overnight. The solvent is removed under reduced pressure and the residue is partitioned between EtOAc (100 mL) and brine (50 mL) The layers are separated and the organic layer is dried and concentrated. The dark brown oil obtained is then purified by Biotage flash column with 6:1 to 4:1 hexane/EtOAc to give 0.49 g (43%) light yellow solid. $^1$H-NMR (CDCl$_3$, 400 MHz) δ (ppm): 7.70 (d, J=20 Hz, 1H), 7.33 (d, J=3.2 Hz, 1H), 7.11 (dd, J=12 Hz, J=32 Hz, 1H), 6.63 (d, J=12 Hz, 1H), 6.33 (d, J=20 Hz, 1H), 4.24 (q, J=10 Hz, 2H), 3.94 (s, br, 2H), 1.32 (t, J=10 Hz, 3H). LCMS RT: 2.24 min, m/z: 226 [M+1]$^+$.

The following intermediates are prepared similarly to Example 13:

TABLE 2

| ID | Structure | Name | $^1$H-NMR (CDCl$_3$, 400 M Hz) δ (ppm): | LC-MS [M + 1]+ |
|---|---|---|---|---|
| Int-18 | 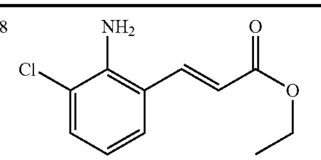 | ethyl (E)-3-(2-amino-3-chlorophenyl)acrylate | 7.77 (d, J = 21 Hz, 1H), 7.25-7.29 (m, 2H), 6.69 (t, J = 10 Hz, 1H), 6.35 (d, J = 21 Hz, 1H), 4.39 (s, br, 2H), 4.26 (q, J = 10 Hz, 2H), 1.33 (t, J = 10 Hz, 3H) | 226 |
| Int-19 | 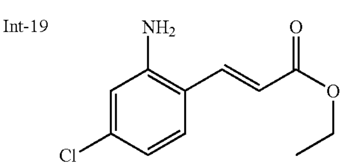 | ethyl (E)-3-(2-amino-4-chlorophenyl)acrylate | 7.71 (d, J = 21 Hz, 1H), 7.25-7.29 (m, 1H), 6.69-6.74 (m, 2H), 6.31 (d, J = 21 Hz, 1H), 4.25 (q, J = 10 Hz, 2H), 4.01 (s, br, 2H), 1.32 (t, J = 10 Hz, 3H) | 226 |
| Int-20 | 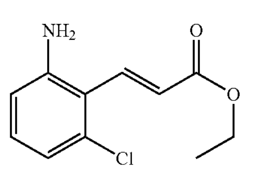 | ethyl (E)-3-(2-amino-6-chlorophenyl)acrylate | 7.85 (d, J = 22 Hz, 1H), 7.02 (t, J = 11 Hz, 1H), 6.81 (d, J = 11 Hz, 1H), 6.60 (d, J = 11 Hz, 1H), 6.45 (d, J = 22 Hz, 1H), 4.27 (q, J = 10 Hz, 2H), 4.06 (s, br, 2H), 1.33 (t, J = 10 Hz, 3H) | 226 |

TABLE 2-continued

| ID | Structure | Name | $^1$H-NMR (CDCl$_3$, 400 M Hz) δ (ppm): | LC-MS [M + 1]+ |
|---|---|---|---|---|
| Int-21 | 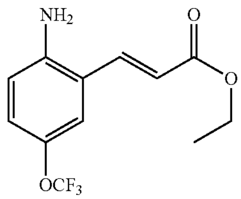 [SMILES: CCOC(=O)/C=C/c1cc(OC(F)(F)F)ccc1N] | ethyl (E)-3-(2-amino-5-(trifluoromethoxy)phenyl)acrylate | 7.72 (d, J = 20 Hz, 1H), 7.22 (s, 1H), 7.02 (d, J = 12 Hz, 1H), 6.67 (d, J = 12 Hz, 1H), 6.34 (d, J = 20 Hz, 1H), 4.26 (q, J = 10 Hz, 2H), 3.98 (s, br, 2H), 1.33 (t, J = 10 Hz, 3H) | 276 |
| Int-22 | 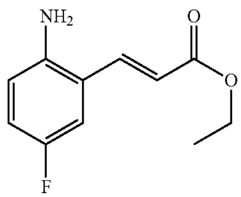 | ethyl (E)-3-(2-amino-5-fluorophenyl)acrylate | 7.74 (d, J = 21 Hz, 1H), 7.07 (m, 1H), 6.86-6.93 (m, 1H), 6.62-6.67 (m, 1H), 6.32 (d, J = 21 Hz, 1H), 4.25 (q, J= 10 Hz, 2H), 3.81 (s, br, 2H), 1.33 (t, J = 10 Hz, 3H) | 210 |
| Int-23 | 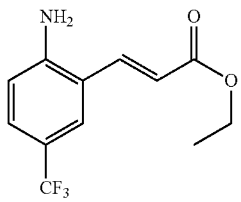 [SMILES: CCOC(=O)/C=C/c1cc(C(F)(F)F)ccc1N] | ethyl (E)-3-(2-amino-5-(trifluoromethyl)phenyl)acrylate | 7.74 (d, J = 21 Hz, 1H), 7.60 (s, 1H), 7.37 (d, J = 12 Hz, 1H), 6.73 (d, J = 12 Hz, 1H), 6.39 (d, J = 21 Hz, 1H), 4.23-4.30 (m, 4H), 1.33 (t, J = 10 Hz, 3H) | 260 |
| Int-24 | 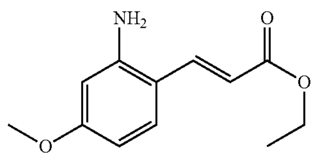 [SMILES: CCOC(=O)/C=C/c1ccc(OC)cc1N] | ethyl (E)-3-(2-amino-4-methoxyphenyl)acrylate | 7.75 (d, J = 21 Hz, 1H), 7.33 (d, J = 11 Hz, 1H), 6.33-6.37 (m, 1H), 6.19-6.25 (m, 2H), 4.24 (q, J = 10 Hz, 2H), 4.00 (s, br, 2H), 3.77 (s, 3H), 1.32 (t, J = 10 Hz, 3H) | 222 |

Example 14—(E)-N-(2-(3-(hydroxyamino)-3-oxo-prop-1-enyl)phenyl)benzamide 2,2,2-trifluoroacetate (I-506)

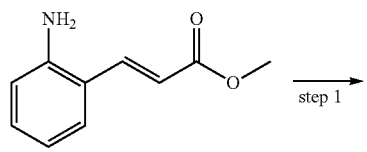

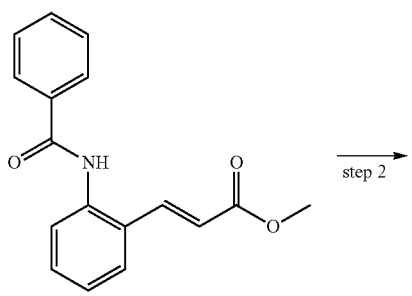

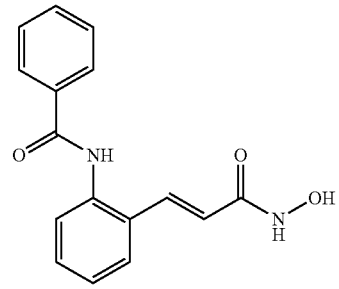

Step-1: Synthesis of (E)-methyl 3-(2-benzamidophenyl)acrylate

Into a 25-mL round-bottom flask, was placed benzoic acid (135 mg, 111 mmol, 1.30 equiv) in dichloromethane (4 mL), HATU (386 mg, 1.02 mmol, 1.20 equiv), DIEA (547 mg, 4.23 mmol, 5.00 equiv) and methyl (2E)-3-(2-aminophenyl)prop-2-enoate (150 mg, 0.85 mmol, 1.00 equiv). The resulting solution was stirred overnight at room temperature. The reaction mixture was then poured into 20 mL of water/ice, extracted with 3×20 mL of dichloromethane, washed with 50 mL of brine, dried over anhydrous sodium sulfate and concentrated under vacuum. The residue was applied onto a silica gel column with ethyl acetate/petroleum ether (1:4). The collected fraction was concentrated under vacuum to give (E)-methyl 3-(2-benzamidophenyl)acrylate (43.2 mg, 18%) as a yellow solid. MS. (ES, m/z): 282[M+H]+.

Step-2: Synthesis of ((E)-N-(2-(3-(hydroxyamino)-3-oxoprop-1-enyl)phenyl)benzamide Into a 10-mL sealed tube, was placed a solution of methyl (2E)-3-(2-benzamidophenyl)prop-2-enoate (74 mg, 0.26 mmol, 1.00 equiv) in THF/MeOH=4/1 (2 mL), NaOH (1 mol/L, 0.527 mL, 2.00 equiv), NH$_2$OH (50% in water, 1.04 g, 60.00 equiv) The resulting solution was stirred for 2 h at room temperature. The pH of the solution was adjusted to 6 with HCl (2 mol/L). The crude product was purified by Prep-HPLC with the following conditions: Column, HSS C18, 2.1*50 mm, 1.8 um; mobile phase, Water with 0.05% trifluoroacetic acid and CH$_3$CN (5% up 95% in 2 min), hold 0.6 min; 0.7 mL/min; Detector, 254, 220 nm. The collected fraction was lyophilized to give (E)-N-(2-(3-(hydroxyamino)-3-oxoprop-1-enyl)phenyl)benzamide (14.1 mg, 14%) as a brown solid. $^1$H-NMR (DMSO, 400 MHz) δ(ppm): 10.74 (s, 1H), 10.25 (s, 1H), 9.09-8.98 (m, 1H), 7.98 (t, J=7.2 Hz, 2H), 7.68-7.50 (m, 1H), 7.48-7.32 (m, 3H), 6.43 (d, J=16 Hz, 1H). MS (ES, m/z): 282[M+H]+.

The following compounds or salts in Table 3 were prepared according to the procedures for the salt (E)-N-(2-(3-(hydroxyamino)-3-oxoprop-1-enyl)phenyl)benzamide 2,2,2-trifluoroacetate. (I-506)

TABLE 3

| Ex. | Structure | Name | $^1$HNMR | (ES, m/z) [M + H]+ |
|---|---|---|---|---|
| 1-41 | 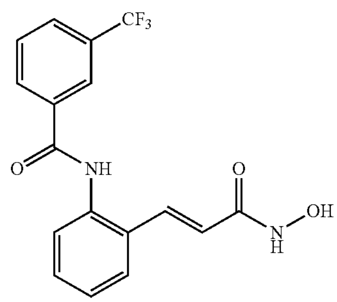 [SMILES: O=C(/C=C/c1ccccc1NC(=O)c1cccc(C(F)(F)F)c1)NO] | (E)-N-(2-(3-(hydroxyamino)-3-oxoprop-1-en-1-yl)phenyl)-3-(trifluoromethyl)benzamide | (DMSO, 400 MHZ, ppm): 10.79 (s, 1H), 10.51 (s, 1H), 8.35 (s, 1H), 8.30 (d, J = 8 Hz, 1H), 8.01 (d, J = 8 Hz, 1H), 7.82 (m, 1H), 7.69 (d, J = 8 Hz, 1H), 7.57 (d, J = 15.6 Hz, 1H), 7.46-7.34 (m, 3H), 6.44 (d, J = 15.6 Hz, 1H) | 351 |
| 1-42 | 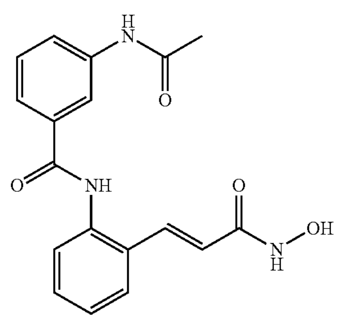 [SMILES: CC(=O)Nc1cccc(C(=O)Nc2ccccc2/C=C/C(=O)NO)c1] | (E)-3-acetamido-N-(2-(3-(hydroxyamino)-3-oxoprop-1-en-1-yl)phenyl)benzamide | (DMSO, 400 MHZ, ppm): 10.76 (s, 1H), 10.24 (s, 1H), 10.15 (s, 1H), 8.11 (s, 1H), 7.86 (d, J = 8 Hz, 1H), 7.68 (m, 2H), 7.57 (d, J = 16 Hz, 1H), 7.49-7.40 (m, 2H), 7.36-7.33 (m, 2H), 6.43 (d, J = 15.6 Hz, 1H), 2.07 (s, 3H). | 340 |
| I-47 | 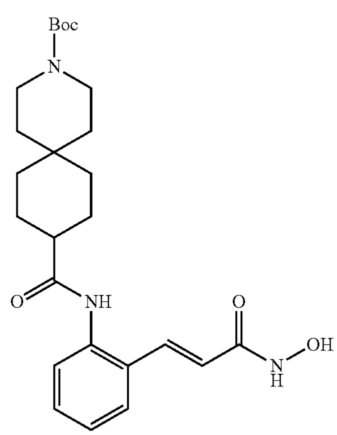 [SMILES: CC(C)(C)OC(=O)N1CCC2(CCC(C(=O)Nc3ccccc3/C=C/C(=O)NO)CC2)CC1] | tert-butyl-(E)-9-((2-(3-(hydroxyamino)-3-oxoprop-1-en-1-yl)phenyl)carbamoyl)-3-azaspiro[5.5]undecane-3-carboxylate | (DMSO, 400 MHZ, ppm): 7.58 (m, 2H), 7.28-7.16 (m, 3H), 6.33 (d, J = 14.4 Hz, 1H), 3.31 (s, 4H), 2.37 (s, 1H), 1.70 (t, J = 22.2 Hz, 6H), 1.48 (s, 2H), 1.36 (3, 9H), 1.25-1.13 (m, 5H), 0.85 (s, 1H) | 458 |

Example 15—(E)-3-cyano-N-(2-(3-(hydroxyamino)-3-oxoprop-1-en-1-yl)phenyl)benzamide (I-44)

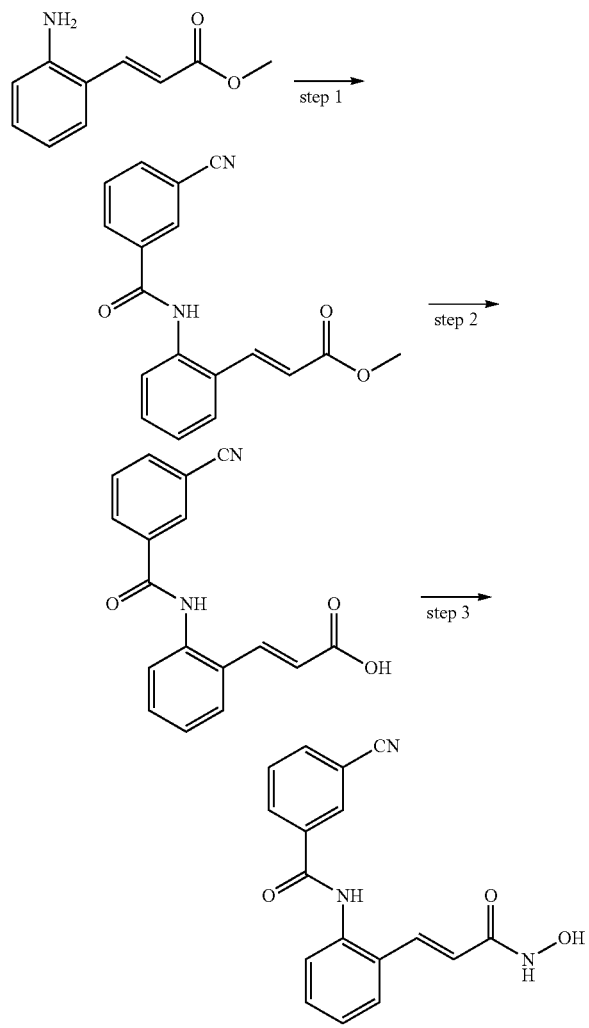

Step-1: Synthesis of (E)-methyl 3-(2-(3-cyanobenzamido)phenyl)acrylate

Into a 25-mL round-bottom flask, was placed 3-cyanobenzoic acid (162 mg, 1.11 mmol, 1.30 equiv), dichloromethane (5 mL), HATU (386 mg, 1.02 mmol, 1.20 equiv), DIEA (547 mg, 4.23 mmol, 5.00 equiv) and methyl (2E)-3-(2-aminophenyl)prop-2-enoate (150 mg, 0.85 mmol, 1.00 equiv). The resulting solution was stirred overnight at room temperature. The reaction mixture was then poured into 30 mL of water/ice, extracted with 3×30 mL of dichloromethane, washed with 50 mL of brine, dried over anhydrous sodium sulfate and concentrated under vacuum to give (E)-methyl 3-(2-(3-cyanobenzamido)phenyl)acrylate (213 mg, crude) as a yellow solid. MS: (ES, m/z): 307[M+H]$^+$.

Step-2 Synthesis of (E)-3-(2-(3-cyanobenzamido)phenyl)acrylic acid

Into a 25-mL round-bottom flask, was placed methyl (2E)-3-[2-[(3-cyanobenzene)amido]phenyl]prop-2-enoate (213 mg, 0.70 mmol, 1.00 equiv), THF (4 mL) and LiOH (145 mg, 5.00 equiv) in 4 mL of water. The resulting solution was stirred overnight at room temperature. The resulting mixture was concentrated under vacuum to remove THF. The residue was diluted with 10 mL of water. The pH value of the solution was adjusted to 5 with HCl (6 mol/L) at 0° C. The resulting solution was extracted with 3×20 mL of dichloromethane, washed with 30 mL of brine, dried over anhydrous sodium sulfate and concentrated under vacuum to give (E)-3-(2-(3-cyanobenzamido)phenyl)acrylic acid (220 mg, crude) as an off-white solid. MS: (ES, m/z): 291 [M−H]$^-$.

Step-3: Synthesis of (E)-3-cyano-N-(2-(3-(hydroxyamino)-3-oxoprop-1-enyl)phenyl)benzamide Into a 10-mL vial, was placed (2E)-3-[2-[(3-cyanobenzene)amido]phenyl]prop-2-enoic acid (100 mg, 0.34 mmol, 1.00 equiv), DMA (3 mL) and NMM (173 mg, 1.71 mmol, 5.00 equiv). This was followed by the addition of IPCF (isopropyl chloroformate) (41.82 mg, 0.34 mmol, 1.00 equiv) dropwise with stirring at 0° C. The mixture was stirred for 2 h at room temperature. To this was added a solution of NH$_2$OH HCl (26 mg, 0.37 mmol, 1.10 equiv) in DMA (1 mL) dropwise with stirring at 0° C. The resulting solution was stirred overnight at room temperature. The crude product was purified by Prep-HPLC with the following conditions: Column, XSelect CSH Prep C18 OBD Column 19*150 mm 5 um 13 nm; mobile phase, water with 0.05% TFA and ACN (28% ACN up to 60% in 9 min), Detector, 254, 220 nm. The collected fraction was lyophilized to give (E)-3-cyano-N-(2-(3-(hydroxyamino)-3-oxoprop-1-enyl)phenyl)benzamide (6.6 mg, 6%) as a pink solid. $^1$H-NMR (DMSO, 400 MHz) δ(ppm): 10.78 (s, 1H), 10.45 (s, 1H), 9.08 (s, 1H), 8.44 (s, 1H), 8.30 (d, J=4 Hz, 1H), 8.11 (d, J=4 Hz, 1H), 7.78 (m, 1H), 7.70 (d, J=4 Hz, 1H), 7.57 (d, J=16 Hz, 1H), 7.44-7.36 (m, 3H), 6.44 (d, J=15.6 Hz, 1H). MS: (ES, m/z): 308[M+H]$^+$.

Example 16—(E)-N-(2-(3-(hydroxyamino)-3-oxoprop-1-enyl)phenyl)-2-phenoxybenzamide (I-71)

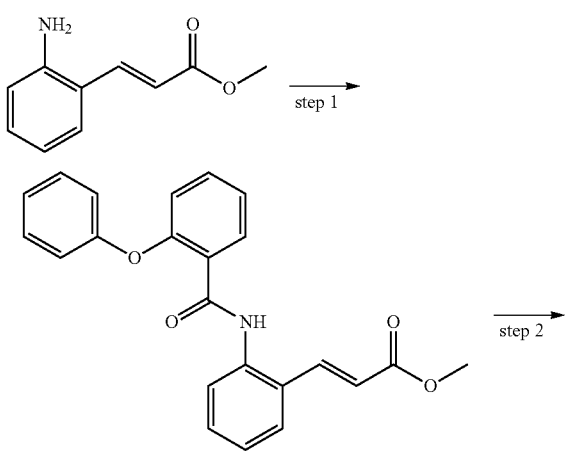

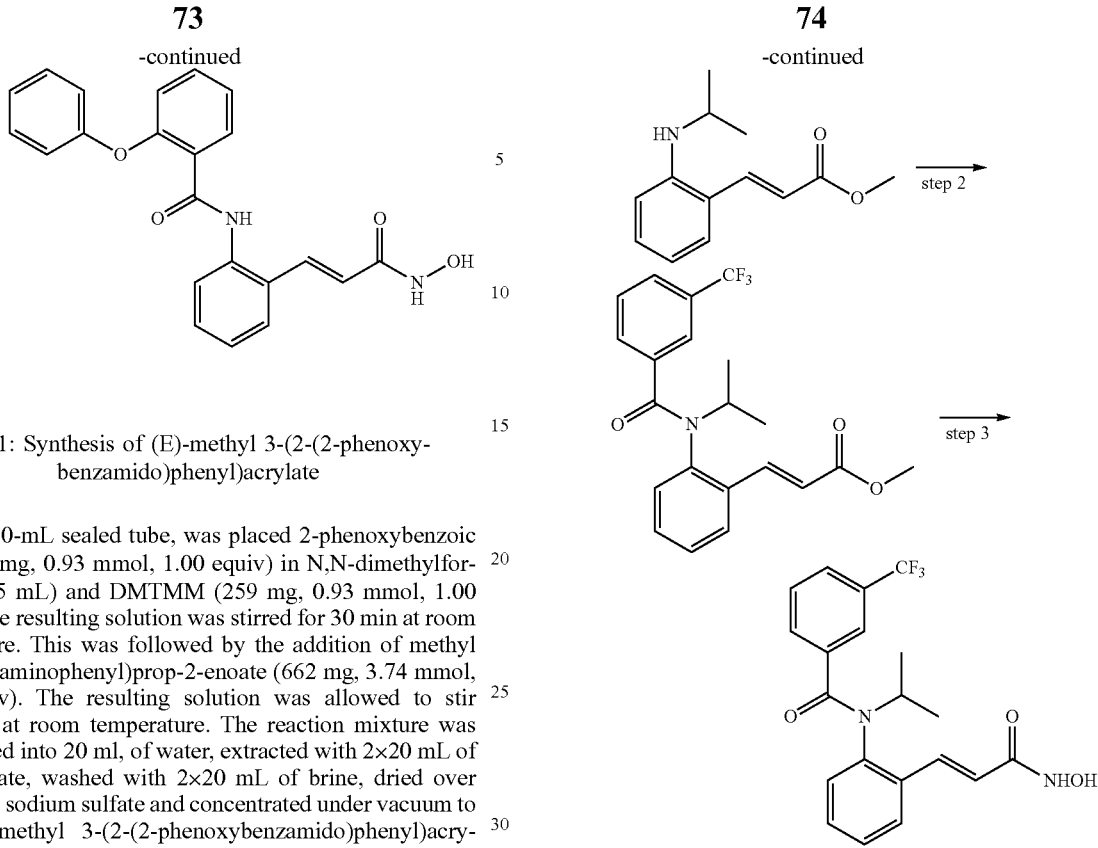

Step-1: Synthesis of (E)-methyl 3-(2-(2-phenoxybenzamido)phenyl)acrylate

Into a 10-mL sealed tube, was placed 2-phenoxybenzoic acid (200 mg, 0.93 mmol, 1.00 equiv) in N,N-dimethylformamide (5 mL) and DMTMM (259 mg, 0.93 mmol, 1.00 equiv). The resulting solution was stirred for 30 min at room temperature. This was followed by the addition of methyl (2E)-3-(2-aminophenyl)prop-2-enoate (662 mg, 3.74 mmol, 4.00 equiv). The resulting solution was allowed to stir overnight at room temperature. The reaction mixture was then poured into 20 ml, of water, extracted with 2×20 mL of ethyl acetate, washed with 2×20 mL of brine, dried over anhydrous sodium sulfate and concentrated under vacuum to give (E)-methyl 3-(2-(2-phenoxybenzamido)phenyl)acrylate (93 mg, 27%) as a solid. MS: (ES, m/z): 374[M+H]⁺.

Step-2: Synthesis of (E)-N-(2-(3-(hydroxyamino)-3-oxoprop-1-enyl)phenyl)-2-phenoxybenzamide Into a 10-mL vial, was placed (E)-methyl 3-(2-(2-phenoxybenzamido)phenyl)acrylate (90 mg, 0.24 mmol, 1.00 equiv), THF/MeOH=4/1 (5 mL), NaOH (1 mol/L, 0.48 mL, 2.00 equiv), NH₂OH (50% in water, 955 mg, 60.00 equiv). The resulting solution was stirred for 2 h at room temperature. The solids were filtered out, the crude product was purified by Prep-HPLC with the following conditions: Column: X Bridge C18, 19*150 mm, 5 urn; Mobile Phase A: Water/0.05% TFA, Mobile Phase B: ACN; Flow rate: 20 mL/min; Gradient: 30% B to 70% B in 10 min; 254 nm. The collected fraction was lyophilized to give (E)-N-(2-(3-(hydroxyamino)-3-oxoprop-1-enyl)phenyl)-2-phenoxybenzamide (61.8 mg, 68%) as a pink solid. ¹H-NMR (DMSO, 400 MI-z) δ(ppm): 10.62 (s, 1H), 10.16 (s, 1H), 9.09 (d, J=5.6 Hz, 1H), 7.75 (m, 2H), 7.61-7.51 (m, 2H), 7.44-7.19 (m, 6H), 7.14-7.00 (m, 4H), 6.40 (d, J=15.61 Hz, 1H). MS: (ES, m/z): 375[M+H]⁺.

Example 17—(E)-N-(2-(3-(hydroxyamino)-3-oxoprop-1-en-1-yl)phenyl)-N-isopropyl-3-(trifluoromethyl)benzamide (I-118)

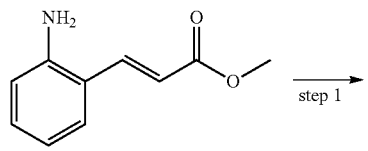

Step-1: Synthesis of (E)-methyl 3-(2-(isopropylamino)phenyl)acrylate

Into a 50-mL round-bottom flask, was placed (E)-methyl 3-(2-aminophenyl)acrylate (150 mg, 0.85 mmol, 1.00 equiv), AcOH (15 mL) and propan-2-one (54 mg, 0.93 mmol, 1.10 equiv) The mixture was stirred for 1 h at room temperature. To this was added NaBH₃CN (160 mg, 2.55 mmol, 3.00 equiv). The resulting solution was stirred overnight at room temperature. The reaction was concentrated under vacuum, diluted with 20 mL of water, extracted with 3×20 mL dichloromethane, washed with 20 mL of brine, dried over anhydrous sodium sulfate and concentrated under vacuum. The residue was applied onto a silica gel column with ethyl acetate/petroleum ether (1:4). The collected fraction was concentrated under vacuum to give (E)-methyl 3-(2-(isopropylamino)phenyl)acrylate (90 mg, 48%) as an off-white solid. MS: (ES, m/z): 220[M+H]⁺.

Step-2: Synthesis of (E)-methyl 3-(2-(N-isopropyl-3-(trifluoromethyl)benzamido)phenyl)acrylate Into a 10-mL sealed tube, was placed a solution of (E)-methyl 3-(2-(isopropylamino)phenyl)acrylate (100 mg, 0.46 mmol, 1.00 equiv) in pyridine (3 mL). This was followed by the addition of 3-(trifluoromethyl)benzoyl chloride (190.8 mg, 0.92 mmol, 2.00 equiv) dropwise at 0° C. The final reaction mixture was heated in the microwave for 30 min at 130° C. The reaction mixture was then cooled to room temperature and poured into 20 mL of water, extracted with 3×20 mL of dichloromethane, washed with 2×20 mL of brine, dried over anhydrous sodium sulfate and concentrated under vacuum. The residue was applied onto a silica gel column with ethyl acetate/petroleum ether (1:2). The collected fraction was concentrated under vacuum to give (E)-methyl 3-(2-(N-isopropyl-3-(trifluoromethyl)benzamido)phenyl)acrylate (55 mg, 30%) as a yellow solid. MS: (ES, m/z): 392[M+H]$^+$.

Step-3: Synthesis or (E)-N-(2-(3-(hydroxyamino)-3-oxoprop-1-enyl)phenyl)-N-isopropyl-3-(trifluoromethyl)benzamide 2,2,2-trifluoroacetate Into a 25-mL round-bottom flask, was placed (E)-methyl 3-(2-(N-isopropyl-3-(trifluoromethyl)benzamido)phenyl) acrylate (55 mg, 0.14 mmol, 1.00 equiv), THF/MeOH=4:1 (5 mL), NH$_2$OH (50% in water, 557 mg, 60.00 equiv), NaOH (1 mol/L, 0.28 mL, 2.00 equiv). The resulting solution was stirred for 2 h at room temperature. The pH of the solution was adjusted to 6 with HCl (6 mol/L) at 0° C. The solids were filtered out, the crude product was purified by Prep-HPLC with the following conditions: Column, HSS C18, 2.1×50 mm, 1.8 um; mobile phase, Water with 0.05% trifluoroacetic acid and CH$_3$CN (5% up 95% in 2 min), hold 0.6 min; 0.7 mL/min; 254 nm. The collected fraction was lyophilized to give (E)-N-(2-(3-(hydroxyamino)-3-oxoprop-1-enyl)phenyl)-N-isopropyl-3-(trifluoromethyl)benzamide 2,2,2-trifluoroacetate (6.8 mg, 10%) as a pink solid. $^1$H-NMR (DMSO, 400 MHz) δ(ppm): 10.88 (s, 1H), 7.60-7.22 (m, 9H), 6.27 (d, J=16 Hz, 1H), 4.86-4.80 (m, 1H), 1.41-1.28 (m, 3H), 1.02-0.94 (m, 3H). MS: (ES, m/z): 393[M+H]$^+$.

The following compounds in Table 4 were prepared according to the procedures for (E)-N-(2-(3-(hydroxyamino)-3-oxoprop-1-en-1-yl)phenyl)-N-isopropyl-3-(trifluoromethyl)benzamide (I-118).

TABLE 4

| Ex. | Structure | Name | $^1$HNMR | (ES, m/z) [M + H]$^+$ |
|---|---|---|---|---|
| I-54 | 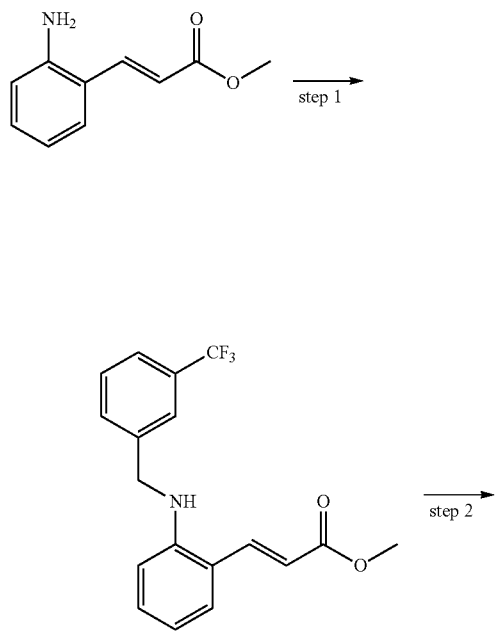 | (E)-N-(2-(3-(hydroxyamino)-3-oxoprop-1-en-1-yl)phenyl)-N-methyl-3-(trifluoromethyl)benzamide | (DMSO, 400 MHz, ppm): 7.58-7.50 (m, 2H), 7.43-7.38 (m, 5H), 7,34-7.25 (m, 2H), 6.32 (d, J = 16 Hz, 1H), 3.32 (s, 3H) | 365 |

Example 18—(E)-N-hydroxy-3-(2-(methyl(3-(trifluoromethyl)benzyl)amino)phenyl)acrylamide (I-119)

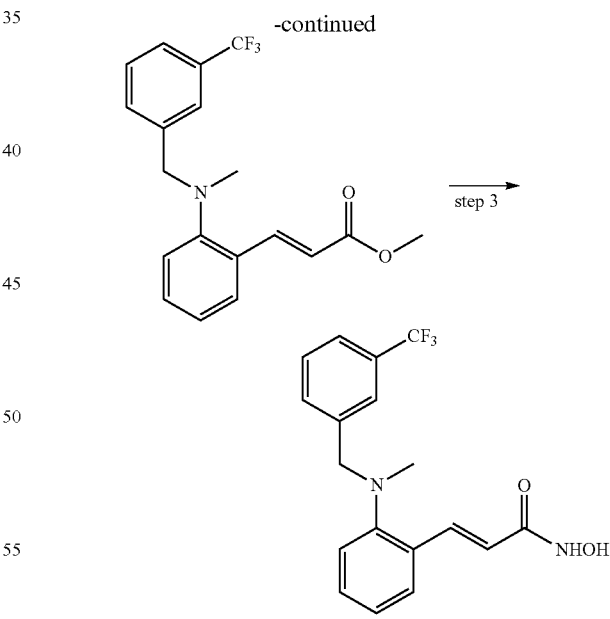

Step-1: Synthesis of (E)-methyl 3-(2-(3-(trifluoromethyl)benzylamino)phenyl)acrylate Into a 100-mL round-bottom flask, was placed (E)-methyl 3-(2-aminophenyl)acrylate (500 mg, 2.82 mmol, 1.00 equiv), N,N-dimethylformamide (25 mL), potassium carbonate (780 mg, 5.64 mmol, 2.00 equiv) and 1-(bromomethyl)-3-(trifluoromethyl)benzene (742 mg, 3.10 mmol, 1.10 equiv). The resulting mixture was stirred overnight at room temperature. The reaction was then quenched by the addition of 20 mL of water, extracted with 3×20 mL of dichloromethane, washed with 3×30 mL of brine, dried over anhydrous sodium sulfate and concentrated under vacuum. The residue was applied onto a silica gel column with ethyl acetate/petroleum ether (1:10). The collected fraction was concentrated under vacuum to give (E)-methyl 3-(2-(3-(trifluoromethyl)benzylamino)phenyl)acrylate (537 mg, 57%) as yellow oil. MS: (ES, m/z): 336[M+H]$^+$.

Step-2: Synthesis of (E)-methyl 3-(2-(methyl(3-(trifluoromethyl)benzyl)amino)phenyl)acrylate Into a 10-mL sealed tube, was placed (E)-methyl 3-(2-(3-(trifluoromethyl)benzylamino)phenyl)acrylate (20 ng, 0.06 mmol, 1.00 equiv), N,N-dimethylformamide (3 mL), potassium carbonate (25 mg, 0.18 mmol, 3.00 equiv) and methyl iodide (10 mg, 0.07 mmol, 1.20 equiv). The resulting solution was stirred overnight at room temperature. The reaction mixture was then poured into 20 mL of water, extracted with 3×20 mL of ethyl acetate, washed with 2×30 mL of brine, dried over anhydrous sodium sulfate and concentrated under vacuum. The residue was applied onto a silica gel column with ethyl acetate/petroleum ether (1:10). The collected fraction was concentrated under vacuum to give (E)-methyl 3-(2-(methyl(3-(trifluoromethyl)benzyl)amino)phenyl)acrylate (18 mg, 86%) as an off-white solid. MS: (ES, m/z): 350[M+H]$^+$.

Step-3: Synthesis of (E)-N-hydroxy-3-(2-(methyl(3-(trifluoromethyl)benzyl)amino)phenyl)acrylamide Into a 25-mL round-bottom flask, was placed (E)-methyl 3-(2-(methyl(3-(trifluoromethyl)benzyl)amino)phenyl)acrylate (42 mg, 0.12 mmol, 1.00 equiv), THF/MeOH=4/1 (3 mL), NH$_2$OH (50% in water, 477 mg, 60.00 equiv), NaOH (1 mol/L, 0.24 mg, 0.01 mmol, 2.00 equiv). The resulting solution was stirred for 3 h at room temperature. The pH of the solution was adjusted to 6 with HCl (6 mol/L) The solids were filtered out, the crude product was purified by Prep-HPLC with the following conditions: Column, HSS C18, 2.1*50 mm, 1.8 um; mobile phase, Water with 0.05% trifluoroacetic acid and CH$_3$CN (5% up 80% in 2 min), hold 0.6 min; 0.7 mL/min, 254 nm. The collected fraction was lyophilized to give (E)-N-hydroxy-3-(2-(methyl(3-(trifluoromethyl)benzyl)amino)phenyl)acrylamide (7 mg, 17%) as a pink solid. $^1$H-NMR (DMSO, 400 MHz) δ(ppm): 10.74 (s, 1H), 7.94 (d, J=15.6 Hz, 1H), 7.61-7.45 (m, 5H), 7.30 (m, 1H), 7.19-7.06 (m, 2H), 6.47 (d, J=7.5 Hz, 1H), 4.18 (s, 2H), 2.72 (s, 3H). MS: (ES, m/z): 351[M+H]$^+$.

The following compounds in Table 5 were prepared according to the procedures for (E)-N-hydroxy-3-(2-(methyl(3-(trifluoromethyl)benzyl)amino)phenyl)acrylamide (I-119).

TABLE 5

| Ex. | Structure | Name | HINMR | (ES, m/z) [M + H]$^+$ |
|---|---|---|---|---|
| I-216 | (structure with CF$_3$, isopropyl N-benzyl, phenyl acrylamide N-OH) | (E)-N-hydroxy-3-(2-(isopropyl(3-(trifluoromethyl)benzylamino)phenyl)acrylamide | (DMSO, 400 MHZ, ppm): 10.73 (br, 1H), 7.97 (d, ) J = 16 Hz, 1H), 7.62-7.59 (m, 2H), 7.44-7.41 (m, 3H), 7.26-7.15 (m, 2H), 6.95 (m,1H), 6.35 (d, J = 16 Hz, 1H), 4.38 (8, 2H), 3.20-3.14 (m, 1H), 1.16 (d, J = 6.4 Hz, 6H). | 379 |

Example 19—(E)-3-(2-(benzylamino)phenyl)-N-hydroxyacrylamide (I-40)

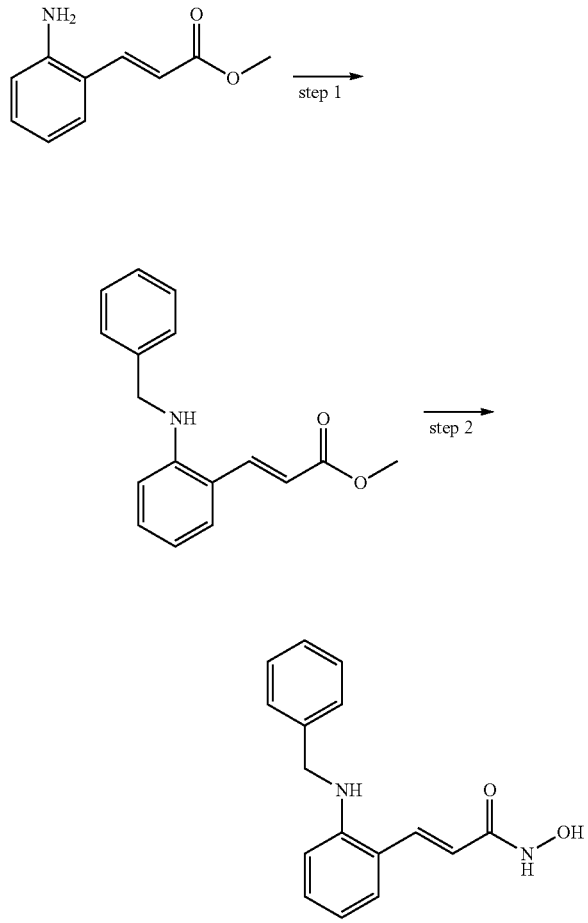

Step-1: Synthesis of (E)-methyl 3-(2-(benzylamino)phenyl)acrylate

Into a 50-mL round-bottom flask, was placed (E)-methyl 3-(2-aminophenyl)acrylate (100 mg, 0.56 mmol, 1.00 equiv), N,N-dimethylformamide (10 mL), (bromomethyl) benzene (96 mg, 0.56 mmol, 0.99 equiv) and potassium carbonate (156 mg, 1.13 mmol, 2.00 equiv). The resulting mixture was stirred overnight at 80° C. The reaction mixture was then poured into 50 mL of water, extracted with 3×50 mL of ethyl acetate, dried over anhydrous sodium sulfate and concentrated under vacuum. The residue was applied onto a silica gel column with ethyl acetate/petroleum ether (1:10-1:1). The collected fraction was concentrated to give (E)-methyl 3-(2-(benzylamino)phenyl)acrylate (60 mg, 40%) as yellow oil. MS: (ES, m/z): 268[M+H]$^+$.

Step-2: Synthesis of (E)-3-(2-(benzylamino)phenyl)-N-hydroxyacrylamide

Into a 100-mL round-bottom flask, was placed a solution of (E)-methyl 3-(2-(benzylamino)phenyl)acrylate (55 mg, 0.21 mmol, 1.00 equiv) in THF/MeOH (2.5 mL), NaOH (1 mol/L, 0.42 mL, 2.00 equiv), NH$_2$OH (50% in water, 1 mL, 60.00 equiv). The resulting solution was stirred for 3 h at room temperature in a water bath. The crude product was purified by Prep-HPLC with the following conditions: Column: XBridge RP C18,19*150 mm, 5 um; Mobile Phase A: Water/0.05% TFA, Mobile Phase B: ACN; Flow rate: 25 mL/min; Gradient: 5% B to 95% B in 2.0 min, hold 0.6 min, 254 nm. The collected fraction was lyophilized to give (E)-3-(2-(benzylamino)phenyl)-N-hydroxyacrylamide (33.1 mg, 42%) as a yellow solid. $^1$H-NMR (DMSO, 400 MHz) δ(ppm): 10.68 (br, 1H), 7.80 (m, 1H), 7.36-7.28 (m, 5H), 7.22-7.19 (m, 1H), 7.06-7.02 (m, 1H), 6.58-6.54 (m, 1H), 6.56-6.54 (m, 1H), 6.31-6.27 (m, 1H), 4.35 (s, 2H). MS: (ES, m/z): 269[M+H]$^+$.

The following compounds in Table 6 were prepared according to the procedures for (E)-3-(2-(benzylamino)phenyl)-N-hydroxyacrylamide (I-40).

TABLE 6

| Ex. | Structure | Name | $^1$HNMR | (ES, m/t) [M + H]$^+$ |
|---|---|---|---|---|
| I-46 | (structure shown) | (E)-N-hydroxy-3-(2-((3-(trifluoromethyl)benzyl) amino)phenyl)acrylamide | (DMSO, 400 MHZ, ppm): 10.71 (s, 1H), 7.63-7.89 (m, 3H), 7.52-7.59 (m, 2H), 7.32 (d, J = 8Hz, 1H), 7.03-7.08 (m, 1H), 6.56-6.61 (m, 1H), 6.45 (d, J = 20 Hz, 1H), 6.32 (d, J = 20 Hz, 1H), 4.45 (s, 2H). | 337 |

TABLE 6-continued

| Ex. | Structure | Name | ¹HNMR | (ES, m/t) [M + H]⁺ |
|---|---|---|---|---|
| I-43 | 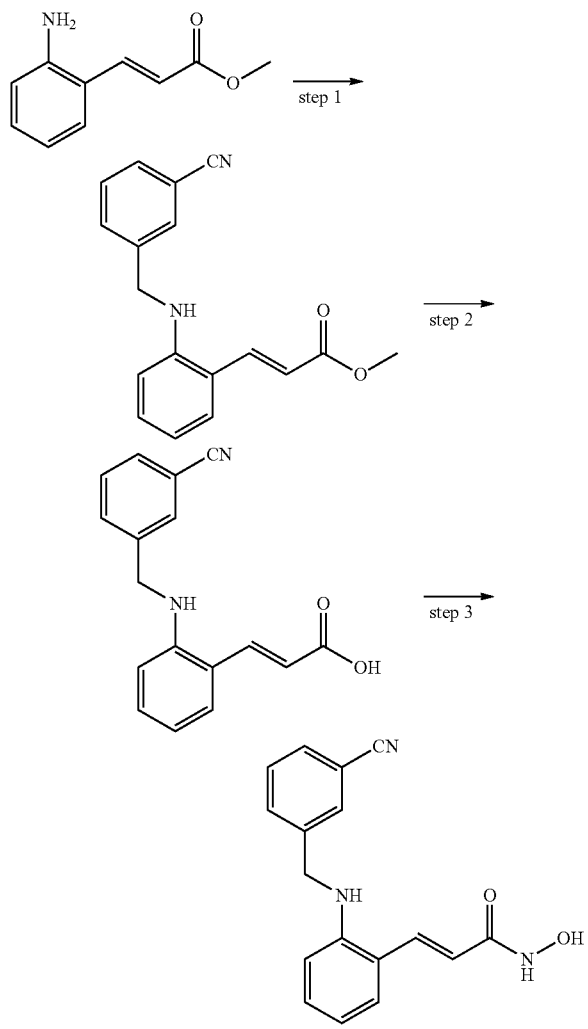 | (E)-3-(2-((3-acetamidobenzyl)amino)phenyl)-N-hydroxyacrylamide | (DMSO, 300 MHZ, ppm): 10.67 (br, 1H), 9.89 (s, 1H), 7.85 (d, J = 9 Hz, 1H), 7,50 (m, 2H), 7.30 (d, J = 7,5 Hz, 1H), 7.22 (m, 1H), 7.08-7.01 (m, 2H), 6.56 (m, 1H), 6.41 (d, J = 8.4 Hz, 1H), 6.32 (m, 1H), 4.35 (s, 2H), 1.99 (s, 3H). | 326 |

Example 20—(E)-3-(2-((3-cyanobenzyl)amino)phenyl)-N-hydroxyacrylamide (I-45)

Step-1: Synthesis of (E)-methyl 3-(2-(3-cyanobenzylamino)phenyl)acrylate

Into a 100-mL round-bottom flask, was placed a solution of (E)-methyl 3-(2-aminophenyl)acrylate (100 mg, 0.56 mmol, 1.00 equiv) in N,N-dimethylformamide (5 mL), 3-(bromomethyl)benzonitrile (132 mg, 0.67 mmol, 1.20 equiv) and potassium carbonate (156 mg, 1.13 mmol, 2.00 equiv). The resulting mixture was stirred overnight at 80° C. in an oil bath. The reaction mixture was cooled to room temperature, diluted with 30 mL of ethyl acetate, washed with 30 mL of water, dried over anhydrous sodium sulfate and concentrated under vacuum. The residue was applied onto a silica gel column with ethyl acetate/petroleum ether (1:3). The collected fraction was concentrated to give (E)-methyl 3-(2-(3-cyanobenzylamino)phenyl)acrylate (120 mg, 73%) as yellow green oil. MS: (ES, m/z): 293[M+H]⁺.

Step-2: Synthesis of (E)-3-(2-(3-cyanobenzylamino)phenyl)acrylic acid

Into a 10-mL vial, was placed a solution of (E)-methyl 3-(2-(3-cyanobenzylamino)phenyl)acrylate (70 mg, 0.24 mmol, 1.00 equiv) in tetrahydrofuran (2 mL) and LiOH (1.12 mL, 1M, 5.00 equiv). The resulting solution was stirred overnight at room temperature and then concentrated under vacuum. The residue was applied onto a C18 column with water/0.05% TFA/ACN (5% B to 60% B). The collected fraction was concentrated to give (E)-3-(2-(3-cyanobenzylamino)phenyl)acrylic acid (43 mg, 65%) as a yellow green solid. MS: (ES, m/z): 279[M+H]⁺.

Step-3: Synthesis of (E)-3-(2-(3-cyanobenzylamino)phenyl)-N-hydroxyacrylamide

Into a 10-mL vial, was placed a solution of (E)-3-(2-(3-cyanobenzylamino)phenyl)acrylic acid (43 mg, 0.15 mmol, 1.00 equiv) in DMA (2.5 mL), NMM (31.2 mg, 0.31 mmol, 5.00 equiv) and IPCF (19 mg, 0.15 mmol, 1.00 equiv). This was followed by the addition of a solution of NH₂OH HCl (11.825 mg, 0.17 mmol, 1.10 equiv) in DMA (0.5 mL) dropwise with stirring at 0° C. The resulting solution was stirred for 4 h at room temperature. The crude product was purified by Prep-HPLC with the following conditions: Column, Waters HSS C18, 2.1*50 mm, 1.8 um; mobile phase, Mobile Phase A: Water/0.05% TFA, Mobile Phase B ACN/0.05% trifluoroacetic acid; Flow rate: 0.7 mL/min; Gradient: 5% B to 95% B in 2.0 min, hold 0.6 min; Detector, 254 nm. The collected fraction was lyophilized to give (E)-3-(2-(3-cyanobenzylamino)phenyl)-N-hydroxyacrylamide (27.3 mg, 43%) as a yellow solid. ¹H-NMR (DMSO, 400 MHz) δ(ppm): 10.69 (br, 1H), 7.72-7.80 (m, 2H), 7.68-7.71 (m, 2H), 7.51-7.55 (m, 1H), 7.32 (d, J=8 Hz 1H), 7.04-7.07 (m, 1H), 6.57-6.61 (m, 1H), 6.44 (d, J=8 Hz, 1H), 6.31 (d, J=16 Hz, 1H), 4.57 (s, 2H). MS: (ES, m/z): 294[M+H]+.

Example 21—(E)-3-(2-((cyclohexylmethyl)amino)phenyl)-N-hydroxyacrylamide (I-55)

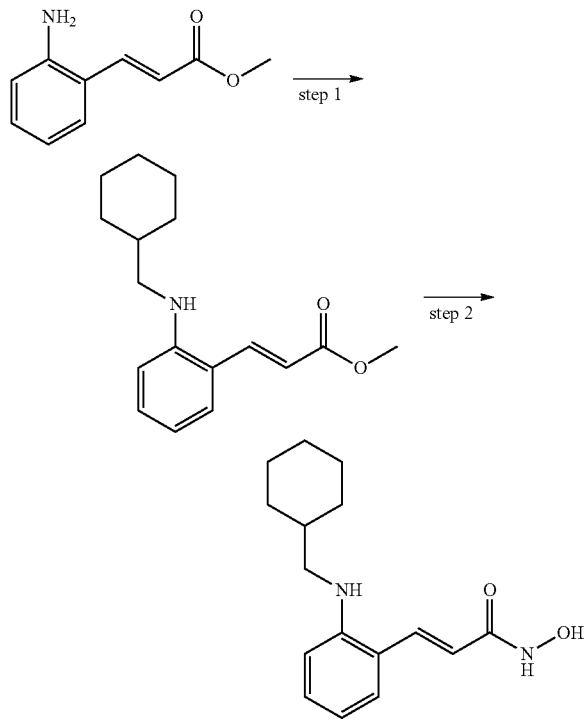 [SMILES: COC(=O)/C=C/c1ccccc1N ; COC(=O)/C=C/c1ccccc1NCC1CCCCC1 ; O=C(/C=C/c1ccccc1NCC1CCCCC1)NO]

Step-1: Synthesis of (E)-methyl 3-(2-(cyclohexylmethylamino)phenyl)acrylate

Into a 25-mL round-bottom flask, was placed (E)-methyl 3-(2-aminophenyl)acrylate (150 mg, 0.85 mmol, 1.00 equiv) and acetic acid (5 mL). This was followed by the addition of cyclohexanecarbaldehyde (95.3 mg, 0.85 mmol, 1.00 equiv). The mixture was stirred for Iii at room temperature. To this was added NaBH₃CN (150 mg, 2.39 mmol, 3.00 equiv), in portions at 0° C. The resulting solution was stirred overnight at room temperature. The reaction mixture was poured into 20 mL of water, the pH of the solution was adjusted to 8 with sodium bicarbonate (sat.). The resulting solution was extracted with 3×50 mL of ethyl acetate, washed with 3×150 mL of brine, and concentrated under vacuum. The residue was applied onto a silica gel column with ethyl acetate/petroleum ether (1:2). The collected fraction was concentrated under vacuum to give (E)-methyl 3-(2-(cyclohexylmethylamino)phenyl)acrylate (107 mg, 46%) as yellow oil. MS: (ES, m/z): 274[M+H]+.

Step-2: Synthesis of (E)-3-(2-(cyclohexylmethylamino)phenyl)-N-hydroxyacrylamide Into a 25-mL round-bottom flask, was placed (E)-methyl 3-(2-(cyclohexylmethylamino)phenyl)acrylate (107 mg, 0.39 mmol, 1.00 equiv), MeOHl/THF=¼ (3 mL), NH₂OH (50% in water, 1.55 g, 60.00 equiv), NaOH (1 mol/L, 0.78 mL, 2.00 equiv). The resulting solution was stirred for 2 h at room temperature. The solids were filtered out. The crude product was purified by Prep-HPLC with the following conditions: Column, sunfire C18 19*150; mobile phase, A: 0.05% TFA. B: ACN 15-60/6 min; Detector, 254 nm. The collected fraction was lyophilized to give (E)-3-(2-(cyclohexylmethylamino)phenyl)-N-hydroxyacrylamide (4.7 mg, 3%) as a yellow solid. ¹H-NMR (DMSO, 400 MHz) δ(ppm): 10.63 (s, 1H), 7.89 (d, J=9.6 Hz, 1H), 7.28 (d, 0.1=7.6 Hz, 1H), 7.16-7.12 (m, 1H), 6.60-6.55 (m, 21H), 6.23 (d, J=15.6 Hz, 1H), 2.92 (d, J=6.8 Hz, 2H), 1.77 (d, J=12.4 Hz, 2H), 1.69-1.58 (m, 4H), 1.23-1.09 (m, 3H), 0.96-0.87 (m, 2H). MS: (ES, m/z): 275[M+H]+.

Example 22—(E)-N-(2-(3-(hydroxyamino)-3-oxoprop-1-en-1-yl)phenyl)cyclohexanecarboxamide (I-56)

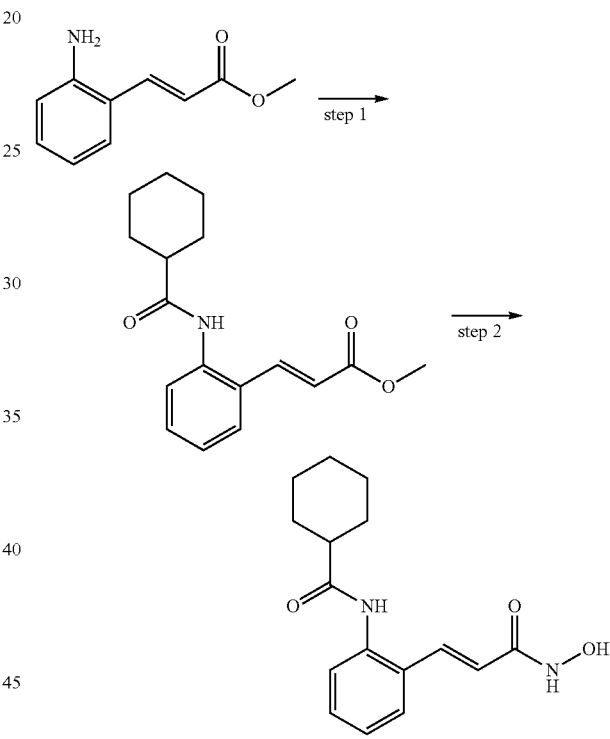

Step-1: Synthesis of (E)-methyl 3-(2-(cyclohexanecarboxamido)phenyl)acrylate

Into a 25-mL round-bottom flask, was placed (E)-methyl 3-(2-aminophenyl)acrylate (150 mg, 0.85 mmol, 1.00 equiv), dichloromethane (5 mL) and triethylamine (255 mg, 2.52 mmol, 3.00 equiv). This was followed by the addition of cyclohexanecarbonyl chloride (123.8 mg, 0.84 mmol, 1.00 equiv) with dropwise at 0° C. The resulting solution was stirred overnight at room temperature. The reaction mixture was then poured into 50 mL of water, extracted with 3×50 mL of ethyl acetate, washed with 1×100 mL of brine, dried over anhydrous sodium sulfate and concentrated under vacuum. The residue was applied onto a silica gel column with ethyl acetate/petroleum ether (1:1). The collected fraction was concentrated under vacuum to give (E)-methyl 3-(2-(cyclohexanecarboxamido)phenyl)acrylate (120 mg, 49%) as a white solid. MS: (ES, m/z): 288[M+H]+.

Step-2: Synthesis of (E)-N-(2-(3-(hydroxyamino)-3-oxoprop-1-enyl)phenyl)cyclohexanecarboxamide Into a 25-mL round-bottom flask, was placed (E)-methyl 3-(2-(cyclohexanecarboxamido)phenyl)acrylate (120 mg, 0.42 mmol, 1.00 equiv), MeOH/THF (¼) (3 mL), NH$_2$OH (50% in water, 1.66 g, 60.00 equiv), NaOH (1 mol/L, 0.84 mL, 2.00 equiv). The resulting solution was stirred for 2 h at room temperature. The solids were filtered out. The crude product was purified by Prep-HPLC with the following conditions: Column, sunfire C18 19*150; mobile phase, A: 0.05% TFA. B: ACN 20-47/8 min; Detector, 254 nm. The collected fraction was lyophilized to give (E)-N-(2-(3-(hydroxyamino)-3-oxoprop-1-enyl)phenyl)cyclohexanecarboxamide (64.1 mg, 38%) as a white solid. $^1$H-NMR (DMSO, 400 MHz) δ(ppm): 10.75 (s, 1H), 9.60 (s, 1H), 9.02 (s, 1H), 7.61-7.57 (m, 2H), 7.36-7.31 (m, 2H), 7.24-7.20 (m, 1H), 6.36 (d, J=16 Hz, 1H), 2.41-2.38 (m, 1H), 1.85-1.64 (m, 5H), 1.47-1.27 (m, 5H). MS: (ES, m/z): 289[M+H]$^+$.

Example 23—(E)-3-(3-amino-3-oxopropyl)-N-(2-(3-(hydroxyamino)-3-oxoprop-1-en-1-yl)phenyl)benzamide (I-107)

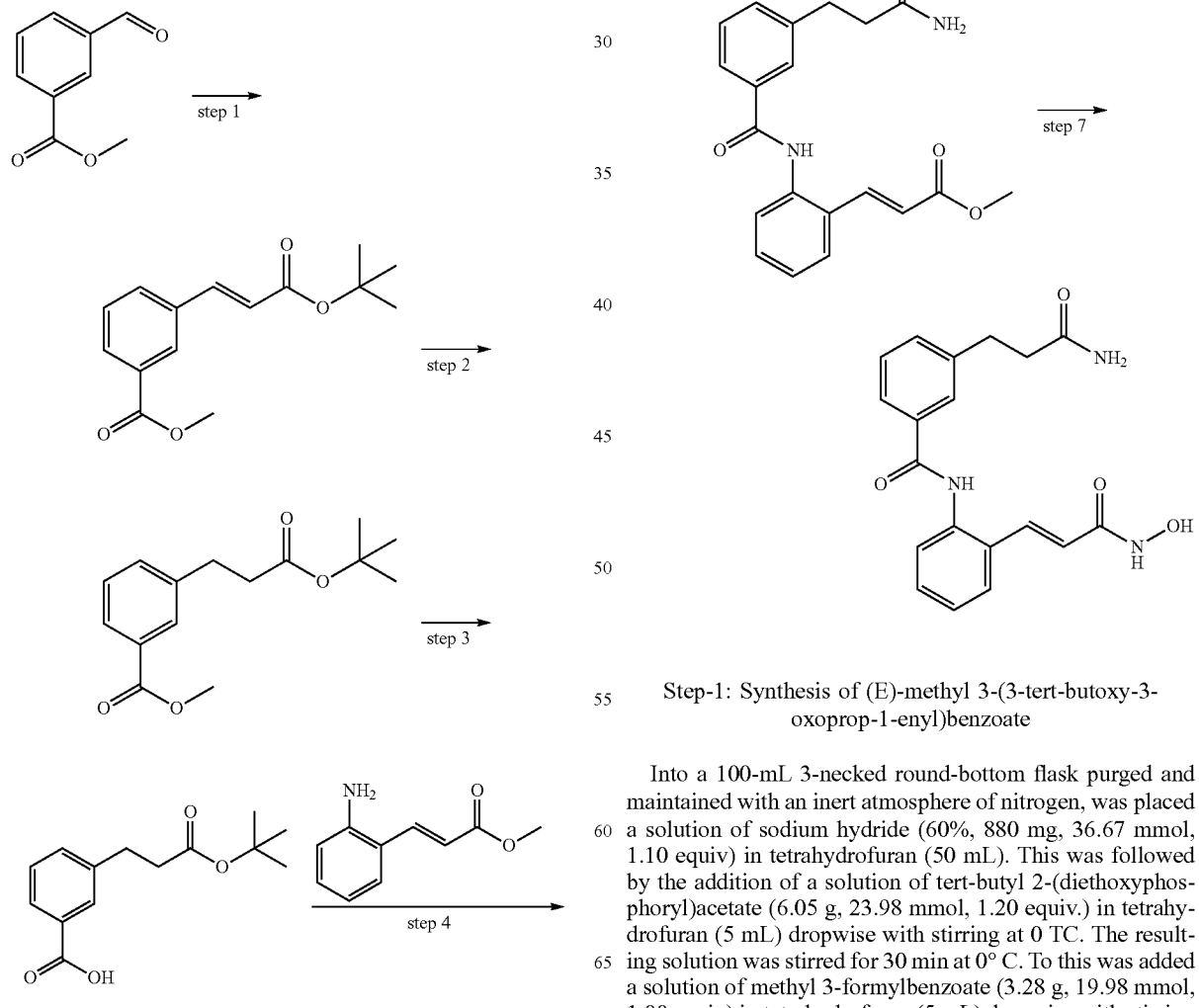

Step-1: Synthesis of (E)-methyl 3-(3-tert-butoxy-3-oxoprop-1-enyl)benzoate

Into a 100-mL 3-necked round-bottom flask purged and maintained with an inert atmosphere of nitrogen, was placed a solution of sodium hydride (60%, 880 mg, 36.67 mmol, 1.10 equiv) in tetrahydrofuran (50 mL). This was followed by the addition of a solution of tert-butyl 2-(diethoxyphosphoryl)acetate (6.05 g, 23.98 mmol, 1.20 equiv.) in tetrahydrofuran (5 mL) dropwise with stirring at 0 TC. The resulting solution was stirred for 30 min at 0° C. To this was added a solution of methyl 3-formylbenzoate (3.28 g, 19.98 mmol, 1.00 equiv) in tetrahydrofuran (5 mL) dropwise with stirring at 0° C. The resulting solution was allowed to react for an additional overnight at room temperature. The reaction mixture was then poured into 200 mL of water, extracted with 2×200 mL of ethyl acetate, washed with 1×500 mL of brine, dried over anhydrous sodium sulfate and concentrated under vacuum. The residue was applied onto a silica gel column with ethyl acetate/petroleum ether (1.10). The collected fraction was concentrated under vacuum to give (E)-methyl 3-(3-tert-butoxy-3-oxoprop-1-enyl)benzoate (4.2 g, 80%) as colorless oil. MS: (ES, m/z): 263[M+H]+.

Step-2: Synthesis of methyl 3-(3-tert-butoxy-3-oxopropyl)benzoate

Into a 100-mL round-bottom flask, was placed a solution of (E)-methyl 3-(3-tert-butoxy-3-oxoprop-1-enyl)benzoate (4.2 g, 16.01 mmol, 1.00 equiv) in methanol (50 mL), Palladium carbon (10%, 1 g). To the above a hydrogen atmosphere was introduced. The resulting solution was stirred overnight at room temperature. The solids were filtered out. The filtrate was concentrated under vacuum to give methyl 3-(3-tert-butoxy-3-oxopropyl)benzoate (3.7 g, crude) as colorless oil which can be used to the next step without any purification. GCMS: (EI, m/z): 264[M].

Step-3: Synthesis of 3-(3-tert-butoxy-3-oxopropyl)benzoic acid

Into a 50-mL round-bottom flask, was placed methyl 3-(3-tert-butoxy-3-oxopropyl)benzoate (2 g, 7.57 mmol, 1.00 equiv) in tetrahydrofuran (20 mL) and a solution of LiOH (900 mg, 37.58 mmol, 5.00 equiv) in 20 ml of water. The resulting solution was stirred overnight at room temperature. The reaction was concentrated under vacuum to remove tetrahydrofuran. The pH of the solution was adjusted to 5 with HCl (6 mmol/L) at 0° C. The resulting solution was extracted with 3×20 mL of dichloromethane, washed with 20 mL of brine, dried over anhydrous sodium sulfate and concentrated under vacuum to give 3-(3-tert-butoxy-3-oxopropyl)benzoic acid (600 mg, 32%) as an off-white solid. MS: (ES, m/z): 249[M−H]−.

Step-4: Synthesis of (E)-methyl 3-(2-(3-(3-tert-butoxy-3-oxopropyl)benzamido)phenyl)acrylate Into a 25-mL round-bottom flask, was placed 3-(3-tert-butoxy-3-oxopropyl)benzoic acid (650 mg, 2.60 mmol, 1.00 equiv), dichloromethane (14 mL), HATU (1185 mg, 976.21 mmol, 1.20 equiv) and DIEA (1342 mg, 10.38 mmol, 4.00 equiv). The resulting solution was stirred for 5 min at room temperature. Then (E)-methyl 3-(2-aminophenyl)acrylate (553 mg, 3.12 mmol, 1.20 equiv) was added. The resulting solution was stirred overnight at room temperature. The reaction mixture was then poured into 20 mL of water, extracted with 3×20 mL of ethyl acetate, washed with 20 mL of brine, dried over anhydrous sodium sulfate and concentrated under vacuum to give (E)-methyl 3-(2-(3-(3-tert-butoxy-3-oxopropyl)benzamido)phenyl)acrylate (510 mg, 48%) as yellow oil. MS: (ES, m/z): 410[M+H]+.

Step-5: Synthesis of (E)-3-(3-(2-(3-methoxy-3-oxoprop-1-enyl)phenylcarbamoyl)phenyl)propanoic acid Into a 10-mL sealed tube, was placed (E)-methyl 3-(2-(3-(3-tert-butoxy-3-oxopropyl)benzamido)phenyl)acrylate (550 mg, 1.34 mmol, 1.00 equiv), dichloromethane (5 mL) and trifluoroacetic acid (1 mL). The resulting solution was stirred for 3 h at room temperature. The reaction was then concentrated under vacuum, and diluted by the addition of 15 mL of water. The resulting solution was extracted with 3×30 mL of ethyl acetate, washed with 30 mL of brine, dried over anhydrous sodium sulfate and concentrated under vacuum to give (E)-3-(3-(2-(3-methoxy-3-oxoprop-1-enyl)phenylcarbamoyl)phenyl)propanoic acid (440 mg, 93%) as yellow oil. MS: (ES, m/z): 354[M+H]+.

Step 6: Synthesis of (E)-methyl 3-(2-(3-(3-amino-3-oxopropyl)benzamido)phenyl)acrylate Into a 50-mL 3-necked round-bottom flask purged and maintained with an inert atmosphere of nitrogen, was placed (E)-3-(3-(2-(3-methoxy-3-oxoprop-1-enyl)phenylcarbamoyl)phenyl)propanoic acid (420 mg, 1.19 mmol, 1.00 equiv), dichloromethane (15 mL), and 1 drop of N,N-dimethylformamide. To the above thionyl chloride (453 mg, 3.00 equiv) was added at 0° C. The resulting solution was stirred for 4 h at room temperature and then concentrated under vacuum. The residue was dissolved in 5 mL of THF to give solution A. Into a another 50-mL 3-necked round-bottom was placed NH3OH·H2O (10 mL) and tetrahydrofuran (10 mL), this was followed by the addition of solution A with dropwise at 0° C. The resulting solution was stirred for 1 h at 0° C. The reaction was then quenched by the addition of 20 mL of water, extracted with 3×20 mL of ethyl acetate, washed with 1×30 mL of brine, dried over anhydrous sodium sulfate and concentrated under vacuum. The residue was applied onto a silica gel column with ethyl acetate/petroleum ether (2:1). The collected fraction was concentrated under vacuum to give (E)-methyl 3-(2-(3-(3-amino-3-oxopropyl)benzamido) phenyl)acrylate (330 mg, 79%) as a white solid. MS: (ES, m/z): 353[M+H]+.

Step-7: Synthesis of (E)-3-(3-amino-3-oxopropyl)-N-(2-(3-(hydroxyamino)-3-oxoprop-1-enyl)phenyl)benzamide Into a 10-mL sealed tube, was placed (E)-methyl 3-(2-(3-(3-amino-3-oxopropyl)benzamido)phenyl)acrylate (120 mg, 0.34 mmol, 1.00 equiv), THF/MeOH (4/1) (3 mL), NH2OH (50% in water, 1.1 g, 50.00 equiv), NaOH (1 mol/L, 0.68 mL, 2.00 equiv). The resulting solution was stirred for 4 h at room temperature. The solids were filtered out. The crude product was purified by Prep-HPLC with the following conditions: Column, XBridge Shield RP18 OBD Column, 5 um, 19*150 mm; mobile phase, Water with 0.05% TFA and ACN (2% ACN up to 14% in 9 min, hold 14% in 7 min); Detector, 220/254 nm. The collected fraction was lyophilized to give (E)-3-(3-amino-3-oxopropyl)-N-(2-(3-(hydroxyamino)-3-oxoprop-1-enyl)phenyl)benzamide (15.2 mg, 13%) as a light pink solid. $^1$H-NMR (DMSO, 400 MHz) δ(ppm) 10.78 (s, 1H), 10.21 (s, 1H), 9.03 (s, 1H), 7.85 (d, J=11.1 Hz, 2H), 7.70-7.58 (m, 2H), 7.48-7.35 (m, 6H), 6.80 (s, 1H), 6.44 (d, J=15.6 Hz, 1H), 2.94-2.89 (m, 2H), 2.43 (d, J=7.5 Hz, 2H) MS. (ES, m/z): 354[M+H]+.

Example 24—(E)-3-(2-(5,6-dichloroisoindolin-2-yl)phenyl)-N-hydroxyacrylamide (I-290)

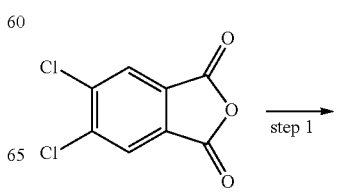

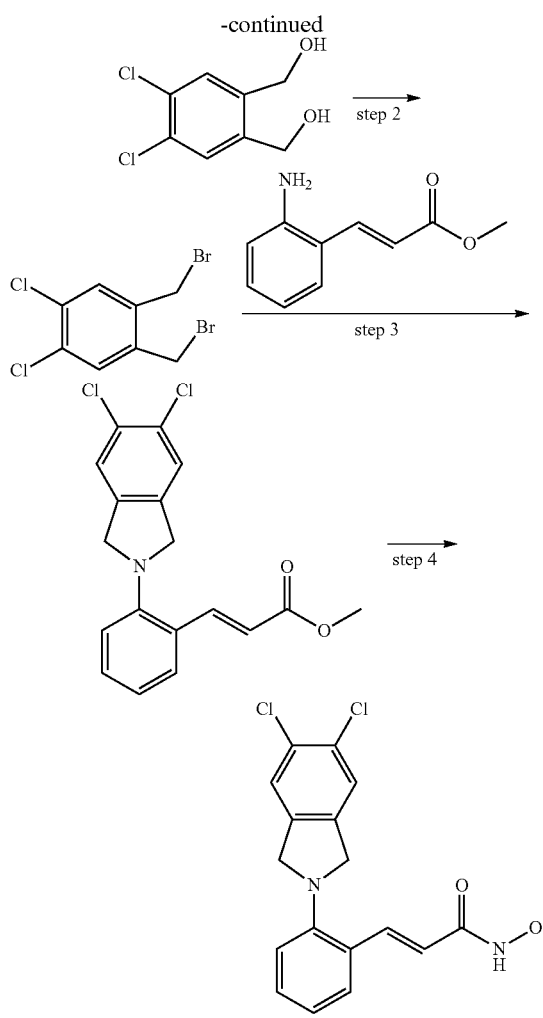

Step-1: Synthesis of (4,5-dichloro-1,2-phenylene)dimethanol

Into a 100-mL round-bottom flask, was placed a solution of 5,6-dichloroisobenzofuran-1,3-dione (0 g, 4.61 mmol, 1.00 equiv) in tetrahydrofuran (40 mL). This was followed by the addition of alumane lithium (440 mg, 12.97 mmol, 2.50 equiv) batchwise at 0° C. The resulting solution was stirred for 2 h at 60° C. The resulting solution was quenched by 40 mL of water at 0° C. The solids were filtered out. The filtrate was extracted with 3×50 mL of ethyl acetate, dried over anhydrous sodium sulfate and concentrated under vacuum. The residue was applied onto a silica gel column with ethyl acetate/petroleum ether (1:1). The collected fraction was concentrated under vacuum to give (4,5-dichloro-1,2-phenylene)dimethanol (500 mg, 52%) of the title compound as a white solid. $^1$H-NMR (DMSO 300 MHz, ppm): δ 7.57 (s, 2H), 4.48 (s, 4H).

Step-2: Synthesis of 1,2-bis(bromomethyl)-4,5-dichlorobenzene

Into a 100-mL round-bottom flask, was placed a solution of (4,5-dichloro-1,2-phenylene)dimethanol (500 mg, 2.41 mmol, 1.00 equiv) in dichloromethane (50 mL) and tribromophosphane (1.30 g, 4.80 mmol, 2.00 equiv). The resulting solution was stirred overnight at room temperature. The mixture was poured into 50 mL of water/ice. The resulting solution was extracted with 3×100 mL of ethyl acetate, dried over anhydrous sodium sulfate and concentrated under vacuum. The residue was applied onto a silica gel column with ethyl acetate/petroleum ether (1:100). The collected fraction was concentrated under vacuum to give 1,2-bis(bromomethyl)-4,5-dichlorobenzene (400 mg, 50%) as off-white oil. $^1$H-NMR (CDCl$_3$, 400 MHz, ppm): δ 7.48 (s, 2H), 4.57 (s, 4H).

Step-3: Synthesis of (E)-methyl 3-(2-(5,6-dichloroisoindolin-2-yl)phenyl)acrylate Into a 10-mL vial, was placed a solution of 1,2-bis(bromomethyl)-4,5-dichlorobenzene (186 mg, 0.56 mmol, 1.00 equiv) in N,N-dimethylformamide (3 mL), (E)-methyl 3-(2-aminophenyl)acrylate (100 mg, 0.56 mmol, 1.00 equiv) and potassium potassium (232 mg, 1.67 mmol, 3.00 equiv). The resulting mixture was stirred for 4 h at room temperature. The resulting solution was diluted with 15 mL of water, extracted with 3×15 mL of ethyl acetate, dried over anhydrous sodium sulfate and concentrated under vacuum. The residue was applied onto a silica gel column with ethyl acetate/petroleum ether (1:10). The collected fraction was concentrated under vacuum to give (E)-methyl 3-(2-(5,6-dichloroisoindolin-2-yl)phenyl)acrylate (60 mg, 31%) as yellow oil. MS. (ES, m/z): 348 [M+H]$^+$.

Step-4: Synthesis of (E)-3-(2-(5,6-dichloroisoindolin-2-yl)phenyl)-N-hydroxyacrylamide Into a 10-mL vial, was placed a solution of (E)-methyl 3-(2-(5,6-dichloroisoindolin-2-yl)phenyl)acrylate (60 mg, 0.17 mmol, 1.00 equiv) in THF/MeOH (4:1) (3 mL), NH$_2$OH (50% in water, 342 mg, 10.35 mmol, 60.00 equiv) and NaOH (1 mol/L, 0.34 mL, 0.34 mmol, 2.00 equiv). The resulting solution was stirred for 2 h at room temperature. The solids were filtered out. The filtrate was purified by Prep-HPLC with the following conditions: Column, Xbridge RP18 5 um, 19*150 mm; mobile phase, water (0.05% TFA) and MeCN (10% CH$_3$CN up to 85% in 7 min); Detector, UV 220/254 nm. The collected fraction was lyophilized to give (E)-3-(2-(5,6-dichloroisoindolin-2-yl)phenyl)-N-hydroxyacrylamide (37.1 mg, 46%) as a yellow solid. $^1$H-NMR (DMSO, 300 MHz) δ (ppm): 10.76 (s, 1H), 767 (s, 311), 7.43 (d, J=7.5 Hz, 1H), 7.35-7.30 (m, 1H), 7.18 (d, J=8.1 Hz, 1H), 6.99-6.88 (m, 1H), 6.33 (d, J=15.6 Hz, 1H), 4.49 (s, 411). MS: (ES, m/z): 349 [M+H]$^+$.

Example 25—(E)-3-(2-((3-(3-amino-3-oxopropyl)benzyl)amino)phenyl)-N-hydroxyacrylamide (I-53)

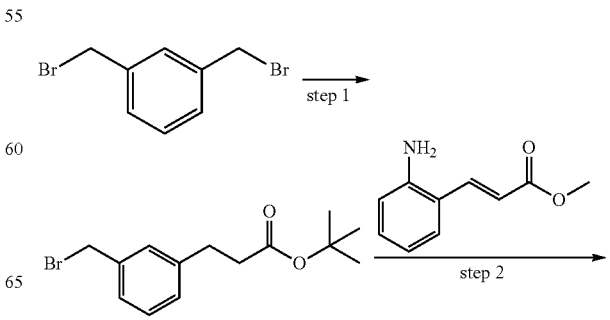

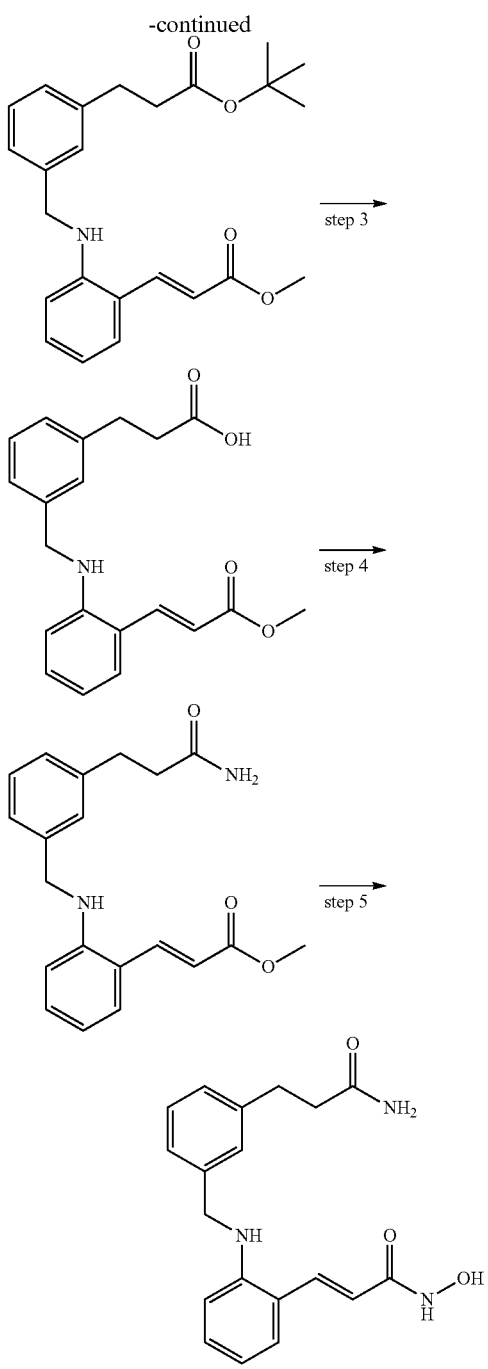

21.97 mmol, 1.00 equiv) and 2-[bis(propan-2-yl)phosphoryl]propane (710 mg, 4.03 mmol, 0.18 equiv) in tetrahydrofuran (20 mL) dropwise with stirring at −78° C. The resulting solution was stirred for 30 min at the same temperature and for an additional 3 h at room temperature. The reaction was then quenched by the addition of 50 mL of water, extracted with 3×50 mL of ethyl acetate, dried over anhydrous sodium sulfate and concentrated under vacuum. The residue was applied onto a silica gel column with ethyl acetate/petroleum ether (1:10-1:1). The collected fraction was concentrated to give tert-butyl 3-(3-(bromomethyl)phenyl)propanoate (3 g, 46%) as colorless oil.

Step-2: Synthesis of (E)-methyl 3-(2-(3-(3-tert-butoxy-3-oxopropyl)benzylamino)phenyl)acrylate Into a 100-mL round-bottom flask, was placed (E)-methyl 3-(2-aminophenyl)acrylate (350 mg, 1.98 mmol, 1.18 equiv), N,N-dimethylformamide (7 mL), potassium carbonate (480 mg, 3.47 mmol, 2.08 equiv) and tert-butyl 3-(3-(bromomethyl)phenyl)propanoate (500 mg, 1.67 mmol, 1.00 equiv). The resulting mixture was stirred overnight at 40° C. The reaction was then quenched by the addition of 30 mL of water, extracted with 3×100 mL of ethyl acetate, washed with 2×100 mL of water, dried over anhydrous sodium sulfate and concentrated under vacuum. The residue was applied onto a silica gel column with ethyl acetate/petroleum ether (1:5). The collected fraction was concentrated to give (E)-methyl 3-(2-(3-(3-tert-butoxy-3-oxopropyl)benzylamino)phenyl)acrylate (0.4 g, 61%) as yellow oil. MS: (ES, m/z): 396 [M+H]$^+$.

Step-3: Synthesis of (E)-3-(3-((2-(3-methoxy-3-oxoprop-1-enyl)phenylamino)methyl)phenyl)propanoic acid Into a 100-mL round-bottom flask, was placed (E)-methyl 3-(2-(3-(3-tert-butoxy-3-oxopropyl)benzylamino)phenyl) acrylate (500 mg, 1.26 mmol, 1.00 equiv), dichloromethane (8 mL) and trifluoroacetic acid (8 mL). The resulting solution was stirred for 3 h at room temperature and then concentrated under vacuum. The residue was applied onto a silica gel column with ethyl acetate/petroleum ether (1:3) The collected fraction was concentrated to give (E)-3-(3-((2-(3-methoxy-3-oxoprop-1-enyl)phenylamino)methyl) phenyl)propanoic acid (260 mg, 61%) as yellow oil MS: (ES, m/z): 340 [M+H]$^+$.

Step-4: Synthesis of (E)-methyl 3-(2-(3-(3-amino-3-oxopropyl)benzylamino)phenyl)acrylate Into a 100-mL round-bottom flask, was placed (E)-3-(3-((2-(3-methoxy-3-oxoprop-1-enyl)phenylamino)methyl) phenyl)propanoic acid (230 mg, 0.68 mmol, 1.00 equiv), methanol (18 mL), NH$_4$Cl (63 mg, 1.18 mmol, 1.74 equiv), triethylamine (50 mg, 0.49 mmol, 0.73 equiv) and DMTMM (240 mg, 0.87 mmol, 1.28 equiv). The resulting solution was stirred for 4 h at room temperature. The resulting mixture was concentrated under vacuum and diluted in 50 mL of water. The resulting solution was extracted with 3×50 mL of dichloromethane, dried over anhydrous sodium sulfate and concentrated. The residue was applied onto a silica gel column with ethyl acetate/petroleum ether (1:1). The collected fraction was concentrated to give (E)-methyl 3-(2-(3-(3-amino-3-oxopropyl)benzylamino)phenyl)acrylate (180 mg, 78%) as yellow oil. MS. (ES, m/z): 339[M+H]$^+$.

Step-1: Synthesis of tert-butyl 3-(3-(bromomethyl)phenyl)propanoate

Into a 250-mL round-bottom flask purged and maintained with an inert atmosphere of nitrogen, was placed bis(propan-2-yl)amine (2.02 g, 19.96 mmol, 0.91 equiv) in tetrahydrofuran (50 mL). This was followed by the addition of n-BuLi (8 mL, 20 mmol, 2.5M) dropwise with stirring at −78° C. The resulting solution was stirred for 30 min at −78° C. To this was added tert-butyl acetate (2.32 g, 19.97 mmol, 0.91 equiv) dropwise with stirring at −78° C. The resulting solution was stirred for 10 min at −78° C. To the mixture was added a solution of 1,3-bis(bromomethyl)benzene (5.8 g, Step-5: Synthesis of (E)-3-(2-((3-(3-amino-3-oxo-propyl)benzyl)amino)phenyl)-N-hydroxyacrylamide Into a 10-mL vial, was placed (E)-methyl 3-(2-(3-(3-amino-3-oxopropyl)benzylamino)phenyl)acrylate (100 mg, 0.30 mmol, 1.00 equiv) in THF/MeOH (4/1) (2.5 mL), NH₂OH (50% in water, 520 mg, 15.74 mmol, 53.28 equiv), NaOH (1 mol/L, 0.6 mL, 0.6 mmoL, 2.00 equiv). The resulting solution was stirred for 2 h at room temperature. The crude product was purified by Prep-HPLC with the following conditions: Column: Waters HSS C18, 2.1*50 mm, 1.8 um; Mobile Phase A: Water/0.05% TFA, Mobile Phase B: ACN/0.05% TFA B: ACN; Flow rate: 0.7 mL/min; Gradient: 5% B to 95% B in 2.0 min, hold 0.6 min; 254 nm. The collected fraction was lyophilized to give (E)-3-(2-((3-(3-amino-3-oxopropyl)benzyl)amino)phenyl)-N-hydroxyacrylamide (42.5 mg, 42%) as a yellow solid. ¹H-NMR (DMSO, 400 MHz) δ (ppm): 10.67 (br, 1H), 7.77 (d, 1H, J=11.6 Hz), 7.38-7.03 (m, 7H), 6.76-6.27 (m, 4H), 4.30 (s, 2H), 2.79-2.75 (m, 2H), 2.35-2.30 (m, 2H). MS: (ES, m/z): 340 [M+H]⁺.

Example 26—(E)-3-(2-(3-(hydroxyamino)-3-oxo-prop-1-en-1-yl)phenyl)-3-azaspiro[5.5]undecane-9-carboxamide (I-108)

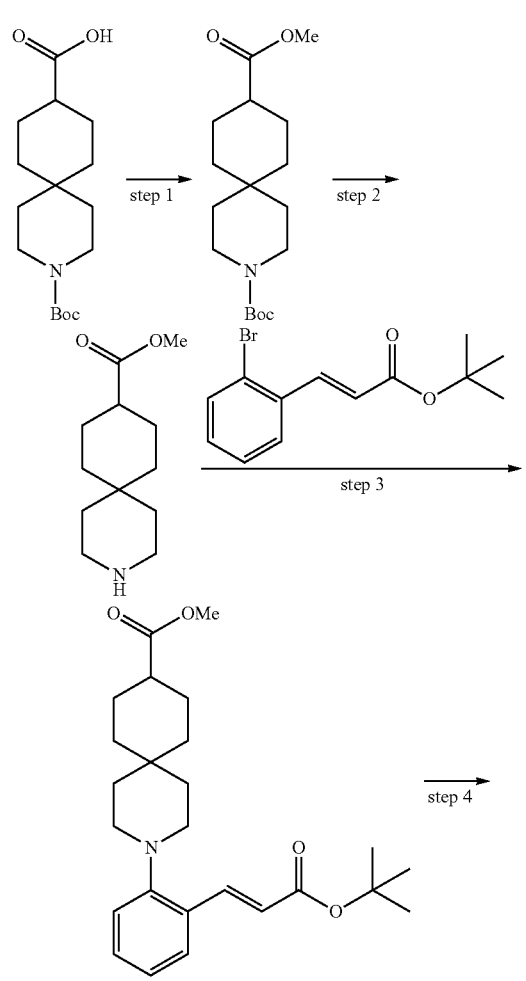

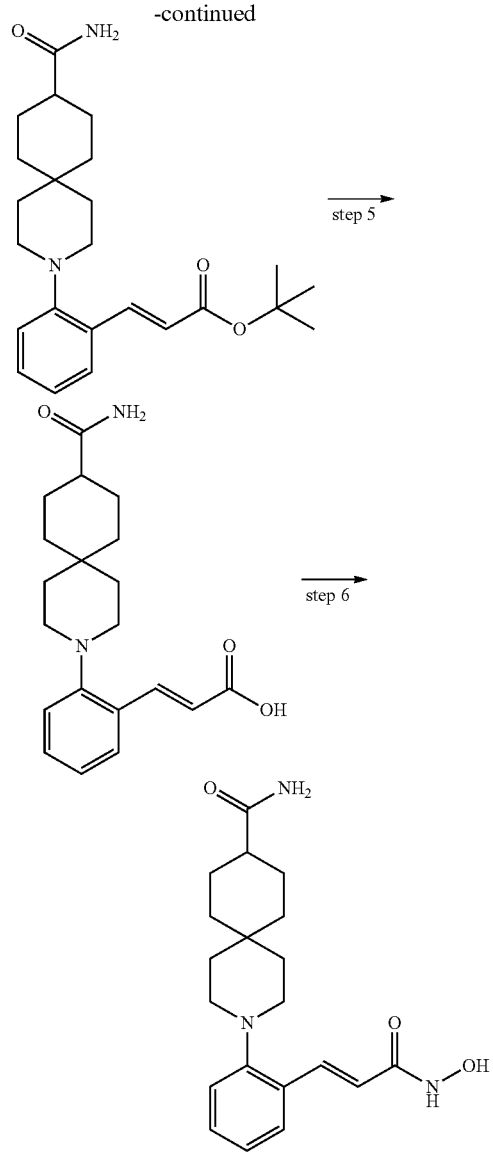

Step-1: Synthesis of 3-tert-butyl 9-methyl 3-azaspiro[5.5]undecane-3,9-dicarboxylate Into a 50-mL, 3-necked round-bottom flask purged and maintained with an inert atmosphere of nitrogen, was placed a solution of 3-[(tert-butoxy)carbonyl]-3-azaspiro[5.5]undecane-9-carboxylic acid (540 mg, 1.82 mmol, 1.00 equiv) in THF/MeOH=4/1 (10 mL). This was followed by the addition of (trimethylsilyl)diazomethane (2M, 1.36 mL, 1.50 equiv) dropwise with stirring at 0° C. The resulting solution was stirred overnight at 0° C. The reaction was concentrated under vacuum and residue was applied onto a silica gel column with ethyl acetate/petroleum ether (1.4). The collected fraction was concentrated under vacuum to give 3-azaspiro[5.5]undecane-3,9-dicarboxylate (525 mg, 93%) as colorless oil MS: (ES, m/z) 312 [M+H]⁺.

Step-2: Synthesis of methyl 3-azaspiro[5.5]undecane-9-carboxylate

Into a 50-mL round-bottom flask, was placed a solution of 3-tert-butyl 9-methyl 3-azaspiro[5.5]undecane-3,9-dicarboxylate (525 mg, 1.69 mmol, 1.00 equiv) in dichloromethane (10 mL) and trifluoroacetic acid (2 mL). The resulting solution was stirred overnight at room temperature. The resulting mixture was concentrated under vacuum. The residue was diluted with 50 mL of sodium bicarbonate (aq, 1M) then extracted with 3×50 mL of dichloromethane, dried over anhydrous sodium sulfate and concentrated under vacuum to give methyl 3-azaspiro[5.5]undecane-9-carboxylate (370 mg, crude) as yellow oil which can be used to the next step with any purification. MS: (ES, m/z): 212 [M+H]+.

Step-3: Synthesis of (E)-methyl 3-(2-(3-(tert-butoxy)-3-oxoprop-1-en-1-yl)phenyl)-3-azaspiro[5.5]undecane-9-carboxylate Into a 30-mL sealed tube purged and maintained with an inert atmosphere of nitrogen, was placed a solution of methyl 3-azaspiro[5.5]undecane-9-carboxylate (211 mg, 1.00 mmol, 1.00 equiv) in toluene (4 mL), (E)-tert-butyl 3-(2-bromophenyl)acrylate (566 mg, 2.00 mmol, 2.00 equiv), Pd₂(dba)₃·CHCl₃ (51.75 mg, 0.05 mmol, 0.05 equiv), XantPhos (57.9 mg, 0.10 mmol, 0.10 equiv) and Cs₂CO₃ (815 mg, 2.50 mmol, 2.50 equiv). The resulting mixture was stirred overnight at 105° C. The reaction was cooled to room temperature and concentrated under vacuum. The residue was then diluted by the addition of 50 mL of water, extracted with 3×50 mL of ethyl acetate, washed with 100 mL of brine, dried over anhydrous sodium sulfate and concentrated under vacuum. The residue was applied onto a silica gel column with ethyl acetate/petroleum ether (1:10). The collected fraction was concentrated under vacuum to give (E)-methyl 3-(2-(3-(tert-butoxy)-3-oxoprop-1-en-1-yl)phenyl)-3-azaspiro[5.5]undecane-9-carboxylate (240 mg, 58%) as yellow oil. MS: (ES, m/z): 414 [M+H]+.

Step-4: Synthesis of (E)-tert-butyl 3-(2-(9-carbamoyl-3-azaspiro[5.5]undecan-3-yl)phenyl)acrylate Into a 50-mL sealed tube, was placed (E)-methyl 3-(2-(3-(tert-butoxy)-3-oxoprop-1-en-1-yl)phenyl)-3-azaspiro[5.5]undecane-9-carboxylate (230 mg, 0.56 mmol, 1.00 equiv), 7 M NH₃ in MeOH (20 mL). The resulting solution was stirred for 72 h at 90° C. The resulting mixture was cooled to room temperature and concentrated under vacuum. The residue was applied onto a silica gel column with dichloromethane/methanol (10.1). The collected fraction was concentrated under vacuum to give (E)-tert-butyl 3-(2-(9-carbamoyl-3-azaspiro[5.5]undecan-3-yl)phenyl)acrylate (100 mg, crude) as yellow oil. MS: (ES, m/z): 399 [M+H]+.

Step-5: Synthesis of (E)-3-(2-(9-carbamoyl-3-azaspiro[5.5]undecan-3-yl)phenyl)acrylic acid Into a 10-mL vial, was placed (E)-tert-butyl 3-(2-(9-carbamoyl-3-azaspiro[5.5]undecan-3-yl)phenyl)acrylate (100 mg, 0.25 mmol, 1.00 equiv), dichloromethane (5 mL) and trifluoroacetic acid (1 mL). The resulting solution was stirred overnight at room temperature. The reaction was concentrated under vacuum. The residue was applied onto a silica gel column with dichloromethane/methanol (10-1). The collected fraction was concentrated under vacuum to give (E)-3-(2-(9-carbamoyl-3-azaspiro[5.5]undecan-3-yl)phenyl)acrylic acid (60 mg, 70%) as yellow oil. MS: (ES, m/z): 343 [M+H]+.

Step-6: Synthesis of (E)-3-(2-(3-(hydroxyamino)-3-oxoprop-1-en-1-yl)phenyl)-3-azaspiro[5.5]undecane-9-carboxamide Into a 10-mL vial, was placed a solution of (E)-3-(2-(9-carbamoyl-3-azaspiro[5.5]undecan-3-yl)phenyl)acrylic acid (60 mg, 0.18 mmol, 1.00 equiv) in DMA (3 mL) and NMM (88.6 mg, 0.88 mmol, 5.00 equiv). This was followed by the addition of IPCF (21.58 mg, 0.18 mmol, 1.00 equiv) dropwise with stirring at 0° C. The resulting solution was stirred for 1 h at room temperature. To the above was added a solution of NH₂OH HCl (13.5 mg, 0.20 mmol, 1.10 equiv) in DMA (1 mL). The resulting solution was stirred overnight at room temperature. The solids were filtered out. The crude product was purified by Prep-HPLC with the following conditions: Column, XBridge RP C18, 19*150 mm, 5 um; mobile phase, Water with 0.05% trifluoroacetic acid and CH₃CN (5% up 36% in 8 min); Detector, 254, 220 nm. The collected fraction was lyophilized to give (E)-3-(2-(3-(hydroxyamino)-3-oxoprop-1-en-1-yl)phenyl)-3-azaspiro[5.5]undecane-9-carboxamide (15 mg, 18%) as a light yellow solid. ¹H-NMR (DMSO, 400 MHz) δ (ppm): 7.70 (d, J=16 Hz, 1H), 7.47 (d, J=8 Hz, 1H), 7.30 (d, J=7.2 Hz, 1H), 7.12 (d, J=8 Hz, 1H), 7.06-7.04 (m, 1H), 6.40 (d, J=16 Hz, 1H), 2.82 (br, 4H), 2.08-2.01 (m, 1H), 1.74 (d, J=13.2 Hz, 2H), 1.65 (br, 2H), 1.54-1.48 (m, 6H), 1.11-1.10 (br, 21H). MS: (ES, m/z): 358 [M+H]+.

Example 27—(E)-N-hydroxy-3-(2-(piperidin-1-yl)phenyl)acrylamide (I-57)

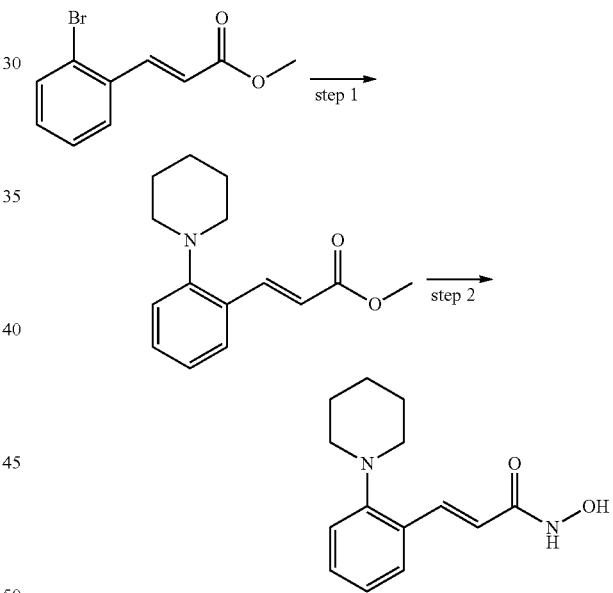

Step-1: Synthesis of (E)-methyl 3-(2-(piperidin-1-yl)phenyl)acrylate

Into a 10-mL sealed tube purged and maintained with an inert atmosphere of nitrogen, was placed methyl (2E)-3-(2-bromophenyl)prop-2-enoate (150 mg, 0.62 mmol, 2.00 equiv) in toluene (5 mL), piperidine (27 mg, 0.32 mmol, 1.00 equiv), Pd(dba)₃·CHCl₃ (16 mg, 0.05 equiv), Xantphos (18 mg, 0.03 mmol, 0.10 equiv) and Cs₂CO₃ (305 mg, 0.94 mmol, 3.00 equiv). The resulting mixture was stirred overnight at 110° C. The reaction mixture was then cooled and poured into 30 mL of water, extracted with 3×20 mL of dichloromethane, washed with 50 mL of brine, dried over anhydrous sodium sulfate and concentrated under vacuum. The residue was applied onto a silica gel column with ethyl acetate/petroleum ether (1:10). The collected fraction was concentrated under vacuum to give (E)-methyl 3-(2-(piperidin-1-yl)phenyl)acrylate (148 mg, crude) as a white solid. MS: (ES, m/z): 246 [M+H]⁺.

Step-2: Synthesis of (E)-N-hydroxy-3-(2-(piperidin-1-yl)phenyl)acrylamide

Into a 25-mL round-bottom flask, was placed methyl (2E)-3-[2-(piperidin-1-yl)phenyl]prop-2-enoate (45 mg, 0.18 mmol, 1.00 equiv), THF/MeOH (4/1) (3 mL), NH$_2$OH (50%/o in water, 0.61 mL, 50.00 equiv), NaOH (1 mol/L, 0.37 mL, 2.00 equiv) The resulting solution was stirred for 3 h at room temperature. The pH value of the solution was adjusted to 6 with HCl (6 mol/L). The resulting mixture was concentrated under vacuum. And the crude product was purified by Prep-HPLC with the following conditions: Column, XBridge Shield RP18 OBD Column, 5 um, 19*150 mm; mobile phase, Water with 0.05% TFA and ACN (5% ACN up to 66% in 7 min); Detector, 220/254 nm. The collected fraction was lyophilized to give (E)-N-hydroxy-3-(2-(piperidin-1-yl)phenyl)acrylamide (11.9 mg, 18%) (as a pink solid ¹H-NMR (DMSO, 400 MHz) δ(ppm): 10.78 (s, 1H), 7.73 (d, J=15.9 Hz, 1H), 7.56 (d, J=3.9 Hz, 1H), 7.49-7.39 (m, 1H), 7.35-7.02 (m, 2H), 6.41 (d, J=15.9 Hz, 1H), 2.78 (d, J=29.4 Hz, 4H), 1.68-1.54 (m, 6H), MS: (ES, m/z): 247 [M+H]⁺.

The following compounds in Table 7 were prepared according to the procedures for (E)-N-hydroxy-3-(2-(piperidin-1-yl)phenyl)acrylamide (I-57).

TABLE 7

| Ex. | Structure | Name | ¹HNMR | (ES, m/z) [M + H]⁺ |
|---|---|---|---|---|
| I-50 | 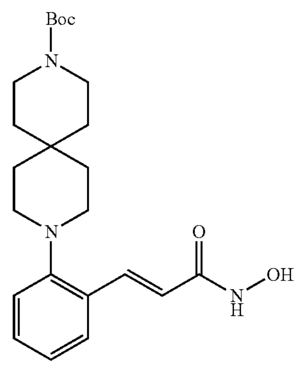 [SMILES: CC(C)(C)OC(=O)N1CCC2(CC1)CCN(c1ccccc1/C=C/C(=O)NO)CC2] | tert-butyl-(E)-9-(2-(3-(hydroxyamino)-3-oxoprop-1-en-1-yl)phenyl)-3,9-diazaspiro[5,5]undecane-3-carboxylate | (DMSO, 400 M Hz, ppm): 7.69 (d, J = 16 Hz, 1H), 7.11 (d, J = 8 Hz, (H), 7.32 (t, J = 6 Hz, 1H), 7.11 (d, J = 8 Hz, 1H), 7.00 (t, J = 12 Hz, 1H), 6.40 (d, J = 16 Hz, 1H), 3.32 (s, 4H), 2.83 (d, J = 4.8 Hz, 4H), 1.62 (s, 4H), 1.45-1.42 (m, 4H), 1.39 (d, J = 6.4 Hz, 9H). | 416 |
| I-58 | 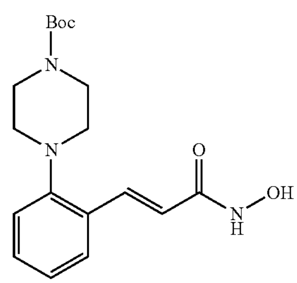 [SMILES: CC(C)(C)OC(=O)N1CCN(c2ccccc2/C=C/C(=O)NO)CC1] | tert-butyl (E)-4-(2-(3-(hydroxyamino)-3-oxoprop-1-en-1-yl)phenyl)piperazine-1-carboxylate | (DMSO, 300 M Hz, ppm); 10.76 (d, J = 11.4 Hz, 1H), 7.74 (d, J = 15.9 Hz, 1H), 7.51 (d, J = 8.1 Hz, 1H), 7.38-7.33 (m, 1HD), 7,13-7.09 (m, 2H), 6.49 (d, J = 15.9 Hz, 1H), 3.51 (s, 4H), 2.84 (8, 4H), 1.44 (s, 9H) | 348 |
| I-60 | 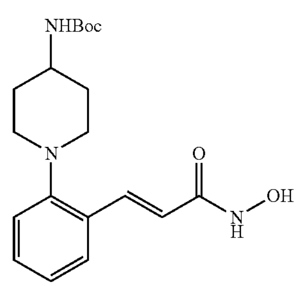 [SMILES: CC(C)(C)OC(=O)NC1CCN(c2ccccc2/C=C/C(=O)NO)CC1] | tert-butyl (E)-(1-(2-(3-(hydroxyamino)-3-oxoprop-1-en-1-yl)phenyl)piperidin-4-yl)carbamate | (DMSO, 300 M Hz, ppm): 10.67 (s, 1H), 7.70(d, J = 15.9 Hz, 1H), 7.47 (d, J = 7.5 Hz, 1H), 7.35-7.30 (m, 1H), 7.11-7.03 (m. 2H), 6.93 (d, J = 7.2 Hz, 1H), 6.45 (d, J = 15.9 Hz, 2H), 3.37 (s, 1H), 3.04 (d, J = 12 Hz, 2H), 2.72-2.65 (m, 2H), 1.82 (d, J = 10.2 Hz, 2H), 1.66-1.54 (m. 2H), 1.38 (d, J = 14.4 Hz, 9H) | 362 |

TABLE 7-continued

| Ex. | Structure | Name | ¹HNMR | (ES, m/z) [M + H]⁺ |
|---|---|---|---|---|
| I-109 | 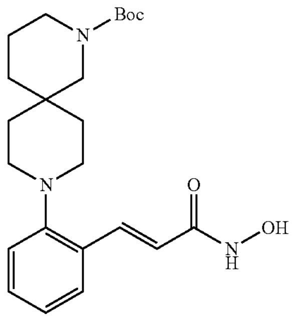 [SMILES: CC(C)(C)OC(=O)N1CCCC2(CCN(c3ccccc3/C=C/C(=O)NO)CC2)C1] | tert-butyl (E)-9-(2-(3-(hydroxyamino)-3-oxoprop-1-en-1-yl)phenyl)-2,9-diazaspiro[5.5]undecane-2-carboxylate | (DMSO, 400 MHZ, ppm): 10.73 (s, 1H), 7.70 (d, J = 16 Hz, 1H), 7.47 (d, J = 7.6 Hz, 1H), 7.35-7.31 (m, 1H), 7.09-7.03 (m, 2H), 6.41 (d, J = 15.6 Hz, 1H), 3.30 (d, J = 9.2 Hz, 4H), 2.85 (s, 4H), 1.57-1.48 (m, 8H), 1.39 (s, 9H) | 416 |
| I-111 | 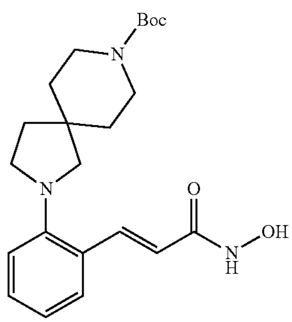 [SMILES: CC(C)(C)OC(=O)N1CCC2(CC1)CCN(c1ccccc1/C=C/C(=O)NO)C2] | tert-butyl (E)-2-(2-(3-(hydroxyamino)-3-oxoprop-1-en-1-yl)phenyl)-2,8-diazaspiro[4.5]decane-8-carboxylate | (DMSO, 400 M Hz, ppm): 10.69 (s, 1H), 7.66 (d, J = 15.6 Hz, 1H), 7.34 (d, J = 7.2 Hz, 1H), 7.24-7.20 (m, 1H), 6.93-6.85 (m, 2H), 6.21 (d, J = 15.6 Hz, 1H), 3.34-3.32 (m, 4H), 3.24-3.21 (m, 2H), 3.01 (s, 2H), 1.79-1.76 (m, 2H), 1.57-1.47 (m, 4H), 1.23 (s, 9H) | 402 |
| I-112 | 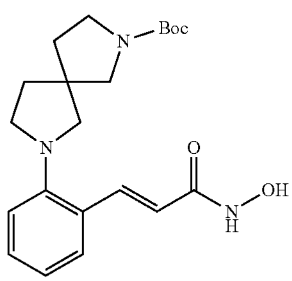 [SMILES: CC(C)(C)OC(=O)N1CCC2(CCN(c3ccccc3/C=C/C(=O)NO)C2)C1] | tert-butyl (E)-7-(2-(3-(hydroxyamino)-3-oxoprop-1-en-1-yl)phenyl)-2,7-diazaspiro[4.4]nonane-2-carboxylate | (DMSO, 400 MHz, ppm): 10.68 (s, 1H), 8.96 (s, 1H), 7.65 (d, J = 15.6 Hz, 1H), 7.34 (d, J = 7.6 Hz, 1H), 7.21 (d, J = 7.2 Hz, 1H), 6.92-6.85 (m, 2H), 6.21 (d, J = 15.6 Hz, 1H), 3.29-3.23 (m, 6H), 3.13-3.10 (m, 2H), 1.90-1.84 (m, 4H), 1.39 (s, 9H) | 402 |

Example 28—(E)-N-hydroxy-3-(2-(piperazin-1-yl)phenyl)acrylamide 2,2,2-trifluoroacetate (I-59)

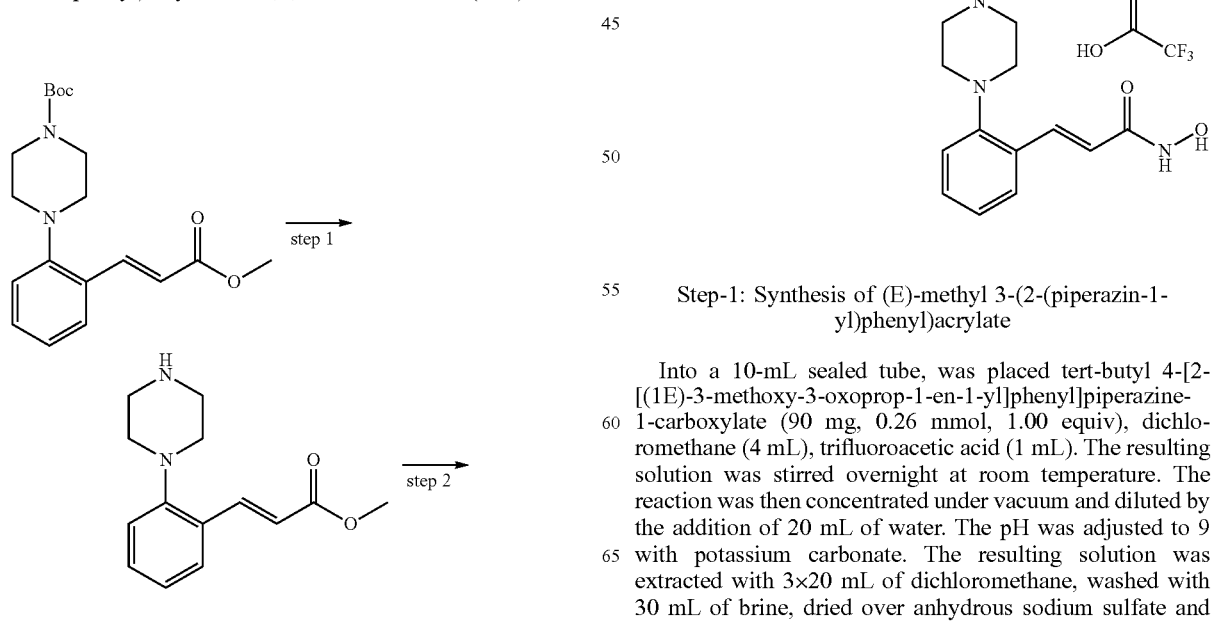

Step-1: Synthesis of (E)-methyl 3-(2-(piperazin-1-yl)phenyl)acrylate

Into a 10-mL sealed tube, was placed tert-butyl 4-[2-[(1E)-3-methoxy-3-oxoprop-1-en-1-yl]phenyl]piperazine-1-carboxylate (90 mg, 0.26 mmol, 1.00 equiv), dichloromethane (4 mL), trifluoroacetic acid (1 mL). The resulting solution was stirred overnight at room temperature. The reaction was then concentrated under vacuum and diluted by the addition of 20 mL of water. The pH was adjusted to 9 with potassium carbonate. The resulting solution was extracted with 3×20 mL of dichloromethane, washed with 30 mL of brine, dried over anhydrous sodium sulfate and concentrated under vacuum to give (E)-methyl 3-(2-(piperazin-1-yl)phenyl)acrylate (60 mg, 94%) as an off-white solid MS: (ES, m/z): 247[M+H]$^+$.

Step-2: Synthesis of (E)-N-hydroxy-3-(2-(piperazin-1-yl)phenyl)acrylamide 2,2,2-trifluoroacetate Into a 25-mL round-bottom flask, was placed methyl (E)-methyl 3-(2-(piperazin-1-yl)phenyl)acrylate (60 mg, 0.24 mmol, 1.00 equiv), THF/MeOH (4/1) (3 mL), NH$_2$OH (50% in water, 0.81 mL, 50.00 equiv), NaOH (1 mol/L, 0.49 mL, 2.00 equiv). The resulting solution was stirred for 4 h at room temperature. The pH was adjusted to 6 with HCl (6 mol/L). The reaction was concentrated under vacuum, and the crude product was purified by Prep-HPLC with the following conditions: Column, XBridge Shield RP18 OBD Column, 5 um, 19*150 mm; mobile phase, Water with 0.05% TFA and ACN (5% ACN up to 66% in 7 min); Detector, 220/254 nm. The collected fraction was lyophilized to give (E)-N-hydroxy-3-(2-(piperazin-1-yl)phenyl)acrylamide 2,2,2-trifluoroacetate (23.8 mg, 27%) as an off-white solid. $^1$H-NMR (DMSO, 300 MHz) δ(ppm): 10.81 (s, 1H), 9.00 (d, J=19.2 Hz, 1H), 8.85 (s, 2H), 7.80-7.60 (m, 1H), 7.52 (d, J=7.5 Hz, 1H), 7.45-7.35 (m, 1H), 7.25-7.03 (m, 2H), 6.47 (d, J=15.6 Hz, 1H), 3.51-3.30 (m, 4H), 3.03 (d, J=19.5 Hz, 4H). MS: (ES, m/z): 248[M-CF$_3$COOH+H]$^+$.

The following compounds or salts in Table 8 were prepared according to the procedures for the salt (E)-N-hydroxy-3-(2-(piperazin-1-yl)phenyl)acrylamide 2,2,2-trifluoroacetate (I-59).

TABLE 8

| Ex. | Structure | Name | $^1$HNMR | (ES, m/z) [M + H]$^+$ |
|---|---|---|---|---|
| I-52 | 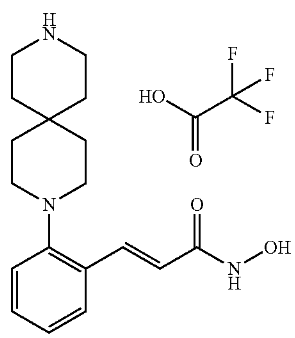 | (E)-3-(2-(3,9-diazaspiro[5.5]undecan-3-yl)phonyl)-N-hydroxyacrylamide 2,2,2-trifluoroacetate | (DMSO, 400 MHZ, ppm): 10.75 (s, 1H), 8.42 (s, 2H), 7.70 (d, J = 16 Hz, 1H), 7.47 (d, J = 7.2 Hz, 1H), 7.35-7.31 (m, 1H), 7.12-7.01 (m, 2H), 6.42 (d, J = 16 Hz, 1H), 3.08 (s, 4H), 2.84 (s, 4H), 1.66 (s, 9H). | 316 |
| I-8 | 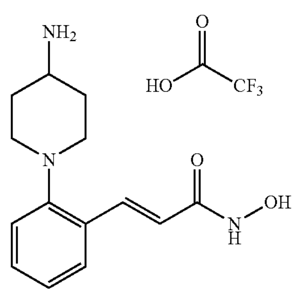 [SMILES: NC1CCN(c2ccccc2/C=C/C(=O)NO)CC1 ; O=C(O)C(F)(F)F] | (E)-3-(2-(4-aminopiperidin-1-yl)phenyl)-N-hydroxyacrylamide 2,2,2-trifluoroacetate | (DMSO, 400 M Hz, ppm): 10.74 (s, 1H), 8.99 (s, 1H), 7.96 (s, 3H), 7.71 (d, J = 12 Hz, 1H), 7.50 (d, J = 7.6 Hz, 1H), 7.34 (t, J = 7 Hz, 1H), 7.09 (t, J = 7.6 Hz, 2H), 6.40 (d, J = 15.6 Hz, 1H), 3.17-3.08 (m, 3H), 2.76-2.67 (m, 2H), 1.99 (d, J = 10.4 HZ, 2H), 1,80-1.77 (m, 2H) | 262 |
| I-110 | 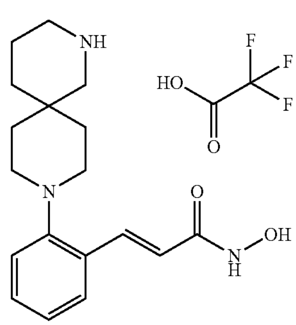 | (E)-3-(2-(2,9-diazaspiro[5.5]undecan-9-yl)phenyl)-N-hydroxyacrylamide 2,2,2-trifluoroacetate | (DMSO, 400 MHz, ppm): 10.75 (s, 1H), 9.01-8.94 (br, 1H), 8.50 (s, 1H), 7.68 (d, J = 16 HZ, 1H), 7.47 (d. J = 7.6 HZ, 1H), 7.35-7.31 (m, 1H), 7.13 (d, J = 7.6 HZ, 1H), 7.07-7.04 (m, 1H), 6.42 (d, J = 16 HZ, 1H), 3.02 (s, 4H), 2.85 (s, 4H), 1.73-1.59 (m, 8H) | 316 |

TABLE 8-continued

| Ex. | Structure | Name | ¹HNMR | (ES, m/z) [M + H]⁺ |
|---|---|---|---|---|
| I-115 | 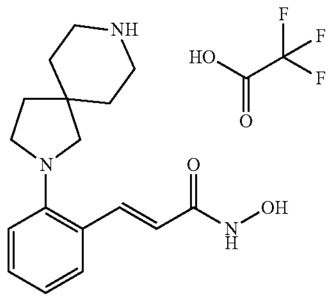 [SMILES: O=C(/C=C/c1ccccc1N1CCC2(CCNCC2)C1)NO ; O=C(O)C(F)(F)F] | (E)-3-(2-(2,8-diazaspiro[4.5]decan-2-yl)phenyl)-N-hydroxyacrylamide 2,2,2-trifluoroacetate | (DMSO, 400 MHz, ppm): 10.75 (s, 1H), 8.97 (s, 1H), 8.40 (s, 2H), 7.66 (d, J = 15.6 Hz, 1H), 7.45 (d, J = 8.4 Hz, 1H), 7.37-7.23 (m, 1H), 6.98-6.89 (m, 2H), 6.25 (d, J = 15.6 Hz, 1H), 3.31-3.22 (m, 2H), 3.10 (s, 4H), 3.04 (s, 2H), 1.85-1.80 (m, 2H), 1.78-1.70 (m, 4H) | 302 |
| I-113 | 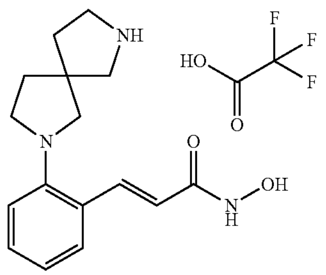 | (E)-3-(2-(2,7-diazaspiro[4.4]nonan-2-yl)pheny])-N-hydroxyacrylamide 2,2,2-trifluoroacetate | (DMSO, 400 MHZ, ppm): 10.72 (s, 1H), 8.97-8.84 (m, 3H), 7.65 (d, J = 15.6 Hz, 1H), 7.36 (d. J = 7.2 Hz, 1H), 7.26-7.23 (m, 1H), 6.93-6.88 (m, 2H), 6.23 (d. J = 15.6 Hz, 1H), 3.29 (s, 4H). 3.18 (s, 4H), 2.04-1.91 (m, 4H) | 288 |

Example 29—benzyl (E)-(2-(2-(3-(hydroxyamino)-3-oxoprop-1-en-1-yl)phenyl)-5,5-dioxido-5-thia-2-aza spiro[3,4]octan-7-yl)carbamate (I-114)

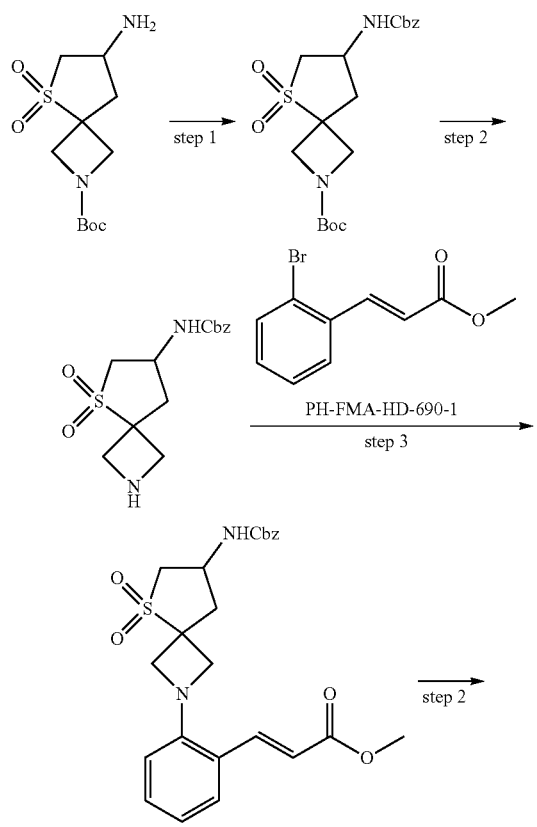

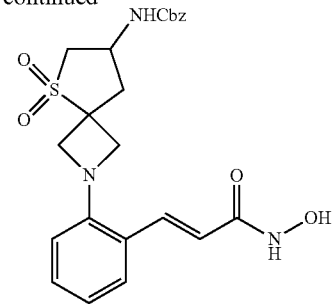

Step-1: Synthesis of tert-butyl 7-(((benzyloxy)carbonyl)amino)-5-thia-2-azaspiro[3.4]octane-2-carboxylate 5,5-dioxide Into a 50-mL 3-necked round-bottom flask purged and maintained with an inert atmosphere of nitrogen, was placed tert-butyl 7-amino-5-thia-2-azaspiro[3.4]octane-2-carboxylate 5,5-dioxide (300 mg, 1.09 mmol, 1.00 equiv), tetrahydrofuran (25 mL) and TEA (218 mg, 2.15 mmol, 2.00 equiv). This was followed by the addition of Cbz-Cl (278.8 mg, 1.63 mmol, 1.50 equiv) dropwised with at stirring at 0° C. The resulting solution was stirred overnight at 0° C. for 3 h. The reaction was then poured into 50 mL of brine, extracted with 3×50 mL of ethyl acetate, dried over anhydrous sodium sulfate and concentrated under vacuum. The residue was applied onto a silica gel column with ethyl acetate/petroleum ether (1.2). The collected fraction was concentrated under vacuum to give tert-butyl 7-(((benzyloxy)carbonyl)amino)-5-thia-2-azaspiro[3.4]octane-2-carboxylate 5,5-dioxide (380 mg, 85%) as a white solid. MS: (ES, m/z): 411 [M+H]⁻.

Step-2: Synthesis of benzyl (5,5-dioxido-5-thia-2-azaspiro[3.4]octan-7-yl)carbamate Into a 25-mL round-bottom flask, was placed tert-butyl 7-(((benzyloxy)carbonyl)amino)-5-thia-2-azaspiro[3.4]octane-2-carboxylate 5,5-dioxide (380 mg, 0.93 mmol, 1.00 equiv), dichloromethane (20 mL) and trifluoroacetic acid (5 mL). The resulting solution was stirred for 3 h at room temperature, and then concentrated under vacuum. The residue was then diluted with 20 mL of water. The pH was adjusted to 8 with saturated aqueous $K_2CO_3$. The resulting solution was extracted with 3×50 mL of dichloromethane, washed with 50 mL of brine, dried over anhydrous sodium sulfate and concentrated under vacuum to give benzyl (5,5-dioxido-5-thia-2-azaspiro[3.4]octan-7-yl)carbamate (270 mg, 94%) as yellow oil. MS: (ES, m/z): 311 [M+H]$^+$.

Step-3: Synthesis of (E)-methyl 3-(2-(7-(((benzyloxy)carbonyl)amino)-5,5-dioxido-5-thia-2-azaspiro[3.4]octan-2-yl)phenyl)acrylate Into a 30-mL sealed tube purged and maintained with an inert atmosphere of nitrogen, was placed benzyl (5,5-dioxido-5-thia-2-azaspiro[3.4]octan-7-yl)carbamate (270 mg, 0.87 mmol, 1.00 equiv) in toluene (6 mL), methyl (2E)-3-(2-bromophenyl)prop-2-enoate (449 mg, 1.86 mmol, 2.00 equiv), $Pd_2(dba)_3$ $CHCl_3$ (49 mg, 0.05 equiv), $Cs_2CO_3$ (766 mg, 2.35 mmol, 2.50 equiv) and XantPhos (4,5-Bis(diphenylphosphino)-9,9-dimethylxanthene) (55 mg, 0.10 mmol, 0.10 equiv) The resulting mixture was stirred overnight at 105° C. in an oil bath. The mixture was cooled to room temperature, concentrated under vacuum and the diluted by the addition of 50 mL of water. The resulting solution was extracted with 3×50 mL of ethyl acetate, washed with 100 mL of brine, dried over anhydrous sodium sulfate and concentrated under vacuum. The residue was applied onto a silica gel column with ethyl acetate/petroleum ether (1:3). The collected fraction was concentrated under vacuum to give (E)-methyl 3-(2-(7-(((benzyloxy)carbonyl)amino)-5,5-dioxido-5-thia-2-azaspiro[3.4]octan-2-yl)phenyl)acrylate (400 mg, 98%) as yellow oil. MS: (ES, m/z): 471[M+H]$^+$.

Step-4: Synthesis of benzyl (E)-(2-(2-(3-(hydroxyamino)-3-oxoprop-1-en-1-yl)phenyl)-5,5-dioxido-5-thia-2-azaspiro[3.4]octan-7-yl)carbamate Into a 10-mL round-bottom flask, was placed (E)-methyl 3-(2-(7-(((benzyloxy)carbonyl)amino)-5,5-dioxido-5-thia-2-azaspiro[3.4]octan-2-yl)phenyl)acrylate (60 mg, 0.13 mmol, 1.00 equiv), MeOH/THF (¼) (3 mL), $NH_2OH$ (50% in water, 506 mg, 60.00 equiv), NaOH (1 mol/L, 0.26 mL, 2.00 equiv). The resulting solution was stirred for 2 h at room temperature. The pH was adjusted to 7 with HCl (6 mol/L). The resulting mixture was concentrated under vacuum. The crude product was purified by Prep-HPLC with the following conditions: Column, X Bridge C18, 19*150 mm, 5 um; mobile phase A, water/0.05% TFA; mobile phase B: ACN; Flow rate: 20 ml/min; Gradient: 10-15% B in 8 min; 254 nm. The collected fraction was lyophilized to give (E)-benzyl (2-(2-(3-(hydroxyamino)-3-oxoprop-1-en-1-yl)phenyl)-5,5-dioxido-5-thia-2-azaspiro[3.4]octan-7-yl)carbamate (15.7 mg, 26%) as a yellow solid. $^1$H-NMR (DMSO, 400 MHz) δ(ppm): 10.72 (s, 1H), 7.71 (s, 1H), 7.49 (d, J=15.6 Hz, 1H), 7.39-7.31 (m, 6H), 7.27-7.23 (m, 1H), 6.88-6.85 (m, 1H), 6.621 (d, J=8 Hz, 1H), 6.21 (d, J=15.6 Hz, 1H), 5.08-5.00 (m, 2H), 4.25 (d, J=8.8 Hz, 2H), 4.15-4.10 (m, 1H), 3.98 (d, J=8.8 Hz, 2H), 3.62-3.57 (m, 4H), 3.11-3.06 (m, 1H), 2.75-2.70 (m, 1H), 2.37-2.32 (m, 1H) MS: (ES, m/z): 472[M+H]$^+$.

Example 30—(E)-3-(2-(7-amino-5,5-dioxido-5-thia-2-azaspiro[3.4]octan-2-yl)phenyl)-N-hydroxyacrylamide 2,2,2-trifluoroacetate (I-117)

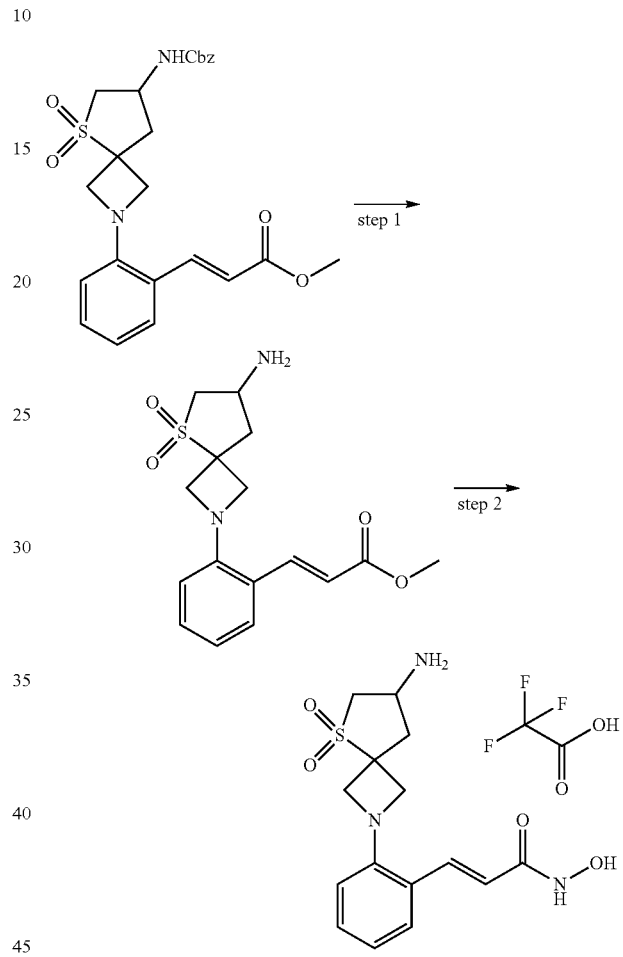

Step-1: Synthesis of (E)-methyl 3-(2-(7-amino-5,5-dioxido-5-thia-2-azaspiro[3.4]octan-2-yl)phenyl)acrylate Into a 10-mL vial, was placed (E)-methyl 3-(2-(7-(((benzyloxy)carbonyl)amino)-5,5-dioxido-5-thia-2-azaspiro[3.4]octan-2-yl)phenyl)acrylate (100 mg, 0.21 mmol, 1.00 equiv), acetonitrile (2 mL) and Iodotrimethylsilane (0.4 mL, 10.00 equiv). The resulting solution was stirred for 5 min at room temperature. The reaction was then quenched by the addition of 0.5 mL of TEA at 0° C. and then diluted with 30 mL of water. The resulting solution was extracted with 3×30 mL of ethyl acetate, dried over anhydrous sodium sulfate and concentrated under vacuum. The residue was purified by prep-TLC with ethyl acetate/petroleum ether (1-3) to give (E)-methyl 3-(2-(7-amino-5,5-dioxido-5-thia-2-azaspiro[3.4]octan-2-yl)phenyl)acrylate (50 mg, 70%) as green oil. MS: (ES, m/z): 337[M+H]$^+$.

Step-2: Synthesis of (E)-3-(2-(7-amino-5,5-dioxido-5-thia-2-azaspiro[3.4]octan-2-yl)phenyl)-N-hydroxy-acrylamide 2,2,2-trifluoroacetate Into a 10-mL round-bottom flask, was placed (E)-methyl 3-(2-(7-amino-5,5-dioxido-5-thia-2-azaspiro[3.4]octan-2-yl)phenyl)acrylate (50 mg, 0.15 mmol, 1.00 equiv), MeOH/THF (¼) (2 mL), NH$_2$OH (50% in water, 590 mg, 60.00 equiv), NaOH (1 mol/L, 0.3 mL, 2.00 equiv). The resulting solution was stirred for 2 h at room temperature. The solids were filtered out. The crude product was purified by Prep-HPLC with the following conditions: Column, sunfire C18 19*150; mobile phase, A: 0.05% TFA, B: ACN 10-23/6 min, Detector, 254 nm. The collected fraction was lyophilized to give (E)-3-(2-(7-amino-5,5-dioxido-5-thia-2-azaspiro[3.4]octan-2-yl)phenyl)-N-hydroxyacrylamide 2,2,2-trifluoroacetate (12.0 mg, 18%) as a yellow solid. $^1$H-NMR (DMSO, 400 MHz) δ(ppm): 10.67 (s, 1H), 9.42-9.27 (br, 2H), 8.97 (s, 1H), 7.67 (d, J=15.2 Hz, 1H), 7.33 (d, J=7.2 Hz, 1H), 7.26-7.19 (m, 1H), 6.78-6.66 (m, 2H), 6.29 (d, J=15.2 Hz, 1H), 5.95-5.89 (m, 1H), 4.52 (s, 1H), 3.85-3.77 (m, 2H), 3.68-3.46 (m, 4H), 2.49-2.26 (m, 1H). MS: (ES, m/z): 338[M+H]$^+$.

Example 31—(E)-2-(3-(hydroxyamino)-3-oxoprop-1-en-1-yl)-N-(3-(trifluoromethyl)phenyl)benzamide (II-36)

2-(3-(hydroxyamino)-3-oxoprop-1-en-1-yl)-N-(3-(trifluoromethyl)phenyl)benzamide

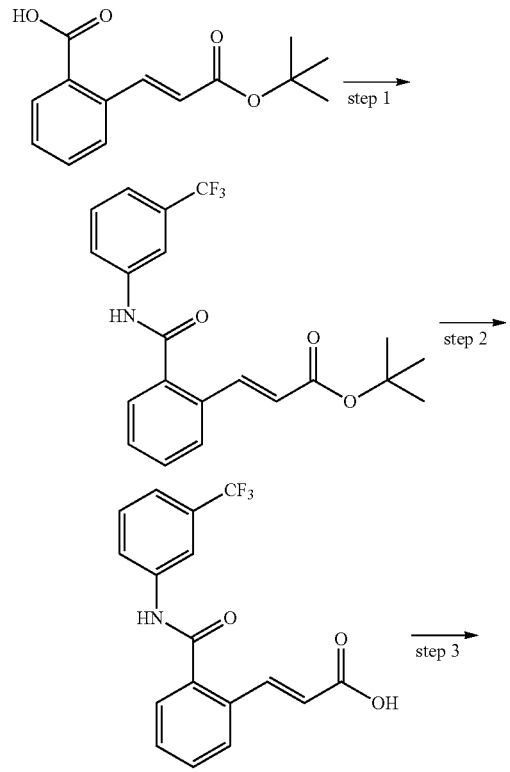

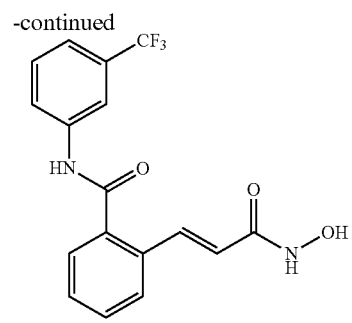

Step-1: Synthesis of (E)-tert-butyl 3-(2-(3-(trifluoromethyl)phenylcarbamoyl)phenyl)acrylate Into a 10-mL sealed tube, was placed (E)-2-(3-tert-butoxy-3-oxoprop-1-enyl)benzoic acid (400 mg, 1.61 mmol, 1.00 equiv) in N,N-dimethylformamide (4 mL) and DMT-MM (447 mg, 1.00 equiv). The resulting solution was stirred for 20 min at room temperature. Then 3-(trifluoromethyl)aniline (368 mg, 2.28 mmol, 1.40 equiv) was added. The resulting solution was stirred overnight at room temperature. The reaction mixture was then poured into 20 mL of water, extracted with 3×20 mL of ethyl acetate, washed with 2×20 mL of brine, dried over anhydrous sodium sulfate and concentrated under vacuum. The residue was applied onto a silica gel column with ethyl acetate/petroleum ether (1:4). The collected fraction was concentrated under vacuum to give (E)-tert-butyl 3-(2-(3-(trifluoromethyl)phenylcarbamoyl)phenyl)acrylate (323 mg, 51%) as a white solid. MS: (ES, m/z): 392[M+H]$^+$.

Step-2: Synthesis of (E)-3-(2-(3-(trifluoromethyl)phenylcarbamoyl)phenyl)acrylic acid Into a 25-mL round-bottom flask, was placed (E)-tert-butyl 3-(2-(3-(trifluoromethyl)phenylcarbamoyl)phenyl)acrylate (323 ng, 0.83 mmol, 1.00 equiv), dichloromethane (4 mL) and trifluoroacetic acid (1 mL). The resulting solution was stirred for 2 h at room temperature. The reaction was the concentrated under vacuum and diluted by 20 mL of water. The resulting solution was extracted with 3×20 mL of ethyl acetate, washed with 1×10 mL of brine, dried over anhydrous sodium sulfate and concentrated under vacuum to give (E)-3-(2-(3-(trifluoromethyl)phenylcarbamoyl)phenyl)acrylic acid (300 mg, 88%) as a white solid. MS: (ES, m/z): 336[M+H]$^+$.

Step-3: Synthesis of (E)-2-(3-(hydroxyamino)-3-oxoprop-1-en-1-yl)-N-(3-(trifluoromethyl)phenyl)benzamide Into a 10-mL sealed tube, was placed (E)-3-(2-(3-(trifluoromethyl)phenylcarbamoyl)phenyl)acrylic acid (200 mg, 0.60 mmol, 1.00 equiv) in DMA (5 mL), NMM (301 mg, 2.98 mmol, 5.00 equiv). This was followed by the addition of IPCF (367 mg, 5.00 equiv) dropwise with stirring at 0° C. The resulting solution was stirred for 5 min at 0° C., then a solution of NH$_2$OH·HCl (209 mg, 5.00 equiv) in DMA (2 mL) was added. The resulting solution was stirred overnight at room temperature. The solids were filtered out. The crude product was purified by Prep-HPLC with the following conditions: Column: X Sunfire C18, 19*150 mm, 5 um; Mobile Phase A: Water/0.05% TFA, Mobile Phase B: ACN;

Flow rate: 20 mL/min; Gradient: 25% B to 50% B in 8 min; 254 nm. The collected fraction was lyophilized to give (E)-2-(3-(hydroxyamino)-3-oxoprop-1-en-1-yl)-N-(3-(trifluoromethyl)phenyl)benzamide (129 mg, 5%) as a pink solid. $^1$H-NMR (DMSO, 400 MHz) δ(ppm): 10.80 (s, 2H), 9.03 (d, J=5.2 Hz, 1H), 8.24 (s, 1H), 7.94 (d, J=8 Hz, 1H), 7.71 (d, J=15.6 Hz, 1H), 7.65-7.61 (m, 1H), 7.59-7.51 (m, 3H), 7.48 (d, J=8.4 Hz, 2H), 6.47 (d, J=15.6 Hz, 1H). MS: (ES, m/z): 351[M+H]$^+$.

The following compounds in Table 9 were prepared according to the procedures for (E)-2-(3-(hydroxyamino)-3-oxoprop-1-enyl)-N-(3-(trifluoromethyl)phen-1-yl)benzamide (I-36).

TABLE 9

| Ex. | Structure | Name | $^1$HNMR | (ES, m/z) [M + H]$^+$ |
|---|---|---|---|---|
| II-13 | 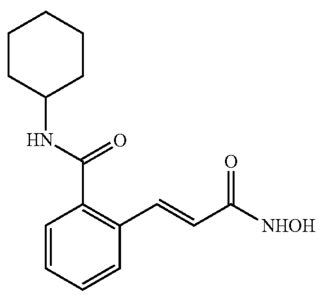 | (E)-N-cyclohexyl-2-(3-(hydroxyamino)-3-oxoprop-1-en-1-yl)benzamide | (DMSO, 400 MHZ, ppm): 10.76 (s, 1H), 8.27 (d, J = 8 Hz, 1H), 7.67-7.63 (m, 2H), 7.48-7.34 (m, 3H), 6.40 (d, J = 15.6 Hz, 1H), 1.84 (d, J = 10.8 Hz, 2H), 1.74-1.70 (m, 2H), 1.59 (d, J = 12.8 Hz, 1H), 1.36-1.19 (m, 4H), 1.16-1.10 (m, 1H) | 289 |
| II-3 | 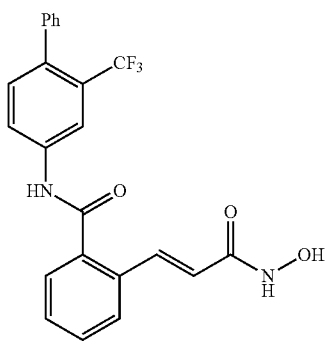 [SMILES: O=C(/C=C/c1ccccc1C(=O)Nc1ccc(-c2ccccc2)c(C(F)(F)F)c1)NO] | (E)-2-(3-(hydroxyamino)-3-oxoprop-1-en-1-yl)-N-(2-(trifluoromethy)-[1,1'-biphenyl]-4-yl)benzamide | (DMSO, 300 MHZ, ppm:): 10.88 (s, 1H), 8.32 (d, J = 1.8 Hz, 1H), 8.02 (d, J = 8.7 Hz, 1H), 7.77-7.49 (m, 5H), 7.47-7.40 (m, 4H), 7.34-7.32 (m, 2H), 6.49 (d, J = 15.9 Hz, 1H) | 427 |

Example 32—(E)-N-(2-(3-(hydroxyamino)-3-oxoprop-1-en-1-yl)phenyl)-3-(3-hydroxypropyl)benzamide (I-49)

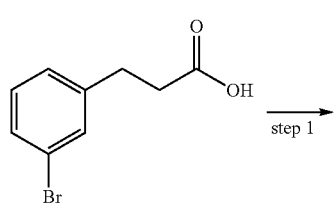

step 1

-continued

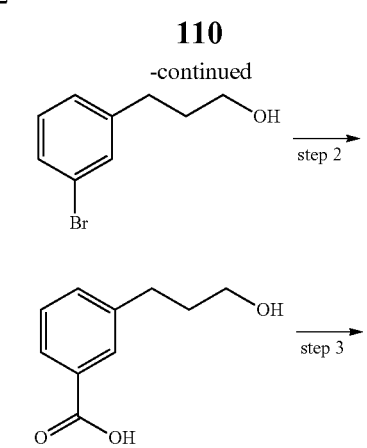

step 2 step 3

-continued step 4

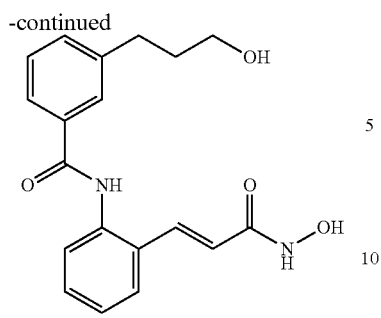

Step-1: Synthesis of 3-(3-bromophenyl)propan-1-ol

Into a 250-mL 3-necked round-bottom flask purged and maintained with an inert atmosphere of nitrogen, was placed a solution of 3-(3-bromophenyl)propanoic acid (5 g, 21.83 mmol, 1.00 equiv) in THF (50 mL). This was followed by the addition of borane tetrahydrofuran complex solution (1moL/L, 75 mL, 74.22mmoL, 3.40 equiv) dropwise with stirring at 0° C. The resulting solution was stirred overnight at room temperature. The reaction mixture was poured into 150 mL of HCl (1moL/L), extracted with 3×200 mL of DCM, washed with 300 mL of brine, dried over anhydrous sodium sulfate and concentrated under vacuum. The residue was applied onto a silica gel column with DCM/MeOH (10:1). The collected fraction was concentrated to afford 3-(3-bromophenyl)propan-1-ol (1.3 g, 28%) as colorless oil. $^1$H-NMR (DMSO, 400 MHz) δ (ppm): 7.41-7.20 (m, 4H), 4.51-4.48 (t, 1H), 3.41-3.34 (m, 2H), 2.67-2.59 (m, 2H), 1.73-1.66 (nm, 2H).

Step-2: Synthesis of 3-(3-hydroxypropyl)benzoic acid

Into a 100-mL 3-necked round-bottom flask purged and maintained with an inert atmosphere of nitrogen, was placed 3-(3-bromophenyl)propan-1-ol (310 mg, 1.44 mmol, 1.00 equiv) in THF (10 mL). This was followed by the addition of n-Butyllithium (2.5moL/L in THF, 1.22 mL, 3.05mmoL, 2.10 equiv) dropwise with stirring at −78° C. After stirring for 1 h at −78° C., dry ice was added. The resulting solution was stirred for 3 h at room temperature. The pH value of the solution was adjusted to 6 with HCl (1 mol/L) at 0° C. The resulting mixture was concentrated under vacuum. The residue was dissolved in 30 mL of DCM/MeOH (10/1) and stirred for a while. Filtration was performed. The filtrate was concentrated under vacuum to give 3-(3-hydroxypropyl) benzoic acid (690 mg, crude) as a light yellow solid which could be used to the next step without any purification. MS: (ES, m/z) 181[M+H]$^+$.

Step-3: Synthesis of methyl (2E)-3-(2-[[3-(3-hydroxypropyl)benzene]amido]phenyl)prop-2-enoate Into a 25-mL round-bottom flask, was placed 3-(3-hydroxypropyl)benzoic acid (180 mg, 1.00 mmol, 1.00 equiv) in dichloromethane (3 mL) Then DIEA (258.48 mg, 2.00 mmol, 2.00 equiv) and DMC (2-Chloro-1,3-dimethylimidazolinium chloride) (202.86 mg, 1.2mmoL, 1.20 equiv) were added at 0° C. After stirred for 5 min at room temperature, methyl (2E)-3-(2-aminophenyl)prop-2-enoate (177 mg, 1.00 mmol, 1.00 equiv) was added. The resulting solution was stirred overnight at room temperature. The reaction was then quenched by the addition of 2 mL of water and extracted with 3×5 mL of dichloromethane, dried over anhydrous sodium sulfate and concentrated under vacuum. The residue was applied onto a silica gel column and eluted with ethyl acetate/petroleum ether (1:1). The collected fraction was concentrated to give methyl (2E)-3-(2-[[3-(3-hydroxypropyl)benzene]amido]phenyl)prop-2-enoate (55.9 mg, 16%) as a yellow solid. MS: (ES, m/z): 340[M+H]$^+$.

Step-4: Synthesis of N-[2-[(1E)-2-(hydroxycarbamoyl)eth-1-en-1-yl]phenyl]-3-(3-hydroxypropyl)benzamide: trifluoroacetic acid Into a 25-mL round-bottom flask, was placed methyl (2E)-3-(2-[[3-(3-hydroxypropyl)benzene]amido]phenyl) prop-2-enoate (55.9 mg, 0.16 mmol, 1.00 equiv), MeOH/THF (¼) (1 mL), then NaOH (1 mol/L, 0.33 mL, 0.33mmoL, 2.00 equiv) and NH$_2$OH (50% in H$_2$O, 544.2 mg, 16.48 mmol, 50.00 equiv) were added at 0° C. After stirred for 1 h at room temperature, the temperature was cooled to 0° C. with a water/ice bath and the pH was adjusted to 6 with HCl (6 mol/L). The mixture was purified by Prep-HPLC with the following conditions: Column, Waters HSS C18; 1.8 um, 2.1*50 mm, mobile phase, Water with 0.05% TFA and CH$_3$CN (20% CH$_3$CN up to 60.0% in 10 min); Detector, 254 nm. The collected fraction was lyophilized to give N-[2-[(1E)-2-(hydroxycarbamoyl)eth-1-en-1-yl]phenyl]-3-(3-hydroxypropyl)benzamide; trifluoroacetic acid (2.9 mg, 4%) as an off-white solid. $^1$H-NMR (DMSO, 400 MHz) δ(ppm): 10.76 (s, 1H), 10.21 (s, 1H), 9.97-9.01 (m, 1H), 7.84-7.25 (m, 9H), 6.45-6.40 (d, J=16 Hz, 1H), 3.47-3.34 (m, 2H), 2.74-2.69 (m, 2H), 1.83-1.73 (m, 2H). MS. (ES, m/z): 341[M+H]$^+$.

Example 33—(E)-3-(2-(((6-(3-amino-3-oxopropyl)-1H-benzo[d]imidazol-2-yl)methyl)amino)phenyl)-N-hydroxyacrylamide (I-385)

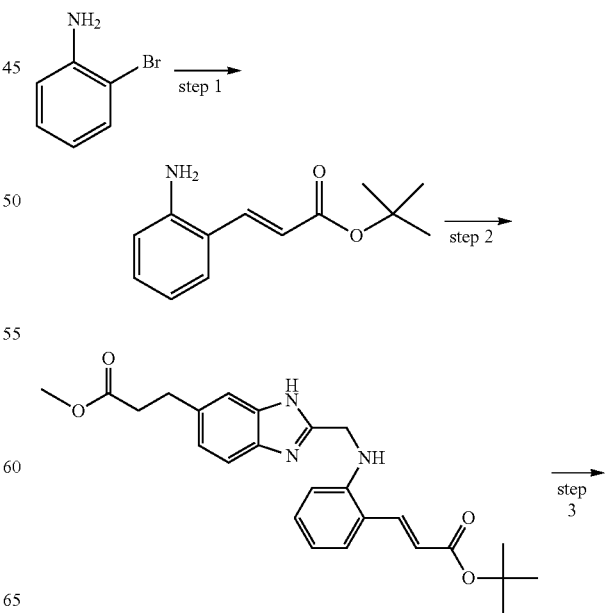

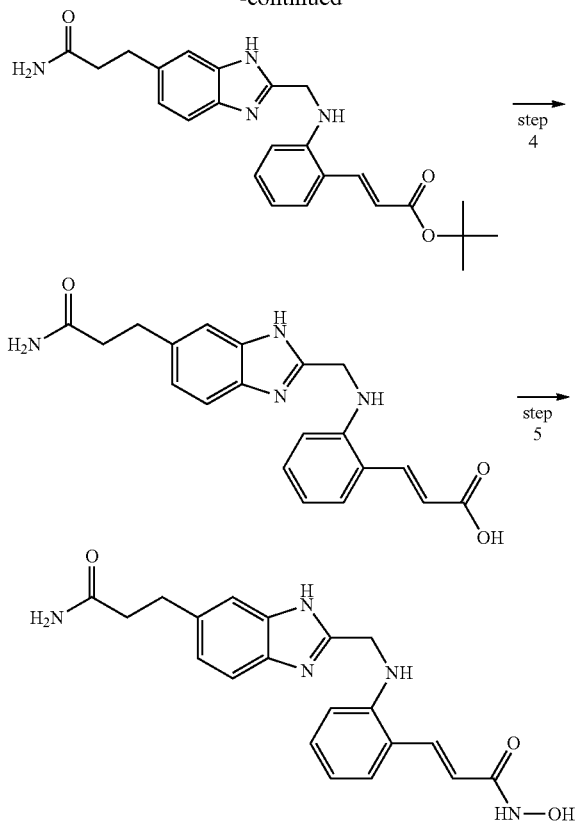

Step-1: Synthesis of (E)-tert-butyl 3-(2-aminophenyl)acrylate

Into a 150-mL sealed tube purged and maintained with an inert atmosphere of nitrogen, was placed a solution of 2-bromoaniline (10 g, 58.13 mmol, 1.00 equiv), water (1 mL), TEA (17.75 g, 175.41 mmol, 3.00 equiv), Pd(dppf)Cl$_2$·CH$_2$Cl$_2$ (2.39 g, 2.90 mmoL, 0.05 equiv) and tert-butyl prop-2-enoate (7.5 g, 58.52 mmol, 1.00 equiv) in DMF (60 mL). The resulting solution was stirred overnight at 100° C. The reaction mixture was then cooled to room temperature and poured into 100 mL of brine. The resulting solution was extracted with 5×50 mL of ethyl acetate, washed with 100 mL of brine, dried over anhydrous Na$_2$SO$_4$ and concentrated under vacuum. The residue was dissolved in 30 mL of DCM/MeOH (10/1) and stirred for a while. Filtration was performed. The filtrate was collected and concentrated to give (E)-tert-butyl 3-(2-aminophenyl)acrylate (10 g, 78%) as a light yellow solid. MS: (ES, m/z): 220 [M+H]$^+$.

Step-2: Synthesis of (E)-tert-butyl 3-(2-(((6-(3-methoxy-3-oxopropyl)-1H-benzo[d]imidazol-2-yl)methyl)amino)phenyl)acrylate Into a 50-mL round-bottom flask, was placed (E)-tert-butyl 3-(2-aminophenyl)acrylate (204.2 mg, 0.93 mmol, 1.00 equiv) in CH$_3$CN (5 mL), potassium carbonate (383.6 mg, 2.78 mmol, 2.00 equiv) and potassium iodide (461.5 mg, 2.78 mmol, 2.00 equiv). Then methyl 3-[2-(chloromethyl)-1H-1,3-benzodiazol-6-yl]propanoate (350 mg, 1.39 mmol, 1.00 equiv) was added by dropwise. The resulting solution was stirred for 5 h at 40° C. The reaction was then quenched by the addition of 20 mL of H$_2$O. The resulting solution was extracted with 3×20 mL of DCM, dried over anhydrous Na$_2$SO$_4$ and concentrated under vacuum. The residue was applied onto a silica gel column with ethyl acetate/petroleum ether (1/1). The collected fraction was concentrated to give (E)-tert-butyl 3-(2-(((6-(3-methoxy-3-oxopropyl)-1H-benzo[d]imidazol-2-yl)methyl)amino)phenyl)acrylate (190 mg, 31%) as a yellow solid. MS: (ES, m/z): 436 [M+H]$^-$.

Step-3: Synthesis of (E)-tert-butyl 3-(2-(((6-(3-amino-3-oxopropyl)-1H-benzo[d]imidazol-2-yl)methyl)amino)phenyl)acrylate Into a 25-mL sealed tube, was placed (E)-tert-butyl 3-(2-(((6-(3-methoxy-3-oxopropyl)-1H-benzo[d]imidazol-2-yl)methyl)amino)phenyl)acrylate (190 mg, 0.44 mmol, 1.00 equiv) and a solution of NH$_3$ in MeOH (7 moL/L, 15 mL). The resulting solution was stirred for 2 days at 80° C. The reaction mixture was cooled to room temperature and concentrated under vacuum. The crude product was applied onto a silica gel column with ethyl acetate/petroleum ether. The collected fraction was concentrated to give (E)-tert-butyl 3-(2-(((6-(3-amino-3-oxopropyl)-1H-benzo[d]imidazol-2-yl)methyl)amino)phenyl)acrylate (125 mg, 68%) as a yellow solid MS. (ES, m/z): 421 [M+H]$^+$ Step-4: Synthesis of (E)-3-(2-(((6-(3-amino-3-oxopropyl)-1H-benzo[d]imidazol-2-yl)methyl)amino)phenyl)acrylic acid Into a 25-mL round-bottom flask, was placed (E)-tert-butyl 3-(2-(((6-(3-amino-3-oxopropyl)-1H-benzo[d]imidazol-2-yl)methyl)amino)phenyl)acrylate (100 mg, 0.24 mmol, 1.00 equiv) and TFA/DCM (½, 3 mL). The resulting solution was stirred for 2 h at room temperature. The reaction was concentrated under vacuum. The residue was dissolved in 2 mL of H$_2$O, and the pH was adjusted to 4 with Na$_2$CO$_3$ (sat. aq.) at 0° C. The mixture was purified by prep-HPLC with the following conditions: Column, C18 silica gel; Mobile phase A: 0.05% TFA in H$_2$O, Mobile phase B: ACN; Gradient: 0%-58% B within 30 min; Detector, UV 254 nm. The collected fraction was concentrated under vacuum to give (E)-3-(2-(((6-(3-amino-3-oxopropyl)-1H-benzo[d]imidazol-2-yl)methyl)amino)phenyl)acrylic acid (65 mg, 75%) as a yellow solid. MS: (ES, m/z): 365 [M+H]$^+$.

Step-5: Synthesis of (E)-3-(2-(((6-(3-amino-3-oxopropyl)-1H-benzo[d]imidazol-2-yl)methyl)amino)phenyl)-N-hydroxyacrylamide Into a 8-mL vial, was placed (E)-3-(2-(((6-(3-amino-3-oxopropyl)-1H-benzo[d]imidazol-2-yl)methyl)amino)phenyl)acrylic acid (33 mg, 0.09 mmol, 1.00 equiv) in DMA (1 mL), NMM (9 mg, 0.09 mmol, 1.00 equiv) and IPCF (11 mg, 0.09 mmol, 1.00 equiv) and stirred at room temperature for 15 mins, then NH$_2$OH·HCl (12.4 mg, 0.18 mmol, 2.00 equiv) was added. The resulting solution was stirred overnight at room temperature. The mixture was purified by Prep-HPLC with the following conditions: Column: X Bridge C18, 19*150 mm, 5 um; Mobile Phase A: H$_2$O/ 0.05% TFA, Mobile Phase B: ACN; Flow rate: 20 mL/min; Gradient: 10-15% B in 8 min; 254 nm. The collected fraction was lyophilized to give (E)-3-(2-(((6-(3-amino-3-oxopropyl)-1H-benzo[d]imidazol-2-yl)methyl)amino)phenyl)-N-hydroxyacrylamide (8.2 mg, 18%) as a yellow oil. 1H-NMR (DMSO, 400 MHz) δ(ppm): 10.73 (s, 1H), 7.86-7.81 (m, 1H), 7.60-7.59 (d, J=4 Hz, 2H), 7.50 (s, 1H), 7.41-7.38 (m, 2H), 7.31-7.29 (m, 2H), 7.16-7.10 (m, 1H), 6.76-6.69 (m, 2H), 6.54-6.48 (d, 2H), 6.48-6.38 (m, 1H), 4.79 (s, 2H), 2.97-2.92 (t, 2H), 2.42-2.37 (t, 2H). MS: (ES, m/z): 380 [M+H]$^+$.

Example 34—of (E)-N-hydroxy-3-(2-(((6-(3-hydroxypropyl)-1H-benzo[d]imidazol-2-yl)methyl) amino)phenyl)acrylamide (I-116)

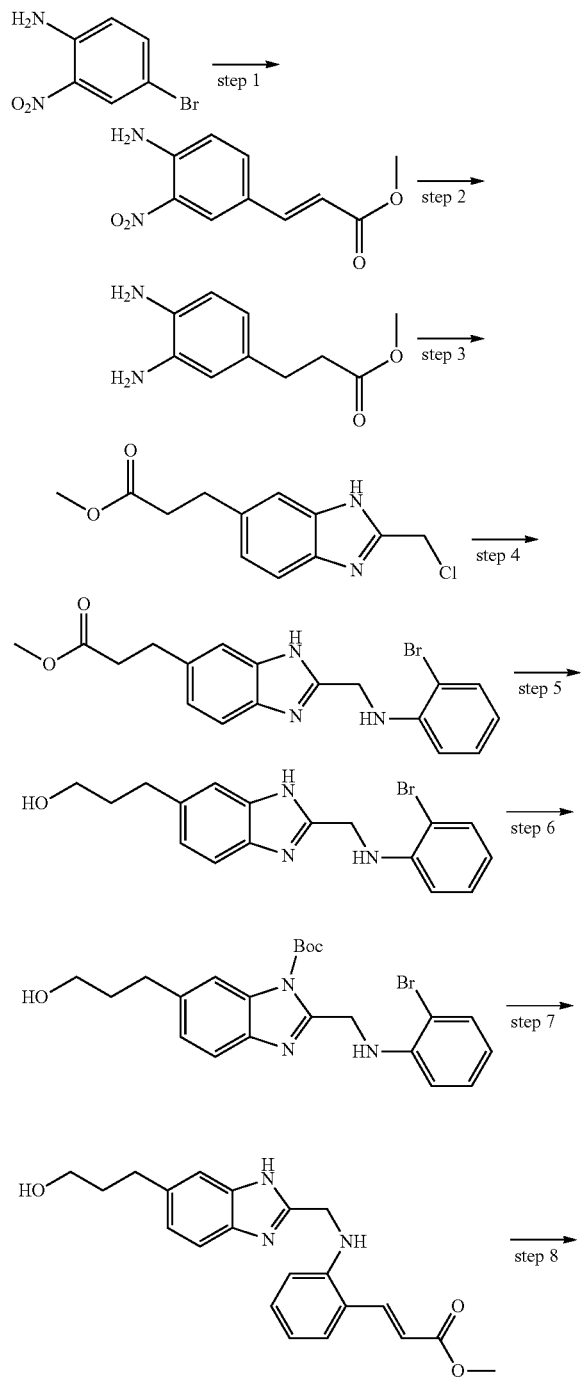

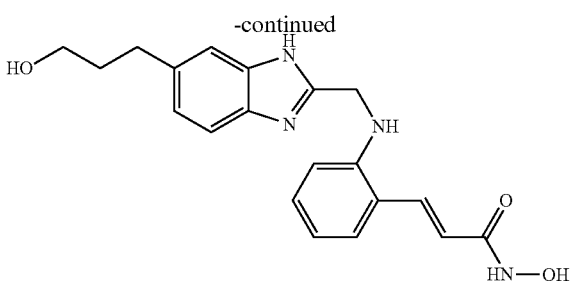

Step-1: Synthesis of methyl (E)-methyl 3-(4-amino-3-nitrophenyl)acrylate

Into a 150-mL sealed tube purged and maintained with an inert atmosphere of nitrogen, was placed 4-bromo-2-nitroaniline (10 g, 46.08 mmol, 1.00 equiv), DMF (60 mL). Pd(dppf)Cl$_2$·CH$_2$Cl$_2$ (1.89 g, 2.30 mmoL, 0.05 equiv), H$_2$O (1 mL), TEA (19.4 mL, 138.24 mmol, 3.00 equiv) and methyl prop-2-enoate (8.4 mL, 92.16 mmol, 2.00 equiv). The resulting solution was stirred overnight at 100° C. The reaction mixture was cooled to r.t and poured into 100 mL of brine. The resulting solution was extracted with 5×50 mL of ethyl acetate, washed with 100 mL of brine, dried over anhydrous Na$_2$SO$_4$ and concentrated under vacuum. The residue was dissolved in 30 mL of DCM/MeOH (10/1) and stirred for a while. Filtration was performed. The filtrate was collected and concentrated to give methyl (E)-methyl 3-(4-amino-3-nitrophenyl)acrylate (5.6 g, 55%) as a yellow green solid. MS: (ES, m/z): 223[M+H]$^+$.

Step-2: Synthesis of methyl 3-(3,4-diaminophenyl)propanoate

Into a 250-ml round-bottom flask, was placed a solution of methyl (E)-methyl 3-(4-amino-3-nitrophenyl)acrylate (850 mg, 3.83 mmol, 1.00 equiv), HOAc (1 mL) and Pd/C (10%, 170 mg) in MeOH (150 mL). To the above an atmosphere of H$_2$ (g) was introduced. The resulting solution was stirred for 1 h at room temperature. The solids were filtered out. The filtrate was concentrated under vacuum. The crude product was applied onto a silica gel column and eluted with ethyl acetate/petroleum ether (0-100%). The collected fraction was concentrated to afford methyl 3-(3,4-diaminophenyl)propanoate (460 mg, 62%) as yellow oil. MS: (ES, m/z): 195 [M+H]$^-$.

Step-3: Synthesis of methyl 3-(2-(chloromethyl)-1H-benzo[d]imidazol-6-yl)propanoate Into a 100-mL round-bottom flask, was placed a solution of methyl 3-(3,4-diaminophenyl)propanoate (460 mg, 2.37 mmol, 1.00 equiv), DCM (10 mL), p-toluenesulfonic acid (40.8 mg, 0.24 mmol, 0.10 equiv) and 2-chloro-1,1,1-trimethoxyethane (1095 mg, 7.08 mmol, 3.00 equiv). The resulting solution was stirred overnight at room temperature. The reaction was then quenched by the addition of 20 mL of H$_2$O. The resulting solution was extracted with 3×20 mL of DCM, dried over anhydrous Na$_2$SO$_4$, and concentrated under vacuum. The crude product was applied onto a silica gel column and eluted with ethyl acetate/petroleum ether. The collected fraction was concentrated to give methyl 3-(2-(chloromethyl)-1H-benzo[d]imidazol-6-yl)propanoate (650 mg, 109%/o) as a yellow solid. MS: (ES, m/z): 253 [M+H]$^-$.

Step-4: Synthesis of methyl 3-(2-(((2-bromophenyl)amino)methyl)-1H-benzo[d]imidazol-6-yl)propanoate Into a 100-mL round-bottom flask, was placed potassium carbonate (711.8 mg, 5.15 mmol, 2.00 equiv), KI (428.1 mg, 2.57mmoL, 1.00 equiv), 2-bromoaniline (882 mg, 5.16 mmol, 2.00 equiv), $CH_3CN$ (40 mL). Then methyl 3-(2-(chloromethyl)-1H-benzo[d]imidazol-6-yl)propanoate (650 mg, 2.57 mmol, 1.00 equiv) was added dropwise. The resulting mixture was stirred for 3 h at room temperature. The solids were filtered out. The filtrate was concentrated under vacuum. The residue was diluted with 20 mL of $H_2O$. The resulting solution was extracted with 3×20 mL of DCM, dried over anhydrous $Na_2SO_4$ and concentrated under vacuum. The crude product was applied onto a silica gel column and eluted with ethyl acetate/petroleum ether (30%-80%). The collected fraction was concentrated to give methyl 3-(2-(((2-bromophenyl)amino)methyl)-1H-benzo[d]imidazol-6-yl)propanoate (370 mg, 37%) as yellow oil. MS: (ES, m/z): 388[M+H]$^+$.

Step-5: Synthesis of 3-(2-(((2-bromophenyl)amino)methyl)-1H-benzo[d]imidazol-6-yl)propan-1-ol Into a 50-mL round-bottom flask, was placed a solution of methyl 3-(2-(((2-bromophenyl)amino)methyl)-1H-benzo[d]imidazol-6-yl)propanoate (370 mg, 0.95 mmol, 1.00 equiv) in THF (5 mL). This was followed by the addition of $LiAlH_4$ (7266 ng, 1.91 mmol, 2.00 equiv) at 0° C. The resulting solution was stirred for 5 min at 0° C. The reaction was then quenched by the addition of 0.07 mL of $H_2O$/0.07 ml NaOH (1 mol/L in $H_2O$)/0.21 mL of $H_2O$ in order. The mixture was stirred for 10 min. The solids were filtered out. The filtrate was concentrated under vacuum at ~20° C. The crude product was applied onto a silica gel column and eluted with DCM/MeOH (0-15%). The collected fraction was concentrated to give 3-(2-(((2-bromophenyl)amino)methyl)-1H-benzo[d]imidazol-6-yl)propan-1-ol (300 mg, 87%) as light yellow oil. MS: (ES, m/z): 360[M+H]$^+$.

Step-6: Synthesis of tert-butyl 2-(((2-bromophenyl)amino)methyl)-6-(3-hydroxypropyl)-1H-benzo[d]imidazole-1-carboxylate Into a 100-mL round-bottom flask, was placed a solution of 3-(2-(((2-bromophenyl)amino)methyl)-1H-benzo[d]imidazol-6-yl)propan-1-ol (300 mg, 0.83 mmol, 1.00 equiv), TEA (253 mg, 2.51 mmol, 3.00 equiv) in DCM (10 mL) Then di-tert-butyl dicarbonate (271 mg, 1.25 mmol, 1.50 equiv) was added at 0° C. The resulting solution was stirred overnight at room temperature. The reaction was concentrated under vacuum. The crude product was applied onto a silica gel column and eluted with ethyl acetate/petroleum ether (0-50%) The collected fraction was concentrated to give tert-butyl 2-(((2-bromophenyl)amino)methyl)-6-(3-hydroxypropyl)-1H-benzo[d]imidazole-1-carboxylate (290 mg, 75%) as an off-white solid. MS. (ES, m/z): 460[M+H]$^+$.

Step-7: Synthesis of (E)-methyl 3-(2-(((6-(3-hydroxypropyl)-1H-benzo[d]imidazol-2-yl)methyl)amino)phenyl)acrylate Into a 10-mL sealed tube purged and maintained with an inert atmosphere of nitrogen, was placed a solution of tert-butyl 2-(((2-bromophenyl)amino)methyl)-6-(3-hydroxypropyl)-1H-benzo[d]imidazole-1-carboxylate (150 mg, 0.33 mmol, 1.00 equiv) in DMF (2 mL) Pd(dppf) $CH_2 \cdot CH_2Cl_2$ (13.3 mg, 0.016mmoL, 0.05 equiv), $H_2O$ (0.03 mL), TEA (98.8 mg, 0.98 mmol, 3.00 equiv) and methyl prop-2-enoate (28.96 mg, 0.34 mmol, 1.00 equiv). The resulting mixture was stirred overnight at 100° C. The reaction was concentrated under vacuum. The crude product was purified by Flash with the following conditions: Column, C18 silica gel; Mobile phase A: 0.05% TFA in water, Mobile phase B: ACN. Gradient: 5%-88% B within 45 min; Detector, UV 254 nm. The collected fraction was concentrated to give (E)-methyl 3-(2-(((6-(3-hydroxypropyl)-1H-benzo[d]imidazol-2-yl)methyl)amino)phenyl)acrylate (50 mg, 35%) as a yellow solid MS: (ES, m/z): 366 [M+H]$^+$.

Step-8: Synthesis of (E)-N-hydroxy-3-(2-(((6-(3-hydroxypropyl)-1H-benzo[d]imidazol-2-yl)methyl)amino)phenyl)acrylamide Into a 25-mL round-bottom flask, was placed a solution of (E)-methyl 3-(2-(((6-(3-hydroxypropyl)-1H-benzo[d]imidazol-2-yl)methyl)amino)phenyl)acrylate (44 mg, 0.12 mmol, 1.00 equiv) in THF/MeOH (4/1) (2 mL). This was followed by the addition of $NH_2OH$ (50% in water, 119.3 mg, 7.2mmoL, 60.00 equiv) and NaOH (1 mol/L, 0.24 mL, 0.24 mmol, 2.00 equiv) at 0° C. The resulting solution was stirred for 1 h at room temperature, the pH was adjusted to 6 with HCl (2 mol/L) at 0° C., the resulting mixture was purified by Prep-HPLC with the following conditions: Column, XBridge Prep Shield RP18 OBD Column, 19*100 mm 5 um 13 nm; mobile phase, $H_2O$ with 0.05% TFA and ACN (15.0% ACN up to 24.0% in 10 min, hold 24.0% in 5 min); Detector, 220/254 nm. The collected fraction was lyophilized to give (E)-N-hydroxy-3-(2-(((6-(3-hydroxypropyl)-1H-benzo[d]imidazol-2-yl)methyl)amino)phenyl)acylamide (5.5 mg, 10%) as a brown solid. $^1$H-NMR (DMSO, 400 MHz) δ(ppm) 10.74 (s, 1H), 7.85-7.81 (m, 1H), 7.60-7.04 (m, 6H), 6.74-6.68 (m, 1H), 6.57-6.49 (m, 2H), 6.36 (d, J=16 Hz, 1H), 4.78 (s, 2H), 3.42-3.39 (t, 2H), 2.77-2.73 (t, 2H), 1.78-1.70 (m, 2H). MS: (ES, m/z): 367 [M+H]$^+$.

The following compounds in Table 10 were prepared according to the procedures for (E)-N-hydroxy-3-(2-(((6-(3-hydroxypropyl)-1H-benzo[d]imidazol-2-yl)methyl)amino) phenyl) acrylamide (I-116)

TABLE 10

| Ex. | Structure | Name | ¹HNMR | (ES, m/z) [M + H]⁺ |
|---|---|---|---|---|
| 1-4 | (structure) | (((6-(trifluoromethyl)-1H-benzo[d]imidazol-2-yl)methyl)amino)phenyl) acrylamide | (DMSO, 400 MHZ, ppm): 10.71 (s, 1H), 7.89 (s, 1H) , 7.84 (d, J = 16 Hz, 1H), 7.72 (d, J = 8 Hz, 1H), 7.52 (d, J = 8 Hz, 1H), 7.36 (d, J = 8 Hz, 1H), 7.10-7.07(m, 1H), 6.54 (d, J = 8 Hz, 1H), 6.35-6.31 (d, J = 16 Hz, 1H), 4.66 (s, 2H) | 377 |

Example 35—(E)-N-hydroxy-3-(2-(3-(trifluoromethyl)phenylsulfonamido)phenyl)acrylamide (I-7)

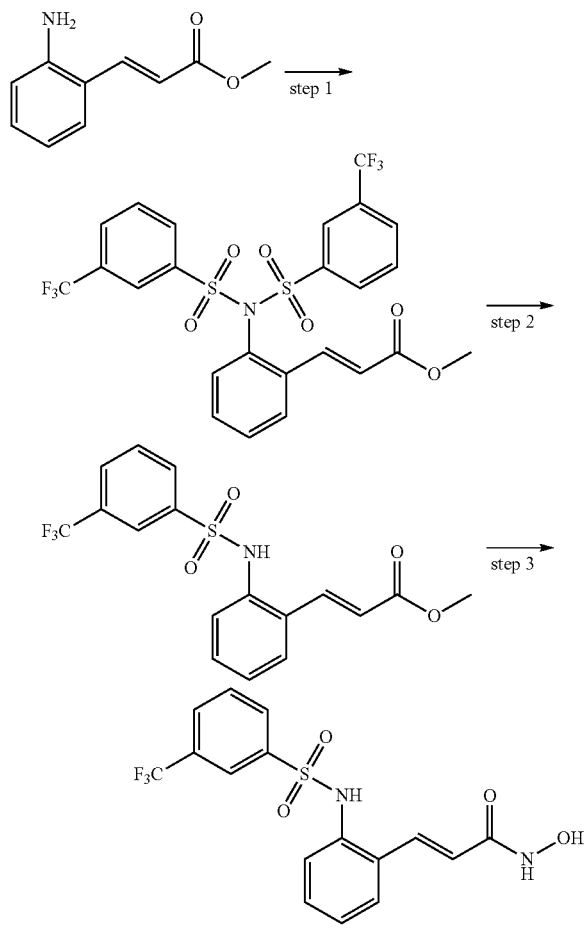

Step-1: Synthesis of (E)-methyl 3-(2-(3-(trifluoromethyl)-N-((3-(trifluoromethyl)phenyl)sulfonyl)phenylsulfonamido)phenyl)acrylate Into a 100-mL round-bottom flask, was placed methyl (2E)-3-(2-aminophenyl)prop-2-enoate (800 mg, 4.51 mmol, 1.10 equiv), TEA (456 mg, 4.51 mmol, 1.10 equiv) and DCM (15 mL) To this was added 3-(trifluoromethyl)benzene-1-sulfonyl chloride (1 g, 4.09 mmol, 1.00 equiv) dropwise with stirring at 0° C. The resulting solution was stirred overnight at room temperature. The reaction was quenched with 15 mL of H₂O, extracted with 3×15 mL of DCM, dried over anhydrous sodium sulfate and concentrated under vacuum. The crude product was purified by Flash with the following conditions: Column, C18 silica gel; mobile phase A: 0.05% TFA, mobile phase B: ACN, Flow rate 5-60% in 20 min; Detector, UV 254 nm. The collected fraction was concentrated under vacuum to give (E)-methyl 3-(2-(3-(trifluoromethyl)-N-((3-(trifluoromethyl)phenyl)sulfonyl) phenylsulfonamido)phenyl)acrylate (130 mg, 5%) as a light yellow solid. MS. (ES, m/z): 594 [M+H]⁺.

Step-2: Synthesis of (E)-methyl 3-(2-(3-(trifluoromethyl)phenylsulfonamido)phenyl)acrylate Into a 10-mL vial, was placed (E)-methyl 3-(2-(3-(trifluoromethyl)-N-((3-(trifluoromethyl)phenyl)sulfonyl)phenylsulfonamido)phenyl)acrylate (130 mg, 0.22 mmol, 1.00 equiv) in THF (2 mL) and tetra-n-butylammonium fluoride (1 mol/L, 0.26 mL, 1.20 equiv) The resulting solution was stirred overnight at room temperature. The reaction was then quenched by the addition of 5 mL of water, extracted with 3×10 mL of ethyl acetate, washed with 3×10 mL of brine, dried over anhydrous sodium sulfate and concentrated under vacuum. The residue was applied onto a silica gel column with ethyl acetate/petroleum ether. The collected fraction was concentrated to give (E)-methyl 3-(2-(3-(trifluoromethyl)phenylsulfonamido)phenyl)acrylate (50 mg, 59%) as a white solid MS: (ES, m/z): 386 [M+H]⁺.

Step-3: Synthesis of (E)-N-hydroxy-3-(2-(3-(trifluoromethyl)phenylsulfonamido)phenyl)acrylamide Into a 8-mL vial, was placed (E)-methyl 3-(2-(3-(trifluoromethyl)phenylsulfonamido)phenyl)acrylate (50 mg, 0.13 mmol, 1.00 equiv) in THF/MeOH (4/1) (1.5 mL). Then NaOH (1 mol/L, 0.26 mL, 0.26 mmoL, 2.00 equiv) and NH₂OH (50% in H₂O, 1.028 g, 15.6mmoL, 120.00 equiv) were added at 0° C. The resulting solution was stirred for 1 h at room temperature. The reaction mixture was cooled with a water/ice bath and the pH was adjusted to 6 with HCl (6 mol/L). The crude product was purified by Prep-HPLC with the following conditions: Column, Waters HSS C18, 2.1*50 mm, 1.8 um; Mobile Phase A: Water/0.05% TFA, Mobile Phase B: ACN; Flow rate: 0.7 mL/min; Gradient: 5% B to 95% B in 2.0 min, hold 0.6 min; 254 nm. The collected fraction was lyophilized to give (E)-N-hydroxy-3-(2-(3-(trifluoromethyl)phenylsulfonamido)phenyl)acrylamide (11.3 mg, 17%) as an off-white solid. $^1$H-NMR (DMSO, 400 MHz) δ(ppm): 10.71 (s, 1H), 10.23 (s, 1H), 9.01 (s, 1H), 8.03-8.01 (d, J=8.0 Hz, 1H), 7.98-7.93 (m, 2H), 7.86-7.72 (m, 2H), 7.68-7.55 (m, 2H), 7.31-7.21 (m, 2H), 6.86-6.84 (m, 1H), 6.27-6.24 (d, J=12.0 Hz, 1H). MS: (ES, m/z): 387 [M+H]$^+$.

Example 36—(E)-N-hydroxy-3-(2-(3-(3-(trifluoromethyl)phenyl)ureido)phenyl)acrylamide (I-5)

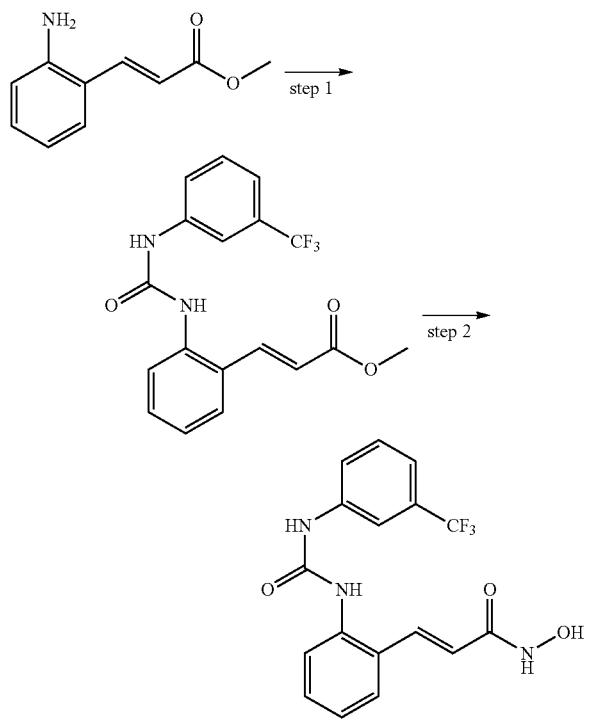

Step-1: Synthesis of (E)-methyl 3-(2-(3-(3-(trifluoromethyl)phenyl)ureido)phenyl)acrylate Into a 50-mL round-bottom flask, was placed a solution of 1-isocyanato-3-(trifluoromethyl)benzene (250 mg, 1.34 mmol, 1.00 equiv) in 1,4-dioxane (5 mL), methyl (E)-methyl 3-(2-aminophenyl)acrylate (238.5 ng, 1.35 mmol, 1.00 equiv) and 4-dimethylaminopyridine (163.5 mg, 1.34 mmol, 1.00 equiv). The resulting solution was stirred overnight at 80° C. The reaction was cooled to room temperature and diluted with 20 mL of water. The resulting solution was extracted with 3×20 mL of DCM, dried over anhydrous Na$_2$SO$_4$ and concentrated under vacuum. The residue was applied onto a silica gel column with DCM/MeOH (20/1). The collected fraction was concentrated to give (E)-methyl 3-(2-(3-(3-(trifluoromethyl)phenyl)ureido)phenyl)acrylate (160 mg, 33%) as a white solid. MS: (ES, m/z): 365 [M+H]$^+$.

Step-2: Synthesis of (E)-N-hydroxy-3-(2-(3-(3-((rifluoromethyl)phenyl)ureido)phenyl)acrylamide Into a 25-mL round-bottom flask, was placed a solution of (E)-methyl 3-(2-(3-(3-(trifluoromethyl)phenyl)ureido)phenyl)acrylate (160 mg, 0.44 mmol, 1.00 equiv) in THF/MeOH (4/1) (2 mL). This was followed by the addition of NaOH (1 mol/L in H$_2$O, 0.88 mL, 0.88mmoL, 2.00 equiv) and NH$_2$OH (50% in H$_2$O, 1.45 g, 22mmoL, 50.00 equiv) at 0° C. The resulting solution was stirred for 1 h at room temperature. The pH of the solution was adjusted to 6 with HCl (6 moL/L) at 0° C. The mixture was purified by Prep-HPLC with the following conditions: Column, Waters HSS C18; 1.8 um, 2.1*50 mm; Mobile phase A: H$_2$O with 0.05% TFA, Mobile phase B: CH$_3$CN; Gradient: 20%-60.0% B in 10 min; Detector, 254 nm. The collected fraction was lyophilized to give (E)-N-hydroxy-3-(2-(3-(3-(trifluoromethyl)phenyl)ureido)phenyl)acrylamide (35.5 mg, 22%) as an off-white solid. $^1$H-NMR (DMSO, 400 MHz) δ(ppm): 10.70 (s, 1H), 10.25 (s, 1H), 9.03 (s, 1H), 8.04-8.02 (m, 1H), 7.96-7.94 (m, 1H), 7.82-7.80 (m, 2H), 7.78-7.57 (m, 2H), 7.32-7.27 (m, 2H) 6.86 (d, J=16.0 Hz, 1H), 6.26 (d, J=16.0 Hz, 1H). MS: (ES, m/z): 366 [M+H]$^+$.

Example 37—(E)-N-hydroxy-3-(2-(((2-(trifluoromethyl)-[1,1'-biphenyl]-4-yl)methyl)amino)phenyl) acrylamide (I-120)

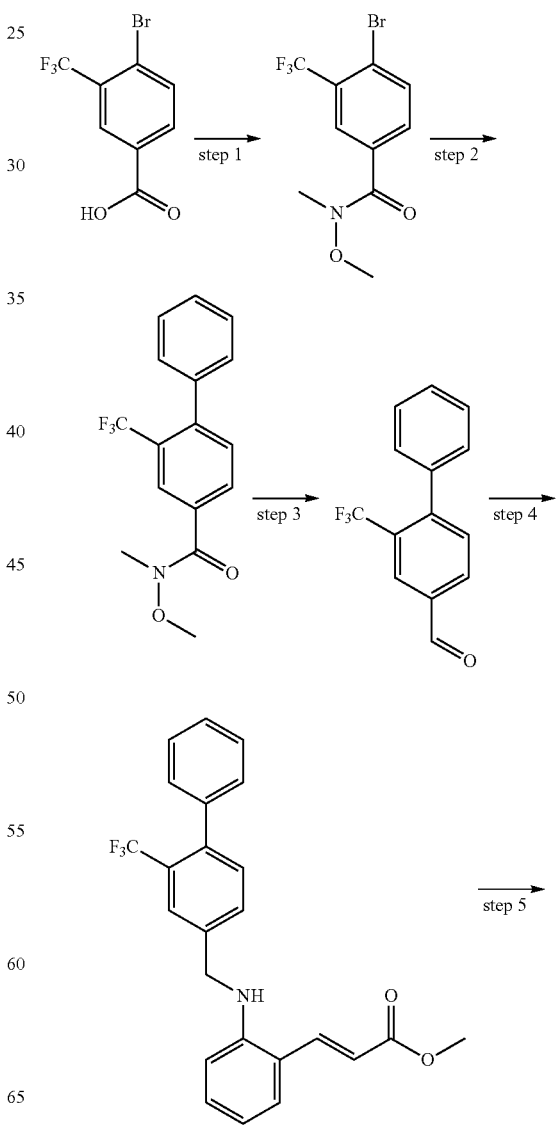

-continued

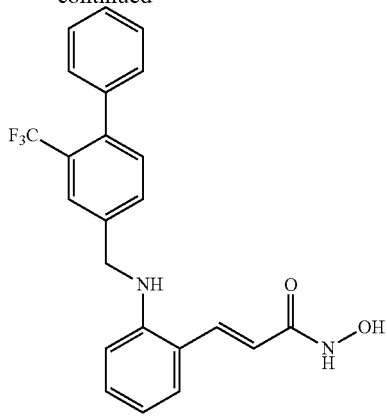

Step-1: Synthesis of 4-bromo-N-methoxy-N-methyl-3-(trifluoromethyl)benzamide Into a 100-mL round-bottom flask, was placed 4-bromo-3-(trifluoromethyl)benzoic acid (2 g, 7.43 mmol, 1.00 equiv) in DMF (20 mL), DIEA (2.89 g, 22.36 mmol, 3.00 equiv), HATU (3.4 g, 8.94 mmol, 1.20 equiv) and methoxy(methyl)amine hydrochloride (723 mg, 7.41 mmol, 1.00 equiv). The resulting solution was stirred overnight at room temperature. The reaction was then quenched by the addition of 20 mL of $H_2O$. The resulting solution was extracted with 3×10 mL of DCM, washed with 4×20 mL of brine, dried over anhydrous sodium sulfate, filtered and concentrated under vacuum. The crude product was applied onto a silica gel column with DCM/MeOH (0-5%). The collected fraction was concentrated to give 4-bromo-N-methoxy-N-methyl-3-(trifluoromethyl)benzamide (2.19 g, 94%) as an off-white solid MS: (ES, m/z): 312 [M+H]$^+$.

Step-2: Synthesis of N-methoxy-N-methyl-4-phenyl-3-(trifluoromethyl)benzamide Into a 250-mL 3-necked round-bottom flask purged and maintained with an inert atmosphere of nitrogen, was placed 4-bromo-N-methoxy-N-methyl-3-(trifluoromethyl)benzamide (1 g, 3.20 mmol, 1.00 equiv), phenylboronic acid (585 mg, 4.8mmoL, 1.5 equiv), 1,4-dioxane (20 mL), Pd(dppf)$CH_2 \cdot CH_2Cl_2$ (130.5 mg, 0.05 equiv), $K_2CO_3$ (883 mg, 6.39 mmol, 2.00 equiv) and $H_2O$ (6 mL). The resulting solution was stirred overnight at 90° C. in an oil bath. The reaction mixture was cooled to room temperature and then poured into 20 mL of water. The resulting solution was extracted with 4×20 mL of EA, dried over anhydrous $Na_2SO_4$, filtered and concentrated under vacuum. The crude product was applied onto a silica gel column with ethyl acetate/petroleum ether (0-70%). The collected fraction was concentrated to afford N-methoxy-N-methyl-4-phenyl-3-(trifluoromethyl)benzamide (960 mg, 69%) as yellow oil. MS: (ES, m/z): 310 [M+H]$^+$.

Step-3: Synthesis of 4-phenyl-3-(trifluoromethyl)benzaldehyde

Into a 100-mL 3-necked bottom flask purged and maintained with an inert atmosphere of nitrogen, was placed a solution of N-methoxy-N-methyl-4-phenyl-3-(trifluoromethyl)benzamide (500 mg, 1.62 mmol, 1.00 equiv) in THF (15 mL). This was followed by the addition of LiAlH$_4$ (123 mg, 3.24 mmol, 2.00 equiv) at −78° C. The resulting solution was stirred for 30 min at −78° C. The reaction was then quenched by the addition of 0.12 mL of $H_2O$, 0.12 ml of NaOH (1 mol/L in $H_2O$) and 0.36 ml of $H_2O$ in order, and stirred for an additional 10 min. The solids were filtered out. The filtrate was concentrated under vacuum. The crude product was applied onto a silica gel column with ethyl acetate/petroleum ether (0-90%). The collected fraction was concentrated to afford 4-phenyl-3-(trifluoromethyl)benzaldehyde (250 mg, 62%) as off-white oil. MS: (ES, m/z): 251 [M+H]$^+$.

Step-4: Synthesis of methyl (2E)-3-[2-([[4-phenyl-3-(trifluoromethyl)phenyl]methyl]amino)phenyl]prop-2-enoate Into a 50-mL round-bottom flask, was placed a solution of 4-phenyl-3-(trifluoromethyl)benzaldehyde (100 mg, 0.40 mmol, 1.00 equiv) and methyl (2E)-3-(2-aminophenyl)prop-2-enoate (70.8 mg, 0.40 mmol, 1.00 equiv) in acetic acid (10 mL). The mixture was stirred for 30 min at room temperature. Then NaBH$_3$CN (75.6 mg, 1.20 mmol, 3.00 equiv) was added at 0° C. The resulting solution was stirred for 30 min at room temperature. The resulting mixture was concentrated under vacuum. The crude product was applied onto a silica gel column with ethyl acetate/petroleum ether (0-70%). The collected fraction was concentrated to afford methyl (2E)-3-[2-([[4-phenyl-3-(trifluoromethyl)phenyl]methyl]amino)phenyl]prop-2-enoate (170 mg, crude) as a yellow solid. MS: (ES, m/z): 412 [M+H]$^+$.

Step-5: Synthesis of (2E)-N-hydroxy-3-[2-([[4-phenyl-3-(trifluoromethyl)phenyl]methyl]amino)phenyl]prop-2-enamide Into a 25-mL round-bottom flask, was placed a solution of methyl (2E)-3-[2-([[4-phenyl-3-(trifluoromethyl)phenyl]methyl]amino)phenyl]prop-2-enoate (80 mg, 0.19 mmol, 1.00 equiv) in THF/MeOH (4/1) (1.5 mL). This was followed by the addition of NaOH (1 mol/L, 0.39 mL, 0.39mmoL, 2.00 equiv) and NH$_2$OH (50% in $H_2O$, 770 mg, 11.4mmoL, 60.00 equiv) at 0° C. The resulting solution was stirred for 3 h at room temperature. The reaction mixture was cooled to 0° C. with a water/ice bath. The pH was adjusted to 6 with HCl (6moL/L). The crude product was purified by Prep-HPLC with the following conditions: Column, Sunfire C18, 19*150 mm; mobile phase, 0.1% TFA in Water and CH$_3$CN (35% CH$_3$CN up to 75% in 7 min, up to 95% in 1 min, hold 95% in 1 min, down to 35% in 2 min, hold 35% in 2 min); Detector, UV 220&254 nm. The collected fraction was lyophilized to give (2E)-N-hydroxy-3-[2-([[4-phenyl-3-(trifluoromethyl)phenyl]methyl]amino)phenyl]prop-2-enamide (21.2 mg, 26%) as a yellow solid. $^1$H-NMR (DMSO, 300 MHz) δ(ppm): δ10.82-10.11 (br, 1H), 8.06-8.02 (m, 2H), 7.84-7.79 (m, 1H), 7.43-7.28 (m, 6H), 7.12-7.07 (t, 1H), 6.63-6.52 (m, 2H), 6.35-6.30 (d, J=15.0 Hz, 1H), 4.49 (s, 2H) MS: (ES, m/z): 413 [M+H]$^+$.

Example 38—(E)-3-(2-(((4,5-dichloro-1 l-imidazol-2-yl)methyl)amino)phenyl)-N-hydroxyacrylamide (I-515)

Step-1: Synthesis of (4,5-dichloro-1H-imidazol-2-yl)methanol

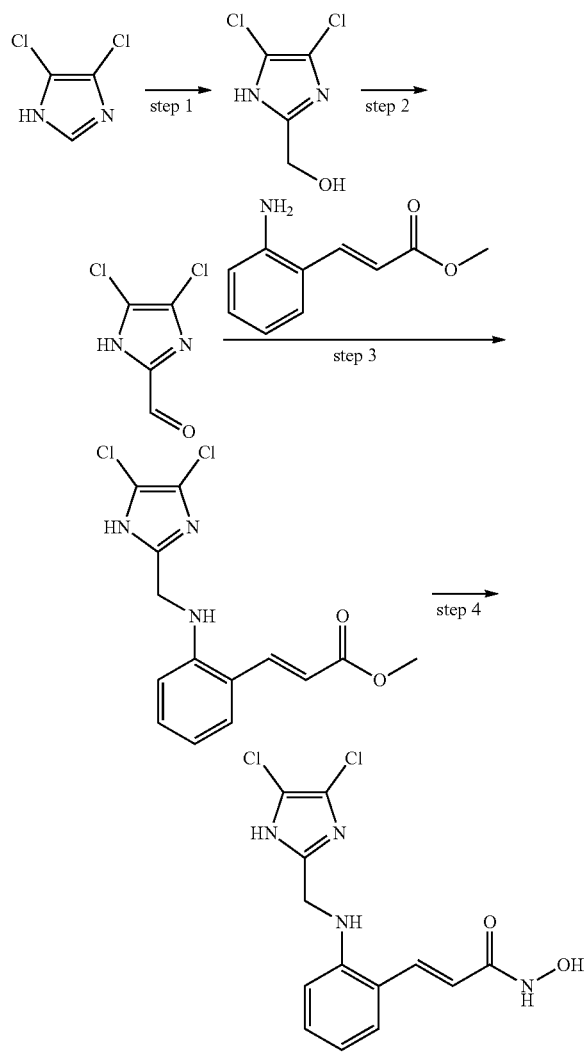

Into a 50-mL round-bottom flask, was placed 4,5-dichloro-1H-imidazole (5 g, 36.51 mmol, 1.00 equiv) in water (36 mL), sodium hydroxide (1.46 g, 36.50 mmol, 1.00 equiv) and formaldehyde (3.65 mL, 36.5 mmol, 1.00 equiv, 37%). The resulting solution was stirred for 2 h at room temperature. The pH was adjusted to 4 with HCl (2 mol/L) at 0° C. The solids were collected by filtration to give (4,5-dichloro-1H-imidazol-2-yl)methanol (4.9 g, 80%) as a white solid. MS: (ES, m/z): 167 [M+H]$^+$.

Step-2: Synthesis of 4,5-dichloro-1H-imidazole-2-carbaldehyde

Into a 100-mL round-bottom flask, was placed (4,5-dichloro-1H-imidazol-2-yl)methanol (1.3 g, 7.78 mmol, 1.00 equiv) in CH$_3$CN (50 mL) and dioxomanganese (3.39 g, 38.99 mmol, 5.00 equiv). The resulting solution was stirred for 16 h at 60° C. in an oil bath. The solids were filtered out. The filtrate was concentrated under vacuum to give 4,5-dichloro-1H-imidazole-2-carbaldehyde (1.3 g, crude) as a yellow solid. MS: (ES, m/z): 165[M+H]$^+$.

Step-3: Synthesis of (E)-methyl 3-(2-(((4,5-dichloro-1H-imidazol-2-yl)methyl)amino)phenyl)acrylate Into a 50-mL round-bottom flask, was placed 4,5-dichloro-1H-imidazole-2-carbaldehyde (500 mg, 3.03 mmol, 1.00 equiv), acetic acid (10 mL) and methyl (2E)-3-(2-aminophenyl)prop-2-enoate (540 mg, 3.05 mmol, 1.00 equiv). After stirring for 1 h at room temperature, Na(CN)BH$_3$ (0.58 g, 9.1 mmoL, 3.00 equiv) was added. The resulting solution was stirred overnight at room temperature and then concentrated under vacuum. The crude product was applied onto a silica gel column with ethyl acetate/petroleum ether (70/30). The collected fraction was concentrated to afford (E)-methyl 3-(2-(((4,5-dichloro-1H-imidazol-2-yl)methyl)amino)phenyl)acrylate (0.33 g, 33%) as a yellow solid. MS: (ES, m/z): 326 [M+H]$^+$.

Step-4: Synthesis of (E)-3-(2-(((4,5-dichloro-1H-imidazol-2-yl)methyl)amino)phenyl)-N-hydroxyacrylamide Into a 25-mL round-bottom flask, was placed (E)-methyl 3-(2-(((4,5-dichloro-1H-imidazol-2-yl)methyl)amino)phenyl)acrylate (100 mg, 0.31 mmol, 1.00 equiv) in THF/MeOH (4/1) (2 mL). Then NH$_2$OH (50% in H$_2$O, 1.22 g, 18.6 mmol, 60.00 equiv) and NaOH (1moL/L, 0.62 mL, 0.62 mmoL, 2.00 equiv) were added at 0° C. The resulting solution was stirred for 1 h at room temperature. The pH was adjusted to 6 with HCl (1 mol/L) at 0° C. The mixture was purified by Prep-HPLC with the following conditions: Column: X Bridge C18, 19*150 mm, 5 um; Mobile Phase A: Water/10 mM NH$_4$HCO$_3$. Mobile Phase B: ACN; Flow rate: 20 mL/min; Gradient: 24-40% B in 8 min; 254 nm. The collected fraction was lyophilized to give (E)-3-(2-(((4,5-dichloro-1H-imidazol-2-yl)methyl)amino)phenyl)-N-hydroxyacrylamide (6.7 mg, 7%) as a yellow solid. $^1$H-NMR (DMSO, 400 MHz) δ(ppm): 11.00-10.40 (br, 1H), 9.01-8.95 (br, 1H), 7.78-7.72 (m, 1H), 7.34-7.32 (m, 1H), 7.16-7.11 (t, 1H), 6.67-6.64 (t, 1H), 6.55-6.49 (t, 1H), 6.32-6.26 (m, 1H), 6.21-6.17 (m, 1H), 4.27-4.25 (d, 2H). MS: (ES, m/z): 327 [M+H]$^+$ Example 39—(E)-3-(2-(((4,5-dichloro-1-methyl-1H-imidazol-2-yl)methyl)amino)phenyl)-N-hydroxyacrylamide (I-121)

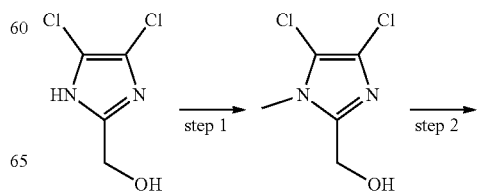

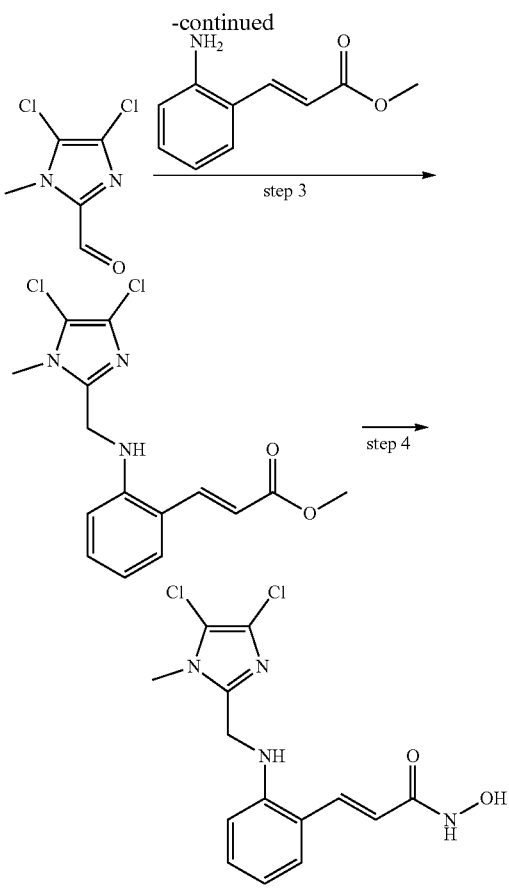

Step-1: Synthesis of (4,5-dichloro-1-methyl-1H-imidazol-2-yl)methanol

Into a 100-mL round-bottom flask, was placed a solution of (4,5-dichloro-1H-imidazol-2-yl)methanol (2 g, 11.98 mmol, 1.00 equiv) in methanol (20 mL). Then sodium hydroxide (241 mg, 6.03 mmol, 1.00 equiv) and CH₃I (1.7 g, 11.98 mmol, 2.00 equiv) were added at 0° C. The resulting solution was stirred for 12 h at room temperature. The resulting mixture was concentrated under vacuum. The crude product was applied onto a silica gel column with MeOH/DCM (0-75%). The collected fraction was concentrated to give (4,5-dichloro-1-methyl-1H-imidazol-2-yl) methanol (600 mg, 28%) as a yellow solid. MS: (ES, m/z): 181 [M+H]⁺.

Step-2: Synthesis of 4,5-dichloro-1-methyl-1H-imidazole-2-carbaldehyde

Into a 100-mL round-bottom flask, was placed a solution of (4,5-dichloro-1-methyl-1H-imidazol-2-yl)methanol (600 mg, 3.31 mmol, 1.00 equiv) and dioxomanganese (1.45 g, 16.68 mmol, 5.00 equiv) in ACN (20 mL). The resulting solution was stirred overnight at 60° C. in an oil bath. The reaction mixture was cooled to room temperature. The solids were filtered out. The filtrate was concentrated under vacuum to give 4,5-dichloro-1-methyl-1H-imidazole-2-carbaldehyde (580 mg, 98%) as a yellow solid. MS: (ES, m/z): 179 [M+H]⁺.

Step-3: Synthesis of (E)-methyl 3-(2-(((4,5-dichloro-1-methyl-1H-imidazol-2-yl)methyl)amino)phenyl)acrylate Into a 50-mL round-bottom flask, was placed a solution of 4,5-dichloro-1-methyl-1H-imidazole-2-carbaldehyde (580 mg, 3.24 mmol, 1.00 equiv) and methyl (2E)-3-(2-aminophenyl)prop-2-enoate (580 mg, 3.27 mmol, 1.00 equiv) in acetic acid (20 mL). After stirring for 1 h at room temperature, Na(CN)BH₃ (615 mg, 9.79 mmol, 3.00 equiv) was added with stirring at 0° C. The resulting solution was stirred for an additional 30 min at 0° C. The resulting mixture was concentrated under vacuum. The crude product was applied onto a silica gel column with ethyl acetate/petroleum ether (0-75%) The collected fraction was concentrated to give (E)-methyl 3-(2-(((4,5-dichloro-1-methyl-1H-imidazol-2-yl)methyl)amino)phenyl)acrylate (680 mg, 62%) as a yellow solid. MS: (ES, m/z): 340 [M+H]⁻.

Step-4: Synthesis of (E)-3-(2-(((4,5-dichloro-1-methyl-1H-imidazol-2-yl)methyl)amino)phenyl)-N-hydroxyacrylamide Into a 25-mL round-bottom flask, was placed a solution of (E)-methyl 3-(2-(((4,5-dichloro-1-methyl-1H-imidazol-2-yl)methyl)amino)phenyl)acrylate (100 mg, 0.29 mmol, 1.00 equiv) in THF/MeOH (4/1) (2 mL). This was followed by the addition of NaOH (1 mol/L in H₂O, 0.59 mL, 0.59mmoL, 2.00 equiv) and NH₂OH (1.17 g, 17.4 mmol, 60.00 equiv, 50% in H₂O) at 0° C. The resulting solution was stirred for 1.5 h at room temperature. The pH was adjusted to 6 with HCl (6 moL/L) at 0° C. The crude product was purified by Prep-HPLC with the following conditions: Column: Sunfire C18, 19*150 mm; Mobile Phase A: Water/0.05% TFA, Mobile Phase B: ACN, Flow rate: 0.7 mL/min; Gradient: 25% B to 50% B in 6.0 min; 254 nm. The collected fraction was lyophilized to give (E)-3-(2-(((4,5-dichloro-1-methyl-1H-imidazol-2-yl)methyl)amino)phenyl)-N-hydroxyacryl-amide (49 mg, 37%) as a yellow solid. ¹H-NMR (DMSO, 300 MHz) δ(ppm): 11.00-9.60 (br, 1H), 7.73-7.67 (m, 1H), 7.33-7.31 (m, 1H), 7.19-7.14 (m, 1H), 6.82 (d, J=12.0 Hz, 1H), 6.67-6.62 (t, 1H), 6.31-6.26 (m, 1H), 4.36 (s, 2H), 3.63 (s, 3H). MS: (ES, m/z): 341[M+H]⁺.

Example 40—(E)-N-hydroxy-3-(2-((4-(methylsulfonyl)benzyl)amino)phenyl)acrylamide (I-95)

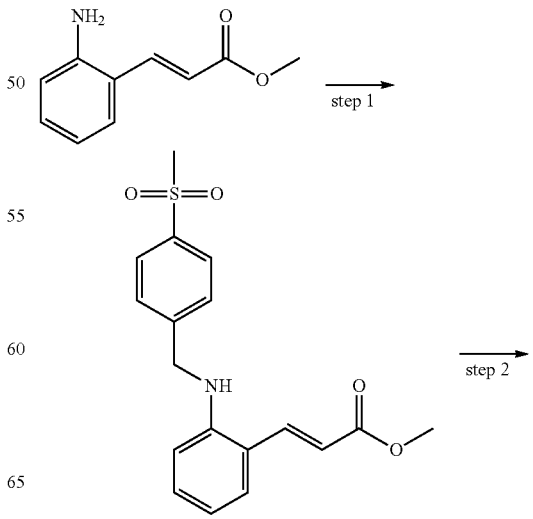

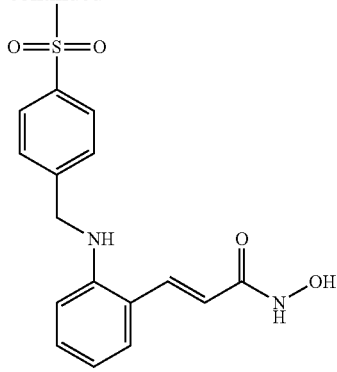

Step-1: Synthesis of (E)-methyl 3-(2-((4-(methylsulfonyl)benzyl)amino)phenyl)acrylate Into a 50-mL round-bottom flask, was placed a solution of 4-methanesulfonylbenzaldehyde (200 mg, L 09 mmol, 1.05 equiv) and methyl (2E)-3-(2-aminophenyl)prop-2-enoate (183.2 mg, 1.03 mmol, 1.00 equiv) in DCM (10 mL). After stirred for 30 min, Na(OAc)₃BH (2.183 g, 17.34 mmol, 10.00 equiv) was added. The resulting solution was stirred for overnight at room temperature. The reaction was then quenched by the addition of 10 mL of H₂O. The resulting solution was extracted with 3×10 mL of DCM, washed with 3×10 mL of brine, dried over anhydrous Na₂SO₄ and concentrated under vacuum. The crude product was purified by Flash with the following conditions: Column, C18 silica gel; Mobile Phase A: H₂O/0.05% TFA, Mobile Phase B: ACN Gradient: 5% B to 10% B within 30 min, Detector, UV 254 nm. The collected fraction was concentrated under vacuum to give (E)-methyl 3-(2-((4-(methylsulfonyl)benzyl)amino)phenyl)acrylate (100 mg, 28%) as a green solid. MS: (ES, m/z): 340 [M+H]⁺.

Step-2: Synthesis of (E)-N-hydroxy-3-(2-((4-(methylsulfonyl)benzyl)amino)phenyl)acrylamide Into a 50-mL round-bottom flask, was placed methyl (2E)-3-(2-[[(4-methanesulfonylphenyl)methyl]amino]phenyl)prop-2-enoate (80 mg, 0.23 mmol, 1.00 equiv) in THF/MeOH (4/1) (1.5 mL). This was followed by the addition of NaOH (1moL/L, 0.46 mL, 0.46moL, 2.00 equiv) and NH₂OH (50% in water, 1.836 g, 27.6mmoL, 120.00 equiv) at 0° C. The resulting solution was stirred for 1 h at room temperature. The pH was adjusted to 6 with HCl (6 mol/L) at 0° C. The crude product was purified by Flash with the following conditions: Column: Waters HSS C18, 2.1*50 mm, 1.8 um; Mobile Phase A: Water/0.05% TFA, Mobile Phase B: ACN; Flow rate: 0.7 mL/min; Gradient: 5% B to 95% B in 2.0 min, hold 0.6 min; 254 nm. The collected fraction was lyophilized to give (E)-N-hydroxy-3-(2-((4-(methylsulfonyl)benzyl)amino)phenyl)acrylamide (31.4 mg, 29%) as a green solid. ¹H-NMR (DMSO, 400 MHz) δ(ppm): 10.67 (s, 1H), 7.87-7.77 (m, 3H), 7.61-7.59 (m, 2H), 7.32-7.30 (m, 1H), 7.05-7.01 (t, 1H), 6.59-6.55 (t, 1H), 6.40 (d, J=8.0 Hz, 1H), 6.30 (d, J=16.0 Hz, 1H), 4.46 (s, 2H), 3.17 (s, 3H). MS: (ES, m/z): 347 [M+H]⁺.

The following compounds in Table 11 were prepared according to the procedures for (E)-N-hydroxy-3-(2-((4-(methylsulfonyl)benzyl)amino)phenyl)acrylamide (I-95)

TABLE 11

| Ex. | Structure | Name | ¹HNMR | (ES, m/z) [M + H]⁺ |
|---|---|---|---|---|
| I-100 | 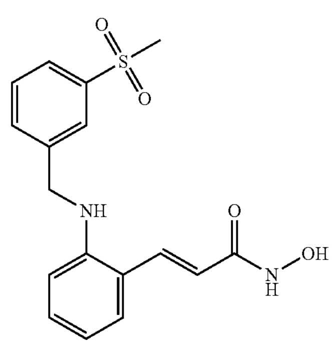 [SMILES: CS(=O)(=O)c1cccc(CNc2ccccc2/C=C/C(=O)NO)c1] | (E)-N-hydroxy-3-(2((3-(methylsulfonyl)benzyl)amino)phenyl)acrylamide | (DMSO, 400 MHz, ppm): 10.66 (s, 1H), 7.93 (s, 1H), 7.81-7.79 (m, 1H), 7.77 (s, 1H), 7.71-7.69 (m, 1H), 7.61-7.57 (1, 1H), 7.33-7.31 (m, 1H), 7.08-7.03(t, 1H), 6.60-6.56 (t, 1H), 6.46-6.44 (d. J = 8.0 Hz, 1H), 6.32-6.29 (d, J = 12.0 Hz, 1H), 4.46 (s, 2H), 3.18 (s, 3H) | 347 |

Example 41—Preparation of (E)-3-(2-(((6-cyano-1H-benzo[d]imidazol-2-yl)methyl)amino)phenyl)-N-hydroxyacrylamide (I-51)

Step-1: Synthesis of 2-(chloromethyl)-1H-1,3-benzodiazole-6-carbonitrile

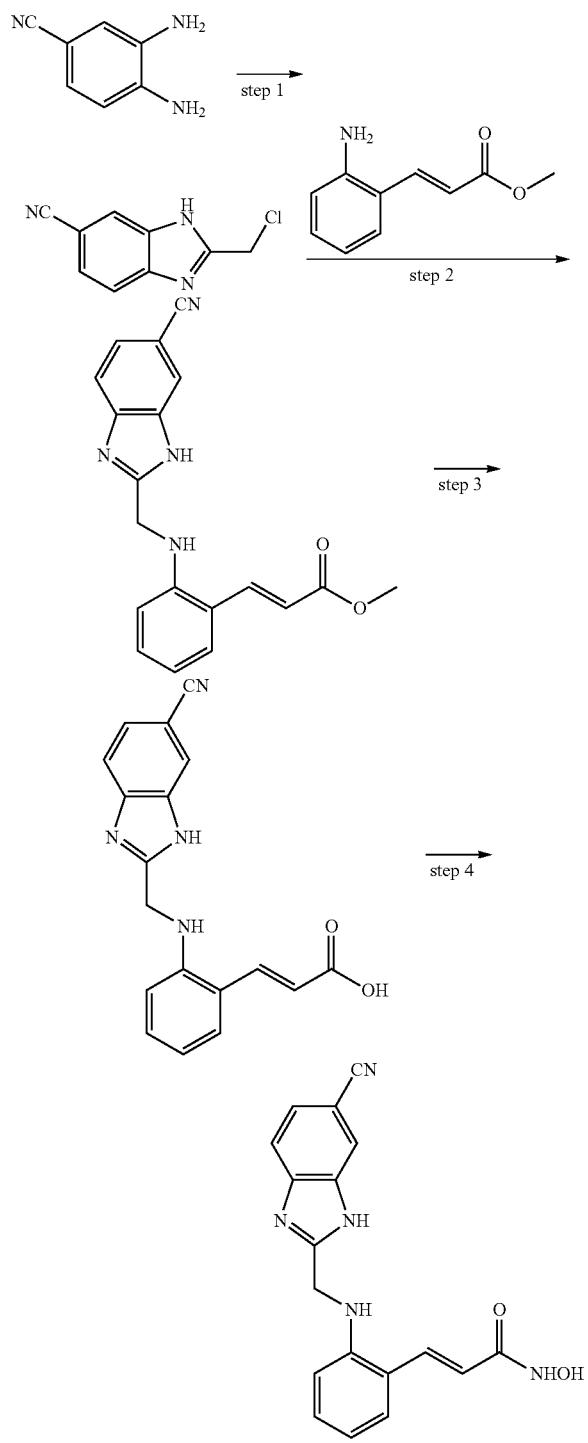

Into a 50-mL round-bottom flask, was placed 3,4-diaminobenzonitrile (500 mg, 3.76 mmol, 1.00 equiv), dichloromethane (10 mL), p-toluenesulfonic acid (64.75 mg, 0.38 mmol, 0.10 equiv), 2-chloro-1,1,1-trimethoxyethane (1.74 g, 11.26 mmol, 3.00 equiv) The resulting solution was stirred for 4 h at room temperature. The reaction was then quenched by the addition of 5 mL of water. The solids were collected by filtration to give 2-(chloromethyl)-1H-1,3-benzodiazole-6-carbonitrile (910 mg, crude) as a brown solid. MS: (ES, m/z) 192 [M+H]$^+$.

Step-2: Synthesis of methyl (2E)-3-(2-[[(6-cyano-1H-1,3-benzodiazol-2-yl)methyl]amino]phenyl)prop-2-enoate Into a 25-mL round-bottom flask, was placed 2-(chloromethyl)-1H-1,3-benzodiazole-6-carbonitrile (150 mg, 0.78 mmol, 1.00 equiv), acetonitrile (3 mL), methyl (2E)-3-(2-aminophenyl)prop-2-enoate (152.8 mg, 0.86 mmol, 1.10 equiv) and potassium carbonate (216.5 mg, 1.56 mmol, 2.00 equiv) The resulting solution was stirred for 5 h at 40° C. in an oil bath. The reaction was then quenched by the addition of 2 mL of water. The resulting solution was extracted with 3×5 mL of dichloromethane, dried over anhydrous sodium sulfate, filtered and concentrated under vacuum. The residue was applied onto a silica gel column with ethyl acetate/petroleum ether. The collected fraction was concentrated to give methyl (2E)-3-(2-[[(6-cyano-1H-1,3-benzodiazol-2-yl)methyl]amino]phenyl)prop-2-enoate (130 mg, 50%) as a yellow solid. MS: (ES, m/z): 333 [M+H]$^+$.

Step-3: Synthesis of (E)-3-(2-(((6-cyano-1H-benzo[d]imidazol-2-yl)methyl)amino)phenyl)acrylic acid Into a 25-mL round-bottom flask, was placed methyl (2E)-3-(2-[[(6-cyano-1H-1,3-benzodiazol-2-yl)methyl]amino]phenyl)prop-2-enoate (130 mg, 0.39 mmol, 1.00 equiv) in tetrahydrofuran (2 mL) and LiOH (1 mol/L in water, 1.2 mL, 1.2 mmoL, 5.00 equiv). The resulting solution was stirred overnight at room temperature. The pH was adjusted to 6 with HCl (6 mol/L) at 0° C. The resulting mixture was concentrated under vacuum. The residue was applied onto a C18 column with 0.05% TFA in $H_2O/CH_3CN$ (5%~60%). The collected fraction was concentrated under vacuum to give (E)-3-(2-(((6-cyano-1H-benzo[d]imidazol-2-yl)methyl)amino)phenyl)acrylic acid (100 mg, 80%) as a yellow solid. MS: (ES, m/z): 319 [M+H]$^+$.

Step-4: Synthesis of (E)-3-(2-(((6-cyano-1H-benzo[d]imidazol-2-yl)methyl)amino)phenyl)-N-hydroxyacrylamide Into a 25-mL round-bottom flask, was placed a solution of (E)-3-(2-(((6-cyano-1H-benzo[d]imidazol-2-yl)methyl)amino)phenyl)acrylic acid (50 mg, 0.16 mmol, 1.00 equiv) in DMA (1 mL), NMM (15.86 mg, 0.16 mmol, 1.00 equiv), isopropyl chloroformate (19.15 ng, 0.16 mmol, 1.00 equiv) and NH2OH·HCl (10.85 mg, 0.16 mmol, 1.00 equiv). The resulting solution was stirred for 30 min at room temperature. The mixture was purified by Prep-HPLC with the following conditions: Column, Waters HSS C18, 2.1*50 mm, 1.8 um; Mobile Phase A: Water/0.05% TFA, Mobile Phase B: ACN, Flow rate: 0.7 mL/min; Gradient: 5% B to 95% B in 2.0 min, hold 0.6 min; 254 nm. The collected fraction was lyophilized to give (E)-3-(2-(((6-cyano-1H-benzo[d]imidazol-2-yl)methyl)amino)phenyl)-N-hydroxyacrylamide (6.8 mg, 10%) as a yellow solid. $^1$H-NMR (DMSO, 400 MHz) δ(ppm): 7.70 (d, J=8.4 Hz, 1H), 7.60 (d, J=8.4 Hz, 1H), 7.36 (d, J=7.5 Hz, 1H), 7.11-7.06 (t, 1H), 6.67-6.62 (t, 1H), 6.54 (d, J=8.1 Hz, 1H), 6.34 (d, J=15.3 Hz, 1H), 4.66 (s, 2H). MS: (ES, m/z): 334 [M+H]⁺.

Example 42—(E)-N-hydroxy-3-(2-((3-(3-hydroxy-propyl)benzyl)amino)phenyl)acrylamide (I-48)

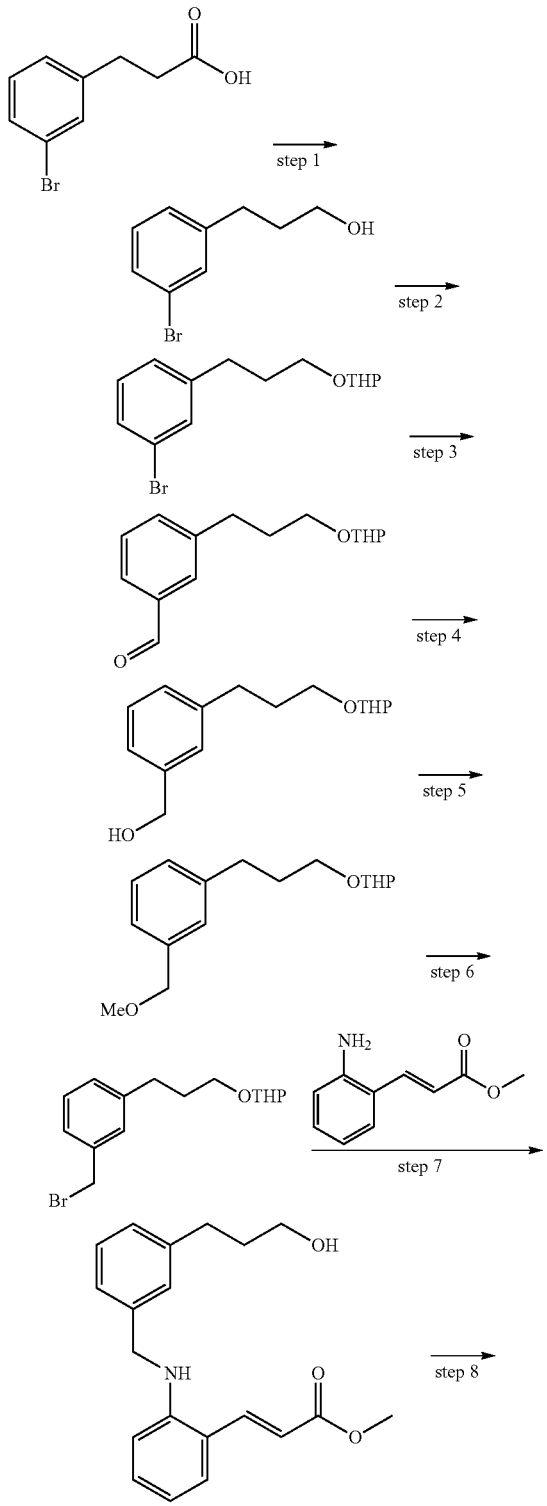

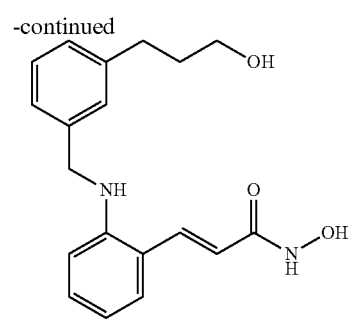

Step-1: Synthesis of 3-(3-bromophenyl)propan-1-ol

Into a 100-mL 3-necked round-bottom flask, was placed 3-(3-bromophenyl)propanoic acid (3 g, 13.10 mmol, 1.00 equiv) in tetrahydrofuran (30 mL). This was followed by the addition of borane dimethyl sulfide complex (1.68 mL) dropwise with stirring at 0° C. The resulting solution was stirred overnight at room temperature. The reaction was then quenched by the addition of 50 mL of NH₄Cl aq. The resulting solution was extracted with 3×50 mL of ethyl acetate, dried over anhydrous sodium sulfate and concentrated under vacuum. The collected fraction was concentrated to give 3-(3-bromophenyl)propan-1-ol (3.2 g, crude) as yellow oil which was used to the next step without any purification.

Step-2: Synthesis of 2-(3-(3-bromophenyl)propoxy)tetrahydro-2H-pyran

Into a 100-mL round-bottom flask, was placed 3-(3-bromophenyl)propan-1-ol (3.2 g, 14.88 mmol, 1.00 equiv) in dichloromethane (30 mL) This was followed by the addition of p-toluenesulfonic acid (260 mg, 1.51 mmol, 0.10 equiv) in portions at 0° C. To this was added dihydropyran (2.51 g, 29.84 mmol, 2.01 equiv) dropwise with stirring at 0° C. The resulting solution was stirred for 1 h at room temperature and then concentrated. The residue was applied onto a silica gel column with ethyl acetate/petroleum ether. The collected fraction was concentrated to give 2-(3-(3-bromophenyl)propoxy)tetrahydro-2H-pyran (2.66 g, 60%) as colorless oil.

Step-3: Synthesis of 3-(3-((tetrahydro-2H-pyran-2-yl)oxy)propyl)benzaldehyde

Into a 100-mL 3-necked bottom flask, was placed 2-(3-(3-bromophenyl)propoxy)tetrahydro-2H-pyran (2.66 g, 8.89 mmol, 1.00 equiv) in tetrahydrofuran (30 mL). This was followed by the addition of n-BuLi (2.5 mol/L in THF, 3.57 mL, 1.00 equiv) dropwise with stirring at −78° C. The resulting solution was stirred for 30 min at −78° C. To this was added N,N-dimethylformamide (2 mL) dropwise with stirring at −78° C. The resulting solution was stirred for an additional 2 h at room temperature. The reaction was then quenched by the addition of 20 mL of water and then diluted with 80 mL of water. The resulting solution was extracted with 3×100 mL of ethyl acetate and concentrated under vacuum. The residue was applied onto a silica gel column with ethyl acetate/petroleum ether (1:10-1:1). The collected fraction was concentrated to give 3-(3-((tetrahydro-2H-pyran-2-yl)oxy)propyl)benzaldehyde (2 g, 91%) as yellow oil. MS: (ES, m/z): 266 [M+H₂O]⁺.

Step-4: Synthesis of (3-(3-((tetrahydro-2H-pyran-2-yl)oxy)propyl)phenyl)methanol Into a 100-mL round-bottom flask, was placed 3-(3-(tetrahydro-2H-pyran-2-yloxy)propyl)benzaldehyde (2 g, 8.05 mmol, 1.00 equiv) in methanol (20 mL), NaBH₄ (310 mg, 8.19 mmol, 1.02 equiv). The resulting solution was stirred for 1 h at room temperature. The reaction was quenched by addition of 20 mL of water. Methanol was removed by concentration under vacuum. The residue was diluted with 20 mL of water, extracted with 3×50 mL of ethyl acetate, dried by anhydrous Na₂SO₄ and concentrated under vacuum. The residue was applied onto a silica gel column with ethyl acetate/petroleum ether. The collected fraction was concentrated to give (3-(3-((tetrahydro-2H-pyran-2-yl)oxy)propyl)phenyl)methanol (1.1 g, 55%) as colorless oil. ¹H-NMR (DMSO, 400 MHz) δ(ppm): 7.23 (t, J=7.5 Hz, 1H), 7.18-7.03 (m, 3H), 5.14 (t, J=5.7 Hz, 1H), 4.54 (t, J=3.7 Hz, 1H), 4.47 (d, J=5.7 Hz, 2H), 3.77-3.71 (m, 1H), 3.66-3.60 (m, 1H), 3.44-3.39 (m, 1H), 3.33-3.28 (m, 1H), 2.69-2.59 (m, 2H), 1.88-1.56 (m, 4H), 1.52-1.43 (m, 4H).

Step-5: Synthesis of 3-(3-((tetrahydro-2H-pyran-2-yl)oxy)propyl)benzyl methanesulfonate Into a 100-mL round-bottom flask, was placed (3-(3-(tetrahydro-2H-pyran-2-yloxy)propyl)phenyl)methanol (550 mg, 2.20 mmol, 1.00 equiv) in dichloromethane (10 mL) and TEA (280 mg, 2.77 mmol, 1.26 equiv) This was followed by the addition of methanesulfonyl chloride (0.31 g, 2.72 mmol, 1.2 equiv) dropwise with stirring at 0° C. The resulting solution was stirred for 1 h at 0° C. The reaction was then quenched by the addition of 50 mL of water. The resulting solution was extracted with 3×50 mL of dichloromethane, dried over anhydrous sodium sulfate and concentrated under vacuum. This gave 3-(3-((tetrahydro-2H-pyran-2-yl)oxy)propyl)benzyl methanesulfonate (800 mg, crude) as a solid which was used to the next step without any purification.

Step-6: Synthesis of 2-(3-(3-(bromomethyl)phenyl)propoxy)tetrahydro-2H-pyran Into a 100-mL round-bottom flask, was placed 3-(3-(tetrahydro-2H-pyran-2-yloxy)propyl)benzyl methanesulfonate (800 mg, 2.44 mmol, 1.00 equiv) in tetrahydrofuran (10 mL), lithium bromide (287 mg) and sodium bicarbonate (369 mg, 4.39 mmol, 1.80 equiv). The resulting mixture was stirred overnight at room temperature. The solids were filtered out. The filtrate was concentrated under vacuum. The residue was applied onto a silica gel column with ethyl acetate/petroleum ether (1:10-1:1). The collected fraction was concentrated to give 2-(3-(3-(bromomethyl)phenyl)propoxy)tetrahydro-2H-pyran (570 mg, 75%) as colorless oil.

Step-7: Synthesis of (E)-methyl 3-(2-((3-(3-hydroxypropyl)benzyl)amino)phenyl)acrylate Into a 100-mL round-bottom flask, was placed 2-(3-(3-(bromomethyl)phenyl)propoxy)-tetrahydro-2H-pyran (570 mg, 1.82 mmol, 1.00 equiv) in N,N-dimethylformamide (10 mL), (E)-methyl 3-(2-aminophenyl)acrylate (324 mg, 1.83 mmol, 1.00 equiv) and potassium carbonate (504 mg, 3.65 mmol, 2.00 equiv). The resulting mixture was stirred for 3 h at 80° C. The reaction was then cooled to room temperature and quenched by the addition of 50 mL of water. The resulting solution was extracted with 3×50 ml, of ethyl acetate, dried over anhydrous sodium sulfate and concentrated under vacuum. The residue was applied onto a silica gel column with ethyl acetate/petroleum ether (1:10-1:1). The collected fraction was concentrated to give (E)-methyl 3-(2-((3-(3-hydroxypropyl)benzyl)amino)phenyl)acrylate (192 in, 32%) as yellow oil MS: (ES, m/z): 326 [M+H]⁺.

Step-8: Synthesis of (E)-N-hydroxy-3-(2-((3-(3-hydroxypropyl)benzyl)amino)phenyl)acrylamide Into a 100-mL round-bottom flask, was placed a solution of (E)-methyl 3-(2-((3-(3-hydroxypropyl)benzyl)amino)phenyl)acrylate (90 mg, 0.28 mmol, 1.00 equiv) in THF/MeOH (4/1) (2.5 mL), NH₂OH (50% in water, 1.05 mL, 60.00 equiv), NaOH (1 mol/L, 0.67 mL, 2.40 equiv). The resulting solution was stirred for 1.5 h at room temperature. The crude product was purified by Prep-HPLC with the following conditions: Column XBridge RP C18,19*150 mm, 5 urn; Mobile Phase A: Water/0.05% TFA, Mobile Phase B: ACN; Flow rate: 25 mL/min; Gradient-S % B to 24% B in 7.0 min, 254 nm. The collected fraction was lyophilized to give (E)-N-hydroxy-3-(2-((3-(3-hydroxypropyl)benzyl)amino)phenyl)acrylamide (34.8 mg, 39%) as a yellow solid. ¹H-NMR (DMSO, 400 MHz) δ(ppm): 10.10 (s, 1H), 7.73 (d, J=8 Hz, 1H), 7.37 (d, J=8 Hz, 1H), 7.12-7.30 (m, 3H), 7.02-7.10 (m, 2H), 6.68-6.76 (m, 1H), 6.57 (d, J=8 Hz, 1H), 6.47 (d, J=8 Hz, 1H), 6.01-6.27 (m, 1H), 4.31-4.36 (m, 2H), 3.37-3.42 (m, 2H), 2.49-2.58 (m, 21H), 1.64-1.71 (m, 2H). MS. (ES, m/z): 327 [M+H]⁺.

Example 43—(E)-N-hydroxy-3-(2-((3-(trifluoromethyl)phenylamino)methyl)pyridin-3-yl)acrylamide (I-516)

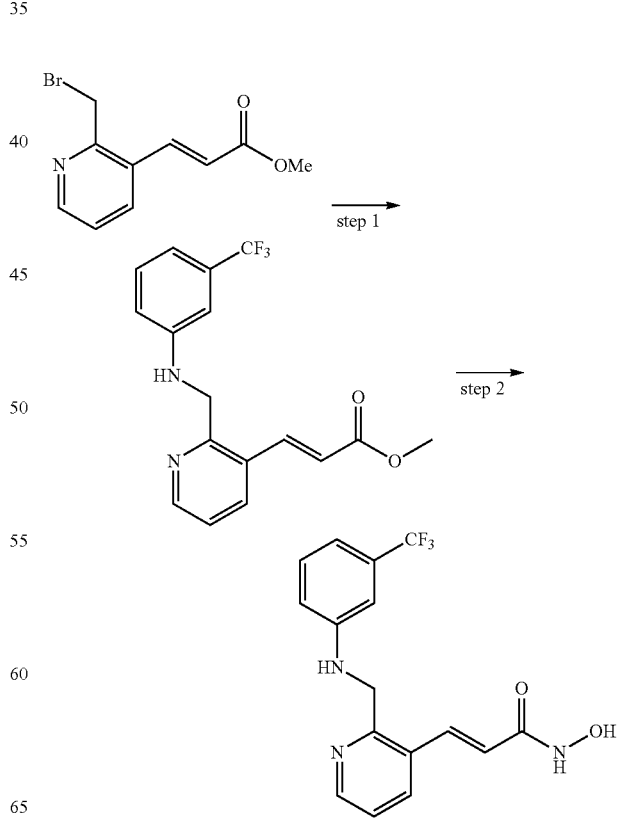

Step-1: Synthesis of (E)-methyl 3-(2-((3-(trifluoromethyl)phenylamino)methyl)pyridin-3-yl)acrylate Into a 10-mL vial, was placed 3-(trifluoromethyl)aniline (47.2 mg, 0.29 mmol, 1.00 equiv), N,N-dimethylformamide (2 mL), potassium carbonate (80.9 mg, 0.59 mmol, 2.00 equiv) and (E)-methyl 3-(2-(bromomethyl)pyridin-3-yl)acrylate (75 mg, 0.29 mmol, 1.00 equiv). The resulting solution was stirred overnight at room temperature. The mixture was then poured into 15 mL of water, extracted with 2×30 mL of ethyl acetate, washed with 2×20 mL of brine, dried over anhydrous sodium sulfate and concentrated under vacuum. The residue was applied onto a silica gel column with ethyl acetate/petroleum ether (1:2). The collected fraction was concentrated under vacuum to give (E)-methyl 3-(2-((3-(trifluoromethyl)phenylamino)methyl)pyridin-3-yl)acrylate (31 mg, 31%) as light yellow oil. MS: (ES, m/z) 337[M+H]$^+$.

Step-2: Synthesis of (E)-N-hydroxy-3-(2-((3-(trifluoromethyl)phenylamino)methyl)pyridin-3-yl)acrylamide Into a 25-mL round-bottom flask, was placed (E)-methyl 3-(2-((3-(trifluoromethyl)phenylamino)methyl)pyridin-3-yl)acrylate (30 mg, 0.09 mmol, 1.00 equiv), MeOH/THF (¼) (2.5 mL), NH$_2$OH (50% in water, 354 mg, 60.00 equiv), NaOH (1 mol/L, 0.18 mL, 2.00 equiv). The resulting solution was stirred for 3 h at room temperature. The solids were filtered out. The crude product was purified by Prep-HPLC with the following conditions: Column, Sunfire C18 19*150 mm, mobile phase, water (0.05% TFA) and ACN (5% up to 40% in 7 min); Detector, UV 220&254 nm. The collected fraction was lyophilized to give (E)-N-hydroxy-3-(2-((3-(trifluoromethyl)phenylamino)methyl)pyridin-3-yl)acrylamide (2.2 mg, 7%) as a yellow solid. $^1$H-NMR (DMSO, 400 MHz) δ(ppm): 10.86 (s, 1H), 8.54 (d, J=4.4 Hz, 1H), 8.00 (d, J=8.0 Hz, 1H), 7.74 (d, J=15.6 Hz, 1H), 7.44-7.40 (m, 1H), 7.29-7.25 (m, 1H), 7.08-6.95 (m, 2H), 6.83 (d, J=7.6 Hz, 1H), 6.46 (d, J=16.0 Hz, 1H), 4.53 (d, J=13.6 Hz, 2H), MS: (ES, m/z): 338[M+H]$^+$.

The following compounds in Table 12 were prepared according to the procedures for (E)-N-hydroxy-3-(2-((3-(trifluoromethyl)phenylamino)methyl)pyridin-3-yl)acrylamide (I-516).

Example 44—(E)-N-(4-(3-(hydroxyamino)-3-oxoprop-1-enyl)pyridin-3-yl)-3-(trifluoromethyl)benzamide (I-123)

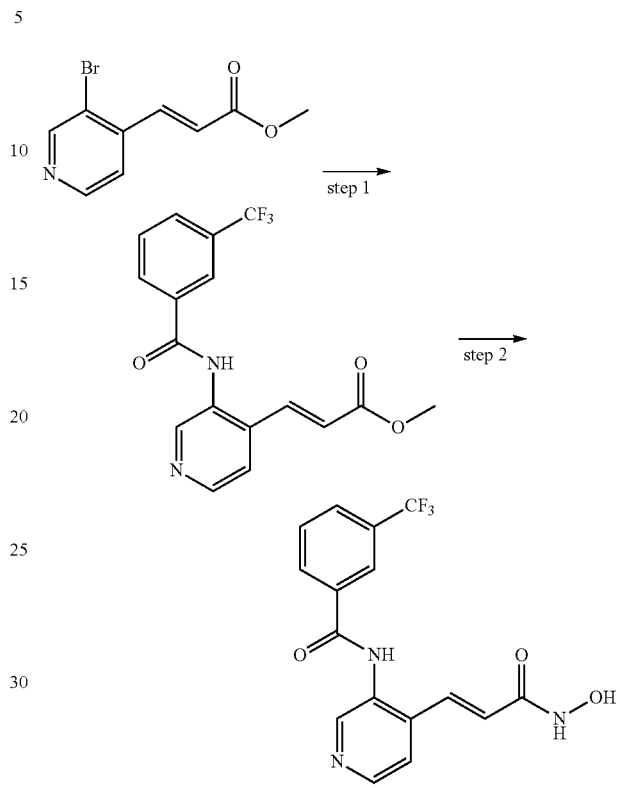

Step-1: Synthesis of (E)-methyl 3-(3-(3-(trifluoromethyl)benzamido)pyridin-4-yl)acrylate Into a 100-mL round-bottom flask purged and maintained with an inert atmosphere of nitrogen, was placed a solution of (E)-methyl 3-(3-bromopyridin-4-yl)acrylate (500 mg, 2.07 mmol, 1.00 equiv) in toluene (30 mL), 3-(trifluoromethyl)benzamide (784 mg, 4.15 mmol, 2.00 equiv), Pd$_2$(dba)$_3$·CHCl$_3$ (107 mg, 0.05 equiv), XantPhos (122 mg, 0.21

TABLE 12

| Ex. | Structure | Name | $^1$HNMR | (ES, m/z) [M + H]$^+$ |
|---|---|---|---|---|
| I-217 | Ph, CF$_3$, HN, N, O, N-OH, H | (E)-N-hydroxy-3-(2-(((2-(trifluoromethyl)-[1,1'-biphenyl]-4-yl)amino)methyl)pyridin-3-yl)acrylamide | (DMSO, 400 M Hz, ppm): 10.87 (s, 1H), 8.55 (d, J = 4.0 Hz, 1H), 8.00 (d, J = 6.8 Hz, 1H), 7.77 (d, J = 15.6 Hz, 1H), 7.43-7.31 (m, 5H), 7.24-7.16 (m, 2H), 7.12-7.06 (m, 2H), 6.97 (d, J = 8.8 Hz, 1H), 6.47 (d, J = 16.0 Hz, 1H), 4.52 (d, J = 15.6 Hz, 2H). | 414 | mmol, 0.10 equiv) and K₃PO₄ (1.32 g, 6.22 mmol, 3.00 equiv). The resulting mixture was stirred overnight at 100° C. The reaction was cooled to room temperature, concentrated under vacuum. The residue was diluted with 100 mL of water, extracted with 3×100 mL of ethyl acetate, dried over anhydrous sodium sulfate and concentrated under vacuum. The residue was applied onto a silica gel column with ethyl acetate/petroleum ether (1:1). The collected fraction was concentrated under vacuum to give (E)-methyl 3-(3-(3-(trifluoromethyl)benzamido)pyridin-4-yl)acrylate (80 mg, 11%) as a yellow solid. MS: (ES, m/z): 351[M+H]⁺.

Step-2: Synthesis of (E)-N-(4-(3-(hydroxyamino)-3-oxoprop-1-enyl)pyridin-3-yl)-3-(trifluoromethyl)benzamide Into a 10-mL round-bottom flask, was placed a solution of (E)-methyl 3-(3-(3-(trifluoromethyl)benzamido)pyridin-4-yl)acrylate (80 mg, 0.23 mmol, 1.00 equiv) in THF/MeOH (4:1) (3 mL), NH₂OH (50% in water, 453 mg, 13.71 mmol, 60.00 equiv), NaOH (1 mol/L, 0.46 mL, 0.46 mmol, 2.00 equiv). The resulting solution was stirred for 2 h at room temperature. The solids were filtered out. The filtrate was purified by Prep-HPLC with the following conditions Column, Xbridge RP18 5 um, 19*150 mm; mobile phase, water (0.05% TFA) and MeCN (5% CH₃CN up to 75% in 6 min); Detector, UV 220/254 nm. The collected fraction was lyophilized to give (E)-N-(4-(3-(hydroxyamino)-3-oxoprop-1-enyl)pyridin-3-yl)-3-(trifluoromethyl)benzamide (28 mg, 26%) as a white solid. ¹H-NMR (DMSO, 300 MHz) δ(ppm): 10.77 (s, 1H), 8.68 (s, 1H), 8.55 (d, J=5.1 Hz, 1H), 8.40 (s, 1H), 8.36-8.30 (m, 1H), 8.04 (d, J=7.8 Hz, 1H), 7.86-7.78 (m, 1H), 7.74 (d, J=5.4 Hz, 1H), 7.50 (d, J=15.6 Hz, 1H), 6.69 (d, J=15.6 Hz, 1H) MS: (ES, m/z): 352[M+H]⁺.

The following compounds in Table 13 were prepared according to the procedures for (E)-N-(4-(3-(hydroxyamino)-3-oxoprop-1-enyl)pyridin-3-yl)-3-(trifluoromethyl)benzamide (I-123)

TABLE 13

| Ex. | Structure | Name | ¹HNMR | (ES, m/z) [M + H]⁺ |
|---|---|---|---|---|
| I-122 | 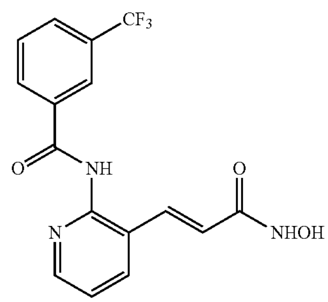 | (E)-N-(3-(3-(hydroxyamino)-3-oxoprop-1-en-1-yl)pyridin 2-yl)-3-(trifluoromethyl)benzamide | (DMSO, 400 MHZ, ppm): 11.10 (s, 1H), 10.84 (s, 1H), 8.51-8.50 (m, 1H), 8.37 (s, 1H), 8.32 (d, J = 7.6 Hz, 1H), 8.14 (d, J = 7.6 Hz, 1H), 8.03 (d, J = 8.0 Hz, 1H), 7.84-7.80 (m, 1H), 7.46-7.43 (m, 1H), 7.37 (d, J = 16.0 Hz, 1H), 6.51 (d, J = 16.0 Hz, 1H). | 352 |
| I-124 | 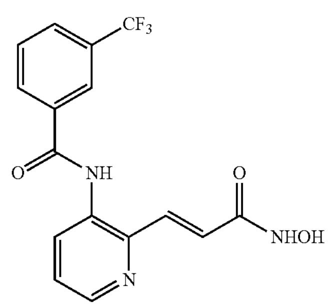 | (E)-N-(2-(3-(hydroxyamino)-3-oxoprop-1-en-1-yl)pyridin-3-yl)-3-(trifluoromethyl)benzamide | (DMSO, 300 MHz, ppm): 10.94 (s, 1H), 10.69 (s, 1H), 8.54-8.52 (m, 1H), 8.37 (s, 1H), 8.32 (d, J = 7.8, 1H) 8.03 (d, J = 8.1 Hz, 1H), 7.88-7.81 (m, 2H), 7.60 (d, J = 15.3 Hz, 1H), 7.05 (d, J = 15.3 Hz, 1H). | 352 |

Example 45—(Z)—N-(2-(2-fluoro-3-(hydroxyamino)-3-oxoprop-1-en-1-yl)phenyl)-3-(trifluoromethyl) benzamide (I-324)

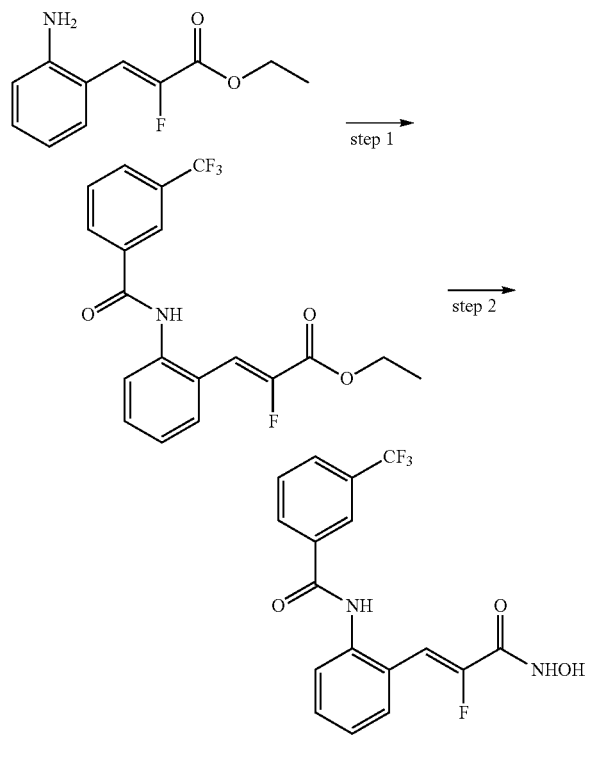

Step-1: Synthesis of (Z)-ethyl 2-fluoro-3-(2-(3-(trifluoromethyl)benzamido)phenyl)acrylate Into a 25-mL round-bottom flask, was placed (Z)-ethyl 3-(2-aminophenyl)-2-fluoroacrylate (200 mg, 0.96 mmol, 1.00 equiv), dichloromethane (5 mL), TEA (290 mg, 2.87 mmol, 3.00 equiv). This was followed by the addition of 3-(trifluoromethyl)benzoyl chloride (300 mg, 1.44 mmol, 1.50 equiv) dropwise with stirring at 0° C. The resulting solution was stirred for 5 h at room temperature. The reaction mixture was then poured into 30 mL of water/ice, extracted with 2×30 mL of dichloromethane, washed with 50 mL of brine, dried over anhydrous sodium sulfate and concentrated under vacuum. The residue was applied onto a silica gel column with ethyl acetate/petroleum ether (1.5). The collected fraction was concentrated under vacuum to give (Z)-ethyl 2-fluoro-3-(2-(3-(trifluoromethyl)benzamido)phenyl)acrylate (110 mg, 30%) as a yellow solid. MS: (ES, m/z): 381[M+H]$^+$.

Step-2: Synthesis of (Z)—N-(2-(2-fluoro-3-(hydroxyamino)-3-oxoprop-1-en-1-yl)phenyl)-3-(trifluoromethyl)benzamide Into a 25-mL round-bottom flask, was placed (Z)-ethyl 2-fluoro-3-(2-(3-(trifluoromethyl)benzamido)phenyl)acrylate (110 mg, 0.29 mmol, 1.00 equiv), MeOH/THF (¼) (2 mL), NH$_2$OH (50% in water, 1143 mg, 60.00 equiv), NaOH (1 mol/L, 0.58 mL, 2.00 equiv). The resulting solution was stirred for 4 h at room temperature. The solids were filtered out. The crude product was purified by Prep-HPLC with the following conditions: Column, Xbridge C18 19*150 mm; mobile phase, water (0.1% FA) and ACN (5% up to 63% in 7 min); Detector, UV 220&254 nm. The collected fraction was lyophilized to give (Z)—N-(2-(2-fluoro-3-(hydroxyamino)-3-oxoprop-1-enyl)phenyl)-3-(trifluoromethyl) benzamide (52.7 mg) as an off-white solid. $^1$H-NMR (DMSO, 400 MHz) δ(ppm): δ 11.46 (s, 1H), 10.49 (s, 1H), 9.27 (s, 1H), 8.33-8.28 (m, 2H), 8.01 (d, J=7.6 Hz, 1H), 7.84-7.78 (m, 2H), 7.45 (d, J=4.4 Hz, 2H), 7.41-7.36 (m, 1H), 6.88 (d, J=38.0 Hz, 1H). MS: (ES, m/z): 369[M+H]$^+$.

Example 46—(Z)—N-(2-(2-fluoro-3-(hydroxyamino)-3-oxoprop-1-enyl)phenyl)-2-phenoxy benzamide hydrochloride (I-325)

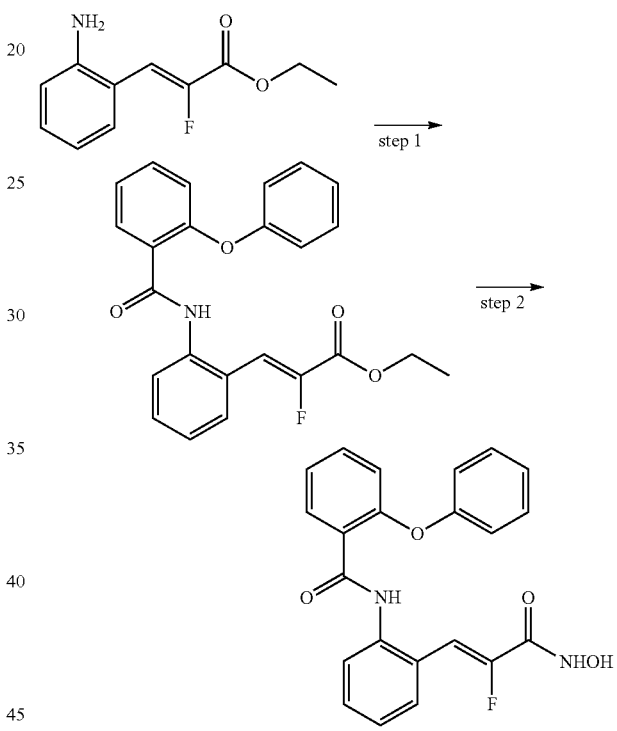

Step-1: Synthesis of (Z)-ethyl 2-fluoro-3-(2-(2-phenoxybenzamido)phenyl)acrylate Into a 25-mL round-bottom flask, was placed 2-phenoxybenzoic acid (307 mg, 1.43 mmol, 1.50 equiv) in N,N-dimethylformamide (3 mL), HATU (545 ng, 1.43 mmol, 1.50 equiv), DIEA (494 mg, 3.82 mmol, 4.00 equiv) and (Z)-ethyl 3-(2-aminophenyl)-2-fluoroacrylate (200 mg, 0.96 mmol, 1.00 equiv). The resulting solution was stirred overnight at room temperature. The reaction was then quenched by the addition of 20 mL of water, extracted with 3×50 mL of ethyl acetate, washed with 2×30 mL of brine, dried over anhydrous sodium sulfate and concentrated under vacuum. The residue was applied onto a silica gel column with ethyl acetate/petroleum ether (1:5). The collected fraction was concentrated under vacuum to give (Z)-ethyl 2-fluoro-3-(2-(2-phenoxybenzamido)phenyl)acrylate (330 mg, 85%) as a brown solid MS: (ES, m/z): 406[M+H]$^+$.

Step-2: Synthesis of (Z)—N-(2-(2-fluoro-3-(hydroxyamino)-3-oxoprop-1-enyl)phenyl)-2-phenoxybenzamide Into a 25-mL round-bottom flask, was placed (Z)-ethyl 2-fluoro-3-(2-(2-phenoxybenzamido)phenyl)acrylate (120 mg, 0.30 mmol, 1.00 equiv), MeOH/THF (¼) (2 mL), NH$_2$OH (50% in water, 1173 mg, 60.00 equiv), NaOH (1 mol/L, 0.59 mL, 2.00 equiv). The resulting solution was stirred for 4 h at room temperature. The solids were filtered out. The crude product was purified by Prep-HPLC with the following conditions Column, Xbride C18 19*150 mm; mobile phase, water (0.1% FA) and ACN (5% up to 69% in 8 min); Detector, UV 220&254 nm. The collected fraction was lyophilized to give (Z)—N-(2-(2-fluoro-3-(hydroxyamino)-3-oxoprop-1-enyl)phenyl)-2-phenoxybenzamide (55.3 mg, 48%) as a off-white solid. $^1$H-NMR (DMSO, 400 MHz) δ(ppm): δ 11.46 (s, 1H), 10.13 (s, 1H), 9.28 (s, 1H), 7.73-7.68 (m, 2H), 7.55-7.51 (m, 2H), 7.46-7.22 (m, 5H), 7.18-6.97 (m, 5H). MS: (ES, n/z): 392[M+H]$^+$.

Example 47—(E)-3-(2-((1H-benzo[d]imidazol-2-yl)amino)phenyl)-N-hydroxyacrylamide (I-1)

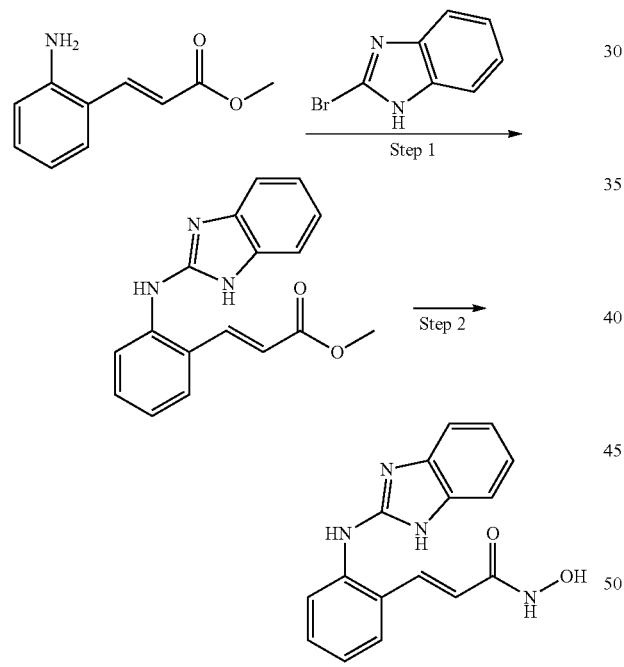

Step-1: Methyl (E)-3-(2-((1H-benzo[d]imidazol-2-yl)amino)phenyl)acrylate

A 10-mL microwave vial was equipped with a stir bar and methyl (E)-3-(2-aminophenyl)acrylate (0.075 g, 0.381 mmol, 1.0 equiv), 2-bromo-1H-benzo[d]imidazole (0.068 g, 0.381 mmol, 1.0 equiv), and hydrochloric acid (1 drop) in ethanol (2.5 mL). The resulting mixture was heated to 155° C. for 80 mins in the microwave. The reaction mixture was concentrated then diluted with 3 mL EtOAC and washed with 5 mL brine. White solid precipitated out of solution and was collected via suction filtration to give Methyl (E)-3-(2-((1H-benzo[d]imidazol-2-yl)amino)phenyl)acrylate and carried on to the next step as crude material. MS (ESI, m/z): 294 [M+H]$^+$.

Step-2: Synthesis of (E)-3-(2-((1H-benzo[d]imidazol-2-yl)amino)phenyl)-N-hydroxyacrylamide Intermediate from Step-1, Methyl (E)-3-(2-((1H-benzo[d]imidazol-2-yl)amino)phenyl)acrylate (0.100 g, 0.34 mmol, 1.0 equiv) was dissolved in Tetrahydrofuran (2.7 mL) and Methanol (0.7 mL) NH$_2$·OH 50% aq. (1.8 ml, 30.7 mmol, 90 equiv), and 1N aq. NaOH (1.0 mL, 3 equiv) were added. The resulting solution was stirred for 18 hours at room temperature. The reaction was concentrated to dryness. The reaction mixture was concentrated then diluted with 3 mL EtOAC and washed with 5 mL brine. A white solid crashed out and was collected by suction filtration then lyophilized to afford (E)-3-(2-((1H-benzo[d]imidazol-2-yl)amino)phenyl)-N-hydroxyacrylamide (0.005 g, 5% yield). MS: (ES, m/r): 295 [M+H]$^+$.

Example 48—(E)-N-hydroxy-3-(2-(((1-(2-methoxyethyl)-1H-benzo[d]imidazol-2-yl)methyl)amino)phenyl)acrylamide (I-2)

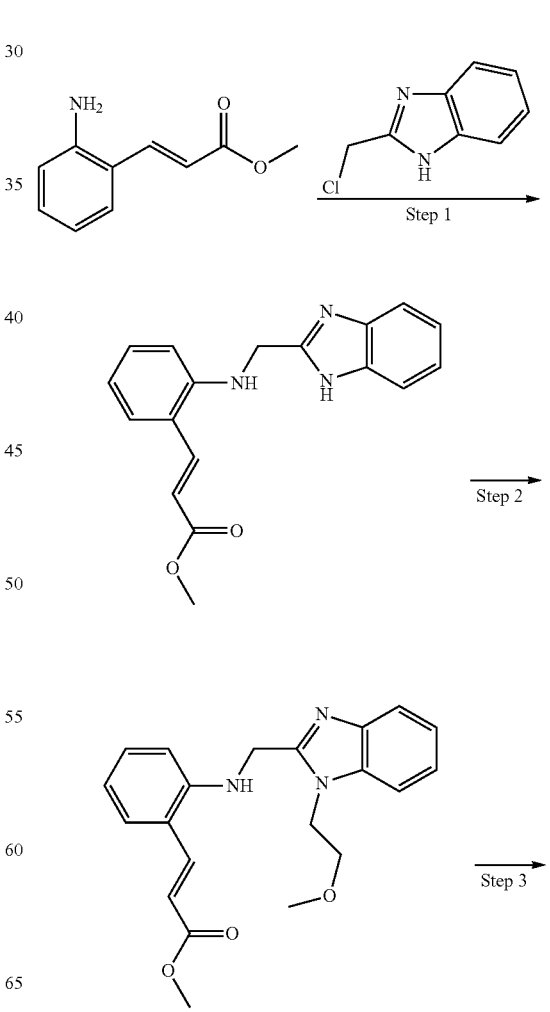

-continued

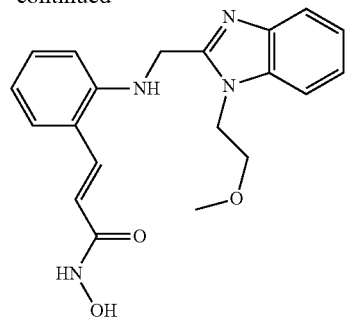

Step-1: methyl (E)-3-(2-(((1H-benzo[d]imidazol-2-yl)methyl)amino)phenyl)acrylate A 20-mL vial was equipped with a stir bar and methyl (E)-3-(2-aminophenyl)acrylate (0.125 g, 0.675 mmol, 1.5 equiv), 2-(chloromethyl)-1H-benzo[d]imidazole (0.075 g, 0.45 mmol, 1.0 equiv), and sodium iodide (0.067 g, 0.45 mmol, 1.0 equiv) in ethanol (7 mL). The resulting mixture was heated at 50° C. overnight. The reaction mixture was concentrated then diluted with 3 mL EtOAC and washed with 5 mL brine. The organic layer is concentrated to dryness and methyl (E)-3-(2-(((1H-benzo[d]imidazol-2-yl)methyl)amino)phenyl)acrylate was carried on to the next step as crude material. MS (ESI, m/z): 308 [M+H]+.

Step-2: methyl (E)-3-(2-(((1-(2-methoxyethyl)-1H-benzo[d]imidazol-2-yl)methyl)amino)phenyl)acrylate A 20-mL vial was equipped with a stir bar and intermediate from Step-1: methyl (E)-3-(2-(((1H-benzo[d]imidazol-2-yl)methyl)amino)phenyl)acrylate (0.040 g, 0.13 mmol, 1.0 equiv), 1-bromo-2-methoxyethane (0.036 g, 0.26 mmol, 2.0 equiv), and cesium carbonate (0.121 g, 0.364 mmol, 2.8 equiv) in DMF (2 mL). The resulting mixture was heated at 80° C. overnight. The reaction mixture was concentrated then diluted with 3 mL EtOAC and washed with 5 mL brine. The organic layer is concentrated purified by normal phase chromatography (Biotage 10 gram column, 25-100% EtOAc in Hex) to afford methyl (E)-3-(2-(((1-(2-methoxyethyl)-1H-benzo[d]imidazol-2-yl)methyl)amino)phenyl)acrylate (35 mg, 76%, 86% purity by uv 254 nm). $^1$H NMR (300 MHz, DMSO-4) δ ppm 8.00 (d, J=15.83 Hz, 1H) 7.51-7.61 (m, 3H) 7.18 (td, J=7.77, 1.17 Hz, 3H) 6.93 (d, J=7.92 Hz, 1H) 6.56-6.68 (m, 2H) 6.45 (d, J=15.54 Hz, 1H) 4.64 (d, J=5.28 Hz, 1H) 4.59-4.60 (m, 1H) 4.53 (t, J=5.28 Hz, 2H) 3.72 (s, 3H) 3.60-3.67 (m, 2H) 3.19 (s, 4H). MS: (ES, m/z): 366 [M+H].

Step-3: Synthesis of (E)-N-hydroxy-3-(2-(((1-(2-methoxyethyl)-H-benzo[d]imidazol-2-yl)methyl)amino)phenyl)acrylamide Intermediate from Step-2, methyl (E)-3-(2-(((1-(2-methoxyethyl)-1H-benzo[d]imidazol-2-yl)methyl)amino)phenyl)acrylate (0.035 g, 0.096 mmol, 1.0 equiv) was dissolved in Tetrahydrofuran (2 mL) and Methanol (0.5 mL). NH$_2$OH 50% aq. (0.29 ml, 4.8 mmol, 50 equiv), and 1N aq. NaOH (0.29 mL, 3 equiv) were added. The resulting solution was stirred for 18 hours at room temperature. The reaction was concentrated to dryness then purified on the Gilson prep-HPLC system with acetonitrile and water to afford (E)-N-hydroxy-3-(2-(((1-(2-methoxyethyl)-1H-benzo[d]imidazol-2-yl)methyl)amino)phenyl)acrylamide (0.0052 g, 15%) as an white solid. MS (ESI, m/z): 367 [M+H]+.

Example 49—(E)-N-hydroxy-3-(2-((1-(2-methoxyethyl)-1H-benzo[d]imidazol-2-yl)amino)phenyl)acrylamide (I-3)

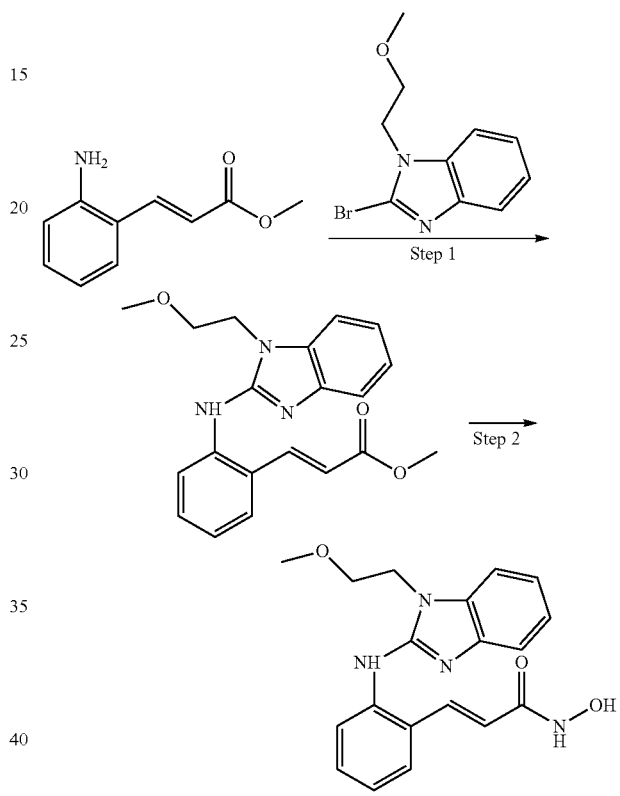

Step-1: methyl (E)-3-(2-((1-(2-methoxyethyl)-11H-benzo[d]imidazol-2-yl)amino)phenyl)acrylate. A 10-mL microwave vial was equipped with a stir bar and methyl (E)-3-(2-aminophenyl)acrylate (0.100 g, 0.392 mmol, 1.0 equiv), 2-bromo-1-(2-methoxyethyl)-1H-benzo[d]imidazole (0.070 g, 0.392 mmol, 1.0 equiv), and hydrochloric acid (1 drop) in ethanol (2.5 mL). The resulting mixture was heated to 130° C. for 60 mins in the microwave. The reaction mixture was concentrated then diluted with 3 mL EtOAC and washed with 5 mL brine. The organic layer is concentrated purified by normal phase chromatography (Biotage 10 gram column, 20-60% EtOAc in Hex) to afford methyl (E)-3-(2-((1-(2-methoxyethyl)-1H-benzo[d]imidazol-2-yl)amino)phenyl)acrylate (0.030 g, 22%) as a white solid. MS (ESI, m/z): 352 [M+H]+.

Step-2: Synthesis of (E)-N-hydroxy-3-(2-((1-(2-methoxyethyl)-1H-benzo[d]imidazol-2-yl)amino)phenyl)acrylamide Intermediate from Step-1, methyl (E)-3-(2-((1-(2-methoxyethyl)-1H-benzo[d]imidazol-2-yl)amino)phenyl)acrylate (0.030 g, 0.085 mmol, 1.0 equiv) was dissolved in tetrahydrofuran (1 mL) and methanol (0.25 mL). NH$_2$OH 50% aq. (0.296 ml, 4.27 mmol, 50 equiv), and 1N aq. NaOH (0.25 mL, 3 equiv) were added. The resulting solution was stirred for 18 hours at room temperature. The reaction was concentrated to dryness then purified on the Gilson prep-HPLC system with acetonitrile and water to afford (E)-N-hydroxy-3-(2-(((1-(2-methoxyethyl)-1H-benzo[d]imidazol-2-yl)methyl)amino)phenyl)acrylamide (0.0039 g, 13%) as an white solid. MS (ESI, m/z): 353 [M+H]+.

Example 50—tert-butyl (E)-3-(2-(3-(hydroxyamino)-3-oxoprop-1-en-1-yl)phenyl)-4-oxoimidazolidine-1-carboxylate (I-261)

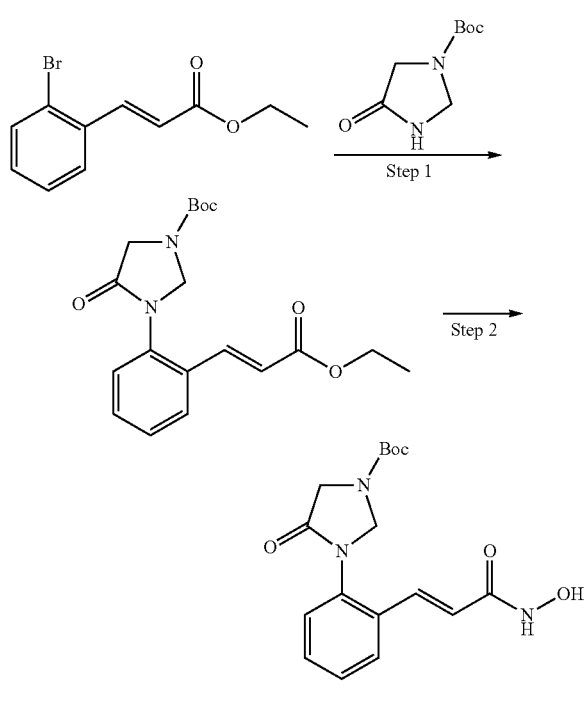

Step-1: Synthesis of tert-butyl (E)-3-(2-(3-ethoxy-3-oxoprop-1-en-1-yl)phenyl)-4-oxoimidazolidine-1-carboxylate A 10-mL microwave vial was equipped with a stir bar and ethyl (E)-3-(2-bromophenyl)acrylate (0.040 g, 0.157 mmol, 1.0 equiv), tert-butyl 4-oxoimidazolidine-1-carboxylate (0.029 g, 0.157 mmol, 1.0 equiv), potassium phosphate tribasic (0.100 g, 0.470 mmol, 3.0 equiv), (1R,2R)—N1,N2-dimethylcyclohexane-1,2-diamine (0.022 g, 0.157 mmol, 1.0 equiv), and copper (I) iodide (0.0307 g, 0.161 mmol, 1.02 equiv) in DMF (5 mL) The resulting mixture was heated to 100° C. for 3 hours in the microwave. The reaction mixture was diluted with 3 mL EtOAC and washed with 2×2 mL H2O. The organic layer was dried over Na2SO4, filtered and concentrated to dryness. Purified using reversed phase HPLC (Column: Waters XBridge Prep C18 OBD 5 um, 19×50 mm column, Mobile Phase A: Water with 0.1% HCO2H, Mobile Phase B: Acetonitrile with 0.1% HCO2H; Flow rate: 23 mL/min, Gradient: 8 min gradient 35% B up to 85% B). Fractions were lyophilized to afford 0.006 g (11% yield) of tert-butyl (E)-3-(2-(3-ethoxy-3-oxoprop-1-en-1-yl)phenyl)-4-oxoimidazolidine-1-carboxylate. MS (ESI, m/z): 361 [M+H]+.

Step-2: Synthesis of tert-butyl (E)-3-(2-(3-(hydroxyamino)-3-oxoprop-1-en-1-yl)phenyl)-4-oxoimidazolidine-1-carboxylate Intermediate from Step-1, tert-butyl (E)-3-(2-(3-ethoxy-3-oxoprop-1-en-1-yl)phenyl)-4-oxoimidazolidine-1-carboxylate (0.006 g, 0.017 mmol, 1.0 equiv) was dissolved in tetrahydrofuran (0.4 mL) and methanol (0.1 mL). NH2OH (0.012 g, 0.175 mmol, 50% in water, 10.00 equiv), and 1N aq. NaOH (0.035 mL, 2.00 equiv) were added. The resulting solution was stirred for 18 hours at room temperature. The reaction was concentrated to dryness. Purified by HPLC (Column: Waters XBridge Prep C18 OBD 5 um, 19×50 mm column: Mobile Phase A: Water with 0.1% HCO2H, Mobile Phase B: Acetonitrile with 0.1% HCO2H; Flow rate: 23 mL/min, Gradient: 8 min gradient 35% B up to 65% B). Fractions were lyophilized to afford 0.0023 g (38% yield) of (E)-3-(2-(3-(hydroxyamino)-3-oxoprop-1-en-1-yl)phenyl)-4-oxoimidazolidine-1-carboxylate MS: (ES, n/z)-348 [M+H]+.

Example 51—tert-butyl (E)-4-(2-(3-(hydroxyamino)-3-oxoprop-1-en-1-yl)phenyl)-3-oxopiperazine-1-carboxylate (I-263)

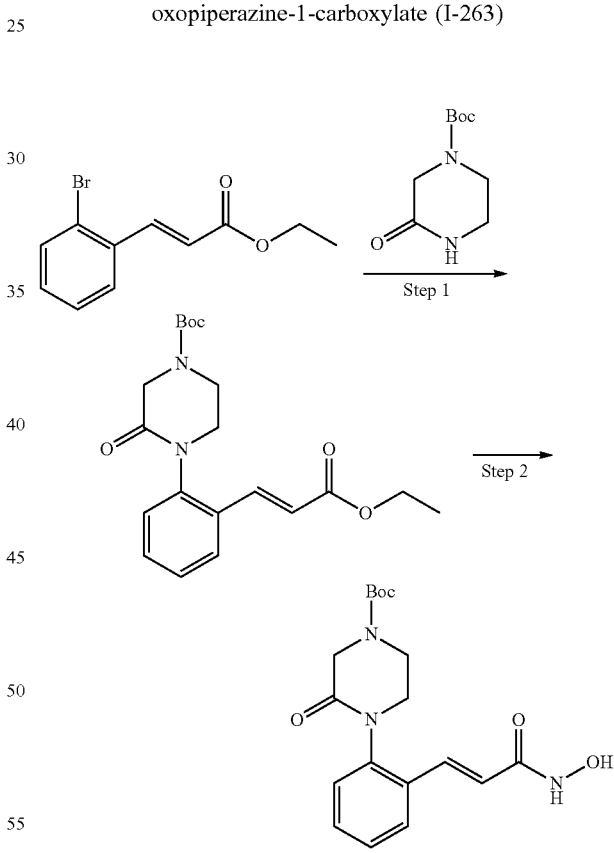

Step-1: Synthesis of tert-butyl (E)-4-(2-(3-ethoxy-3-oxoprop-1-en-1-yl)phenyl)-3-oxopiperazine-1-carboxylate A 10-mL microwave vial was equipped with a stir bar and ethyl (E)-3-(2-bromophenyl)acrylate (0.050 g, 0.196 mmol, 1.0 equiv), tert-butyl 3-oxopiperazine-1-carboxylate (0.039 g, 0.196 mmol, 1.0 equiv), potassium phosphate tribasic (0.125 g, 0.588 mmol, 3.0 equiv), (1R,2R)—N1,N2-dimethylcyclohexane-1,2-diamine (0.028 g, 0.196 mmol, 1.0 equiv), and copper (I) iodide (0.008 g, 0.039 mmol, 0.2 equiv) in DMF (1 mL). The resulting mixture was heated to 100° C. for 3 hours in the microwave. The reaction mixture was diluted with 3 mL EtOAC and washed with 2×2 mL H₂O. The organic layer was dried over Na2SO4, filtered and concentrated to dryness. Purified using reversed phase HPLC (Column: Waters XBridge Prep C18 OBD 5 um, 19×50 mm column; Mobile Phase A: Water with 0.1% HCO₂H, Mobile Phase B: Acetonitrile with 0.1% HCO₂H; Flow rate: 23 m/min, Gradient: 8 min gradient 15% B up to 65% B). Fractions were lyophilized to afford 0.021 g (29% yield) of tert-butyl (E)-4-(2-(3-ethoxy-3-oxoprop-1-en-1-yl)phenyl)-3-oxopiperazine-1-carboxylate. MS (ESI, m/z): 376 [M+H]⁻.

Step-2: Synthesis of tert-butyl (E)-4-(2-(3-(hydroxyamino)-3-oxoprop-1-en-1-yl)phenyl)-3-oxopiperazine-1-carboxylate Intermediate from Step-1, tert-butyl (E)-4-(2-(3-ethoxy-3-oxoprop-1-en-1-yl)phenyl)-3-oxopiperazine-1-carboxylate (0.012 g, 0.032 mmol, 1.0 equiv) was dissolved in Tetrahydrofuran (0.4 mL) and Methanol (0.1 mL). NH₂OH (0.007 g, 0.320 mmol, 50% in water, 10.00 equiv), and 1N aq. NaOH (0.064 mL, 2.00 equiv) were added. The resulting solution was stirred for 4 hours at room temperature. The reaction was concentrated to dryness. Purified by HPLC (Column: Waters XBridge Prep C18 OBD 5 um, 19×50 mm column; Mobile Phase A. Water with 0.1% HCO₂H, Mobile Phase B: Acetonitrile with 0.1% HCO₂H; Flow rate: 23 mL/min, Gradient: 8 min gradient 0% B up to 35% B). Fractions were lyophilized to afford 0.004 g (35% yield) of tert-butyl (E)-4-(2-(3-(hydroxyamino)-3-oxoprop-1-en-1-yl)phenyl)-3-oxopiperazine-1-carboxylate. MS. (ES, m/z): 362 [M+H]⁺.

Example 52—(E)-N-hydroxy-3-(2-(3-(4-methoxybenzyl)-5-oxoimidazolidin-1-yl)phenyl)acrylamide (I-292)

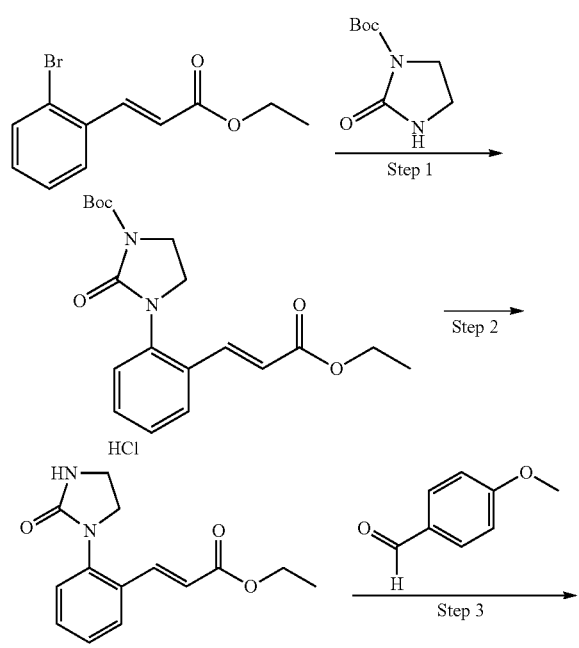

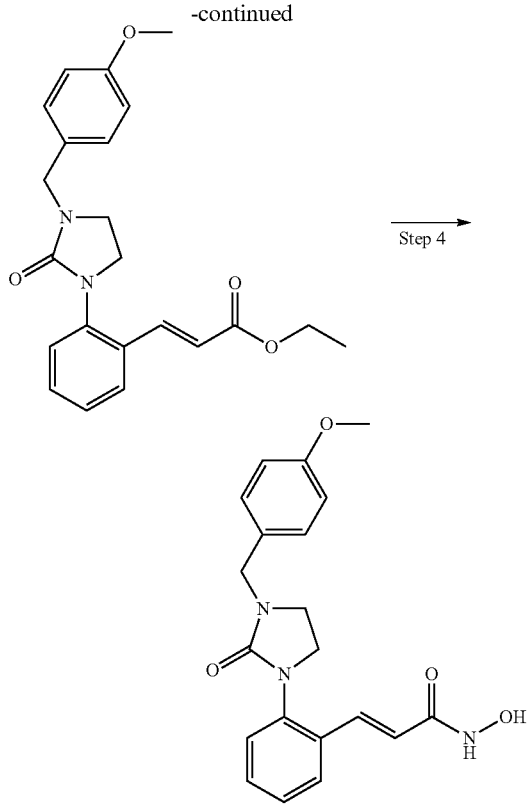

Step-1: Synthesis of tert-butyl (E)-3-(2-(3-ethoxy-3-oxoprop-1-en-1-yl)phenyl)-2-oxoimidazolidine-1-carboxylate A 10-mL microwave vial was equipped with a stir bar and ethyl (E)-3-(2-bromophenyl)acrylate (0.206 g, 0.806 mmol, 1.0 equiv), tert-butyl 2-oxoimidazolidine-1-carboxylate (0.15 g, 0.806 mmol, 1.0 equiv), potassium phosphate tribasic (0.513 g, 2.42 mmol, 3.0 equiv), (1R,2R)—N1,N2-dimethylcyclohexane-1,2-diamine (0.115 g 0.806 mmol, 1.0 equiv), and copper (I) iodide (0.0307 g, 0.161 mmol, 0.2 equiv) in DMF (3 mL). The resulting mixture was heated to 100° C. for 3 hours in the microwave. The reaction mixture was diluted with 25 mL EtOAC and washed with 20 mL, H₂O. The organic layer was separated and the aqueous layer was extracted twice with 10 mL EtOAc. Organic layers were combined and filtered through a 5 g Silicycle SiliaMetS-DMT column. EtOAc was removed under reduced pressure to afford 0.208 g (72% crude yield) of crude tert-butyl (E)-3-(2-(3-ethoxy-3-oxoprop-1-en-1-yl)phenyl)-2-oxoimidazolidine-1-carboxylate MS (ESI, m/z) 361 [M+H]⁺.

Step-2: Synthesis of ethyl (E)-3-(2-(2-oxoimidazolidin-1-yl)phenyl)acrylate hydrochloride Intermediate from Step-1, (E)-3-(2-(3-ethoxy-3-oxoprop-1-en-1-yl)phenyl)-2-oxoimidazolidine-1-carboxylate (0.208 g, 0.577 mmol, 1.0 equiv) was dissolved in EtOAc (3 mL). 4M HCl in 1,4-Dioxane (1.44 mL, 5.77 mmol, 10.0 equiv) was added. The reaction was heated at 50° C. for 18 hours. The reaction was concentrated to dryness. The residue was brought up in 3 mL of Et2O and warmed to 35° C. Upon cooling to room temperature, a precipitate formed. The precipitate was collected by vacuum filtration to afford 0.135 g (79% crude yield) of ethyl (E)-3-(2-(2-oxoimidazolidin-1-yl)phenyl)acrylate hydrochloride as a pale yellow-brown solid. MS (ES, m/z): 261 [M+H]+.

Step-3: Synthesis of ethyl (E)-3-(2-(3-(4-methoxybenzyl)-2-oxoimidazolidin-1-yl)phenyl)acrylate Intermediate from Step-2, ethyl (E)-3-(2-(2-oxoimidazolidin-1-yl)phenyl)acrylate hydrochloride (0.028 g, 0.109 mmol, 1.0 equiv) was combined with triethylamine (0.011 g, 0.109 mmol, 1.0 equiv) in DCE (1 mL). After 15 minutes at room temperature, 1 drop of acetic acid and 4-methoxybenzaldehyde (0.018 g, 0.131 mmol, 1.2 equiv) were added and allowed to shake at room temperature for 30 minutes Lastly, sodium triacetoxyborohydride (0.058 g, 0.273 mmol, 2.5 equiv) was added and the reaction was heated at 50° C. for 2 hours with stirring. The reaction was washed with 1 mL H₂O and the organic layer was separated and concentrated to dryness. Purified by HPLC (Column: Waters XBridge Prep C18 OBD 5 um, 19×50 mm column; Mobile Phase A: Water with 0.1% HCO₂H, Mobile Phase B: Acetonitrile with 0.1% HCO₂H; Flow rate: 23 mL/min, Gradient: 8 min gradient 0% B up to 35% B). Isolated fractions were lyophilized to afford 0.014 g (35% yield) of ethyl (E)-3-(2-(3-(4-methoxybenzyl)-2-oxoimidazolidin-1-yl)phenyl)acrylate. MS (EST, m/z): 381 [M+H]+.

Step-4: Synthesis of (E)-N-hydroxy-3-(2-(3-(4-methoxybenzyl)-2-oxoimidazolidin-1-yl)phenyl)acrylamide Intermediate from Step-3, ethyl (E)-3-(2-(3-(4-methoxybenzyl)-2-oxoimidazolidin-1-yl)phenyl)acrylate (0.014 g, 0.038 mmol, 1.0 equiv) was dissolved in Tetrahydrofuran (0.8 mL) and Methanol (0.2 ml). NH₂OH (0.028 g, 0.376 mmol, 50%4 in water, 10.00 equiv), and NaOH (0.075 mL, 1 mol/L, 2.00 equiv) were added. The resulting solution was stirred for 3 hours at room temperature. The reaction was concentrated to dryness. Purified by HPLC (Column: Waters XBridge Prep C18 OBD 5 um, 19×50 mm column; Mobile Phase A: Water with 0.1% HCO₂H, Mobile Phase B: Acetonitrile with 0.1% HCO₂H; Flow rate: 23 mL/min, Gradient: 8 min gradient 0% B up to 35% B). The collected fractions were lyophilized to afford 0.0072 g (52% yield) of (E)-N-hydroxy-3-(2-(3-(4-methoxybenzyl)-2-oxoimidazolidin-1-yl)phenyl)acrylamide. MS: (ES, m/z): 368 [M+H]+. ¹H NMR (DMSO) δ: 10.83 (br s, 1H), 8.14 (s, 1H), 7.74-8.05 (m, 1H), 7.63-7.73 (m, 1H), 7.14-7.50 (m, 4H), 6.77-7.11 (m, 2H), 6.67 (br d, J=16.1 Hz, 1H), 6.34-6.56 (m, 1H), 4.17-4.49 (m, 21H), 3.54-3.92 (m, 5H), 3.26-3.43 (m, 2H).

Example 53—(E)-N-hydroxy-3-(2-(4-(4-methoxybenzyl)-2-oxopiperazin-1-yl)phenyl)acrylamide (I-293)

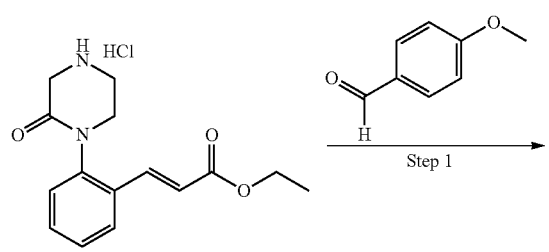

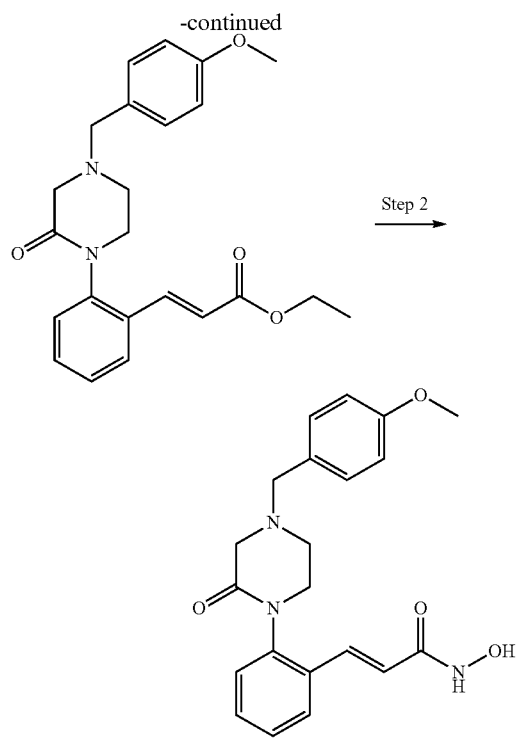

Step-1: Synthesis of ethyl (E)-3-(2-(4-(4-methoxybenzyl)-2-oxopiperazin-1-yl)phenyl)acrylate Ethyl (E)-3-(2-(2-oxopiperazin-1-yl)phenyl)acrylate hydrochloride (0.031 g, 0.113 mmol, 1.0 equiv) was combined with triethylamine (0.011 g, 0.113 mmol, 1.0 equiv) in DCE (1 mL) After 15 minutes at room temperature, 1 drop of acetic acid and 4-methoxybenzaldehyde (0.018 g, 0.131 mmol, 1.2 equiv) were added and allowed to shake at room temperature for 30 minutes. Lastly, sodium triacetoxyborohydride (0.058 g, 0.273 mmol, 2.5 equiv) was added and the reaction was heated at 50° C. for 2 hours with stirring. The reaction was washed with 1 mL H₂O and the organic layer was separated and concentrated the dryness. The residue was purified by HPLC (Column: Waters XBridge Prep C18 OBD 5 um, 19×50 mm column; Mobile Phase A: Water with 0.1% HCO₂H, Mobile Phase B: Acetonitrile with 0.1% HCO₂H; Flow rate: 23 mL/min, Gradient: 8 min gradient 0% B up to 35% B). Isolated fractions were lyophilized to afford 0.0155 g (36% yield) of ethyl (E)-3-(2-(4-(4-methoxybenzyl)-2-oxopiperazin-1-yl)phenyl)acrylate. MS (ESI, m/z): 395 [M+H]+.

Step-2: Synthesis of (E)-N-hydroxy-3-(2-(4-(4-methoxybenzyl)-2-oxopiperazin-1-yl)phenyl)acrylamide Intermediate from Step-1, ethyl (E)-3-(2-(4-(4-methoxybenzyl)-2-oxopiperazin-1-yl)phenyl)acrylate (0.015 g, 0.039 mmol, 1.0 equiv) was dissolved in Tetrahydrofuran (0.8 mL) and Methanol (0.2 mL). NH₂OH (0.028 g, 0.376 mmol, 50% in water, 10.00 equiv), and 1N aq. NaOH (0.075 mL, 2.00 equiv) were added. The resulting solution was stirred for 3 hours at room temperature. The reaction was concentrated to dryness. Purified by HPLC (Column: Waters XBridge Prep C18 OBD 5 um, 19×50 mm column. Mobile Phase A: Water with 0.1% HCO₂H, Mobile Phase B:

Acetonitrile with 0.1% HCO₂H; Flow rate: 23 mL/min, Gradient 8 min gradient 0% B up to 35% B). The collected fraction was lyophilized to afford 0.0035 g (24% yield) of (E)-N-hydroxy-3-(2-(4-(4-methoxybenzyl)-2-oxopiperazin-1-yl)phenyl)acrylamide. MS: (ES, m/z): 382 [M+H]⁺.

The following compounds in Table 14 were prepared according to the procedures for (E)-N-hydroxy-3-(2-(4-(4-methoxybenzyl)-2-oxopiperazin-1-yl)phenyl)acrylamide (I-293)

TABLE 14

| Example # | Structure | Name | (ES, m/z) [M + H]⁺ |
|---|---|---|---|
| I-495 | 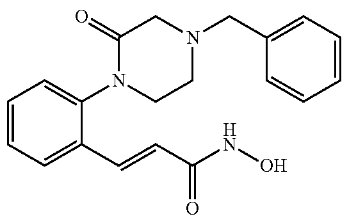 [SMILES: O=C(/C=C/c1ccccc1N1CCN(Cc2ccccc2)CC1=O)NO] | (E)-3-(2-(4-benzyl-2-oxopiperazin-1-yl)phenyl)-N-hydroxyacrylamide | 352 |
| I-630 | | (E)-3-(2-(4-(4-fluorobenzyl)-2-oxopiperazin-1-yl)phenyl)-N-hydroxyacrylamide | 370 |

Example 54—(E)-N-hydroxy-3-(2-(2-oxo-3-phenylimidazolidin-1-yl)phenyl)acrylamide (I-302)

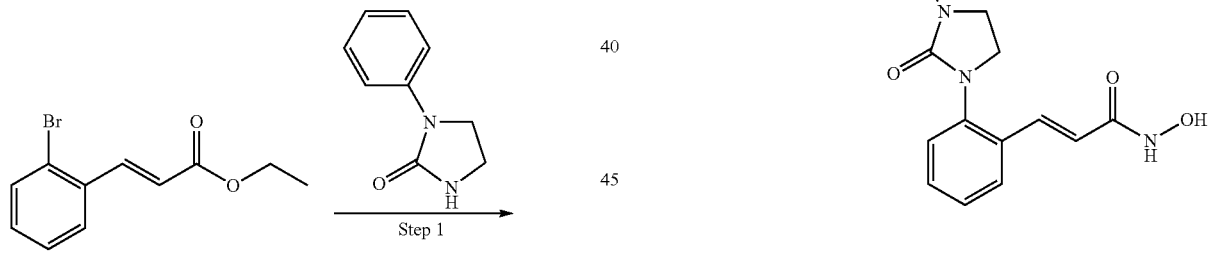

Step-1: Synthesis of ethyl (E)-3-(2-(2-oxo-3-phenylimidazolidin-1-yl)phenyl)acrylate A 10-mL microwave vial was equipped with a stir bar and ethyl (E)-3-(2-bromophenyl)acrylate (0.070 g, 0.274 mmol, 1.0 equiv), 1-phenylimidazolidin-2-one (0.053 g, 0.329 mmol, 1.2 equiv), potassium phosphate tribasic (0.146 g, 0.686 mmol, 2.5 equiv), (1R,2R)—N1,N2-dimethylcyclohexane-1,2-diamine (0.020 g, 0.137 mmol, 0.5 equiv), and copper (1) iodide (0.011 g, 0.055 mmol, 0.2 equiv) in DMF (2.5 mL). Nitrogen was bubbled through the reaction for 10 minutes. The resulting mixture was heated to 100° C. for 3 hours in the microwave. The reaction mixture was diluted with 3 mL EtOAC and washed with 2×2 mL H₂O. The organic layers was combined and concentrated to dryness to afford 0.024 g (26% crude yield) of ethyl (E)-3-(2-(2-oxo-3-phenylimidazolidin-1-yl)phenyl)acrylate. MS (ESI, m/z): 337 [M+H]⁺.

Step-2: Synthesis of (E)-N-hydroxy-3-(2-(2-oxo-3-phenylimidazolidin-1-yl)phenyl)acrylamide Intermediate from Step-1: ethyl (E)-3-(2-(2-oxo-3-phenylimidazolidin-1-yl)phenyl)acrylate (0.024 g, 0.071 mmol, 1.0 equiv) was dissolved in Tetrahydrofuran (0.8 mL) and Methanol (0.2 mL). NH$_2$OH (0.047 g, 0.713 mmol, 50/o in water, 10.00 equiv) and 1N aq. NaOH (0.143 mL, 2.00 equiv) were added. The resulting solution was stirred for 18 hours at room temperature. The reaction was concentrated to dryness. Purified by HPLC (Column: Waters XBridge Prep C18 OBD 5 um, 19×50 mm column; Mobile Phase A: Water with 0.1% HCO2H, Mobile Phase B: Acetonitrile with 0.1% HCO2H; Flow rate: 23 mL/min, Gradient: 8 min gradient 0% B up to 35% B). Fractions were lyophilized to afford 0.011 g (49% yield) of (E)-N-hydroxy-3-(2-(2-oxo-3-phenylimidazolidin-1-yl)phenyl)acrylamide. $^1$H NMR (DMSO) δ: 8.32 (br s, 1H), 7.55-7.69 (m, 3H), 7.27-7.53 (m, 7H), 6.82-7.17 (m, 3H), 6.62 (s, 1H), 6.45 (d, J=15.8 Hz, 1H), 3.97-4.07 (m, 3H), 3.59-3.93 (m, 9H), 2.97-3.28 (m, 3H), 2.52-2.84 (m, 2H). MS: (ES, m/z): 324 [M+H]$^+$.

Example 55—(E)-N-hydroxy-3-(2-(1-oxoisoindolin-2-yl)phenyl)acrylamide (I-308)

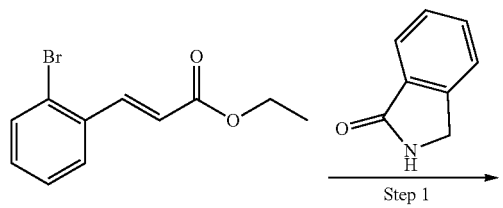

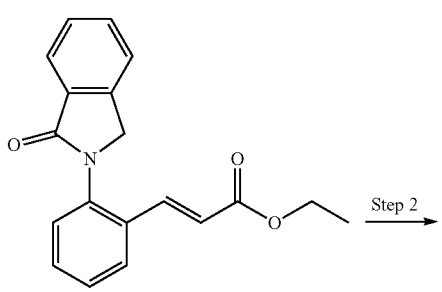

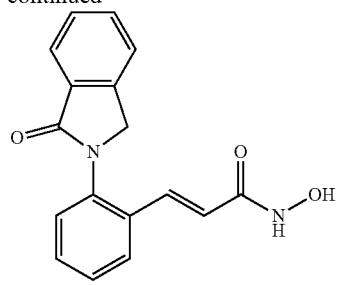

Step-1: Synthesis of ethyl (E)-3-(2-(1-oxoisoindolin-2-yl)phenyl)acrylate

A 10-mL microwave vial was equipped with a stir bar and ethyl (E)-3-(2-bromophenyl)acrylate (0.050 g, 0.235 mmol, 1.0 equiv), isoindolin-1-one (0.031 g, 0.235 mmol, 1.0 equiv), potassium phosphate tribasic (0.104 g, 0.490 mmol, 2.1 equiv), (1R,2R)—N1,N2-dimethylcyclohexane-1,2-diamine (0.006 g, 0.039 mmol, 0.16 equiv), and copper (I) iodide (0.004 g, 0.020 mmol, 0.08 equiv) in DMF (5 mL). Nitrogen was bubbled through the reaction for 10 minutes. The resulting mixture was heated to 120° C. for 3 hours in the microwave. The reaction mixture was diluted with 3 mL EtOAC and washed with 2 mL H$_2$O. The organic layers was separated and filtered through a 5 g Silicycle SiliaMetS-DMT column. Purified by HPLC (Column: Waters XBridge Prep C18 OBD 5 um, 19×50 mm column; Mobile Phase A: Water with 0.1% HCO$_2$-1, Mobile Phase B: Acetonitrile with 0.1% HCO$_2$H; Flow rate: 23 mL/min, Gradient: 8 min gradient 15% B up to 65% B). Fractions were lyophilized to afford 0.017 g (28% yield) ethyl (E)-3-(2-(1-oxoisoindolin-2-yl)phenyl)acrylate. MS (ESI, m/z): 308 [M+H]$^+$.

Step-2: Synthesis of (E)-N-hydroxy-3-(2-(1-oxoisoindolin-2-yl)phenyl)acrylamide Intermediate from Step-1: ethyl (E)-3-(2-(1-oxoisoindolin-2-yl)phenyl)acrylate (0.017 g, 0.055 mmol, 1.0 equiv) was dissolved in Tetrahydrofuran (0.8 mL) and Methanol (0.2 mL). NH$_2$OH (0.037 g, 0.553 mmol, 50% in water, 10.00 equiv) and 1N aq. NaOH (0.111 mL, 2.00 equiv) were added. The resulting solution was stirred for 4 hours at room temperature. The reaction was concentrated to dryness. Purified by HPLC (Column: Waters XBridge Prep C18 OBD 5 um, 19×50 mm column, Mobile Phase A: Water with 0.1% HCO$_2$H, Mobile Phase B: Acetonitrile with 0.1% HCO$_2$H; Flow rate: 23 mL/min. Gradient: 8 min gradient 0% B up to 35% B). Fractions were lyophilized to afford 0.004 g (49% yield) of (E)-N-hydroxy-3-(2-(1-oxoisoindolin-2-yl)phenyl)acrylamide MS: (ES, m/z): 295 [M+H]$^+$.

The following compounds in Table 15 were prepared according to the procedures for (E)-N-hydroxy-3-(2-(1-oxoisoindolin-2-yl)phenyl)acrylamide (I-308)

TABLE 15

| Ex. | Structure | Name | (ES, m/z) [M + H]+ | 1H NMR |
|---|---|---|---|---|
| I-309 | 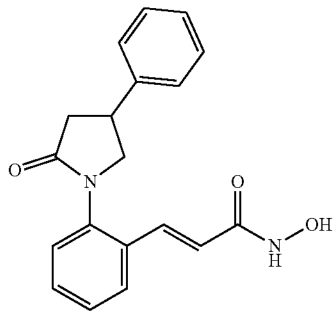 [SMILES: O=C(/C=C/c1ccccc1N1CC(c2ccccc2)CC1=O)NO] | (E)-N-hydroxy-3-(2-(2-oxo-4-phenylpyrrolidin-1-yl)phenyl)acrylamide | 323 | (DMSO) δ: 10.83 (br s,1H), 8.15 (s, 1H), 7.53-7.92 (m, 2H), 7.24-7.52 (m, 9H), 6.43 (d, J = 15.8 Hz, 1H), 3.94-4.09 (m, 2H), 3.54-3.92 (m, 6H), 2.79-3.05 (m, 2H), 2.58-2.79 (m, 2H), 1.40 (d, J = 5.0 Hz, 1H) |
| I-310 | 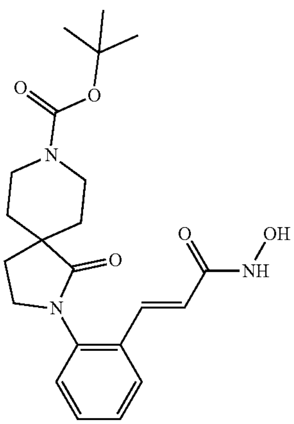 [SMILES: CC(C)(C)OC(=O)N1CCC2(CC1)CCN(c1ccccc1/C=C/C(=O)NO)C2=O] | tert-butyl (E)-2-(2-(3-(hydroxyamino)-3-oxoprop-1-en-1-yl)phenyl)-1-oxo-2,8-diazaspiro[4.5]decane-8-carboxylate | 416 | |

Example 56—Ethyl (E)-3-(2-(2-oxo-3-phenylpyrrolidin-1-yl)phenyl)acrylate (I-521)

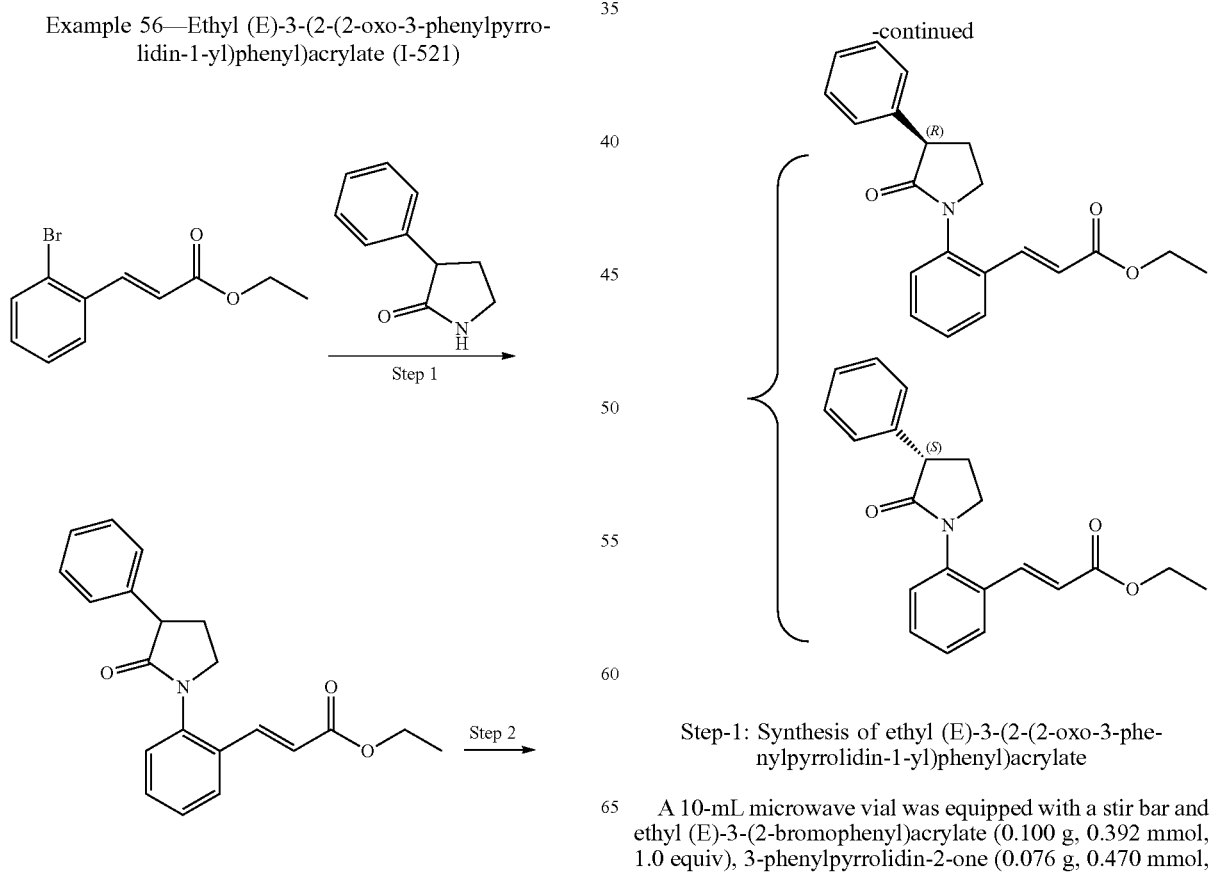

Step-1: Synthesis of ethyl (E)-3-(2-(2-oxo-3-phenylpyrrolidin-1-yl)phenyl)acrylate A 10-mL microwave vial was equipped with a stir bar and ethyl (E)-3-(2-bromophenyl)acrylate (0.100 g, 0.392 mmol, 1.0 equiv), 3-phenylpyrrolidin-2-one (0.076 g, 0.470 mmol, 1.2 equiv), potassium phosphate tribasic (0.208 g, 0.980 mmol, 2.5 equiv), (1R,2R)—N1,N2-dimethylcyclohexane-1,2-diamine (0.028 g, 0.196 mmol, 0.5 equiv), and copper (1) iodide (0.015 g, 0.078 mmol, 0.2 equiv) in DMF (5 mL). Nitrogen was bubbled through the reaction for 10 minutes. The resulting mixture was heated to 100° C. for 3 hours in the microwave. The reaction mixture was diluted with 3 mL EtOAC and washed with 2×2 mL H$_2$O The organic layer was combined and filtered through a 5 g Silicycle SiliaMetS-DMT column. Purified using reversed phase HPLC (Column: Waters XBridge Prep C18 OBD 5 um, 19×50 mm column; Mobile Phase A: Water with 0.1% HCO$_2$H. Mobile Phase B: Acetonitrile with 0.1% HCO$_2$H; Flow rate: 23 mL/min, Gradient: 8 min gradient 15% B up to 65% B). Fractions were lyophilized to afford 0.069 g (53% yield) of ethyl (E)-3-(2-(2-oxo-3-phenylpyrrolidin-1-yl)phenyl)acrylate MS (ESI, m/z) 336 [M+H]$^+$.

Step-2: Synthesis of ethyl (R,E)-3-(2-(2-oxo-3-phenylpyrrolidin-1-yl)phenyl) and ethyl (S,E)-3-(2-(2-oxo-3-phenylpyrrolidin-1-yl)phenyl)acrylate The racemate of ethyl (E)-3-(2-(2-oxo-3-phenylpyrrolidin-J-yl)phenyl)acrylate (0.040 g) was purified by Chiral HPLC with the following conditions Column: Chiralpak IA 4.6*25 mm, 5 um; Mobile Phase A: Hexanes, Mobile Phase B: IPA; Flow rate: 5 nil/min; Gradient: 30% B hold, Detector: 220 nm. The first peak was collected and concentrated to give 0.016 g and arbitrarily assigned as ethyl (R,E)-3-(2-(2-oxo-3-phenylpyrrolidin-1-yl)phenyl). MS: (ES, m/z): 336 [M+H]$^+$. The second peak was collected and concentrated to give 0.016 g arbitrarily assigned as ethyl (S,E)-3-(2-(2-oxo-3-phenylpyrrolidin-1-yl)phenyl). MS: (ES, m/z): 336 [M+H]$^+$.

Example 57—(E)-N-hydroxy-3-(2-(2-oxo-3-phenylpyrrolidin-1-yl)phenyl)acrylamide (I-327, I-328)

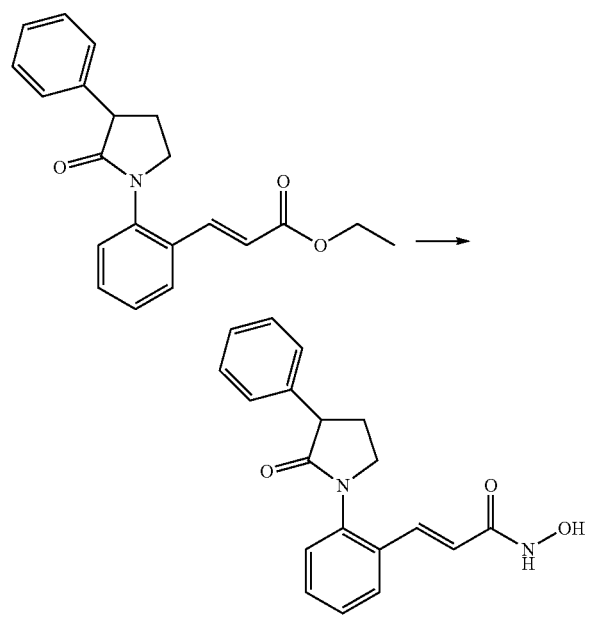

Racemic intermediate ethyl (E)-3-(2-(2-oxo-3-phenylpyrrolidin-1-yl)phenyl)acrylate (0.010 g, 0.031 mmol, 1.0 equiv) was dissolved in Tetrahydrofuran (0.4 mL) and Methanol (0.1 mL). NH$_2$OH (0.021 g, 0.310 mmol, 50% in water, 10.00 equiv) and 1N aq. NaOH (0.062 mL, 2.00 equiv) were added. The resulting solution was stirred for 1 hour at room temperature. The reaction was concentrated to dryness. Purified by HPLC (Column Waters XBridge Prep C18 OBD 5 um, 19×50 mm column; Mobile Phase A: Water with 0.1% HCO$_2$H, Mobile Phase B: Acetonitrile with 0.1% HCO$_2$H; Flow rate: 23 mL/min, Gradient: 8 min gradient 15% B up to 65% B). Fractions were lyophilized to afford 0.006 g (62% yield) of (E)-N-hydroxy-3-(2-(2-oxo-3-phenylpyrrolidin-1-yl)phenyl)acrylamide. MS: (ES, m/z): 323 [M+H]$^+$.

Example 58—(R,E)-N-hydroxy-3-(2-(2-oxo-3-phenylpyrrolidin-1-yl)phenyl)acrylamide (I-327)

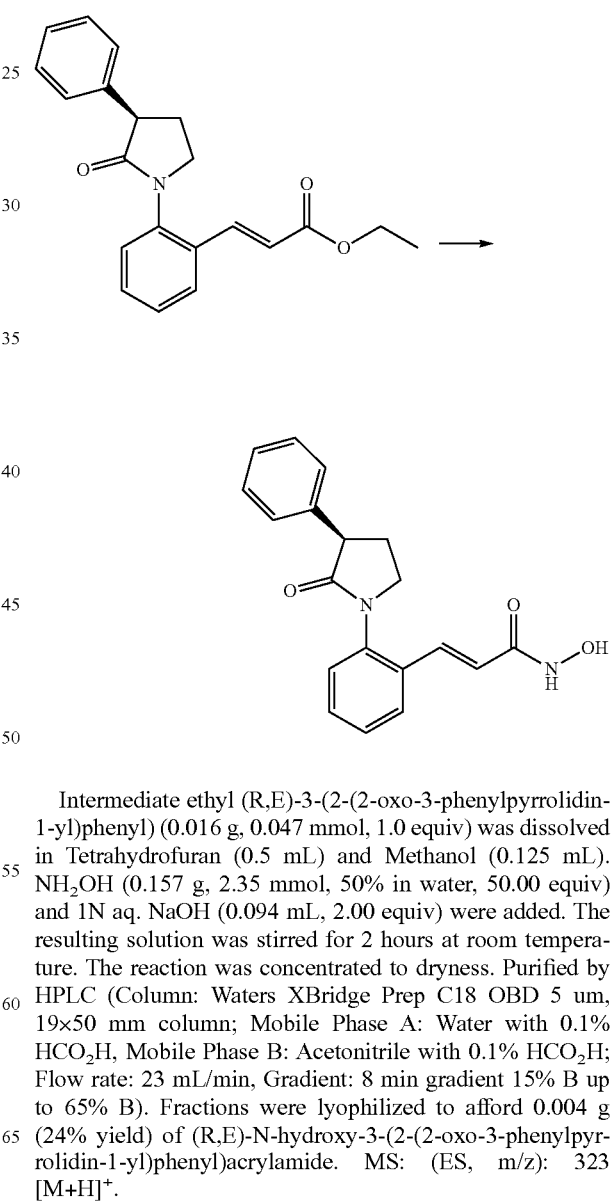

Intermediate ethyl (R,E)-3-(2-(2-oxo-3-phenylpyrrolidin-1-yl)phenyl) (0.016 g, 0.047 mmol, 1.0 equiv) was dissolved in Tetrahydrofuran (0.5 mL) and Methanol (0.125 mL). NH$_2$OH (0.157 g, 2.35 mmol, 50% in water, 50.00 equiv) and 1N aq. NaOH (0.094 mL, 2.00 equiv) were added. The resulting solution was stirred for 2 hours at room temperature. The reaction was concentrated to dryness. Purified by HPLC (Column: Waters XBridge Prep C18 OBD 5 um, 19×50 mm column; Mobile Phase A: Water with 0.1% HCO$_2$H, Mobile Phase B: Acetonitrile with 0.1% HCO$_2$H; Flow rate: 23 mL/min, Gradient: 8 min gradient 15% B up to 65% B). Fractions were lyophilized to afford 0.004 g (24% yield) of (R,E)-N-hydroxy-3-(2-(2-oxo-3-phenylpyrrolidin-1-yl)phenyl)acrylamide. MS: (ES, m/z): 323 [M+H]$^+$.

Example 59—(S,E)-N-hydroxy-3-(2-(2-oxo-3-phenylpyrrolidin-1-yl)phenyl)acrylamide (I-327)

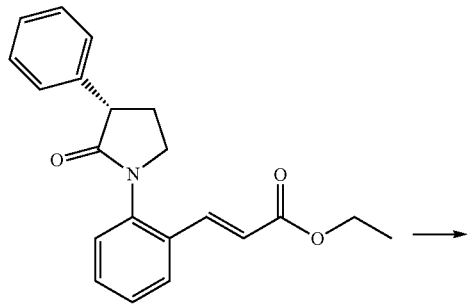

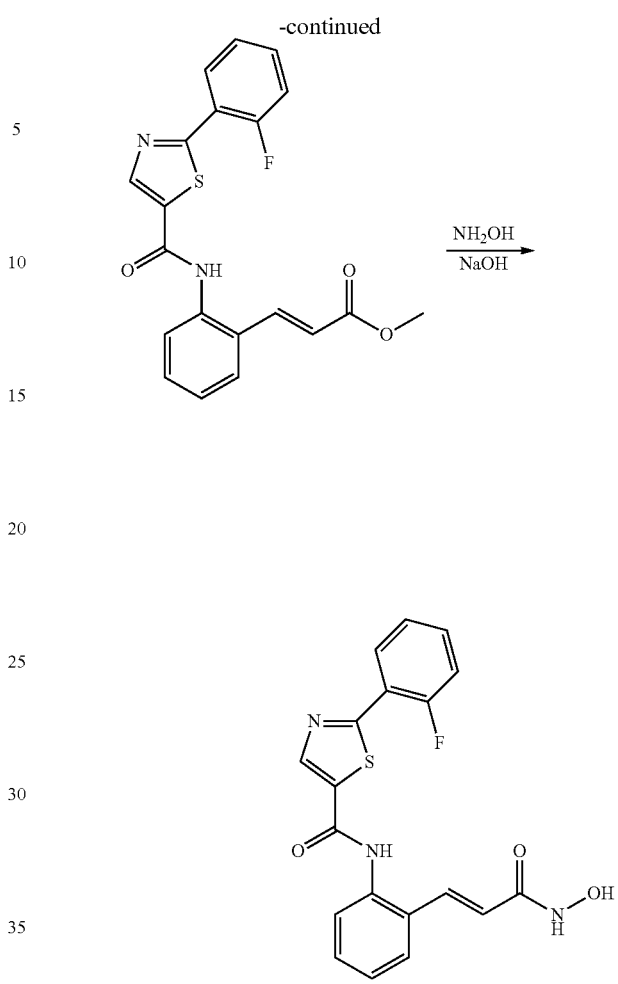

Intermediate ethyl (S,E)-3-(2-(2-oxo-3-phenylpyrrolidin-1-yl)phenyl) (0.016 g, 0.047 mmol, 1.0 equiv) was dissolved in Tetrahydrofuran (0.5 mL) and Methanol (0.125 mL). NH$_2$OH (0.157 g, 2.37 mmol, 50% in water, 50.00 equiv) and 1N aq. NaOH (0.094 mL, 2.00 equiv) were added. The resulting solution was stirred for 2 hours at room temperature. The reaction was concentrated to dryness Purified by HPLC (Column. Waters XBridge Prep C18 OBD 5 um, 19×50 mm column; Mobile Phase A: Water with 0.1% HCO$_2$H, Mobile Phase B: Acetonitrile with 0.1% HCO$_2$H; Flow rate 23 mL/min, Gradient: 8 min gradient 15% B up to 65% B). Fractions were lyophilized to afford 0.008 g (51% yield) of (S,E)-N-hydroxy-3-(2-(2-oxo-3-phenylpyrrolidin-1-yl)phenyl)acrylamide. MS. (ES, m/z): 323 [M+H]$^+$.

Example 60—(E)-2-(2-fluorophenyl)-N-(2-(3-(hydroxyamino)-3-oxoprop-1-en-1-yl)phenyl)thiazole-5-carboxamide (I-311)

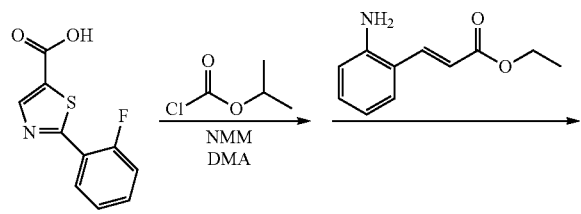

To a 2 mL reaction vial charged with 2-(2-fluorophenyl)thiazole-5-carboxylic acid (0.2M in DMA, 150 uL, 30umol) and N-methylmorpholine (neat, 24.7 uL, 225umol) was added isopropyl chloroformate (1M in toluene, 45 uL, 45umol). The mixture was shaken at RT for 20 min. and to this mixture was added methyl (E)-3-(2-aminophenyl)acrylate (0.2M in DMA, 150 uL, 30umol). The resulting reaction mixture was shaken at RT for 2 h then at 50° C. for overnight, after which time it was diluted with brine (500 uL) and extracted with ethyl acetate (2×500 uL). The combined organic layers were evaporated to dryness under reduced pressure. Mixed solvent of THF/MeOH (3:1, 180 uL) was added to the vial and it was shaken at 50° C. for 15 min to dissolve the residue. NH$_2$OH (50% in water, 125 uL) was added followed by NaOH (1N in water, 85 uL) and the vial was sealed and shaken at RT overnight. The solvent was evaporated under reduce pressure and the residue was dissolved in DMSO (500 uL) then purified by HPLC to yield (E)-2-(2-fluorophenyl)-N-(2-(3-(hydroxyamino)-3-oxoprop-1-en-1-yl)phenyl)thiazole-5-carboxamide (1 mg, 8.69% yield). LCMS RT: 1.12 min, m/z: 384[M+H]$^+$.

The following compounds in Table 16 were prepared according to the procedures for (E)-2-(2-fluorophenyl)-N-(2-(3-(hydroxyamino)-3-oxoprop-1-en-1-yl)phenyl)thiazole-5-carboxamide (I-311)

TABLE 16

| ID | Structure | Name | LC-MS [M + 1]+ | HPLC RT (min) |
|---|---|---|---|---|
| I-312 | 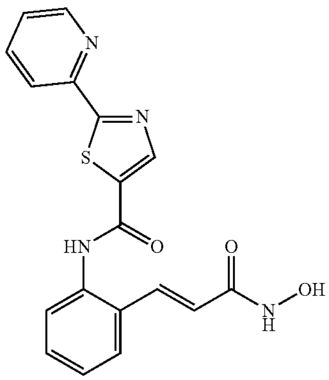 [SMILES: O=C(/C=C/c1ccccc1NC(=O)c1cnc(-c2ccccn2)s1)NO] | (E)-N-(2-(3-(hydroxyamino)-3-oxoprop-1-en-1-yl)phenyl)-2-(pyridin-2-yl)thiazole-5-carboxamide | 367 | 0.90 |
| I-313 | 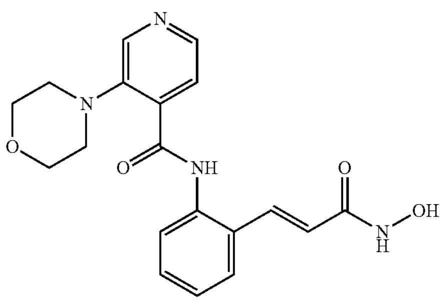 [SMILES: O=C(/C=C/c1ccccc1NC(=O)c1ccncc1N1CCOCC1)NO] | (E)-N-(2-(3-(hydroxyamino)-3-oxoprop-1-en-1-yl)phenyl)-3-morpholinoisonicotinamide | 369 | 0.71 |
| I-314 | 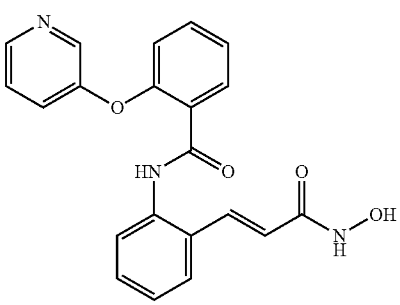 [SMILES: O=C(/C=C/c1ccccc1NC(=O)c1ccccc1Oc1cccnc1)NO] | (E)-N-(2-(3-(bydroxyamino)-3-oxoprop-1-en-1-yl]pheny])-2-(pyridin-3-yloxy)benzamide | 376 | 0.85 |
| I-319 | 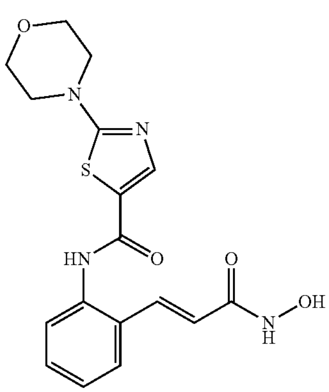 [SMILES: O=C(/C=C/c1ccccc1NC(=O)c1cnc(N2CCOCC2)s1)NO] | (E)-N-(2-(3-(hydroxyamino)-3-oxoprop-1-en-1-yl)phenyl)-2-morpholinothiazole-5-carboxamide | 375 | 0.76 |

TABLE 16-continued

| ID | Structure | Name | LC-MS [M + 1]+ | HPLC RT (min) |
|---|---|---|---|---|
| I-320 | | (E)-3-(2-chlorophenyl)-N-(2-(3-(hydroxyamino)-3-oxoprop-1-en-1-yl)phenyl)-5-methylisoxazole-4-carboxamide | 398 | 1.07 |
| I-323 | 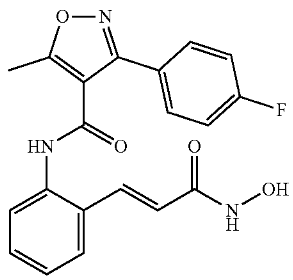 [SMILES: Cc1onc(-c2ccc(F)cc2)c1C(=O)Nc1ccccc1/C=C/C(=O)NO] | (E)-3-(4-fluorophenyl)-N-(2-(3-(hydroxyamino)-3-oxoprop-1-en-1-yl)phenyl)-5-methylisoxazole-4-carboxamide | 382 | 1.05 |
| I-38 | 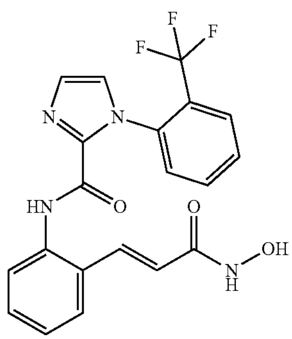 [SMILES: O=C(/C=C/c1ccccc1NC(=O)c1nccn1-c1ccccc1C(F)(F)F)NO] | (E)-N-(2-(3-(hydroxyamino)-3-oxoprop-1-en-1-yl)phenyl)-1-(2-(trifluoromethyl)phenyl)-1H-imidazole-2-carboxamide | 417 | 0.83 |
| I-61 | 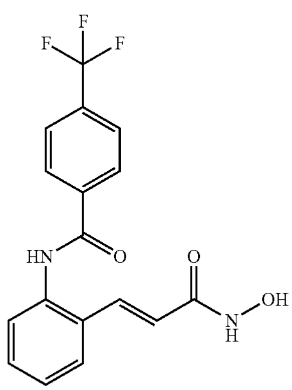 [SMILES: O=C(/C=C/c1ccccc1NC(=O)c1ccc(C(F)(F)F)cc1)NO] | (E)-N-(2-(3-(hydroxyamino)-3-oxoprop-1-en-1-yl)phenyl)-4-(trifluoromethyl)benzamide | 351 | 1.1 |
| I-62 | 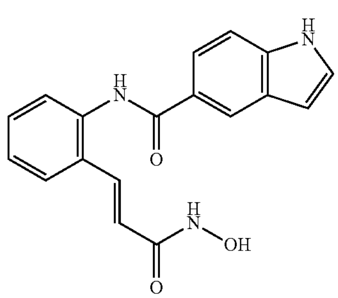 [SMILES: O=C(/C=C/c1ccccc1NC(=O)c1ccc2[nH]ccc2c1)NO] | (E)-N-(2-(3-(hydroxyamino)-3-oxoprop-1-en-1-yl)phenyl)-1H-indole-5-carboxamide | 322 | 0.82 |

TABLE 16-continued

| ID | Structure | Name | LC-MS [M + 1]+ | HPLC RT (min) |
| --- | --- | --- | --- | --- |
| I-63 | 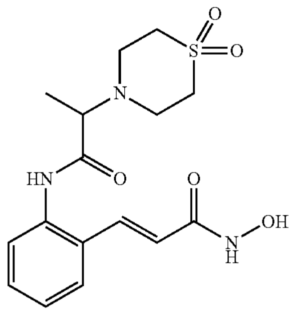 [SMILES: CC(C(=O)Nc1ccccc1/C=C/C(=O)NO)N1CCS(=O)(=O)CC1] | (E)-3-(2-(2-(1,1-dioxidothiomorpholino)propanamido)phenyl)-N-hydroxyacrylamide | 368 | 0.65 |
| I-64 | 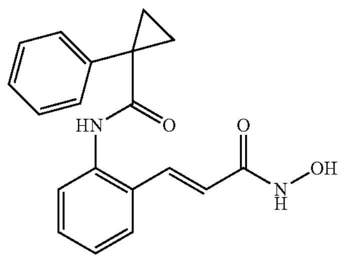 [SMILES: O=C(/C=C/c1ccccc1NC(=O)C1(c2ccccc2)CC1)NO] | (E)-N-(2-(3-(hydroxyamino)-3-oxoprop-1-en-1-yl)phenyl)-1-phenylcyclopropane-1-carboxamide | 323 | 1.02 |
| I-65 | 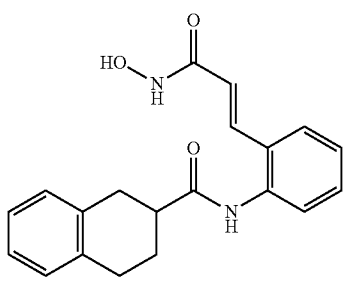 [SMILES: O=C(/C=C/c1ccccc1NC(=O)C1CCc2ccccc2C1)NO] | (E)-N-(2-(3-(hydroxyamino)-3-oxoprop-1-en-1-yl)phenyl)-1,2,3,4-tetrahydronaphthalene-2-carboxamide | 337 | 1.11 |
| I-66 | 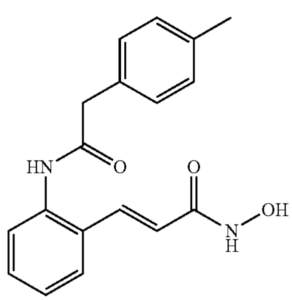 [SMILES: Cc1ccc(CC(=O)Nc2ccccc2/C=C/C(=O)NO)cc1] | (E)-N-hydroxy-3-(2-(2-(p-tolyl)acetamido)phenyl)acrylamide | 311 | 0.99 |
| I-67 | 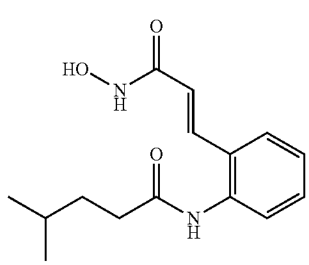 [SMILES: CC(C)CCC(=O)Nc1ccccc1/C=C/C(=O)NO] | (E)-N-(2-(3-(hydroxyamino)-3-oxoprop-1-en-1-yl)phenyl)-4-methylpentanamide | 277 | 0.93 |

TABLE 16-continued

| ID | Structure | Name | LC-MS [M + 1]+ | HPLC RT (min) |
|---|---|---|---|---|
| I-68 | 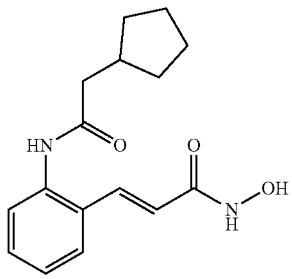 [SMILES: O=C(/C=C/c1ccccc1NC(=O)CC1CCCC1)NO] | (E)-3-(2-(2-cyclopentylacctamido)phenyl)-N-hydroxyacrylamide | 289 | 0.94 |
| I-69 | 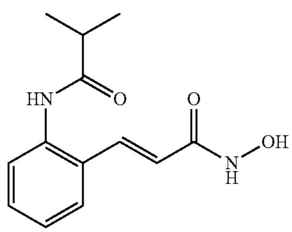 [SMILES: CC(C)C(=O)Nc1ccccc1/C=C/C(=O)NO] | (E)-N-hydroxy-3-(2-isobutyramidopbenyl)acrylamide | 249 | 0.64 |
| I-70 | 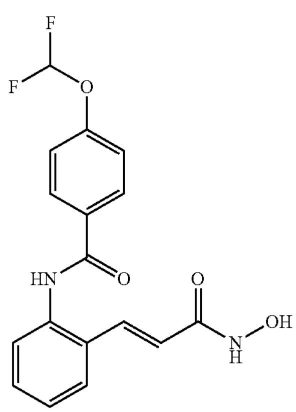 [SMILES: O=C(/C=C/c1ccccc1NC(=O)c1ccc(OC(F)F)cc1)NO] | (E)-4-(difluoromethoxy)-N-(2-(3-(hydroxyamino)-3-oxoprop-1-n-1-yl)phenyl)bonzamide | 349 | 1 |
| I-71 | 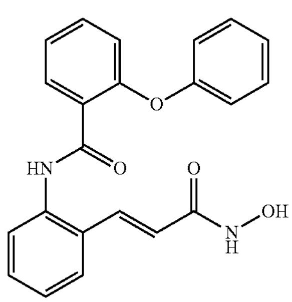 [SMILES: O=C(/C=C/c1ccccc1NC(=O)c1ccccc1Oc1ccccc1)NO] | (E)-N-(2-(3-(hydroxyamino)-3-oxoprop-1-en-1-yl)phenyl)-2-phenoxybenzamide | 375 | 1.23 |

TABLE 16-continued

| ID | Structure | Name | LC-MS [M + 1]+ | HPLC RT (min) |
|---|---|---|---|---|
| I-72 | 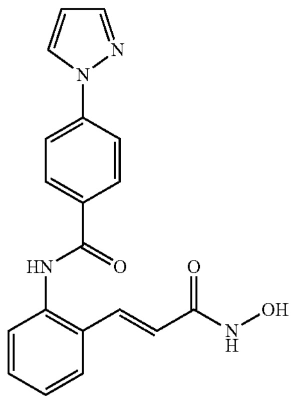 [SMILES: O=C(/C=C/c1ccccc1NC(=O)c1ccc(-n2cccn2)cc1)NO] | (E)-N-(2-(3-(hydroxyamino)-3-oxoprop-1-en-1-yl)phenyl)-4-(1H-pyrazol-1-yl)benzamide | 349 | 0.89 |
| I-73 | 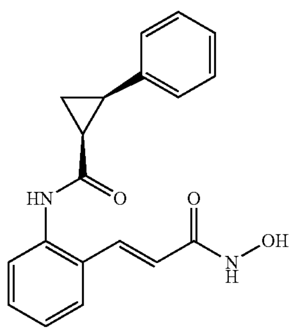 [SMILES: O=C(/C=C/c1ccccc1NC(=O)[C@H]1C[C@H]1c1ccccc1)NO] | (1S,2R)-N-(2-((E)-3-(hydroxyamino)-3-oxoprop-1-en-1-yl)phenyl)-2-phenylcyclopropane-1-carboxamide | 323 | 1.07 |
| I-74 | 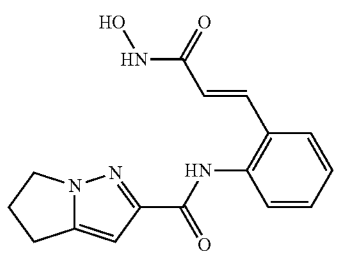 [SMILES: O=C(/C=C/c1ccccc1NC(=O)c1cc2n(n1)CCC2)NO] | (E)-N-(2-(3-(hydroxyamino)-3-oxoprop-1-cn-1-yl)phonyl)-5,6-dihydro-4H-pyrrolo[1,2-b]pyrazole-2-carboxamide | 313 | 0.76 |
| I-6 | 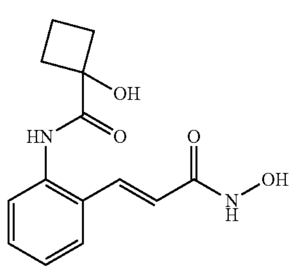 [SMILES: O=C(/C=C/c1ccccc1NC(=O)C1(O)CCC1)NO] | (E)-1-hydroxy-N-(2-(3-(hydroxyamino)-3-oxoprop-1-en-1-yl)phenyl)cyclobutane-1-carboxamide | 277 | 0.64 |

TABLE 16-continued

| ID | Structure | Name | LC-MS [M + 1]+ | HPLC RT (min) |
|---|---|---|---|---|
| I-75 | 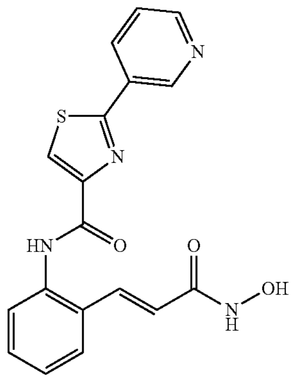 [SMILES: O=C(/C=C/c1ccccc1NC(=O)c1csc(-c2cccnc2)n1)NO] | (E)-N-(2-(3-(hydroxyamino)-3-oxoprop-1-en-1-yl)phenyl)-2-(pyridin-3-yl)thiazole-4-carboxamide | 367 | 0.86 |
| I-76 | 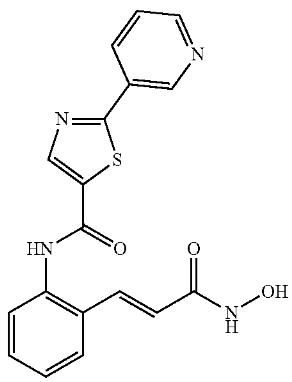 [SMILES: O=C(/C=C/c1ccccc1NC(=O)c1cnc(-c2cccnc2)s1)NO] | (E)-N-(2-(3-(hydroxyamino)-3-oxoprop-1-en-1-yl)phenyl)-2-(pyridin-3-yl)thiazole-5-carboxamide | 367 | 0.87 |
| I-77 | 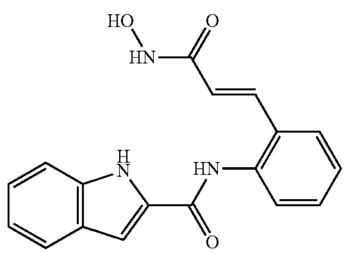 [SMILES: O=C(/C=C/c1ccccc1NC(=O)c1cc2ccccc2[nH]1)NO] | (E)-N-(2-(3-(hydroxyamino)-3-oxoprop-1-en-1-yl)phenyl)-1H-indole-2-carboxamide | 322 | 0.98 |
| I-78 | 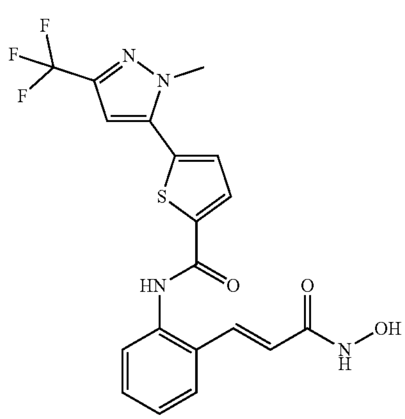 [SMILES: Cn1nc(C(F)(F)F)cc1-c1ccc(C(=O)Nc2ccccc2/C=C/C(=O)NO)s1] | (E)-N-(2-(3-(hydroxyamino)-3-oxoprop-1-en-1-yl)phenyl)-5-(1-methyl-3-(trifluoromethyl)-1H-pyrazol-5-yl)thiophene-2-carboxamide | 437 | 1.24 |

TABLE 16-continued

| ID | Structure | Name | LC-MS [M + 1]+ | HPLC RT (min) |
|---|---|---|---|---|
| I-79 | 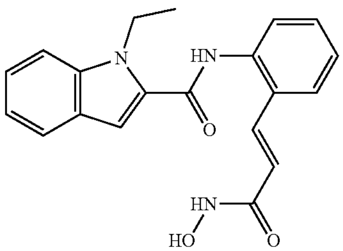 [SMILES: CCn1c(C(=O)Nc2ccccc2/C=C/C(=O)NO)cc2ccccc21] | (E)-1-ethyl-N-(2-(3-(hydroxyamino)-3-oxoprop-1-en-1-yl)phenyl)-1H-indole-2-carboxamide | 350 | 1.22 |
| I-80 | 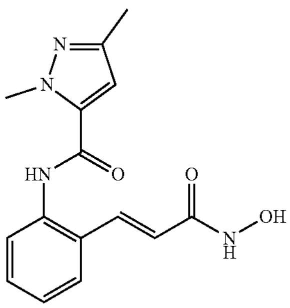 [SMILES: Cc1cc(C(=O)Nc2ccccc2/C=C/C(=O)NO)n(C)n1] | (E)-N-(2-(3-(hydroxyamino)-3-oxoprop-1-en-1-yl)phenyl)-1,3-dimethyl-1H-pyrazole-5-carboxamide | 301 | 0.73 |
| I-81 | 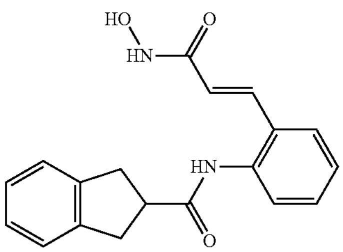 [SMILES: O=C(/C=C/c1ccccc1NC(=O)C1Cc2ccccc2C1)NO] | (E)-N-(2-(3-(hydroxyamino)-3-oxoprop-1-en-1-yl)phenyl)-2,3-dihydro-1H-indene-2-carboxamide | 323 | 1.04 |
| I-82 | 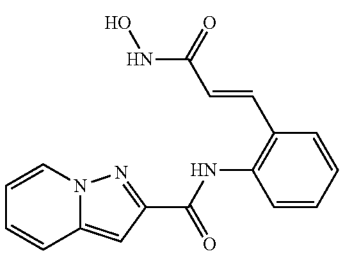 [SMILES: O=C(/C=C/c1ccccc1NC(=O)c1cc2ccccn2n1)NO] | (E)-N-(2-(3-(hydroxyamino)-3-oxoprop-1-en-1-yl)phenyl)pyrazolo[1,5-a]pyridine-2-carboxamide | 323 | 0.85 |
| I-83 | 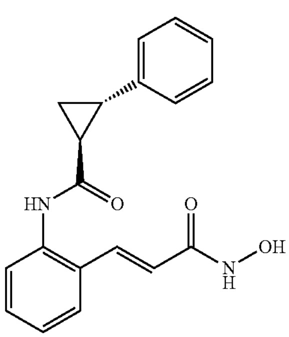 [SMILES: O=C(/C=C/c1ccccc1NC(=O)[C@H]1C[C@@H]1c1ccccc1)NO] | (1S,2S)-N-(2-((E)-3-(hydroxyamino)-3-oxoprop-1-en-1-yl)phenyl)-2-phenylcyclopropane-1-carboxamide | 323 | 1.08 |

TABLE 16-continued

| ID | Structure | Name | LC-MS [M + 1]+ | HPLC RT (min) |
|---|---|---|---|---|
| I-84 | 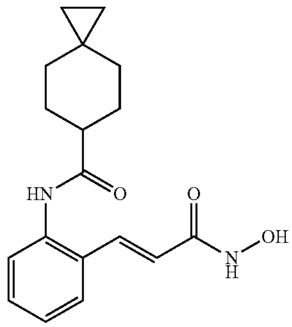 [SMILES: O=C(/C=C/c1ccccc1NC(=O)C1CCC2(CC1)CC2)NO] | (E)-N-(2-(3-(hydroxyamino)-3-oxoprop-1-en-1-yl)phenyl)spiro[2,5]octane-6-carboxamide | 315 | 1.08 |
| I-85 | 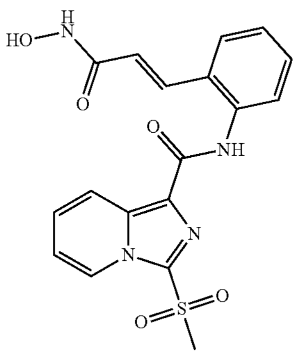 [SMILES: CS(=O)(=O)c1nc(C(=O)Nc2ccccc2/C=C/C(=O)NO)c2ccccn12] | (E)-N-(2-(3-(hydroxyamino)-3-oxoprop-1-en-1-yl)phenyl)-3-(methylsulfonyl])imidazo[1,5-a]pyridine-1-carboxamide | 401 | 0.9 |
| I-265 | 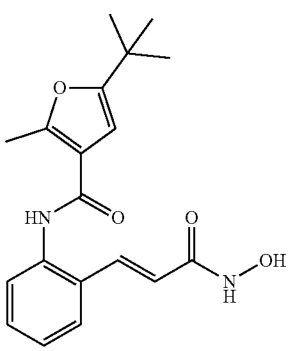 [SMILES: Cc1oc(C(C)(C)C)cc1C(=O)Nc1ccccc1/C=C/C(=O)NO] | (E)-5-(tert-butyl)-N-(2-(3-(hydroxyamino)-3-oxoprop-1-en-1-yl)phenyl)-2-methylfuran-3-carboxamide | 343 | 1.26 |
| I-266 | 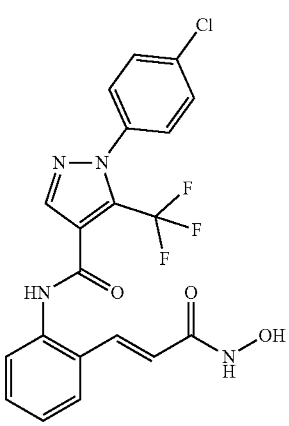 [SMILES: O=C(/C=C/c1ccccc1NC(=O)c1cnn(-c2ccc(Cl)cc2)c1C(F)(F)F)NO] | (E)-1-(4-chlorophenyl)-N-(2-(3-(hydroxyamino)-3-oxoprop-1-en-1-yl)phenyl)-5-(trifluoromethyl)-1H-pyrazole-4-carboxamide | 451 | 1.28 |

TABLE 16-continued

| ID | Structure | Name | LC-MS [M + 1]+ | HPLC RT (min) |
|---|---|---|---|---|
| I-267 | 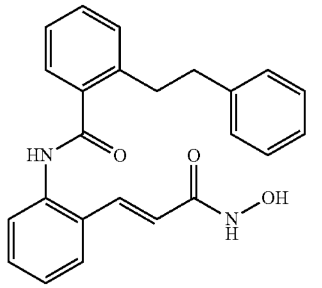 [SMILES: O=C(/C=C/c1ccccc1NC(=O)c1ccccc1CCc1ccccc1)NO] | (E)-N-(2-(3-(hydroxyamino)-3-oxoprop-1-en-1-yl)phenyl)-2-phenethylbenzamide | 387 | 1.31 |
| I-268 | 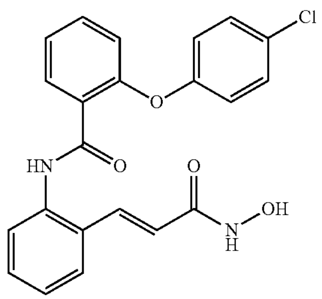 [SMILES: O=C(/C=C/c1ccccc1NC(=O)c1ccccc1Oc1ccc(Cl)cc1)NO] | (E)-2-(4-chlorophenoxy)-N-(2-(3-(hydroxyamino)-3-oxoprop-1-en-1-y)phenyl)benzamide | 409 | 1.34 |
| I-269 | 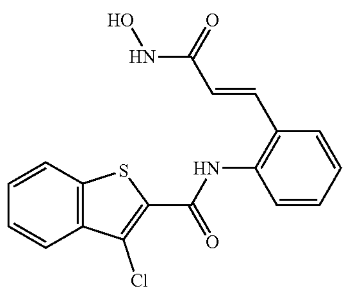 [SMILES: O=C(/C=C/c1ccccc1NC(=O)c1sc2ccccc2c1Cl)NO] | (E)-3-chloro-N-(2-(3-(hydroxyamino)-3-oxoprop-1-en-1-yl)phenyl)benzo[b]thiophene-2-carboxamide | 373 | 1.22 |
| I-270 | 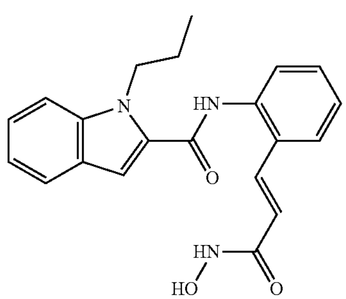 [SMILES: CCCn1c(C(=O)Nc2ccccc2/C=C/C(=O)NO)cc2ccccc21] | (E)-N-(2-(3-(hydroxyamino)-3-oxoprop-1-en-1-yl)phenyl)-1-propyl-1H-indole-2-carboxamide | 364 | 1.29 |
| I-271 | 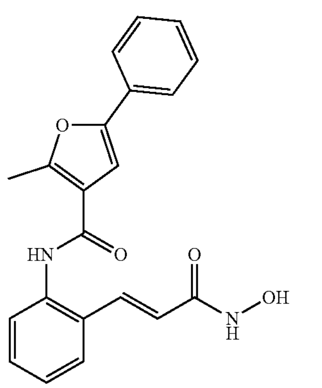 [SMILES: Cc1oc(-c2ccccc2)cc1C(=O)Nc1ccccc1/C=C/C(=O)NO] | (E)-N-(2-(3-(hydroxyamino)-3-oxoprop-1-en-1-yl)phenyl)-2-methyl-5-phenylfuran-3-carboxamide | 363 | 1.24 |

TABLE 16-continued

| ID | Structure | Name | LC-MS [M + 1]+ | HPLC RT (min) |
|---|---|---|---|---|
| I-272 | 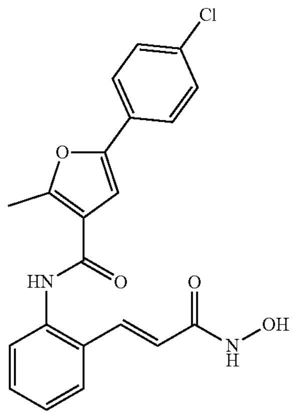 [SMILES: Cc1oc(-c2ccc(Cl)cc2)cc1C(=O)Nc1ccccc1/C=C/C(=O)NO] | (E)-5-(4-chlorophenyl)-N-(2-(3-(hydroxyamino)-3-oxoprop-1-en-1-yl)phenyl)-2-methylfuran-3-carboxamide | 397 | 1.4 |
| I-273 | 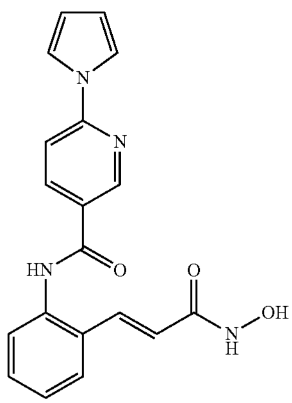 [SMILES: O=C(/C=C/c1ccccc1NC(=O)c1ccc(-n2cccc2)nc1)NO] | (E)-N-(2-(3-(hydroxyamino)-3-oxoprop-1-en-1-yl)phenyl)-6-(1H-pyrrol-1-yl)nicotinamide | 349 | 1 |
| I-274 | 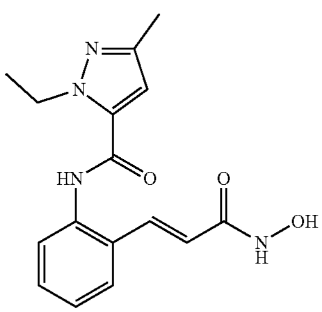 [SMILES: CCn1nc(C)cc1C(=O)Nc1ccccc1/C=C/C(=O)NO] | (E)-1-ethyl-N-(2-(3-(hydroxyamino)-3-oxoprop-1-en-1-yl)phenyl)-3-methyl-1H-pyrazole-5-carboxamide | 315 | 0.81 |
| I-275 | 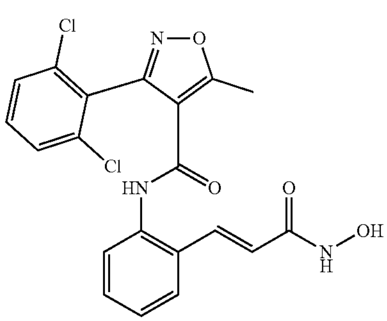 [SMILES: Cc1onc(-c2c(Cl)cccc2Cl)c1C(=O)Nc1ccccc1/C=C/C(=O)NO] | (E)-3-(2,6-dichlorophenyl)-N-(2-(3-(hydroxyamino)-3-oxoprop-1-en-1-yl)phenyl)-5-methylisoxazole-4-carboxamide | 432 | 115 |

TABLE 16-continued

| ID | Structure | Name | LC-MS [M + 1]+ | HPLC RT (min) |
|---|---|---|---|---|
| I-276 | 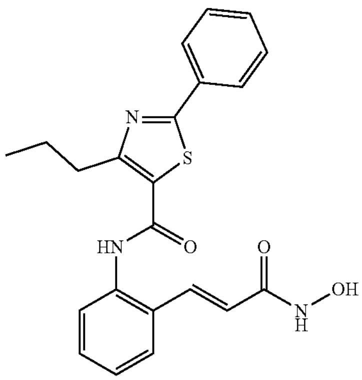 [SMILES: CCCc1nc(-c2ccccc2)sc1C(=O)Nc1ccccc1/C=C/C(=O)NO] | (E)-N-(2-(3-(hydroxyamino)-3-oxoprop-1-en-1-yl)phenyl)-2-phenyl-4-propylthiazole-5-carboxamide | 408 | 1.35 |
| I-277 | 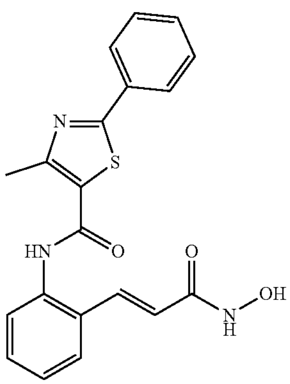 [SMILES: Cc1nc(-c2ccccc2)sc1C(=O)Nc1ccccc1/C=C/C(=O)NO] | (E)-N-(2-(3-(bydroxyamino)-3-oxoprop-1-en-1-yl)phenyl)-4-methyl-2-phenylthiazole-5-carboxamide | 380 | 1.11 |
| I-278 | 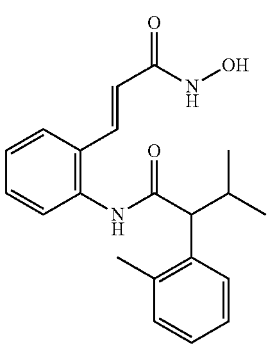 [SMILES: Cc1ccccc1C(C(=O)Nc1ccccc1/C=C/C(=O)NO)C(C)C] | (E)-N-(2-(3-(hydroxyamino)-3-oxoprop-1-en-1-yl)phenyl)-3-methyl-2-(o-tolyl)butanamide | 353 | 1.2 |
| I-279 | 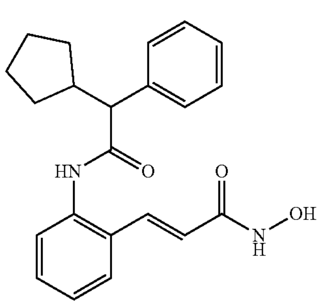 [SMILES: O=C(/C=C/c1ccccc1NC(=O)C(c1ccccc1)C1CCCC1)NO] | (E)-3-(2-(2-cyclopentyl-2-phenylacetamide)phenyl)-N-hydroxyacrylamide | 365 | 1.29 |

TABLE 16-continued

| ID | Structure | Name | LC-MS [M + 1]+ | HPLC RT (min) |
|---|---|---|---|---|
| I-280 | 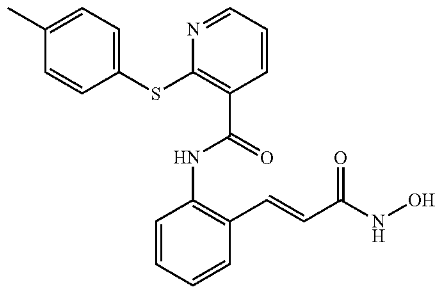 [SMILES: Cc1ccc(Sc2ncccc2C(=O)Nc2ccccc2/C=C/C(=O)NO)cc1] | (E)-N-(2-(3-(hydroxyamino)-3-oxoprop-1-en-1-yl)phenyl)-2-(p-tolylthio)nicotinamide | 406 | 1.16 |
| I-281 | 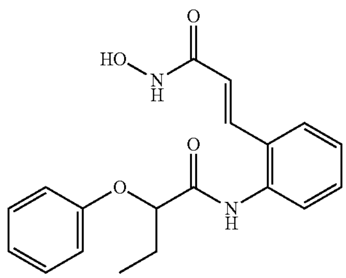 [SMILES: CCC(Oc1ccccc1)C(=O)Nc1ccccc1/C=C/C(=O)NO] | (E)-N-(2-(3-(hydroxyamino)-3-oxoprop-1-en-1-yl)phenyl)-2-phenoxybutanamide | 341 | 1.07 |
| I-282 | 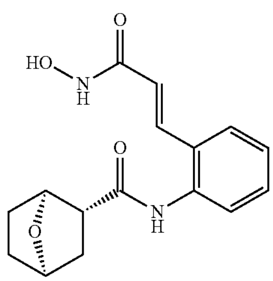 [SMILES: O=C(/C=C/c1ccccc1NC(=O)[C@@H]1C[C@H]2CC[C@@H]1O2)NO] | (1S,2R,4R)-N-(2-((E)-3-(hydroxyauxino)-3-oxoprop-1-en-1-yl)phenyl)-7-oxabicyclo[2.2.1]heptane-2-carboxamide | 303 | 0.65 |
| I-283 | 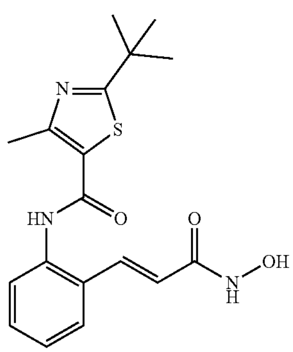 [SMILES: Cc1nc(C(C)(C)C)sc1C(=O)Nc1ccccc1/C=C/C(=O)NO] | (E)-2-(tert-butyl)-N-(2-(3-(hydroxyamino)-3-oxoprop-1-en-1-yl)phenyl)-4-methylthiazole-5-carboxamide | 360 | 1.04 |
| I-284 | 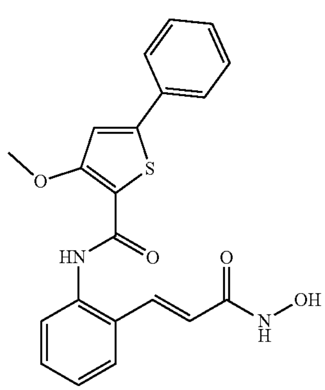 [SMILES: COc1cc(-c2ccccc2)sc1C(=O)Nc1ccccc1/C=C/C(=O)NO] | (E)-N-(2-(3-(hydroxyamino)-3-oxoprop-1-en-1-yl)phenyl)-3-methoxy-5-phenylthiophene-2-carboxamide | 395 | 1.37 |

TABLE 16-continued

| ID | Structure | Name | LC-MS [M + 1]+ | HPLC RT (min) |
|---|---|---|---|---|
| I-285 | 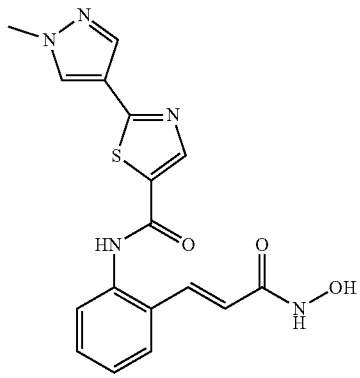 [SMILES: Cn1cc(-c2ncc(C(=O)Nc3ccccc3/C=C/C(=O)NO)s2)cn1] | (E)-N-(2-(3-(hydroxyamino)-3-oxoprop-1-en-1-yl)phenyl)-2-(1-methyl-1H-pyrazol-4-yl)thiazole-5-carboxamide | 370 | 0.86 |
| I-286 | 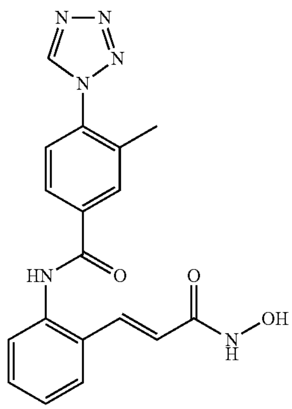 [SMILES: Cc1cc(C(=O)Nc2ccccc2/C=C/C(=O)NO)ccc1-n1cnnn1] | (E)-N-(2-(3-(hydroxyamino)-3-oxoprop-1-en-1-yl)phenyl)-3-methyl-4-(1H-tetrazol-1-yl)benzamide | 365 | 0.82 |
| I-287 | 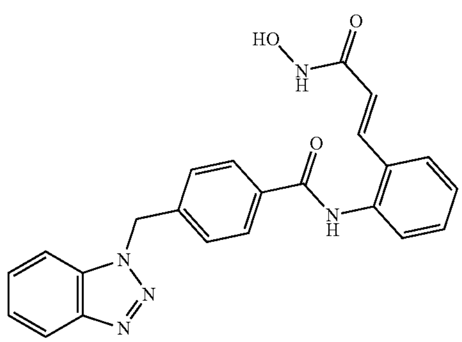 [SMILES: O=C(/C=C/c1ccccc1NC(=O)c1ccc(Cn2nnc3ccccc32)cc1)NO] | (E)-4-((1H-benzo[d][1,2,3]triazol-1-yl)methyl)-N-(2-(3-(hydroxyamino)-3-oxoprop-1-en-1-yl)phenyl)benzamide | 414 | 0.98 |
| I-288 | 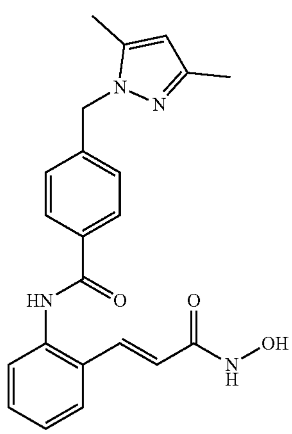 [SMILES: Cc1cc(C)n(Cc2ccc(C(=O)Nc3ccccc3/C=C/C(=O)NO)cc2)n1] | (E)-4-((3,5-dimethyl-1H-pyrazol-1-yl)methyl)-N-(2-(3-(hydroxyamino)-3-oxoprop-1-en-1-yl)phenyl)benzamide | 391 | 0.96 |

TABLE 16-continued

| ID | Structure | Name | LC-MS [M + 1]+ | HPLC RT (min) |
|---|---|---|---|---|
| I-303 | 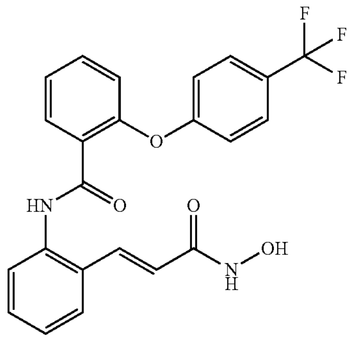 [SMILES: O=C(/C=C/c1ccccc1NC(=O)c1ccccc1Oc1ccc(C(F)(F)F)cc1)NO] | (E)-N-(2-(3-(hydroxyamino)-3-oxoprop-1-en-1-yl)pheny])-2-(4-(trifluoromethyl)phenoxy)benzamide | 443 | 1.37 |
| I-304 | 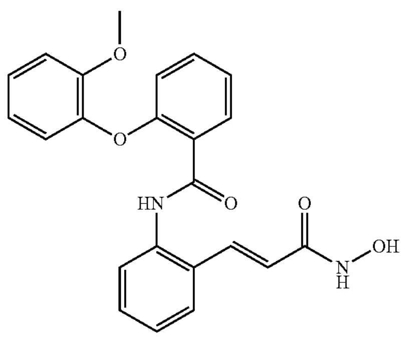 [SMILES: COc1ccccc1Oc1ccccc1C(=O)Nc1ccccc1/C=C/C(=O)NO] | (E)-N-(2-(3-(hydroxyamino)-3-oxoprop-1-en-1-yl)phenyl)-2-(2-methoxyphenoxy)benzamide | 405 | 1.22 |
| I-305 | 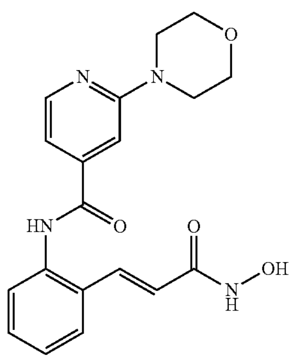 [SMILES: O=C(/C=C/c1ccccc1NC(=O)c1ccnc(N2CCOCC2)c1)NO] | (E)-N-(2-(3-(hydroxyamino)-3-oxoprop-1-en-1-yl)phenyl)-2-morpholinoisonicotinamide | 369 | 0.71 |
| I-306 | 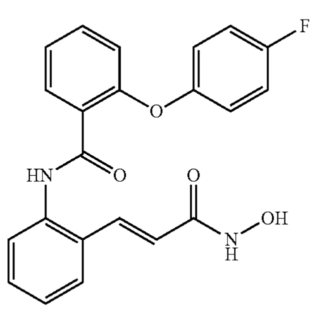 [SMILES: O=C(/C=C/c1ccccc1NC(=O)c1ccccc1Oc1ccc(F)cc1)NO] | (E)-2-(4-fluorophenoxy)-N-(2-(3-(hydroxyamino)-3-oxoprop-1-en-1-yl)phenyl)benzamide | 393 | 1.24 |

TABLE 16-continued

| ID | Structure | Name | LC-MS [M + 1]+ | HPLC RT (min) |
|---|---|---|---|---|
| I-534 | 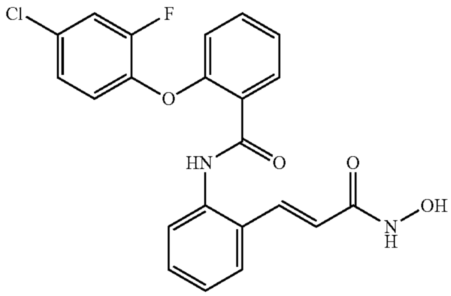 [SMILES: O=C(/C=C/c1ccccc1NC(=O)c1ccccc1Oc1ccc(Cl)cc1F)NO] | (E)-2-(4-chloro-2-fluorophenoxy)-N-(2-(3-(hydroxyamino)-3-oxoprop-1-en-1-yl)phenyl)benzamide | 427 | 1.39 |
| I-535 | 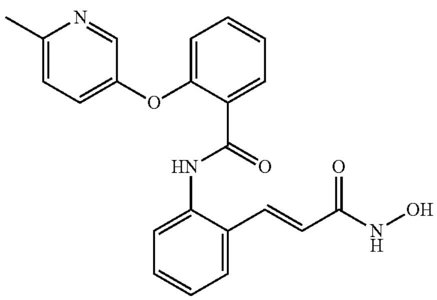 [SMILES: Cc1ccc(Oc2ccccc2C(=O)Nc2ccccc2/C=C/C(=O)NO)cn1] | (E)-N-(2-(3-(hydroxyamino)-3-oxoprop-1-en-1-yl)phenyl)-2-((6-methylpyridin-3-yl)oxy)benzamide | 390 | 0.67 |
| I-540 | 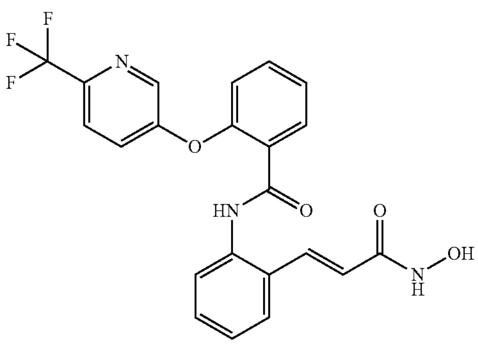 [SMILES: O=C(/C=C/c1ccccc1NC(=O)c1ccccc1Oc1ccc(C(F)(F)F)nc1)NO] | (E)-N-(2-(3-(hydroxyamino)-3-oxoprop-1-en-1-yl)phenyl)-2-((6-(trifluoromethyl)pyridin-3-yl)oxy)benzamide | 444 | 1.25 |
| I-537 | 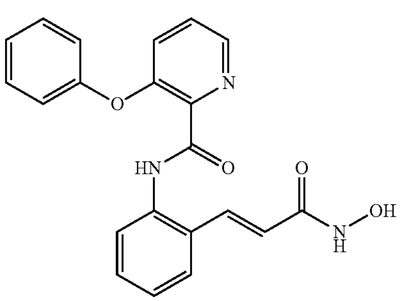 [SMILES: O=C(/C=C/c1ccccc1NC(=O)c1ncccc1Oc1ccccc1)NO] | N-{2-[(1E)-2-(hydroxycarbamoyl)eth-1-en-1-yl]phenyl}-3-phenoxypyridine-2-carboxamide | 376 | 1.07 |
| I-548 | 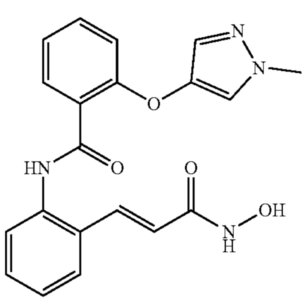 [SMILES: Cn1cc(Oc2ccccc2C(=O)Nc2ccccc2/C=C/C(=O)NO)cn1] | N-{2-[(1E)-2-(hydroxycarbamoyl)eth-1-en-1-yl]phenyl}-2-[(1-methyl-1H-pyrazol-4-yl)oxy]benzamide | 379 | 0.96 |

TABLE 16-continued
| ID | Structure | Name | LC-MS [M + 1]+ | HPLC RT (min) |
|---|---|---|---|---|
| I-549 | 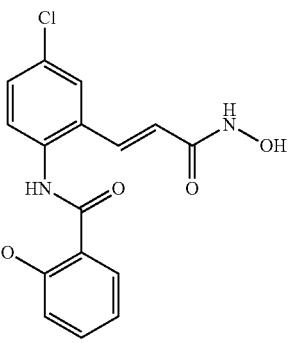 | N-{4-chloro-2-[(1E)-2-(hydroxycarbamoyl)eth-1-en-1-yl]phenyl}-2-(4-fluorophenoxy)benzamide | 427 | 1.43 |
| I-552 | 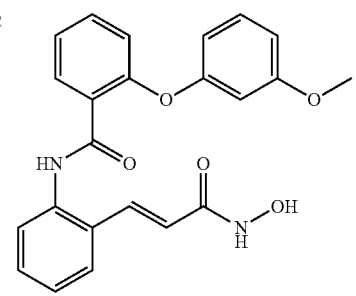 | N-{2-[(1E)-2-(hydroxycarbamoyl)eth-1-en-1-yl]phenyl}-2-(3-methoxyphenoxy)benzamide | 405 | 1.27 |
| I-539 | 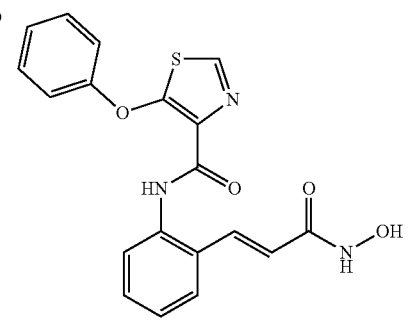 | N-{2-[(1E)-2-(hydroxycarbamoyl)eth-1-en-1-yl]phenyl}-5-phenoxy-1,3-thiazole-4-carboxamide | 382 | 1.11 |
| I-544 | 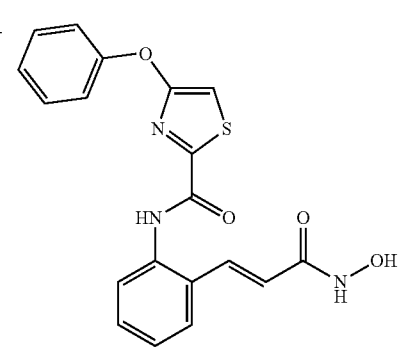 | N-{2-[(1B)-2-(hydroxycarbamoyl)eth-1-en-1-yl]phenyl}-4-phenoxy-1,3-thiazole-2-carboxamide | 382 | 1.25 |

TABLE 16-continued

| ID | Structure | Name | LC-MS [M + 1]+ | HPLC RT (min) |
|---|---|---|---|---|
| I-555 | 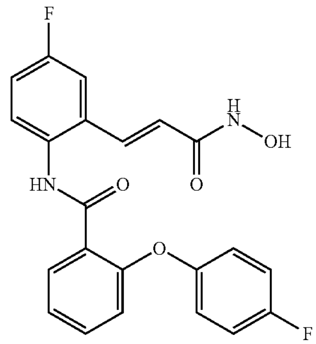 [SMILES: O=C(/C=C/c1cc(F)ccc1NC(=O)c1ccccc1Oc1ccc(F)cc1)NO] | N-{4-fluoro-2-[(1E)-2-(hydroxycarbamoyl)eth-1-en-1-yl]phenyl}-2-(4-fluorophenoxy)benzamide | 411 | 1.31 |
| I-556 | 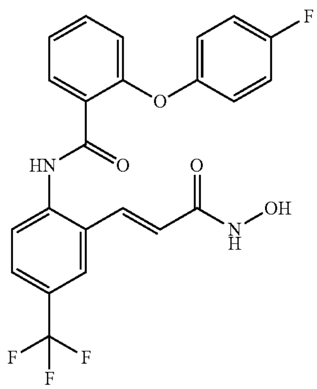 [SMILES: O=C(/C=C/c1cc(C(F)(F)F)ccc1NC(=O)c1ccccc1Oc1ccc(F)cc1)NO] | 2-(4-fluorophenoxy)-N-{2-[(1E)-2-(hydroxycarbamoyl)eth-1-en-1-yl]-4-(trifluoromethyl)phenyl}benzamide | 461 | 1.53 |
| I-557 | 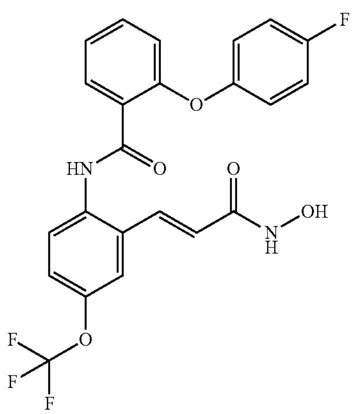 [SMILES: O=C(/C=C/c1cc(OC(F)(F)F)ccc1NC(=O)c1ccccc1Oc1ccc(F)cc1)NO] | 2-(4-fluorophenoxy)-N-{2-[(1E)-2-(hydroxycarbamoyl)eth-1-en-1-yl]-4-(trifluoromethoxy)phenyl}benzamide | 477 | 1.53 |
| I-558 | 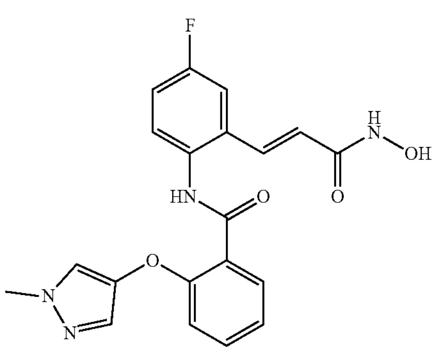 [SMILES: Cn1cc(Oc2ccccc2C(=O)Nc2ccc(F)cc2/C=C/C(=O)NO)cn1] | N-{4-fluoro-2-[(1E)-2-(hydroxycarbamoyl)eth-1-en-1-yl]phenyl}-2-[(1-methyl-1H-pyrazol-4-yl)oxy]benzamide | 397 | 1 |

TABLE 16-continued

| ID | Structure | Name | LC-MS [M + 1]+ | HPLC RT (min) |
|---|---|---|---|---|
| I-559 | 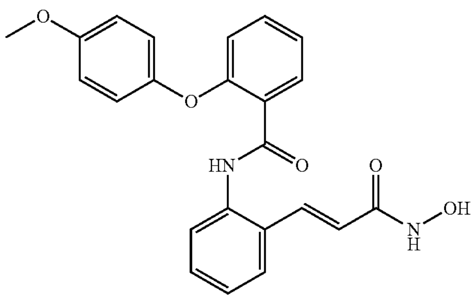 [SMILES: COc1ccc(Oc2ccccc2C(=O)Nc2ccccc2/C=C/C(=O)NO)cc1] | N-{2-[(1E)-2-(hydroxycarbamoyl)eth-1-en-1-yl]phenyl)-2-(4-methoxyphenoxy)benzamide | 405 | 127 |
| I-563 | 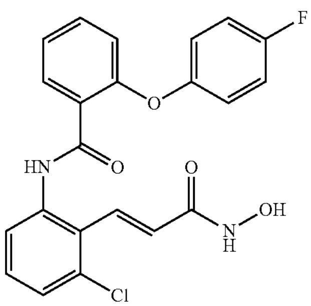 [SMILES: O=C(/C=C/c1c(Cl)cccc1NC(=O)c1ccccc1Oc1ccc(F)cc1)NO] | N-{3-chloro-2-[(1E)-2-(hydroxycarbamoyl)eth-1-en-1-yl]phenyl}-2-(4-fluorophenoxy)benzamide | 427 | 1.4 |
| I-564 | 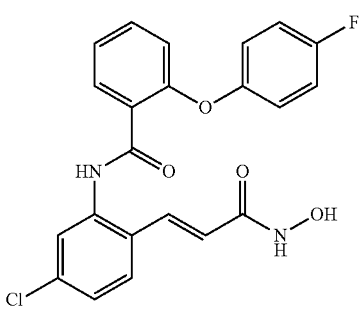 [SMILES: O=C(/C=C/c1ccc(Cl)cc1NC(=O)c1ccccc1Oc1ccc(F)cc1)NO] | N-{5-chloro-2-[(1E)-2-(hydroxycarbamoyl)eth-1-en-1-yl]phenyl}-2-(4-fluorophenoxy)benzamide | 427 | 1.47 |
| I-570 | 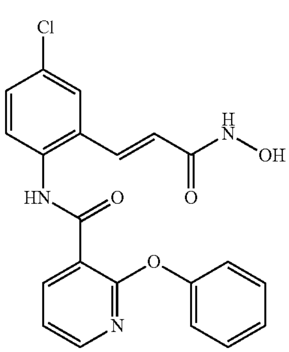 [SMILES: O=C(/C=C/c1cc(Cl)ccc1NC(=O)c1cccnc1Oc1ccccc1)NO] | N-{4-chloro-2-[(1E)-2-(hydroxycarbamoyl)eth-1-en-1-yl]phenyl}-2-phenoxypyridine-3-carboxamide | 410 | 1.26 |

TABLE 16-continued

| ID | Structure | Name | LC-MS [M + 1]+ | HPLC RT (min) |
|---|---|---|---|---|
| I-571 | 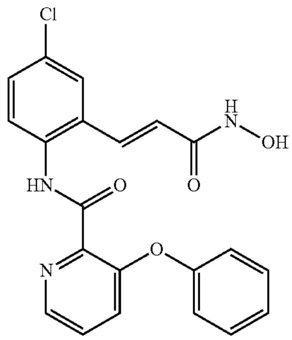 [SMILES: O=C(/C=C/c1cc(Cl)ccc1NC(=O)c1ncccc1Oc1ccccc1)NO] | N-{4-chloro-2-[(1E)-2-(hydroxycarbamoyl)eth-1-en-1-yl]phenyl}-3-phenoxypyridine-2-carboxamide | 410 | 1.23 |
| I-572 | 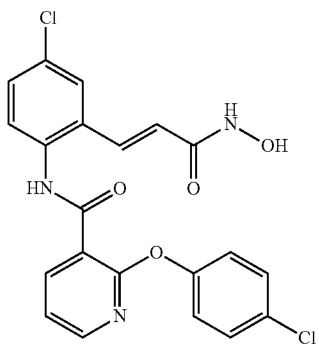 [SMILES: O=C(/C=C/c1cc(Cl)ccc1NC(=O)c1cccnc1Oc1ccc(Cl)cc1)NO] | N-(4-chloro-2-[(1E)-2-(hydroxycarbamoyl)eth-1-en-1-yl]phenyl)-2-(4-chlorophenoxy)pyridine-3-carboxamide | 444 | 1.39 |
| I-573 | 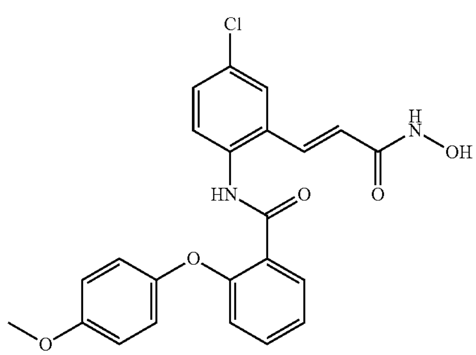 [SMILES: COc1ccc(Oc2ccccc2C(=O)Nc2ccc(Cl)cc2/C=C/C(=O)NO)cc1] | N-{4-chloro-2-[(1E)-2-(hydroxycarbamoyl)eth-1-en-1-yl]phenyl}-2-(4-methoxyphenoxy)benzamide | 439 | 1.42 |
| II-37 | 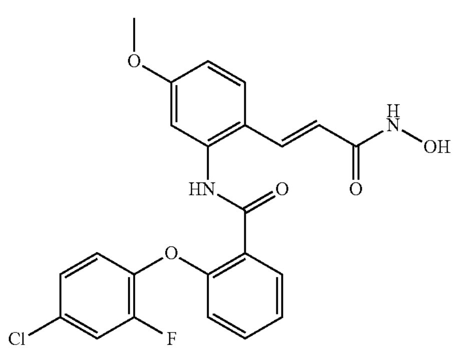 [SMILES: COc1ccc(/C=C/C(=O)NO)c(NC(=O)c2ccccc2Oc2ccc(Cl)cc2F)c1] | 2-(4-chloro-2-fluorophenoxy)-N-{2-[(1E)-2-(hydroxycarbamoyl)eth-1-en-1-yl]-5-methoxyphenyl}benzamide | 457 | 1.4 |

TABLE 16-continued

| ID | Structure | Name | LC-MS [M + 1]+ | HPLC RT (min) |
|---|---|---|---|---|
| I-560 | 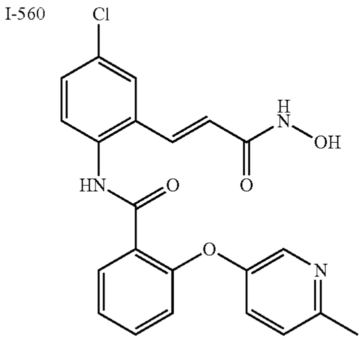 | N-{4-chloro-2-[(1E)-2-(hydroxycarbamoyl)eth-1-en-1-yl]phenyl}-2-[(6-methylpyridin-3-yl)oxy]benzamide | 424 | 1.21 |

Example 61—(E)-N-hydroxy-3-(2-(2-oxo-3-(4-(trifluoromethoxy)phenyl)imidazolidin-1-yl)phenyl)acrylamide (I-500)

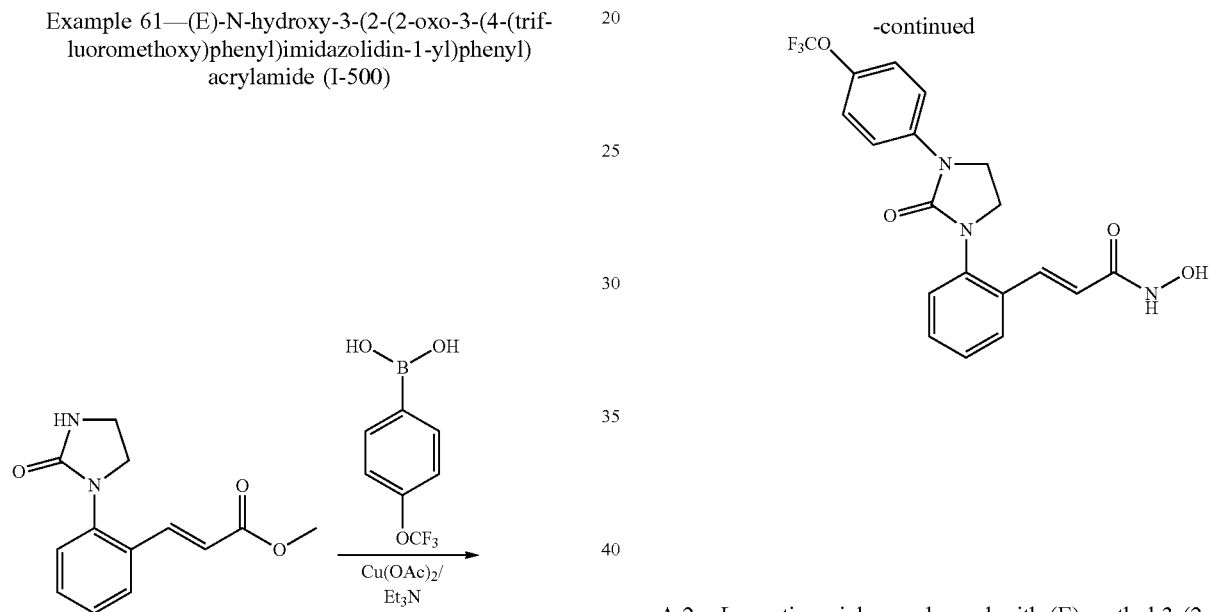

A 2 mL reaction vial was charged with (E)-methyl 3-(2-(2-oxoimidazolidin-1-yl)phenyl)acrylate (30umol, 7.39 mg), (4-(trifluoromethoxy)phenyl)boronic acid (12.36 mg, 60umol), copper(II) acetate (60umol, 10.9 mg), DCM (500 uL) and triethylamine (neat, 12.5 uL, 90 umol). The vial was sealed and shaken at RT for two days. The solvent was evaporated under reduced pressure and the residue was diluted with brine (500 uL), NH₄OH (100 uL) and extracted with ethyl acetate (2×600 uL). The combined organic layers were evaporated to dryness under reduced pressure. Mixed solvent of THF/MeOH (3:1, 180 uL) was added to the vial and it was shaken at 50° C. for 15 min to dissolve the residue. NH₂OH (50% in water, 125 uL) was added followed by NaOH (1N in water, 85 uL) and the vial was sealed and shaken at RT overnight. The solvent was evaporated under reduce pressure and the residue was dissolved in DMSO (500 uL) then purified by HPLC to yield (E)-N-hydroxy-3-(2-(2-oxo-3-(4-(trifluoro ethoxy)phenyl)imidazolidin-1-yl)phenyl)acrylamide (0.9 mg, 7.36% yield) LCMS RT. 1.27 min, m/z: 408 [M+H]⁺.

The following compounds in Table 17 were prepared according to the procedures for (E)-N-hydroxy-3-(2-(2-oxo-3-(4-(trifluoromethoxy)phenyl)imidazolidin-1-yl)phenyl)acrylamide (I-500).

TABLE 17

| ID | Structure | Name | LC-MS [M + 1]+ | HPLC RT (min) |
|---|---|---|---|---|
| I-501 | 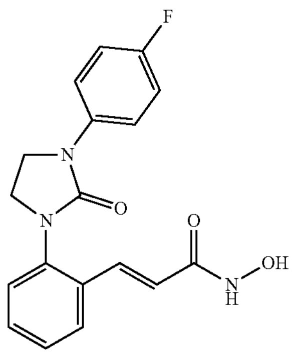 [SMILES: O=C(/C=C/c1ccccc1N1CCN(c2ccc(F)cc2)C1=O)NO] | (E)-3-(2-(3-(4-fluorophonyl)-2-oxoimidazolidin-1-yl)phenyl)-N-hydroxyacrylamide | 342 | 1.02 |
| I-502 | 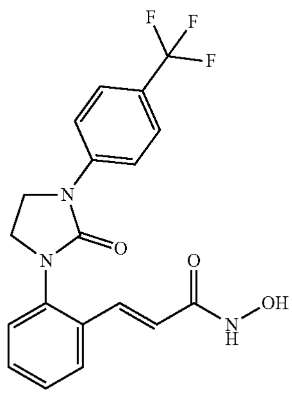 [SMILES: O=C(/C=C/c1ccccc1N1CCN(c2ccc(C(F)(F)F)cc2)C1=O)NO] | (E)-N-hydroxy-3-(2-(2-oxo-3-(4-(trifluoromethyl)phenyl)imidazolidin-1-yl)phenyl)acrylamide | 392 | 1.24 |
| I-503 | 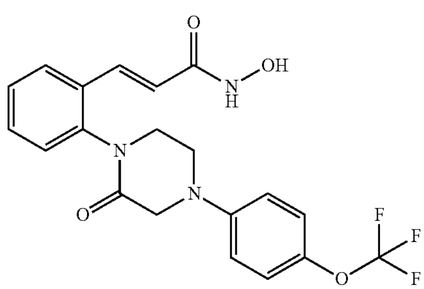 [SMILES: O=C(/C=C/c1ccccc1N1CCN(c2ccc(OC(F)(F)F)cc2)CC1=O)NO] | (E)-N-hydroxy-3-(2-(2-oxo-4-(4-(trifluoromethoxy)phenyl)piperazin-1-yl)phenyl)acrylamide | 422 | 1.24 |
| I-504 | 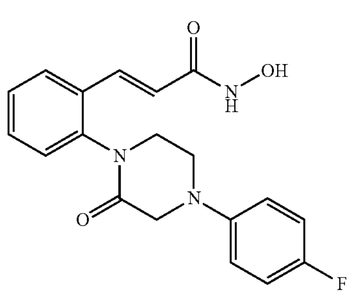 [SMILES: O=C(/C=C/c1ccccc1N1CCN(c2ccc(F)cc2)CC1=O)NO] | (E)-3-(2-(4-(4-fluorophenyl)-2-oxopipemazin-1-yl)phenyl)-N-hydroxyacrylantide | 356 | 0.8 |

TABLE 17-continued

| ID | Structure | Name | LC-MS [M + 1]+ | HPLC RT (min) |
|---|---|---|---|---|
| I-505 | 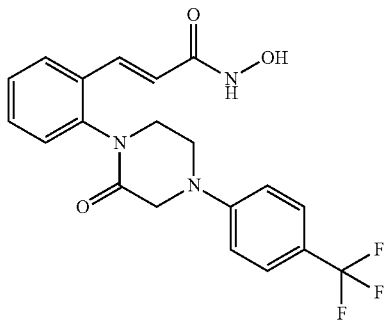 [SMILES: O=C(/C=C/c1ccccc1N1CCN(c2ccc(C(F)(F)F)cc2)CC1=O)NO] | (B)-N-hydroxy-3-(2-(2-oxo-4-(4-(trifluoromethyl)phenyl)piperazin-1-yl)phenyl)acrylamide | 406 | 1.21 |
| I-533 | | (E)-N-bydroxy-3-(2-(2-oxo-4-(p-tolyl)piperazin-1-yl)phenyl)acrylamide | 352 | 1.08 |

Example 62—(E)-3-(2-(4,4-difluoropiperidine-1-carbonyl)phenyl)-N-hydroxyacrylamide (II-17)

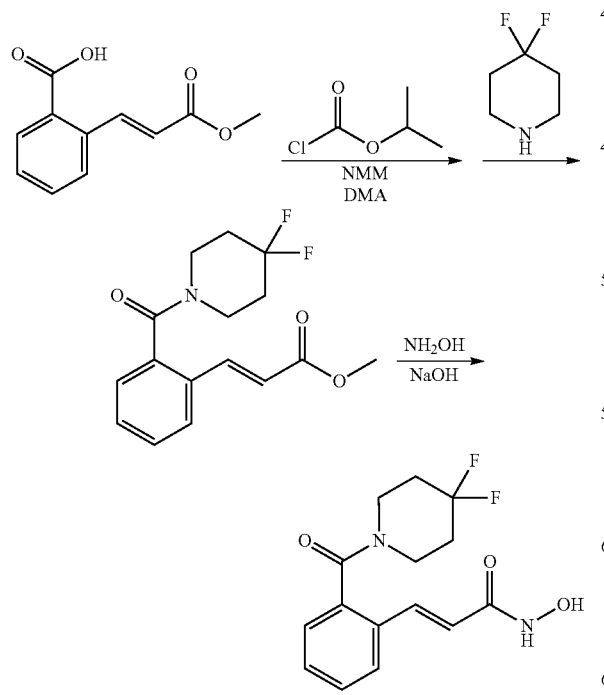

A 2 mL reaction vial was charged (E)-2-(3-methoxy-3-oxoprop-1-en-1-yl)benzoic acid (0.2M in DCE, 150 uL, 30umol) and N-methylmorpholine (neat, 24.7 uL, 225umol), under N₂ add isopropyl chloroformate 45 uL (1M in toluene, 45umol), the mixture was shaken at RT for 20 min. To this mixture was then added 4,4-difluoropiperidine (150 uL, 0.2M in DCE, 30umol) and the resulting reaction mixture was shaken at RT for 2 h then at 50° C. for overnight, after which time it was diluted with brine (500 uL) and extracted with ethyl acetate (2×500 uL). The combined organic layers were evaporated to dryness under reduced pressure. Mixed solvent of THF/MeOH (3.1, 180 uL) was added to the vial and it was shaken at 50° C. for 15 min to dissolve the residue. NH₂OH (50% in water, 125 uL) was added followed by NaOH (1N in water, 85 uL) and the vial was sealed and shaken at RT overnight. The solvent was evaporated under reduce pressure and the residue was dissolved in DMSO (500 uL) then purified by HPLC to yield (E)-3-(2-(4,4-difluoropiperidine-1-carbonyl)phenyl)-N-hydroxyacrylamide (0.7 mg, 7.52% yield). LCMS RT: 0.84 min, m/z: 311[M+H]⁺.

The following compounds in Table 18 were prepared according to the procedures for (E)-3-(2-(4,4-difluoropiperidine-1-carbonyl)phenyl)-N-hydroxyacrylamide (II-17)

TABLE 18

| ID | Structure | Name | LC-MS [M + 1]+ | RT (min) |
|---|---|---|---|---|
| II-2 | 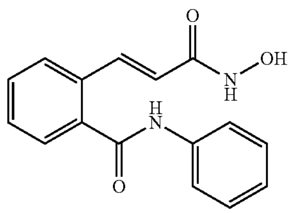 [SMILES: O=C(/C=C/c1ccccc1C(=O)Nc1ccccc1)NO] | (E)-2-(3-(hydroxyamino)-3-oxoprop-1-en-1-yl)-N-phenylbenzamide | 283 | 0.71 |
| II-3 | 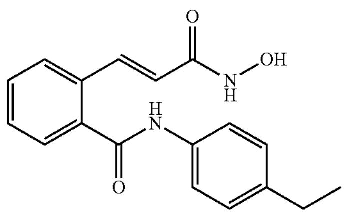 [SMILES: CCc1ccc(NC(=O)c2ccccc2/C=C/C(=O)NO)cc1] | (E)-N-(4-ethylphenyl)-2-(3-(hydroxyamino)-3-oxoprop-1-en-1-yl)benzamide | 311 | 0.96 |
| II-14 | 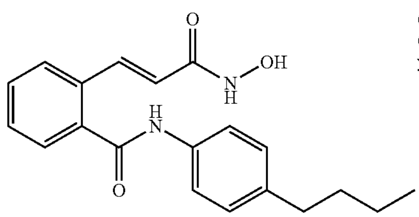 [SMILES: CCCCc1ccc(NC(=O)c2ccccc2/C=C/C(=O)NO)cc1] | (E)-N-(4-butylphenyl)-2-(3-(hydroxyamino)-3-oxoprop-1-en-1-yl)benzamide | 339 | 1.23 |
| II-4 | 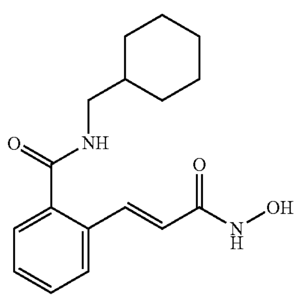 [SMILES: O=C(/C=C/c1ccccc1C(=O)NCC1CCCCC1)NO] | (E)-N-(cyclohexylmethyl)-2-(3-(hydroxyamino)-3-oxoprop-1-en-1-yl)benzamoide | 303 | 0.98 |
| II-5 | 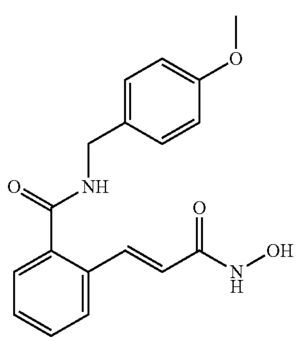 [SMILES: COc1ccc(CNC(=O)c2ccccc2/C=C/C(=O)NO)cc1] | (E)-2-(3-(hydroxyamino)-3-oxoprop-1-en-1-yl)-N-(4-methoxybenzyl)benzamide | 327 | 0.84 |
| II-6 | 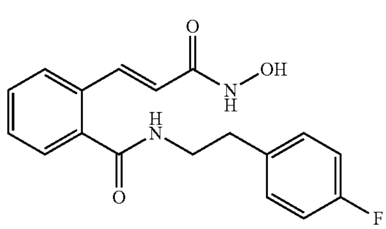 [SMILES: O=C(/C=C/c1ccccc1C(=O)NCCc1ccc(F)cc1)NO] | (E)-N-(4-fluorophenethyl)-2-(3-(hydroxyamino)-3-oxoprop-1-en-1-yl)benzamide | 329 | 0.92 |

TABLE 18-continued

| ID | Name | LC-MS [M + 1]+ | RT (min) |
|---|---|---|---|
| II-7 | (E)-N-([1,1'-biphenyl]-4-ylmethyl)-2-(3-(hydroxyamino)-3-oxoprop-1-en-1-yl)benzamide | 373 | 1.20 |
| II-15 | (E)-N-hydroxy-3-(2-(pyrrolidine-1-carbonyl)phenyl)acrylamide | 261 | 0.70 |
| II-16 | (E)-N-hydroxy-3-(2-(piperidine-1-carbonyl)phenyl)acrylamide | 275 | 0.83 |
| II-18 | (E)-2-(3.(hydroxyamino)-3-oxoprop-1-en-1-yl)-N-methyl-N-(3-(trifluoromethyl)benzyl)benzamide | 379 | 1.19 |
| II-19 | (E)-N-hydroxy-3-(2-(4-phenylpiperazine-1-carbonyl)phenyl)acrylamide | 352 | 1.03 |

TABLE 18-continued

| ID | Structure | Name | LC-MS [M + 1]+ | RT (min) |
|---|---|---|---|---|
| II-8 | 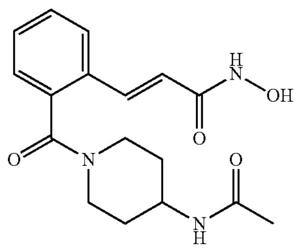 [SMILES: CC(=O)NC1CCN(C(=O)c2ccccc2/C=C/C(=O)NO)CC1] | (E)-3-(2-(4-acetamidopiperidine-1-carbonyl)phenyl)-N-hydroxyacrylamide | 332 | 0.57 |
| II-20 | 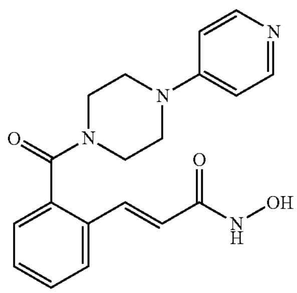 [SMILES: O=C(/C=C/c1ccccc1C(=O)N1CCN(c2ccncc2)CC1)NO] | (E)-N-hydroxy-3-(2-(4-(pyridin-4-yl)piperazine-1-carbonyl)phenyl)acrylamide | 353 | 0.48 |
| II-21 | 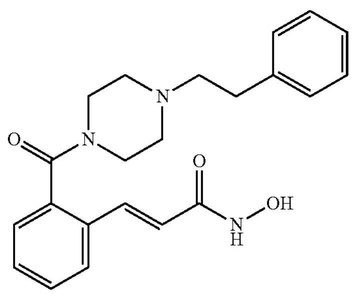 [SMILES: O=C(/C=C/c1ccccc1C(=O)N1CCN(CCc2ccccc2)CC1)NO] | (E)-N-hydroxy-3-(2-(4-phenethylpiperazine-1-carbonyl)phenyl)acrylamide | 380 | 0.68 |
| II-9 | 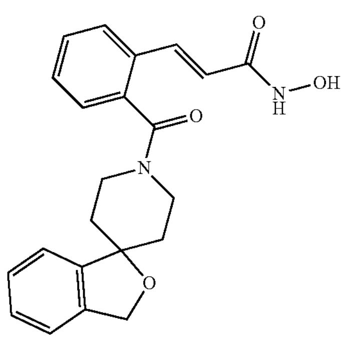 [SMILES: O=C(/C=C/c1ccccc1C(=O)N1CCC2(CC1)OCc1ccccc12)NO] | (E)-3-(2-(3H-spiro[isobenzofuran-1,4'-piperidine]-1'-carbonyl)phenyl)-N-hydroxyacrylamide | 379 | 1.08 |
| II-22 | 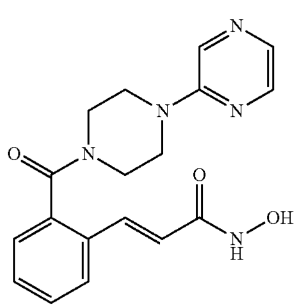 [SMILES: O=C(/C=C/c1ccccc1C(=O)N1CCN(c2cnccn2)CC1)NO] | (E)-N-hydroxy-3-(2-(4-(pyrazin-2-yl)piperazine-1-carbonyl)phenyl)acrylamide | 354 | 0.73 |

TABLE 18-continued

| ID | Structure | Name | LC-MS [M + 1]+ | RT (min) |
|---|---|---|---|---|
| II-23 | 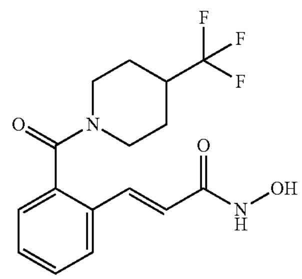 [SMILES: O=C(/C=C/c1ccccc1C(=O)N1CCC(C(F)(F)F)CC1)NO] | (E)-N-hydroxy-3-(2-(4-(trifluoromethyl)piperidine-1-carbonyl)phenylacrylamide | 343 | 0.99 |
| II-24 | 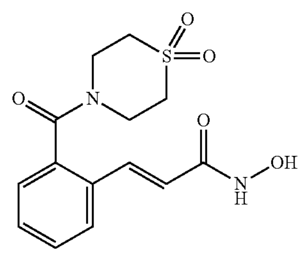 [SMILES: O=C(/C=C/c1ccccc1C(=O)N1CCS(=O)(=O)CC1)NO] | (E)-3-(2-(1,1-dioxidothiomorpholine-4-carbonyl)phenyl)-N-hydroxyacrylamide | 325 | 0.55 |
| II-25 | 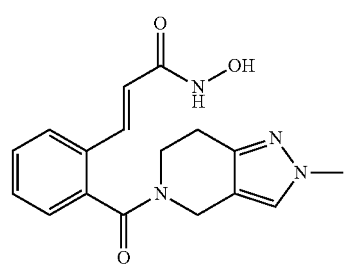 [SMILES: Cn1cc2c(n1)CCN(C(=O)c1ccccc1/C=C/C(=O)NO)C2] | (E)-N-hydroxy-3-(2-(2-methyl-4,5,6,7-tetrahydro-2H-pyrazolo[4,3-c]pyridine-5-carbonyl)phenylacrylamide | 327 | 0.66 |
| II-10 | 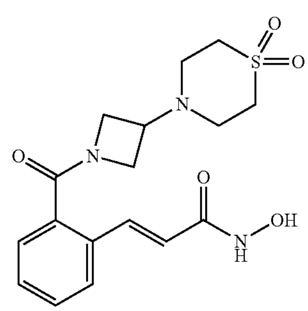 [SMILES: O=C(/C=C/c1ccccc1C(=O)N1CC(N2CCS(=O)(=O)CC2)C1)NO] | (E)-3-(2-(3-(1,1-dioxidothiomorpholino)azetidine-1-carbonyl)phenyl)-N-hydroxyacrylamide | 380 | 0.59 |
| II-26 | 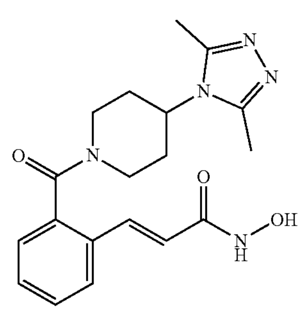 [SMILES: Cc1nnc(C)n1C1CCN(C(=O)c2ccccc2/C=C/C(=O)NO)CC1] | (E)-3-(2-(4-(3,5-dimethyl-4H-1,2,4-triazol-4-yl)piperidine-1-carbonyl)phenyl)-N-hydroxyacrylamide | 370 | 0.62 |

TABLE 18-continued

| ID | Structure | Name | LC-MS [M + 1]+ | RT (min) |
|---|---|---|---|---|
| (R)-II-27 | 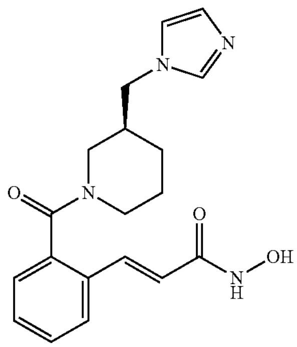 [SMILES: O=C(/C=C/c1ccccc1C(=O)N1CCC[C@H](Cn2ccnc2)C1)NO] | (R,E)-3-(2-(3-((1H-imidazol-1-yl)methyl)piperidine-1-carbonyl)phenyl)-N-hydroxyacrylamide | 355 | 0.54 |
| II-11 | 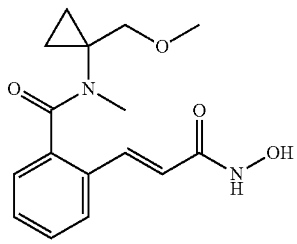 [SMILES: COCC1(N(C)C(=O)c2ccccc2/C=C/C(=O)NO)CC1] | (E)-2-(3-(hydroxyamino)-3-oxoprop-1-en-1-yl)-N-(1-(methoxymethyl)cyclopropyl)-N-methylbenzamide | 305 | 0.76 |
| II-12 | 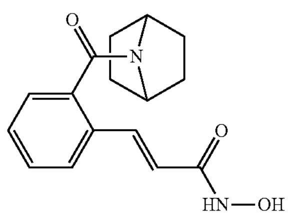 [SMILES: O=C(/C=C/c1ccccc1C(=O)N1C2CCC1CC2)NO] | (E)-3-(2-(7-azabicyclo[2.2.1]heptane-7-carbonyl)phenyl)-N-hydroxyacrylamide | 287 | 0.81 |
| II-28 | 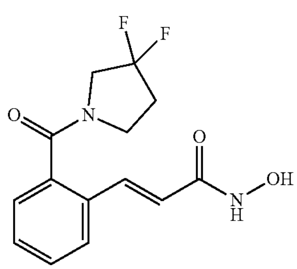 [SMILES: O=C(/C=C/c1ccccc1C(=O)N1CCC(F)(F)C1)NO] | (E)-3-(2-(3,3-difluoropyrrolidine-1-carbonyl)phenyl)-N-hydroxyacrylamide | 297 | 0.77 |

Example 63—(E)-3-(2-((4-chlorobenzyl)amino)phenyl)-N-hydroxyacrylamide (I-86)

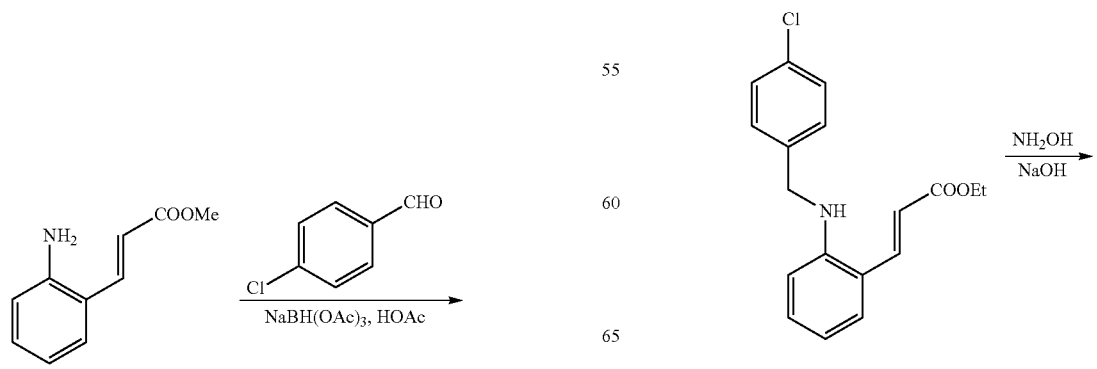

-continued

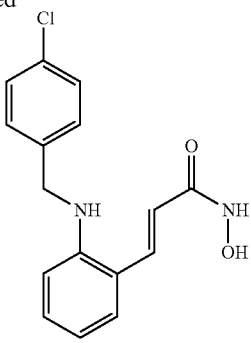

To a 2 mL reaction vial charged with methyl (E)-3-(2-aminophenyl)acrylate (0.2M in DCE, 150 uL, 30umol) and HOAc (neat, 25 uL, 437 umol) was added 4-chlorobenzaldehyde (0.2M in DCE, 250 uL, 50umol). The mixture was shaken at RT for 10 min then 50° C. for 2 h and to this mixture was added NaBH(OAc)$_3$ (0.2M in DCE, 500 uL, 100umol). The resulting reaction mixture was shaken at RT for overnight, after which time it was diluted with 1 N NaOH in brine (500 uL) and extracted with ethyl acetate (2×600 uL). The combined organic layers were evaporated to dryness under reduced pressure. Mixed solvent of THF/MeOH (3:1, 180 uL) was added to the vial and it was shaken at 50° C. for 15 min to dissolve the residue. NH$_2$OH (50% in water, 125 uL) was added followed by NaOH (1N in water, 85 uL) and the vial was sealed and shaken at RT overnight. The solvent was evaporated under reduce pressure and the residue was dissolved in DMSO (500 uL) then purified by HPLC to yield (2E)-3-(2-{[(4-chlorophenyl)methyl]amino}phenyl)-N-hydroxyprop-2-enamide (1.9 mg, 20.9% yield). LCMS RT: 1.38 min, m/z: 303[M+H]$^+$.

The following compounds in Table 19 were prepared according to the procedures for (E)-3-(2-((4-chlorobenzyl)amino)phenyl)-N-hydroxyacrylamide (I-86)

TABLE 19

| ID | Structure | Name | LC-MS [M + 1]+ | HPLC RT (min) |
| --- | --- | --- | --- | --- |
| I-87 | 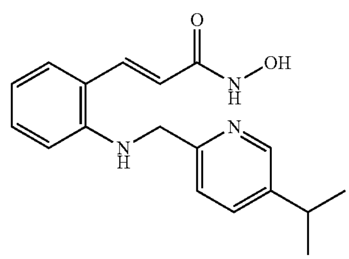 [SMILES: CC(C)c1ccc(CNc2ccccc2/C=C/C(=O)NO)nc1] | (E)-N-hydroxy-3-(2-(((5-isopropylpyridin-2-yl)methyl)amino)phenyl)acrylamide | 312 | 0.92 |
| I-88 | 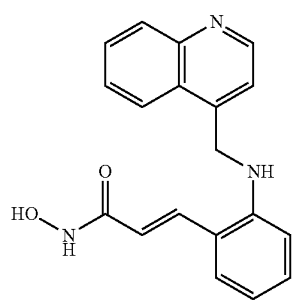 [SMILES: O=C(/C=C/c1ccccc1NCc1ccnc2ccccc12)NO] | (E)-N-hydroxy-3-(2-((quinolin-4-ylmethyl)amino)phenyl)acrylamide | 320 | 0.85 |
| I-89 | 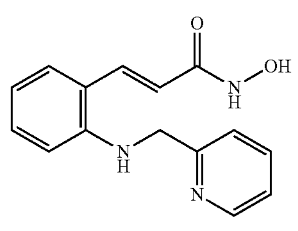 [SMILES: O=C(/C=C/c1ccccc1NCc1ccccn1)NO] | (E)-N-hydroxy-3-(2-((pyridin-2-ylmethyl)amino)phenyl)acrylamide | 270 | 0.65 |
| I-90 | 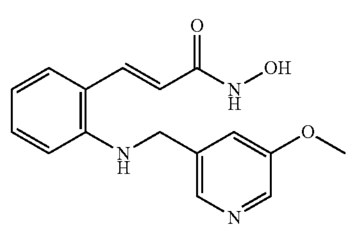 [SMILES: COc1cncc(CNc2ccccc2/C=C/C(=O)NO)c1] | (E)-N-hydroxy-3-(2-(((5-methoxypyridin-3-yl)methyl)amino)phenyl)acrylamide | 300 | 0.75 |

TABLE 19-continued

| ID | Structure | Name | LC-MS [M + 1]+ | HPLC RT (min) |
|---|---|---|---|---|
| I-91 | 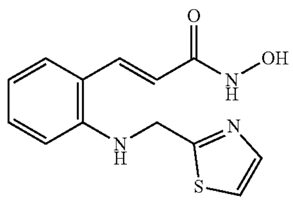 [SMILES: O=C(/C=C/c1ccccc1NCc1nccs1)NO] | (E)-N-hydroxy-3-(2-((thiazol-2-ylmethyl)amino)phenyl)acrylamide | 276 | 0.87 |
| I-92 | 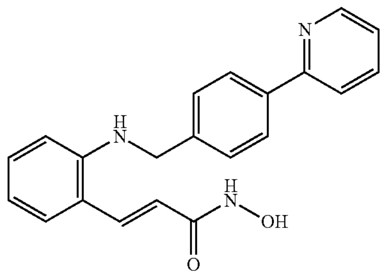 [SMILES: O=C(/C=C/c1ccccc1NCc1ccc(-c2ccccn2)cc1)NO] | (E)-N-hydroxy-3-(2-((4-(pyridin-2-yl)benzyl)amino)phenyl)acrylamide | 346 | 1,13 |
| I-93 | 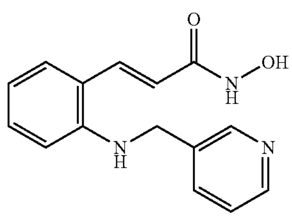 [SMILES: O=C(/C=C/c1ccccc1NCc1cccnc1)NO] | (E)-N-hydroxy-3-(2-((pyridin-3-ylmethyl)amino)phenyl)acrylamide | 270 | 0.59 |
| I-94 | 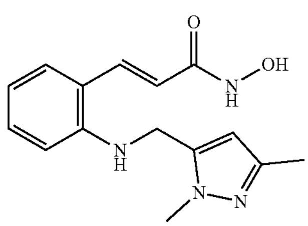 [SMILES: Cc1cc(CNc2ccccc2/C=C/C(=O)NO)n(C)n1] | (E)-3-(2-(((1,3-dimethyl-1H-pyrazol-5-yl)methyl)amino)phenyl)-N-hydroxyacrylamide | 287 | 0.88 |
| I-95 | 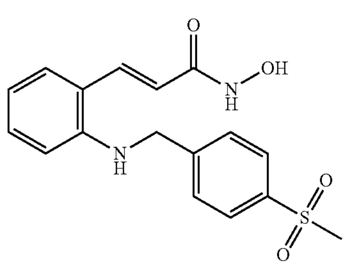 [SMILES: CS(=O)(=O)c1ccc(CNc2ccccc2/C=C/C(=O)NO)cc1] | (E)-N-hydroxy-3-(2-((4-(methylsulfonyl)benzyl)amino)phenyl)acrylamide | 347 | 0.97 |
| I-96 | 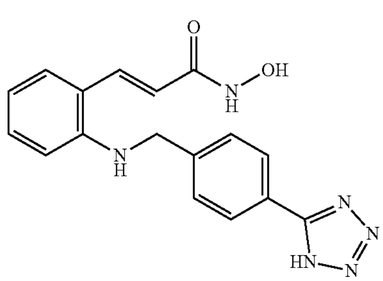 [SMILES: O=C(/C=C/c1ccccc1NCc1ccc(-c2nnn[nH]2)cc1)NO] | (E)-3-(2-((4-(1H-tetrazol-5-yl)benzylamino)phenyl)-N-hydroxyacrylamide | 337 | 0.91 |

TABLE 19-continued

| ID | Structure | Name | LC-MS [M + 1]+ | HPLC RT (min) |
|---|---|---|---|---|
| I-97 | 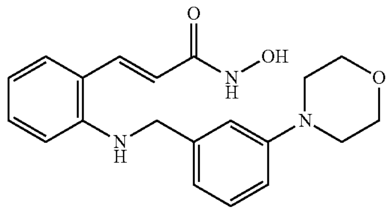 [SMILES: O=C(/C=C/c1ccccc1NCc1cccc(N2CCOCC2)c1)NO] | (E)-N-hydroxy-3-(2-((3-morpholinobenzyl)amino)phenyl)actylamide | 354 | 1.16 |
| I-98 | 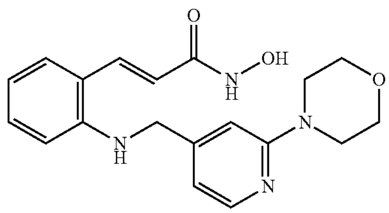 [SMILES: O=C(/C=C/c1ccccc1NCc1ccnc(N2CCOCC2)c1)NO] | (E)-N-hydroxy-3-(2-(((2-morpholinopyridin-4-yl)methyl)amino)phenyl)acrylamide | 355 | 0.68 |
| I-99 | 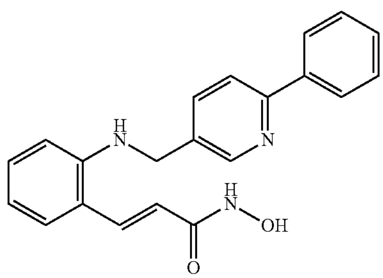 [SMILES: O=C(/C=C/c1ccccc1NCc1ccc(-c2ccccc2)nc1)NO] | (E)-N-hydroxy-3-(2-(((6-phenylpyridin-3-yl)methyl)amino)phenylacrylamide | 346 | 1.22 |
| I-100 | 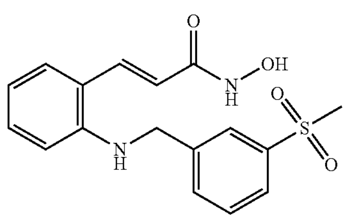 [SMILES: CS(=O)(=O)c1cccc(CNc2ccccc2/C=C/C(=O)NO)c1] | (E)-N-hydroxy-3-(2-((3-(methylsulfonyl)benzyl)amino)phenyl)acrylamide | 347 | 0.98 |
| I-101 | 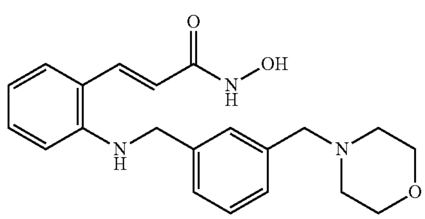 [SMILES: O=C(/C=C/c1ccccc1NCc1cccc(CN2CCOCC2)c1)NO] | (E)-N-hydroxy-3-(2-((3-(morpholinomethyl)benzyl)amino)phenyl)acrylamide | 368 | 0.74 |
| I-102 | 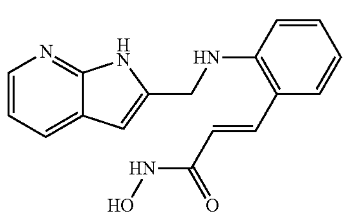 [SMILES: O=C(/C=C/c1ccccc1NCc1cc2cccnc2[nH]1)NO] | (E)-3-(2-(((1H-pyrrolo[2,3-b]pyridin-2-yl)methyl)amino)phenyl)-N-hydroxyacrylamide | 309 | 0.93 |
| I-103 | 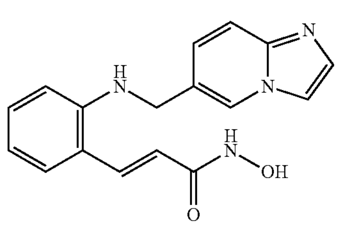 [SMILES: O=C(/C=C/c1ccccc1NCc1ccc2nccn2c1)NO] | (E)-N-hydroxy-3-(2-((imidazo[1,2-a]pyridin-6-ylmethyl)amino)phenyl)acrylamide | 309 | 0.6 |

TABLE 19-continued

| ID | Structure | Name | LC-MS [M + 1]+ | HPLC RT (min) |
|---|---|---|---|---|
| I-104 | 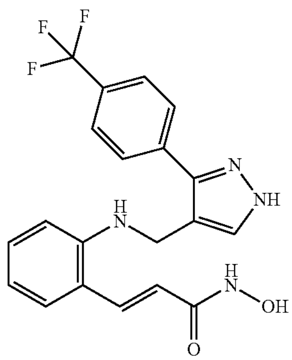 [SMILES: O=C(/C=C/c1ccccc1NCc1c[nH]nc1-c1ccc(C(F)(F)F)cc1)NO] | (E)-N-hydroxy-3-(2-(((3-(4-(trifluoromethyl)phenyl)-1H-pyrazol-4-yl)methyl)amino)phenyl)acrylamide | 403 | 1,32 |
| I-105 | 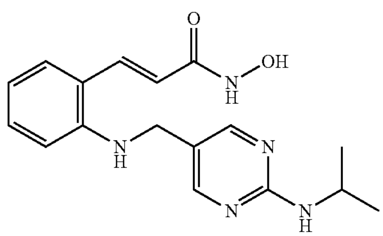 [SMILES: CC(C)Nc1ncc(CNc2ccccc2/C=C/C(=O)NO)cn1] | (E)-N-hydroxy-3-(2-(((2-(isopropylamino)pyrimidin-5-yl)methyl)amino)phenyl)acrylamide | 328 | 0.98 |
| I-106 | 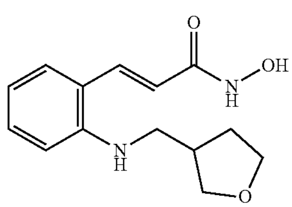 [SMILES: O=C(/C=C/c1ccccc1NCC1CCOC1)NO] | (E)-N-hydroxy-3-(2-(((tetrahydrofuran-3-yl)methyl)amino)phenyl)acrylamide | 263 | 0.91 |

Example 64—(E)-3-(2-(4-(3,3-difluorocyclobutane-1-carbonyl)piperazin-1-yl)phenyl)-N-hydroxyacrylamide (I-205)

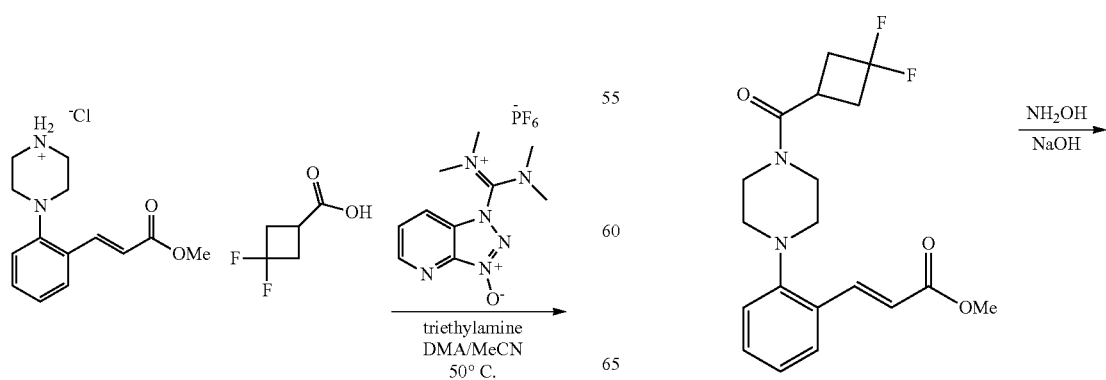

-continued

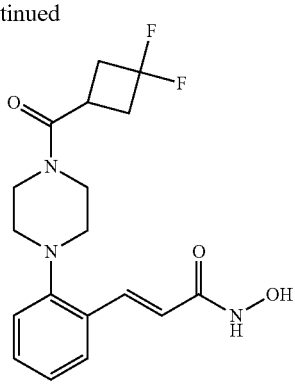

Step-1: A 2 mL vial was charged with a solution of (E)-4-(2-(3-methoxy-3-oxoprop-1-en-1-yl)phenyl)piperazin-1-ium chloride (0.2 M in 10:1 DMA:TEA, 200 μL, 0.040 mmol) and 3,3-difluorocyclobutane-1-carboxylic acid (0.2 M in 10:1 DMA:TEA, 200 μL, 0.040 mmol), followed by a solution of 1-((dimethylamino)(dimethyliminio)methyl)-1H-[1,2,3]triazolo[4,5-b]pyridine-3-oxide hexafluorophosphate (0.2 NM in acetonitrile, 200 μL, 0.040 mmol). The vial was sealed and shaken at room temperature for 18 h, then the solvent was removed under a stream of $N_2$. The residue was diluted with brine (500 μL) and extracted with ethyl acetate (2×500 μL) The combined organic layers were dried under a stream of $N_2$ revealing a pale yellow residue, which was used without further purification. $^1$H NMR (400 MHz, CDCl$_3$) δ 8.08 (d, J=16.4 Hz, 1H), 7.56 (dd, J=7.8, 1.6 Hz, 1H), 7.37 (dt, J=7.4, 1.6 Hz, 1H), 7.12 (t, J=7.8 Hz, 1H), 7.02 (dd, J=8.2, 1.2 Hz, 1H), 6.44 (d, J=16.0 Hz, 1H), 3.85-3.82 (m, 3H), 3.61-3.53 (m, 2H), 3.12-3.06 (m, 1H), 3.00-2.89 (m, 6H), 2.81-2.69 (m, 2H). $^{13}$C NMR (100 MHz, CDCl$_3$) δ 167.6, 151.6, 141.6, 131.0, 128.9, 128.0, 123.8, 119.1, 118.1, 53.2, 52.2, 51.7, 45.5, 42.3, 38.4 (t, J=24 Hz), 25.4 (dd, J=15, 4.6 Hz); LRMS (ESI, m/z) calculated for $C_{18}H_{22}F_2N_3O_3$ [M+H]$^+$ 365.17, found 365.01.

Step-2: The residue was dissolved in 3:1 THF/methanol (200 μL). The vial was sealed and shaken at 50° C. for 15 min to dissolve the residue, then cooled to room temperature Hydroxylamine (150 μL, 50% v/v solution in water) was added, followed by 1 N NaOH (100 μL) The mixture was sealed and shaken at room temperature for 18 h. The reaction mixture was concentrated under a stream of $N_2$ at room temperature, then dissolved in 500 μL of DMSO and purified by mass triggered prep HPLC (Column: Waters Sunfire C18, 5 μm, 19×50 mm, Mobile Phase: water (0.1% formic acid) and acetonitrile (0.1% formic acid) (15% to 100% acetonitrile in 6 min; flow rate: 23 mL/min), Detector: UV 254/220 nm) The product-containing fractions were combined and concentrated in a Genevac to afford (E)-3-(2-(4-(3,3-difluorocyclobutane-1-carbonyl)piperazin-1-yl)phenyl)-N-hydroxyacrylamide (0.90 mg, 6.8% yield). $^1$H NMR (400 MHz, DMSO-d$_6$) δ 7.73 (d, J=16.0 Hz, 1H), 7.49 (d, J=7.4 Hz, 1H), 7.34 (t, J=7.4 Hz, 1H), 7.12-7.08 (m, 2H), 6.51 (d, J=15.6 Hz, 1H), 3.65 (br s, 2H), 3.34-3.24 (m, 1H), 2.88-2.76 (m, 8H); $^{13}$C NMR (100 MHz, DMSO-d$_6$) δ 162.9, 151.3, 135.2, 130.2, 128.8, 127.7, 123.4, 119.32, 119.27, 52.6, 51.8, 44.8, 41.8, 37.6 (t, J=24 Hz), 24.2 (dd, J=15, 4.6 Hz); (LRMS (ESI, m/z) calculated for $C_{18}H_{22}F_2N_3O_3$ [M+H]$^+$ 366.16, found 366.24; $R_t$ 1.07 min.

The following compounds in Table 20 were prepared according to the procedures for (F)-3-(2-(4-(3,3-difluorocyclobutane-1-carbonyl)piperazin-1-yl)phenyl)-N-hydroxyacrylamide (I-205)

TABLE 20

| ID | Structure | Name | LC-MS [M + H]$^+$ | RT (min) | Purity (% UV220) |
|---|---|---|---|---|---|
| I-125 | 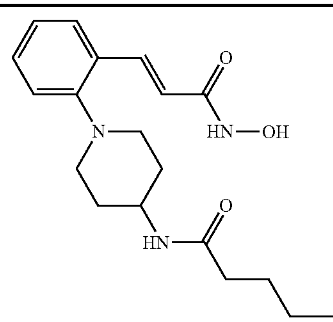 | (E)-N-(1-(2-(3-(hydroxyamino)-3-oxoprop-1-en-1-yl)phenyl)piperidin-4-yl)pentanamide | 346.32 | 1.05 | 100 |
| I-126 | 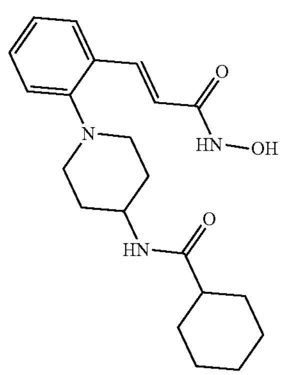 [SMILES: O=C(/C=C/c1ccccc1N1CCC(NC(=O)C2CCCCC2)CC1)NO] | (E)-N-(1-(2-(3-(hydroxyamino)-3-oxoprop-1-en-1-yl)phenyl)piperidin-4-yl)cyclohexanecarboxamide | 372.31 | 1.15 | 100 |

TABLE 20-continued

| ID | Structure | Name | LC-MS [M + H]+ | RT (min) | Purity (% UV220) |
|---|---|---|---|---|---|
| I-9 | 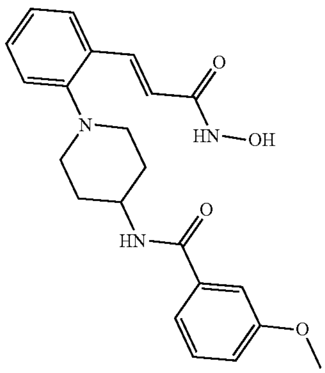 [SMILES: COc1cccc(C(=O)NC2CCN(c3ccccc3/C=C/C(=O)NO)CC2)c1] | (E)-N-hydroxy-3-(2-(4-(2-(4-methoxyphenyl)acetamido)piperidin-1-yl)phenyl)acrylamide | 410.33 | 0.69 | 94.71 |
| I-127 | 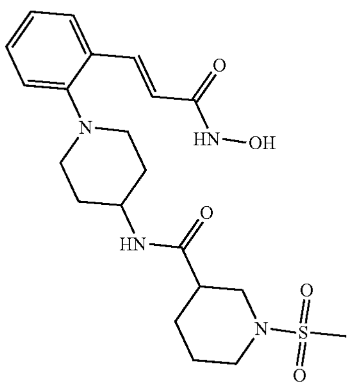 [SMILES: CS(=O)(=O)N1CCCC(C(=O)NC2CCN(c3ccccc3/C=C/C(=O)NO)CC2)C1] | (E)-N-(1-(2-(3-(hydroxyamino)-3-oxoprop-1-en-1-yl)phenyl)piperidin-4-yl)-1-(methylsulfonyl)piperidine-3-carboxamide | 451.34 | 0.96 | 100 |
| I-128 | 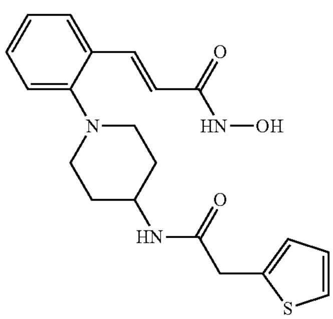 [SMILES: O=C(/C=C/c1ccccc1N1CCC(NC(=O)Cc2cccs2)CC1)NO] | (E)-N-hydroxy-3-(2-(4-(2-(thiophen-2-yl)acetamido)piperidin-1-yl)phenyl)acrylamide | 386.25 | 1.08 | 100 |
| I-129 | 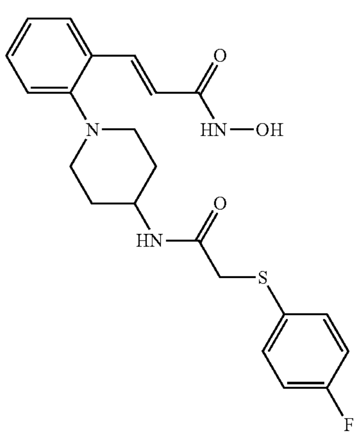 [SMILES: O=C(/C=C/c1ccccc1N1CCC(NC(=O)CSc2ccc(F)cc2)CC1)NO] | (E)-3-(2-(4-(2-((4-fluorophenyl)thio)acetamido)piperidin-1-yl)phenyl)-N-hydroxyacrylamide | 430.23 | 1.20 | 100 |

TABLE 20-continued

| ID | Structure | Name | LC-MS [M + H]+ | RT (min) | Purity (% UV220) |
|---|---|---|---|---|---|
| I-10 | 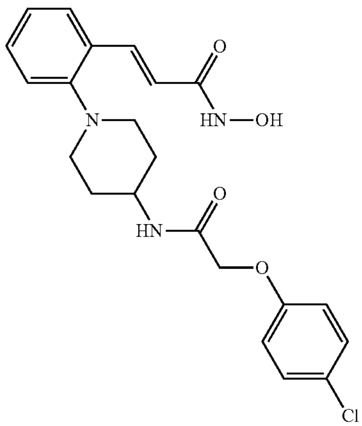 [SMILES: O=C(/C=C/c1ccccc1N1CCC(NC(=O)COc2ccc(Cl)cc2)CC1)NO] | (E)-3-(2-(4-(2-(4-chlorophenoxy)acetamido)piperidin-1-yl)phenyl)-N-hydroxyacrylamide | 430.27 | 0.88 | 85.87 |
| I-130 | 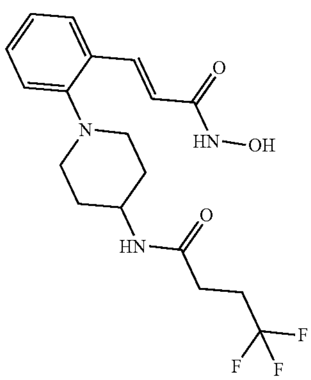 [SMILES: O=C(/C=C/c1ccccc1N1CCC(NC(=O)CCC(F)(F)F)CC1)NO] | (E)-4,4,4-trifluoro-N-(1-(2-(3-(hydroxyamino)-3-oxoprop-1-en-1-yl)phenyl)piperidin-4-yl)butanamide | 386.29 | 1.08 | 100 |
| I-131 | 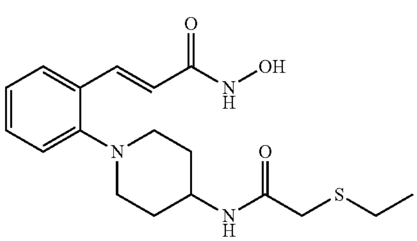 [SMILES: CCSCC(=O)NC1CCN(c2ccccc2/C=C/C(=O)NO)CC1] | (E)-3-(2-(4-(2-(ethylthio)acetamido)piperidin-1-yl)phenyl)-N-hydroxyacrylamide | 364.26 | 1.00 | 100 |
| I-132 | 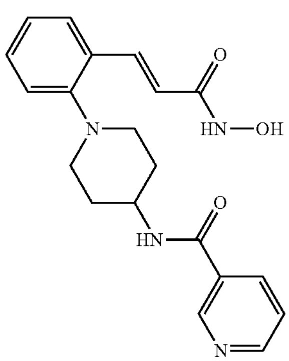 [SMILES: O=C(/C=C/c1ccccc1N1CCC(NC(=O)c2cccnc2)CC1)NO] | (E)-N-(1-(2-(3-(hydroxyamino)-3-oxoprop-1-en-1-yl)phenyl)piperidin-4-yl)nicotinamide | 367.26 | 0.88 | 100 |

TABLE 20-continued

| ID | Structure | Name | LC-MS [M + H]+ | RT (min) | Purity (% UV220) |
|---|---|---|---|---|---|
| I-133 | 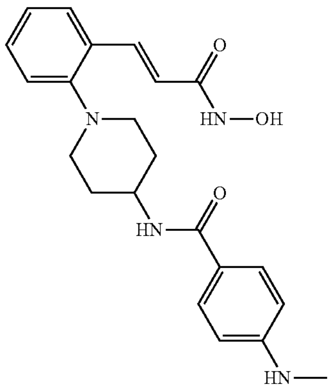 [SMILES: CNc1ccc(C(=O)NC2CCN(c3ccccc3/C=C/C(=O)NO)CC2)cc1] | (E)-N-(1-(2-(3-(hydroxyamino)-3-oxoprop-1-en-1-yl)phenyl)piperidin-4-yl)-4-(methylamino)benzamido | 395.14 | 1.04 | 93.81 |
| I-134 | 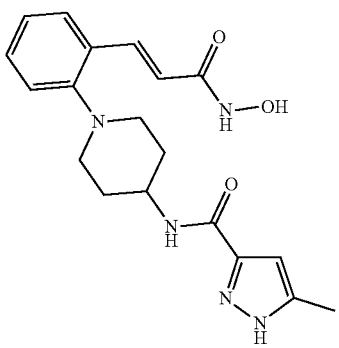 [SMILES: Cc1cc(C(=O)NC2CCN(c3ccccc3/C=C/C(=O)NO)CC2)n[nH]1] | (E)-N-(1-(2-(3-(hydroxyamino)-3-oxoprop-1-en-1-yl)phenyl)piperidin-4-yl)-5-methyl-1H-pyrazole-3-carboxamide | 370.28 | 0.9 | 100 |
| I-135 | 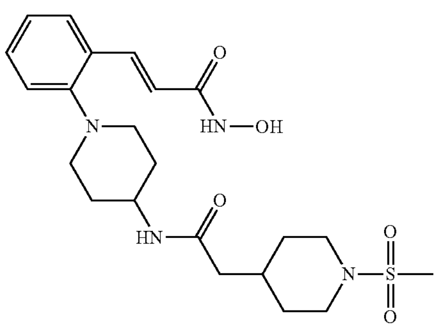 [SMILES: CS(=O)(=O)N1CCC(CC(=O)NC2CCN(c3ccccc3/C=C/C(=O)NO)CC2)CC1] | (E)-N-hydroxy-3-(2-(4-(2-(1-(methylsulfonyl)piperidin-4-yl)acetamido)piperidin-1-yl)phenyl)acrylamide | 465.32 | 0.93 | 100 |
| I-136 | 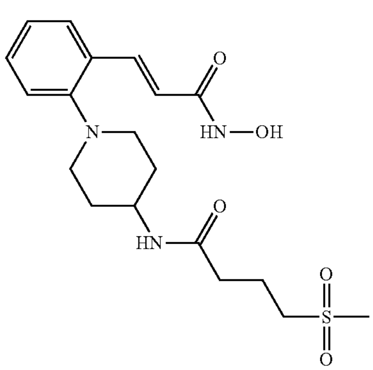 [SMILES: CS(=O)(=O)CCCC(=O)NC1CCN(c2ccccc2/C=C/C(=O)NO)CC1] | (E)-N-(1-(2-(3-(hydroxyamino)-3-oxoprop-1-en-1-yl)phenyl)piperidin-4-yl)-4-(methylsulfonyl)butanamide | 410.27 | 0.82 | 100 |

TABLE 20-continued

| ID | Structure | Name | LC-MS [M + H]+ | RT (min) | Purity (% UV220) |
|---|---|---|---|---|---|
| I-137 | 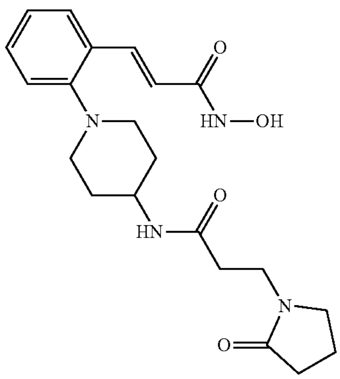 [SMILES: O=C(/C=C/c1ccccc1N1CCC(NC(=O)CCN2CCCC2=O)CC1)NO] | (E)-N-hydroxy-3-(2-(4-(3-(2-oxopyrrolidin-1-yl)propanamido)piperidin-1-yl)phenyl)acrylamide | 401.31 | 0.81 | 100 |
| I-138 | 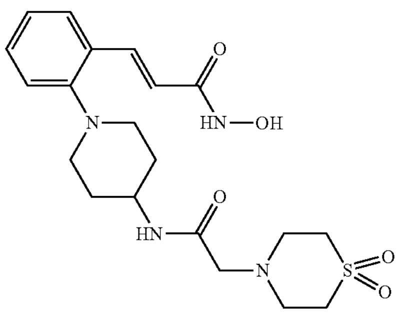 [SMILES: O=C(/C=C/c1ccccc1N1CCC(NC(=O)CN2CCS(=O)(=O)CC2)CC1)NO] | (E)-3-(2-(4-(2-(1,1-dioxidothiomorpholino)acetamido)piperidin-1-yl)phenyl)-N-hydroxyacrylamide | 437.30 | 0.84 | 100 |
| I-139 | 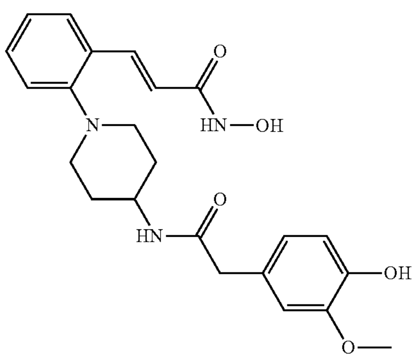 [SMILES: COc1cc(CC(=O)NC2CCN(c3ccccc3/C=C/C(=O)NO)CC2)ccc1O] | (E)-N-hydroxy-3-(2-(4-(2-(4-hydroxy-3-methoxyphenyl)acetamido)piperidin-1-yl)phenyl)acrylamide | 426.32 | 0.94 | 93.62 |
| I-140 | 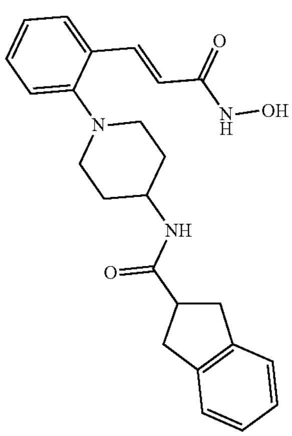 [SMILES: O=C(/C=C/c1ccccc1N1CCC(NC(=O)C2Cc3ccccc3C2)CC1)NO] | (E)-N-(1-(2-(3-(hydroxyamino)-3-oxoprop-1-en-1-yl)phenyl)piperidin-4-yl)-2,3-dihydro-1H-indene-2-carboxamide | 406.30 | 1.24 | 100 |

TABLE 20-continued

| ID | Structure | Name | LC-MS [M + H]⁺ | RT (min) | Purity (% UV220) |
|---|---|---|---|---|---|
| I-141 | 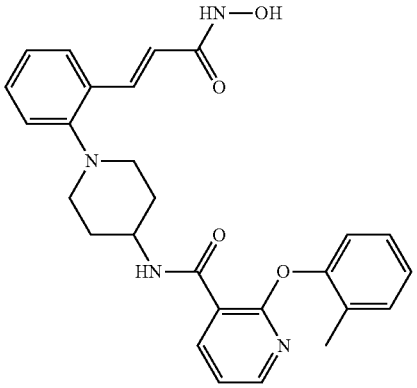 [SMILES: Cc1ccccc1Oc1ncccc1C(=O)NC1CCN(c2ccccc2/C=C/C(=O)NO)CC1] | (E)-N-(1-(2-(3-(hydroxyamino)-3-oxoprop-1-en-1-yl)phenyl)piperidin-4-yl)-2-(o-tolyloxy)nicotinamide | 473.31 | 1.34 | 100 |
| I-142 | 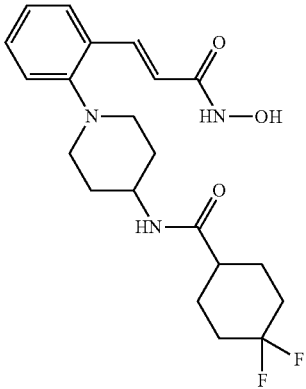 [SMILES: O=C(/C=C/c1ccccc1N1CCC(NC(=O)C2CCC(F)(F)CC2)CC1)NO] | (E)-4,4-difluoro-N-(1-(2-(3-(hydroxyamino)-3-oxoprop-1-en-1-yl)phenyl)piperidin-4-yl)cyclohexane-1-carboxamide | 408.32 | 1.12 | 97.06 |
| I-143 | 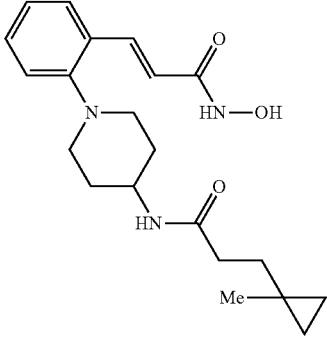 [SMILES: CC1(CCC(=O)NC2CCN(c3ccccc3/C=C/C(=O)NO)CC2)CC1] | (E)-N-hydroxy-3-(2-(4-(3-(1-methylcyclopropyl)propanamido)piperidin-1-yl)phenyl)acrylamide | 372.31 | 1.16 | 100 |
| I-144 | 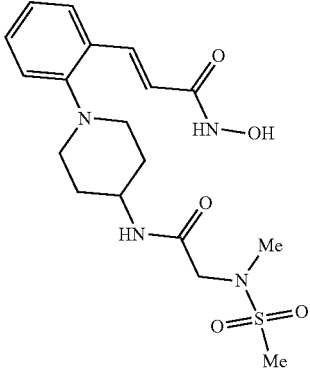 [SMILES: CN(CC(=O)NC1CCN(c2ccccc2/C=C/C(=O)NO)CC1)S(C)(=O)=O] | (E)-N-hydroxy-3-(2-(4-(2-(N-methylmethylsulfonamido)acetamido)piperidin-1-yl)phenyl)acrylamide | 411.24 | 0.89 | 97.35 |

TABLE 20-continued
| ID | Structure | Name | LC-MS [M + H]+ | RT (min) | Purity (% UV220) |
|---|---|---|---|---|---|
| I-145 | 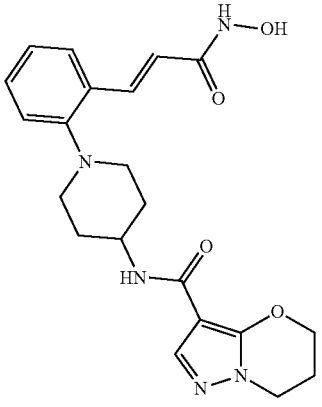 [SMILES: O=C(/C=C/c1ccccc1N1CCC(NC(=O)c2cnn3c2OCCC3)CC1)NO] | (E)-N-(1-(2-(3-(hydroxyamino)-3-oxoprop-1-en-1-yl)phenyl)piperidin-4-yl)-6,7-dihydro-5H-pyrazolo[5,1-b][1,3]oxazine-3-carboxamide | 412.28 | 0.88 | 100 |
| I-146 | 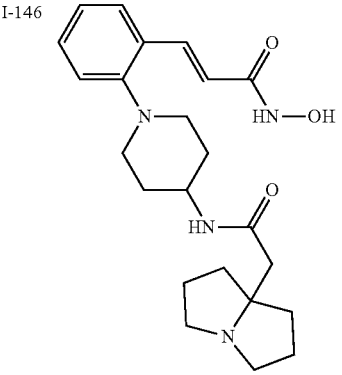 | (E)-N-hydroxy-3-(2-(4-(2-(tetrahydro-1H-pyrrolizin-7a(5H)-yl)acetamido)piperidin-1-yl)phenyl)acrylamide | 413.36 | 0.77 | 97.3 |
| I-11 | 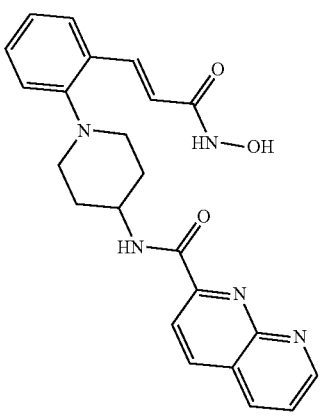 [SMILES: O=C(/C=C/c1ccccc1N1CCC(NC(=O)c2ccc3cccnc3n2)CC1)NO] | (E)-N-(1-(2-(3-(hydroxyamino)-3-oxoprop-1-en-1-yl)phenyl)piperidin-4-yl)-1,8-naphthyridine-2-carboxamide | 418.29 | 0.61 | 86.95 |

TABLE 20-continued

| ID | Structure | Name | LC-MS [M + H]+ | RT (min) | Purity (% UV220) |
|---|---|---|---|---|---|
| I-147 | 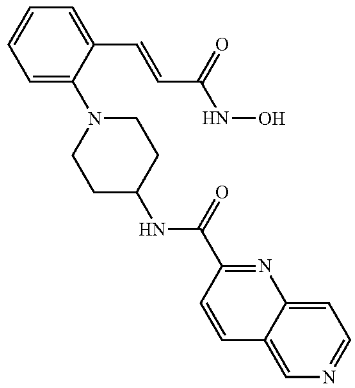 [SMILES: O=C(/C=C/c1ccccc1N1CCC(NC(=O)c2ccc3cnccc3n2)CC1)NO] | (E)-N-(1-(2-(3-(hydroxyamino)-3-oxoprop-1-en-1-yl)phenyl)piperidin-4-yl)-1,6-naphthyridine-2-carboxamide | 418.28 | 1.03 | 100 |
| I-148 | 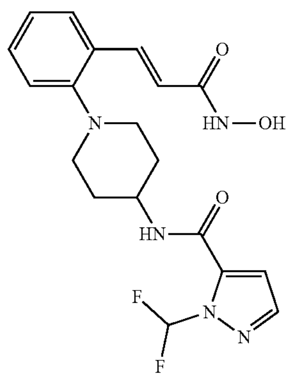 [SMILES: O=C(/C=C/c1ccccc1N1CCC(NC(=O)c2ccnn2C(F)F)CC1)NO] | (E)-1-(difluoromethyl)-N-(1-(2-(3-(hydroxyamino)-3-oxoprop-1-en-1-yl)phenyl)piperidin-4-yl)-1H-pyrazole-5-carboxamide | 406.24 | 1.05 | 100 |
| I-12 | 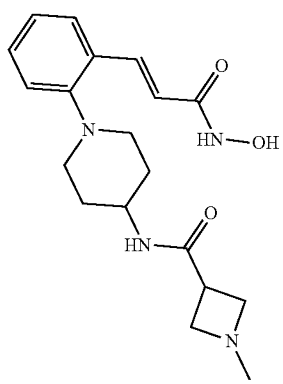 [SMILES: CN1CC(C(=O)NC2CCN(c3ccccc3/C=C/C(=O)NO)CC2)C1] | (E)-N-(1-(2-(3-(hydroxyamino)-3-oxoprop-1-en-1-yl)phenyl)piperidin-4-yl)-1-methylazetidine-3-carboxamide | 359.27 | 0.69 | 88.09 |
| I-149 | 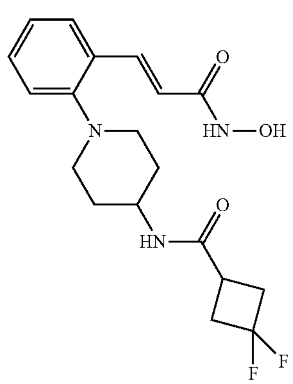 [SMILES: O=C(/C=C/c1ccccc1N1CCC(NC(=O)C2CC(F)(F)C2)CC1)NO] | (E)-3,3-difluoro-N-(1-(2-(3-(hydroxyamino)-3-oxoprop-1-en-1-yl)phenyl)piperidin-4-yl)cyclobutane-1-carboxamide | 380.31 | 1.07 | 100 |

TABLE 20-continued

| ID | Structure | Name | LC-MS [M + H]+ | RT (min) | Purity (% UV220) |
|---|---|---|---|---|---|
| I-150 | 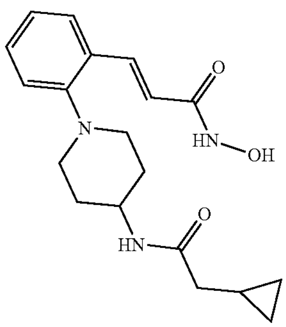 [SMILES: O=C(/C=C/c1ccccc1N1CCC(NC(=O)CC2CC2)CC1)NO] | (E)-3-(2-(4-(2-cyclopropylacetamido)piperidin-1-yl)phenyl)-N-hydroxyacrylamide | 344.31 | 0.97 | 100 |
| I-151 | 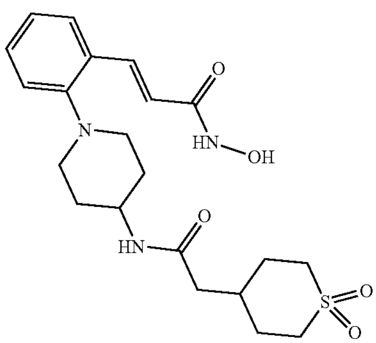 [SMILES: O=C(/C=C/c1ccccc1N1CCC(NC(=O)CC2CCS(=O)(=O)CC2)CC1)NO] | (E)-3-(2-(4-(2-(1,1-dioxidotetrahydro-2H-thiopyran-4-yl)acetamido)piperidin-1-yl)phenyl)-N-hydroxyacrylamide | 436.28 | 0.84 | 100 |
| I-152 | 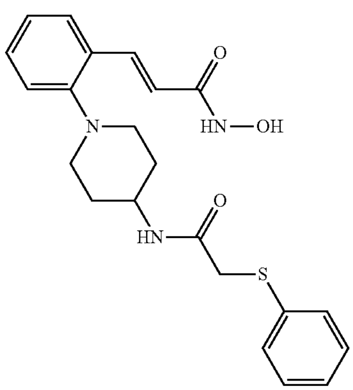 [SMILES: O=C(/C=C/c1ccccc1N1CCC(NC(=O)CSc2ccccc2)CC1)NO] | (E)-N-hydroxy-3-(2-(4-(2-(phenylthio)acetamido)piperidin-1-yl)phenyl)acrylamide | 412.22 | 1.18 | 100 |
| I-153 | 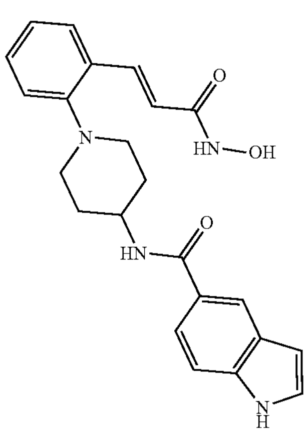 [SMILES: O=C(/C=C/c1ccccc1N1CCC(NC(=O)c2ccc3[nH]ccc3c2)CC1)NO] | (E)-N-(1-(2-(3-(hydroxyamino)-3-oxoprop-1-en-1-yl)phenyl)piperidin-4-yl)-1H-indole-5-carboxamide | 405.31 | 1.06 | 100 |

TABLE 20-continued

| ID | Structure | Name | LC-MS [M + H]+ | RT (min) | Purity (% UV220) |
|---|---|---|---|---|---|
| I-154 | 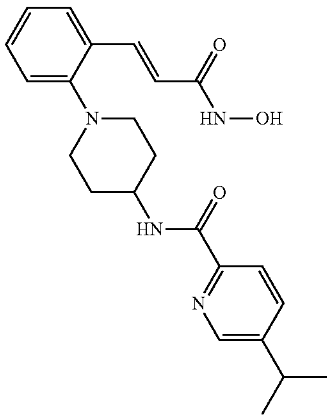 [SMILES: CC(C)c1ccc(C(=O)NC2CCN(c3ccccc3/C=C/C(=O)NO)CC2)nc1] | (E)-N-(1-(2-(3-(hydroxyamino)-3-oxoprop-1-en-1-yl)phenyl)piperidin-4-yl)-5-isopropylpicolinamide | 409.36 | 1.34 | 89.53 |
| I-155 | 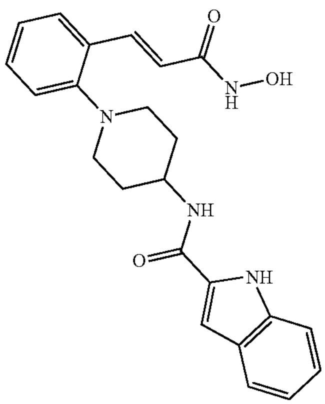 [SMILES: O=C(/C=C/c1ccccc1N1CCC(NC(=O)c2cc3ccccc3[nH]2)CC1)NO] | (E)-N-(1-(2-(3-(hydroxyamino)-3-oxoprop-1-en-1-yl)phenyl)piperidin-4-yl)-1H-indole-2-carboxamide | 405.26 | 1.20 | 95.31 |
| I-156 | 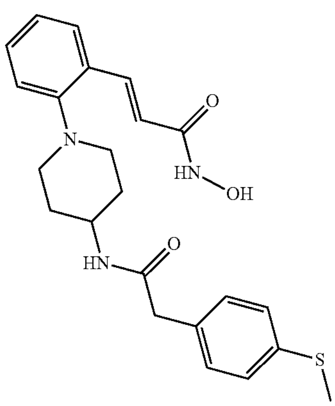 [SMILES: CSc1ccc(CC(=O)NC2CCN(c3ccccc3/C=C/C(=O)NO)CC2)cc1] | (E)-N-hydroxy-3-(2-(4-(2-(4-(methylthio)phenyl)acetamido)piperidin-1-yl)phenyl)acrylamide | 426.26 | 1.22 | 100 |
| I-331 | 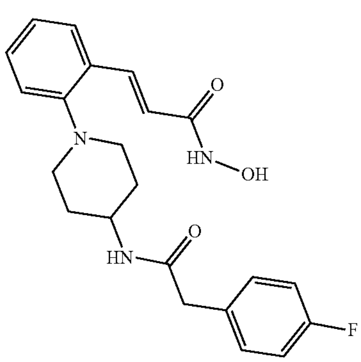 [SMILES: O=C(/C=C/c1ccccc1N1CCC(NC(=O)Cc2ccc(F)cc2)CC1)NO] | (E)-3-(2-(4-(2-(4-fluorophenyl)acetamido)piperidin-1-yl)phenyl)-N-hydroxyacrylamide | 398.31 | 1.14 | 100 |

TABLE 20-continued

| ID | Structure | Name | LC-MS [M + H]+ | RT (min) | Purity (% UV220) |
|---|---|---|---|---|---|
| I-13 | 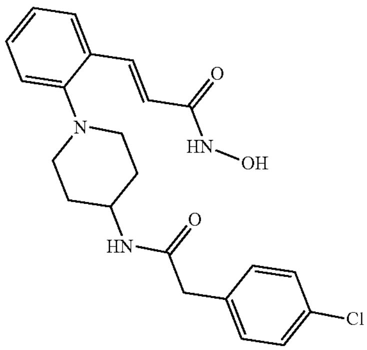 [SMILES: O=C(/C=C/c1ccccc1N1CCC(NC(=O)Cc2ccc(Cl)cc2)CC1)NO] | (E)-3-(2-(4-(2-(4-chlorophenyl)acetamido)piperidin-1-yl)phenyl)-N-hydroxyacrylamide | 414.21 | 1.72 | 100 |
| I-157 | 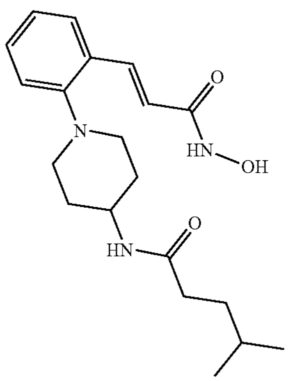 [SMILES: CC(C)CCC(=O)NC1CCN(c2ccccc2/C=C/C(=O)NO)CC1] | (E)-N-(1-(2-(3-(hydroxyamino)-3-oxoprop-1-en-1-yl)phenyl)piperidin-4-yl)-4-methylpentanamide | 360.36 | 1.15 | 100 |
| I-158 | 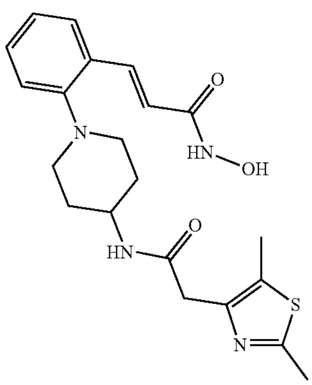 [SMILES: Cc1nc(CC(=O)NC2CCN(c3ccccc3/C=C/C(=O)NO)CC2)c(C)s1] | (E)-3-(2-(4-(2-(2,5-dimethylthiazol-4-yl)acetamido)piperidin-1-yl)phenyl)-N-hydroxyacrylamide | 415.27 | 1.00 | 100 |
| I-14 | 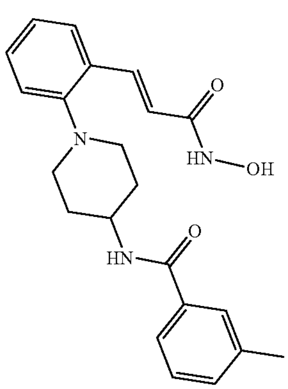 [SMILES: Cc1cccc(C(=O)NC2CCN(c3ccccc3/C=C/C(=O)NO)CC2)c1] | (E)-N-(1-(2-(3-(hydroxyamino)-3-oxoprop-1-en-1-yl)phenyl)piperidin-4-yl)-3-methylbenzamide | 380.31 | 0.76 | 96.3 |

TABLE 20-continued

| ID | Structure | Name | LC-MS [M + H]+ | RT (min) | Purity (% UV220) |
|---|---|---|---|---|---|
| I-15 | 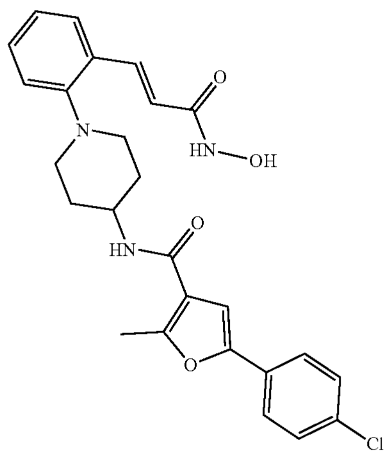 [SMILES: Cc1oc(-c2ccc(Cl)cc2)cc1C(=O)NC1CCN(c2ccccc2/C=C/C(=O)NO)CC1] | (E)-5-(4-chlorophenyl)-N-(1-(2-(3-(hydroxyamino)-3-oxoprop-1-en-1-yl)phenyl)piperidin-4-yl)-2-methylfuran-3-carboxamide | 480.31 | 1.62 | 84.46 |
| I-159 | 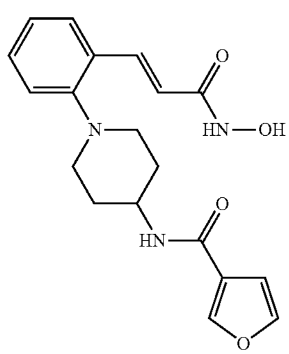 [SMILES: O=C(/C=C/c1ccccc1N1CCC(NC(=O)c2ccoc2)CC1)NO] | (E)-N-(1-(2-(3-(hydroxyamino)-3-oxoprop-1-en-1-yl)phenyl)piperidin-4-yl)furan-3-carboxamide | 356.26 | 0.99 | 100 |
| I-160 | 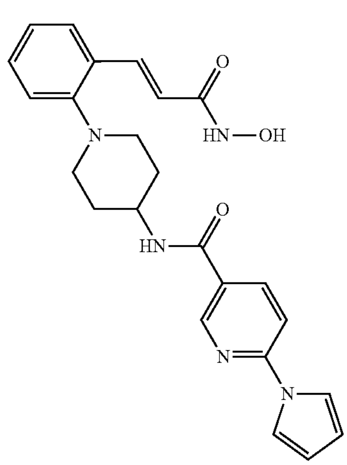 [SMILES: O=C(/C=C/c1ccccc1N1CCC(NC(=O)c2ccc(-n3cccc3)nc2)CC1)NO] | (E)-N-(1-(2-(3-(hydroxyamino)-3-oxoprop-1-en-1-yl)phenyl)piperidin-4-yl)-6-(1H-pyrrol-1-yl)nicotinamide | 432.30 | 1.24 | 100 |

TABLE 20-continued

| ID | Structure | Name | LC-MS [M + H]+ | RT (min) | Purity (% UV220) |
|---|---|---|---|---|---|
| I-16 | 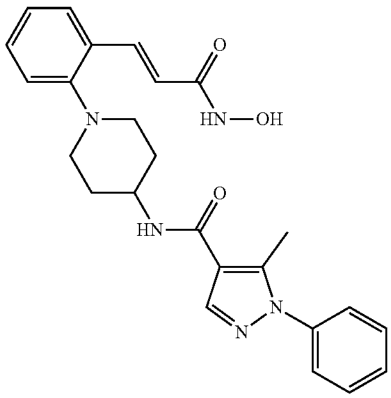 [SMILES: Cc1c(C(=O)NC2CCN(c3ccccc3/C=C/C(=O)NO)CC2)cnn1-c1ccccc1] | (E)-N-(1-(2-(3-(hydroxyamino)-3-oxoprop-1-en-1-yl)phenyl)piperidin-4-yl)-3-methyl-1-phenyl-1H-pyrazole-4-carboxamide | 446.34 | 0.80 | 90.62 |
| I-161 | 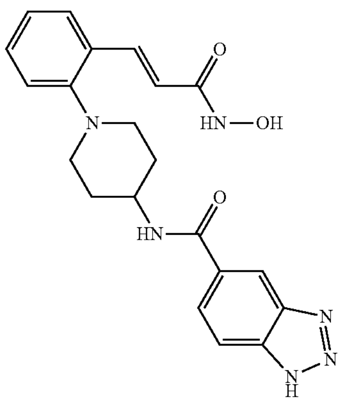 [SMILES: O=C(/C=C/c1ccccc1N1CCC(NC(=O)c2ccc3[nH]nnc3c2)CC1)NO] | (E)-N-(1-(2-(3-(hydroxyamino)-3-oxoprop-1-en-1-yl)phenyl)piperidin-4-yl)-1H-benzo[d][1,2,3]triazole-5-carboxamide | 407.28 | 0.93 | 97.32 |
| I-193 | 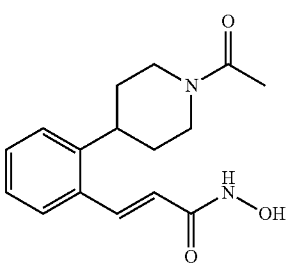 [SMILES: CC(=O)N1CCC(c2ccccc2/C=C/C(=O)NO)CC1] | (E)-3-(2-(4-acetylpiperazin-1-yl)phenyl)-N-hydroxyacrylamide | 290.25 | 0.78 | 100 |
| I-19 | 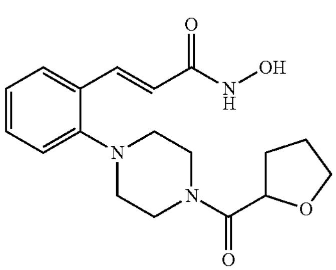 [SMILES: O=C(/C=C/c1ccccc1N1CCN(C(=O)C2CCCO2)CC1)NO] | (E)-N-hydroxy-3-(2-(4-(tetrahydrofuran-2-carbonyl)piperazin-1-yl)phenyl)acrylamide | 346.32 | 0.71 | 86.23 |

TABLE 20-continued

| ID | Structure | Name | LC-MS [M + H]+ | RT (min) | Purity (% UV220) |
|---|---|---|---|---|---|
| I-194 | 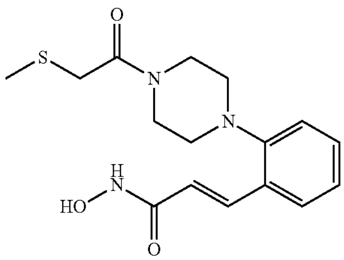 [SMILES: CSCC(=O)N1CCN(c2ccccc2/C=C/C(=O)NO)CC1] | (E)-N-hydroxy-3-(2-(4-(2-(methylthio)acetyl)piperazin-1-yl)phenylacrylamide | 336.25 | 0.85 | 95.50 |
| I-195 | 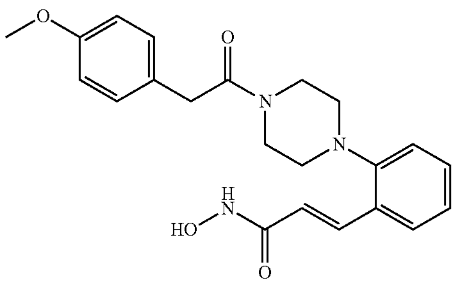 | (E)-N-hydroxy-3-(2-(4-(2-(4-methoxyphenyl)acetyl)piperazin-1-yl)phenyl)acrylamide | 396.29 | 1.11 | 89.77 |
| I-196 | 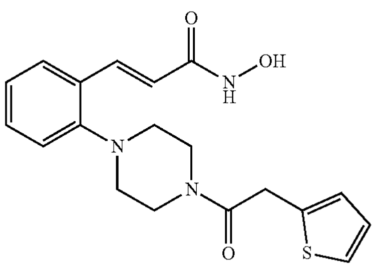 [SMILES: O=C(/C=C/c1ccccc1N1CCN(C(=O)Cc2cccs2)CC1)NO] | (E)-N-hydroxy-3-(2-(4-(2-(thiophen-2-yl)acetyl)piperazin-1-yl)phenyl)acrylamide | 372.23 | 1.08 | 92.44 |
| I-197 | 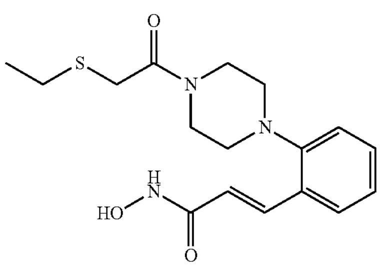 [SMILES: CCSCC(=O)N1CCN(c2ccccc2/C=C/C(=O)NO)CC1] | (E)-3-(2-(4-(2-(ethylthio)acetyl)piperazin-1-yl)phenyl)-N-hydroxyacrylamide | 350.28 | 1.03 | 100 |
| I-198 | 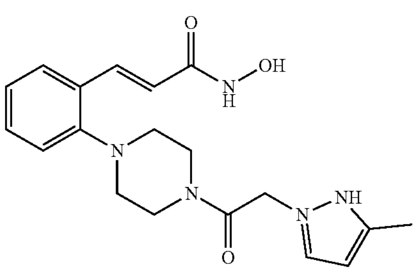 | (E)-N-hydroxy-3-(2-(4-(5-methyl-1H-pyrazole-3-carbonyl)piperazin-1-yl)phenyl)acrylamide | 356.26 | 0.85 | 94.00 |

TABLE 20-continued

| ID | Structure | Name | LC-MS [M + H]+ | RT (min) | Purity (% UV220) |
|---|---|---|---|---|---|
| I-199 | 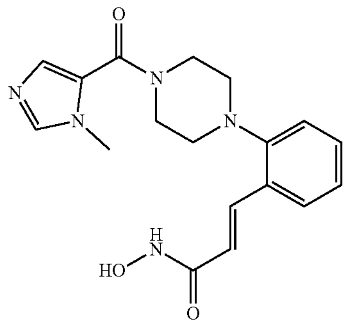 [SMILES: Cn1cncc1C(=O)N1CCN(c2ccccc2/C=C/C(=O)NO)CC1] | (E)-N-bydroxy-3-(2-(4-(1-methyl-1H-imidazole-5-carbonyl)piperazin-1-yl)phenyl)acrylamide | 356.25 | 0.67 | 97.22 |
| I-200 | 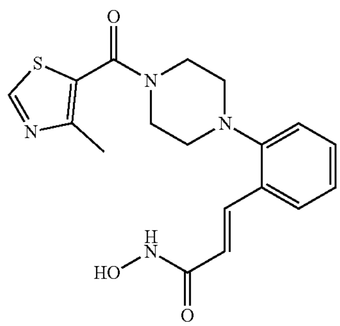 [SMILES: Cc1ncsc1C(=O)N1CCN(c2ccccc2/C=C/C(=O)NO)CC1] | (E)-N-hydroxy-3-(2-(4-(4-methylthiazole-5-carbonyl)piperazin-1-yl)phenyl)acrylamide | 372.33 | 0.88 | 100 |
| I-201 | 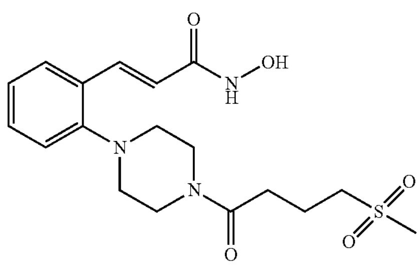 [SMILES: CS(=O)(=O)CCCC(=O)N1CCN(c2ccccc2/C=C/C(=O)NO)CC1] | (E)-N-hydroxy-3-(2-(4-(4-(methylsulfonyl)butanoyl)piperazin-1-yl)phenyl)acrylamide | 396.27 | 0.80 | 100 |
| I-202 | 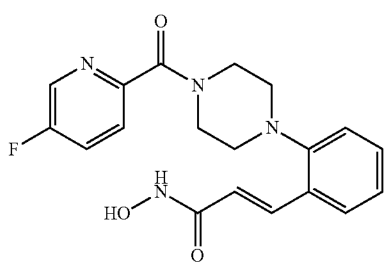 [SMILES: O=C(/C=C/c1ccccc1N1CCN(C(=O)c2ccc(F)cn2)CC1)NO] | (E)-3-(2-(4-(5-fluoropicolinoyl)piperazin-1-yl)phenyl)-N-hydroxyacrylamide | 371.27 | 0.95 | 100 |
| I-203 | 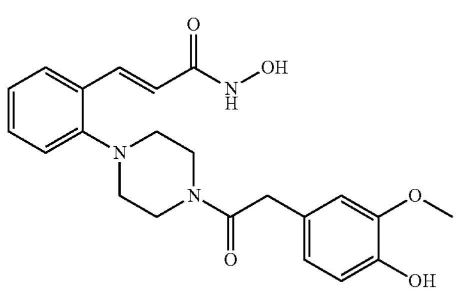 [SMILES: COc1cc(CC(=O)N2CCN(c3ccccc3/C=C/C(=O)NO)CC2)ccc1O] | (E)-N-hydroxy-3-(2-(4-(2-(4-hydroxy-3-methoxyphenyl)acetyl)piperazin-1-yl)phenylacrylamide | 412.28 | 0.91 | 100 |

TABLE 20-continued

| ID | Structure | Name | LC-MS [M + H]+ | RT (min) | Purity (% UV220) |
|---|---|---|---|---|---|
| I-20 | 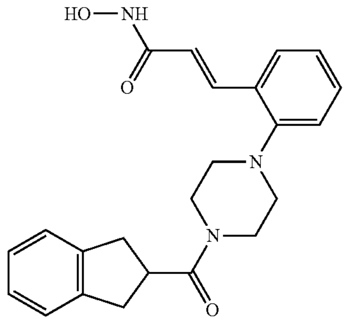 [SMILES: O=C(/C=C/c1ccccc1N1CCN(C(=O)C2Cc3ccccc3C2)CC1)NO] | (E)-3-(2-(4-(2,3-dihydro-1H-indene-2-carbonyl)piperazin-1-yl)phenyl)-N-hydroxyacrylamide | 392.30 | 0.84 | 87.29 |
| I-21 | 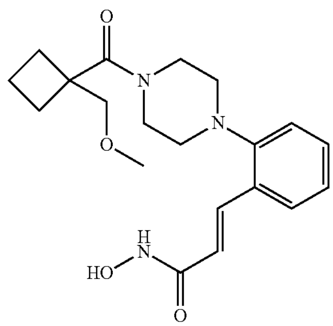 [SMILES: COCC1(C(=O)N2CCN(c3ccccc3/C=C/C(=O)NO)CC2)CCC1] | (E)-N-hydroxy-3-(2-(4-(methoxymethyl)cyclobutane-1-carbonyl)piperazin-1-yl)phenyl)acrylamide | 374.30 | 0.65 | 85.15 |
| I-22 | 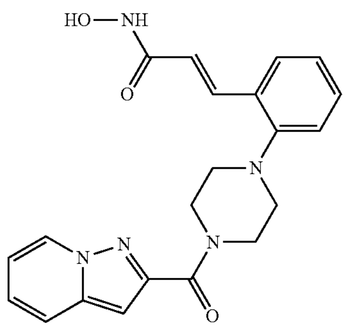 [SMILES: O=C(/C=C/c1ccccc1N1CCN(C(=O)c2cc3ccccn3n2)CC1)NO] | (E)-N-hydroxy-3-(2-(4-(pyrazolo[1,5-a]pyridine-2-carbonyl)piperazin-1-yl)phenyl)acrylamide | 392.26 | 0.63 | 100 |
| I-23 | 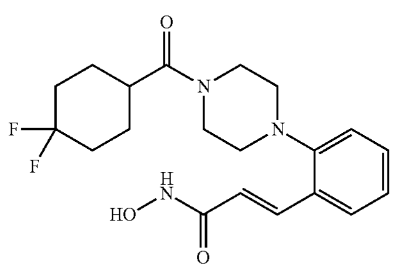 [SMILES: O=C(/C=C/c1ccccc1N1CCN(C(=O)C2CCC(F)(F)CC2)CC1)NO] | (E)-3-(2-(4-(4,4-difluorocyclohexane-1-carbonyl)piperazin-1-yl)phenyl)-N-hydroxyacrylamide | 394.28 | 0.69 | 96.18 |
| I-204 | 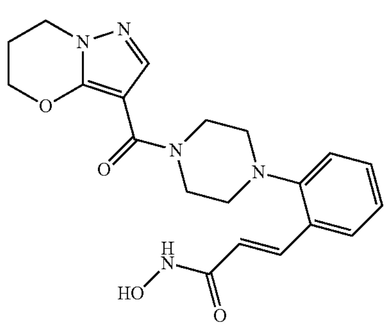 [SMILES: O=C(/C=C/c1ccccc1N1CCN(C(=O)c2cnn3c2OCCC3)CC1)NO] | (E)-3-(2-(4-(6,7-dihydro-5H-pyrazolo[5,1-b][1,3]oxazine-3-carbonyl)piperazin-1-yl)phenyl)-N-hydroxyacrylamide | 398.25 | 0.82 | 85.83 |

TABLE 20-continued

| ID | Structure | Name | LC-MS [M + H]+ | RT (min) | Purity (% UV220) |
|---|---|---|---|---|---|
| I-24 | 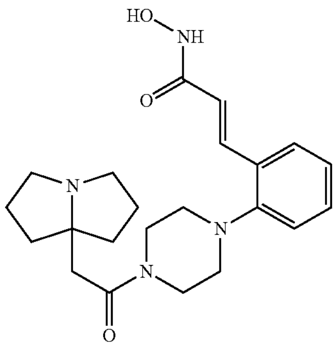 [SMILES: O=C(/C=C/c1ccccc1N1CCN(C(=O)CC23CCCN2CCC3)CC1)NO] | (E)-N-hydroxy-3-(2-(4-(2-(tetrahydro-1H-pyrrolizin-7a(5H)-yl)acetyl)piperazin-1-yl)phenyl)acrylamide | 399.35 | 0.72 | 91.65 |
| I-35 | 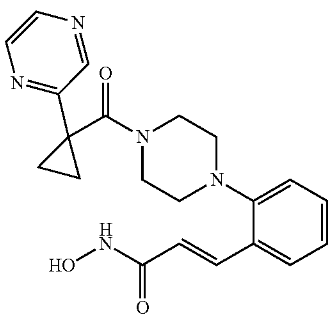 [SMILES: O=C(/C=C/c1ccccc1N1CCN(C(=O)C2(c3cnccn3)CC2)CC1)NO] | (2E)-N-hydroxy-3-(2-{4-[1-(pyrazin-2-yl)cyclopropanecarbonyl]piperazin-1-yl}phenyl)prop-2-enamide | 392.20 | 0.78 | 100 |
| I-206 | 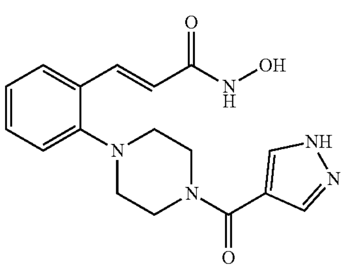 [SMILES: O=C(/C=C/c1ccccc1N1CCN(C(=O)c2cn[nH]c2)CC1)NO] | (E)-3-(2-(4-(1H-pyrazole-4-carbonyl)piperazin-1-yl)phenyl)-N-hydroxyacrylamide | 342.23 | 0.67 | 89.43 |
| I-207 | 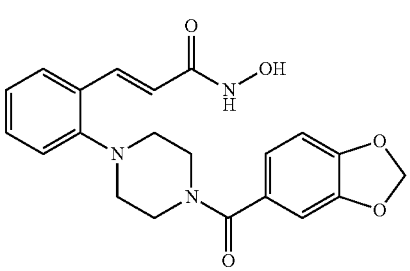 [SMILES: O=C(/C=C/c1ccccc1N1CCN(C(=O)c2ccc3c(c2)OCO3)CC1)NO] | (E)-3-(2-(4-(benzo[d][1,3]dioxole-5-carbonyl)piperazin-1-yl)phenyl-N-hydroxyacrylamide | 396.24 | 1.06 | 89.65 |
| I-208 | 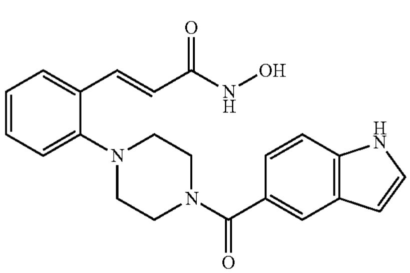 [SMILES: O=C(/C=C/c1ccccc1N1CCN(C(=O)c2ccc3[nH]ccc3c2)CC1)NO] | (E)-3-(2-(4-(1H-indole-5-carbonyl)piperazin-1-yl)phenyl)-N-hydroxyacrylamide | 391.28 | 1.01 | 100 |

TABLE 20-continued

| ID | Structure | Name | LC-MS [M + H]+ | RT (min) | Purity (% UV220) |
|---|---|---|---|---|---|
| I-209 | 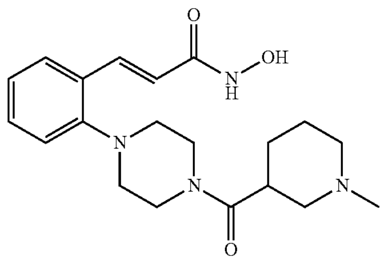 [SMILES: CN1CCCC(C(=O)N2CCN(c3ccccc3/C=C/C(=O)NO)CC2)C1] | (E)-N-hydroxy-3-(2-(4-(1-methylpiperidine-3-carbonyl)piperazin-1-yl)phenyl)acrylamide | 373.29 | 0.66 | 87.04 |
| I-25 | 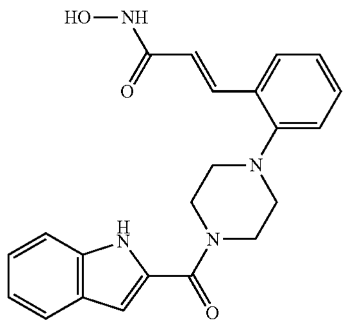 [SMILES: O=C(/C=C/c1ccccc1N1CCN(C(=O)c2cc3ccccc3[nH]2)CC1)NO] | (E)-3-(2-(4-(1H-indole-2-carbonyl)piperazin-1-yl)phenyl)-N-hydroxyacrylamide | 391.26 | 0.81 | 100 |
| I-210 | 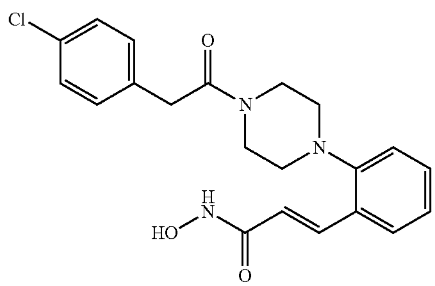 | (E)-3-(2-(4-(2-(4-chlorophenylacetyl)piperazin-1-yl)phenyl)-N-hydroxyacrylamide | 400.20 | 1.24 | 86.54 |
| I-211 | 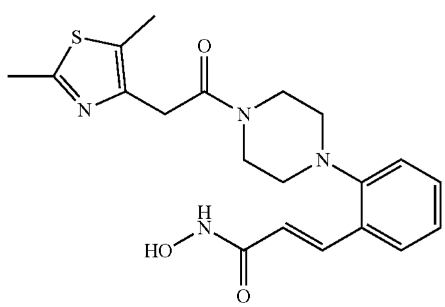 [SMILES: Cc1nc(CC(=O)N2CCN(c3ccccc3/C=C/C(=O)NO)CC2)c(C)s1] | (E)-3-(2-(4-(2-(2,5-dimethylthiazol-4-yl)acetyl)piperazin-1-yl)phenyl)-N-hydroxyacrylamide | 401.23 | 0.98 | 86.65 |
| I-212 | 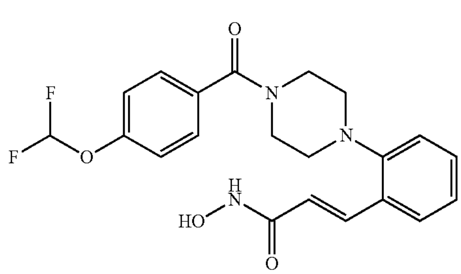 [SMILES: O=C(/C=C/c1ccccc1N1CCN(C(=O)c2ccc(OC(F)F)cc2)CC1)NO] | (E)-3-(2-(4-(4-(difluoromethoxy)benzoyl)piperazin-1-yl)phenyl)-N-hydroxyacrylamide | 418.25 | 1.18 | 86.1 |

TABLE 20-continued

| ID | Structure | Name | LC-MS [M + H]+ | RT (min) | Purity (% UV220) |
|---|---|---|---|---|---|
| I-213 | 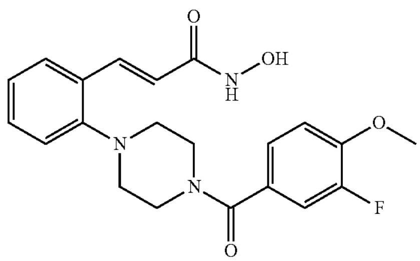 [SMILES: COc1ccc(C(=O)N2CCN(c3ccccc3/C=C/C(=O)NO)CC2)cc1F] | (E)-3-(2-(4-(3-fluoro-4-methoxybenzoyl)piperazin-1-yl)phenyl)-N-hydroxyacrylamide | 400.26 | 1.11 | 87.67 |
| I-214 | 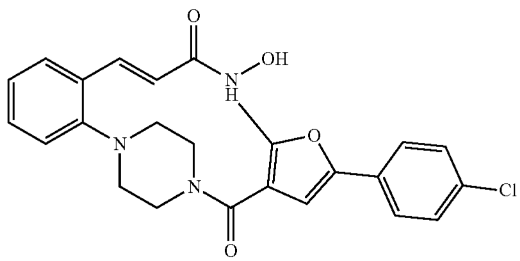 [SMILES: O=C1c2cc(-c3ccc(Cl)cc3)oc2N(O)C(=O)/C=C/c2ccccc2N2CCN1CC2] | (E)-3-(2-(4-(5-(4-chlorophenyl)-2-methylfuran-3-carbonyl)piperazin-1-yl)phenyl)-N-hydroxyacrylamide | 466.23 | 1.16 | 100 |
| I-215 | 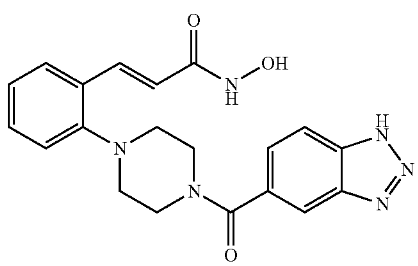 [SMILES: O=C(/C=C/c1ccccc1N1CCN(C(=O)c2ccc3[nH]nnc3c2)CC1)NO] | (E)-3-(2-(4-(1H-benzo[d][1,2,3]triazole-5-carbonyl)piperazin-1-yl)phenyl)-N-hydroxyacrylamide | 393.24 | 0.83 | 89.66 |
| I-387 | 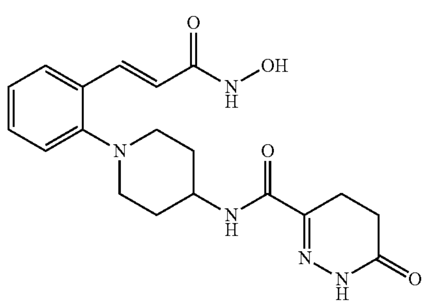 [SMILES: O=C(/C=C/c1ccccc1N1CCC(NC(=O)C2=NNC(=O)CC2)CC1)NO] | (E)-N-(1-(2-(3-(hydroxyamino)-3-oxoprop-1-en-1-yl)phenyl)piperidin-4-yl)-6-oxo-1,4,5,6-tetrahydropyridazine-3-carboxamide | 386.29 | 0.44 | 57.63 |
| I-388 | 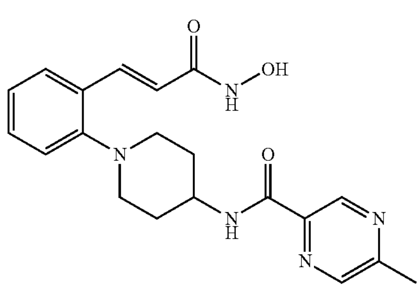 [SMILES: Cc1cnc(C(=O)NC2CCN(c3ccccc3/C=C/C(=O)NO)CC2)cn1] | (E)-N-(1-(2-(3-(hydroxyamino)-3-oxoprop-1-en-1-yl)phenyl)piperidio-4-yl)-5-methylpyrazine-2-carboxamide | 382.28 | 0.53 | 68.59 |

TABLE 20-continued

| ID | Structure | Name | LC-MS [M + H]+ | RT (min) | Purity (% UV220) |
|---|---|---|---|---|---|
| I-389 | 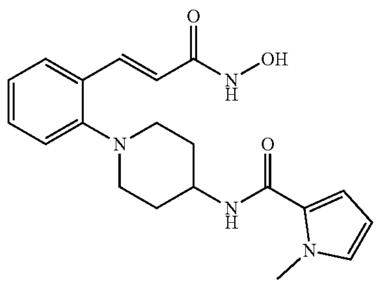 [SMILES: Cn1cccc1C(=O)NC1CCN(c2ccccc2/C=C/C(=O)NO)CC1] | N-(1-(2-{(1E)-2-(hydroxycarbamoyl)eth-1-en-1-yl]phenyl)piperidin-4-yl)-1-methyl-1H-imidazole-5-carboxamide | 347.31 | 0.69 | 100 |
| I-390 | 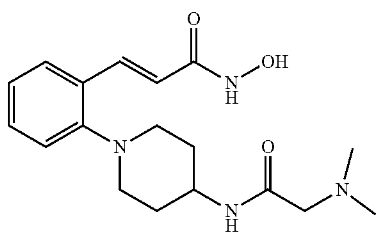 [SMILES: CN(C)CC(=O)NC1CCN(c2ccccc2/C=C/C(=O)NO)CC1] | (E)-3-(2-(4-(2-(dimethylamino)acetamido)piperidin-1-yl)phenyl)-N-hydroxyacrylamide | | | |
| I-391 | 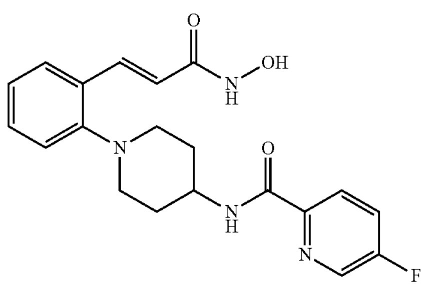 [SMILES: O=C(/C=C/c1ccccc1N1CCC(NC(=O)c2ccc(F)cn2)CC1)NO] | (E)-5-fluoro-N-(1-(2-(3-(hydroxyamino)-3-oxoprop-1-en-1-yl)phenyl)piperidin-4-yl)picolinamide | 385.25 | 0.63 | 57.67 |
| I-392 | 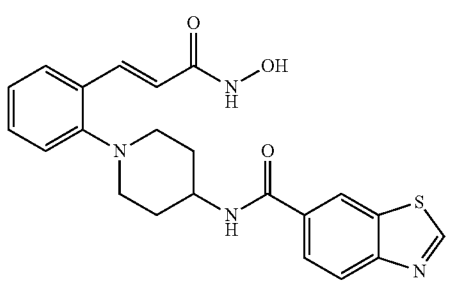 [SMILES: O=C(/C=C/c1ccccc1N1CCC(NC(=O)c2ccc3ncsc3c2)CC1)NO] | N-(1-(2-((1E)-2-(hydroxycarbamoyl)eth-1-en-1-yl]phenyl)piperidin-4-yl)-1,3-benzothiazole-6-carboxamide | 423.24 | 0.63 | 61.23 |
| I-393 | 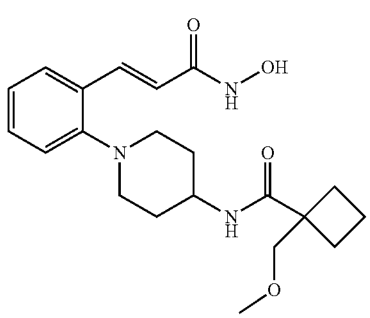 [SMILES: COCC1(C(=O)NC2CCN(c3ccccc3/C=C/C(=O)NO)CC2)CCC1] | (E)-N-(1-(2-(3-(hydroxyamino)-3-oxoprop-1-en-1-yl)phenyl)piperidin-4-yl)-1-(methoxymethyl)cyclobutane-1-carboxamide | 388.31 | 0.60 | 37.02 |

TABLE 20-continued

| ID | Structure | Name | LC-MS [M + H]+ | RT (min) | Purity (% UV220) |
|---|---|---|---|---|---|
| I-394 | 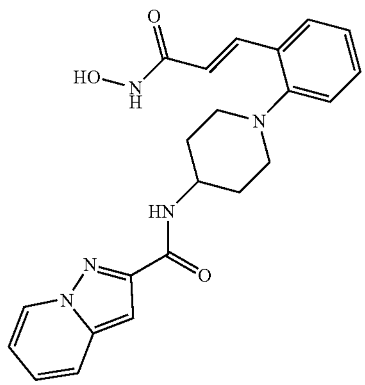 [SMILES: O=C(/C=C/c1ccccc1N1CCC(NC(=O)c2cc3ccccn3n2)CC1)NO] | (E)-N-(1-(2-(3-(hydroxyamino)-3-oxoprop-1-en-1-yl)phenyl)piperidin-4-yl)pyrazolo[1,5-a]pyridine-2-carboxamide | 406.30 | 0.65 | 70.14 |
| I-438 | 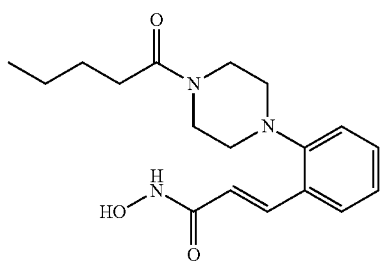 [SMILES: CCCCC(=O)N1CCN(c2ccccc2/C=C/C(=O)NO)CC1] | (E)-N-hydroxy-3-(2-(4-pentanoylpiperazin-1-yl)phenyl)acrylamide | 332.29 | 0.63 | 54.35 |
| I-439 | 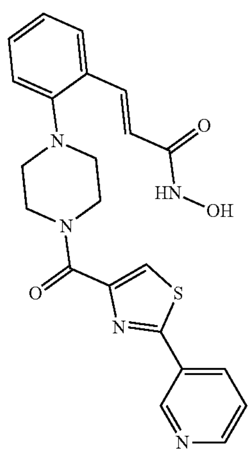 [SMILES: O=C(/C=C/c1ccccc1N1CCN(C(=O)c2csc(-c3cccnc3)n2)CC1)NO] | (E)-N-hydroxy-3-(2-(4-(2-(pyridin-3-yl)thiazole-4-carbonyl)piperazin-1-yl)phenyl)acrylamide | 436.25 | 0.97 | 82.64 |
| I-440 | 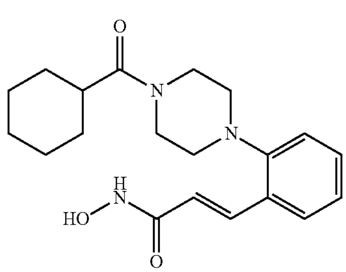 [SMILES: O=C(/C=C/c1ccccc1N1CCN(C(=O)C2CCCCC2)CC1)NO] | (E)-3-(2-(4-(cyclohexanecarbonyl)piperazin-1-yl)phenyl)-N-hydroxyacrylamide | 358.34 | 0.74 | 73 |

TABLE 20-continued

| ID | Structure | Name | LC-MS [M + H]+ | RT (min) | Purity (% UV220) |
|---|---|---|---|---|---|
| I-441 | 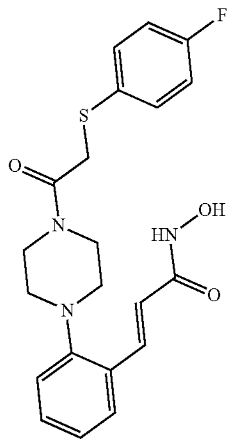 [SMILES: O=C(/C=C/c1ccccc1N1CCN(C(=O)CSc2ccc(F)cc2)CC1)NO] | (E)-3-(2-(4-(2-((4-fluorophenyl)thio)acetyl)piperazin-1-yl)phenyl)-N-hydroxyacrylamide | 416.25 | 0.83 | 52.77 |
| I-442 | 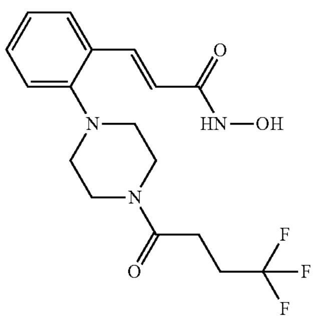 [SMILES: O=C(/C=C/c1ccccc1N1CCN(C(=O)CCC(F)(F)F)CC1)NO] | (E)-N-hydroxy-3-(2-(4-(4,4,4-trifluorobutanoyl)piperazin-1-yl)phenyl)acrylamide | 372.25 | 0.64 | 55 |
| I-443 | 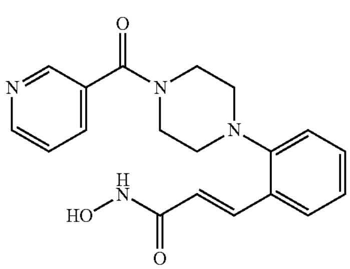 [SMILES: O=C(/C=C/c1ccccc1N1CCN(C(=O)c2cccnc2)CC1)NO] | (E)-N-hydroxy-3-(2-(4-nicotinoylpiperazin-1-yl)phenyl)acrylamide | 353.27 | 0.38 | 68.99 |
| I-444 | 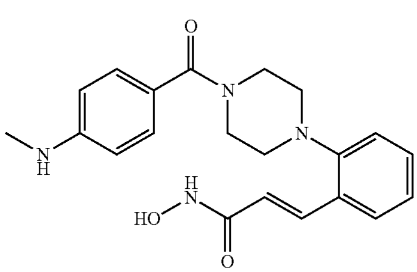 [SMILES: CNc1ccc(C(=O)N2CCN(c3ccccc3/C=C/C(=O)NO)CC2)cc1] | (E)-N-hydroxy-3-(2-(4-(4-(methylamino)benzoyl)piperazin-1-yl)phenyl)acrylamide | 381.28 | 0.60 | 60.24 |

TABLE 20-continued

| ID | Structure | Name | LC-MS [M + H]+ | RT (min) | Purity (% UV220) |
|---|---|---|---|---|---|
| I-445 | 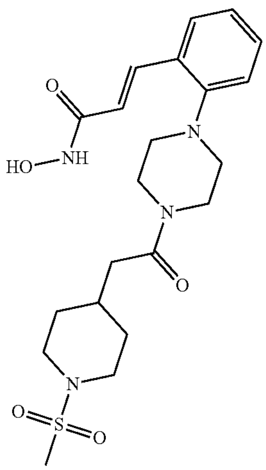 [SMILES: CS(=O)(=O)N1CCC(CC(=O)N2CCN(c3ccccc3/C=C/C(=O)NO)CC2)CC1] | (E)-N-hydroxy-3-(2-(4-(2-(1-(methylsulfonyl)piperidin-4-yl)acetyl)piperazin-1-yl)phenyl)acrylamide | 451.28 | 0.54 | 67.36 |
| I-447 | 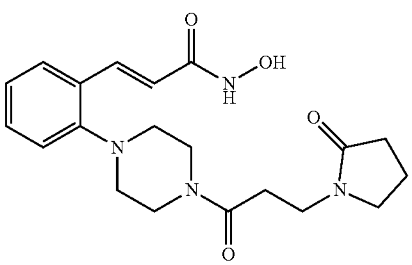 [SMILES: O=C(/C=C/c1ccccc1N1CCN(C(=O)CCN2CCCC2=O)CC1)NO] | (E)-N-hydroxy-3-(2-(4-(3-(2-oxopyrrolidin-1-yl)propanoyl)piperazin-1-yl)phenyl)acrylamide | 387.29 | 0.44 | 43.01 |
| I-448 | 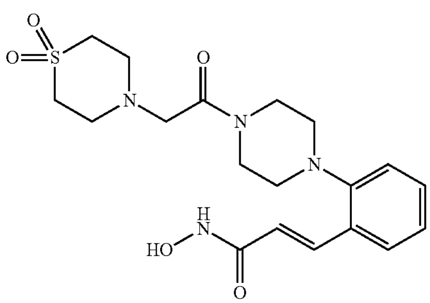 [SMILES: O=C(/C=C/c1ccccc1N1CCN(C(=O)CN2CCS(=O)(=O)CC2)CC1)NO] | (E)-3-(2-(4-(2-(1,1-dioxidothiomorpholino)acetyl)piperazin-1-yl)phenyl)-N-hydroxyacrylamide | 423.25 | 0.77 | 42.45 |
| I-449 | 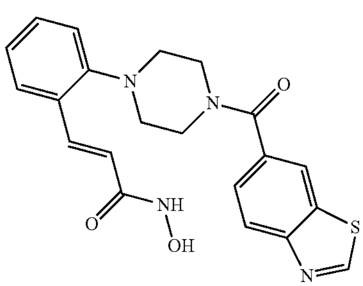 [SMILES: O=C(/C=C/c1ccccc1N1CCN(C(=O)c2ccc3ncsc3c2)CC1)NO] | (E)-3-(2-(4-(benzo[d]thiazole-6-carbonyl)piperazin-1-yl)phenyl)-N-hydroxyacrylamide | 409.19 | 0.97 | 83.37 |

TABLE 20-continued

| ID | Structure | Name | LC-MS [M + H]+ | RT (min) | Purity (% UV220) |
|---|---|---|---|---|---|
| I-450 | 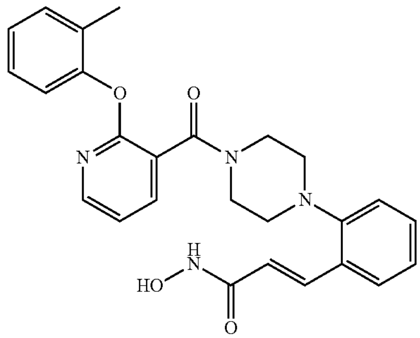 [SMILES: Cc1ccccc1Oc1ncccc1C(=O)N1CCN(c2ccccc2/C=C/C(=O)NO)CC1] | (E)-N-hydroxy-3-(2-(4-(2-(o-tolyloxy)nicotinoyl)piperazin-1-yl)phenyl)acrylamide | 459.34 | 0.83 | 71.48 |
| I-454 | 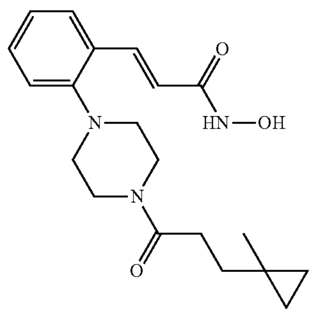 [SMILES: CC1(CCC(=O)N2CCN(c3ccccc3/C=C/C(=O)NO)CC2)CC1] | (E)-N-hydroxy-3-(2-(4-(3-(1-methylcyclopropyl)propanoyl)piperazin-1-yl)phenyl)acrylamide | 358.28 | 0.76 | 67.51 |
| I-456 | 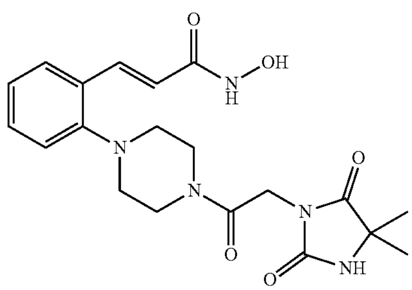 [SMILES: CC1(C)NC(=O)N(CC(=O)N2CCN(c3ccccc3/C=C/C(=O)NO)CC2)C1=O] | (E)-3-(2-(4-(2-(4,4-dimethyl-2,5-dioxoimidazolidin-1-yl)acetyl)piperazin-1-yl)phenyl)-N-hydroxyacrylamide | 416.25 | 0.46 | 71.07 |
| I-457 | 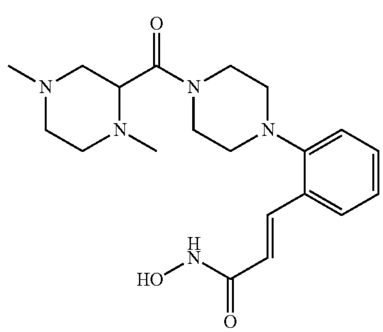 [SMILES: CN1CCN(C)C(C(=O)N2CCN(c3ccccc3/C=C/C(=O)NO)CC2)C1] | (E)-3-(2-(4-(1,4-dimethylpiperazine-2-carbonyl)piperazin-1-yl)phenyl)-N-hydroxyacrylamide | 388.30 | 0.64 | 54.44 |
| I-458 | 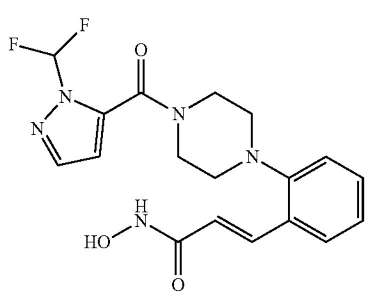 [SMILES: O=C(/C=C/c1ccccc1N1CCN(C(=O)c2ccnn2C(F)F)CC1)NO] | (E)-3-(2-(4-(1-(difluoromethyl)-1H-pyrazole-5-carbonyl)piperazin-1-yl)phenyl)-N-hydroxyacrylamide | 392.23 | 0.57 | 64.56 |

TABLE 20-continued

| ID | Structure | Name | LC-MS [M + H]+ | RT (min) | Purity (% UV220) |
|---|---|---|---|---|---|
| I-459 | 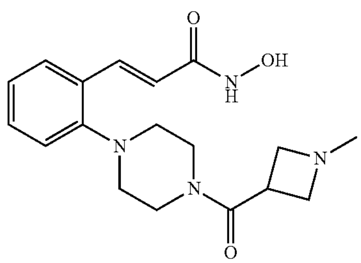 [SMILES: CN1CC(C(=O)N2CCN(c3ccccc3/C=C/C(=O)NO)CC2)C1] | (E)-N-hydroxy-3-(2-(4-(1-methylazetidine-3-carbonyl)piperazin-1-yl)phenyl)acrylamide | 345.28 | 1.08 | 45.93 |
| I-460 | 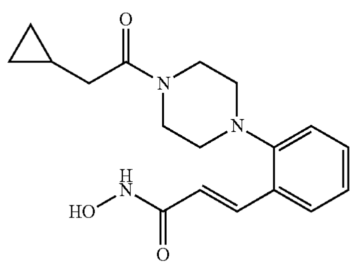 [SMILES: O=C(/C=C/c1ccccc1N1CCN(C(=O)CC2CC2)CC1)NO] | (E)-3-(2-(4-(2-cyclopropylacetyl)piperazin-1-yl)phenyl)-N-hydroxyacrylamide | 330.27 | 0.52 | 78 |
| I-461 | 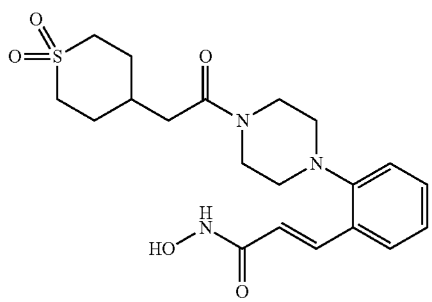 [SMILES: O=C(/C=C/c1ccccc1N1CCN(C(=O)CC2CCS(=O)(=O)CC2)CC1)NO] | (E)-3-(2-(4-(2-(1,1-dioxidotetrahydro-2H-thiopyran-4-yl)acetyl)piperazin-1-yl)phenyl)-N-hydroxyacrylamide | 422.23 | 0.42 | 76.58 |
| I-462 | 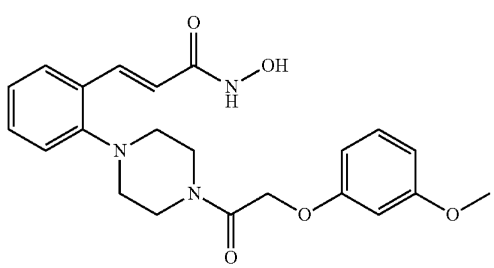 [SMILES: COc1cccc(OCC(=O)N2CCN(c3ccccc3/C=C/C(=O)NO)CC2)c1] | (E)-N-hydroxy-3-(2-(4-(2-(3-methoxyphenoxy)acetyl)piperazin-1-yl)phenyl)acrylamide | 412.28 | 0.76 | 52.62 |
| I-463 | 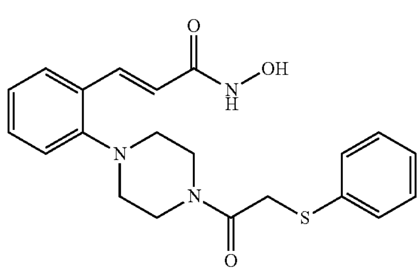 [SMILES: O=C(/C=C/c1ccccc1N1CCN(C(=O)CSc2ccccc2)CC1)NO] | (E)-N-hydroxy-3-(2-(4-(2-(phenylthio)acetyl)piperazin-1-yl)phenyl)acrylamide | 398.33 | 1.23 | 67.74 |

TABLE 20-continued

| ID | Structure | Name | LC-MS [M + H]+ | RT (min) | Purity (% UV220) |
|---|---|---|---|---|---|
| I-464 | 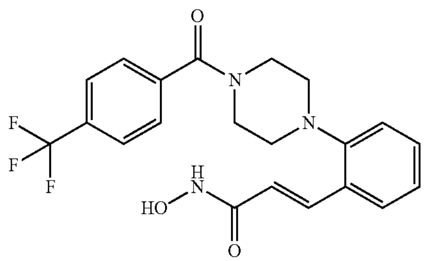 [SMILES: O=C(/C=C/c1ccccc1N1CCN(C(=O)c2ccc(C(F)(F)F)cc2)CC1)NO] | (E)-N-hydroxy-3-(2-(4-(4-(trifluoromethyl)benzoyl)piperazin-1-yl)phenyl)acrylamide | 420.21 | 1.28 | 68.11 |
| I-465 | 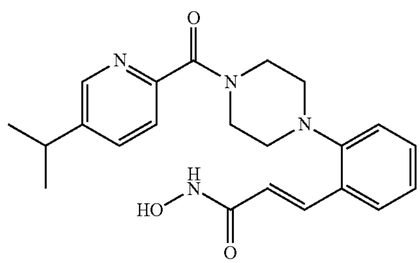 [SMILES: CC(C)c1ccc(C(=O)N2CCN(c3ccccc3/C=C/C(=O)NO)CC2)nc1] | (E)-N-hydroxy-3-(2-(4-(5-isopropylpicolinoyl)piperazin-1-yl)phenyl)acrylamide | 395.32 | 0.79 | 10.83 |
| I-466 | 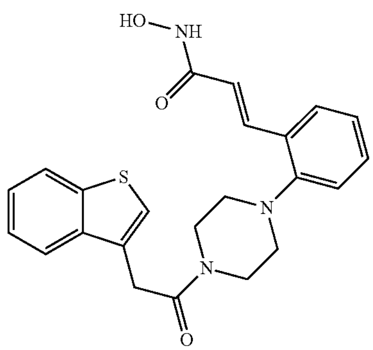 [SMILES: O=C(/C=C/c1ccccc1N1CCN(C(=O)Cc2csc3ccccc23)CC1)NO] | (E)-3-(2-(4-(2-(benzo[b]thiophen-3-yl)acetyl)piperazin-1-yl)phenyl)-N-hydroxyacrylamide | 422.23 | 1.28 | 69.94 |
| I-467 | 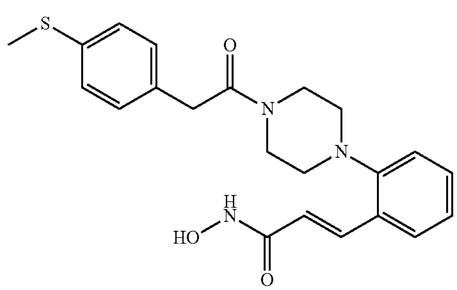 [SMILES: CSc1ccc(CC(=O)N2CCN(c3ccccc3/C=C/C(=O)NO)CC2)cc1] | (E)-N-hydroxy-3-(2-(4-(2-(4-(methylthio)phenyl)acetyl)piperazin-1-yl)phenyl)acrylamide | 412.22 | 1.22 | 80.02 |
| I-468 | 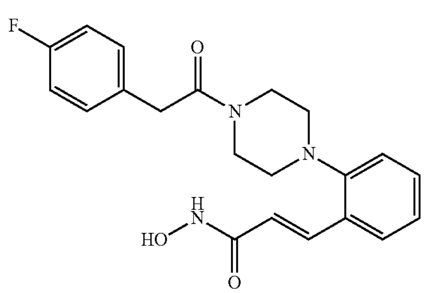 [SMILES: O=C(/C=C/c1ccccc1N1CCN(C(=O)Cc2ccc(F)cc2)CC1)NO] | (E)-3-(2-(4-(2-(4-fluorophenyl)acetyl)piperazin-1-yl)phenyl)-N-hydroxyacrylamide | 384.27 | 1.14 | 79.95 |

TABLE 20-continued

| ID | Structure | Name | LC-MS [M + H]+ | RT (min) | Purity (% UV220) |
|---|---|---|---|---|---|
| I-469 | 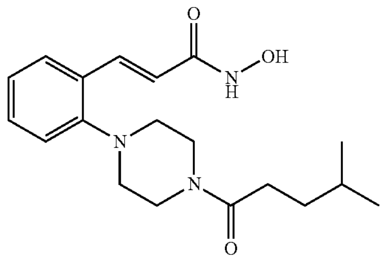 [SMILES: CC(C)CCC(=O)N1CCN(c2ccccc2/C=C/C(=O)NO)CC1] | (E)-N-hydroxy-3-(2-(4-(4-methylpentanoyl)piperazin-1-yl)phenyl)acrylamide | 346.32 | 0.75 | 74.56 |
| I-470 | 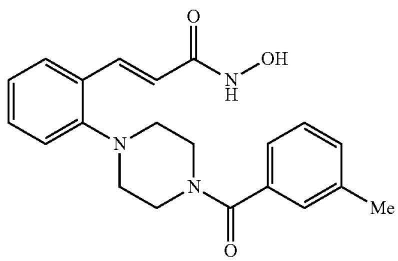 [SMILES: Cc1cccc(C(=O)N2CCN(c3ccccc3/C=C/C(=O)NO)CC2)c1] | (E)-N-hydroxy-3-(2-(4-(3-methylbenzoyl)piperazin-1-yl)phenyl)acrylamide | 366.27 | 1.16 | 80.43 |
| I-471 | 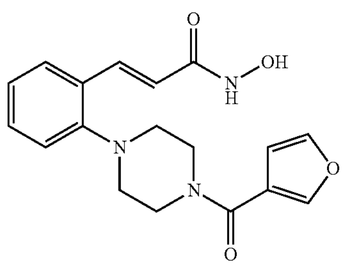 [SMILES: O=C(/C=C/c1ccccc1N1CCN(C(=O)c2ccoc2)CC1)NO] | (E)-3-(2-(4-(furan-3-carbonyl)piperazin-1-yl)phenyl)-N-hydroxyacrylamide | 342.23 | 0.49 | 52.08 |
| I-472 | 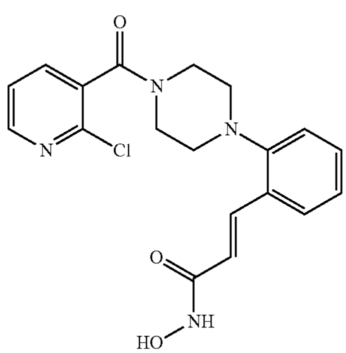 [SMILES: O=C(/C=C/c1ccccc1N1CCN(C(=O)c2cccnc2Cl)CC1)NO] | (E)-3-(2-(4-(2-chloronicotinoyl)piperazin-1-yl)phenyl)-N-hydroxyacrylamide | 387.20 | 0.49 | 11.77 |
| I-473 | 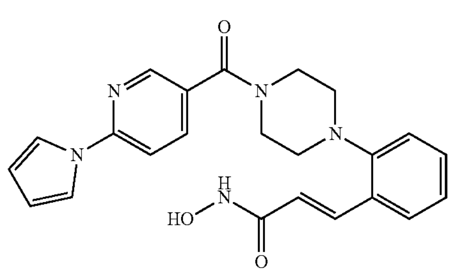 [SMILES: O=C(/C=C/c1ccccc1N1CCN(C(=O)c2ccc(-n3cccc3)nc2)CC1)NO] | (E)-3-(2-(4-(6-(1H-pyrrol-1-yl)nicotinoyl)piperazin-1-yl)phenyl)-N-hydroxyacrylamide | 418.29 | 0.80 | 82.7 |

TABLE 20-continued

| ID | Structure | Name | LC-MS [M + H]+ | RT (min) | Purity (% UV220) |
|---|---|---|---|---|---|
| I-474 | 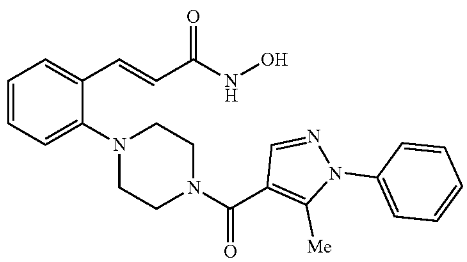 [SMILES: Cc1c(C(=O)N2CCN(c3ccccc3/C=C/C(=O)NO)CC2)cnn1-c1ccccc1] | (E)-N-hydroxy-3-(2-(4-(5-methyl-1-phenyl-1H-pyrazole-4-carbonyl)piperazin-1-yl)phenyl)acrylamide | 432.30 | 1.11 | 83.91 |
| I-475 | 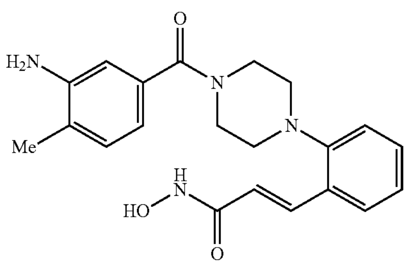 [SMILES: Cc1ccc(C(=O)N2CCN(c3ccccc3/C=C/C(=O)NO)CC2)cc1N] | (E)-3-(2-(4-(3-amino-4-methylbenzoyl)piperazin-1-yl)phenyl)-N-hydroxyacrylamide | 381.27 | 0.96 | 41.94 |
| I-477 | 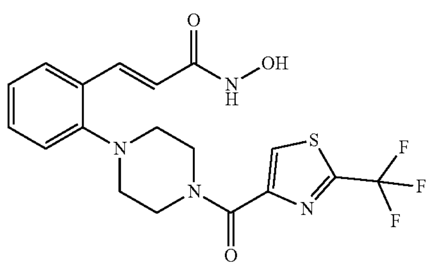 [SMILES: O=C(/C=C/c1ccccc1N1CCN(C(=O)c2csc(C(F)(F)F)n2)CC1)NO] | (E)-N-hydroxy-3-(2-(4-(2-(trifluoromethyl)thiazole-4-carbonyl)piperazin-1-yl)phenyl)acrylamide | 427.16 | 1.19 | 30 |
| I-478 | 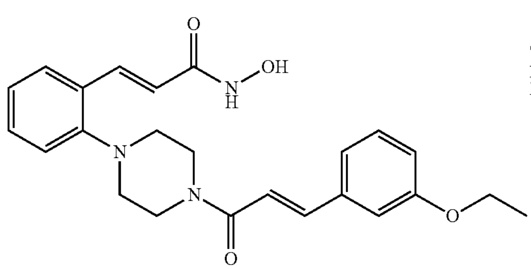 [SMILES: CCOc1cccc(/C=C/C(=O)N2CCN(c3ccccc3/C=C/C(=O)NO)CC2)c1] | (E)-3-(2-(4-((E)-3-(3-ethoxyphenyl)acryloyl)piperazin-1-yl)phenyl)-N-hydroxyacrylamide | 422.29 | 0.96 | 41.77 |
| I-36 | 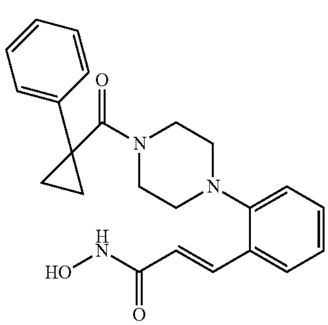 [SMILES: O=C(/C=C/c1ccccc1N1CCN(C(=O)C2(c3ccccc3)CC2)CC1)NO] | (E)-N-hydroxy-3-(2-(4-(1-phenylcyclopropane-1-carbonyl)piperazin-1-yl)phenyl)acrylamide | 392.20 | 0.78 | 100 |

TABLE 20-continued

| ID | Structure | Name | LC-MS [M + H]⁺ | RT (min) | Purity (% UV220) |
|---|---|---|---|---|---|
| I-37 | 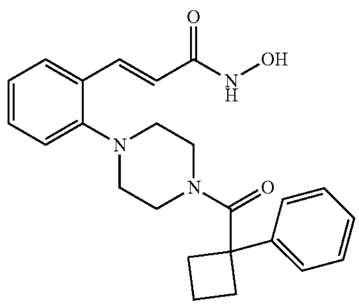 [SMILES: O=C(/C=C/c1ccccc1N1CCN(C(=O)C2(c3ccccc3)CCC2)CC1)NO] | (E)-N-hydroxy-3-(2-(4-(1-phenylcyclobutane-1-carbonyl)piperazin-1-yl)phenyl)acrylamide | 406.24 | 0.89 | 100 |
| I-289 | 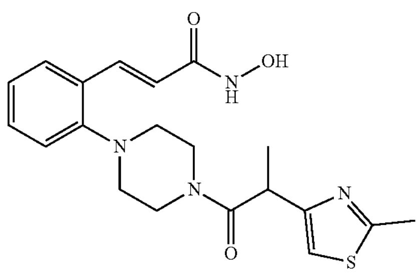 [SMILES: Cc1nc(C(C)C(=O)N2CCN(c3ccccc3/C=C/C(=O)NO)CC2)cs1] | (E)-N-hydroxy-3-(2-(4-(2-(2-methylthiazol-4-yl)propanoyl)piperazin-1-yl)phenyl)acrylamide | 401.22 | 0.99 | 100 |
| I-291 | 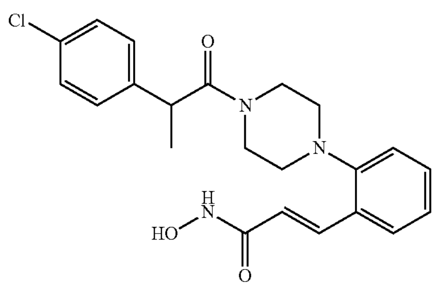 [SMILES: CC(C(=O)N1CCN(c2ccccc2/C=C/C(=O)NO)CC1)c1ccc(Cl)cc1] | (E)-3-(2-(4-(2-(4-chlorophenyl)propanoyl)piperazin-1-yl)phenyl)-N-hydroxyacrylamide | 414.23 | 1.34 | 100 |
| I-294 | 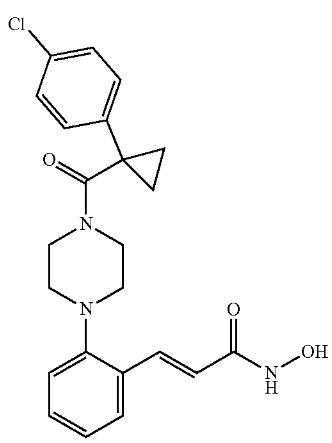 [SMILES: O=C(/C=C/c1ccccc1N1CCN(C(=O)C2(c3ccc(Cl)cc3)CC2)CC1)NO] | (E)-3-(2-(4-(1-(4-chlorophenyl)cyclopropane-1-carbonyl)piperazin-1-yl)phenyl)-N-hydroxyacrylamide | 426.19 | 1.34 | 78.93 |

TABLE 20-continued

| ID | Structure | Name | LC-MS [M + H]+ | RT (min) | Purity (% UV220) |
|---|---|---|---|---|---|
| I-295 | 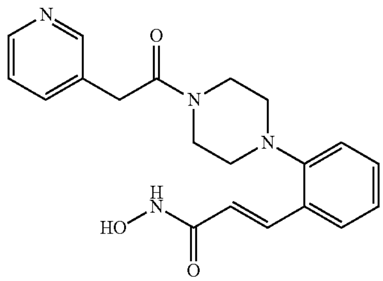 [SMILES: O=C(/C=C/c1ccccc1N1CCN(C(=O)Cc2cccnc2)CC1)NO] | (E)-N-hydroxy-3-(2-(4-(2-(pyridin-3-yl)acetyl)piperazin-1-yl)phenyl)acrylamide | 367.21 | 0.68 | 100 |
| I-296 | 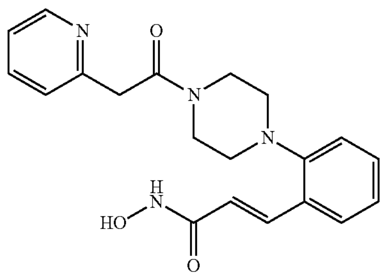 [SMILES: O=C(/C=C/c1ccccc1N1CCN(C(=O)Cc2ccccn2)CC1)NO] | (E)-N-hydroxy-3-(2-(4-(2-(pyridin-2-yl)acetyl)piperazin-1-yl)phenyl)acrylamide | 367.22 | 0.73 | 95.13 |
| I-297 | 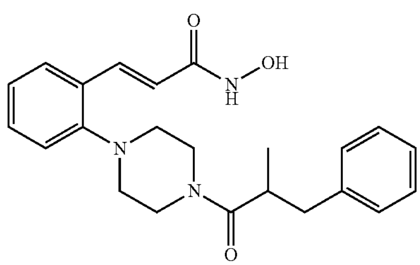 [SMILES: CC(Cc1ccccc1)C(=O)N1CCN(c2ccccc2/C=C/C(=O)NO)CC1] | (E)-N-hydroxy-3-(2-(4-(2-methyl-3-phenylpropanoyl)piperazin-1-yl)phenyl)acrylamide | 394.28 | 1.24 | 91.38 |
| I-298 | 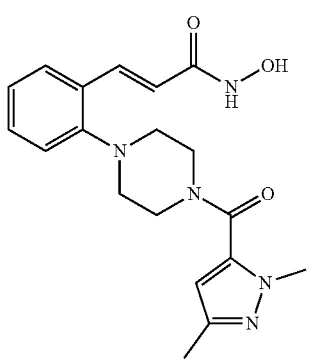 [SMILES: Cc1cc(C(=O)N2CCN(c3ccccc3/C=C/C(=O)NO)CC2)n(C)n1] | (1)-3-(2-(4-(1,3-dimethyl-1H-pyrazole-5-carbonyl)piperazin-1-yl)phenyl)-N-hydroxyacrylamide | 370.23 | 0.91 | 100 |
| I-321 | 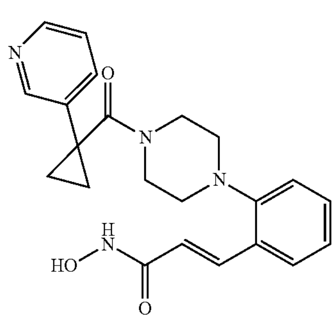 [SMILES: O=C(/C=C/c1ccccc1N1CCN(C(=O)C2(c3cccnc3)CC2)CC1)NO] | (E)-N-hydroxy-3-(2-(4-(1-(pyridin-3-yl)cyclopropane-1-carbonyl)piperazin-1-yl)phenyl)acrylamide | 393.22 | 0.79 | 100 |

TABLE 20-continued

| ID | Structure | Name | LC-MS [M + H]+ | RT (min) | Purity (% UV220) |
|---|---|---|---|---|---|
| I-322 | 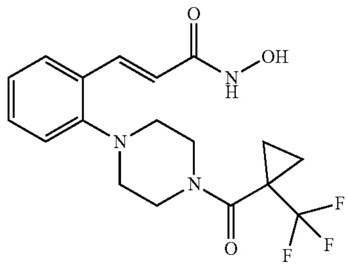 [SMILES: O=C(/C=C/c1ccccc1N1CCN(C(=O)C2(C(F)(F)F)CC2)CC1)NO] | (E)-N-hydroxy-3-(2-(4-(1-(trifluoromethyl)cyclopropane-1-carbonyl)piperazin-1-yl)phenyl)acrylamide | 384.17 | 1.10 | 100 |
| I-316 | 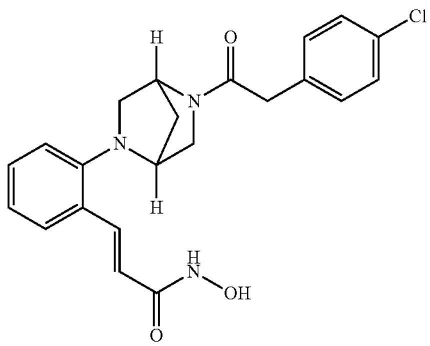 [SMILES: O=C(/C=C/c1ccccc1N1CC2CC1CN2C(=O)Cc1ccc(Cl)cc1)NO] | (E)-3-(2-((1S,4S)-5-(2-(4-chlorophenyl)acetyl)-2,5-diazabicyclo[2.2.1]heptan-2-yl)phenyl)-N-hydroxyacrylamide | 412.16 | 1.11 | 100 |
| I-329 | 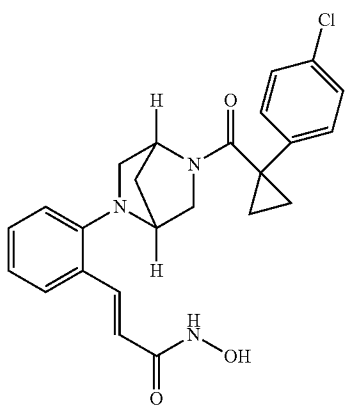 [SMILES: O=C(/C=C/c1ccccc1N1CC2CC1CN2C(=O)C1(c2ccc(Cl)cc2)CC1)NO] | (E)-3-(2-((1S,4S)-5-(1-(4-chlorophenyl)cyclopropane-1-carbonyl)-2,5-diazabicyclo[2.2.1]heptan-2-yl)phenyl)-N-hydroxyacrylamide | 438.04 | 1.23 | 92.55 |
| I-307 | 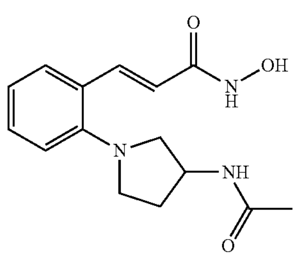 [SMILES: CC(=O)NC1CCN(c2ccccc2/C=C/C(=O)NO)C1] | (E)-3-(2-(3-acetamidopyrrolidin-1-yl)phenyl)-N-hydroxyacrylamide | 290.22 | 100 | 0.75 |
| I-318 | 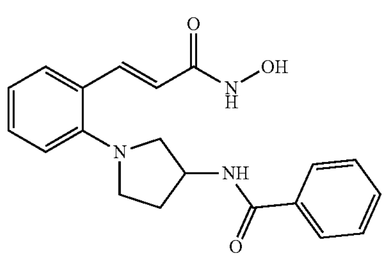 [SMILES: O=C(/C=C/c1ccccc1N1CCC(NC(=O)c2ccccc2)C1)NO] | (E)-N-(1-(2-(3-(hydroxyamino)-3-oxoprop-1-en-1-yl)phenyl)pyrrolidin-3-yl)benzamide | 352.22 | 3.04 | 100 |

TABLE 20-continued

| ID | Structure | Name | LC-MS [M + H]+ | RT (min) | Purity (% UV220) |
|---|---|---|---|---|---|
| II-29 | 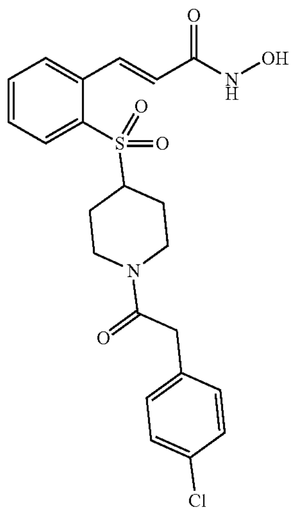 [SMILES: O=C(/C=C/c1ccccc1S(=O)(=O)C1CCN(C(=O)Cc2ccc(Cl)cc2)CC1)NO] | (E)-3-(2-((1-(2-(4-chlorophenyl)acetyl)piperidin-4-yl)sulfonyl)phenyl)-N-hydroxyacrylamide | 463.15 | 1.10 | 100 |
| I-532 | 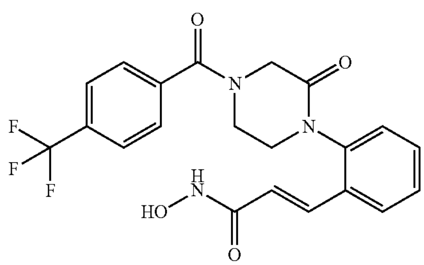 [SMILES: O=C(/C=C/c1ccccc1N1CCN(C(=O)c2ccc(C(F)(F)F)cc2)CC1=O)NO] | (E)-N-hydroxy-3-(2-(2-oxo-4-(4-(trifluoromethyl)benzoyl)piperazin-1-yl)phenyl)acrylamide | 434 | 1.04 | 87.77 |
| I-545 | 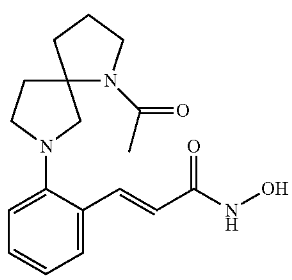 [SMILES: CC(=O)N1CCCC12CCN(c1ccccc1/C=C/C(=O)NO)C2] | (E)-3-(2-(1-acetyl-1,7-diazaspiro[4.4]nonan-7-yl)phenyl)-N-hydroxyacrylamide | 330 | 0.67 | 100 |
| I-547 | 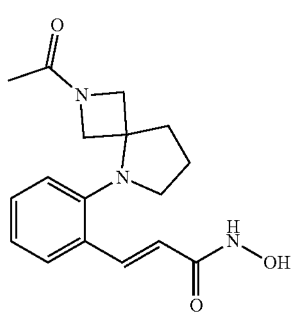 [SMILES: CC(=O)N1CC2(CCCN2c2ccccc2/C=C/C(=O)NO)C1] | (E)-3-(2-(2-acetyl-2,5-diazaspiro[3.4]octan-5-yl)phenyl)-N-hydroxyacrylamide | 316 | 0.86 | 100 |

TABLE 20-continued

| ID | Structure | Name | LC-MS [M + H]+ | RT (min) | Purity (% UV220) |
|---|---|---|---|---|---|
| I-554 | 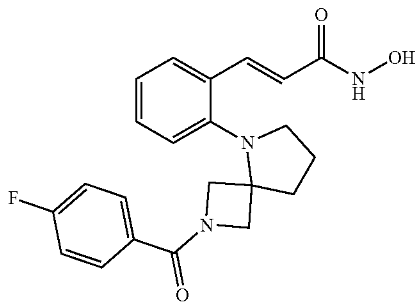 [SMILES: O=C(/C=C/c1ccccc1N1CCCC12CN(C(=O)c1ccc(F)cc1)C2)NO] | (E)-3-(2-(2-(4-fluorobenzoyl)-2,5-diazaspiro[3.4]octan-5-yl)phenyl)-N-hydroxyacrylamide | 396 | 0.57 | 100 |
| I-561 | 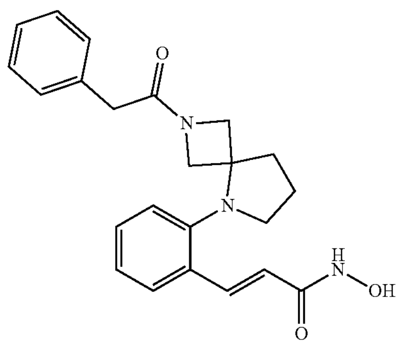 [SMILES: O=C(/C=C/c1ccccc1N1CCCC12CN(C(=O)Cc1ccccc1)C2)NO] | (E)-N-hydroxy-3-(2-(2-(2-phenylacetyl)-2,5-diazaspiro[3.4]octan-5-yl)phenyl)acrylamide | 392 | 1.14 | 93.93 |
| I-562 | 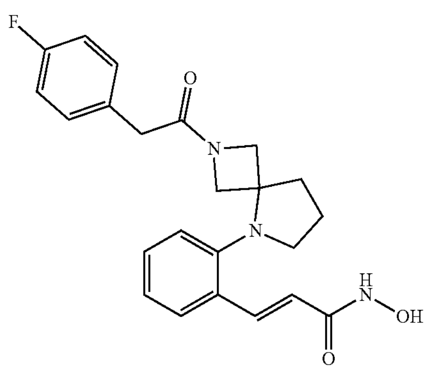 [SMILES: O=C(/C=C/c1ccccc1N1CCCC12CN(C(=O)Cc1ccc(F)cc1)C2)NO] | (E)-3-(2-(2-(2-(4-fluorophenylacetyl)-2,5-diazaspiro[3.4]octan-5-yl)phenyl)-N-hydroxyacrylamide | 410 | 1.18 | 92.87 |
| I-565 | 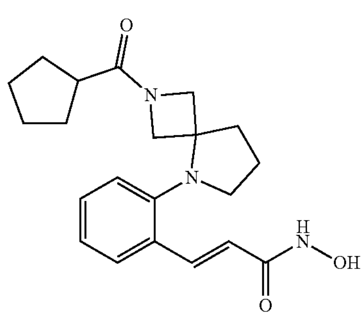 [SMILES: O=C(/C=C/c1ccccc1N1CCCC12CN(C(=O)C1CCCC1)C2)NO] | (E)-3-(2-(2-(cyclopentanecarbonyl)-2,5-diazaspiro[3.4]octan-5-yl)phenyl)-N-hydroxyacrylamide | 370 | 1.16 | 100 |

TABLE 20-continued

| ID | Structure | Name | LC-MS [M + H]+ | RT (min) | Purity (% UV220) |
|---|---|---|---|---|---|
| I-566 | 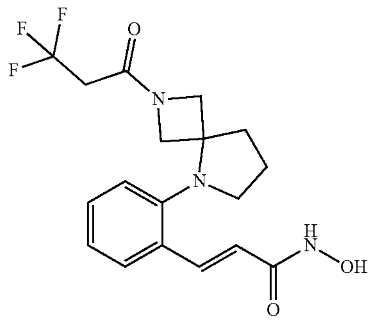 [SMILES: O=C(/C=C/c1ccccc1N1CCCC12CN(C(=O)CC(F)(F)F)C2)NO] | (E)-N-hydroxy-3-(2-(2-(3,3,3-trifluoropropanoyl)-2,5-diazaspiro[3.4]octan-5-yl)phenyl)acrylamide | 384 | 1.06 | 100 |
| I-567 | 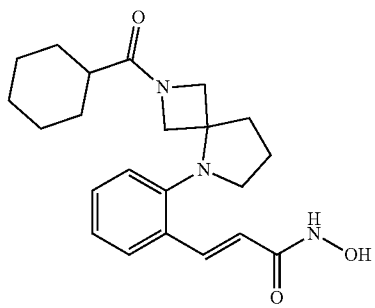 [SMILES: O=C(/C=C/c1ccccc1N1CCCC12CN(C(=O)C1CCCCC1)C2)NO] | (E)-3-(2-(2-(cyclohexanecarbonyl)-2,5-diazaspiro[3.4]octan-5-yl)phenyl)-N-hydroxyacrylamide | 384 | 0.61 | 100 (ELSD) |
| I-568 | 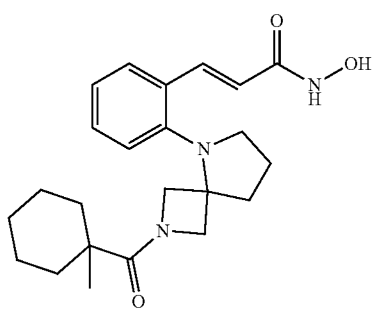 [SMILES: CC1(C(=O)N2CC3(CCCN3c3ccccc3/C=C/C(=O)NO)C2)CCCCC1] | (E)-N-hydroxy-3-(2-(2-(1-methylcyclohexane-1-carbonyl)-2,5-diazaspiro[3.4]octan-5-yl)phenyl)acrylamide | 398 | 1.34 | 100 |
| I-569 | 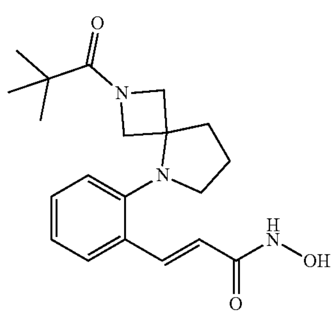 [SMILES: CC(C)(C)C(=O)N1CC2(CCCN2c2ccccc2/C=C/C(=O)NO)C1] | (E)-N-hydroxy-3-(2-(2-pivaloyl-2,5-diazaspiro[3.4]octan-5-yl)phenyl)acrylamide | 358 | 1.12 | 93.71 |

Example 65—(E)-3-(2-(4-(cyclopropylsulfonyl)piperazin-1-yl)phenyl)-N-hydroxyacrylamide (I-260)

Step-1: A 2 mL vial was charged with (A)-4-(2-(3-methoxy-3-oxoprop-1-en-1-yl)phenyl)piperazin-1-ium chloride as a 0.2 M solution in 10.1 DCE:diisopropylethyl amine (200 µL, 0.40 µmol). Then a solution of cyclopropanesulfonyl chloride (0.2 M in DCE, 200 µL, 0.40 µmol) was added. The vial was sealed and shaken at room temperature for 18 h, then the solvent was removed under a stream of $N_2$. The residue was diluted with brine (500 µL) and extracted with ethyl acetate (2×500 µL). The combined organic layers were dried under a stream of $N_2$, and the residue was used without an further purification. $^1$H NMR (400 MHz CDCl$_3$) δ 8.08 (d, J=16.4 Hz, 1H),

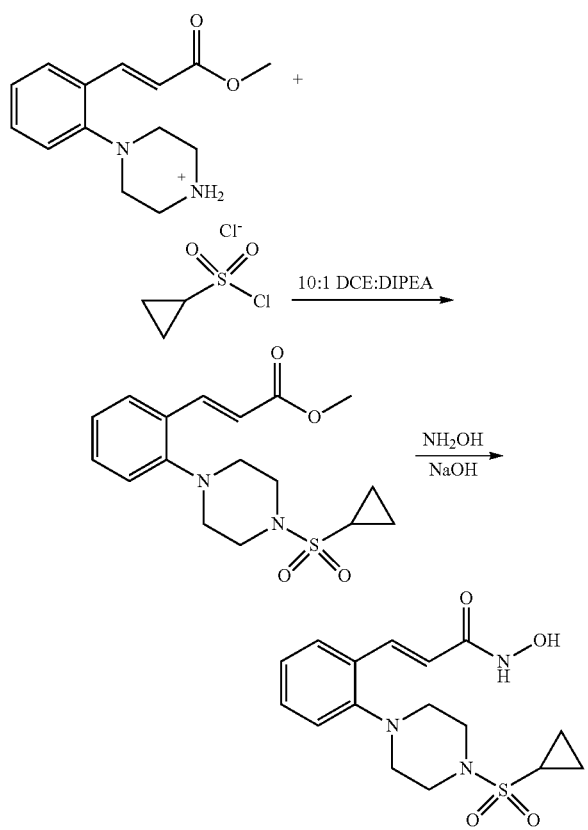

7.57 (dd, J=7.44, 1.2 Hz, 1H), 7.38 (dt, J=7.8, 1.6 Hz, 1H), 7.14-7.06 (m, 2H), 6.03 (d, J=16, Hz, 1H), 3.82 (s, 3 H), 3.51-3.49 (m, 4H), 3.06-3.03 (m, 4H), 2.38-2.31 (m, 1H), 1.24-1.19 (m, 2H), 1.08-1.04 (m, 2H); $^{13}$C NMR (100 MHz, CDCl$_3$) δ 167.7, 151.6, 141.7, 131.1, 128.8, 127.9, 123.8, 119.3, 117.9, 52.4, 51.6, 46.3, 25 5, 4.3; LRMS (ESI, m/z) calculated for C$_{17}$H$_{23}$N$_2$O$_4$S [M+H]$^+$ 351.14, found 351.05.

Step-2: 3:1 THF/methanol (200 μL) was added to the residue. The vial was sealed and shaken at 50° C. for 15 min to dissolve the residue, then cooled to room temperature. Hydroxylamine (150 μL, 50% v/v solution in water) was added, followed by 1 N NaOH (100 μL). The mixture was sealed and then shaken at room temperature for 18 h. The reaction mixture was concentrated under a stream of N$_2$ at room temperature, then dissolved in 500 μL of DMSO and purified by mass triggered prep HPLC (Column: Waters Sunfire C18, 5 μm, 19×50 mm; Mobile Phase: water (0.1% formic acid) and acetonitrile (0.1% formic acid) (15% to 100%/o acetonitrile in 6 min; flow rate: 23 mL/min), Detector: UV 254/220 nm). The product-containing fractions were combined and concentrated in a Genevac to afford (A)-3-(2-(4-(cyclopropylsulfonyl)piperazin-1-yl)phenyl)-N-hydroxyacrylamide (2.7 mg, 19% yield) $^1$H NMR (400 MHz, DMSO-d$_6$) δ 10.83 (br s, 1H), 9.04 (br S, 1H), 7.74 (d, J=16.0 Hz, 1H), 7.51 (d, J=7.0 Hz, 1H), 7.36 (t, J=8.2 Hz, 1H), 7.16-7.10 (m, 2H), 6.46 (d, J=16.0 Hz, 1H), 3.39-3.35 (m, 4H), 2.96-2.93 (m, 4H), 2.74-2.68 (m, 1H), 1.08-0.95 (m, 4H); $^{13}$C NMR (100 MHz, DMSO-d$_6$) δ 162.9, 151.1, 135.0, 130.2, 128.8, 127.4, 123.6, 119.42, 119.30, 51.6, 46.0, 24.9, 3.97; LRMS (ESI, m/z) calculated for C$_{16}$H$_{22}$N$_3$O$_4$S [M+H]$^+$ 352.13, found 352.23; R$_t$ 1.01 min.

The following compounds in Table 21 were prepared according to the procedures for (E)-3-(2-(4-(cyclopropylsulfonyl)piperazin-1-yl)phenyl)-N-hydroxyacrylamide (I-260)

TABLE 21

| ID | Structure | Name | LC-MS [M + H]$^+$ | RT (min) | Purity (% UV220) |
|---|---|---|---|---|---|
| I-218 | 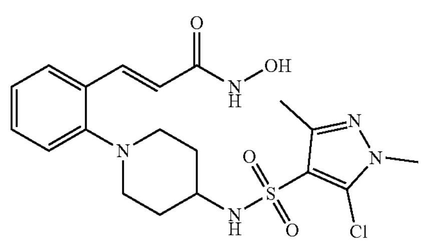 [SMILES: Cc1nn(C)c(Cl)c1S(=O)(=O)NC1CCN(c2ccccc2/C=C/C(=O)NO)CC1] | (E)-3-(2-(4-((5-chloro-1,3-dimethyl-1H-pyrazole)-4-sulfonamido)piperidin-1-yl)phenyl)-N-hydroxyacrylamide | 454.20 | 1.12 | 100 |
| I-219 | 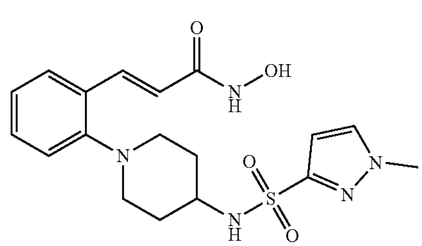 [SMILES: Cn1ccc(S(=O)(=O)NC2CCN(c3ccccc3/C=C/C(=O)NO)CC2)n1] | (E)-N-hydroxy-3-(2-(4-((1-methyl-1H-pyrazole)-3-sulfonamido)piperidin-1-yl)phenyl)acrylamide | 406.21 | 0.98 | 100 |

TABLE 21-continued

| ID | Structure | Name | LC-MS [M + H]+ | RT (min) | Purity (% UV220) |
|---|---|---|---|---|---|
| I-220 | 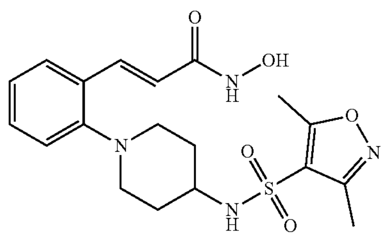 [SMILES: Cc1noc(C)c1S(=O)(=O)NC1CCN(c2ccccc2/C=C/C(=O)NO)CC1] | (E)-3-(2-(4-((3,5-dimethylisoxazole)-4-sulfonamido)piperidin-1-yl)phenyl)-N-hydroxyacrylamide | 421.19 | 1.20 | 100 |
| I-221 | 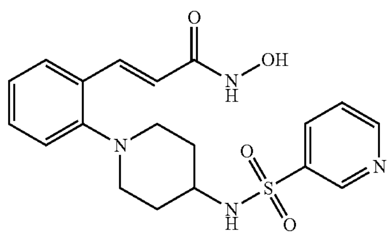 [SMILES: O=C(/C=C/c1ccccc1N1CCC(NS(=O)(=O)c2cccnc2)CC1)NO] | (E)-N-hydroxy-3-(2-(4-(pyridine-3-sulfonamido)piperidin-1-yl)phenyl)acrylamide | 403.18 | 1.02 | 100 |
| I-222 | 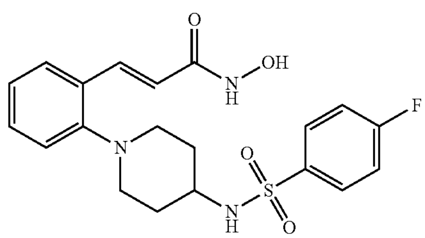 [SMILES: O=C(/C=C/c1ccccc1N1CCC(NS(=O)(=O)c2ccc(F)cc2)CC1)NO] | (E)-3-(2-(4-((4-fluorophenyl)sulfonamido)piperidin-1-yl)phenyl)-N-hydroxyacrylamide | 420.21 | 1.28 | 96.15 |
| I-223 | 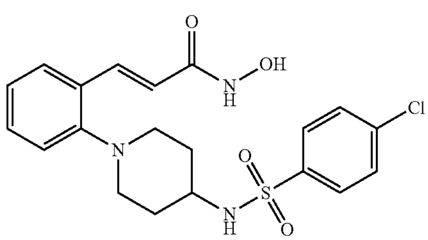 [SMILES: O=C(/C=C/c1ccccc1N1CCC(NS(=O)(=O)c2ccc(Cl)cc2)CC1)NO] | (E)-3-(2-(4-((4-chlorophenyl)sulfonamido)piperidin-1-yl)phenyl)-N-hydroxyacrylamide | 436.20 | 1.38 | 100 |
| I-224 | 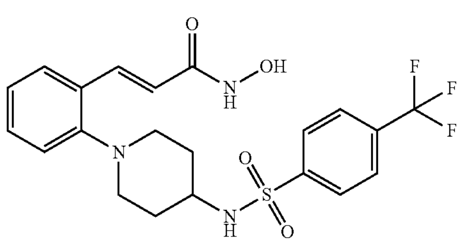 [SMILES: O=C(/C=C/c1ccccc1N1CCC(NS(=O)(=O)c2ccc(C(F)(F)F)cc2)CC1)NO] | (E)-N-hydroxy-3-(2-(4-((4-(trifluoromethyl)phenyl)sulfonamido)piperidin-1-yl)phenyl)acrylamide | 470.24 | 1.45 | 96.74 |
| I-225 | 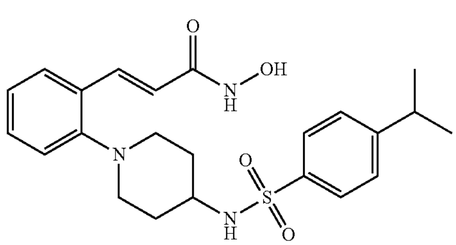 [SMILES: CC(C)c1ccc(S(=O)(=O)NC2CCN(c3ccccc3/C=C/C(=O)NO)CC2)cc1] | (E)-N-hydroxy-3-(2-(4-((4-isopropyl-phenyl)sulfonamido)piperidin-1-yl)phenyl)acrylamide | 444.26 | 1.51 | 100 |

TABLE 21-continued

| ID | Structure | Name | LC-MS [M + H]+ | RT (min) | Purity (% UV220) |
|---|---|---|---|---|---|
| I-226 | 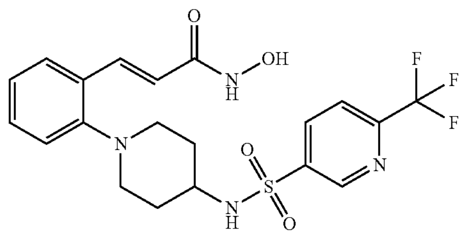 [SMILES: O=C(/C=C/c1ccccc1N1CCC(NS(=O)(=O)c2ccc(C(F)(F)F)nc2)CC1)NO] | (E)-N-hydroxy-3-(2-(4-((6-(trifluoromethyl)pyridine)-3-sulfonamido)piperidin-1-yl)phenyl)acrylamide | 471.22 | 1.35 | 97.55 |
| I-227 | 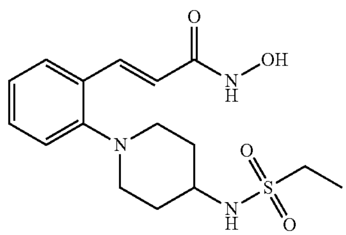 [SMILES: CCS(=O)(=O)NC1CCN(c2ccccc2/C=C/C(=O)NO)CC1] | (E)-3-(2-(4-(ethylsulfonamido)piperidin-1-yl)phenyl)-N-hydroxyacrylamide | 354.21 | .98 | 100 |
| I-26 | 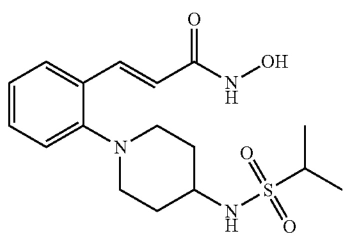 [SMILES: CC(C)S(=O)(=O)NC1CCN(c2ccccc2/C=C/C(=O)NO)CC1] | (E)-N-hydroxy-3-(2-(4-(((1-methylethyl)sulfonamido)piperidin-1-yl)phenyl)acrylamide | 368.22 | 1.07 | 93.8 |
| I-27 | 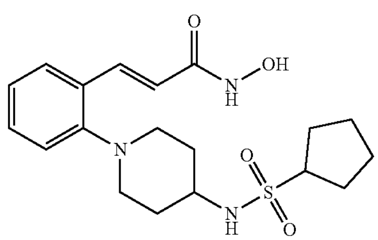 [SMILES: O=C(/C=C/c1ccccc1N1CCC(NS(=O)(=O)C2CCCC2)CC1)NO] | (E)-3-(2-(4-(cyclopentane-sulfonamido)piperidin-1-yl)phenyl)-N-hydroxyacrylamide | 394.24 | 1.19 | 94.63 |
| I-228 | 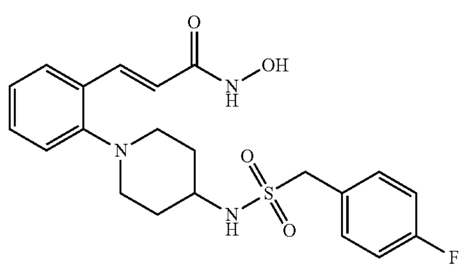 [SMILES: O=C(/C=C/c1ccccc1N1CCC(NS(=O)(=O)Cc2ccc(F)cc2)CC1)NO] | (E)-3-(2-(4-(((4-fluorophenyl)methyl)sulfonamido)piperidin-1-yl)phenyl)-N-hydroxyacrylamide | 434.22 | 1.27 | 100 |
| I-229 | 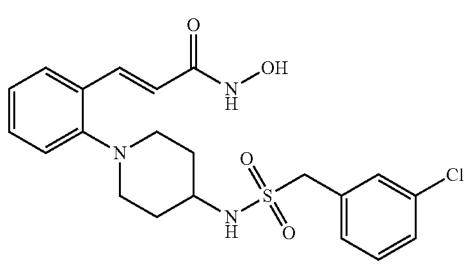 [SMILES: O=C(/C=C/c1ccccc1N1CCC(NS(=O)(=O)Cc2cccc(Cl)c2)CC1)NO] | (E)-3-(2-(4-(((3-chlorophenyl)methyl)sulfonamido)piperidin-1-yl)phenyl)-N-hydroxyacrylamide | 450.17 | 1.36 | 96.72 |

TABLE 21-continued

| ID | Name | LC-MS [M + H]+ | RT (min) | Purity (% UV220) |
|---|---|---|---|---|
| I-231 | (E)-3-(2-(4-((2,3-dihydrobenzo[b][1,4]dioxine)-6-sulfonamido)piperidin-1-yl)phenyl)-N-hydroxyacrylamide | 460.25 | 1.22 | 97.43 |
| I-232 | (E)-N-hydroxy-3-(2-(4-(isoquinoline-5-sulfonamido)piperidin-1-yl)phenyl)acrylamide | 453.23 | 1.12 | 97.35 |
| I-233 | (E)-3-(2-(4-((3,4-dimethoxyphenyl)sulfonamido)piperidin-1-yl)phenyl)-N-hydroxyacrylamide | 462.26 | 1.17 | 100 |
| I-234 | (E)-3-(2-(4-((4-(difluoromethoxy)phenyl)sulfonamido)piperidin-1-yl)phenyl)-N-hydroxyacrylamide | 468.24 | 1.34 | 97.11 |
| I-235 | (E)-3-(2-(4-(((3-fluorophenyl)methyl)sulfonamido)piperidin-1-yl)phenyl)-N-hydroxyacrylamide | 432.46 | 1.27 | 100 |

TABLE 21-continued

| ID | Structure | Name | LC-MS [M + H]+ | RT (min) | Purity (% UV220) |
|---|---|---|---|---|---|
| I-236 | 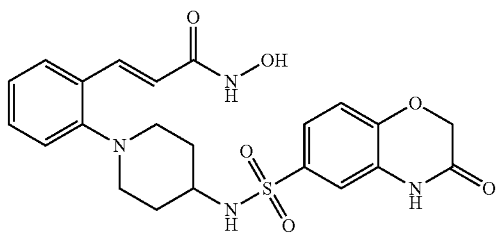 [SMILES: O=C(/C=C/c1ccccc1N1CCC(NS(=O)(=O)c2ccc3c(c2)NC(=O)CO3)CC1)NO] | (E)-N-hydroxy-3-(2-(4-((3-oxo-3,4-dihydro-2H-benzo[b][1,4]oxazine)-6-sulfonamido)piperidin-1-yl)phenyl)acrylamide | 473.25 | 1.08 | 96.28 |
| I-237 | 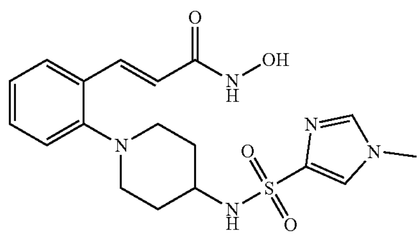 [SMILES: Cn1cnc(S(=O)(=O)NC2CCN(c3ccccc3/C=C/C(=O)NO)CC2)c1] | (E)-N-hydroxy-3-(2-(4-((1-methyl-1H-imidazole)-4-sulfonamido)piperidin-1-yl)phenyl)acrylamide | 406.24 | 0.90 | 100 |
| I-238 | 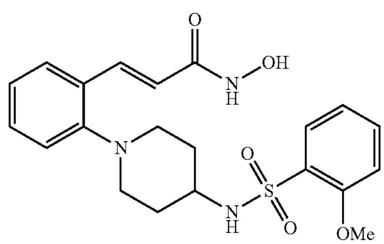 [SMILES: COc1ccccc1S(=O)(=O)NC1CCN(c2ccccc2/C=C/C(=O)NO)CC1] | (E)-N-hydroxy-3-(2-(4-((2-methoxyphenyl)sulfonamido)piperidin-1-yl)phenyl)acrylamide | 432.23 | 1.23 | 100 |
| I-239 | 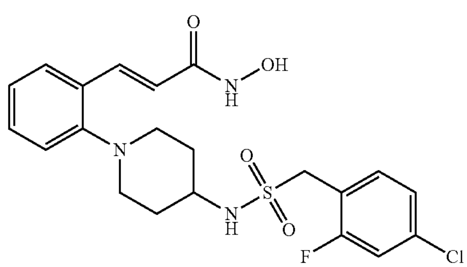 [SMILES: O=C(/C=C/c1ccccc1N1CCC(NS(=O)(=O)Cc2ccc(Cl)cc2F)CC1)NO] | (E)-3-(2-(4-(((4-chloro-2-fluorophenyl)methyl)sulfonamido)piperidin-1-yl)phenyl)-N-hydroxyacrylamide | 468.18 | 1.39 | 94.37 |
| I-240 | 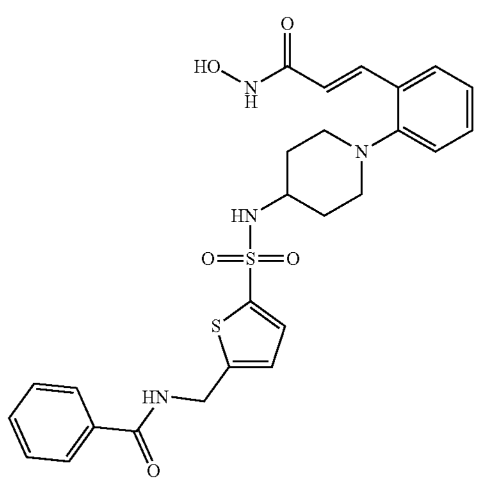 [SMILES: O=C(/C=C/c1ccccc1N1CCC(NS(=O)(=O)c2ccc(CNC(=O)c3ccccc3)s2)CC1)NO] | (E)-N-((5-(N-(1-(2-(3-(hydroxyamino)-3-oxoprop-1-en-1-yl)phenyl)piperidin-4-yl)sulfamoyl)thiophen-2-yl)methyl)benzamide | 541.29 | 1.24 | 97.23 |

TABLE 21-continued

| ID | Structure | Name | LC-MS [M + H]+ | RT (min) | Purity (% UV220) |
|---|---|---|---|---|---|
| I-241 | 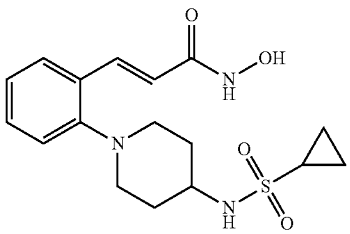 [SMILES: O=C(/C=C/c1ccccc1N1CCC(NS(=O)(=O)C2CC2)CC1)NO] | (E)-3-(2-(4-(cyclopropane-sulfonamido)piperidin-1-yl)phenyl)-N-hydroxyacrylamide | 366.21 | 1.03 | 100 |
| I-242 | 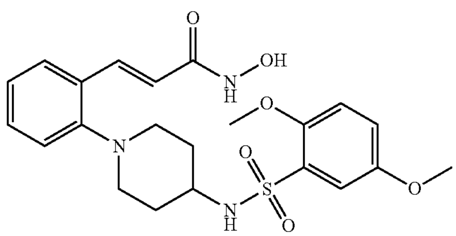 [SMILES: COc1ccc(OC)c(S(=O)(=O)NC2CCN(c3ccccc3/C=C/C(=O)NO)CC2)c1] | (E)-3-(2-(4-((2,5-dimethoxyphenyl)sulfonamido)piperidin-1-yl)phenyl)-N-hydroxyacrylamide | 462.26 | 1.25 | 100 |
| I-243 | 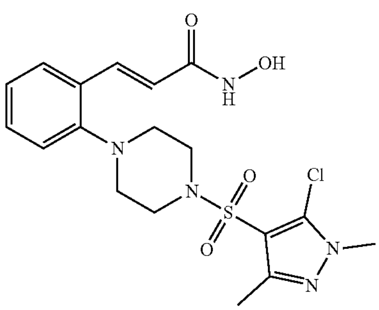 [SMILES: Cc1nn(C)c(Cl)c1S(=O)(=O)N1CCN(c2ccccc2/C=C/C(=O)NO)CC1] | (E)-3-(2-(4-((5-chloro-1,3-dimethyl-1H-pyrazol-4-yl)sulfonyl)piperazin-1-yl)phenyl)-N-hydroxyacrylamide | 440.16 | 1.15 | 100 |
| I-244 | 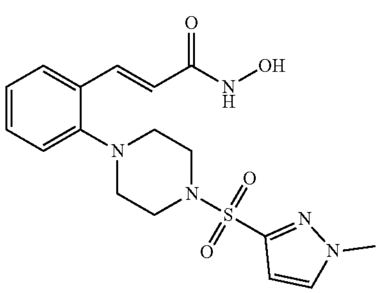 [SMILES: Cn1ccc(S(=O)(=O)N2CCN(c3ccccc3/C=C/C(=O)NO)CC2)n1] | (E)-N-hydroxy-3-(2-(4-((1-methyl-1H-pyrazol-3-yl)sulfonyl)piperazin-1-yl)phenyl)acrylamide | 392.20 | 1.00 | 100 |
| I-247 | 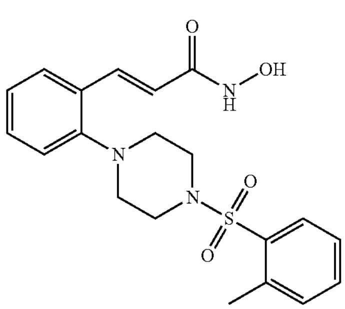 [SMILES: Cc1ccccc1S(=O)(=O)N1CCN(c2ccccc2/C=C/C(=O)NO)CC1] | (E)-N-hydroxy-3-(2-(4-(o-tolylsulfonyl)piperazin-1-yl)phenyl)acrylamide | 407.20 | 1.19 | 100 |

TABLE 21-continued

| ID | Structure | Name | LC-MS [M + H]+ | RT (min) | Purity (% UV220) |
|---|---|---|---|---|---|
| I-248 | | (E)-N-hydroxy-3-(2-(4-((6-(trifluoromethyl)pyridin-3-yl)sulfonyl)piperazin-1-yl)phenyl)acrylamide | 389.21 | 1.03 | 100 |
| I-247 | 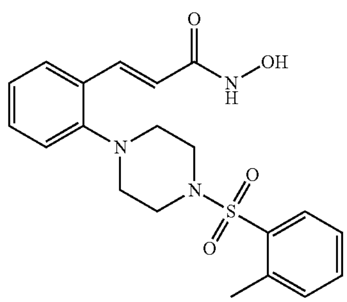 [SMILES: Cc1ccccc1S(=O)(=O)N1CCN(c2ccccc2/C=C/C(=O)NO)CC1] | (E)-N-hydroxy-3-(2-(4-(o-tolylsulfonyl)piperazin-1-yl)phenyl)acrylamide | 402.21 | 1.30 | 94.29 |
| I-248 | | (E)-N-hydroxy-3-(2-(4-((6-(trifluoromethyl)pyridin-3-yl)sulfonyl)piperazin-1-yl)phenyl)acrylamide | 457.19 | 1.32 | 100 |
| I-249 | 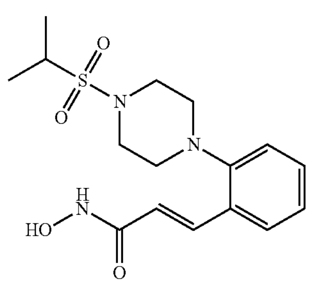 [SMILES: CC(C)S(=O)(=O)N1CCN(c2ccccc2/C=C/C(=O)NO)CC1] | (E)-N-hydroxy-3-(2-(4-(isopropylsulfonyl)piperazin-1-yl)phenyl)acrylamide | 354.25 | 1.04 | 100 |
| I-250 | 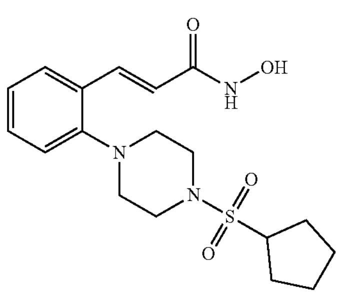 [SMILES: O=C(/C=C/c1ccccc1N1CCN(S(=O)(=O)C2CCCC2)CC1)NO] | (E)-3-(2-(4-(cyclopentylsulfonyl)piperazin-1-yl)phenyl)-N-hydroxyacrylamide | 380.24 | 1.16 | 95.65 |

TABLE 21-continued

| ID | Name | LC-MS [M + H]+ | RT (min) | Purity (% UV220) |
|---|---|---|---|---|
| I-251 | (E)-3-(2-(4-((4-fluorobenzyl)sulfonyl)piperazin-1-yl)phenyl)-N-hydroxyacrylamide | 420.21 | 1.25 | 100 |
| I-252 | (E)-N-hydroxy-3-(2-(4-((1-methyl-1H-imidazol-2-yl)sulfonyl)piperazin-1-yl)phenyl)acrylamide | 392.20 | 1.00 | 100 |
| I-253 | (E)-3-(2-(4-((5-chlorothiophen-2-yl)sulfonyl)piperazin-1-yl)phenyl)-N-hydroxyacrylamide | 428.14 | 1.37 | 100 |
| I-28 | (E)-3-(2-(4-((2,3-dihydrobenzo[b][1,4]dioxin-6-yl)sulfonyl)piperazin-1-yl)phenyl)-N-hydroxyacrylamide | 446.21 | 0.78 | 100 |

TABLE 21-continued

| ID | Name | LC-MS [M + H]+ | RT (min) | Purity (% UV220) |
|---|---|---|---|---|
| I-254 | (E)-N-hydroxy-3-(2-(4-(isoquinolin-5-ylsulfonyl)piperazin-1-yl)phenyl)acrylamide | 439.25 | 1.10 | 88.97 |
| I-255 | (E)-N-hydroxy-3-(2-(4-((tetrahydro-2H-pyran-4-yl)sulfonyl)piperazin-1-yl)phenyl)acrylamide | 396.27 | 0.97 | 100 |
| I-256 | (E)-3-(2-(4-((3,4-dimethoxyphenyl)sulfonyl)piperazin-1-yl)phenyl)-N-hydroxyacrylamide | 448.22 | 1.17 | 100 |
| I-29 | (E)-N-hydroxy-3-(2-(4-((2-(trifluoromethoxy)phenyl)sulfonyl)piperazin-1-yl)phenyl)acrylamide | 472.21 | 0.95 | 100 |

TABLE 21-continued

| ID | Structure | Name | LC-MS [M + H]+ | RT (min) | Purity (% UV220) |
|---|---|---|---|---|---|
| I-30 | 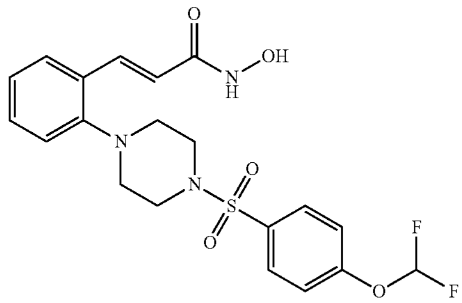 [SMILES: O=C(/C=C/c1ccccc1N1CCN(S(=O)(=O)c2ccc(OC(F)F)cc2)CC1)NO] | (E)-3-(2-(4-((4-(difluoromethoxy)phenyl)sulfonyl)piperazin-1-yl)phenyl)-N-hydroxyacrylamide | 454.20 | 0.88 | 96.24 |
| I-257 | 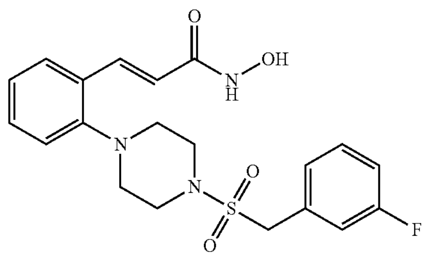 [SMILES: O=C(/C=C/c1ccccc1N1CCN(S(=O)(=O)Cc2cccc(F)c2)CC1)NO] | (E)-3-(2-(4-((3-fluorobenzyl)sulfonyl)piperazin-1-yl)phenyl)-N-hydroxyacrylamide | 420.21 | 1.25 | 100 |
| I-258 | 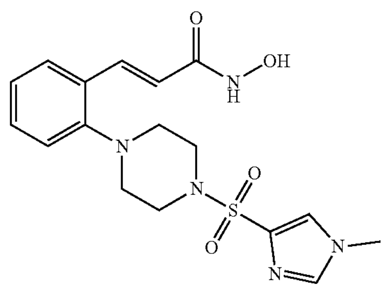 [SMILES: Cn1cnc(S(=O)(=O)N2CCN(c3ccccc3/C=C/C(=O)NO)CC2)c1] | (E)-N-hydroxy-3-(2-(4-((1-methyl-1H-imidazol-4-yl)sulfonyl)piperazin-1-yl)phenyl)acrylamide | 392.26 | 0.90 | 100 |
| I-31 | 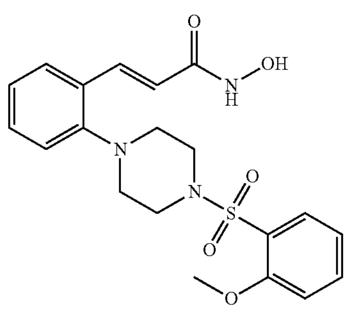 [SMILES: COc1ccccc1S(=O)(=O)N1CCN(c2ccccc2/C=C/C(=O)NO)CC1] | (E)-N-hydroxy-3-(2-(4-((2-methoxyphenyl)sulfonyl)piperazin-1-yl)phenyl)acrylamide | 418.24 | 0.73 | 100 |
| I-259 | 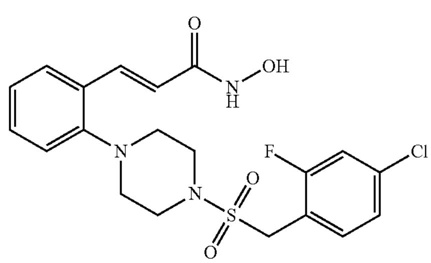 [SMILES: O=C(/C=C/c1ccccc1N1CCN(S(=O)(=O)Cc2ccc(Cl)cc2F)CC1)NO] | (E)-3-(2-(4-((4-chloro-2-fluorobenzyl)sulfonyl)piperazin-1-yl)phenyl)-N-hydroxyacrylamide | 454.20 | 1.36 | 100 |

TABLE 21-continued

| ID | Structure | Name | LC-MS [M + H]+ | RT (min) | Purity (% UV220) |
|---|---|---|---|---|---|
| I-32 | 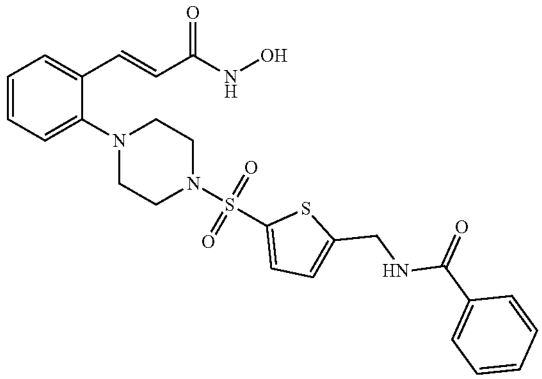 [SMILES: O=C(/C=C/c1ccccc1N1CCN(S(=O)(=O)c2ccc(CNC(=O)c3ccccc3)s2)CC1)NO] | (E)-N-((5-((4-(2-(3-(hydroxyamino)-3-oxoprop-1-en-1-yl)phenyl)piperazin-1-yl)sulfonyl)thiophen-2-yl)methyl)benzamide | 527.31 | 0.88 | 93.54 |
| I-33 | 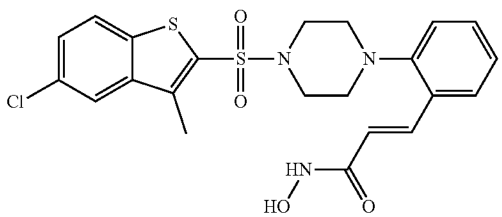 [SMILES: Cc1c(S(=O)(=O)N2CCN(c3ccccc3/C=C/C(=O)NO)CC2)sc2ccc(Cl)cc12] | (E)-3-(2-(4-((5-chloro-3-methylbenzo[b]thiophen-2-yl)sulfonyl)piperazin-1-yl)phenyl)-N-hydroxyacrylamide | 492.22 | 1.17 | 86.17 |
| I-34 | 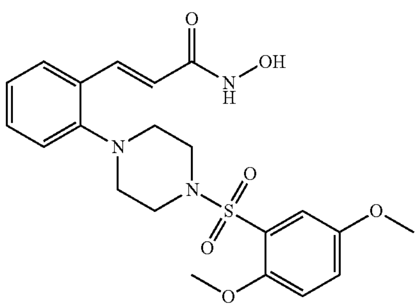 [SMILES: COc1ccc(OC)c(S(=O)(=O)N2CCN(c3ccccc3/C=C/C(=O)NO)CC2)c1] | (E)-3-(2-(4-((2,5-dimethoxyphenyl)sulfonyl)piperazin-1-yl)phenyl)-N-hydroxyacrylamide | 488.22 | 0.80 | 100 |
| I-526 | 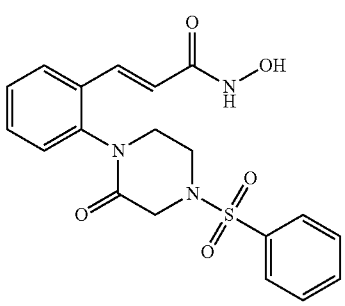 [SMILES: O=C(/C=C/c1ccccc1N1CCN(S(=O)(=O)c2ccccc2)CC1=O)NO] | (E)-N-hydroxy-3-(2-(2-oxo-4-(phenylsulfonyl)piperazin-1-yl)phenyl)acrylamide | 402 | 0.92 | 100 |
| I-527 | 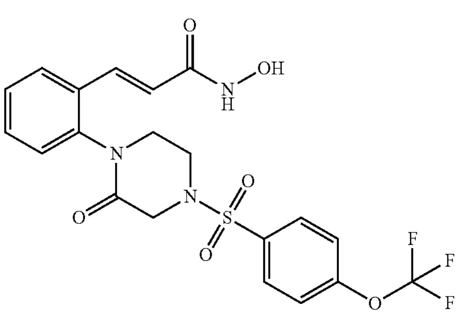 [SMILES: O=C(/C=C/c1ccccc1N1CCN(S(=O)(=O)c2ccc(OC(F)(F)F)cc2)CC1=O)NO] | (E)-N-hydroxy-3-(2-(2-oxo-4-((4-(trifluoromethoxy)phenyl)sulfonyl)piperazin-1-yl)phenyl)acrylamide | 486 | 1.20 | 100 |

315

Example 66—(E)-N-hydroxy-3-(2-(4-(4-iso-propoxybenzyl)piperazin-1-yl)phenyl)acrylamide (I-401)

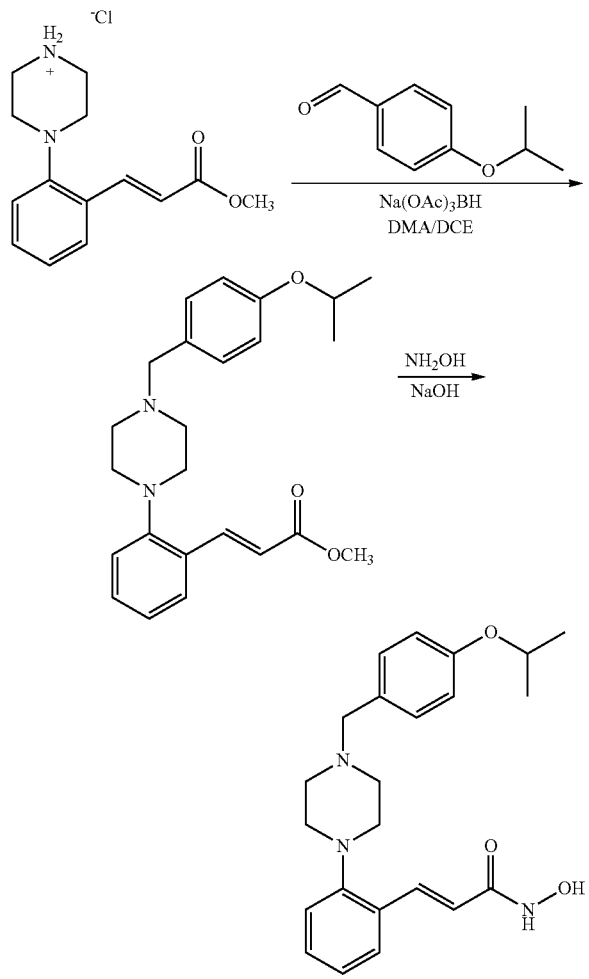

Step-1: A 2 mL vial was charged with a solution of (E)-4-(2-(3-methoxy-3-oxoprop-1-en-1-yl)phenyl)piperazin-1-ium chloride (0.2 M in 10:1 DMA:TEA, 200 μL, 0.040 mmol), and 4-isopropoxybenzaldehyde (0.2 M in DCE, 200 μL, 0.040 mmol), followed by a slurry of Na(OAc)$_3$BH in DCE (0.2M, 200 μL, 0.040 mmol). The vial was sealed and shaken at room temperature for 18 h, then the solvent was removed under a stream of N$_2$. The residue was diluted with brine (500 μL) and extracted with ethyl acetate (2×500 μL). The combined organic layers were dried under a stream of N$_2$ revealing a pale yellow residue, which was used without further purification. $^1$H NMR (400 MHz, CDCl$_3$) δ 8.09 (d, J=16.4 Hz, 1H), 7.52 (dd, 0.1=8.2, 1.9 Hz, 1H), 7.35 (t, J=7.4 Hz, 1H), 7.25 (d, J=8.6 Hz, 2H), 7.07-7.03 (m, 2H), 6.85 (d, J=8.6 Hz, 2H), 6.41 (d, J=16.0 Hz, 1H), 4.54 (sept, 1H), 3.82 (s, 3H), 3.53 (2H), 3.00-2.97 (m, 4H), 2.65 (br s, 4H), 1.34 (d, J=6.2 Hz, 6H); $^{13}$C NMR (100 MHz, CDCl$_3$) δ 167.9, 157.0, 152.7, 142.5, 130.9, 130.4, 129.9, 128.6, 127.9, 122.8, 118.9, 117.2, 115.6, 69.8, 62.5, 53.3, 52.8, 51.6, 22.1; LRMS (ESI, m/z) calculated for C$_{24}$H$_{31}$N$_2$O$_3$ [M+H]$^+$ 395.23, found 395.11.

Step-2: The crude residue of methyl-(E)-3-(2-(4-(4-isopropoxybenzyl)piperazin-1-yl)phenyl)acrylate was dissolved in 3:1 THF/methanol (200 μL). The vial was sealed and shaken at 50° C. for 15 min to dissolve the residue, then cooled to room temperature. Hydroxylamine (150 μL, 50% v/v solution in water) was added, followed by 1 N NaOH (100 μL). The mixture was sealed and shaken at room temperature for 18 h. The reaction mixture was concentrated under a stream of N$_2$ at room temperature, then dissolved in 500 μL of DMSO and purified by mass triggered prep HPLC (Column: Waters Sunfire C18, 5 μm, 19×50 mm; Mobile Phase: water (0.1% formic acid) and acetonitrile (0.1% formic acid) (15% to 100% acetonitrile in 6 min, flow rate: 23 mL/min); Detector UV 254/220 nm). The product-containing fractions were combined and concentrated in a Genevac to afford (E)-N-hydroxy-3-(2-(4-(4-isopropoxybenzyl)piperazin-1-yl)phenyl)acrylamide (5.2 mg, 33% yield). $^1$H NMR (400 MHz, DMSO-d$_6$) δ 9.85 (br s, 1H), 7.64 (d, J=16 Hz, 1H), 7.44 (d, J=6.6 Hz, 1H), 7.27 (t, J=7.0 Hz, 1H), 7.18 (d, J=8.6 Hz, 2H), 7.05-6.99 (m, 2H), 6.83 (d, J=8.6 Hz, 2H), 6.38 (d, J=16 Hz, 1H), 4.54 (sept, J=6.3 Hz, 1H), 3.43 (s, 2H), 2.82 (br s, 4H), 2.52 (br s, 4H), 1.23 (d, J=5.8 Hz, 6H); $^{13}$C NMR (100 MHz, DMSO-d$_6$) δ 163.6, 156.5, 151.6, 134.4, 130.2, 129.8, 129.6, 128.9, 127.1, 122.8, 119.4, 118.8, 115.2, 69.0, 52.67, 52.22, 21.9, LRMS (ESI, m/z) calculated for C$_{23}$H$_{29}$N$_3$O$_3$ [M+H]$^+$ 395.22, found 394.58; R$_t$ 0.92 min.

The following compounds in Table 22 were prepared according to the procedures for (E)-N-hydroxy-3-(2-(4-(4-isopropoxybenzyl)piperazin-1-yl)phenyl)acrylamide (I-401)

TABLE 22

| ID | Structure | Name | LC-MS [M + H]$^+$ | RT (min) | Purity (% UV220) |
|---|---|---|---|---|---|
| I-395 | ![structure] | (E)-3-(2-(4-(3-((dimethylamino)methyl)benzyl)piperazin-1-yl)phenyl)-N-hydroxyacrylamide | 393.47 | 0.48 | 72.68 |

TABLE 22-continued

| ID | Name | LC-MS [M + H]+ | RT (min) | Purity (% UV220) |
|---|---|---|---|---|
| I-396 | (E)-3-(2-(4-(4-(2-(dimethylamino)ethoxy)benzyl)piperazin-1-yl)phenyl)-N-hydroxyacrylamide | 423.53 | 0.50 | 51.72 |
| I-397 | (E)-N-hydroxy-3-(2-(4-(4-isopropylbenzyl)piperazin-1-yl)phenyl)acrylamide | 380.31 | 0.99 | 79.1 |
| I-398 | (E)-N-hydroxy-3-(2-(4-(3-methylbenzyl)piperazin-1-yl)phenyl)acrylamide | 352.30 | 0.80 | 82.05 |
| I-399 | ((E)-N-hydroxy-3-(2-(4-((5-isopropylpyridin-2-yl)methyl)piperazin-1-yl)phenyl)acrylamide | 381.28 | 0.60 | 71.87 |
| I-400 | (E)-N-hydroxy-3-(2-(4-(pyridin-4-ylmethyl)piperazin-1-yl)phenyl)acrylamide | 339.26 | 0.55 | 70.55 |
| I-402 | (E)-3-(2-(4-(benzo[d][1,3]dioxol-5-ylmethyl)piperazin-1-yl)phenyl)-N-hydroxyacrylamide | 382.26 | 0.73 | 81.76 |
| I-403 | (E)-N-hydroxy-3-(2-(4-((6-morpholinopyridin-3-yl)methyl)piperazin-1-yl)phenyl)acrylamide | 424.31 | 0.46 | 77.1 |

TABLE 22-continued

| ID | Structure | Name | LC-MS [M + H]+ | RT (min) | Purity (% UV220) |
|---|---|---|---|---|---|
| I-404 | 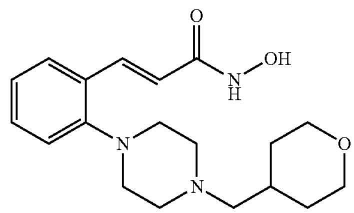 [SMILES: O=C(/C=C/c1ccccc1N1CCN(CC2CCOCC2)CC1)NO] | (E)-N-hydroxy-3-(2-(4-((tetrahydro-2H-pyran-4-yl)methyl)piperazin-1-yl)phenyl)acrylamide | 346.32 | 0.57 | 48.89 |
| I-406 | 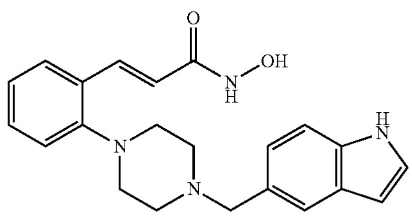 [SMILES: O=C(/C=C/c1ccccc1N1CCN(Cc2ccc3[nH]ccc3c2)CC1)NO] | (E)-3-(2-(4-((1H-indol-5-yl)methyl)piperazin-1-yl)phenyl)-N-hydroxyacrylamide | 377.28 | 0.57 | 80.00 |
| I-522 | 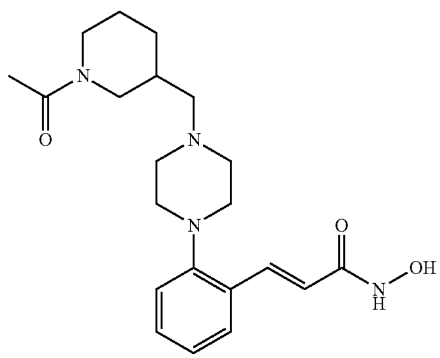 [SMILES: CC(=O)N1CCCC(CN2CCN(c3ccccc3/C=C/C(=O)NO)CC2)C1] | (E)-3-(2-(4-((1-acetylpiperidin-3-yl)methyl)piperazin-1-yl)phenyl)-N-hydroxyacrylamide | 387.33 | 0.58 | 61.00 |
| I-523 | 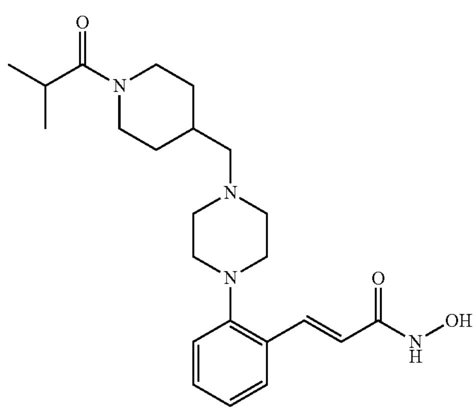 [SMILES: CC(C)C(=O)N1CCC(CN2CCN(c3ccccc3/C=C/C(=O)NO)CC2)CC1] | (E)-N-hydroxy-3-(2-(4-((1-isobutyrylpiperidin-4-yl)methyl)piperazin-1-yl)phenyl)acrylamide | 415.36 | 0.65 | 53.15 |
| I-409 | 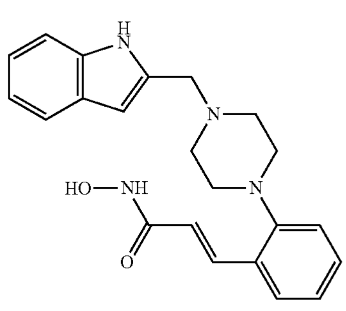 [SMILES: O=C(/C=C/c1ccccc1N1CCN(Cc2cc3ccccc3[nH]2)CC1)NO] | (2E)-N-hydroxy-3-{2-[4-(1H-indol-2-ylmethyl)piperazin-1-yl]phenyl}prop-2-enamide | 377.31 | 0.89 | 52.85 |

TABLE 22-continued

| ID | Structure | Name | LC-MS [M + H]+ | RT (min) | Purity (% UV220) |
|---|---|---|---|---|---|
| I-410 | 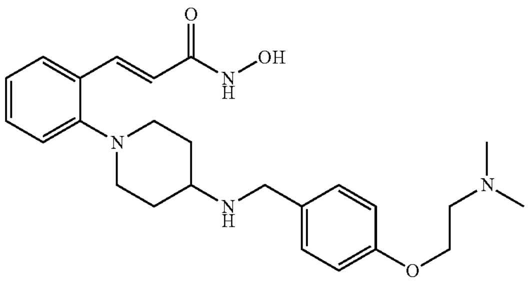 [SMILES: CN(C)CCOc1ccc(CNC2CCN(c3ccccc3/C=C/C(=O)NO)CC2)cc1] | E)-3-(2-(4-((4-(2-(dimethylamino)ethoxy)benzyl)amino)piperidin-1-yl)phenyl)-N-hydroxyacrylamide | 439.38 | 0.62 | 100 |
| I-411 | 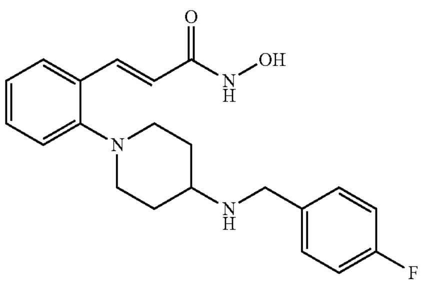 [SMILES: O=C(/C=C/c1ccccc1N1CCC(NCc2ccc(F)cc2)CC1)NO] | (E)-3-(2-(4-((4-fluorobenzyl)amino)piperidin-1-yl)phenyl)-N-hydroxyacrylamide | 370.30 | 0.88 | 49.47 |
| I-412 | 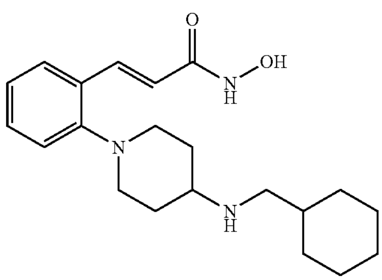 [SMILES: O=C(/C=C/c1ccccc1N1CCC(NCC2CCCCC2)CC1)NO] | (E)-3-(2-(4-((cyclohexylmethyl)amino)piperidin-1-yl)phenyl)-N-hydroxyacrylamide | 358.34 | 0.87 | 27 |
| I-413 | 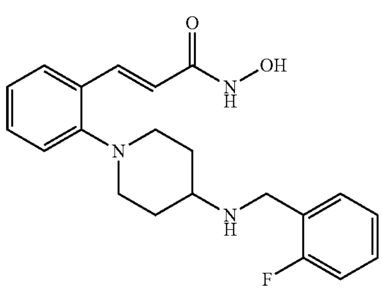 [SMILES: O=C(/C=C/c1ccccc1N1CCC(NCc2ccccc2F)CC1)NO] | (E)-3-(2-(4-((2-fluorobenzyl)amino)piperidin-1-yl)phenyl)-N-hydroxyacrylamide | 370.29 | 0.76 | 32 |
| I-414 | 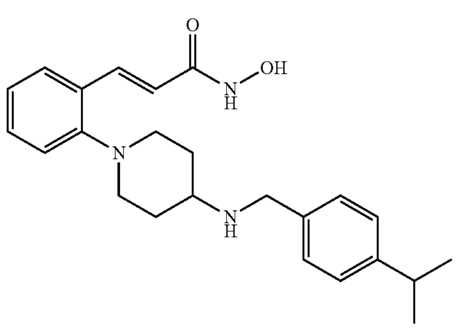 [SMILES: CC(C)c1ccc(CNC2CCN(c3ccccc3/C=C/C(=O)NO)CC2)cc1] | (E)-N-hydroxy-3-(2-(4-((4-isopropylbenzyl)amino)piperidin-1-yl)phenyl)acrylamide | 394.34 | 1.03 | 36 |

TABLE 22-continued

| ID | Structure | Name | LC-MS [M + H]+ | RT (min) | Purity (% UV220) |
|---|---|---|---|---|---|
| I-415 | 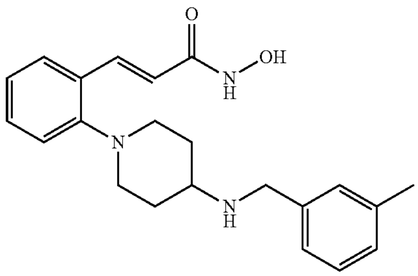 [SMILES: Cc1cccc(CNC2CCN(c3ccccc3/C=C/C(=O)NO)CC2)c1] | (E)-N-hydroxy-3-(2-(4-((3-methylbenzyl)amino)piperidin-1-yl)phenyl)acrylamide | 366.34 | 0.95 | 53 |
| I-416 | 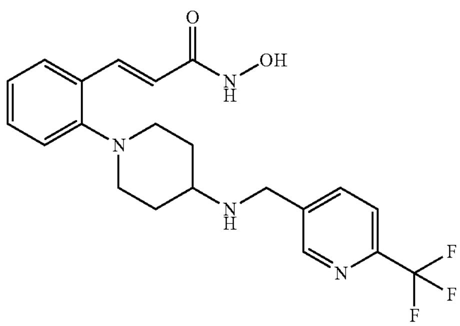 [SMILES: O=C(/C=C/c1ccccc1N1CCC(NCc2ccc(C(F)(F)F)nc2)CC1)NO] | (E)-N-hydroxy-3-(2-(4-(((6-(trifluoromethyl)pyridin-3-yl)methyl)amino)piperidin-1-yl)phenyl)acrylamide | 421.25 | 0.87 | 36.39 |
| I-417 | 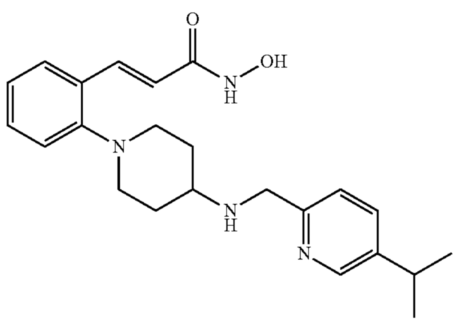 [SMILES: CC(C)c1ccc(CNC2CCN(c3ccccc3/C=C/C(=O)NO)CC2)nc1] | (E)-N-hydroxy-3-(2-(4-(((5-isopropylpyridin-2-yl)methyl)amino)piperidin-1-yl)phenyl)acrylamide | 395.32 | 0.99 | 68 |
| I-418 | 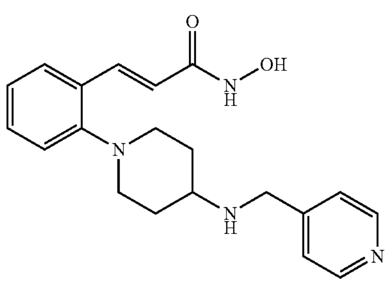 [SMILES: O=C(/C=C/c1ccccc1N1CCC(NCc2ccncc2)CC1)NO] | (E)-N-hydroxy-3-(2-(4-((pyridin-4-ylmethyl)amino)piperidin-1-yl)phenyl)acrylamide | 353.32 | 0.64 | 56.16 |
| I-419 | 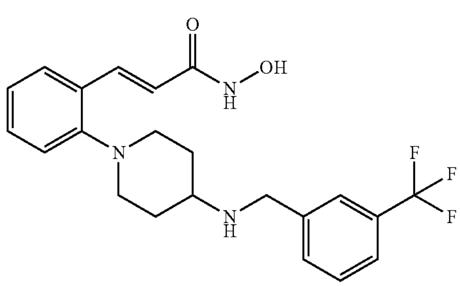 [SMILES: O=C(/C=C/c1ccccc1N1CCC(NCc2cccc(C(F)(F)F)c2)CC1)NO] | (E)-N-hydroxy-3-(2-(4-((3-(trifluoromethyl)benzyl)amino)piperidin-1-yl)phenyl)acrylamide | 420.29 | 1.15 | 19 |

TABLE 22-continued

| ID | Structure | Name | LC-MS [M + H]+ | RT (min) | Purity (% UV220) |
|---|---|---|---|---|---|
| I-420 | 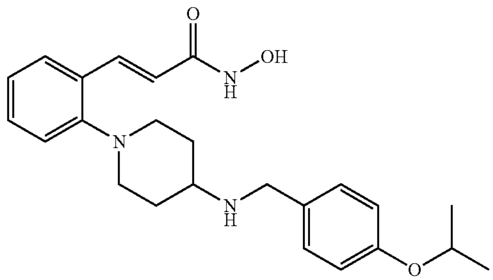 [SMILES: CC(C)Oc1ccc(CNC2CCN(c3ccccc3/C=C/C(=O)NO)CC2)cc1] | (E)-N-hydroxy-3-(2-(4-((4-isopropoxybenzyl)amino)piperidin-1-yl)phenyl)acrylamide | 410.33 | 0.96 | 25.49 |
| I-423 | 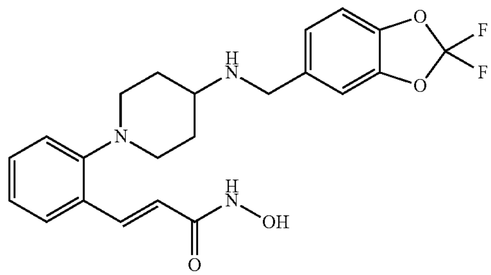 [SMILES: O=C(/C=C/c1ccccc1N1CCC(NCc2ccc3c(c2)OC(F)(F)O3)CC1)NO] | (E)-3-(2-(4-(((2,2-difluorobenzo[d][1,3]dioxol-5-yl)methyl)amino)piperidin-1-yl)phenyl)-N-hydroxyacrylamide | 432.28 | 1.04 | 32 |
| I-424 | 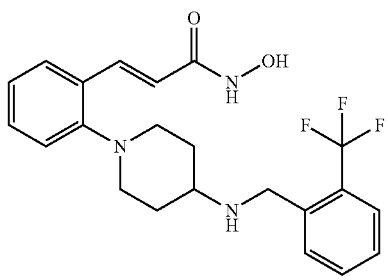 [SMILES: O=C(/C=C/c1ccccc1N1CCC(NCc2ccccc2C(F)(F)F)CC1)NO] | (E)-N-hydroxy-3-(2-(4-((2-(trifluoromethyl)benzyl)amino)piperidin-1-yl)phenyl)acrylamide | 420.28 | 0.54 | 75.86 |
| I-427 | 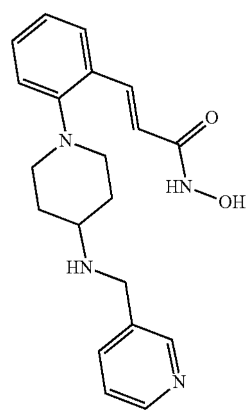 [SMILES: O=C(/C=C/c1ccccc1N1CCC(NCc2cccnc2)CC1)NO] | (E)-N-hydroxy-3-(2-(4-((pyridin-3-ylmethyl)amino)piperidin-1-yl)phenyl)acrylamide | 353.28 | 0.67 | 63.35 |
| I-428 | 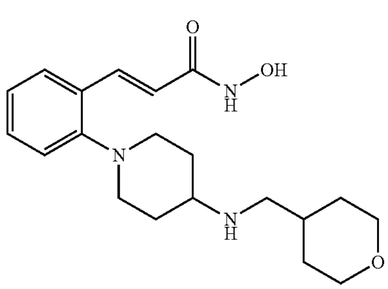 [SMILES: O=C(/C=C/c1ccccc1N1CCC(NCC2CCOCC2)CC1)NO] | (E)-N-hydroxy-3-(2-(4-(((tetrahydro-2H-pyran-4-yl)methyl)amino)piperidin-1-yl)phenyl)acrylamide | 360.29 | 0.70 | 32 |

TABLE 22-continued

| ID | Structure | Name | LC-MS [M + H]+ | RT (min) | Purity (% UV220) |
|---|---|---|---|---|---|
| I-429 | 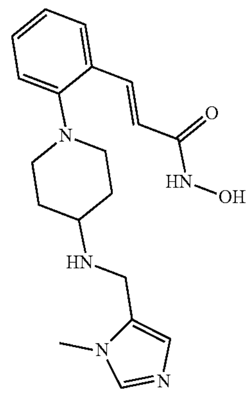 [SMILES: Cn1cncc1CNC1CCN(c2ccccc2/C=C/C(=O)NO)CC1] | (E)-N-hydroxy-3-(2-(4-(((1-methyl-1H-imidazol-5-yl)methyl)amino)piperidin-1-yl)phenyl)acrylamide | 356.30 | 0.52 | 100 |
| I-432 | 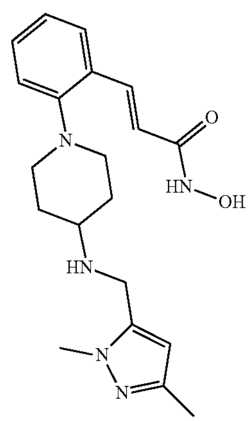 [SMILES: Cc1cc(CNC2CCN(c3ccccc3/C=C/C(=O)NO)CC2)n(C)n1] | (E)-3-(2-(4-(((1,3-dimethyl-1H-pyrazol-5-yl)methyl)amino)piperidin-1-yl)phenyl)-N-hydroxyacrylamide | 370.32 | 0.61 | 42 |
| I-524 | 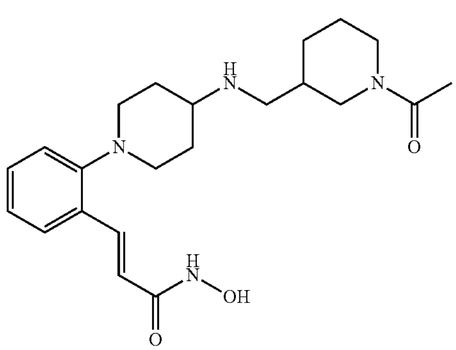 [SMILES: CC(=O)N1CCCC(CNC2CCN(c3ccccc3/C=C/C(=O)NO)CC2)C1] | (E)-3-(2-(4-(((1-acetylpiperidin-3-yl)methyl)amino)piperidin-1-yl)phenyl)-N-hydroxyacrylamide | 401.34 | 0.70 | 36 |

TABLE 22-continued

| ID | Structure | Name | LC-MS [M + H]+ | RT (min) | Purity (% UV220) |
|---|---|---|---|---|---|
| I-514 | 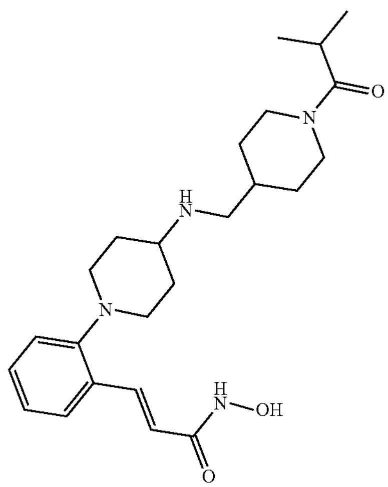 [SMILES: CC(C)C(=O)N1CCC(CNC2CCN(c3ccccc3/C=C/C(=O)NO)CC2)CC1] | (E)-N-hydroxy-3-(2-(4-(((1-isobutytylpiperidin-4-yl)methyl)amino)piperidin-1-yl)phenyl)acrylamide | 429.33 | 0.41 | 57.56 |
| I-435 | 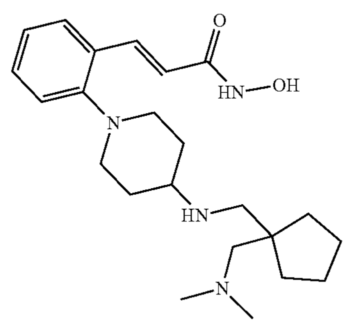 [SMILES: CN(C)CC1(CNC2CCN(c3ccccc3/C=C/C(=O)NO)CC2)CCCC1] | (E)-3-(2-(4-(((1-((dimethylamino)methyl)cyclopentyl)methyl)amino)piperidin-1-yl)phenyl)-N-hydroxyacrylamide | 401.36 | 0.66 | 59.99 |
| I-437 | 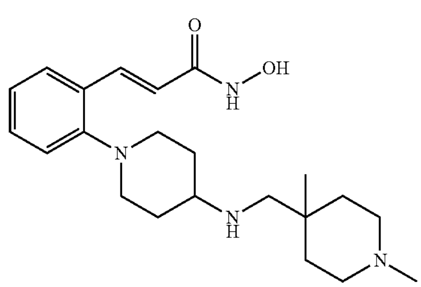 [SMILES: CN1CCC(C)(CNC2CCN(c3ccccc3/C=C/C(=O)NO)CC2)CC1] | (E)-3-(2-(4-(((1,4-dimethylpiperidin-4-yl)methyl)amino)piperidin-1-yl)phenyl)-N-hydroxyacrylamide | 387.33 | 0.54 | 69.74 |
| I-299 | 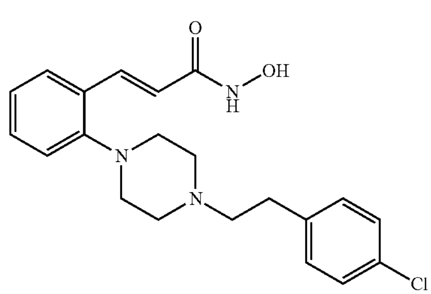 [SMILES: O=C(/C=C/c1ccccc1N1CCN(CCc2ccc(Cl)cc2)CC1)NO] | (E)-3-(2-(4-(4-chlorophenethyl)piperazin-1-yl)phenyl)-N-hydroxyacrylamide | 386.22 | 0.88 | 95 |

TABLE 22-continued

| ID | Structure | Name | LC-MS [M + H]⁺ | RT (min) | Purity (% UV220) |
|---|---|---|---|---|---|
| I-300 | 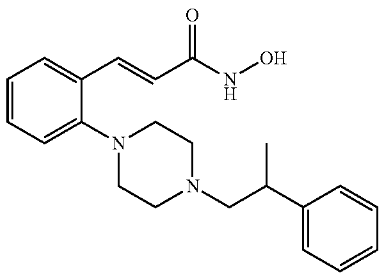 [SMILES: CC(CN1CCN(c2ccccc2/C=C/C(=O)NO)CC1)c1ccccc1] | (E)-N-hydroxy-3-(2-(4-(2-phenylpropyl)piperazin-1-yl)phenyl)acrylamide | 366.27 | 0.82 | 94 |
| I-315 | 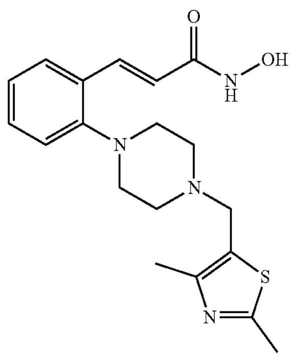 [SMILES: Cc1nc(C)c(CN2CCN(c3ccccc3/C=C/C(=O)NO)CC2)s1] | (E)-3-(2-(4-((2,4-dimethyltiazol-5-yl)methyl)piperazin-1-yl)phenyl)-N-hydroxyacrylamide | 373.16 | 0.56 | 85 |
| I-317 | 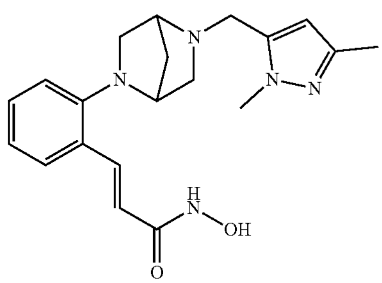 [SMILES: Cc1cc(CN2CC3CC2CN3c2ccccc2/C=C/C(=O)NO)n(C)n1] | (E)-3-(2-((1S,4S)-5-((1,3-dimethyl-1H-pyrazol-5-yl)methyl)-2,5-diazabicyclo[2.2.1]heptan-2-yl)phenyl)-N-hydroxyacrylamide | 368.28 | 0.62 | 100 |
| II-30 | 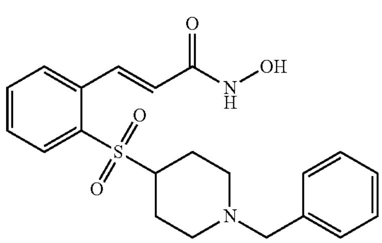 [SMILES: O=C(/C=C/c1ccccc1S(=O)(=O)C1CCN(Cc2ccccc2)CC1)NO] | (E)-3-(2-((1-benzylpiperidin-4-yl)sulfonyl)phenyl)-N-hydroxyacrylamide | 401.17 | 0.67 | 96.59 |
| I-326 | 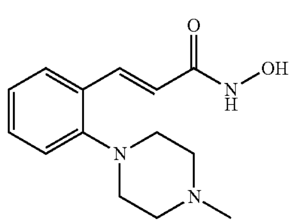 [SMILES: CN1CCN(c2ccccc2/C=C/C(=O)NO)CC1] | (E)-N-hydroxy-3-(2-(4-methylpiperazin-1-yl)phenyl)acrylamide | 262.21 | 0.50 | 100 |

TABLE 22-continued

| ID | Structure | Name | LC-MS [M + H]⁺ | RT (min) | Purity (% UV220) |
|---|---|---|---|---|---|
| I-330 | 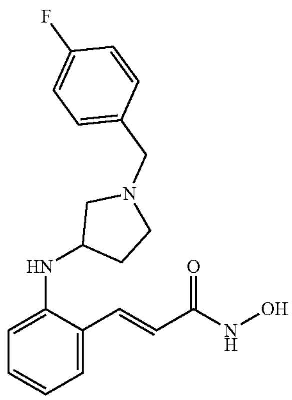 [SMILES: O=C(/C=C/c1ccccc1NC1CCN(Cc2ccc(F)cc2)C1)NO] | (E)-3-(2-((1-(4-fluorobenzyl)pyrrolidin-3-yl)amino)phenyl)-N-hydroxyacrylamide | 356.08 | 0.79 | 87.81 |
| I-498 | 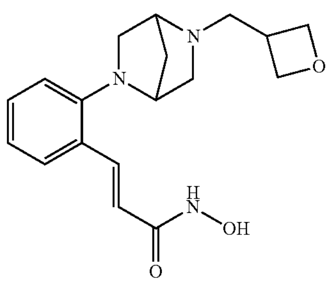 [SMILES: O=C(/C=C/c1ccccc1N1CC2CC1CN2CC1COC1)NO] | (E)-N-hydroxy-3-(2-((1S,4S)-5-(oxetan-3-ylmethyl)-2,5-diazabicyclo[2.2.1]heptan-2-yl)phenyl)acrylamide | 330.13 | 0.52 | 71.9 |

Example 67—tert-butyl(E)-7-(2-(3-(hydroxyamino)-3-oxoprop-1-en-1-yl)phenyl)-1,7-diazaspiro[4.4]nonane-1-carboxylate

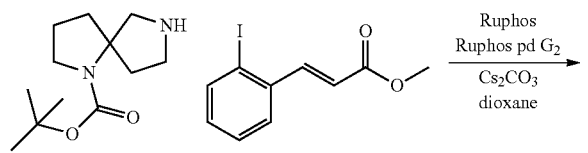

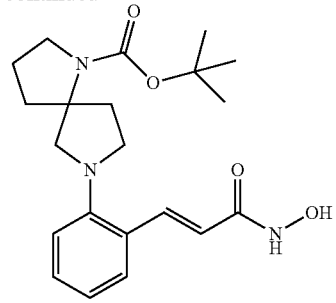

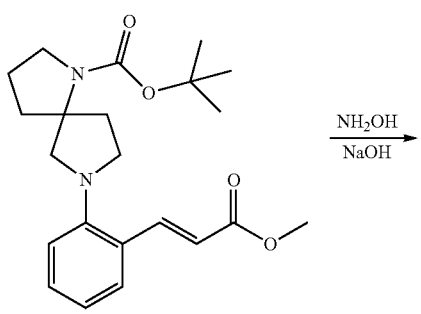

Under N₂, to a 2 mL reaction vial were charged tert-butyl 1,7-diazaspiro[4.4]nonane-1-carboxylate (0.2M in dioxane, 400 uL, 80umol), methyl (E)-3-(2-iodophenyl)acrylate (0.2M in dioxane, 400 uL, 80umol), Ruphos Pd G₂ (16umol, 12.4 mg), Ruphos (16umol, 7.5 mg) and Cs₂CO₃ (240umol, 78 mg), then the vial was sealed and heated at 100° C. for overnight. The solvent was removed under reduced pressure. The residue was diluted with brine (600 uL) and extracted with ethyl acetate (2×800 uL). The combined organic layers were evaporated to dryness under reduced presssure. Mixed solvent of THF/MeOH (3:1, 300 uL) was added to the vial and it was shaken at 50° C. for 15 min to dissolve the residue. NH₂OH (50% in water, 200 uL) was added followed by NaOH (1N in water, 160 uL) and the vial was sealed and shaken at RT for overnight. The solvent was evaporated under reduce presssure. The residue was dissolved in DMSO (500 uL), then purified by HPLC to yield the title compound (3.3 mg, 10.65% yield). LCMS Rt: 1.42 min, m/z: 388[M+H]⁺.

The following compounds were synthesized according to the above protocol:

TABLE 23

| ID | Structure | Name | LC-MS [M + 1]+ | HPLC RT (min) |
|---|---|---|---|---|
| I-538 | 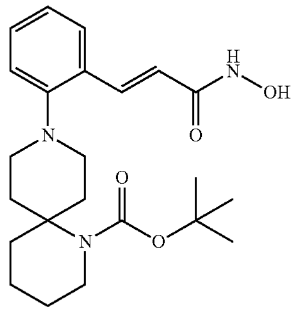 [SMILES: CC(C)(C)OC(=O)N1CCCCC12CCN(c1ccccc1/C=C/C(=O)NO)CC2] | tert-butyl (E)-9-(2-(3-(hydroxyamino)-3-oxoprop-1-en-1-yl)phenyl)-1,9-diazaspiro[5.5]undecane-1-carboxylate | 416 | 1.47 |
| I-584 | 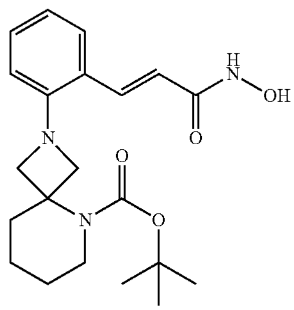 [SMILES: CC(C)(C)OC(=O)N1CCCCC12CN(c1ccccc1/C=C/C(=O)NO)C2] | ter-butyl (E)-2-(2-(3-(hydroxyamino)-3-oxoprop-1-en-1-yl)phenyl)-2,5-diazaspiro[3.5]nonane-5-carboxylate | 388 | 1.09 |
| I-542 | 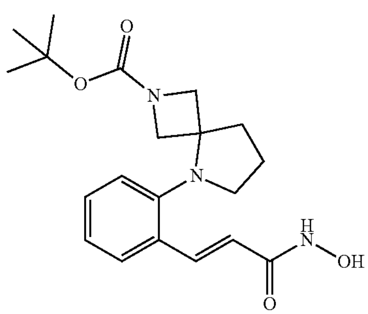 [SMILES: CC(C)(C)OC(=O)N1CC2(CCCN2c2ccccc2/C=C/C(=O)NO)C1] | tert-butyl (E)-5-(2-(3-(hydroxyamino)-3-oxoprop-1-en-1-yl)phenyl)-2,5-diazaspiro[3.4]octane-2-carboxylate | 374 | 1.35 |
| I-543 | 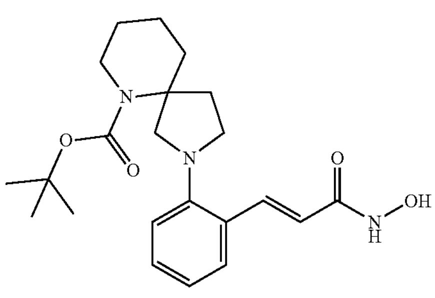 [SMILES: CC(C)(C)OC(=O)N1CCCCC12CCN(c1ccccc1/C=C/C(=O)NO)C2] | ter-butyl (E)-2-(2-(3-(hydroxyamino)-3-oxoprop-1-en-1-yl)phenyl)-2,6-diazaspiro[4.5]decane-6-carboxylate | 402 | 1.58 |

TABLE 23-continued

| ID | Structure | Name | LC-MS [M + 1]+ | HPLC RT (min) |
|---|---|---|---|---|
| I-550 | 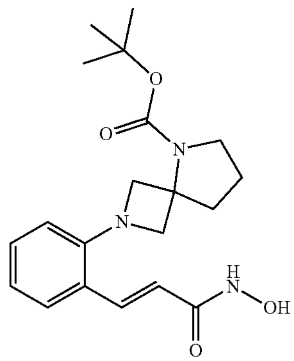 [SMILES: CC(C)(C)OC(=O)N1CCCC12CN(c1ccccc1/C=C/C(=O)NO)C2] | tert-butyl (E)-2-(2-(3-(hydroxyamino)-3-oxoprop-1-en-1-yl)phenyl)-2,5-diazaspiro[3.4]octane-5-carboxylate | 374 | 1.32 |

Example 68—(E)-4-(2-(3-(hydroxyamino)-3-oxoprop-1-en-1-yl)phenyl)-3-oxo-N-(4-(trifluoromethoxy)phenyl)piperazine-1-carboxamide

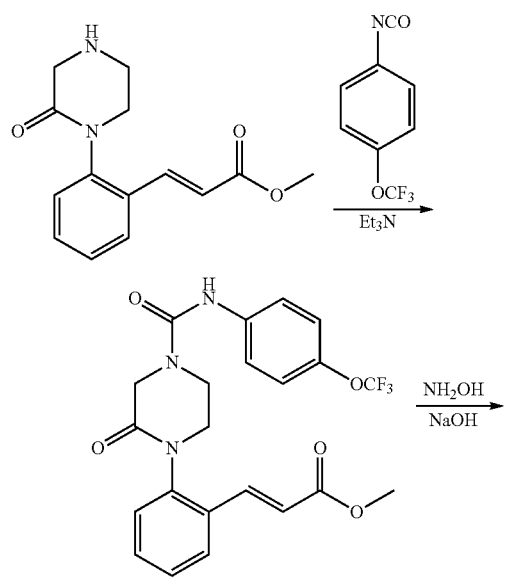

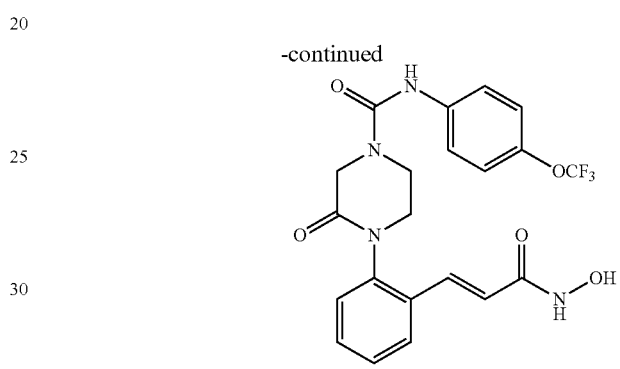

A 2 mL reaction vial was charged with 0.2M 1,2-Dichloroethane solutions of methyl (E)-3-(2-(2-oxopiperazin-1-yl)phenyl)acrylate (150 uL, 30 umol) and 1-isocyanato-4-(trifluoromethoxy)benzene (225 uL, 45 umol), then triethylamine (neat, 10 uL, 71umol) was added, the vial was sealed and shaken at RT for overnight. The mixture was diluted with brine (500 uL) and extracted with ethyl acetate (2×500 uL), the combined organic layers was dried under a stream of nitrogen Solvent THF/MeOH (3:1, 200 uL) was added to the vial, sealed and shaken at 50° C. for 15 min to dissolve the residue, cool to RT, the solutions of NH$_2$OH (150 uL, 50% in water) and NaOH (60 uL, 1N) were added, the vial was sealed and shaken at RT for overnight. The vial was dried under a stream of nitrogen, dissolved in DMSO (500 uL), and purified by HPLC to yield the title compound (6.7 mg, 48.1% yield). LCMS Rt 1.13 min, m/z 465 [M+H]$^+$.

The following compounds were synthesized according to the above protocol.

TABLE 24

| ID | Structure | Name | LC-MS [M + 1]+ | HPLC RT (min) |
|---|---|---|---|---|
| I-529 | 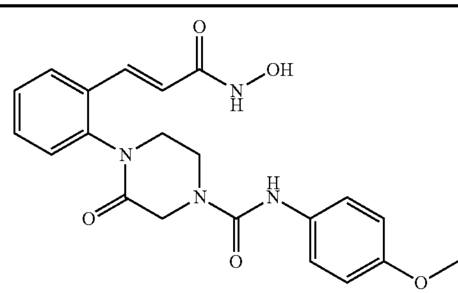 | (E)-4-(2-(3-(hydroxyamino)-3-oxoprop-1-en-1-yl)phenyl)-N-(4-methoxyphenyl)-3-oxopiperazine-1-carboxamide | 411 | 0.82 |

Example 69—2-(4-fluoro-2-methoxyphenoxy)-N-{2-[(1E)-2-(hydroxycarbamoyl)eth-1-en-1-yl]phenyl}benzamide

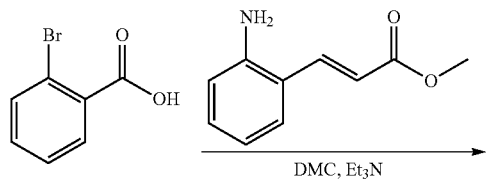

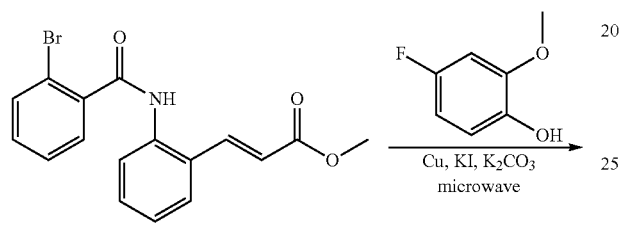

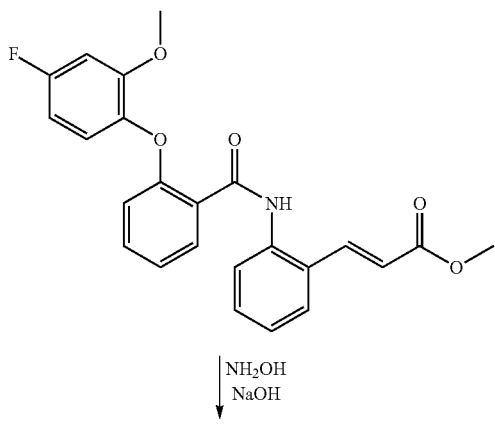

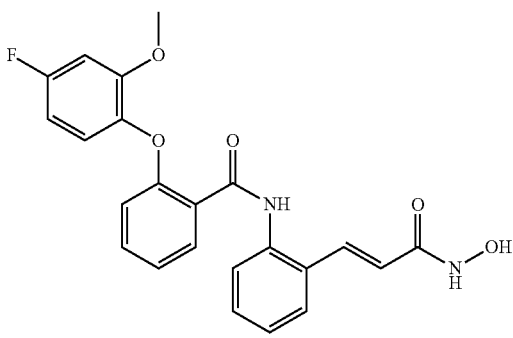

Step 1: Synthesis of methyl (E)-3-(2-(2-bromobenzamido)phenyl)acrylate

To a solution of 2-bromobenzoic acid (0.68 g, 3.39 mmol) and methyl (E)-3-(2-aminophenyl)acrylate (545 mg, 3.08 mmol) in DCE (20 mL) is added Et$_3$N (1.29 ml, 9.24 mmol) followed by DMC (592 mg, 3.5 mmol). The mixture is stirred at RT overnight and DCM (50 mL) and brine are added and the layers are separated. The organic layer is concentrated and the residue is purified by Biotage flash column (8:1 to 6:1 Hexanes/EtOAc) to give 782 mg (70%) white solid. $^1$H-NMR (CDCl$_3$, 400 MHz) δ (ppm): 7.92-8.02 (m, 2H), 7.59-7.72 (m, 41), 7.22-7.48 (m, 4H), 6.43 (d, J=21 Hz, 1H), 3.79 (s, 31H). LCMS RT: 1.91 min, m/z: 361 [M+1]$^+$.

Step 2: Synthesis of methyl (E)-3-(2-(2-(4-fluoro-2-methoxyphenoxy)benzamido)phenyl)acrylate To a solution of 4-fluoro-2-methoxyphenol (42 mg, 0.30 mmol) and methyl (E)-3-(2-(2-bromobenzamido)phenyl) acrylate (72 mg, 0.20 mmol) in DMF (2 mL) is added Cu (7 mg, 0.1 mmol), KI (17 mg, 0.1 mmol) and K$_2$CO$_3$ (83 mg, 0.6 mmol) The mixture is heated by microwave at 120° C. for 2 h. EtOAc (15 mL) and water (10 mL) is added and the layers are separated. The organic layer is washed with water (10 mL) and concentrated. The residue is purified by HPLC to give 13 mg (15%) of titled compound as light yellow oil $^1$H-NMR (CDCl$_3$, 400 MHz) δ (ppm): 9.73 (s, br, 1H), 8.21 (d, J=11 Hz, 1H), 8.06 (d, J=11 Hz, 1H), 7.82 (d, J=21 Hz, 1H), 7.27-7.47 (m, 3H), 7.09-7.17 (m, 3H), 6.62-6.69 (m, 3H), 6.28 (d, J=21 Hz, 1H), 3.64 (s, 3H), 3.56 (s, 3H) LCMS RT: 2.48 min, m/z: 422 [M+1]$^+$.

Step 3: Synthesis of 2-(4-fluoro-2-methoxyphenoxy)-N-{2-[(1E)-2-(hydroxycarbamoyl)eth-1-en-1-yl]phenyl}benzamide To a solution of methyl (E)-3-(2-(2-(4-fluoro-2-methoxyphenoxy)benzamido)phenyl)acrylate (13 mg, 0.03 mmol) in THF/MeOH (3:1, 180 uL) is added NH$_2$OH (50% in water, 125 uL) followed by NaOH (1N in water, 85 uL). The mixture is stirred at RT overnight. The solvent is evaporated under reduce pressure and the residue is dissolved in DMSO (500 uL) then purified by HPLC to yield 2-(4-fluoro-2-methoxyphenoxy)-N-{2-[(1E)-2-(hydroxycarbamoyl)eth-1-en-1-yl]phenyl}benzamide (6.2 mg, 47%). LCMS RT: 1.30 min, m/z: 423 [M+H]$^+$.

The following compounds are prepared by similar ways.

TABLE 25

| ID | Structure | Name | LC-MS [M + 1]+ | HPLC RT (min) |
|---|---|---|---|---|
| I-551 | 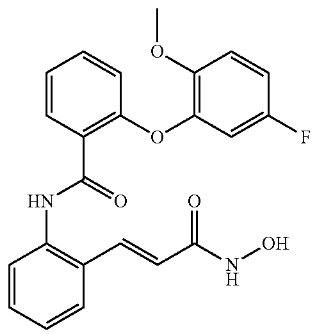 [SMILES: COc1ccc(F)cc1Oc1ccccc1C(=O)Nc1ccccc1/C=C/C(=O)NO] | 2-(5-fluoro-2-methoxy-phenoxy)-N-{2-[(1E)-2-(hydroxycarbamoyl)eth-1-en-1-yl]phenyl}benzamide | 423 | 1.17 |
| I-553 | 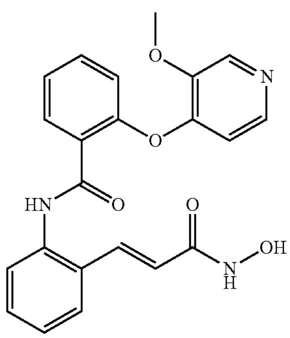 [SMILES: COc1cnccc1Oc1ccccc1C(=O)Nc1ccccc1/C=C/C(=O)NO] | N-{2-[(1E)-2-(hydroxy-carbamoyl)eth-1-en-1-yl]phenyl}-2-[(3-methoxypyridin-4-yl)oxy]benzamide | 406 | 0.63 |

Example 70—In Vitro Histone Deacetylase Assay

The enzymatic HDAC8 assay was performed using electrophoretic mobility shift assay. Full length human recombinant HDAC8 protein was expressed in baculoviral system and purified by affinity chromatography. The enzymatic reactions were assembled in 384 well plates in a total volume of 25 μL in a reaction buffer composing: 100 mM HEPES, pH 7.5, 25 mM KCl, 0.1% bovine serum albumin, 0.01% Triton X-100, 1% DMSO (from compounds) 2 μM of the fluorescently labeled peptide substrate and enzyme. The enzyme was added at a final concentration of 1 nM. The peptide substrate RHKK(Ac)-NH2 was used. The compounds were tested at 12 concentrations spaced by 3× dilution intervals. Negative control samples (0%—inhibition in the absence of inhibitor) and positive control samples (100%-inhibition) were assembled in replicates of four in each assay plate. The reactions were incubated at 25° C. and quenched by the addition of 45 μL, of termination buffer (100 mM HEPES, pH 7.5, 0.01% Triton X-100, 0.05% SDS).

The terminated assay plates were analyzed on LabChip® 3000 microfluidic electrophoresis instrument (Perkin Elmer/Caliper Life Sciences) The fluorescence intensity of the electrophoretically separated de-acetylated product and substrate peptide was measured. Activity in each sample was determined as the product to sum ratio (PSR): P/(S+P), where P is the peak height of the product peptide and S is the peak height of the substrate peptide. Percent inhibition (Pinh) is determined using the following equation: Pinh= (PSR0%−PSRinh)/(PSR0%−PSR100%)*100, where PSRinh is the product sum ratio in the presence of inhibitor, PSR0% is the average product sum ration in the absence of inhibitor and PSR100% is the average product sum ratio in 100%-inhibition control samples. The $IC_{50}$ values of inhibitors were determined by fitting the %-inhibition curves with 4 parameter dose-response model using XLfit 4 software. Ranges of $IC_{50}$ values for compounds of the invention are disclosed in Table 26.

Table 26 provides the compounds arranged according to Inhibition of proliferation of HDAC8. The compounds are separated into two groups: $IC_{50}$>1.0 μM≤10 μM and $IC_{50}$<1 μM

TABLE 26

Exemplary compounds arranged according to inhibition of proliferation of HDAC8.

| Compounds with HDAC8 $IC_{50}$ >1.0 μM ≤ 10 μM | | |
|---|---|---|
| Compounds with HDAC8 $IC_{50}$ >1.0 μM ≤ 10 μM | Compounds with HDAC8 $IC_{50}$ >1.0 μM ≤ 10 μM | Compounds with HDAC8 $IC_{50}$ >1.0 μM ≤ 10 μM |
| I-1 | I-18 | II-1 |
| I-2 | I-19 | II-2 |
| I-3 | I-20 | II-3 |
| I-4 | I-21 | II-4 |
| I-5 | I-22 | II-5 |
| I-6 | I-23 | II-6 |
| I-7 | I-24 | II-7 |
| I-8 | I-25 | II-8 |
| I-9 | I-26 | II-9 |
| I-10 | I-27 | II-10 |
| I-11 | I-28 | II-11 |
| I-12 | I-29 | II-12 |
| I-13 | I-30 | I-35 |
| I-14 | I-31 | I-36 |
| I-15 | I-32 | I-37 |

TABLE 26-continued

Exemplary compounds arranged according to inhibition of proliferation of HDAC8.

| | | |
|---|---|---|
| I-16 | I-33 | I-38 |
| I-17 | I-34 | |

Compounds with HDAC8 IC$_{50}$ < 1 μM

| Compounds with HDAC8 IC$_{50}$ <1 μM | Compounds with HDAC8 IC$_{50}$ <1 μM | Compounds with HDAC8 IC$_{50}$ <1 μM |
|---|---|---|
| I-39 | I-150 | I-262 |
| I-40 | I-151 | I-263 |
| I-41 | I-152 | II-36 |
| I-42 | I-153 | I-265 |
| I-43 | I-154 | I-266 |
| I-44 | I-155 | I-267 |
| I-45 | I-156 | I-268 |
| I-46 | I-157 | I-269 |
| I-47 | I-158 | I-270 |
| I-48 | I-159 | I-271 |
| I-49 | I-160 | I-272 |
| I-50 | I-161 | I-273 |
| I-51 | I-162 | I-274 |
| I-52 | I-163 | I-275 |
| I-53 | I-164 | I-276 |
| I-54 | I-165 | I-277 |
| I-55 | I-166 | I-278 |
| I-56 | I-167 | I-279 |
| I-57 | I-168 | I-280 |
| I-58 | I-169 | I-281 |
| I-59 | I-170 | I-282 |
| I-60 | I-171 | I-283 |
| I-61 | I-172 | I-284 |
| I-62 | I-173 | I-285 |
| I-63 | I-174 | I-286 |
| I-64 | I-175 | I-287 |
| I-65 | I-176 | I-288 |
| I-66 | I-177 | I-289 |
| I-67 | I-178 | I-290 |
| I-68 | I-179 | I-291 |
| I-69 | I-180 | I-292 |
| I-70 | I-181 | I-293 |
| I-71 | I-182 | I-294 |
| I-72 | I-183 | I-295 |
| I-73 | I-184 | II-14 |
| I-74 | I-185 | I-296 |
| I-75 | I-186 | I-297 |
| I-76 | I-187 | I-298 |
| I-77 | I-188 | II-15 |
| I-78 | I-189 | II-16 |
| I-79 | I-190 | II-17 |
| I-80 | I-191 | II-18 |
| I-81 | I-192 | I-299 |
| I-82 | I-193 | I-300 |
| I-83 | I-194 | I-301 |
| I-84 | I-195 | I-302 |
| I-85 | I-196 | I-303 |
| I-86 | I-197 | I-304 |
| I-87 | I-198 | I-305 |
| I-88 | I-199 | I-306 |
| I-89 | I-200 | I-307 |
| I-90 | I-201 | I-308 |
| I-91 | I-202 | I-309 |
| I-92 | I-203 | I-310 |
| I-93 | I-204 | I-311 |
| I-94 | I-205 | I-312 |
| I-95 | I-206 | I-313 |
| I-96 | I-207 | I-314 |
| I-97 | I-208 | I-315 |
| I-98 | I-209 | I-316 |
| I-99 | I-210 | I-317 |
| I-100 | I-211 | II-19 |
| I-101 | I-212 | II-20 |
| I-102 | I-213 | II-21 |
| I-103 | I-214 | II-22 |
| I-104 | I-215 | II-23 |
| I-105 | I-216 | II-24 |
| I-106 | I-217 | II-25 |
| I-107 | I-218 | II-26 |
| I-108 | I-219 | II-27 |
| I-109 | I-220 | II-28 |
| I-110 | I-221 | I-318 |
| I-111 | I-222 | I-319 |
| I-112 | I-223 | I-320 |
| I-113 | I-224 | I-321 |
| I-114 | I-225 | I-322 |
| I-115 | I-226 | I-323 |
| I-116 | I-227 | II-29 |
| I-117 | I-228 | II-30 |
| I-118 | I-229 | I-324 |
| I-119 | I-230 | I-325 |
| II-13 | I-231 | I-326 |
| I-120 | I-232 | I-327 |
| I-121 | I-233 | I-328 |
| I-122 | I-234 | I-329 |
| I-123 | I-235 | I-330 |
| I-124 | I-236 | I-331 |
| I-125 | I-237 | I-506 |
| I-126 | I-238 | I-526 |
| I-127 | I-239 | I-527 |
| I-128 | I-240 | I-528 |
| I-129 | I-241 | I-529 |
| I-130 | I-242 | I-530 |
| I-131 | I-243 | I-532 |
| I-132 | I-244 | I-533 |
| I-133 | I-245 | I-534 |
| I-134 | I-246 | I-535 |
| I-135 | I-247 | I-536 |
| I-136 | I-248 | I-537 |
| I-137 | I-249 | I-538 |
| I-138 | I-250 | I-539 |
| I-139 | I-251 | I-540 |
| I-140 | I-252 | I-541 |
| I-141 | I-253 | I-542 |
| I-142 | I-254 | I-543 |
| I-143 | I-255 | I-544 |
| I-144 | I-256 | I-545 |
| I-145 | I-257 | I-547 |
| I-146 | I-258 | I-556 |
| I-147 | I-259 | I-557 |
| I-148 | I-260 | II-37 |
| I-149 | I-261 | |

Example 71—HDAC8 Probe Binding Assay

The HDAC8 probe binding assay was performed using a time resolved fluorescence (TRF) assay format. Recombinant N-terminal GST tag full-length human HDAC8 was expressed and purified from baculovirus in Sf9 insect cells (SignalChem, #H90-30G-1000). Each assay was performed in 1536 black well microplates (Corning, #3936) in a final volume of 4 μL in assay buffer containing 50 mM HEPES (pH 7.5), 50 mM KCl, 50 mM NaCl, 0.5 mM GSH (L-Glutathione reduced, Sigma #G4251), 0.03% BGG (0.22 μM filtered, Sigma, #G7516-25G), and 0.01% Triton X-100 (Sigma, #T9284-10L) 20 nL of 10-point, 3-fold serial dilution in DMSO was pre-dispensed into respective wells of 1536 assay plates for a final test concentration range of 25 μM to 1.3 nM respectively. The final concentration in the assay of HDAC8 and probe (a fluorescein labeled pan-HDAC inhibitor) was 2.5 nM and 1.5 nM respectively. 2 μL of 2× probe and 2× anti-GST Terbium (Cisbio, #61GSTXLB) was added to assay plates followed by 2 μL of 2× HDAC8. Plates were incubated for 16 hours at room temperature before time resolved fluorescence was read on the Envision (Excitation at 340 nm, and Emission at 485 nm and 535 nm, Perkin Elmer).

Data from HDAC8 Assays were reported as percent inhibition (inh) compared with control wells based on the following equation: % inh=1−((FLU−AveLow)/(AveHigh−AveLow)) where FLU=measured time resolved fluorescence. AveLow=average time resolved fluorescence of no enzyme control (n=32). AveHigh=average time resolved fluorescence of DMSO control (n=32). $IC_{50}$ values were determined by curve fitting of the standard 4 parameter logistic fitting algorithm included in the Activity Base software package. IDBS XE Designer Model205. Data is fitted using the Levenburg Marquardt algorithm.

TABLE 27

Exemplary compounds arranged according to inhibition of proliferation of HDAC8 determined in a time resolved fluorescence (TRF) assay.

| Compounds with HDAC8 TRF $IC_{50}$ ≤1 μM | Compounds with HDAC8 TRF $IC_{50}$ ≤1 μM | Compounds with HDAC8 TRF $IC_{50}$ ≤1 μM |
|---|---|---|
| I-40 | I-200 | I-529 |
| I-41 | I-204 | I-530 |
| I-44 | I-206 | I-533 |
| I-49 | I-208 | I-534 |
| I-54 | I-219 | I-535 |
| I-61 | I-246 | I-536 |
| I-62 | I-252 | I-537 |
| I-65 | I-262 | I-538 |
| I-66 | I-263 | I-539 |
| I-67 | I-265 | I-540 |
| I-68 | I-266 | I-541 |
| I-69 | I-268 | I-542 |
| I-70 | I-270 | I-543 |
| I-71 | I-274 | I-544 |
| I-72 | I-275 | I-545 |
| I-73 | I-281 | I-546 |
| I-75 | I-282 | I-547 |
| I-76 | I-288 | I-548 |
| I-77 | I-292 | I-549 |
| I-79 | I-293 | I-550 |
| I-81 | I-298 | I-551 |
| I-83 | I-303 | I-552 |
| I-84 | I-304 | I-553 |
| I-85 | I-306 | I-555 |
| I-89 | I-307 | I-556 |
| I-91 | I-309 | I-557 |
| I-93 | I-310 | I-558 |
| I-94 | I-311 | I-559 |
| I-95 | I-312 | I-560 |
| I-96 | I-313 | I-561 |
| I-97 | I-314 | I-562 |
| I-98 | I-315 | I-563 |
| I-100 | I-317 | I-564 |
| I-101 | I-319 | I-565 |
| I-103 | I-320 | I-566 |
| I-104 | I-321 | I-568 |
| I-107 | I-323 | I-569 |
| I-113 | I-324 | I-570 |
| I-115 | I-325 | I-572 |
| I-123 | I-326 | I-573 |
| I-134 | I-327 | I-575 |
| I-148 | I-328 | I-576 |
| I-153 | I-495 | II-15 |
| I-170 | I-501 | II-22 |
| I-179 | I-503 | II-27 |
| I-180 | I-504 | II-28 |
| I-182 | I-526 | II-29 |
| I-183 | I-527 | II-37 |

| Compounds with HDAC8 TRF $IC_{50}$ >1 μM ≤ 100 μM | Compounds with HDAC8 TRF $IC_{50}$ >1 μM ≤ 10 μM | Compounds with HDAC8 TRF $IC_{50}$ >1 μM ≤ 10 μM |
|---|---|---|
| I-43 | I-554 | I-579 |
| I-45 | I-567 | I-582 |
| I-48 | | |

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A method of treating, inhibiting, or eliminating a disease or disorder associated with inhibition of HDAC8, the method comprising administering to a patient in need thereof a therapeutically effective amount of a compound of formula (I):

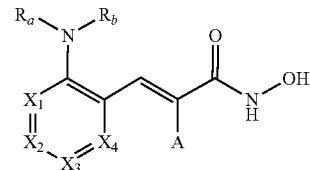

Formula I or a pharmaceutically acceptable salt thereof,
wherein:
$X_1$, $X_2$, $X_3$, and $X_4$ are each CH;
$R_a$ is hydrogen;
$R_b$ is —C(O)$R_c$;
or alternatively, $R_a$ and $R_b$ are combined to form a heterocycle, wherein said heterocycle is optionally substituted with one or more $R_d$;
$R_c$ is aryl, optionally substituted with one or more $R_d$ or $R_e$;
$R_d$ is hydrogen, $C_1$-$C_6$ alkyl, oxo, $C_3$-$C_8$ cycloalkyl, or —O$R_e$,
or two $R_d$ when attached to the same carbon atom can form a $C_3$-$C_{12}$ spirocycle or a 3- to 12-membered spiroheterocycle;
$R_e$ is aryl; and
A is hydrogen;
with the proviso that:
when $R_a$ is H and $R_b$ is —C(O)$R_c$, then $R_c$ cannot be phenyl, 1-naphthyl, 2-naphthyl, or 4-biphenyl.

2. The method of claim 1, wherein $R_a$ and $R_b$ are combined to form a heterocycle, wherein said heterocycle is optionally substituted with one or more $R_d$.

3. The method of claim 2, wherein $R_d$ is at least one of hydrogen, $C_1$-$C_6$ alkyl, oxo, or $C_3$-$C_8$ cycloalkyl.

4. The method of claim 2, wherein $R_d$ is at least one of hydrogen, oxo, $C_3$-$C_8$ cycloalkyl, or two $R_d$ when attached to the same carbon atom can form a $C_3$-$C_{12}$ spirocycle or a 3- to 12-membered spiroheterocycle.

5. The method of claim 1, wherein $R_c$ is aryl, optionally substituted with one or more $R_d$.

6. The method of claim 5, wherein $R_d$ is —O$R_e$.

7. The method of claim 1, wherein the compound is (E)-N-(2-(3-(hydroxyamino)-3-oxoprop-1-en-1-yl)phenyl)-2-phenoxybenzamide, or a pharmaceutically acceptable salt thereof.

8. The method according to claim 1, wherein the disease or disorder associated with HDAC8 inhibition is cancer, neurological disease, inflammatory disease, autoimmune disease, infection, metabolic disease, hematological disease, or cardiovascular disease.

9. The method according to claim 8, wherein the cancer is colon cancer, lung cancer, neuroblastoma, ovarian cancer, hepatocellular carcinoma, gastric cancer, prostate cancer, pancreatic cancer, renal cancer, cervical cancer, ovarian cancer, head and neck cancer, lymphoma, colorectal cancer, non-small cell lung carcinoma, breast cancer, bladder cancer, acute myeloid leukemia, acute lymphoblastic leukemia, cutaneous T-cell lymphoma, peripheral T-cell lymphoma, or multiple myeloma.

10. The method according to claim 8, wherein the neurological disease is epilepsy, attention deficit disorder (ADD), Alzheimer's disease, Parkinson's Disease, Huntington's Disease, Muscular dystrophy, essential tremor, central nervous system trauma caused by tissue injury, oxidative stress-induced neuronal or axonal degeneration, ALS, or multiple sclerosis.

11. The method according to claim 8, wherein the autoimmune disease is rheumatoid arthritis, Crohn's disease, type-1 diabetes, systemic juvenile idiopathic arthritis; inflammatory bowel disease; allograft transplantation; eczema, psoriasis, idiopathic thrombocytopenic purpura, autoimmune thrombocytopenia, acquired immune thrombocytopenia, autoimmune neutropenia, autoimmune hemolytic anemia, parvovirus B19-associated red cell aplasia, acquired antifactor VIII autoimmunity, acquired von Willebrand disease, monoclonal gammopathy, aplastic anemia, pure red cell aplasia, Diamond-Blackfan anemia, hemolytic disease of the newborn, immune mediated-refractoriness to platelet transfusion, hemolytic uremic syndrome, Evan's syndrome, Guillain-Barre syndrome, chronic demyelinating polyradiculoneuropathy, paraproteinemic IgM demyelinating polyneuropathy, Lamber-Eaton myasthenic syndrome, myasthenia gravis, multifocal motor neuropathy, stiff man syndrome, paraneoplastic encephalomyelitis, sensory neuropathy with anti-Hu antibodies, myelitis, autoimmune diabetic neuropathy, acute idiopathic neuropathy, toxic epidermal necrolysis, gangrene, granuloma, pemphigus vulgaris, bullous pemphigoid, vitiligo, scleroderma, atopic dermatitis, systemic and diffuse sclerosis, primary biliary cirrhosis, Celiac disease, dermatitis herpetiformis, cryptogenic cirrhosis, reactive arthritis, Hashimoto's thyroiditis, Wegener's granulomatosis, micropolyarterits, Churg-Strauss syndrome Type I and Type II autoimmune polyglandular syndromes, linear IgA disease, epidermolysis bullosa acquisita, erythema nodosa, pemphigoid gestationis, cicatricial pemphigoid, mixed essential cryoglobulinemia, chronic bullous disease of childhood, Goodpasture's syndrome, sclerosis cholangitis, ankylosing spondylitis, Behcet's syndrome temporal arteritis, Takayasu's arteritis, autoimmune urticaria, or Kawasaki disease.

12. The method of claim 8, wherein the cardiovascular disease is cardiovascular stress, pressure overload, chronic ischemia, infarction-reperfusion injury, hypertension, Brain infarct after cerebral artery occlusion; atherosclerosis, peripheral artery disease, cardiac hypertrophy, cardiac arrhythmias, stroke, or heart failure.

13. The method of claim 8, wherein the metabolic disease is metabolic syndrome, diabetes, obesity, high blood pressure, non-alcoholic fatty liver disease or heart failure.

14. A method of treating, inhibiting, or eliminating a disease or disorder associated with inhibition of HDAC8, the method comprising administering to a patient in need thereof an effective amount of a compound selected from:
(E)-3-(2-((1H-benzo[d]imidazol-2-yl)amino)phenyl)-N-hydroxyacrylamide (I-1);
(E)-N-hydroxy-3-(2-(((1-(2-methoxyethyl)-1H-benzo[d]imidazol-2-yl)methyl)amino)phenyl)acrylamide (I-2);
(E)-N-hydroxy-3-(2-((1-(2-methoxyethyl)-1H-benzo[d]imidazol-2-yl)amino)phenyl)acrylamide (I-3);
(E)-N-hydroxy-3-(2-(((6-(trifluoromethyl)-1H-benzo[d]imidazol-2-yl)methyl)amino)phenyl)acrylamide (I-4);
(E)-N-hydroxy-3-(2-(3-(3-(trifluoromethyl)phenyl)ureido)phenyl)acrylamide (I-5);
(E)-1-hydroxy-N-(2-(3-(hydroxyamino)-3-oxoprop-1-en-1-yl)phenyl)cyclobutane-1-carboxamide (I-6);
(E)-N-hydroxy-3-(2-((3-(trifluoromethyl)phenyl)sulfonamido)phenyl)acrylamide (I-7);
(E)-3-(2-(4-aminopiperidin-1-yl)phenyl)-N-hydroxyacrylamide (I-8);
(E)-N-hydroxy-3-(2-(4-(2-(4-methoxyphenyl)acetamido)piperidin-1-yl)phenyl)acrylamide (I-9);
(E)-3-(2-(4-(2-(4-chlorophenoxy)acetamido)piperidin-1-yl)phenyl)-N-hydroxyacrylamide (I-10);
(E)-N-(1-(2-(3-(hydroxyamino)-3-oxoprop-1-en-1-yl)phenyl)piperidin-4-yl)-1,8-naphthyridine-2-carboxamide (I-11);
(E)-N-(1-(2-(3-(hydroxyamino)-3-oxoprop-1-en-1-yl)phenyl)piperidin-4-yl)-1-methylazetidine-3-carboxamide (I-12);
(E)-3-(2-(4-(2-(4-chlorophenyl)acetamido)piperidin-1-yl)phenyl)-N-hydroxyacrylamide (I-13);
(E)-N-(1-(2-(3-(hydroxyamino)-3-oxoprop-1-en-1-yl)phenyl)piperidin-4-yl)-3-methylbenzamide (I-14);
(E)-5-(4-chlorophenyl)-N-(1-(2-(3-(hydroxyamino)-3-oxoprop-1-en-1-yl)phenyl)piperidin-4-yl)-2-methylfuran-3-carboxamide (I-15);
(E)-N-(1-(2-(3-(hydroxyamino)-3-oxoprop-1-en-1-yl)phenyl)piperidin-4-yl)-5-methyl-1-phenyl-1H-pyrazole-4-carboxamide (I-16);
(E)-3-(2-(4-((2-((dimethylamino)methyl)benzyl)amino)piperidin-1-yl)phenyl)-N-hydroxyacrylamide (I-17);
(E)-3-(2-(4-((3-((dimethylamino)methyl)benzyl)amino)piperidin-1-yl)phenyl)-N-hydroxyacrylamide (I-18);
(E)-N-hydroxy-3-(2-(4-(tetrahydrofuran-2-carbonyl)piperazin-1-yl)phenyl)acrylamide (I-19);
(E)-3-(2-(4-(2,3-dihydro-1H-indene-2-carbonyl)piperazin-1-yl)phenyl)-N-hydroxyacrylamide (I-20);
(E)-N-hydroxy-3-(2-(4-(1-(methoxymethyl)cyclobutane-1-carbonyl)piperazin-1-yl)phenyl)acrylamide (I-21);
(E)-N-hydroxy-3-(2-(4-(pyrazolo[1,5-a]pyridine-2-carbonyl)piperazin-1-yl)phenyl)acrylamide (I-22);
(E)-3-(2-(4-(4,4-difluorocyclohexane-1-carbonyl)piperazin-1-yl)phenyl)-N-hydroxyacrylamide (I-23);
(E)-N-hydroxy-3-(2-(4-(2-(tetrahydro-1H-pyrrolizin-7a(5H)-yl)acetyl)piperazin-1-yl)phenyl)acrylamide (I-24);
(E)-3-(2-(4-(1H-indole-2-carbonyl)piperazin-1-yl)phenyl)-N-hydroxyacrylamide (I-25);
(E)-N-hydroxy-3-(2-(4-((1-methylethyl)sulfonamido)piperidin-1-yl)phenyl)acrylamide (I-26);
(E)-3-(2-(4-(cyclopentanesulfonamido)piperidin-1-yl)phenyl)-N-hydroxyacrylamide (I-27);
(E)-3-(2-(4-((2,3-dihydrobenzo[b][1,4]dioxin-6-yl)sulfonyl)piperazin-1-yl)phenyl)-N-hydroxyacrylamide (I-28);
(E)-N-hydroxy-3-(2-(4-((2-(trifluoromethoxy)phenyl)sulfonyl)piperazin-1-yl)phenyl)acrylamide (I-29);
(E)-3-(2-(4-((4-(difluoromethoxy)phenyl)sulfonyl)piperazin-1-yl)phenyl)-N-hydroxyacrylamide (I-30);
(E)-N-hydroxy-3-(2-(4-((2-methoxyphenyl)sulfonyl)piperazin-1-yl)phenyl)acrylamide (I-31);
(E)-N-((5-((4-(2-(3-(hydroxyamino)-3-oxoprop-1-en-1-yl)phenyl)piperazin-1-yl)sulfonyl)thiophen-2-yl)methyl)benzamide (I-32);

(E)-3-(2-(4-((5-chloro-3-methylbenzo[b]thiophen-2-yl)sulfonyl)piperazin-1-yl)phenyl)-N-hydroxyacrylamide (I-33);
(E)-3-(2-(4-((2,5-dimethoxyphenyl)sulfonyl)piperazin-1-yl)phenyl)-N-hydroxyacrylamide (I-34);
(E)-N-hydroxy-3-(2-(4-(1-(pyrazin-2-yl)cyclopropane-1-carbonyl)piperazin-1-yl)phenyl)acrylamide (I-35);
(E)-N-hydroxy-3-(2-(4-(1-phenylcyclopropane-1-carbonyl)piperazin-1-yl)phenyl)acrylamide (I-36);
(E)-N-hydroxy-3-(2-(4-(1-phenylcyclobutane-1-carbonyl)piperazin-1-yl)phenyl)acrylamide (I-37);
(E)-N-(2-(3-(hydroxyamino)-3-oxoprop-1-en-1-yl)phenyl)-1-(2-(trifluoromethyl)phenyl)-1H-imidazole-2-carboxamide (I-38);
(E)-3-(2-(((1H-benzo[d]imidazol-2-yl)methyl)amino)phenyl)-N-hydroxyacrylamide (I-39);
(E)-3-(2-(benzylamino)phenyl)-N-hydroxyacrylamide (I-40);
(E)-N-(2-(3-(hydroxyamino)-3-oxoprop-1-en-1-yl)phenyl)-3-(trifluoromethyl)benzamide (I-41);
(E)-3-acetamido-N-(2-(3-(hydroxyamino)-3-oxoprop-1-en-1-yl)phenyl)benzamide (I-42);
(E)-3-(2-((3-acetamidobenzyl)amino)phenyl)-N-hydroxyacrylamide (I-43);
(E)-3-cyano-N-(2-(3-(hydroxyamino)-3-oxoprop-1-en-1-yl)phenyl)benzamide (I-44);
(E)-3-(2-((3-cyanobenzyl)amino)phenyl)-N-hydroxyacrylamide (I-45);
(E)-N-hydroxy-3-(2-((3-(trifluoromethyl)benzyl)amino)phenyl)acrylamide (I-46);
tert-butyl-(E)-9-((2-(3-(hydroxyamino)-3-oxoprop-1-en-1-yl)phenyl)carbamoyl)-3-azaspiro[5.5]undecane-3-carboxylate (I-47);
(E)-N-hydroxy-3-(2-((3-(3-hydroxypropyl)benzyl)amino)phenyl)acrylamide (I-48);
(E)-N-(2-(3-(hydroxyamino)-3-oxoprop-1-en-1-yl)phenyl)-3-(3-hydroxypropyl)benzamide (I-49);
tert-butyl-(E)-9-(2-(3-(hydroxyamino)-3-oxoprop-1-en-1-yl)phenyl)-3,9-diazaspiro[5.5]undecane-3-carboxylate (I-50)
(E)-3-(2-(((6-cyano-1H-benzo[d]imidazol-2-yl)methyl)amino)phenyl)-N-hydroxyacrylamide (I-51);
(E)-3-(2-(3,9-diazaspiro[5.5]undecan-3-yl)phenyl)-N-hydroxyacrylamide (I-52);
(E)-3-(2-((3-(3-amino-3-oxopropyl)benzyl)amino)phenyl)-N-hydroxyacrylamide (I-53);
(E)-N-(2-(3-(hydroxyamino)-3-oxoprop-1-en-1-yl)phenyl)-N-methyl-3-(trifluoromethyl)benzamide (I-54)
(E)-3-(2-((cyclohexylmethyl)amino)phenyl)-N-hydroxyacrylamide (I-55);
(E)-N-(2-(3-(hydroxyamino)-3-oxoprop-1-en-1-yl)phenyl)cyclohexanecarboxamide (I-56);
(E)-N-hydroxy-3-(2-(piperidin-1-yl)phenyl)acrylamide (I-57);
tert-butyl (E)-4-(2-(3-(hydroxyamino)-3-oxoprop-1-en-1-yl)phenyl)piperazine-1-carboxylate (I-58);
(E)-N-hydroxy-3-(2-(piperazin-1-yl)phenyl)acrylamide (I-59);
tert-butyl (E)-(1-(2-(3-(hydroxyamino)-3-oxoprop-1-en-1-yl)phenyl)piperidin-4-yl)carbamate (I-60);
(E)-N-(2-(3-(hydroxyamino)-3-oxoprop-1-en-1-yl)phenyl)-4-(trifluoromethyl)benzamide (I-61);
(E)-N-(2-(3-(hydroxyamino)-3-oxoprop-1-en-1-yl)phenyl)-1H-indole-5-carboxamide (I-62);
(E)-3-(2-(2-(1,1-dioxidothiomorpholino)propanamido)phenyl)-N-hydroxy acrylamide (I-63);
(E)-N-(2-(3-(hydroxyamino)-3-oxoprop-1-en-1-yl)phenyl)-1-phenylcyclopropane-1-carboxamide (I-64);
(E)-N-(2-(3-(hydroxyamino)-3-oxoprop-1-en-1-yl)phenyl)-1,2,3,4-tetrahydronaphthalene-2-carboxamide (I-65);
(E)-N-hydroxy-3-(2-(2-(p-tolyl)acetamido)phenyl)acrylamide (I-66);
(E)-N-(2-(3-(hydroxyamino)-3-oxoprop-1-en-1-yl)phenyl)-4-methylpentanamide (I-67);
(E)-3-(2-(2-cyclopentylacetamido)phenyl)-N-hydroxyacrylamide (I-68);
(E)-N-hydroxy-3-(2-isobutyramidophenyl)acrylamide (I-69);
(E)-4-(difluoromethoxy)-N-(2-(3-(hydroxyamino)-3-oxoprop-1-en-1-yl)phenyl)benzamide (I-70);
(E)-N-(2-(3-(hydroxyamino)-3-oxoprop-1-en-1-yl)phenyl)-2-phenoxybenzamide (I-71);
(E)-N-(2-(3-(hydroxyamino)-3-oxoprop-1-en-1-yl)phenyl)-4-(1H-pyrazol-1-yl)benzamide (I-72);
(1S,2R)—N-(2-((E)-3-(hydroxyamino)-3-oxoprop-1-en-1-yl)phenyl)-2-phenylcyclopropane-1-carboxamide (I-73);
(E)-N-(2-(3-(hydroxyamino)-3-oxoprop-1-en-1-yl)phenyl)-5,6-dihydro-4H-pyrrolo[1,2-b]pyrazole-2-carboxamide (I-74);
(E)-N-(2-(3-(hydroxyamino)-3-oxoprop-1-en-1-yl)phenyl)-2-(pyridin-3-yl)thiazole-4-carboxamide (I-75);
(E)-N-(2-(3-(hydroxyamino)-3-oxoprop-1-en-1-yl)phenyl)-2-(pyridin-3-yl)thiazole-5-carboxamide (I-76);
(E)-N-(2-(3-(hydroxyamino)-3-oxoprop-1-en-1-yl)phenyl)-1H-indole-2-carboxamide (I-77);
(E)-N-(2-(3-(hydroxyamino)-3-oxoprop-1-en-1-yl)phenyl)-5-(1-methyl-3-(trifluoromethyl)-1H-pyrazol-5-yl)thiophene-2-carboxamide (I-78);
(E)-1-ethyl-N-(2-(3-(hydroxyamino)-3-oxoprop-1-en-1-yl)phenyl)-1H-indole-2-carboxamide (I-79);
(E)-N-(2-(3-(hydroxyamino)-3-oxoprop-1-en-1-yl)phenyl)-1,3-dimethyl-1H-pyrazole-5-carboxamide (I-80);
(E)-N-(2-(3-(hydroxyamino)-3-oxoprop-1-en-1-yl)phenyl)-2,3-dihydro-1H-indene-2-carboxamide (I-81);
(E)-N-(2-(3-(hydroxyamino)-3-oxoprop-1-en-1-yl)phenyl)pyrazolo[1,5-a]pyridine-2-carboxamide (I-82);
(1S,2S)—N-(2-((E)-3-(hydroxyamino)-3-oxoprop-1-en-1-yl)phenyl)-2-phenylcyclopropane-1-carboxamide (I-83);
(E)-N-(2-(3-(hydroxyamino)-3-oxoprop-1-en-1-yl)phenyl)spiro[2.5]octane-6-carboxamide (I-84);
(E)-N-(2-(3-(hydroxyamino)-3-oxoprop-1-en-1-yl)phenyl)-3-(methylsulfonyl)imidazo[1,5-a]pyridine-1-carboxamide (I-85);
(E)-3-(2-((4-chlorobenzyl)amino)phenyl)-N-hydroxyacrylamide (I-86);
(E)-N-hydroxy-3-(2-(((5-isopropylpyridin-2-yl)methyl)amino)phenyl)acrylamide (I-87);
(E)-N-hydroxy-3-(2-((quinolin-4-ylmethyl)amino)phenyl)acrylamide (I-88);
(E)-N-hydroxy-3-(2-((pyridin-2-ylmethyl)amino)phenyl)acrylamide (I-89);
(E)-N-hydroxy-3-(2-(((5-methoxypyridin-3-yl)methyl)amino)phenyl)acrylamide (I-90);
(E)-N-hydroxy-3-(2-((thiazol-2-ylmethyl)amino)phenyl)acrylamide (I-91);
(E)-N-hydroxy-3-(2-((4-(pyridin-2-yl)benzyl)amino)phenyl)acrylamide (I-92);
(E)-N-hydroxy-3-(2-((pyridin-3-ylmethyl)amino)phenyl)acrylamide (I-93);

(E)-3-(2-(((1,3-dimethyl-1H-pyrazol-5-yl)methyl)amino)phenyl)-N-hydroxyacrylamide (I-94);
(E)-N-hydroxy-3-(2-((4-(methylsulfonyl)benzyl)amino)phenyl)acrylamide (I-95);
(E)-3-(2-((4-(1H-tetrazol-5-yl)benzyl)amino)phenyl)-N-hydroxyacrylamide (I-96);
(E)-N-hydroxy-3-(2-((3-morpholinobenzyl)amino)phenyl)acrylamide (I-97);
(E)-N-hydroxy-3-(2-(((2-morpholinopyridin-4-yl)methyl)amino)phenyl)acrylamide (I-98);
(E)-N-hydroxy-3-(2-(((6-phenylpyridin-3-yl)methyl)amino)phenyl)acrylamide (I-99);
(E)-N-hydroxy-3-(2-((3-(methylsulfonyl)benzyl)amino)phenyl)acrylamide (I-100);
(E)-N-hydroxy-3-(2-((3-(morpholinomethyl)benzyl)amino)phenyl)acrylamide (I-101);
(E)-3-(2-(((1H-pyrrolo[2,3-b]pyridin-2-yl)methyl)amino)phenyl)-N-hydroxyacrylamide (I-102);
(E)-N-hydroxy-3-(2-((imidazo[1,2-a]pyridin-6-ylmethyl)amino)phenyl)acrylamide (I-103);
(E)-N-hydroxy-3-(2-(((3-(4-(trifluoromethyl)phenyl)-1H-pyrazol-4-yl)methyl)amino)phenyl)acrylamide (I-104);
(E)-N-hydroxy-3-(2-(((2-(isopropylamino)pyrimidin-5-yl)methyl)amino)phenyl)acrylamide (I-105);
(E)-N-hydroxy-3-(2-(((tetrahydrofuran-3-yl)methyl)amino)phenyl)acrylamide (I-106);
(E)-3-(3-amino-3-oxopropyl)-N-(2-(3-(hydroxyamino)-3-oxoprop-1-en-1-yl)phenyl)benzamide (I-107);
(E)-3-(2-(3-(hydroxyamino)-3-oxoprop-1-en-1-yl)phenyl)-3-azaspiro[5.5]undecane-9-carboxamide (I-108);
tert-butyl (E)-9-(2-(3-(hydroxyamino)-3-oxoprop-1-en-1-yl)phenyl)-2,9-diazaspiro[5.5]undecane-2-carboxylate (I-109);
(E)-3-(2-(2,9-diazaspiro[5.5]undecan-9-yl)phenyl)-N-hydroxyacrylamide (I-110);
tert-butyl (E)-2-(2-(3-(hydroxyamino)-3-oxoprop-1-en-1-yl)phenyl)-2,8-diazaspiro[4.5]decane-8-carboxylate (I-111);
tert-butyl (E)-7-(2-(3-(hydroxyamino)-3-oxoprop-1-en-1-yl)phenyl)-2,7-diazaspiro[4.4]nonane-2-carboxylate (I-112);
(E)-3-(2-(2,7-diazaspiro[4.4]nonan-2-yl)phenyl)-N-hydroxyacrylamide (I-113);
benzyl (E)-(2-(2-(3-(hydroxyamino)-3-oxoprop-1-en-1-yl)phenyl)-5,5-dioxido-5-thia-2-azaspiro[3.4]octan-7-yl)carbamate (I-114);
(E)-3-(2-(2,8-diazaspiro[4.5]decan-2-yl)phenyl)-N-hydroxyacrylamide (I-115);
(E)-N-hydroxy-3-(2-(((6-(3-hydroxypropyl)-1H-benzo[d]imidazol-2-yl)methyl)amino)phenyl)acrylamide (I-116);
(E)-3-(2-(7-amino-5,5-dioxido-5-thia-2-azaspiro[3.4]octan-2-yl)phenyl)-N-hydroxyacrylamide (I-117);
(E)-N-(2-(3-(hydroxyamino)-3-oxoprop-1-en-1-yl)phenyl)-N-isopropyl-3-(trifluoromethyl)benzamide (I-118);
(E)-N-hydroxy-3-(2-(methyl(3-(trifluoromethyl)benzyl)amino)phenyl)acrylamide (I-119);
(E)-N-hydroxy-3-(2-(((2-(trifluoromethyl)-[1,1'-biphenyl]-4-yl)methyl)amino)phenyl)acrylamide (I-120);
(E)-3-(2-(((4,5-dichloro-1-methyl-1H-imidazol-2-yl)methyl)amino)phenyl)-N-hydroxyacrylamide (I-121);
(E)-N-(3-(3-(hydroxyamino)-3-oxoprop-1-en-1-yl)pyridin-2-yl)-3-(trifluoromethyl)benzamide (I-122);
(E)-N-(4-(3-(hydroxyamino)-3-oxoprop-1-en-1-yl)pyridin-3-yl)-3-(trifluoromethyl)benzamide (I-123);
(E)-N-(2-(3-(hydroxyamino)-3-oxoprop-1-en-1-yl)pyridin-3-yl)-3-(trifluoromethyl)benzamide (I-124);
(E)-N-(1-(2-(3-(hydroxyamino)-3-oxoprop-1-en-1-yl)phenyl)piperidin-4-yl)pentanamide (I-125);
(E)-N-(1-(2-(3-(hydroxyamino)-3-oxoprop-1-en-1-yl)phenyl)piperidin-4-yl)cyclohexanecarboxamide (I-126);
(E)-N-(1-(2-(3-(hydroxyamino)-3-oxoprop-1-en-1-yl)phenyl)piperidin-4-yl)-1-(methylsulfonyl)piperidine-3-carboxamide (I-127);
(E)-N-hydroxy-3-(2-(4-(2-(thiophen-2-yl)acetamido)piperidin-1-yl)phenyl)acrylamide (I-128);
(E)-3-(2-(4-(2-((4-fluorophenyl)thio)acetamido)piperidin-1-yl)phenyl)-N-hydroxyacrylamide (I-129);
(E)-4,4,4-trifluoro-N-(1-(2-(3-(hydroxyamino)-3-oxoprop-1-en-1-yl)phenyl)piperidin-4-yl)butanamide (I-130);
(E)-3-(2-(4-(2-(ethylthio)acetamido)piperidin-1-yl)phenyl)-N-hydroxyacrylamide (I-131);
(E)-N-(1-(2-(3-(hydroxyamino)-3-oxoprop-1-en-1-yl)phenyl)piperidin-4-yl)nicotinamide (I-132);
(E)-N-(1-(2-(3-(hydroxyamino)-3-oxoprop-1-en-1-yl)phenyl)piperidin-4-yl)-4-(methylamino)benzamide (I-133);
(E)-N-(1-(2-(3-(hydroxyamino)-3-oxoprop-1-en-1-yl)phenyl)piperidin-4-yl)-5-methyl-1H-pyrazole-3-carboxamide (I-134);
(E)-N-hydroxy-3-(2-(4-(2-(1-(methylsulfonyl)piperidin-4-yl)acetamido)piperidin-1-yl)phenyl)acrylamide (I-135);
(E)-N-(1-(2-(3-(hydroxyamino)-3-oxoprop-1-en-1-yl)phenyl)piperidin-4-yl)-4-(methylsulfonyl)butanamide (I-136);
(E)-N-hydroxy-3-(2-(4-(3-(2-oxopyrrolidin-1-yl)propanamido)piperidin-1-yl)phenyl)acrylamide (I-137);
(E)-3-(2-(4-(2-(1,1-dioxidothiomorpholino)acetamido)piperidin-1-yl)phenyl)-N-hydroxyacrylamide (I-138);
(E)-N-hydroxy-3-(2-(4-(2-(4-hydroxy-3-methoxyphenyl)acetamido)piperidin-1-yl)phenyl)acrylamide (I-139);
(E)-N-(1-(2-(3-(hydroxyamino)-3-oxoprop-1-en-1-yl)phenyl)piperidin-4-yl)-2,3-dihydro-1H-indene-2-carboxamide (I-140);
(E)-N-(1-(2-(3-(hydroxyamino)-3-oxoprop-1-en-1-yl)phenyl)piperidin-4-yl)-2-(o-tolyloxy)nicotinamide (I-141);
(E)-4,4-difluoro-N-(1-(2-(3-(hydroxyamino)-3-oxoprop-1-en-1-yl)phenyl)piperidin-4-yl)cyclohexane-1-carboxamide (I-142);
(E)-N-hydroxy-3-(2-(4-(3-(1-methylcyclopropyl)propanamido)piperidin-1-yl)phenyl)acrylamide (I-143);
(E)-N-hydroxy-3-(2-(4-(2-(N-methylmethylsulfonamido)acetamido)piperidin-1-yl)phenyl)acrylamide (I-144);
(E)-N-(1-(2-(3-(hydroxyamino)-3-oxoprop-1-en-1-yl)phenyl)piperidin-4-yl)-6,7-dihydro-5H-pyrazolo[5,1-b][1,3]oxazine-3-carboxamide (I-145);
(E)-N-hydroxy-3-(2-(4-(2-(tetrahydro-1H-pyrrolizin-7a(5H)-yl)acetamido)piperidin-1-yl)phenyl)acrylamide (I-146);
(E)-N-(1-(2-(3-(hydroxyamino)-3-oxoprop-1-en-1-yl)phenyl)piperidin-4-yl)-1,6-naphthyridine-2-carboxamide (I-147);
(E)-1-(difluoromethyl)-N-(1-(2-(3-(hydroxyamino)-3-oxoprop-1-en-1-yl)phenyl)piperidin-4-yl)-1H-pyrazole-5-carboxamide (I-148);
(E)-3,3-difluoro-N-(1-(2-(3-(hydroxyamino)-3-oxoprop-1-en-1-yl)phenyl)piperidin-4-yl)cyclobutane-1-carboxamide (I-149);

(E)-3-(2-(4-(2-cyclopropylacetamido)piperidin-1-yl)phenyl)-N-hydroxyacrylamide (I-150);
(E)-3-(2-(4-(2-(1,1-dioxidotetrahydro-2H-thiopyran-4-yl)acetamido)piperidin-1-yl)phenyl)-N-hydroxyacrylamide (I-151);
(E)-N-hydroxy-3-(2-(4-(2-(phenylthio)acetamido)piperidin-1-yl)phenyl)acrylamide (I-152);
(E)-N-(1-(2-(3-(hydroxyamino)-3-oxoprop-1-en-1-yl)phenyl)piperidin-4-yl)-1H-indole-5-carboxamide (I-153);
(E)-N-(1-(2-(3-(hydroxyamino)-3-oxoprop-1-en-1-yl)phenyl)piperidin-4-yl)-5-isopropylpicolinamide (I-154);
(E)-N-(1-(2-(3-(hydroxyamino)-3-oxoprop-1-en-1-yl)phenyl)piperidin-4-yl)-1H-indole-2-carboxamide (I-155);
(E)-N-hydroxy-3-(2-(4-(2-(4-(methylthio)phenyl)acetamido)piperidin-1-yl)phenyl)acrylamide (I-156);
(E)-N-(1-(2-(3-(hydroxyamino)-3-oxoprop-1-en-1-yl)phenyl)piperidin-4-yl)-4-methylpentanamide (I-157);
(E)-3-(2-(4-(2-(2,5-dimethylthiazol-4-yl)acetamido)piperidin-1-yl)phenyl)-N-hydroxyacrylamide (I-158);
(E)-N-(1-(2-(3-(hydroxyamino)-3-oxoprop-1-en-1-yl)phenyl)piperidin-4-yl)furan-3-carboxamide (I-159);
(E)-N-(1-(2-(3-(hydroxyamino)-3-oxoprop-1-en-1-yl)phenyl)piperidin-4-yl)-6-(1H-pyrrol-1-yl)nicotinamide (I-160);
(E)-N-(1-(2-(3-(hydroxyamino)-3-oxoprop-1-en-1-yl)phenyl)piperidin-4-yl)-1H-benzo[d][1,2,3]triazole-5-carboxamide (I-161);
(E)-3-(2-(4-(2-((dimethylamino)methyl)benzyl)piperazin-1-yl)phenyl)-N-hydroxyacrylamide (I-162);
(E)-3-(2-(4-(4-fluorobenzyl)piperazin-1-yl)phenyl)-N-hydroxyacrylamide (I-163);
(E)-3-(2-(4-(2-fluorobenzyl)piperazin-1-yl)phenyl)-N-hydroxyacrylamide (I-164);
(E)-N-hydroxy-3-(2-(4-((6-(trifluoromethyl)pyridin-3-yl)methyl)piperazin-1-yl)phenyl)acrylamide (I-165);
(E)-N-hydroxy-3-(2-(4-(3-phenylpropyl)piperazin-1-yl)phenyl)acrylamide (I-166);
(E)-N-hydroxy-3-(2-(4-((tetrahydrofuran-3-yl)methyl)piperazin-1-yl)phenyl)acrylamide (I-167);
(E)-N-hydroxy-3-(2-(4-(pyridin-2-ylmethyl)piperazin-1-yl)phenyl)acrylamide (I-168);
(E)-N-hydroxy-3-(2-(4-((5-methoxypyridin-3-yl)methyl)piperazin-1-yl)phenyl)acrylamide (I-169);
(E)-N-hydroxy-3-(2-(4-(thiazol-2-ylmethyl)piperazin-1-yl)phenyl)acrylamide (I-170);
(E)-N-hydroxy-3-(2-(4-(3-(trifluoromethyl)benzyl)piperazin-1-yl)phenyl)acrylamide (I-171);
(E)-N-hydroxy-3-(2-(4-(4-methoxybenzyl)piperazin-1-yl)phenyl)acrylamide (I-172);
(E)-3-(2-(4-((2,2-difluorobenzo[d][1,3]dioxol-5-yl)methyl)piperazin-1-yl)phenyl)-N-hydroxyacrylamide (I-173);
(E)-N-hydroxy-3-(2-(4-(2-(trifluoromethyl)benzyl)piperazin-1-yl)phenyl)acrylamide (I-174);
(E)-3-(2-(4-((6-chlorobenzo[d][1,3]dioxol-5-yl)methyl)piperazin-1-yl)phenyl)-N-hydroxyacrylamide (I-175);
(E)-3-(2-(4-(2-(difluoromethoxy)benzyl)piperazin-1-yl)phenyl)-N-hydroxyacrylamide (I-176);
(E)-3-(2-(4-butylpiperazin-1-yl)phenyl)-N-hydroxyacrylamide (I-177);
(E)-3-(2-(4-hexylpiperazin-1-yl)phenyl)-N-hydroxyacrylamide (I-178);
(E)-N-hydroxy-3-(2-(4-(pyridin-3-ylmethyl)piperazin-1-yl)phenyl)acrylamide (I-179);
(E)-N-hydroxy-3-(2-(4-((1-methyl-1H-imidazol-5-yl)methyl)piperazin-1-yl)phenyl)acrylamide (I-180);
(E)-N-hydroxy-3-(2-(4-((1-methyl-1H-imidazol-2-yl)methyl)piperazin-1-yl)phenyl)acrylamide (I-181);
(E)-N-hydroxy-3-(2-(4-((6-(pyrrolidin-1-yl)pyridin-3-yl)methyl)piperazin-1-yl)phenyl)acrylamide (I-182);
(E)-3-(2-(4-((1,3-dimethyl-1H-pyrazol-5-yl)methyl)piperazin-1-yl)phenyl)-N-hydroxyacrylamide (I-183);
(E)-N-hydroxy-3-(2-(4-(4,4,4-trifluorobutyl)piperazin-1-yl)phenyl)acrylamide (I-184);
(E)-N-hydroxy-3-(2-(4-((4-methylthiazol-2-yl)methyl)piperazin-1-yl)phenyl)acrylamide (I-185);
(E)-3-(2-(4-((1-((dimethylamino)methyl)cyclopentyl)methyl)piperazin-1-yl)phenyl)-N-hydroxyacrylamide (I-186);
(E)-3-(2-(4-((1,4-dimethylpiperidin-4-yl)methyl)piperazin-1-yl)phenyl)-N-hydroxyacrylamide (I-187);
(E)-N-hydroxy-3-(2-(4-(imidazo[1,2-a]pyridin-2-ylmethyl)piperazin-1-yl)phenyl)acrylamide (I-188);
(E)-3-(2-(4-(benzo[d]thiazol-2-ylmethyl)piperazin-1-yl)phenyl)-N-hydroxyacrylamide (I-189);
(E)-N-hydroxy-3-(2-(4-((thiazol-2-ylmethyl)amino)piperidin-1-yl)phenyl)acrylamide (I-190);
(E)-3-(2-(4-((2-(difluoromethoxy)benzyl)amino)piperidin-1-yl)phenyl)-N-hydroxyacrylamide (I-191);
(E)-3-(2-(4-((benzo[d]thiazol-2-ylmethyl)amino)piperidin-1-yl)phenyl)-N-hydroxyacrylamide (I-192);
(E)-3-(2-(4-acetylpiperazin-1-yl)phenyl)-N-hydroxyacrylamide (I-193);
(E)-N-hydroxy-3-(2-(4-(2-(methylthio)acetyl)piperazin-1-yl)phenyl)acrylamide (I-194);
(E)-N-hydroxy-3-(2-(4-(2-(4-methoxyphenyl)acetyl)piperazin-1-yl)phenyl)acrylamide (I-195);
(E)-N-hydroxy-3-(2-(4-(2-(thiophen-2-yl)acetyl)piperazin-1-yl)phenyl)acrylamide (I-196);
(E)-3-(2-(4-(2-(ethylthio)acetyl)piperazin-1-yl)phenyl)-N-hydroxyacrylamide (I-197);
(E)-N-hydroxy-3-(2-(4-(5-methyl-1H-pyrazole-3-carbonyl)piperazin-1-yl)phenyl)acrylamide (I-198);
(E)-N-hydroxy-3-(2-(4-(1-methyl-1H-imidazole-5-carbonyl)piperazin-1-yl)phenyl)acrylamide (I-199);
(E)-N-hydroxy-3-(2-(4-(4-methylthiazole-5-carbonyl)piperazin-1-yl)phenyl)acrylamide (I-200);
(E)-N-hydroxy-3-(2-(4-(4-(methylsulfonyl)butanoyl)piperazin-1-yl)phenyl)acrylamide (I-201);
(E)-3-(2-(4-(5-fluoropicolinoyl)piperazin-1-yl)phenyl)-N-hydroxyacrylamide (I-202);
(E)-N-hydroxy-3-(2-(4-(2-(4-hydroxy-3-methoxyphenyl)acetyl)piperazin-1-yl)phenyl)acrylamide (I-203);
(E)-3-(2-(4-(6,7-dihydro-5H-pyrazolo[5,1-b][1,3]oxazine-3-carbonyl)piperazin-1-yl)phenyl)-N-hydroxyacrylamide (I-204);
(E)-3-(2-(4-(3,3-difluorocyclobutane-1-carbonyl)piperazin-1-yl)phenyl)-N-hydroxyacrylamide (I-205);
(E)-3-(2-(4-(1H-pyrazole-4-carbonyl)piperazin-1-yl)phenyl)-N-hydroxyacrylamide (I-206);
(E)-3-(2-(4-(benzo[d][1,3]dioxole-5-carbonyl)piperazin-1-yl)phenyl)-N-hydroxyacrylamide (I-207);
(E)-3-(2-(4-(1H-indole-5-carbonyl)piperazin-1-yl)phenyl)-N-hydroxyacrylamide (I-208);
(E)-N-hydroxy-3-(2-(4-(1-methylpiperidine-3-carbonyl)piperazin-1-yl)phenyl)acrylamide (I-209);
(E)-3-(2-(4-(2-(4-chlorophenyl)acetyl)piperazin-1-yl)phenyl)-N-hydroxyacrylamide (I-210);
(E)-3-(2-(4-(2-(2,5-dimethylthiazol-4-yl)acetyl)piperazin-1-yl)phenyl)-N-hydroxyacrylamide (I-211);

(E)-3-(2-(4-(4-(difluoromethoxy)benzoyl)piperazin-1-yl)phenyl)-N-hydroxyacrylamide (I-212);
(E)-3-(2-(4-(3-fluoro-4-methoxybenzoyl)piperazin-1-yl)phenyl)-N-hydroxyacrylamide (I-213);
(E)-3-(2-(4-(5-(4-chlorophenyl)-2-methylfuran-3-carbonyl)piperazin-1-yl)phenyl)-N-hydroxyacrylamide (I-214);
(E)-3-(2-(4-(1H-benzo[d][1,2,3]triazole-5-carbonyl)piperazin-1-yl)phenyl)-N-hydroxyacrylamide (I-215);
(E)-N-hydroxy-3-(2-(isopropyl(3-(trifluoromethyl)benzyl)amino)phenyl)acrylamide (I-216);
(E)-N-hydroxy-3-(2-(((2-(trifluoromethyl)-[1,1'-biphenyl]-4-yl)amino)methyl)pyridin-3-yl)acrylamide (I-217);
(E)-3-(2-(4-((5-chloro-1,3-dimethyl-1H-pyrazole)-4-sulfonamido)piperidin-1-yl)phenyl)-N-hydroxyacrylamide (I-218);
(E)-N-hydroxy-3-(2-(4-((1-methyl-1H-pyrazole)-3-sulfonamido)piperidin-1-yl)phenyl)acrylamide (I-219);
(E)-3-(2-(4-((3,5-dimethylisoxazole)-4-sulfonamido)piperidin-1-yl)phenyl)-N-hydroxyacrylamide (I-220);
(E)-N-hydroxy-3-(2-(4-(pyridine-3-sulfonamido)piperidin-1-yl)phenyl)acrylamide (I-221);
(E)-3-(2-(4-((4-fluorophenyl)sulfonamido)piperidin-1-yl)phenyl)-N-hydroxyacrylamide (I-222);
(E)-3-(2-(4-((4-chlorophenyl)sulfonamido)piperidin-1-yl)phenyl)-N-hydroxyacrylamide (I-223);
(E)-N-hydroxy-3-(2-(4-((4-(trifluoromethyl)phenyl)sulfonamido)piperidin-1-yl)phenyl)acrylamide (I-224);
(E)-N-hydroxy-3-(2-(4-((4-isopropylphenyl)sulfonamido)piperidin-1-yl)phenyl)acrylamide (I-225);
(E)-N-hydroxy-3-(2-(4-((6-(trifluoromethyl)pyridine)-3-sulfonamido)piperidin-1-yl)phenyl)acrylamide (I-226);
(E)-3-(2-(4-(ethylsulfonamido)piperidin-1-yl)phenyl)-N-hydroxyacrylamide (I-227);
(E)-3-(2-(4-(((4-fluorophenyl)methyl)sulfonamido)piperidin-1-yl)phenyl)-N-hydroxyacrylamide (I-228);
(E)-3-(2-(4-(((3-chlorophenyl)methyl)sulfonamido)piperidin-1-yl)phenyl)-N-hydroxyacrylamide (I-229);
(E)-N-hydroxy-3-(2-(4-((1-methyl-1H-imidazole)-2-sulfonamido)piperidin-1-yl)phenyl)acrylamide (I-230);
(E)-3-(2-(4-((2,3-dihydrobenzo[b][1,4]dioxine)-6-sulfonamido)piperidin-1-yl)phenyl)-N-hydroxyacrylamide (I-231);
(E)-N-hydroxy-3-(2-(4-(isoquinoline-5-sulfonamido)piperidin-1-yl)phenyl)acrylamide (I-232);
(E)-3-(2-(4-((3,4-dimethoxyphenyl)sulfonamido)piperidin-1-yl)phenyl)-N-hydroxyacrylamide (I-233);
(E)-3-(2-(4-((4-(difluoromethoxy)phenyl)sulfonamido)piperidin-1-yl)phenyl)-N-hydroxyacrylamide (I-234);
(E)-3-(2-(4-(((3-fluorophenyl)methyl)sulfonamido)piperidin-1-yl)phenyl)-N-hydroxyacrylamide (I-235);
(E)-N-hydroxy-3-(2-(4-((3-oxo-3,4-dihydro-2H-benzo[b][1,4]oxazine)-6-sulfonamido)piperidin-1-yl)phenyl)acrylamide (I-236);
(E)-N-hydroxy-3-(2-(4-((1-methyl-1H-imidazole)-4-sulfonamido)piperidin-1-yl)phenyl)acrylamide (I-237);
(E)-N-hydroxy-3-(2-(4-((2-methoxyphenyl)sulfonamido)piperidin-1-yl)phenyl)acrylamide (I-238);
(E)-3-(2-(4-(((4-chloro-2-fluorophenyl)methyl)sulfonamido)piperidin-1-yl)phenyl)-N-hydroxyacrylamide (I-239);
(E)-N-((5-(N-(1-(2-(3-(hydroxyamino)-3-oxoprop-1-en-1-yl)phenyl)piperidin-4-yl)sulfamoyl)thiophen-2-yl)methyl)benzamide (I-240);
(E)-3-(2-(4-(cyclopropanesulfonamido)piperidin-1-yl)phenyl)-N-hydroxyacrylamide (I-241);
(E)-3-(2-(4-((2,5-dimethoxyphenyl)sulfonamido)piperidin-1-yl)phenyl)-N-hydroxyacrylamide (I-242);
(E)-3-(2-(4-((5-chloro-1,3-dimethyl-1H-pyrazol-4-yl)sulfonyl)piperazin-1-yl)phenyl)-N-hydroxyacrylamide (I-243);
(E)-N-hydroxy-3-(2-(4-((1-methyl-1H-pyrazol-3-yl)sulfonyl)piperazin-1-yl)phenyl)acrylamide (I-244);
(E)-3-(2-(4-((3,5-dimethylisoxazol-4-yl)sulfonyl)piperazin-1-yl)phenyl)-N-hydroxyacrylamide (I-245);
(E)-N-hydroxy-3-(2-(4-(pyridin-3-ylsulfonyl)piperazin-1-yl)phenyl)acrylamide (I-246);
(E)-N-hydroxy-3-(2-(4-(o-tolylsulfonyl)piperazin-1-yl)phenyl)acrylamide (I-247);
(E)-N-hydroxy-3-(2-(4-((6-(trifluoromethyl)pyridin-3-yl)sulfonyl)piperazin-1-yl)phenyl)acrylamide (I-248);
(E)-N-hydroxy-3-(2-(4-(isopropylsulfonyl)piperazin-1-yl)phenyl)acrylamide (I-249);
(E)-3-(2-(4-(cyclopentylsulfonyl)piperazin-1-yl)phenyl)-N-hydroxyacrylamide (I-250);
(E)-3-(2-(4-((4-fluorobenzyl)sulfonyl)piperazin-1-yl)phenyl)-N-hydroxyacrylamide (I-251);
(E)-N-hydroxy-3-(2-(4-((1-methyl-1H-imidazol-2-yl)sulfonyl)piperazin-1-yl)phenyl)acrylamide (I-252);
(E)-3-(2-(4-((5-chlorothiophen-2-yl)sulfonyl)piperazin-1-yl)phenyl)-N-hydroxyacrylamide (I-253);
(E)-N-hydroxy-3-(2-(4-(isoquinolin-5-ylsulfonyl)piperazin-1-yl)phenyl)acrylamide (I-254);
(E)-N-hydroxy-3-(2-(4-((tetrahydro-2H-pyran-4-yl)sulfonyl)piperazin-1-yl)phenyl)acrylamide (I-255);
(E)-3-(2-(4-((3,4-dimethoxyphenyl)sulfonyl)piperazin-1-yl)phenyl)-N-hydroxyacrylamide (I-256);
(E)-3-(2-(4-((3-fluorobenzyl)sulfonyl)piperazin-1-yl)phenyl)-N-hydroxyacrylamide (I-257);
(E)-N-hydroxy-3-(2-(4-((1-methyl-1H-imidazol-4-yl)sulfonyl)piperazin-1-yl)phenyl)acrylamide (I-258);
(E)-3-(2-(4-((4-chloro-2-fluorobenzyl)sulfonyl)piperazin-1-yl)phenyl)-N-hydroxyacrylamide (I-259);
(E)-3-(2-(4-(cyclopropylsulfonyl)piperazin-1-yl)phenyl)-N-hydroxyacrylamide (I-260);
tert-butyl (E)-3-(2-(3-(hydroxyamino)-3-oxoprop-1-en-1-yl)phenyl)-4-oxoimidazolidine-1-carboxylate (I-261);
(E)-N-hydroxy-3-(2-(2-oxo-3-phenylpyrrolidin-1-yl)phenyl)acrylamide (I-262);
tert-butyl (E)-4-(2-(3-(hydroxyamino)-3-oxoprop-1-en-1-yl)phenyl)-3-oxopiperazine-1-carboxylate (I-263);
(E)-5-(tert-butyl)-N-(2-(3-(hydroxyamino)-3-oxoprop-1-en-1-yl)phenyl)-2-methylfuran-3-carboxamide (I-265);
(E)-1-(4-chlorophenyl)-N-(2-(3-(hydroxyamino)-3-oxoprop-1-en-1-yl)phenyl)-5-(trifluoromethyl)-1H-pyrazole-4-carboxamide (I-266);
(E)-N-(2-(3-(hydroxyamino)-3-oxoprop-1-en-1-yl)phenyl)-2-phenethylbenzamide (I-267);
(E)-2-(4-chlorophenoxy)-N-(2-(3-(hydroxyamino)-3-oxoprop-1-en-1-yl)phenyl)benzamide (I-268);
(E)-3-chloro-N-(2-(3-(hydroxyamino)-3-oxoprop-1-en-1-yl)phenyl)benzo[b]thiophene-2-carboxamide (I-269);
(E)-N-(2-(3-(hydroxyamino)-3-oxoprop-1-en-1-yl)phenyl)-1-propyl-1H-indole-2-carboxamide (I-270);
(E)-N-(2-(3-(hydroxyamino)-3-oxoprop-1-en-1-yl)phenyl)-2-methyl-5-phenylfuran-3-carboxamide (I-271);

(E)-5-(4-chlorophenyl)-N-(2-(3-(hydroxyamino)-3-oxoprop-1-en-1-yl)phenyl)-2-methylfuran-3-carboxamide (I-272);
(E)-N-(2-(3-(hydroxyamino)-3-oxoprop-1-en-1-yl)phenyl)-6-(1H-pyrrol-1-yl)nicotinamide (I-273);
(E)-1-ethyl-N-(2-(3-(hydroxyamino)-3-oxoprop-1-en-1-yl)phenyl)-3-methyl-1H-pyrazole-5-carboxamide (I-274);
(E)-3-(2,6-dichlorophenyl)-N-(2-(3-(hydroxyamino)-3-oxoprop-1-en-1-yl)phenyl)-5-methylisoxazole-4-carboxamide (I-275);
(E)-N-(2-(3-(hydroxyamino)-3-oxoprop-1-en-1-yl)phenyl)-2-phenyl-4-propylthiazole-5-carboxamide (I-276);
(E)-N-(2-(3-(hydroxyamino)-3-oxoprop-1-en-1-yl)phenyl)-4-methyl-2-phenylthiazole-5-carboxamide (I-277);
(E)-N-(2-(3-(hydroxyamino)-3-oxoprop-1-en-1-yl)phenyl)-3-methyl-2-(o-tolyl)butanamide (I-278);
(E)-3-(2-(2-cyclopentyl-2-phenylacetamido)phenyl)-N-hydroxyacrylamide (I-279);
(E)-N-(2-(3-(hydroxyamino)-3-oxoprop-1-en-1-yl)phenyl)-2-(p-tolylthio)nicotinamide (I-280);
(E)-N-(2-(3-(hydroxyamino)-3-oxoprop-1-en-1-yl)phenyl)-2-phenoxybutanamide (I-281);
(1S,2R,4R)—N-(2-((E)-3-(hydroxyamino)-3-oxoprop-1-en-1-yl)phenyl)-7-oxabicyclo[2.2.1]heptane-2-carboxamide (I-282);
(E)-2-(tert-butyl)-N-(2-(3-(hydroxyamino)-3-oxoprop-1-en-1-yl)phenyl)-4-methylthiazole-5-carboxamide (I-283);
(E)-N-(2-(3-(hydroxyamino)-3-oxoprop-1-en-1-yl)phenyl)-3-methoxy-5-phenylthiophene-2-carboxamide (I-284);
(E)-N-(2-(3-(hydroxyamino)-3-oxoprop-1-en-1-yl)phenyl)-2-(1-methyl-1H-pyrazol-4-yl)thiazole-5-carboxamide (I-285);
(E)-N-(2-(3-(hydroxyamino)-3-oxoprop-1-en-1-yl)phenyl)-3-methyl-4-(1H-tetrazol-1-yl)benzamide (I-286);
(E)-4-((1H-benzo[d][1,2,3]triazol-1-yl)methyl)-N-(2-(3-(hydroxyamino)-3-oxoprop-1-en-1-yl)phenyl)benzamide (I-287);
(E)-4-((3,5-dimethyl-1H-pyrazol-1-yl)methyl)-N-(2-(3-(hydroxyamino)-3-oxoprop-1-en-1-yl)phenyl)benzamide (I-288);
(E)-N-hydroxy-3-(2-(4-(2-(2-methylthiazol-4-yl)propanoyl)piperazin-1-yl)phenyl)acrylamide (I-289);
(E)-3-(2-(5,6-dichloroisoindolin-2-yl)phenyl)-N-hydroxyacrylamide (I-290);
(E)-3-(2-(4-(2-(4-chlorophenyl)propanoyl)piperazin-1-yl)phenyl)-N-hydroxyacrylamide (I-291);
(E)-N-hydroxy-3-(2-(3-(4-methoxybenzyl)-5-oxoimidazolidin-1-yl)phenyl)acrylamide (I-292);
(E)-N-hydroxy-3-(2-(4-(4-methoxybenzyl)-2-oxopiperazin-1-yl)phenyl)acrylamide (I-293);
(E)-3-(2-(4-(1-(4-chlorophenyl)cyclopropane-1-carbonyl)piperazin-1-yl)phenyl)-N-hydroxyacrylamide (I-294);
(E)-N-hydroxy-3-(2-(4-(2-(pyridin-3-yl)acetyl)piperazin-1-yl)phenyl)acrylamide (I-295);
(E)-N-hydroxy-3-(2-(4-(2-(pyridin-2-yl)acetyl)piperazin-1-yl)phenyl)acrylamide (I-296);
(E)-N-hydroxy-3-(2-(4-(2-methyl-3-phenylpropanoyl)piperazin-1-yl)phenyl)acrylamide (I-297);
(E)-3-(2-(4-(1,3-dimethyl-1H-pyrazole-5-carbonyl)piperazin-1-yl)phenyl)-N-hydroxyacrylamide (I-298);
(E)-3-(2-(4-(4-chlorophenethyl)piperazin-1-yl)phenyl)-N-hydroxyacrylamide (I-299);
(E)-N-hydroxy-3-(2-(4-(2-phenylpropyl)piperazin-1-yl)phenyl)acrylamide (I-300);
tert-butyl (E)-(1-(2-(3-(hydroxyamino)-3-oxoprop-1-en-1-yl)phenyl)pyrrolidin-3-yl)carbamate (I-301);
(E)-N-hydroxy-3-(2-(2-oxo-3-phenylimidazolidin-1-yl)phenyl)acrylamide (I-302);
(E)-N-(2-(3-(hydroxyamino)-3-oxoprop-1-en-1-yl)phenyl)-2-(4-(trifluoromethyl)phenoxy)benzamide (I-303);
(E)-N-(2-(3-(hydroxyamino)-3-oxoprop-1-en-1-yl)phenyl)-2-(2-methoxyphenoxy)benzamide (I-304);
(E)-N-(2-(3-(hydroxyamino)-3-oxoprop-1-en-1-yl)phenyl)-2-morpholinoisonicotinamide (I-305);
(E)-2-(4-fluorophenoxy)-N-(2-(3-(hydroxyamino)-3-oxoprop-1-en-1-yl)phenyl)benzamide (I-306);
(E)-3-(2-(3-acetamidopyrrolidin-1-yl)phenyl)-N-hydroxyacrylamide (I-307);
(E)-N-hydroxy-3-(2-(1-oxoisoindolin-2-yl)phenyl)acrylamide (I-308);
(E)-N-hydroxy-3-(2-(2-oxo-4-phenylpyrrolidin-1-yl)phenyl)acrylamide (I-309);
tert-butyl (E)-2-(2-(3-(hydroxyamino)-3-oxoprop-1-en-1-yl)phenyl)-1-oxo-2,8-diazaspiro[4.5]decane-8-carboxylate (I-310);
(E)-2-(2-fluorophenyl)-N-(2-(3-(hydroxyamino)-3-oxoprop-1-en-1-yl)phenyl)thiazole-5-carboxamide (I-311);
(E)-N-(2-(3-(hydroxyamino)-3-oxoprop-1-en-1-yl)phenyl)-2-(pyridin-2-yl)thiazole-5-carboxamide (I-312);
(E)-N-(2-(3-(hydroxyamino)-3-oxoprop-1-en-1-yl)phenyl)-3-morpholinoisonicotinamide (I-313);
(E)-N-(2-(3-(hydroxyamino)-3-oxoprop-1-en-1-yl)phenyl)-2-(pyridin-3-yloxy)benzamide (I-314);
(E)-3-(2-(4-((2,4-dimethylthiazol-5-yl)methyl)piperazin-1-yl)phenyl)-N-hydroxyacrylamide (I-315);
(E)-3-(2-((1S,4S)-5-(2-(4-chlorophenyl)acetyl)-2,5-diazabicyclo[2.2.1]heptan-2-yl)phenyl)-N-hydroxyacrylamide (I-316);
(E)-3-(2-((1S,4S)-5-((1,3-dimethyl-1H-pyrazol-5-yl)methyl)-2,5-diazabicyclo[2.2.1]heptan-2-yl)phenyl)-N-hydroxyacrylamide (I-317);
(E)-N-(1-(2-(3-(hydroxyamino)-3-oxoprop-1-en-1-yl)phenyl)pyrrolidin-3-yl)benzamide (I-318);
(E)-N-(2-(3-(hydroxyamino)-3-oxoprop-1-en-1-yl)phenyl)-2-morpholinothiazole-5-carboxamide (I-319);
(E)-3-(2-chlorophenyl)-N-(2-(3-(hydroxyamino)-3-oxoprop-1-en-1-yl)phenyl)-5-methylisoxazole-4-carboxamide (I-320);
(E)-N-hydroxy-3-(2-(4-(1-(pyridin-3-yl)cyclopropane-1-carbonyl)piperazin-1-yl)phenyl)acrylamide (I-321);
(E)-N-hydroxy-3-(2-(4-(1-(trifluoromethyl)cyclopropane-1-carbonyl)piperazin-1-yl)phenyl)acrylamide (I-322);
(E)-3-(4-fluorophenyl)-N-(2-(3-(hydroxyamino)-3-oxoprop-1-en-1-yl)phenyl)-5-methylisoxazole-4-carboxamide (I-323);
(Z)—N-(2-(2-fluoro-3-(hydroxyamino)-3-oxoprop-1-en-1-yl)phenyl)-3-(trifluoromethyl)benzamide (I-324);
(Z)—N-(2-(2-fluoro-3-(hydroxyamino)-3-oxoprop-1-en-1-yl)phenyl)-2-phenoxybenzamide (I-325);
(E)-N-hydroxy-3-(2-(4-methylpiperazin-1-yl)phenyl)acrylamide (I-326);
(R,E)-N-hydroxy-3-(2-(2-oxo-3-phenylpyrrolidin-1-yl)phenyl)acrylamide (I-327);

(S,E)-N-hydroxy-3-(2-(2-oxo-3-phenylpyrrolidin-1-yl)phenyl)acrylamide (I-328);
(E)-3-(2-((1s,4S)-5-(1-(4-chlorophenyl)cyclopropane-1-carbonyl)-2,5-diazabicyclo[2.2.1]heptan-2-yl)phenyl)-N-hydroxyacrylamide (I-329);
(E)-3-(2-((1-(4-fluorobenzyl)pyrrolidin-3-yl)amino)phenyl)-N-hydroxyacrylamide (I-330);
(E)-3-(2-(4-(2-(4-fluorophenyl)acetamido)piperidin-1-yl)phenyl)-N-hydroxyacrylamide (I-331);
(E)-N-(2-(3-(hydroxyamino)-3-oxoprop-1-en-1-yl)phenyl)-4-methoxybenzamide (I-332);
(E)-N-(2-(3-(hydroxyamino)-3-oxoprop-1-en-1-yl)phenyl)-1-methylpiperidine-3-carboxamide (I-333);
(E)-3-(2-(2-(benzo[d][1,3]dioxol-5-yl)acetamido)phenyl)-N-hydroxyacrylamide (I-334);
(E)-N-(2-(3-(hydroxyamino)-3-oxoprop-1-en-1-yl)phenyl)-2,3-dihydrobenzofuran-5-carboxamide (I-335);
(E)-N-(2-(3-(hydroxyamino)-3-oxoprop-1-en-1-yl)phenyl)furan-3-carboxamide (I-336);
(E)-N-(2-(3-(hydroxyamino)-3-oxoprop-1-en-1-yl)phenyl)quinoline-4-carboxamide (I-337);
(E)-N-hydroxy-3-(2-(2-(2-oxopiperidin-1-yl)acetamido)phenyl)acrylamide (I-338);
(E)-N-(2-(3-(hydroxyamino)-3-oxoprop-1-en-1-yl)phenyl)-2-(1H-pyrrol-1-yl)benzamide (I-339);
(E)-3-(2-(2-cyanoacetamido)phenyl)-N-hydroxyacrylamide (I-340);
(E)-N-(2-(3-(hydroxyamino)-3-oxoprop-1-en-1-yl)phenyl)quinoline-2-carboxamide (I-341);
(S,E)-N-(2-(3-(hydroxyamino)-3-oxoprop-1-en-1-yl)phenyl)tetrahydrofuran-2-carboxamide (I-342);
(E)-N-(2-(3-(hydroxyamino)-3-oxoprop-1-en-1-yl)phenyl)-1-methyl-1H-indole-2-carboxamide (I-343);
(E)-N-(2-(3-(hydroxyamino)-3-oxoprop-1-en-1-yl)phenyl)-5-methyl-1-phenyl-1H-pyrazole-4-carboxamide (I-344);
(E)-N-(2-(3-(hydroxyamino)-3-oxoprop-1-en-1-yl)phenyl)-1-phenyl-5-propyl-1H-pyrazole-4-carboxamide (I-345);
(E)-N-(2-(3-(hydroxyamino)-3-oxoprop-1-en-1-yl)phenyl)-2-methyl-4-phenylthiazole-5-carboxamide (I-346);
(E)-N-(2-(3-(hydroxyamino)-3-oxoprop-1-en-1-yl)phenyl)-4-(5-oxo-4,5-dihydro-1H-pyrazol-1-yl)benzamide (I-347);
(E)-N-(2-(3-(hydroxyamino)-3-oxoprop-1-en-1-yl)phenyl)-5,6,7,8-tetrahydroquinoline-3-carboxamide (I-348);
(E)-5-chloro-N-(2-(3-(hydroxyamino)-3-oxoprop-1-en-1-yl)phenyl)-1H-indole-3-carboxamide (I-349);
(E)-6-fluoro-N-(2-(3-(hydroxyamino)-3-oxoprop-1-en-1-yl)phenyl)quinoline-2-carboxamide (I-350);
(E)-N-(2-(3-(hydroxyamino)-3-oxoprop-1-en-1-yl)phenyl)furo[3,2-b]pyridine-2-carboxamide (I-351);
(E)-N-(2-(3-(hydroxyamino)-3-oxoprop-1-en-1-yl)phenyl)-3-phenylisoxazole-5-carboxamide (I-352);
(E)-N-(2-(3-(hydroxyamino)-3-oxoprop-1-en-1-yl)phenyl)-4-(1H-imidazol-2-yl)benzamide (I-353);
(E)-N-(2-(3-(hydroxyamino)-3-oxoprop-1-en-1-yl)phenyl)-4-(1H-1,2,4-triazol-5-yl)benzamide (I-354);
(E)-N-(2-(3-(hydroxyamino)-3-oxoprop-1-en-1-yl)phenyl)-4-(1H-imidazol-1-yl)benzamide (I-355);
(E)-3-(2-((4-((dimethylamino)methyl)benzyl)amino)phenyl)-N-hydroxyacrylamide (I-356);
(E)-3-(2-((3-(2-(dimethylamino)ethyl)benzyl)amino)phenyl)-N-hydroxyacrylamide (I-357);
(E)-N-hydroxy-3-(2-((4-isopropylbenzyl)amino)phenyl)acrylamide (I-358);
(E)-N-hydroxy-3-(2-((pyridin-4-ylmethyl)amino)phenyl)acrylamide (I-359);
(E)-3-(2-(((5-fluoropyridin-2-yl)methyl)amino)phenyl)-N-hydroxyacrylamide (I-360);
(E)-3-(2-((2,5-difluorobenzyl)amino)phenyl)-N-hydroxyacrylamide (I-361);
(E)-3-(2-((3,5-dichlorobenzyl)amino)phenyl)-N-hydroxyacrylamide (I-362);
(E)-N-hydroxy-3-(2-((4-(trifluoromethoxy)benzyl)amino)phenyl)acrylamide (I-363);
(E)-N-hydroxy-3-(2-((3-phenoxybenzyl)amino)phenyl)acrylamide (I-364);
(E)-N-hydroxy-3-(2-((4-phenoxybenzyl)amino)phenyl)acrylamide (I-365);
(E)-N-hydroxy-3-(2-((3-(trifluoromethoxy)benzyl)amino)phenyl)acrylamide (I-366);
(E)-N-hydroxy-3-(2-((2-(trifluoromethoxy)benzyl)amino)phenyl)acrylamide (I-367);
(E)-N-hydroxy-3-(2-((quinolin-2-ylmethyl)amino)phenyl)acrylamide (I-368);
(E)-N-hydroxy-3-(2-(((1-methyl-1H-imidazol-5-yl)methyl)amino)phenyl)acrylamide (I-369);
(E)-N-hydroxy-3-(2-((imidazo[1,2-a]pyridin-2-ylmethyl)amino)phenyl)acrylamide (I-370);
(E)-N-hydroxy-3-(2-((isoquinolin-5-ylmethyl)amino)phenyl)acrylamide (I-371);
(E)-N-hydroxy-3-(2-(((2-morpholinothiazol-5-yl)methyl)amino)phenyl)acrylamide (I-372);
(E)-N-hydroxy-3-(2-((naphthalen-2-ylmethyl)amino)phenyl)acrylamide (I-373);
(E)-3-(2-((4-(1,3,4-oxadiazol-2-yl)benzyl)amino)phenyl)-N-hydroxyacrylamide (I-374);
(E)-N-hydroxy-3-(2-((naphthalen-1-ylmethyl)amino)phenyl)acrylamide (I-375);
(E)-3-(2-(((1H-pyrrolo[2,3-b]pyridin-3-yl)methyl)amino)phenyl)-N-hydroxyacrylamide (I-376);
(E)-N-hydroxy-3-(2-((4-morpholinobenzyl)amino)phenyl)acrylamide (I-377);
(E)-3-(2-((4-(1,1-dioxidothiomorpholino)benzyl)amino)phenyl)-N-hydroxyacrylamide (I-378);
(E)-3-(2-(((1H-indazol-6-yl)methyl)amino)phenyl)-N-hydroxyacrylamide (I-379);
(E)-3-(2-((4-(1H-1,2,4-triazol-1-yl)benzyl)amino)phenyl)-N-hydroxyacrylamide (I-380);
(E)-N-hydroxy-3-(2-(((6-oxo-1,6-dihydropyridin-3-yl)methyl)amino)phenyl)acrylamide (I-381);
(E)-N-hydroxy-3-(2-(((6-isopropylpyridin-3-yl)methyl)amino)phenyl)acrylamide (I-382);
(E)-3-(2-((4-(tert-butoxy)benzyl)amino)phenyl)-N-hydroxyacrylamide (I-383);
(E)-N-hydroxy-3-(2-(((1-isopropylpiperidin-4-yl)methyl)amino)phenyl)acrylamide (I-384);
(E)-3-(2-(((6-(3-amino-3-oxopropyl)-1H-benzo[d]imidazol-2-yl)methyl)amino)phenyl)-N-hydroxyacrylamide (I-385);
(E)-N-(1-(2-(3-(hydroxyamino)-3-oxoprop-1-en-1-yl)phenyl)piperidin-4-yl)cyclobutanecarboxamide (I-386);
(E)-N-(1-(2-(3-(hydroxyamino)-3-oxoprop-1-en-1-yl)phenyl)piperidin-4-yl)-6-oxo-1,4,5,6-tetrahydropyridazine-3-carboxamide (I-387);
(E)-N-(1-(2-(3-(hydroxyamino)-3-oxoprop-1-en-1-yl)phenyl)piperidin-4-yl)-5-methylpyrazine-2-carboxamide (I-388);

(E)-N-(1-(2-(3-(hydroxyamino)-3-oxoprop-1-en-1-yl)phenyl)piperidin-4-yl)-1-methyl-1H-imidazole-5-carboxamide (I-389);
(E)-3-(2-(4-(2-(dimethylamino)acetamido)piperidin-1-yl)phenyl)-N-hydroxyacrylamide (I-390);
(E)-5-fluoro-N-(1-(2-(3-(hydroxyamino)-3-oxoprop-1-en-1-yl)phenyl)piperidin-4-yl)picolinamide (I-391);
(E)-N-(1-(2-(3-(hydroxyamino)-3-oxoprop-1-en-1-yl)phenyl)piperidin-4-yl)benzo[d]thiazole-6-carboxamide (I-392);
(E)-N-(1-(2-(3-(hydroxyamino)-3-oxoprop-1-en-1-yl)phenyl)piperidin-4-yl)-1-(methoxymethyl)cyclobutane-1-carboxamide (I-393);
(E)-N-(1-(2-(3-(hydroxyamino)-3-oxoprop-1-en-1-yl)phenyl)piperidin-4-yl)pyrazolo[1,5-a]pyridine-2-carboxamide (I-394);
(E)-3-(2-(4-(3-((dimethylamino)methyl)benzyl)piperazin-1-yl)phenyl)-N-hydroxyacrylamide (I-395);
(E)-3-(2-(4-(4-(2-(dimethylamino)ethoxy)benzyl)piperazin-1-yl)phenyl)-N-hydroxyacrylamide (I-396);
(E)-N-hydroxy-3-(2-(4-(4-isopropylbenzyl)piperazin-1-yl)phenyl)acrylamide (I-397);
(E)-N-hydroxy-3-(2-(4-(3-methylbenzyl)piperazin-1-yl)phenyl)acrylamide (I-398);
(E)-N-hydroxy-3-(2-(4-((5-isopropylpyridin-2-yl)methyl)piperazin-1-yl)phenyl)acrylamide (I-399);
(E)-N-hydroxy-3-(2-(4-(pyridin-4-ylmethyl)piperazin-1-yl)phenyl)acrylamide (I-400);
(E)-N-hydroxy-3-(2-(4-(4-isopropoxybenzyl)piperazin-1-yl)phenyl)acrylamide (I-401);
(E)-3-(2-(4-(benzo[d][1,3]dioxol-5-ylmethyl)piperazin-1-yl)phenyl)-N-hydroxyacrylamide (I-402);
(E)-N-hydroxy-3-(2-(4-((6-morpholinopyridin-3-yl)methyl)piperazin-1-yl)phenyl)acrylamide (I-403);
(E)-N-hydroxy-3-(2-(4-((tetrahydro-2H-pyran-4-yl)methyl)piperazin-1-yl)phenyl)acrylamide (I-404);
(E)-3-(2-(4-((1H-pyrrol-2-yl)methyl)piperazin-1-yl)phenyl)-N-hydroxyacrylamide (I-405);
(E)-3-(2-(4-((1H-indol-5-yl)methyl)piperazin-1-yl)phenyl)-N-hydroxyacrylamide (I-406);
(E)-3-(2-(4-(1-((S)-3-formylpiperidin-1-yl)ethyl)piperazin-1-yl)phenyl)-N-hydroxyacrylamide (I-407);
(E)-3-(2-(4-(1-(4-formylpiperidin-1-yl)-2-methylpropyl)piperazin-1-yl)phenyl)-N-hydroxyacrylamide (I-408);
(E)-3-(2-(4-((1H-indol-2-yl)methyl)piperazin-1-yl)phenyl)-N-hydroxyacrylamide (I-409);
(E)-3-(2-(4-((4-(2-(dimethylamino)ethoxy)benzyl)amino)piperidin-1-yl)phenyl)-N-hydroxyacrylamide (I-410);
(E)-3-(2-(4-((4-fluorobenzyl)amino)piperidin-1-yl)phenyl)-N-hydroxyacrylamide (I-411);
(E)-3-(2-(4-((cyclohexylmethyl)amino)piperidin-1-yl)phenyl)-N-hydroxyacrylamide (I-412);
(E)-3-(2-(4-((2-fluorobenzyl)amino)piperidin-1-yl)phenyl)-N-hydroxyacrylamide (I-413);
(E)-N-hydroxy-3-(2-(4-((4-isopropylbenzyl)amino)piperidin-1-yl)phenyl)acrylamide (I-414);
(E)-N-hydroxy-3-(2-(4-((3-methylbenzyl)amino)piperidin-1-yl)phenyl)acrylamide (I-415);
(E)-N-hydroxy-3-(2-(4-(((6-(trifluoromethyl)pyridin-3-yl)methyl)amino)piperidin-1-yl)phenyl)acrylamide (I-416);
(E)-N-hydroxy-3-(2-(4-(((5-isopropylpyridin-2-yl)methyl)amino)piperidin-1-yl)phenyl)acrylamide (I-417);
(E)-N-hydroxy-3-(2-(4-((pyridin-4-ylmethyl)amino)piperidin-1-yl)phenyl)acrylamide (I-418);
(E)-N-hydroxy-3-(2-(4-((3-(trifluoromethyl)benzyl)amino)piperidin-1-yl)phenyl)acrylamide (I-419);
(E)-N-hydroxy-3-(2-(4-((4-isopropoxybenzyl)amino)piperidin-1-yl)phenyl)acrylamide (I-420);
(E)-N-hydroxy-3-(2-(4-((4-methoxybenzyl)amino)piperidin-1-yl)phenyl)acrylamide (I-421);
(E)-3-(2-(4-((benzo[d][1,3]dioxol-5-ylmethyl)amino)piperidin-1-yl)phenyl)-N-hydroxyacrylamide (I-422);
(E)-3-(2-(4-(((2,2-difluorobenzo[d][1,3]dioxol-5-yl)methyl)amino)piperidin-1-yl)phenyl)-N-hydroxyacrylamide (I-423);
(E)-N-hydroxy-3-(2-(4-((2-(trifluoromethyl)benzyl)amino)piperidin-1-yl)phenyl)acrylamide (I-424);
(E)-3-(2-(4-(((6-chlorobenzo[d][1,3]dioxol-5-yl)methyl)amino)piperidin-1-yl)phenyl)-N-hydroxyacrylamide (I-425);
(E)-N-hydroxy-3-(2-(4-(((6-morpholinopyridin-3-yl)methyl)amino)piperidin-1-yl)phenyl)acrylamide (I-426);
(E)-N-hydroxy-3-(2-(4-((pyridin-3-ylmethyl)amino)piperidin-1-yl)phenyl)acrylamide (I-427);
(E)-N-hydroxy-3-(2-(4-(((tetrahydro-2H-pyran-4-yl)methyl)amino)piperidin-1-yl)phenyl)acrylamide (I-428);
(E)-N-hydroxy-3-(2-(4-(((1-methyl-1H-imidazol-5-yl)methyl)amino)piperidin-1-yl)phenyl)acrylamide (I-429);
(E)-3-(2-(4-(((1H-pyrrol-2-yl)methyl)amino)piperidin-1-yl)phenyl)-N-hydroxyacrylamide (I-430);
(E)-3-(2-(4-(((1H-indol-5-yl)methyl)amino)piperidin-1-yl)phenyl)-N-hydroxyacrylamide (I-431)
(E)-3-(2-(4-(((1,3-dimethyl-1H-pyrazol-5-yl)methyl)amino)piperidin-1-yl)phenyl)-N-hydroxyacrylamide (I-432);
(E)-3-(2-(4-((1-((S)-3-formylpiperidin-1-yl)ethyl)amino)piperidin-1-yl)phenyl)-N-hydroxyacrylamide (I-433);
(E)-3-(2-(4-((1-(4-formylpiperidin-1-yl)-2-methylpropyl)amino)piperidin-1-yl)phenyl)-N-hydroxyacrylamide (I-434);
(E)-3-(2-(4-(((1-((dimethylamino)methyl)cyclopentyl)methyl)amino)piperidin-1-yl)phenyl)-N-hydroxyacrylamide (I-435);
(E)-3-(2-(4-(((1H-indol-2-yl)methyl)amino)piperidin-1-yl)phenyl)-N-hydroxyacrylamide (I-436)
(E)-3-(2-(4-(((1,4-dimethylpiperidin-4-yl)methyl)amino)piperidin-1-yl)phenyl)-N-hydroxyacrylamide (I-437);
(E)-N-hydroxy-3-(2-(4-pentanoylpiperazin-1-yl)phenyl)acrylamide (I-438);
(E)-N-hydroxy-3-(2-(4-(2-(pyridin-3-yl)thiazole-4-carbonyl)piperazin-1-yl)phenyl)acrylamide (I-439);
(E)-3-(2-(4-(cyclohexanecarbonyl)piperazin-1-yl)phenyl)-N-hydroxyacrylamide (I-440);
(E)-3-(2-(4-(2-((4-fluorophenyl)thio)acetyl)piperazin-1-yl)phenyl)-N-hydroxyacrylamide (I-441);
(E)-N-hydroxy-3-(2-(4-(4,4,4-trifluorobutanoyl)piperazin-1-yl)phenyl)acrylamide (I-442);
(E)-N-hydroxy-3-(2-(4-nicotinoylpiperazin-1-yl)phenyl)acrylamide (I-443);
(E)-N-hydroxy-3-(2-(4-(4-(methylamino)benzoyl)piperazin-1-yl)phenyl)acrylamide (I-444);
(E)-N-hydroxy-3-(2-(4-(2-(1-(methylsulfonyl)piperidin-4-yl)acetyl)piperazin-1-yl)phenyl)acrylamide (I-445);
(E)-3-(2-(4-(dimethylglycyl)piperazin-1-yl)phenyl)-N-hydroxyacrylamide (I-446);
(E)-N-hydroxy-3-(2-(4-(3-(2-oxopyrrolidin-1-yl)propanoyl)piperazin-1-yl)phenyl)acrylamide (I-447);

(E)-3-(2-(4-(2-(1,1-dioxidothiomorpholino)acetyl)piperazin-1-yl)phenyl)-N-hydroxyacrylamide (I-448);
(E)-3-(2-(4-(benzo[d]thiazole-6-carbonyl)piperazin-1-yl)phenyl)-N-hydroxyacrylamide (I-449);
(E)-N-hydroxy-3-(2-(4-(2-(o-tolyloxy)nicotinoyl)piperazin-1-yl)phenyl)acrylamide (I-450);
(E)-N-hydroxy-3-(2-(4-(1-(pyrrolidin-1-yl)cyclopentane-1-carbonyl)piperazin-1-yl)phenyl)acrylamide (I-451);
(E)-N-hydroxy-3-(2-(4-(1-methyl-1H-pyrazole-5-carbonyl)piperazin-1-yl)phenyl)acrylamide (I-452);
ethyl (E)-(4-(4-(2-(3-(hydroxyamino)-3-oxoprop-1-en-1-yl)phenyl)piperazin-1-yl)-4-oxobutyl)carbamate (I-453);
(E)-N-hydroxy-3-(2-(4-(3-(1-methylcyclopropyl)propanoyl)piperazin-1-yl)phenyl)acrylamide (I-454);
(E)-N-hydroxy-3-(2-(4-(N-methyl-N-(methylsulfonyl)glycyl)piperazin-1-yl)phenyl)acrylamide (I-455);
(E)-3-(2-(4-(2-(4,4-dimethyl-2,5-dioxoimidazolidin-1-yl)acetyl)piperazin-1-yl)phenyl)-N-hydroxyacrylamide (I-456);
(E)-3-(2-(4-(1,4-dimethylpiperazine-2-carbonyl)piperazin-1-yl)phenyl)-N-hydroxyacrylamide (I-457);
(E)-3-(2-(4-(1-(difluoromethyl)-1H-pyrazole-5-carbonyl)piperazin-1-yl)phenyl)-N-hydroxyacrylamide (I-458);
(E)-N-hydroxy-3-(2-(4-(1-methylazetidine-3-carbonyl)piperazin-1-yl)phenyl)acrylamide (I-459);
(E)-3-(2-(4-(2-cyclopropylacetyl)piperazin-1-yl)phenyl)-N-hydroxyacrylamide (I-460);
(E)-3-(2-(4-(2-(1,1-dioxidotetrahydro-2H-thiopyran-4-yl)acetyl)piperazin-1-yl)phenyl)-N-hydroxyacrylamide (I-461);
(E)-N-hydroxy-3-(2-(4-(2-(3-methoxyphenoxy)acetyl)piperazin-1-yl)phenyl)acrylamide (I-462);
(E)-N-hydroxy-3-(2-(4-(2-(phenylthio)acetyl)piperazin-1-yl)phenyl)acrylamide (I-463);
(E)-N-hydroxy-3-(2-(4-(4-(trifluoromethyl)benzoyl)piperazin-1-yl)phenyl)acrylamide (I-464);
(E)-N-hydroxy-3-(2-(4-(5-isopropylpicolinoyl)piperazin-1-yl)phenyl)acrylamide (I-465);
(E)-3-(2-(4-(2-(benzo[b]thiophen-3-yl)acetyl)piperazin-1-yl)phenyl)-N-hydroxyacrylamide (I-466);
(E)-N-hydroxy-3-(2-(4-(2-(4-(methylthio)phenyl)acetyl)piperazin-1-yl)phenyl)acrylamide (I-467);
(E)-3-(2-(4-(2-(4-fluorophenyl)acetyl)piperazin-1-yl)phenyl)-N-hydroxyacrylamide (I-468);
(E)-N-hydroxy-3-(2-(4-(4-methylpentanoyl)piperazin-1-yl)phenyl)acrylamide (I-469);
(E)-N-hydroxy-3-(2-(4-(3-methylbenzoyl)piperazin-1-yl)phenyl)acrylamide (I-470);
(E)-3-(2-(4-(furan-3-carbonyl)piperazin-1-yl)phenyl)-N-hydroxyacrylamide (I-471);
(E)-3-(2-(4-(2-chloronicotinoyl)piperazin-1-yl)phenyl)-N-hydroxyacrylamide (I-472);
(E)-3-(2-(4-(6-(1H-pyrrol-1-yl)nicotinoyl)piperazin-1-yl)phenyl)-N-hydroxyacrylamide (I-473);
(E)-N-hydroxy-3-(2-(4-(5-methyl-1-phenyl-1H-pyrazole-4-carbonyl)piperazin-1-yl)phenyl)acrylamide (I-474);
(E)-3-(2-(4-(3-amino-4-methylbenzoyl)piperazin-1-yl)phenyl)-N-hydroxyacrylamide (I-475);
(E)-3-(2-(4-(3-aminobenzoyl)piperazin-1-yl)phenyl)-N-hydroxyacrylamide (I-476);
(E)-N-hydroxy-3-(2-(4-(2-(trifluoromethyl)thiazole-4-carbonyl)piperazin-1-yl)phenyl)acrylamide (I-477);
(E)-3-(2-(4-((E)-3-(3-ethoxyphenyl)acryloyl)piperazin-1-yl)phenyl)-N-hydroxyacrylamide (I-478);
(E)-3-(2-(4-((4-butylphenyl)sulfonamido)piperidin-1-yl)phenyl)-N-hydroxyacrylamide (I-479);
(E)-N-hydroxy-3-(2-(4-((4-isopropylphenyl)sulfonyl)piperazin-1-yl)phenyl)acrylamide (I-480);
(E)-N-hydroxy-3-(2-(4-((5-(2-(methylthio)pyrimidin-4-yl)thiophen-2-yl)sulfonyl)piperazin-1-yl)phenyl)acrylamide (I-481);
(E)-3-(2-(4-((4-acetamido-3-chlorophenyl)sulfonyl)piperazin-1-yl)phenyl)-N-hydroxyacrylamide (I-482);
(E)-N-(2-(3-(hydroxyamino)-3-oxoprop-1-en-1-yl)phenyl)-2,4-diphenylthiazole-5-carboxamide (I-483);
(E)-2-(2,4-dimethylphenoxy)-N-(2-(3-(hydroxyamino)-3-oxoprop-1-en-1-yl)phenyl)nicotinamide (I-484);
(E)-N-(2-(3-(hydroxyamino)-3-oxoprop-1-en-1-yl)phenyl)-2-(o-tolyloxy)nicotinamide (I-485);
(E)-2-(4-chloro-2-methylphenoxy)-N-(2-(3-(hydroxyamino)-3-oxoprop-1-en-1-yl)phenyl)nicotinamide (I-486);
(E)-N-(2-(3-(hydroxyamino)-3-oxoprop-1-en-1-yl)phenyl)-3-methyl-1-phenyl-1H-pyrazole-4-carboxamide (I-487);
(E)-N-(2-(3-(hydroxyamino)-3-oxoprop-1-en-1-yl)phenyl)-6,7-dihydro-5H-pyrazolo[5,1-b][1,3]oxazine-3-carboxamide (I-488);
(E)-5-chloro-N-(2-(3-(hydroxyamino)-3-oxoprop-1-en-1-yl)phenyl)-3-methylbenzofuran-2-carboxamide (I-489);
(3S,4S)-1-(2-ethoxyethyl)-N-(2-((E)-3-(hydroxyamino)-3-oxoprop-1-en-1-yl)phenyl)-4-(trifluoromethyl)pyrrolidine-3-carboxamide (I-490);
(E)-N-(2-(3-(hydroxyamino)-3-oxoprop-1-en-1-yl)phenyl)-4-(2-methyl-1H-imidazol-1-yl)benzamide (I-491);
(E)-N-hydroxy-3-(2-(2-(2-methylindolin-1-yl)acetamido)phenyl)acrylamide (I-492);
(E)-3-((1H-imidazol-1-yl)methyl)-N-(2-(3-(hydroxyamino)-3-oxoprop-1-en-1-yl)phenyl)benzamide (I-493);
(E)-N-(2-(3-(hydroxyamino)-3-oxoprop-1-en-1-yl)phenyl)-3-((2-methyl-1H-imidazol-1-yl)methyl)benzamide (I-494);
(E)-3-(2-(4-benzyl-2-oxopiperazin-1-yl)phenyl)-N-hydroxyacrylamide (I-495);
(E)-3-(4-chlorophenyl)-N-(2-(3-(hydroxyamino)-3-oxoprop-1-en-1-yl)phenyl)isoxazole-4-carboxamide (I-496);
(E)-3-(2-(3-(2-(4-chlorophenyl)acetamido)-2-oxopyrrolidin-1-yl)phenyl)-N-hydroxyacrylamide (I-497);
(E)-N-hydroxy-3-(2-((1S,4S)-5-(oxetan-3-ylmethyl)-2,5-diazabicyclo[2.2.1]heptan-2-yl)phenyl)acrylamide (I-498);
(E)-3-(2-((1-(4-fluorophenyl)pyrrolidin-3-yl)amino)phenyl)-N-hydroxyacrylamide (I-499);
(E)-N-hydroxy-3-(2-(2-oxo-3-(4-(trifluoromethoxy)phenyl)imidazolidin-1-yl)phenyl)acrylamide (I-500);
(E)-3-(2-(3-(4-fluorophenyl)-2-oxoimidazolidin-1-yl)phenyl)-N-hydroxyacrylamide (I-501);
(E)-N-hydroxy-3-(2-(2-oxo-3-(4-(trifluoromethyl)phenyl)imidazolidin-1-yl)phenyl)acrylamide (I-502);
(E)-N-hydroxy-3-(2-(2-oxo-4-(4-(trifluoromethoxy)phenyl)piperazin-1-yl)phenyl)acrylamide (I-503);
(E)-3-(2-(4-(4-fluorophenyl)-2-oxopiperazin-1-yl)phenyl)-N-hydroxyacrylamide (I-504);
(E)-N-hydroxy-3-(2-(2-oxo-4-(4-(trifluoromethyl)phenyl)piperazin-1-yl)phenyl)acrylamide (I-505);
(E)-N-(2-(3-(hydroxyamino)-3-oxoprop-1-enyl)phenyl)benzamide (I-506);
(E)-3-(2-(((4,5-dichloro-1H-imidazol-2-yl)methyl)amino)phenyl)-N-hydroxyacrylamide (I-515);

(E)-N-hydroxy-3-(2-((3-(trifluoromethyl)phenylamino)methyl)pyridin-3-yl)acrylamide (I-516);
Ethyl (E)-3-(2-(2-oxo-3-phenylpyrrolidin-1-yl)phenyl)acrylate (I-521);
(E)-3-(2-(4-((1-acetylpiperidin-3-yl)methyl)piperazin-1-yl)phenyl)-N-hydroxyacrylamide (I-522);
(E)-N-hydroxy-3-(2-(4-((1-isobutyrylpiperidin-4-yl)methyl)piperazin-1-yl)phenyl)acrylamide (I-523);
(E)-3-(2-(4-(((1-acetylpiperidin-3-yl)methyl)amino)piperidin-1-yl)phenyl)-N-hydroxyacrylamide (I-524);
ethyl (E)-3-(2-(4-bromobenzamido)phenyl)acrylate (I-525);
(E)-N-hydroxy-3-(2-(2-oxo-4-(phenylsulfonyl)piperazin-1-yl)phenyl)acrylamide (I-526);
(E)-N-hydroxy-3-(2-(2-oxo-4-((4-(trifluoromethoxy)phenyl)sulfonyl)piperazin-1-yl)phenyl)acrylamide (I-527);
(E)-4-(2-(3-(hydroxyamino)-3-oxoprop-1-en-1-yl)phenyl)-3-oxo-N-(4-(trifluoromethoxy)phenyl)piperazine-1-carboxamide (I-528);
(E)-4-(2-(3-(hydroxyamino)-3-oxoprop-1-en-1-yl)phenyl)-N-(4-methoxyphenyl)-3-oxopiperazine-1-carboxamide (I-529);
(E)-3-(2-(4-(4-fluorobenzyl)-2-oxopiperazin-1-yl)phenyl)-N-hydroxyacrylamide (I-530);
(E)-N-hydroxy-3-(2-(4-(4-methoxybenzoyl)-2-oxopiperazin-1-yl)phenyl)acrylamide (I-531);
(E)-N-hydroxy-3-(2-(2-oxo-4-(4-(trifluoromethyl)benzoyl)piperazin-1-yl)phenyl)acrylamide (I-532);
(E)-N-hydroxy-3-(2-(2-oxo-4-(p-tolyl)piperazin-1-yl)phenyl)acrylamide (I-533);
(E)-2-(4-chloro-2-fluorophenoxy)-N-(2-(3-(hydroxyamino)-3-oxoprop-1-en-1-yl)phenyl)benzamide (I-534);
(E)-N-(2-(3-(hydroxyamino)-3-oxoprop-1-en-1-yl)phenyl)-2-((6-methylpyridin-3-yl)oxy)benzamide (I-535);
(E)-N-(2-(3-(hydroxyamino)-3-oxoprop-1-en-1-yl)phenyl)-3-phenoxybenzamide (I-536);
N-{2-[(1E)-2-(hydroxycarbamoyl)eth-1-en-1-yl]phenyl}-3-phenoxypyridine-2-carboxamide (I-537);
tert-butyl (E)-9-(2-(3-(hydroxyamino)-3-oxoprop-1-en-1-yl)phenyl)-1,9-diazaspiro[5.5]undecane-1-carboxylate (I-538);
N-{2-[(1E)-2-(hydroxycarbamoyl)eth-1-en-1-yl]phenyl}-5-phenoxy-1,3-thiazole-4-carboxamide (I-539);
(E)-N-(2-(3-(hydroxyamino)-3-oxoprop-1-en-1-yl)phenyl)-2-((6-(trifluoromethyl)pyridin-3-yl)oxy)benzamide (I-540);
tert-butyl (E)-7-(2-(3-(hydroxyamino)-3-oxoprop-1-en-1-yl)phenyl)-1,7-diazaspiro[4.4]nonane-1-carboxylate (I-541);
tert-butyl (E)-5-(2-(3-(hydroxyamino)-3-oxoprop-1-en-1-yl)phenyl)-2,5-diazaspiro[3.4]octane-2-carboxylate (I-542);
tert-butyl (E)-2-(2-(3-(hydroxyamino)-3-oxoprop-1-en-1-yl)phenyl)-2,6-diazaspiro[4.5]decane-6-carboxylate (I-543);
N-{2-[(1E)-2-(hydroxycarbamoyl)eth-1-en-1-yl]phenyl}-4-phenoxy-1,3-thiazole-2-carboxamide (I-544);
(E)-3-(2-(1-acetyl-1,7-diazaspiro[4.4]nonan-7-yl)phenyl)-N-hydroxyacrylamide (I-545);
(E)-2-(4-fluoro-2-methoxyphenoxy)-N-(2-(3-(hydroxyamino)-3-oxoprop-1-en-1-yl)phenyl)benzamide (I-546);
(E)-3-(2-(2-acetyl-2,5-diazaspiro[3.4]octan-5-yl)phenyl)-N-hydroxyacrylamide (I-547);
N-{2-[(1E)-2-(hydroxycarbamoyl)eth-1-en-1-yl]phenyl}-2-[(1-methyl-1H-pyrazol-4-yl)oxy]benzamide (I-548);
N-{4-chloro-2-[(1E)-2-(hydroxycarbamoyl)eth-1-en-1-yl]phenyl}-2-(4-fluorophenoxy)benzamide (I-549);
tert-butyl (E)-2-(2-(3-(hydroxyamino)-3-oxoprop-1-en-1-yl)phenyl)-2,5-diazaspiro[3.4]octane-5-carboxylate (I-550);
2-(5-fluoro-2-methoxyphenoxy)-N-{2-[(1E)-2-(hydroxycarbamoyl)eth-1-en-1-yl]phenyl}benzamide (I-551);
N-{2-[(1E)-2-(hydroxycarbamoyl)eth-1-en-1-yl]phenyl}-2-(3-methoxyphenoxy)benzamide (I-552);
N-{2-[(1E)-2-(hydroxycarbamoyl)eth-1-en-1-yl]phenyl}-2-[(3-methoxypyridin-4-yl)oxy]benzamide (I-553);
(E)-3-(2-(2-(4-fluorobenzoyl)-2,5-diazaspiro[3.4]octan-5-yl)phenyl)-N-hydroxyacrylamide (I-554);
N-{4-fluoro-2-[(1E)-2-(hydroxycarbamoyl)eth-1-en-1-yl]phenyl}-2-(4-fluorophenoxy)benzamide (I-555);
2-(4-fluorophenoxy)-N-{2-[(1E)-2-(hydroxycarbamoyl)eth-1-en-1-yl]-4-(trifluoromethyl)phenyl}benzamide (I-556);
2-(4-fluorophenoxy)-N-{2-[(1E)-2-(hydroxycarbamoyl)eth-1-en-1-yl]-4-(trifluoromethoxy)phenyl}benzamide (I-557);
N-{4-fluoro-2-[(1E)-2-(hydroxycarbamoyl)eth-1-en-1-yl]phenyl}-2-[(1-methyl-1H-pyrazol-4-yl)oxy]benzamide (I-558);
N-{2-[(1E)-2-(hydroxycarbamoyl)eth-1-en-1-yl]phenyl}-2-(4-methoxyphenoxy)benzamide (I-559);
N-{4-chloro-2-[(1E)-2-(hydroxycarbamoyl)eth-1-en-1-yl]phenyl}-2-[(6-methylpyridin-3-yl)oxy]benzamide (I-560);
(E)-N-hydroxy-3-(2-(2-(2-phenylacetyl)-2,5-diazaspiro[3.4]octan-5-yl)phenyl)acrylamide (I-561);
(E)-3-(2-(2-(2-(4-fluorophenyl)acetyl)-2,5-diazaspiro[3.4]octan-5-yl)phenyl)-N-hydroxyacrylamide (I-562);
N-{3-chloro-2-[(1E)-2-(hydroxycarbamoyl)eth-1-en-1-yl]phenyl}-2-(4-fluorophenoxy)benzamide (I-563);
N-{5-chloro-2-[(1E)-2-(hydroxycarbamoyl)eth-1-en-1-yl]phenyl}-2-(4-fluorophenoxy)benzamide (I-564);
(E)-3-(2-(2-(cyclopentanecarbonyl)-2,5-diazaspiro[3.4]octan-5-yl)phenyl)-N-hydroxyacrylamide (I-565);
(E)-N-hydroxy-3-(2-(2-(3,3,3-trifluoropropanoyl)-2,5-diazaspiro[3.4]octan-5-yl)phenyl)acrylamide (I-566);
(E)-3-(2-(2-(cyclohexanecarbonyl)-2,5-diazaspiro[3.4]octan-5-yl)phenyl)-N-hydroxyacrylamide (I-567);
(E)-N-hydroxy-3-(2-(2-(1-methylcyclohexane-1-carbonyl)-2,5-diazaspiro[3.4]octan-5-yl)phenyl)acrylamide (I-568);
(E)-N-hydroxy-3-(2-(2-pivaloyl-2,5-diazaspiro[3.4]octan-5-yl)phenyl)acrylamide (I-569);
N-{4-chloro-2-[(1E)-2-(hydroxycarbamoyl)eth-1-en-1-yl]phenyl}-2-phenoxypyridine-3-carboxamide (I-570);
N-{4-chloro-2-[(1E)-2-(hydroxycarbamoyl)eth-1-en-1-yl]phenyl}-3-phenoxypyridine-2-carboxamide (I-571);
N-{4-chloro-2-[(1E)-2-(hydroxycarbamoyl)eth-1-en-1-yl]phenyl}-2-(4-chlorophenoxy)pyridine-3-carboxamide (I-572);
N-{4-chloro-2-[(1E)-2-(hydroxycarbamoyl)eth-1-en-1-yl]phenyl}-2-(4-methoxyphenoxy)benzamide (I-573);
(E)-3-(2-(1-(cyclopentanecarbonyl)-1,7-diazaspiro[4.4]nonan-7-yl)phenyl)-N-hydroxyacrylamide (I-574);
(E)-3-(2-(1-(4-fluorobenzoyl)-1,7-diazaspiro[4.4]nonan-7-yl)phenyl)-N-hydroxyacrylamide (I-575);
(E)-N-hydroxy-3-(2-(1-(3,3,3-trifluoropropanoyl)-1,7-diazaspiro[4.4]nonan-7-yl)phenyl)acrylamide (I-576);

(E)-3-(2-(1-(cyclohexanecarbonyl)-1,7-diazaspiro[4.4]
nonan-7-yl)phenyl)-N-hydroxyacrylamide (I-577);
(E)-3-(2-(1-benzoyl-1,7-diazaspiro[4.4]nonan-7-yl)phe-
nyl)-N-hydroxyacrylamide (I-578);
(E)-N-hydroxy-3-(2-(1-(2-phenylacetyl)-1,7-diazaspiro
[4.4]nonan-7-yl)phenyl)acrylamide (I-579);
(E)-N-hydroxy-3-(2-(1-(3-phenylpropanoyl)-1,7-diaz-
aspiro[4.4]nonan-7-yl)phenyl)acrylamide (I-580);
(E)-N-hydroxy-3-(2-(1-(4-(trifluoromethyl)benzoyl)-1,7-
diazaspiro[4.4]nonan-7-yl)phenyl)acrylamide (I-581);
(E)-3-(2-(4-(4-chloro-3-(trifluoromethyl)phenyl)-2-
oxopiperazin-1-yl)phenyl)-N-hydroxyacrylamide
(I-582);
(E)-3-(2-(4-(3,4-dichlorophenyl)-2-oxopiperazin-1-yl)
phenyl)-N-hydroxyacrylamide (I-583); and
tert-butyl (E)-2-(2-(3-(hydroxyamino)-3-oxoprop-1-en-1-
yl)phenyl)-2,5-diazaspiro[3.5]nonane-5-carboxylate
(I-584);
(E)-2-(3-(hydroxyamino)-3-oxoprop-1-en-1-yl)-N-(2-
(trifluoromethyl)-[1,1'-biphenyl]-4-yl)benzamide (II-
1);
(E)-2-(3-(hydroxyamino)-3-oxoprop-1-en-1-yl)-N-phe-
nylbenzamide (II-2);
(E)-N-(4-ethylphenyl)-2-(3-(hydroxyamino)-3-oxoprop-
1-en-1-yl)benzamide (II-3);
(E)-N-(cyclohexylmethyl)-2-(3-(hydroxyamino)-3-oxo-
prop-1-en-1-yl)benzamide (II-4);
(E)-2-(3-(hydroxyamino)-3-oxoprop-1-en-1-yl)-N-(4-
methoxybenzyl)benzamide (II-5);
(E)-N-(4-fluorophenethyl)-2-(3-(hydroxyamino)-3-oxo-
prop-1-en-1-yl)benzamide (II-6);
(E)-N-([1,1'-biphenyl]-4-ylmethyl)-2-(3-(hy-
droxyamino)-3-oxoprop-1-en-1-yl)benzamide (II-7);
(E)-3-(2-(4-acetamidopiperidine-1-carbonyl)phenyl)-N-
hydroxyacrylamide (II-8);
(E)-3-(2-(3H-spiro[isobenzofuran-1,4'-piperidine]-1'-car-
bonyl)phenyl)-N-hydroxyacrylamide (II-9);
(E)-3-(2-(3-(1,1-dioxidothiomorpholino)azetidine-1-car-
bonyl)phenyl)-N-hydroxyacrylamide (II-10);
(E)-2-(3-(hydroxyamino)-3-oxoprop-1-en-1-yl)-N-(1-
(methoxymethyl)cyclopropyl)-N-methylbenzamide
(II-11);
(E)-3-(2-(7-azabicyclo[2.2.1]heptane-7-carbonyl)phe-
nyl)-N-hydroxyacrylamide (II-12);
(E)-N-cyclohexyl-2-(3-(hydroxyamino)-3-oxoprop-1-en-
1-yl)benzamide (II-13);
(E)-N-(4-butylphenyl)-2-(3-(hydroxyamino)-3-oxoprop-
1-en-1-yl)benzamide (II-14)
(E)-N-hydroxy-3-(2-(pyrrolidine-1-carbonyl)phenyl)
acrylamide (II-15);
(E)-N-hydroxy-3-(2-(piperidine-1-carbonyl)phenyl)acry-
lamide (II-16);
(E)-3-(2-(4,4-difluoropiperidine-1-carbonyl)phenyl)-N-
hydroxyacrylamide (II-17);
(E)-2-(3-(hydroxyamino)-3-oxoprop-1-en-1-yl)-N-
methyl-N-(3-(trifluoromethyl)benzyl)benzamide (II-
18);
(E)-N-hydroxy-3-(2-(4-phenylpiperazine-1-carbonyl)
phenyl)acrylamide (II-19);
(E)-N-hydroxy-3-(2-(4-(pyridin-4-yl)piperazine-1-carbo-
nyl)phenyl)acrylamide (II-20);
(E)-N-hydroxy-3-(2-(4-phenethylpiperazine-1-carbonyl)
phenyl)acrylamide (II-21);
(E)-N-hydroxy-3-(2-(4-(pyrazin-2-yl)piperazine-1-carbo-
nyl)phenyl)acrylamide (II-22);
(E)-N-hydroxy-3-(2-(4-(trifluoromethyl)piperidine-1-
carbonyl)phenyl)acrylamide (II-23);
(E)-3-(2-(1,1-dioxidothiomorpholine-4-carbonyl)phe-
nyl)-N-hydroxyacrylamide (II-24);
(E)-N-hydroxy-3-(2-(2-methyl-4,5,6,7-tetrahydro-2H-
pyrazolo[4,3-c]pyridine-5-carbonyl)phenyl)acrylam-
ide (II-25);
(E)-3-(2-(4-(3,5-dimethyl-4H-1,2,4-triazol-4-yl)piperi-
dine-1-carbonyl)phenyl)-N-hydroxyacrylamide (II-
26);
(E)-3-(2-(3-((1H-imidazol-1-yl)methyl)piperidine-1-car-
bonyl)phenyl)-N-hydroxyacrylamide (II-27);
(E)-3-(2-(3,3-difluoropyrrolidine-1-carbonyl)phenyl)-N-
hydroxyacrylamide (II-28);
(E)-3-(2-((1-(2-(4-chlorophenyl)acetyl)piperidin-4-yl)
sulfonyl)phenyl)-N-hydroxyacrylamide (II-29);
(E)-3-(2-((1-benzylpiperidin-4-yl)sulfonyl)phenyl)-N-
hydroxyacrylamide (II-30);
(E)-N-hydroxy-3-(2-(3-(2-hydroxypropan-2-yl)azetidine-
1-carbonyl)phenyl)acrylamide (II-31);
(E)-N-hydroxy-3-(2-(3-oxopiperazine-1-carbonyl)phe-
nyl)acrylamide (II-32);
(E)-2-(3-(hydroxyamino)-3-oxoprop-1-en-1-yl)-N-((6-
isopropylpyridin-3-yl)methyl)-N-methylbenzamide
(II-33);
(E)-2-(3-(hydroxyamino)-3-oxoprop-1-en-1-yl)-N-
methyl-N-(1-methylpiperidin-4-yl)benzamide (II-34);
(E)-N-hydroxy-3-(2-((1-phenylpiperidin-4-yl)sulfonyl)
phenyl)acrylamide (II-35);
(E)-2-(3-(hydroxyamino)-3-oxoprop-1-en-1-yl)-N-(3-
(trifluoromethyl)phenyl)benzamide (II-36); and
2-(4-chloro-2-fluorophenoxy)-N-{2-[(1E)-2-(hydroxy-
carbamoyl)eth-1-en-1-yl]-5-
methoxyphenyl}benzamide (II-37).

15. The method of claim 14, wherein the disease or disorder associated with inhibition of HDAC8 is a cancer selected from: colon cancer, lung cancer, neuroblastoma, ovarian cancer, hepatocellular carcinoma, gastric cancer, prostate cancer, pancreatic cancer, renal cancer, cervical cancer, ovarian cancer, head and neck cancer, lymphoma, colorectal cancer, non-small cell lung carcinoma, breast cancer, bladder cancer, acute myeloid leukemia, acute lymphoblastic leukemia, cutaneous T-cell lymphoma, peripheral T-cell lymphoma, and multiple myeloma.

16. The method of claim 14, wherein the disease or disorder associated with inhibition of HDAC8 is a neurological disease selected from: epilepsy, attention deficit disorder (ADD), Alzheimer's disease, Parkinson's Disease, Huntington's Disease, Muscular dystrophy, essential tremor, central nervous system trauma caused by tissue injury, oxidative stress-induced neuronal or axonal degeneration, ALS, and multiple sclerosis.

17. The method of claim 14, wherein the disease or disorder associated with inhibition of HDAC8 is an autoimmune disease selected from: rheumatoid arthritis, Crohn's disease, type-1 diabetes, systemic juvenile idiopathic arthritis; inflammatory bowel disease; allograft transplantation; eczema, psoriasis, idiopathic thrombocytopenic purpura, autoimmune thrombocytopenia, acquired immune thrombocytopenia, autoimmune neutropenia, autoimmune hemolytic anemia, parvovirus B19-associated red cell aplasia, acquired antifactor VIII autoimmunity, acquired von Willebrand disease, monoclonal gammopathy, aplastic anemia, pure red cell aplasia, Diamond-Blackfan anemia, hemolytic disease of the newborn, immune mediated-refractoriness to platelet transfusion, hemolytic uremic syndrome, Evan's syndrome, Guillain-Barre syndrome, chronic demyelinating polyradiculoneuropathy, paraproteinemic IgM demyelinating polyneuropathy, Lamber-Eaton myasthenic syndrome, myasthenia gravis, multifocal motor neuropathy, stiff man syndrome, paraneoplastic encephalomyelitis, sensory neuropathy with anti-Hu antibodies, myelitis, autoimmune diabetic neuropathy, acute idiopathic neuropathy, toxic epidermal necrolysis, gangrene, granuloma, pemphigus vulgaris, bullous pemphigoid, vitiligo, scleroderma, atopic dermatitis, systemic and diffuse sclerosis, primary biliary cirrhosis, Celiac disease, dermatitis herpetiformis, cryptogenic cirrhosis, reactive arthritis, Hashimoto's thyroiditis, Wegener's granulomatosis, micropolyarterits, Churg-Strauss syndrome Type I and Type II autoimmune polyglandular syndromes, linear IgA disease, epidermolysis bullosa acquisita, erythema nodosa, pemphigoid gestationis, cicatricial pemphigoid, mixed essential cryoglobulinemia, chronic bullous disease of childhood, Goodpasture's syndrome, sclerosis cholangitis, ankylosing spondylitis, Behcet's syndrome temporal arteritis, Takayasu's arteritis, autoimmune urticaria, and Kawasaki disease.

18. The method of claim 14, wherein the disease or disorder associated with inhibition of HDAC8 is a hematological disease selected from: anemia, multiple myeloma, lymphoma and leukemia.

19. The method of claim 14, wherein the disease or disorder associated with inhibition of HDAC8 is a cardiovascular disease selected from: cardiovascular stress, pressure overload, chronic ischemia, infarction-reperfusion injury, hypertension, Brain infarct after cerebral artery occlusion; atherosclerosis, peripheral artery disease, cardiac hypertrophy, cardiac arrhythmias, stroke, and heart failure.

20. The method of claim 14, wherein the disease or disorder associated with inhibition of HDAC8 is a metabolic disease selected from: metabolic syndrome, diabetes, obesity, high blood pressure, non-alcoholic fatty liver disease and heart failure.

* * * * *